United States Patent
Kida et al.

(10) Patent No.: US 12,043,872 B2
(45) Date of Patent: Jul. 23, 2024

(54) KIT, DEVICE, AND METHOD FOR DETECTING LUNG CANCER

(71) Applicants: TORAY INDUSTRIES, INC., Tokyo (JP); NATIONAL CANCER CENTER, Tokyo (JP)

(72) Inventors: Yuho Kida, Kamakura (JP); Satoko Kozono, Kamakura (JP); Hiroko Sudo, Kamakura (JP); Satoshi Kondou, Kamakura (JP); Junpei Kawauchi, Kamakura (JP); Takahiro Ochiya, Tokyo (JP); Shun-ichi Watanabe, Tokyo (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 0 days.

(21) Appl. No.: 18/120,059

(22) Filed: Mar. 10, 2023

(65) Prior Publication Data
US 2023/0193402 A1    Jun. 22, 2023

Related U.S. Application Data

(62) Division of application No. 16/626,781, filed as application No. PCT/JP2018/024834 on Jun. 29, 2018, now Pat. No. 11,634,778.

(30) Foreign Application Priority Data

Jun. 29, 2017 (JP) ................... 2017-126933

(51) Int. Cl.
*C12Q 1/6886* (2018.01)
*C12Q 1/6816* (2018.01)

(52) U.S. Cl.
CPC ......... *C12Q 1/6886* (2013.01); *C12Q 1/6816* (2013.01); *C12Q 2600/112* (2013.01); *C12Q 2600/178* (2013.01); *G01N 2800/7028* (2013.01)

(58) Field of Classification Search
None
See application file for complete search history.

(56) References Cited

U.S. PATENT DOCUMENTS

| | | |
|---|---|---|
| 2001/0053519 A1 | 12/2001 | Fodor et al. |
| 2010/0233704 A1 | 9/2010 | Michot et al. |
| 2011/0053158 A1 | 3/2011 | Mambo et al. |
| 2011/0117565 A1 | 5/2011 | Zhang et al. |
| 2012/0108462 A1 | 5/2012 | Keller et al. |
| 2015/0080243 A1 | 3/2015 | Whitney et al. |
| 2015/0337332 A1 | 11/2015 | Ruohoa-Baker et al. |
| 2017/0121779 A1 | 5/2017 | Kondou et al. |
| 2017/0130275 A1 | 5/2017 | Kondou et al. |
| 2017/0130278 A1 | 5/2017 | Sudo et al. |
| 2017/0166975 A1 | 6/2017 | Kondou et al. |

FOREIGN PATENT DOCUMENTS

| | | |
|---|---|---|
| CN | 103173448 A | 6/2013 |
| CN | 106471132 A | 3/2017 |
| CN | 106488986 A | 3/2017 |
| EP | 3156500 A1 | 4/2017 |
| JP | 2011-505143 A | 2/2011 |
| JP | 2013-502931 A | 1/2013 |
| WO | WO 2007/081720 A2 | 7/2007 |
| WO | WO 2009/070653 A1 | 6/2009 |
| WO | WO 2010/139810 A1 | 12/2010 |
| WO | WO 2011/025919 A1 | 3/2011 |
| WO | WO 2011/076144 A1 | 6/2011 |
| WO | WO 2011/146937 A1 | 11/2011 |
| WO | WO 2014/013258 A1 | 1/2014 |
| WO | WO 2014/192907 A1 | 12/2014 |
| WO | WO 2015/012175 A1 | 1/2015 |
| WO | WO 2015/115923 A2 | 8/2015 |
| WO | WO 2015/190542 A1 | 12/2015 |
| WO | WO 2015/190584 A1 | 12/2015 |
| WO | WO 2015/194610 A1 | 12/2015 |
| WO | WO 2015/194615 A1 | 12/2015 |

OTHER PUBLICATIONS

Liu et al., "MicroRNA expression profile of gastric cancer stem cells in the MKN-45 cancer cell line", Acta Biochim Biophys Sin, vol. 46, Issue 2, 2014, pp. 92-99.

Volinia et al., "A microRNA expression signature of human solid tumors defines cancer gene targets" PNAS, vol. 103, No. 7, Feb. 14, 2006, pp. 2257-2261.

Chinese Office Action and Search Report for Chinese Application No. 201880042985.0, dated Sep. 27, 2023.

Chinese Office Action and Search Report dated May 19, 2023 for Application No. 202010875727.X.

Song et al., "The role of deregulated microRNAs in high metastatic hepatocellular carcinoma", Chinese Journal Clinicians (Electronic Edition), vol. 7, No. 22, Nov. 15, 2013, pp. 10092-10097 with an English abstract.

Zhai et al., "Differential expressions of microRNAs in the CD138+ cells of multiple myeloma patients with deletion of Chromosome 13", Journal of Shandong University (Health Sciences), vol. 51, No. 5, May 2013, pp. 80-84 with an English abstract.

American Cancer Society, "Lung Cancer (Non-Small Cell)", 2013, total 77 pages, pp. 2-7 and 37-56.

Bai et al., "MiR-296-3p regulates cell growth and multi-drug resistance of human glioblastoma by targeting ether-á-go-go (EAG1)," European Journal of Cancer, vol. 49, No. 3, 2013 (available online Sep. 18, 2012), pp. 710-724.

(Continued)

*Primary Examiner* — Katherine D Salmon
(74) *Attorney, Agent, or Firm* — Birch, Stewart, Kolasch & Birch, LLP

(57) ABSTRACT

This application provides a kit or a device for detection of lung cancer, comprising a nucleic acid(s) for detecting a miRNA(s) in a sample from a subject, and a method for detecting lung cancer, comprising measuring the miRNA(s) in vitro.

7 Claims, 3 Drawing Sheets
Specification includes a Sequence Listing.

(56) References Cited

OTHER PUBLICATIONS

Chen et al., "Identification of ten serum microRNAs from a genome-wide serum microRNA expression profile as novel noninvasive biomarkers for nonsmall cell lung cancer diagnosis", International Journal Cancer, vol. 130, May 9, 2011, pp. 1620-1628.
Cheung et al., "Natural variation in human gene expression assessed in lymphoblastoid cells", Nature Genetics, vol. 33, Mar. 2003, pp. 422-425.
Cobb et al., "Sepsis gene expression profiling: Murine splenic compared with hepatic responses determined by using complementary DNA microarrays," Crit. Care Med. (2002), vol. 30, No. 12, pp. 2711-2721.
Dissertation of Xin Wang, "MicroRNA: Profiling and Functional Implications in Cancer and Metabolism" from University of Houston, Dec. 2012, available online at https://uh-ir.tdl.org/bitstream/handle/10657/540/Diss_XinWang_20121.pdf?sequence=1&isAllowed=y.
Enard et al., "Intra- and Interspecific Variation in Primate Gene Expression Patterns," Science (2002), vol. 296, pp. 340-343.
Eto et al., "Prospect of microRNA toward laboratory medicine Gastrointestinal Cancer and microRNA" Clinical Chemistry, 2014, vol. 43, pp. 99-105.
Foss et al., "miR-1254 and miR-574-5p Serum-Based microRNA Biomarkers for Early-Stage Non-small Cell Lung Cancer", Journal of Thoracic Oncology, Mar. 2011, vol. 6, No. 3, pp. 482-488.
Gen Bank Locus NR_ 106826, "*Homo sapiens* micro RNA 6768 (MIR6768), micro RNA", (Apr. 3, 2014) from /www.ncbi.nlm.nih.gov, printed pp. 1-3.
Hoshikawa et al., "Hypoxia induces different genes in the lungs of rats compared with mice", Physiological Genomics, vol. 12, 2003, pp. 209-219.
International Search Report, issued in PCT/JP2015/067533, dated Sep. 15, 2015.
International Search Report, issued in PCT/JP2018/024834, dated Oct. 2, 2018.
Japanese Office Action for Japanese Application No. 2019-527064, dated Jun. 7, 2022.
Jin et al., "Circulating microRNA: a novel potential biomarker for early diagnosis of Intracranial Aneurysm Rupture a case control study," Journal of Translational Medicine (2013), vol. 11, No. 296, pp. 1-9.
Keller et al., "Stable serum miRNA profiles as potential tool for non-invasive lung cancer diagnosis", RNA Biology, May 1, 2011, vol. 8, No. 3, pp. 506-516, Supplemental Content.
Kozomara et al., "miRBase: annotating high confidence microRNAs using deep sequencing data" Nucleic Acids Research, Nov. 25, 2013, vol. 42, Database issue, pp. D68-D73.
Leidinger et al., "What makes a blood cell based miRNA expression pattern disease specific?—A miRNome analysis of blood cell subsets in lung cancer patients and healthy controls"; Oncotarget, Sep. 19, 2014, vol. 5, No. 19, pp. 9484-9497.
MiScript™ miRNA PCR Array (384-well, 384HC) Human miRBase Profiler HC Plate 5, Qiagen, 2012, 10 pages, from https://b2b.qiagen.com/-/media/genetable/mi/hs/34/mihs-3403z.
Office Action issued Aug. 23, 2021, in Republic of Korea Patent Application No. 10-2017-7000867.
Okamura et al., "Diagnostic value of CEA and CYFRA 21-1 tumor markers in primary lung cancer", Lung Cancer, 2013, vol. 80, pp. 45-49.
Ondracek et al., "Global MicroRNA Expression Profiling Identifies Unique MicroRNA Pattern of Radioresistant Glioblastoma Cells", Anticancer Research 37, pp. 1099-1104, 2017.
Partial Supplementary European Search Report, dated Dec. 14, 2017, for European Application No. 15809623.0.
Persson et al., "Identification of New MicroRNAs in Paired Normal and Tumor Breast Tissue Suggests a Dual Role for the ERBB2/Her2 Gene", Cancer Research 71(1), pp. 78-86, 2011.
Qiagen Product Description "miScript™ miRNA PCR Array (384-well, 384HC) Human miRBase Profiler HC Plate 3" document 1073798, Aug. 2012, from https://b2b.qiagen.com/~media/genetable/mi/hs/34/mihs-3403z.
Rani et al., "Global analysis of serum microRNAs as potential biomarkers for lung adenocarcinoma", Cancer Biology & Therapy, 2013; vol. 14, Issue 12, pp. 1104-1112.
Roth et al., "Low Levels of Cell-Free Circulating miR-361-3p and miR-625* as Blood-Based Markers for Discriminating Malignant from Benign Lung Tumors", PLoS One, Jun. 2012, vol. 7, Issue 6, e38248, pp. 1-10.
Schmidt et al., "Liquid Profiling in Lung Cancer—Quantification of Extracellular miRNAs in Bronchial Lavage", Adv Exp Med Biol., 2016, vol. 924, pp. 33-37.
Shen et al., "Applications of MicroRNAs in the Diagnosis and Prognosis of Lung Cancer," Expert Opin. Med. Diagn. (2012), vol. 6, No. 3, pp. 197-207.
Sobin et al., "TNM Classification of Malignant Tumours, the 7th edition", International Union Against Cancer, 2010, pp. 129-134.
Supplementary Partial European Search Report issued in Application No. 18823484.3 dated Mar. 12, 2021.
Tai et al., "Blood-borne miRNA profile-based diagnostic classifier for lung adenocarcinoma", Scientific Reports, Aug. 10, 2016, 6: 31389, total 9 pages.
Takizawa et al., "miRNA Profiling in Serum Samples Using DNA Chip 3D-Gene®", BIO Clinica, Jun. 10, 2014, vol. 29, No. 6, pp. 588-589.
U.S. Office Action for U.S. Appl. No. 16/800,755, dated Feb. 2, 2022.
U.S. Office Action for U.S. Appl. No. 16/800,755, dated Oct. 8, 2021.
Written Opinion of the International Searching Authority, issued in PCT/JP2015/067533, dated Sep. 15, 2015.
Written Opinion of the International Searching Authority, issued in PCT/JP2018/024834, dated Oct. 2, 2018.
Yanaihara et al., "Unique microRNA molecular profiles in lung cancer diagnosis and prognosis," Cancer Cell, vol. 9, No. 3, Mar. 13, 2006, pp. 189-198.
Korean Office Action for Korean Application No. 10-2019-7033142, dated Jan. 22, 2024.

KIT, DEVICE, AND METHOD FOR DETECTING LUNG CANCER

CROSS-REFERENCE TO RELATED APPLICATIONS

This application is a Divisional of copending application Ser. No. 16/626,781, filed on Dec. 26, 2019, which is the National Phase under 35 U.S.C. § 371 of International Application No. PCT/JP2018/024834, filed on Jun. 29, 2018, which claims the benefit under 35 U.S.C. § 119(a) to Patent Application No. 2017-126933, filed in Japan on Jun. 29, 2017, all of which are hereby expressly incorporated by reference into the present application.

REFERENCE TO ELECTRONIC SEQUENCE LISTING

The application contains a Sequence Listing which has been submitted electronically in .XML format and is hereby incorporated by reference in its entirety. Said .XML copy, created on Feb. 28, 2023, is named "PH-7402-PCT_Sequence Listing" and is 277,496 bytes in size. The sequence listing contained in this .XML file is part of the specification and is hereby incorporated by reference herein in its entirety.

TECHNICAL FIELD

The present invention relates to a kit or a device for detection of lung cancer, comprising a nucleic acid capable of specifically binding to a particular polynucleotide or a polynucleotide complementary to that of the polynucleotide, which is used for examining the presence or absence of lung cancer in a subject, and a method for detecting lung cancer by measuring an expression level of the miRNA using the nucleic acid.

BACKGROUND ART

Lung cancer is a cancerous change of some cells of the trachea, bronchi, or alveoli of the lungs for some reasons. According to the cancer statistics in the year of 2012 by site in Japan disclosed by the Center for Cancer Control and Information Services, National Cancer Center, the number of people affected by lung cancer is 107,241 people, and 1 out of every 10 men and 1 out of every 22 women are supposedly affected. The number of deaths from lung cancer in men and women all together climbed to 71,518 people which is the top cause of deaths among cancer types. In the United States, the estimated number of people affected by lung cancer in 2014 climbed to 224,210 people, out of which about 159,260 people are expected to die.

Lung cancer has several different tissue types, of which about 15% is small cell lung carcinoma, whereas the remaining tissue types are called non-small cell lung carcinoma. Non-small cell lung carcinoma contains various tissue types, including three major tissue types that are adenocarcinoma, squamous cell carcinoma, and large cell carcinoma. Depending on the tissue type of lung cancer, development site, form and speed of progression, and their symptoms notably vary, and appropriate approaches to therapy are accordingly different. For example, small cell carcinoma quickly grows and is highly malignant, but is said to be more susceptible to anticancer agents and radiation treatment than non-small cell carcinoma. Furthermore, classification by the development site of lung cancer primarily includes hilar type and lung field type. The hilar type which develops near the hilar area at which various tracheas come together is not easily detected by a typical X-ray examination compared to the lung field type which develops in the periphery of the lung.

A stage of progression of lung cancer is classified into stages 0, IA, IB, IIA, IIB, IIIA, IIIB, and IV according to spread of tumors (T1 to T4), lymph node metastasis (N0 to N3), and distant metastasis (M0, M1). Survival rate in lung cancer varies depending on the stage of progression. Five-year relative survival rates in non-small cell lung carcinoma are reported to be 45 to 49% in the case of stage I (IA and IB), 30 to 31% in the case of stage II (IIA and 1113), 5 to 14% in the case of stage III (IIIA and IIIB), and 1% in the case of stage IV. Thus, detection of lung cancer in an early stage, i.e., detection in stage 0 or stage I, and treatment thereof notably contribute to improvement in survival rate.

Lung cancer is mainly treated by surgery, radiation therapy, and anticancer agents. Particularly, surgery is suitable for an early stage lung cancer, and it is likely to be cured in such case. Furthermore, in the case of an early stage lung cancer, there are several treatment selections that are less burden on a patient are available; such treatment includes thoracoscopic surgery, stereotactic body radiation treatment (SBRT), photodynamic treatment, laser treatment, brachytherapy for irradiating radiation from inside the body, or the like.

Many lung cancer cases are, regardless of a stage of progression, almost asymptomatic, which makes early detection at routine health checkups important. The most common lung cancer screening is chest X-ray examination. When a suspecting result is obtained from chest X-ray examination, a more precise image diagnoses such as CT test, MRI test, PET test, or the like, are carried out. Additionally, in recent years effectiveness of low dose CT on lung cancer screening has been recognized. National Lung Screening Trial conducted in the United States revealed that a test subject group of high-risk for lung cancer such as chain smokers who took CT checkups had reduced mortalities compared to those who took chest X-ray checkups.

When an individual is strongly suspected of having lung cancer by an image diagnosis, final diagnosis would be made that includes determination of the lung cancer tissue type by collecting cells and tissues for a microscopic examination. Cytodiagnosis and tissue diagnosis include sputum cytodiagnosis, pleural effusion examination, bronchoscopy, percutaneous needle biopsy, and the like.

In conventional diagnostic methods, lung cancers are often found in a progressed state, and they were found by the methods that impose an innegligible burden on the examinee, such as biopsy test. Under the circumstance, there is an effort to detect lung cancers earlier in a simpler manner using tumor markers in blood. Examples of the lung cancer tumor markers used at present include CEA, CYFRA21-1, NSE, SCC, and the like. As shown in Patent Literatures 1 to 6 and Non-Patent Literatures 1 to 6, there are reports, albeit at a research stage, on the detection of lung cancer using the expression levels of microRNAs (miRNAs) in biological samples including blood.

Specifically, Patent Literature 1 discloses a method for discriminating lung cancer patients from healthy subjects and patients with cancers other than lung cancer using miR-1343-3p, miR-6746-5p, miR-187-5p, miR-4632-5p and the like in serum.

Patent Literature 2 discloses a method for discriminating lung cancer using a pair of expression levels of miR-296-5p, miR-422a, miR-638, miR-191-5p, miR-23a-3p, miR-24-3p, miR-320a, miR-29b-3p, miR-92-3p and the like in serum or plasma.

Patent Literature 3 discloses miR-150-3p, miR-103a-3p, miR-107 and the like in peripheral blood as biomarkers for non-small cell lung carcinoma.

Patent Literature 4 discloses a method for discriminating non-small cell lung carcinoma using miR-23b-3p, miR-29b-3p, miR-625-3p, miR-17-3p and the like in peripheral blood.

Patent Literature 5 discloses a method for diagnosing lung cancer or predicting prognosis for lung cancer using miR-1249-3p, miR-1275, miR-191-5p, miR-423-5p, miR-744, miR-874-3p and the like in tracheal cells.

Patent Literature 6 discloses a method for detecting lung cancer patients from high-risk people for lung cancer with high smoking amount using miR-23b-3p, miR-107, miR-103a-3p, miR-17-5p and the like in plasma.

Non-Patent Literature 1 discloses a method for discriminating lung adenocarcinoma from healthy subjects and lung benign diseases using twenty miRNAs including miR-1290 and miR-24-3p in serum.

Non-Patent Literature 2 discloses that expression levels of five miRNAs including miR-650 in bronchoalveolar lavage samples significantly increase in lung cancer patients whereby these miRNAs have potential for the use as lung cancer markers.

Non-Patent Literature 3 discloses a method for discriminating lung cancer patients from healthy subjects using expression levels of miR-3180-3p, miR-342-5p, miR-150 and the like contained in neutrophilic granulocyte.

Non-Patent Literature 4 discloses miR-550 and the like in serum as biomarkers for lung adenocarcinoma.

Non-Patent Literature 5 discloses miR-1229 and the like in serum as biomarkers for non-small cell lung carcinoma.

Non-Patent Literature 6 discloses miR-1254, miR-1275, miR-320a and the like in serum as biomarkers for non-small cell lung carcinoma.

PRIOR ART LITERATURE

Patent Literature

Patent Literature 1: International Publication No. WO 2015/194610
Patent Literature 2: JP Patent Publication (Kohyo) No. 2013-502931 A (2013)
Patent Literature 3: JP Patent Publication (Kohyo) No. 2011-505143 A (2011)
Patent Literature 4: Published U.S. Patent Application No. 2012/108462
Patent Literature 5: Published U.S. Patent Application No. 2015/080243
Patent Literature 6: International Publication No. WO 2015/115923

Non-Patent Literature

Non-Patent Literature 1: Tai M C et al. Sci Rep. 2016 Aug. 10; 6: 31389
Non-Patent Literature 2: Schmidt B et al. Adv Exp Med Biol. 2016; 924: 33-37.
Non-Patent Literature 3: Leidinger P et al. Oncotarget. 2014 Oct. 15; 5(19): 9484-97.
Non-Patent Literature 4: Rani S et al. Cancer Biol Ther. 2013 December; 14(12): 1104-12.
Non-Patent Literature 5: Roth C et al. PLoS One. 2012; 7(6): e38248
Non-Patent Literature 6: Foss K M et al. J Thorac Oncol. 2011 March; 6(3): 482-8

SUMMARY OF INVENTION

Problem to be Solved by Invention

An object of the present invention is to find a novel tumor marker(s) for lung cancer practically usable in primary tests of lung cancer and to provide a method that can effectively detect lung cancer using a nucleic acid(s) that specifically bind(s) to the marker(s). Effective primary tests of lung cancer require four factors: 1. ability to detect early stages, 2. Ability to detect any histological type of lung cancer, 3. high detection sensitivity and specificity for lung cancer, and 4. low invasiveness to examinees. An object of the present invention is to provide a test method that satisfies these factors.

X-ray examination, which is currently used as a main primary test of lung cancer, has the difficulty in the early detection of small cell carcinoma or squamous cell carcinoma which develops mainly in the hilar area. Large cell carcinoma grows rapidly and often already has a large tumor size when detected. Furthermore, some who are detected as abnormal in low-dose CT examination often turn out to be non-cancer (false-positive) by additional examination. Such case could lead to more highly invasive needle biopsy or surgery if unattended.

For detection of lung cancer, CEA and CYFRA21-1 are known examples as tumor markers in blood. These tumor markers in blood, however, have been reported to have general lung cancer detection sensitivity of 69% (CEA) and 43% (CYFRA21-1), and are thus not very useful in lung cancer examination. Furthermore, the tumor markers such as CEA and CYFRA21-1 may elevate for reasons other than lung cancer, and therefore have the difficulty in identifying cancer types. The false diagnosis of other cancers as lung cancer wastes appropriate therapeutic opportunity or places unnecessary economical and physical burdens on patients due to the application of wrong medical approaches.

As described below, there are reports, albeit at a research stage, on the determination of lung cancer using the expression levels of microRNAs (miRNAs) in biological samples including blood, none of which, however, have yet been brought into practical use.

Patent Literature 1 discloses a method for discriminating a lung cancer patient from a healthy subject or a patient having a cancer other than lung cancer using miR-1343-3p, miR-6746-5p, miR-187-5p, miR-4632-5p and the like in serum. However, lung cancer sample groups include only adenocarcinoma and squamous cell carcinoma samples. Therefore, this method might be unable to detect the other types of lung cancers.

Patent Literature 2 discloses a method for determining lung cancer using a pair of expression levels of miR-296-5p, miR-422a, miR-638, miR-191-5p, miR-23a-3p, miR-24-3p, miR-320a, miR-29b-3p, miR-92-3p and the like in serum or plasma. However, any cancer sample other than lung cancer was not used in the Examples. Therefore, the method might misdiagnose lung cancer as another cancer.

Patent Literature 3 discloses miR-150-3p, miR-103a-3p, miR-107 and the like in peripheral blood as biomarkers for non-small cell lung carcinoma; however, it does not describe the specific detection performance, such as accuracy, sensitivity, or specificity, for determining lung cancer, making these miRNAs poor in industrially practical use.

Patent Literature 4 discloses a method for determining non-small cell lung carcinoma using miR-23b-3p, miR-29b-3p, miR-625-3p, miR-17-3p and the like in peripheral blood. However, any cancer sample other than lung cancer, or any other cancer type other than small cell carcinoma was not used in the Examples. Therefore, the method might misdiagnose lung cancer as another cancer, or might be unable to detect some types of lung cancers such as small cell carcinoma.

Patent Literature 5 discloses a method for diagnosing lung cancer or predicting prognosis for lung cancer using miR-1249-3p, miR-1275, miR-191-5p, miR-423-5p, miR-744, miR-874-3p and the like in tracheal cells. However, obtaining tissue samples requires tissue resection by surgery, and this step causes an undue physical burden on a patient, hence not preferable as a test method.

Patent Literature 6 discloses a method for detecting a lung cancer patient from people who have a large quantity of smoking and have a high risk of lung cancer using miR-23b-3p, miR-107, miR-103a-3p, miR-17-5p and the like in plasma. However, any cancer sample other than lung cancer was not used in the Examples. Therefore, the method might misdiagnose lung cancer as another cancer.

Non-Patent Literature 1 discloses a method for discriminating lung adenocarcinoma from normal health or benign lung disease using twenty miRNAs including miR-1290 and miR-24-3p in serum. However, the discriminant performance for squamous cell carcinoma or small cell carcinoma is as low as approximately 70%. Therefore, the method might overlook some histological types of lung cancer patients.

Non-Patent Literature 2 discloses that expression levels of five miRNAs including miR-650 in bronchoalveolar lavage samples were significantly increased in lung cancer patients, indicating their potentiality as lung cancer markers; however, it does not describe the specific detection performance, such as accuracy, sensitivity, or specificity, for determining lung cancer, making these miRNAs poor in industrially practical use.

Non-Patent Literature 3 discloses a method for discriminating a lung cancer patient from a healthy subject using expression levels of miR-3180-3p, miR-342-5p, miR-150 and the like contained in neutrophilic granulocytes. However, separation of immunocytes on a cell type basis from blood is laborious, making these miRNAs poor in industrially practical use.

Non-Patent Literature 4 discloses miR-550 and the like in serum as biomarkers for lung adenocarcinoma. However, any cancer sample other than lung cancer, or any lung cancer type other than adenocarcinoma was not used in the Examples. Therefore, use of these miRNAs as biomarkers might misdiagnose lung cancer as another cancer or might be unable to detect some histological types of lung cancers.

Non-Patent Literature 5 discloses miR-1229 and the like in serum as biomarkers for non-small cell lung carcinoma. However, any cancer sample other than lung cancer, or any small cell carcinoma sample was not used in the Examples. Therefore, use of these miRNAs as the biomarker might misdiagnose lung cancer as another cancer or might be unable to detect some histological types of lung cancers.

Non-Patent Literature 6 discloses miR-1254, miR-1275, miR-320a and the like in serum as biomarkers for non-small cell lung carcinoma. However, any cancer sample other than lung cancer, or any small cell carcinoma sample was not used in the Examples. Therefore, use of these miRNAs as the biomarker might misdiagnose lung cancer as another cancer, or might be unable to detect some types of lung cancers such as small cell carcinoma.

As mentioned above, chest X-ray examination or low-dose CT for use in lung cancer examination has the difficulty in detection of lung cancer, depending on the site of origin, and in some case detect non-cancer abnormality in an image that might lead to the execution of needless extra examination. Furthermore, the existing tumor markers exhibit low detection performance for lung cancer and cannot distinguish lung cancer from other cancers. Neither validation using samples of cancers other than lung cancer nor validation using some histological types of lung cancers such as small cell carcinoma or large cell carcinoma has been conducted as to the markers at a research stage. Therefore, use of these markers might require carrying out needless extra examination due to the false detection of normal subjects or other cancer patients as being lung cancer patients, or might waste therapeutic opportunity because of overlooking lung cancer patients. Furthermore, the collection of lung tissues for measuring the tumor markers is highly invasive to patients and is not favorable. Hence, there is a demand for a highly accurate lung cancer marker that is detectable from blood, which can be collected with less invasiveness, and is capable of correctly determining the presence or absence of lung cancer. Particularly, the early detection of lung cancer increases the applicability of surgery in treatment, and drastically improve the survival rates. For early-stage lung cancers, there are several therapeutic options available that place less burden on patients, such as thoracoscopic surgery and stereotactic body radiotherapy. Therefore, a highly sensitive lung cancer marker that can detect lung cancer even at a low stage of progression is desired.

Means for Solution of Problem

The present inventors have conducted diligent studies to attain the object and consequently completed the present invention by finding gene markers usable as markers for detection of lung cancer from blood, which can be collected with limited invasiveness, and finding that lung cancer such as lung adenocarcinoma, lung squamous cell carcinoma, large cell lung carcinoma, or small cell lung carcinoma can be significantly, preferably specifically, detected, using nucleic acids to detect such markers, for example, at least one nucleic acid selected from probes capable of specifically binding to any of these markers and primers for amplifying these markers.

SUMMARY OF INVENTION

The present invention has the following features:
(1) A kit for detection of lung cancer, comprising a nucleic acid(s) capable of specifically binding to at least one polynucleotide selected from the group consisting of the following lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-

3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p, or to a polynucleotide consisting of a nucleotide sequence complementary to that of the polynucleotide.

(2) The kit according to (1), wherein the nucleic acid(s) is a polynucleotide(s) selected from the group consisting of the following polynucleotides (a) to (e):
  (a) a polynucleotide consisting of a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;
  (b) a polynucleotide comprising a nucleotide sequence represented by any of SEQ ID NOs: 1 to 163;
  (c) a polynucleotide consisting of a nucleotide sequence complementary to a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;
  (d) a polynucleotide comprising a nucleotide sequence complementary to a nucleotide sequence represented by any of SEQ ID NOs: 1 to 163 or a nucleotide sequence derived from the nucleotide sequence in which the nucleic acid u is replaced with t; and
  (e) a polynucleotide hybridizing under stringent conditions to any of the polynucleotides (a) to (d).

(3) The kit according to (1) or (2), wherein the kit further comprises a nucleic acid(s) capable of specifically binding to at least one polynucleotide selected from the group consisting of the following other lung cancer markers: miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, or to a polynucleotide consisting of a nucleotide sequence complementary to that of the polynucleotide.

(4) The kit according to (3), wherein the nucleic acid(s) is a polynucleotide(s) selected from the group consisting of the following polynucleotides (f) to (j):
  (f) a polynucleotide consisting of a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;
  (g) a polynucleotide comprising a nucleotide sequence represented by any of SEQ ID NOs: 164 to 329;
  (h) a polynucleotide consisting of a nucleotide sequence complementary to a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;
  (i) a polynucleotide comprising a nucleotide sequence complementary to a nucleotide sequence represented by any of SEQ ID NOs: 164 to 329 or a nucleotide sequence derived from the nucleotide sequence in which the nucleic acid u is replaced with t; and
  (j) a polynucleotide hybridizing under stringent conditions to any of the polynucleotides (f) to (i).

(5) A device for detection of lung cancer, comprising a nucleic acid(s) capable of specifically binding to at least one polynucleotide selected from the group consisting of the following lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p, or to a polynucleotide consisting of a nucleotide sequence complementary to that of the polynucleotide.

(6) The device according to (5), wherein the nucleic acid(s) is a polynucleotide(s) selected from the group consisting of the following polynucleotides (a) to (e):
  (a) a polynucleotide consisting of a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;
  (b) a polynucleotide comprising a nucleotide sequence represented by any of SEQ ID NOs: 1 to 163;
  (c) a polynucleotide consisting of a nucleotide sequence complementary to a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;
  (d) a polynucleotide comprising a nucleotide sequence complementary to a nucleotide sequence represented by any of SEQ ID NOs: 1 to 163 or a nucleotide sequence derived from the nucleotide sequence in which the nucleic acid u is replaced with t; and
  (e) a polynucleotide hybridizing under stringent conditions to any of the polynucleotides (a) to (d).

(7) The device according to (5) or (6), wherein the device further comprises a nucleic acid(s) capable of specifically binding to at least one polynucleotide selected from the group consisting of the following other lung cancer markers: miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, or to a polynucleotide consisting of a nucleotide sequence complementary to that of the polynucleotide.

(8) The device according to (7), wherein the nucleic acid(s) is a polynucleotide(s) selected from the group consisting of the following polynucleotides (f) to (j):
  (f) a polynucleotide consisting of a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;
(g) a polynucleotide comprising a nucleotide sequence represented by any of SEQ ID NOs: 164 to 329;
(h) a polynucleotide consisting of a nucleotide sequence complementary to a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 164 to 329 or a nucleotide sequence derived from the nucleotide sequence in which the nucleic acid u is replaced with t; and
(j) a polynucleotide hybridizing under stringent conditions to any of the polynucleotides (f) to (i).

(9) The device according to any of (5) to (8), wherein the device is for measurement by a hybridization technique.

(10) The device according to (9), wherein the hybridization technique is a nucleic acid array technique.

(11) A method for detecting lung cancer, comprising: measuring an expression level(s) of at least one polynucleotide selected from the group consisting of the following lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p in a sample from a subject; and evaluating in vitro whether or not the subject has lung cancer using the measured expression level(s).

(12) A method for detecting lung cancer, comprising: measuring an expression level(s) of at least one polynucleotide selected from the group consisting of the following lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p in a sample from a subject; and evaluating in vitro whether or not the subject has lung cancer using both of the measured expression level(s) and a control expression level(s) from healthy subjects measured in the same way.

(13) A method for detecting lung cancer, comprising: measuring an expression level(s) of at least one polynucleotide selected from the group consisting of the following lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-

5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p in a sample from a subject; and assigning the expression level(s) of the at least one polynucleotide in the sample from the subject to a discriminant, which is capable of discriminatorily determining the presence or absence of lung cancer, and is prepared with gene expression levels in samples from subjects known to have lung cancer and samples from subjects without lung cancer as training samples, and thereby evaluating in vitro the presence or absence of lung cancer.

(14) The method according to any of (11) to (13), wherein the measurement of the expression level(s) of the polynucleotide(s) is performed using a nucleic acid(s) capable of specifically binding to the polynucleotide(s) or a polynucleotide(s) consisting of a nucleotide sequence(s) complementary to the polynucleotide(s), wherein the nucleic acid(s) is a polynucleotide(s) selected from the group consisting of the following polynucleotides (a) to (e):
(a) a polynucleotide consisting of a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;
(b) a polynucleotide comprising a nucleotide sequence represented by any of SEQ ID NOs: 1 to 163;
(c) a polynucleotide consisting of a nucleotide sequence complementary to a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;
(d) a polynucleotide comprising a nucleotide sequence complementary to a nucleotide sequence represented by any of SEQ ID NOs: 1 to 163 or a nucleotide sequence derived from the nucleotide sequence in which the nucleic acid u is replaced with t; and
(e) a polynucleotide hybridizing under stringent conditions to any of the polynucleotides (a) to (d).

(15) The method according to any of (11) to (14), wherein the method further comprises measuring an expression level(s) of at least one polynucleotide selected from the group consisting of the following other lung cancer markers: miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p.

(16) The method according to (15), wherein the measurement of the expression level(s) of the polynucleotide(s) is performed using a nucleic acid(s) capable of specifically binding to the polynucleotide(s) or a polynucleotide(s) consisting of a nucleotide sequence(s) complementary to the polynucleotide(s), wherein the nucleic acid(s) is a polynucleotide(s) selected from the group consisting of the following polynucleotides (f) to (j):
(f) a polynucleotide consisting of a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;
(g) a polynucleotide comprising a nucleotide sequence represented by any of SEQ ID NOs: 164 to 329;
(h) a polynucleotide consisting of a nucleotide sequence complementary to a nucleotide sequence represented by any of SEQ ID NOs: 164 to 329 or a nucleotide sequence derived from the nucleotide sequence in which the nucleic acid u is replaced with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 164 to 329 or a nucleotide sequence derived from the nucleotide sequence in which the nucleic acid u is replaced with t; and
(j) a polynucleotide hybridizing under stringent conditions to any of the polynucleotides (f) to (i).
(17) The method according to any of (11) to (16), wherein the expression level(s) of the polynucleotide(s) in the sample from the subject is measured using a kit according to any of (1) to (4) or a device according to any of (5) to (10), comprising a nucleic acid(s) capable of specifically binding to the polynucleotide(s) or a polynucleotide(s) consisting of a nucleotide sequence(s) complementary to the polynucleotide(s).
(18) The method according to any of (11) to (17), wherein the subject is a human.
(19) The method according to any of (11) to (18), wherein the sample is blood, serum, or plasma.

In one preferred aspect of the present invention, the kit, the device or the method for detecting lung cancer according to the present invention is a kit, a device or a method for detecting lung cancer, wherein a histological type of the lung cancer is adenocarcinoma, squamous cell carcinoma, large cell carcinoma or small cell carcinoma.

In another preferred aspect of the present invention, the kit, the device or the method for detecting lung cancer according to the present invention is a kit, a device or a method for detecting lung cancer, wherein as the lung cancer markers, miR-6787-5p is hsa-miR-6787-5p, miR-920 is hsa-miR-920, miR-3622a-5p is hsa-miR-3622a-5p, miR-1185-1-3p is hsa-miR-1185-1-3p, miR-4327 is hsa-miR-4327, miR-5739 is hsa-miR-5739, miR-937-5p is hsa-miR-937-5p, miR-1181 is hsa-miR-1181, miR-1185-2-3p is hsa-miR-1185-2-3p, miR-1193 is hsa-miR-1193, miR-1207-5p is hsa-miR-1207-5p, miR-1238-5p is hsa-miR-1238-5p, miR-1246 is hsa-miR-1246, miR-1249-5p is hsa-miR-1249-5p, miR-1292-3p is hsa-miR-1292-3p, miR-1469 is hsa-miR-1469, miR-1470 is hsa-miR-1470, miR-197-5p is hsa-miR-197-5p, miR-208a-5p is hsa-miR-208a-5p, miR-2110 is hsa-miR-2110, miR-211-3p is hsa-miR-211-3p, miR-2467-3p is hsa-miR-2467-3p, miR-3122 is hsa-miR-3122, miR-3141 is hsa-miR-3141, miR-3156-5p is hsa-miR-3156-5p, miR-3158-5p is hsa-miR-3158-5p, miR-3160-5p is hsa-miR-3160-5p, miR-3180-3p is hsa-miR-3180-3p, miR-3191-3p is hsa-miR-3191-3p, miR-3194-3p is hsa-miR-3194-3p, miR-320b is hsa-miR-320b, miR-328-5p is hsa-miR-328-5p, miR-3610 is hsa-miR-3610, miR-3619-3p is hsa-miR-3619-3p, miR-3620-5p is hsa-miR-3620-5p, miR-370-3p is hsa-miR-370-3p, miR-373-5p is hsa-miR-373-5p, miR-3917 is hsa-miR-3917, miR-3937 is hsa-miR-3937, miR-4259 is hsa-miR-4259, miR-4281 is hsa-miR-4281, miR-4294 is hsa-miR-4294, miR-4419b is hsa-miR-4419b, miR-4428 is hsa-miR-4428, miR-4429 is hsa-miR-4429, miR-4433a-3p is hsa-miR-4433a-3p, miR-4447 is hsa-miR-4447, miR-4449 is hsa-miR-4449, miR-4459 is hsa-miR-4459, miR-4480 is hsa-miR-4480, miR-4485-5p is hsa-miR-4485-5p, miR-4486 is hsa-miR-4486, miR-4488 is hsa-miR-4488, miR-4489 is hsa-miR-4489, miR-4505 is hsa-miR-4505, miR-4513 is hsa-miR-4513, miR-4515 is hsa-miR-4515, miR-4530 is hsa-miR-4530, miR-4535 is hsa-miR-4535, miR-4635 is hsa-miR-4635, miR-4640-5p is hsa-miR-4640-5p, miR-4646-5p is hsa-miR-4646-5p, miR-4656 is hsa-miR-4656, miR-4663 is hsa-miR-4663, miR-4665-5p is hsa-miR-4665-5p, miR-4706 is hsa-miR-4706, miR-4707-5p is hsa-miR-4707-5p, miR-4708-3p is hsa-miR-4708-3p, miR-4710 is hsa-miR-4710, miR-4718 is hsa-miR-4718, miR-4722-5p is hsa-miR-4722-5p, miR-4727-3p is hsa-miR-4727-3p, miR-4730 is hsa-miR-4730, miR-4734 is hsa-miR-4734, miR-4740-5p is hsa-miR-4740-5p, miR-4747-3p is hsa-miR-4747-3p, miR-4749-5p is hsa-miR-4749-5p, miR-4755-3p is hsa-miR-4755-3p, miR-4763-5p is hsa-miR-4763-5p, miR-4787-3p is hsa-miR-4787-3p, miR-5008-5p is hsa-miR-5008-5p, miR-5010-5p is hsa-miR-5010-5p, miR-504-3p is hsa-miR-504-3p, miR-5090 is hsa-miR-5090, miR-5100 is hsa-miR-5100, miR-5196-5p is hsa-miR-5196-5p, miR-551b-5p is hsa-miR-551b-5p, miR-557 is hsa-miR-557, miR-5787 is hsa-miR-5787, miR-6090 is hsa-miR-6090, miR-6124 is hsa-miR-6124, miR-6132 is hsa-miR-6132, miR-6510-5p is hsa-miR-6510-5p, miR-6511b-5p is hsa-miR-6511b-5p, miR-6515-3p is hsa-miR-6515-3p, miR-654-5p is hsa-miR-654-5p, miR-658 is hsa-miR-658, miR-668-5p is hsa-miR-668-5p, miR-6722-5p is hsa-miR-6722-5p, miR-6724-5p is hsa-miR-6724-5p, miR-6729-3p is hsa-miR-6729-3p, miR-6737-5p is hsa-miR-6737-5p, miR-6756-5p is hsa-miR-6756-5p, miR-6762-5p is hsa-miR-6762-5p, miR-6763-3p is hsa-miR-6763-3p, miR-6766-5p is hsa-miR-6766-5p, miR-6769a-5p is hsa-miR-6769a-5p, miR-6771-5p is hsa-miR-6771-5p, miR-6786-5p is hsa-miR-6786-5p, miR-6789-5p is hsa-miR-6789-5p, miR-6794-5p is hsa-miR-6794-5p, miR-6796-3p is hsa-miR-6796-3p, miR-6797-5p is hsa-miR-6797-5p, miR-6800-3p is hsa-miR-6800-3p, miR-6802-5p is hsa-miR-6802-5p, miR-6803-5p is hsa-miR-6803-5p, miR-6805-3p is hsa-miR-6805-3p, miR-6805-5p is hsa-miR-6805-5p, miR-6807-5p is hsa-miR-6807-5p, miR-6812-5p is hsa-miR-6812-5p, miR-6819-5p is hsa-miR-6819-5p, miR-6822-5p is hsa-miR-6822-5p, miR-6824-5p is hsa-miR-6824-5p, miR-6826-5p is hsa-miR-6826-5p, miR-6850-5p is hsa-miR-6850-5p, miR-6858-5p is hsa-miR-6858-5p, miR-6861-5p is hsa-miR-6861-5p, miR-6880-3p is hsa-miR-6880-3p, miR-7107-5p is hsa-miR-7107-5p, miR-7109-5p is hsa-miR-7109-5p, miR-7114-5p is hsa-miR-7114-5p, miR-7704 is hsa-miR-7704, miR-7846-3p is hsa-miR-7846-3p, miR-8052 is hsa-miR-8052, miR-8060 is hsa-miR-8060, miR-8071 is hsa-miR-8071, miR-8073 is hsa-miR-8073, miR-874-5p is hsa-miR-874-5p, miR-204-3p is hsa-miR-204-3p, miR-3154 is hsa-miR-3154, miR-3960 is hsa-miR-3960, miR-4433a-5p is hsa-miR-4433a-5p, miR-4455 is hsa-miR-4455, miR-4462 is hsa-miR-4462, miR-4476 is hsa-miR-4476, miR-4508 is hsa-miR-4508, miR-4687-3p is hsa-miR-4687-3p, miR-4687-5p is hsa-miR-4687-5p, miR-4732-5p is hsa-miR-4732-5p, miR-4771 is hsa-miR-4771, miR-642a-3p is hsa-miR-642a-3p, miR-6732-5p is hsa-miR-6732-5p, miR-6760-5p is hsa-miR-6760-5p, miR-6799-5p is hsa-miR-6799-5p, miR-6820-5p is hsa-miR-6820-5p, miR-6821-5p is hsa-miR-6821-5p, miR-6829-5p is hsa-miR-6829-5p, miR-6893-5p is hsa-miR-6893-5p, miR-7108-3p is hsa-miR-7108-3p, miR-7111-5p is hsa-miR-7111-5p, miR-8089 is hsa-miR-8089, miR-885-3p is hsa-miR-885-3p, miR-92b-3p is hsa-miR-92b-3p, miR-1343-3p is hsa-miR- 1343-3p, miR-6746-5p is hsa-miR-6746-5p, miR-422a is hsa-miR-422a, miR-187-5p is hsa-miR-187-5p, miR-4632-5p is hsa-miR-4632-5p, miR-6791-5p is hsa-miR-6791-5p, miR-103a-3p is hsa-miR-103a-3p, miR-107 is hsa-miR-107, miR-1199-5p is hsa-miR-1199-5p, miR-1225-3p is hsa-miR-1225-3p, miR-1225-5p is hsa-miR-1225-5p, miR-1228-5p is hsa-miR-1228-5p, miR-1229-5p is hsa-miR-1229-5p, miR-1233-5p is hsa-miR-1233-5p, miR-1237-5p is hsa-miR-1237-5p, miR-1247-3p is hsa-miR-1247-3p, miR-1249-3p is hsa-miR-1249-3p, miR-1254 is hsa-miR-1254, miR-1260b is hsa-miR-1260b, miR-1268a is hsa-miR-1268a, miR-1268b is hsa-miR-1268b, miR-1273g-3p is hsa-miR-1273g-3p, miR-128-1-5p is hsa-miR-128-1-5p, miR-128-2-5p is hsa-miR-128-2-5p, miR-1290 is hsa-miR-1290, miR-150-3p is hsa-miR-150-3p, miR-17-3p is hsa-miR-17-3p, miR-1908-5p is hsa-miR-1908-5p, miR-1909-3p is hsa-miR-1909-3p, miR-1914-3p is hsa-miR-1914-3p, miR-1915-3p is hsa-miR-1915-3p, miR-191-5p is hsa-miR-191-5p, miR-22-3p is hsa-miR-22-3p, miR-23b-3p is hsa-miR-23b-3p, miR-24-3p is hsa-miR-24-3p, miR-296-3p is hsa-miR-296-3p, miR-296-5p is hsa-miR-296-5p, miR-3131 is hsa-miR-3131, miR-3162-5p is hsa-miR-3162-5p, miR-3188 is hsa-miR-3188, miR-3196 is hsa-miR-3196, miR-3197 is hsa-miR-3197, miR-320a is hsa-miR-320a, miR-342-5p is hsa-miR-342-5p, miR-3621 is hsa-miR-3621, miR-3648 is hsa-miR-3648, miR-3656 is hsa-miR-3656, miR-365a-5p is hsa-miR-365a-5p, miR-3665 is hsa-miR-3665, miR-3679-5p is hsa-miR-3679-5p, miR-371a-5p is hsa-miR-371a-5p, miR-3940-5p is hsa-miR-3940-5p, miR-423-5p is hsa-miR-423-5p, miR-4257 is hsa-miR-4257, miR-4270 is hsa-miR-4270, miR-4271 is hsa-miR-4271, miR-4286 is hsa-miR-4286, miR-4298 is hsa-miR-4298, miR-4417 is hsa-miR-4417, miR-4442 is hsa-miR-4442, miR-4446-3p is hsa-miR-4446-3p, miR-4448 is hsa-miR-4448, miR-4454 is hsa-miR-4454, miR-4467 is hsa-miR-4467, miR-4472 is hsa-miR-4472, miR-4507 is hsa-miR-4507, miR-4516 is hsa-miR-4516, miR-451a is hsa-miR-451a, miR-4649-5p is hsa-miR-4649-5p, miR-4651 is hsa-miR-4651, miR-4665-3p is hsa-miR-4665-3p, miR-4674 is hsa-miR-4674, miR-4675 is hsa-miR-4675, miR-4689 is hsa-miR-4689, miR-4695-5p is hsa-miR-4695-5p, miR-4697-5p is hsa-miR-4697-5p, miR-4725-3p is hsa-miR-4725-3p, miR-4739 is hsa-miR-4739, miR-4745-5p is hsa-miR-4745-5p, miR-4763-3p is hsa-miR-4763-3p, miR-4792 is hsa-miR-4792, miR-486-3p is hsa-miR-486-3p, miR-5001-5p is hsa-miR-5001-5p, miR-5195-3p is hsa-miR-5195-3p, miR-550a-5p is hsa-miR-550a-5p, miR-5698 is hsa-miR-5698, miR-6075 is hsa-miR-6075, miR-6088 is hsa-miR-6088, miR-6089 is hsa-miR-6089, miR-6125 is hsa-miR-6125, miR-6126 is hsa-miR-6126, miR-614 is hsa-miR-614, miR-615-5p is hsa-miR-615-5p, miR-619-5p is hsa-miR-619-5p, miR-638 is hsa-miR-638, miR-642b-3p is hsa-miR-642b-3p, miR-650 is hsa-miR-650, miR-663a is hsa-miR-663a, miR-663b is hsa-miR-663b, miR-6717-5p is hsa-miR-6717-5p, miR-6721-5p is hsa-miR-6721-5p, miR-6726-5p is hsa-miR-6726-5p, miR-6727-5p is hsa-miR-6727-5p, miR-6738-5p is hsa-miR-6738-5p, miR-6741-5p is hsa-miR-6741-5p, miR-6749-5p is hsa-miR-6749-5p, miR-6752-5p is hsa-miR-6752-5p, miR-675-5p is hsa-miR-675-5p, miR-6757-5p is hsa-miR-6757-5p, miR-6763-5p is hsa-miR-6763-5p, miR-6765-5p is hsa-miR-6765-5p, miR-6775-5p is hsa-miR-6775-5p, miR-6780b-5p is hsa-miR-6780b-5p, miR-6782-5p is hsa-miR-6782-5p, miR-6784-5p is hsa-miR-6784-5p, miR-6800-5p is hsa-miR-6800-5p, miR-6806-5p is hsa-miR-6806-5p, miR-6840-3p is hsa-miR-6840-3p, miR-6848-5p is hsa-miR-6848-5p, miR-6851-5p is hsa-miR-6851-5p, miR-6870-5p is hsa-miR-6870-5p, miR-6872-3p is hsa-miR-6872-3p, miR-6875-5p is hsa-miR-6875-5p, miR-6877-5p is hsa-miR-6877-5p, miR-6879-5p is hsa-miR-6879-5p, miR-6880-5p is hsa-miR-6880-5p, miR-6885-5p is hsa-miR-6885-5p, miR-6887-5p is hsa-miR-6887-5p, miR-7108-5p is hsa-miR-7108-5p, miR-711 is hsa-miR-711, miR-7113-3p is hsa-miR-7113-3p, miR-744-5p is hsa-miR-744-5p, miR-760 is hsa-miR-760, miR-7845-5p is hsa-miR-7845-5p, miR-7847-3p is hsa-miR-7847-3p, miR-7977 is hsa-miR-7977, miR-8059 is hsa-miR-8059, miR-8063 is hsa-miR-8063, miR-8072 is hsa-miR-8072, miR-874-3p is hsa-miR-874-3p, miR-92a-2-5p is hsa-miR-92a-2-5p, miR-92b-5p is hsa-miR-92b-5p, miR-940 is hsa-miR-940, miR-1228-3p is hsa-miR-1228-3p, miR-1275 is hsa-miR-1275, miR-1307-3p is hsa-miR-1307-3p, miR-1343-5p is hsa-miR-1343-5p, miR-23a-3p is hsa-miR-23a-3p, miR-29b-3p is hsa-miR-29b-3p, miR-3135b is hsa-miR-3135b, miR-3185 is hsa-miR-3185, miR-4532 is hsa-miR-4532, miR-4690-5p is hsa-miR-4690-5p, miR-4758-5p is hsa-miR-4758-5p, miR-4783-3p is hsa-miR-4783-3p, miR-6131 is hsa-miR-6131, miR-625-3p is hsa-miR-625-3p, miR-6511a-5p is hsa-miR-6511a-5p, miR-6765-3p is hsa-miR-6765-3p, miR-6816-5p is hsa-miR-6816-5p, miR-6825-5p is hsa-miR-6825-5p, miR-6845-5p is hsa-miR-6845-5p, miR-7150 is hsa-miR-7150, miR-7641 is hsa-miR-7641, miR-7975 is hsa-miR-7975, and miR-92a-3p is hsa-miR-92a-3p.

Definition of Terms

The terms used herein are defined as described below.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Here the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotides (i.e., a variant sequence) and a sequence comprising one or more modified nucleotides (i.e., a modified sequence), which are different from the natural sequence. Herein, the term "polynucleotide" is used interchangeably with the term "nucleic acid."

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus(+) strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand), cDNA, microRNA (miRNA), their fragments, and human genome, and their transcripts, unless otherwise specified. The "gene" includes not only a "gene" represented by a particular nucleotide sequence (or SEQ ID N0) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 1000 or a nucleotide sequence derived from the nucleotide sequence in which the nucleic acid u is replaced with t. Regardless whether or not there is a difference in functional region, the "gene" can comprise, for example, expression control regions, coding region, exons, or introns. The "gene" may be contained in a cell or may exist alone after being released from a cell. Alternatively, the "gene" may be in a state enclosed in a vesicle called exosome.

The term "exosome" used herein is a vesicle that is encapsulated by lipid bilayer and secreted from a cell. The exosome is derived from a multivesicular endosome and may incorporate biomaterials such as "genes" (e.g., RNA or DNA) or proteins when released into an extracellular environment. The exosome is known to be contained in a body fluid such as blood, serum, plasma or lymph.

The term "transcript" used herein refers to an RNA synthesized from the DNA sequence of a gene as a template. RNA polymerase binds to a site called promoter located upstream of the gene and adds ribonucleotides complementary to the nucleotide sequence of the DNA to the 3' end to synthesize an RNA. This RNA contains not only the gene itself but the whole sequence from a transcription initiation site to the end of a polyA sequence, including expression control regions, coding region, exons, or introns.

Unless otherwise specified, the term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, and integrated into a protein complex called RISC, and that is involved in the suppression of translation of mRNA. The term "miRNA" used herein includes not only a "miRNA" represented by a particular nucleotide sequence (or SEQ ID N0) but a "miRNA" comprising a precursor of the "miRNA" (pre-miRNA or pri-miRNA) and having biological functions equivalent to miRNAs encoded by these, for example, a "miRNA" encoding a congener (i.e., a homolog or an ortholog), a variant such as a genetic polymorph, and a derivative. Such a "miRNA" encoding a precursor, a congener, a variant, or a derivative can be specifically identified using miRBase Release 21 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 1000. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes consecutive polynucleotides that specifically recognize and amplify an RNA resulting from the expression of a gene or a polynucleotide derived from the RNA, and/or a polynucleotide complementary thereto.

The term "complementary polynucleotide" or "polynucleotide consisting of a complementary nucleotide sequence" (complementary strand or reverse strand) used herein means a polynucleotide in a complementary relationship based on A:T (U) and G:C base pairs with the full-length sequence of the nucleotide sequence of the target polynucleotide or a nucleotide sequence derived from the nucleotide sequence in which the nucleic acid u is replaced with t, or a partial sequence thereof (herein, these nucleotide sequences are referred to as a plus strand for the sake of convenience). Such a complementary polynucleotide is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a detectably larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence 100% complementary to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1, 2 or 3 or more (e.g., 1 to several) nucleotides in a nucleotide sequence represented by a SEQ ID N0 or a nucleotide sequence derived from the nucleotide sequence in which the nucleic acid u is replaced with t, or a partial sequence thereof; a variant containing the deletion, substitution, addition, or insertion of 1 or 2 or more nucleotides in a nucleotide sequence of a premature miRNA of the sequence of any of SEQ ID NOs 1 to 329 or a nucleotide sequence derived from the nucleotide sequence in which the nucleic acid u is replaced with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant used herein can be prepared by use of a well-known technique such as site-directed mutagenesis or mutagenesis using PCR.

The term "percent (%) identity" used herein can be determined with or without an introduced gap, using a protein or gene search system based on BLAST (https://blast.ncbi.nlm.nih.gov/Blast.cgi) or FASTA (http://www.genome.jp/tools/fasta/) (Zheng Zhang et al., 2000, J. Comput. Biol., Vol. 7, p. 203-214; Altschul, S. F. et al., 1990, Journal of Molecular Biology, Vol. 215, p. 403410; and Pearson, W. R. et al., 1988, Proc. Natl. Acad. Sci. U.S.A, Vol. 85, p. 2444-2448).

The term "derivative" used herein is meant to include modified nucleic acids, unlimitedly for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404).

As used herein, the "nucleic acid" capable of specifically binding to a polynucleotide selected from the lung cancer marker miRNAs described above or to a polynucleotide consisting of a nucleotide sequence complementary to that of the polynucleotide is a synthesized or prepared nucleic acid and, for example, includes a "nucleic acid probe" or a "primer" capable of detecting the polynucleotide. These nucleic acids are utilized directly or indirectly for detecting the presence or absence of lung cancer in a subject, for diagnosing the presence or absence or the severity of lung cancer, the presence or absence or the degree of amelioration of lung cancer, or the therapeutic sensitivity of lung cancer, or for screening for a candidate substance useful in the prevention, amelioration, or treatment of lung cancer. The "nucleic acid" includes a nucleotide, an oligonucleotide, and a polynucleotide capable of specifically recognizing and binding to a transcript represented by any of SEQ ID NOs: 1 to 1000 or a synthetic cDNA nucleic acid thereof in vivo, particularly, in a sample such as a body fluid (e.g., blood or urine), in relation to the development of lung cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". As used herein, the term "evaluation" is meant to include diagnosing- or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, a rodent including a mouse and a rat, and animals raised in a zoo. The subject is preferably a human. The term "subject" herein may be optionally referred to as "test subject". The term "healthy subject" also means such a mammal, which is an animal or a subject without the cancer to be detected. The healthy subject is preferably a human.

The "lung cancer" used herein is malignant tumor that develops in the lungs, and is broadly divided into small cell lung carcinoma and non-small cell lung carcinoma. The non-small cell lung carcinoma is generic name for lung cancer other than the small cell lung carcinoma and, for example, includes lung adenocarcinoma, lung squamous cell carcinoma, and large cell lung carcinoma.

The term "lung adenocarcinoma" or "adenocarcinoma" used herein is lung cancer in which differentiation into a duct of the gland or mucus production is found.

The term "lung squamous cell carcinoma" or "squamous cell carcinoma" used herein is lung cancer that exhibits cornification or intercellular bridge.

The term "large cell lung carcinoma" or "large cell carcinoma" used herein is lung cancer that is undifferentiated malignant epithelial tumor, and that is not categorized to any of small cell carcinoma, adenocarcinoma, and squamous cell carcinoma.

The term "small cell lung carcinoma" or "small cell carcinoma" used herein is lung cancer consisting of cells having a small size. The tumor cells exhibit a round, oval, or spindle form or the like with poor cytoplasms and unclear boundaries between the cells.

The term "other lung cancers" used herein is lung cancers other than adenocarcinoma, squamous cell carcinoma, large cell carcinoma, and small cell carcinoma and, for example, includes carcinoid tumor, adenosquamous carcinoma, polymorphic cell cancer, and salivary gland-type cancer.

The term "P" or "P value" used herein refers to a probability at which a more extreme statistic than that actually calculated from data under null hypothesis is observed in a statistical test. Thus, smaller "P" or "P value" is regarded as being a more significant difference between subjects to be compared.

The term "sensitivity" used herein means a value of (the number of true positives)/(the number of true positives+the number of false negatives). High sensitivity allows lung cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being lung cancer patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

As used herein, the "sample" that is subjected to determination, detection, or diagnosis refers to a tissue and a biological material in which the expression of the gene of the present invention varies as lung cancer develops, as lung cancer progresses, or as therapeutic effects on lung cancer are exerted. Specifically, the sample refers to a lung tissue, lymph node and a surrounding organ thereof, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-6787-5p gene" or "hsa-miR-6787-5p" used herein includes the hsa-miR-6787-5p gene (miRBase Accession No. MIMAT0027474) described in SEQ ID NO: 1, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 330) having a hairpin-like structure is known as a precursor of "hsa-miR-6787-5p".

The term "hsa-miR-920 gene" or "hsa-miR-920" used herein includes the hsa-miR-920 gene (miRBase Accession No. MIMAT0004970) described in SEQ ID NO: 2, a homolog or an ortholog of a different organism species, and the like. The hsa-miR-920 gene can be obtained by a method described in Novotny G W et al., 2007, Int J Androl, Vol. 30, p. 316-326. Also, "hsa-mir-920" (miRBase Accession No. MI0005712, SEQ ID NO: 331) having a hairpin-like structure is known as a precursor of "hsa-miR-920".

The term "hsa-miR-3622a-5p gene" or "hsa-miR-3622a-5p" used herein includes the hsa-miR-3622a-5p gene (miRBase Accession No. MIMAT0018003) described in SEQ ID NO: 3, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 332) having a hairpin-like structure is known as a precursor of "hsa-miR-3622a-5p".

The term "hsa-miR-1185-1-3p gene" or "hsa-miR-1185-1-3p" used herein includes the hsa-miR-1185-1-3p gene (miRBase Accession No. MIMAT0022838) described in SEQ ID NO: 4, a homolog or an ortholog of a different organism species, and the like. The hsa-miR-1185-1-3p gene can be obtained by a method described in Berezikov E et al., 2006, Genome Res, Vol. 16, p. 1289-1298. Also, "hsa-mir-1185-1" (miRBase Accession No. MI0003844, SEQ ID NO: 333) having a hairpin-like structure is known as a precursor of "hsa-miR-1185-1-3p".

The term "hsa-miR-4327 gene" or "hsa-miR-4327" used herein includes the hsa-miR-4327 gene (miRBase Accession No. MIMAT0016889) described in SEQ ID NO: 5, a homolog or an ortholog of a different organism species, and the like. The hsa-miR-4327 gene can be obtained by a method described in Goff L A et al., 2009, PLoS One, Vol. 4, e7192. Also, "hsa-mir-4327" (miRBase Accession No. MI0015867, SEQ ID NO: 334) having a hairpin-like structure is known as a precursor of "hsa-miR-4327".

The term "hsa-miR-5739 gene" or "hsa-miR-5739" used herein includes the hsa-miR-5739 gene (miRBase Accession No. MIMAT0023116) described in SEQ ID NO: 6, a homolog or an ortholog of a different organism species, and the like. The hsa-miR-5739 gene can be obtained by a method described in Yoo J K et al., 2011, Biochem Biophys Res Commun., Vol. 415, p. 258-262. Also, "hsa-mir-5739" (miRBase Accession No. MI0019412, SEQ ID NO: 335) having a hairpin-like structure is known as a precursor of "hsa-miR-5739".

The term "hsa-miR-937-5p gene" or "hsa-miR-937-5p" used herein includes the hsa-miR-937-5p gene (miRBase Accession No. MIMAT0022938) described in SEQ ID NO: 7, a homolog or an ortholog of a different organism species, and the like. The hsa-miR-937-5p gene can be obtained by a method described in Lui W O et al., 2007, Cancer Res, Vol. 67, p. 6031-6043. Also, "hsa-mir-937" (miRBase Accession No. MI0005759, SEQ ID NO: 336) having a hairpin-like structure is known as a precursor of "hsa-miR-937-5p".

The term "hsa-miR-1181 gene" or "hsa-miR-1181" used herein includes the hsa-miR-1181 gene (miRBase Accession No. MIMAT0005826) described in SEQ ID NO: 8, a homolog or an ortholog of a different organism species, and the like. The hsa-miR-1181 gene can be obtained by a method described in Subramanian S et al., 2008, Oncogene, Vol. 27, p. 2015-2026. Also, "hsa-mir-1181" (miRBase Accession No. MI0006274, SEQ ID NO: 337) having a hairpin-like structure is known as a precursor of "hsa-miR-1181".

The term "hsa-miR-1185-2-3p gene" or "hsa-miR-1185-2-3p" used herein includes the hsa-miR-1185-2-3p gene (miRBase Accession No. MIMAT0022713) described in SEQ ID NO: 9, a homolog or an ortholog of a different organism species, and the like. The hsa-miR-1185-2-3p gene can be obtained by a method described in Berezikov E et al., 2006, Genome Res, Vol. 16, p. 1289-1298. Also, "hsa-mir-1185-2" (miRBase Accession No. MI0003821, SEQ ID NO: 338) having a hairpin-like structure is known as a precursor of "hsa-miR-1185-2-3p".

The term "hsa-miR-1193 gene" or "hsa-miR-1193" used herein includes the hsa-miR-1193 gene (miRBase Accession No. MIMAT0015049) described in SEQ ID NO: 10, a homolog or an ortholog of a different organism species, and the like. The hsa-miR-1193 gene can be obtained by a method described in Stark M S et al., 2010, PLoS One, Vol. 5, e9685. Also, "hsa-mir-1193" (miRBase Accession No. MI0014205, SEQ ID NO: 339) having a hairpin-like structure is known as a precursor of "hsa-miR-1193".

The term "hsa-miR-1207-5p gene" or "hsa-miR-1207-5p" used herein includes the hsa-miR-1207-5p gene (miRBase Accession No. MIMAT0005871) described in SEQ ID NO: 11, a homolog or an ortholog of a different organism species, and the like. The hsa-miR-1207-5p gene can be obtained by a method described in Huppi K et al., 2008, Mol Cancer Res, Vol. 6, p. 212-221. Also, "hsa-mir-1207" (miRBase Accession No. MI0006340, SEQ ID NO: 340) having a hairpin-like structure is known as a precursor of "hsa-miR-1207-5p".

The term "hsa-miR-1238-5p gene" or "hsa-miR-1238-5p" used herein includes the hsa-miR-1238-5p gene (miRBase Accession No. MIMAT0022947) described in SEQ ID NO: 12, a homolog or an ortholog of a different organism species, and the like. The hsa-miR-1238-5p gene can be obtained by a method described in Berezikov E et al., 2007, Mol Cell, Vol. 28, p. 328-336. Also, "hsa-mir-1238" (miRBase Accession No. MI0006328, SEQ ID NO: 341) having a hairpin-like structure is known as a precursor of "hsa-miR-1238-5p".

The term "hsa-miR-1246 gene" or "hsa-miR-1246" used herein includes the hsa-miR-1246 gene (miRBase Accession No. MIMAT0005898) described in SEQ ID NO: 13, a homolog or an ortholog of a different organism species, and the like. The hsa-miR-1246 gene can be obtained by a method described in Morin R D et al., 2008, Genome Res, Vol. 18, p. 610-621. Also, "hsa-mir-1246" (miRBase Accession No. MI0006381, SEQ ID NO: 342) having a hairpin-like structure is known as a precursor of "hsa-miR-1246".

The term "hsa-miR-1249-5p gene" or "hsa-miR-1249-5p" used herein includes the hsa-miR-1249-5p gene (miRBase Accession No. MIMAT0032029) described in SEQ ID NO: 14, a homolog or an ortholog of a different organism species, and the like. The hsa-miR-1249-5p gene can be obtained by a method described in Morin R D et al., 2008, Genome Res, Vol. 18, p. 610-621. Also, "hsa-mir-1249" (miRBase Accession No. MI0006384, SEQ ID NO: 343) having a hairpin-like structure is known as a precursor of "hsa-miR-1249-5p".

The term "hsa-miR-1292-3p gene" or "hsa-miR-1292-3p" used herein includes the hsa-miR-1292-3p gene (miRBase Accession No. MIMAT0022948) described in SEQ ID NO: 15, a homolog or an ortholog of a different organism species, and the like. The hsa-miR-1292-3p gene can be obtained by a method described in Morin R D et al., 2008, Genome Res, Vol. 18, p. 610-621. Also, "hsa-mir-1292" (miRBase Accession No. MI0006433, SEQ ID NO: 344) having a hairpin-like structure is known as a precursor of "hsa-miR-1292-3p".

The term "hsa-miR-1469 gene" or "hsa-miR-1469" used herein includes the hsa-miR-1469 gene (miRBase Accession No. MIMAT0007347) described in SEQ ID NO: 16, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 345) having a hairpin-like structure is known as a precursor of "hsa-miR-1469".

The term "hsa-miR-1470 gene" or "hsa-miR-1470" used herein includes the hsa-miR-1470 gene (miRBase Accession No. MIMAT0007348) described in SEQ ID NO: 17, a homolog or an ortholog of a different organism species, and the like. The hsa-miR-1470 gene can be obtained by a method described in Kawaji H et al., 2008, BMC Genomics, Vol. 9, p. 157. Also, "hsa-mir-1470" (miRBase Accession No. MI0007075, SEQ ID NO: 346) having a hairpin-like structure is known as a precursor of "hsa-miR-1470".

The term "hsa-miR-197-5p gene" or "hsa-miR-197-5p" used herein includes the hsa-miR-197-5p gene (miRBase Accession No. MIMAT0022691) described in SEQ ID NO: 18, a homolog or an ortholog of a different organism species, and the like. The hsa-miR-197-5p gene can be obtained by a method described in 'Lagos-Quintana M et al., 2003, RNA, Vol. 9, p. 175-179'. Also, "hsa-mir-197" (miRBase Accession No. MI0000239, SEQ ID NO: 347) having a hairpin-like structure is known as a precursor of "hsa-miR-197-5p".

The term "hsa-miR-208a-5p gene" or "hsa-miR-208a-5p" used herein includes the hsa-miR-208a-5p gene (miRBase Accession No. MIMAT0026474) described in SEQ ID NO: 19, a homolog or an ortholog of a different organism species, and the like. The hsa-miR-208a-5p gene can be obtained by a method described in Lagos-Quintana M et al., 2003, RNA, Vol. 9, p. 175-179. Also, "hsa-mir-208a" (miRBase Accession No. MI0000251, SEQ ID NO: 348) having a hairpin-like structure is known as a precursor of "hsa-miR-208a-5p".

The term "hsa-miR-2110 gene" or "hsa-miR-2110" used herein includes the hsa-miR-2110 gene (miRBase Accession No. MIMAT0010133) described in SEQ ID NO: 20, a homolog or an ortholog of a different organism species, and the like. The hsa-miR-2110 gene can be obtained by a method described in Zhu J Y et al., 2009, J Virol, Vol. 83, p. 3333-3341. Also, "hsa-mir-2110" (miRBase Accession No. MI0010629, SEQ ID NO: 349) having a hairpin-like structure is known as a precursor of "hsa-miR-2110".

The term "hsa-miR-211-3p gene" or "hsa-miR-211-3p" used herein includes the hsa-miR-211-3p gene (miRBase Accession No. MIMAT0022694) described in SEQ ID NO: 21, a homolog or an ortholog of a different organism species, and the like. The hsa-miR-211-3p gene can be obtained by a method described in Lim L P et al., 2003, Science, Vol. 299, p. 1540. Also, "hsa-mir-211" (miRBase Accession No. MI0000287, SEQ ID NO: 350) having a hairpin-like structure is known as a precursor of "hsa-miR-211-3p".

The term "hsa-miR-2467-3p gene" or "hsa-miR-2467-3p" used herein includes the hsa-miR-2467-3p gene (miRBase Accession No. MIMAT0019953) described in SEQ ID NO: 22, a homolog or an ortholog of a different organism species, and the like. The hsa-miR-2467-3p gene can be obtained by a method described in Persson H et al., 2011, Cancer Res, Vol. 71, p. 78-86. Also, "hsa-mir-2467" (miRBase Accession No. MI0017432, SEQ ID NO: 351) having a hairpin-like structure is known as a precursor of "hsa-miR-2467-3p".

The term "hsa-miR-3122 gene" or "hsa-miR-3122" used herein includes the hsa-miR-3122 gene (miRBase Accession No. MIMAT0014984) described in SEQ ID NO: 23, a homolog or an ortholog of a different organism species, and the like. The hsa-miR-3122 gene can be obtained by a method described in Stark M S et al., 2010, PLoS One., Vol. 5, e9685. Also, "hsa-mir-3122" (miRBase Accession No. MI0014138, SEQ ID NO: 352) having a hairpin-like structure is known as a precursor of "hsa-miR-3122".

The term "hsa-miR-3141 gene" or "hsa-miR-3141" used herein includes the hsa-miR-3141 gene (miRBase Accession No. MIMAT0015010) described in SEQ ID NO: 24, a homolog or an ortholog of a different organism species, and the like. The hsa-miR-3141 gene can be obtained by a method described in Stark M S et al., 2010, PLoS One, Vol. 5, e9685. Also, "hsa-mir-3141" (miRBase Accession No. MI0014165, SEQ ID NO: 353) having a hairpin-like structure is known as a precursor of "hsa-miR-3141".

The term "hsa-miR-3156-5p gene" or "hsa-miR-3156-5p" used herein includes the hsa-miR-3156-5p gene (miRBase Accession No. MIMAT0015030) described in SEQ ID NO: 25, a homolog or an ortholog of a different organism species, and the like. The hsa-miR-3156-5p gene can be obtained by a method described in Stark M S et al., 2010, PLoS One., Vol. 5, e9685. Also, "hsa-mir-3156-1, hsa-mir-3156-2, and hsa-mir-3156-3" (miRBase Accession Nos. MI0014184, MI0014230, and MI0014242, SEQ ID NOs: 354, 355, and 356) having a hairpin-like structure are known as precursors of "hsa-miR-3156-5p".

The term "hsa-miR-3158-5p gene" or "hsa-miR-3158-5p" used herein includes the hsa-miR-3158-5p gene (miRBase Accession No. MIMAT0019211) described in SEQ ID NO: 26, a homolog or an ortholog of a different organism species, and the like. The hsa-miR-3158-5p gene can be obtained by a method described in Creighton C J et al., 2010, PLoS One, Vol. 5, e9637. Also, "hsa-mir-3158-1 and hsa-mir-3158-2" (miRBase Accession Nos. MI0014186 and MI0014187, SEQ ID NOs: 357 and 358) having a hairpin-like structure are known as precursors of "hsa-miR-3158-5p".

The term "hsa-miR-3160-5p gene" or "hsa-miR-3160-5p" used herein includes the hsa-miR-3160-5p gene (miRBase Accession No. MIMAT0019212) described in SEQ ID NO: 27, a homolog or an ortholog of a different organism species, and the like. The hsa-miR-3160-5p gene can be obtained by a method described in Stark M S et al., 2010, PLoS One, Vol. 5, e9685. Also, "hsa-mir-3160-1 and hsa-mir-3160-2" (miRBase Accession Nos. MI0014189 and MI0014190, SEQ ID NOs: 359 and 360) having a hairpin-like structure are known as precursors of "hsa-miR-3160-5p".

The term "hsa-miR-3180-3p gene" or "hsa-miR-3180-3p" used herein includes the hsa-miR-3180-3p gene (miRBase Accession No. MIMAT0015058) described in SEQ ID NO: 28, a homolog or an ortholog of a different organism species, and the like. The hsa-miR-3180-3p gene can be obtained by a method described in Creighton C J et al., 2010, PLoS One, Vol. 5, e9637. Also, "hsa-mir-3180-1, hsa-mir-3180-2, and hsa-mir-3180-3" (miRBase Accession Nos. MI0014214, MI0014215, and MI0014217, SEQ ID NOs: 361, 362, and 363) having a hairpin-like structure are known as precursors of "hsa-miR-3180-3p".

The term "hsa-miR-3191-3p gene" or "hsa-miR-3191-3p" used herein includes the hsa-miR-3191-3p gene (miRBase Accession No. MIMAT0015075) described in SEQ ID NO: 29, a homolog or an ortholog of a different organism species, and the like. The hsa-miR-3191-3p gene can be obtained by a method described in Stark M S et al., 2010, PLoS One, Vol. 5, e9685. Also, "hsa-mir-3191" (miRBase Accession No. MI0014236, SEQ ID NO: 364) having a hairpin-like structure is known as a precursor of "hsa-miR-3191-3p".

The term "hsa-miR-3194-3p gene" or "hsa-miR-3194-3p" used herein includes the hsa-miR-3194-3p gene (miRBase Accession No. MIMAT0019218) described in SEQ ID NO: 30, a homolog or an ortholog of a different organism species, and the like. The hsa-miR-3194-3p gene can be obtained by a method described in Stark M S et al., 2010, PLoS One, Vol. 5, e9685. Also, "hsa-mir-3194" (miRBase Accession No. MI0014239, SEQ ID NO: 365) having a hairpin-like structure is known as a precursor of "hsa-miR-3194-3p".

The term "hsa-miR-320b gene" or "hsa-miR-320b" used herein includes the hsa-miR-320b gene (miRBase Accession No. MIMAT0005792) described in SEQ ID NO: 31, a homolog or an ortholog of a different organism species, and the like. The hsa-miR-320b gene can be obtained by a method described in Berezikov E et al., 2006, Genome Res, Vol. 16, p. 1289-1298. Also, "hsa-mir-320b-1 and hsa-mir-320b-2" (miRBase Accession Nos. MI0003776 and MI0003839, SEQ ID NOs: 366 and 367) having a hairpin-like structure are known as precursors of "hsa-miR-320b".

The term "hsa-miR-328-5p gene" or "hsa-miR-328-5p" used herein includes the hsa-miR-328-5p gene (miRBase Accession No. MIMAT0026486) described in SEQ ID NO: 32, a homolog or an ortholog of a different organism species, and the like. The hsa-miR-328-5p gene can be obtained by a method described in Kim J et al., 2004, Proc Natl Acad Sci USA, Vol. 101, p. 360-365. Also, "hsa-mir-328" (miRBase Accession No. MI0000804, SEQ ID NO: 368) having a hairpin-like structure is known as a precursor of "hsa-miR-328-5p".

The term "hsa-miR-3610 gene" or "hsa-miR-3610" used herein includes the hsa-miR-3610 gene (miRBase Accession No. MIMAT0017987) described in SEQ ID NO: 33, a homolog or an ortholog of a different organism species, and the like. The hsa-miR-3610 gene can be obtained by a method described in Witten D et al., 2010, BMC Biol., Vol. 8, 58. Also, "hsa-mir-3610" (miRBase Accession No. MI0016000, SEQ ID NO: 369) having a hairpin-like structure is known as a precursor of "hsa-miR-3610".

The term "hsa-miR-3619-3p gene" or "hsa-miR-3619-3p" used herein includes the hsa-miR-3619-3p gene (miRBase Accession No. MIMAT0019219) described in SEQ ID NO: 34, a homolog or an ortholog of a different organism species, and the like. The hsa-miR-3619-3p gene can be obtained by a method described in Witten D et al., 2010, BMC Biol, Vol. 8, p. 58. Also, "hsa-mir-3619" (miRBase Accession No. MI0016009, SEQ ID NO: 370) having a hairpin-like structure is known as a precursor of "hsa-miR-3619-3p".

The term "hsa-miR-3620-5p gene" or "hsa-miR-3620-5p" used herein includes the hsa-miR-3620-5p gene (miRBase Accession No. MIMAT0022967) described in SEQ ID NO: 35, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 371) having a hairpin-like structure is known as a precursor of "hsa-miR-3620-5p".

The term "hsa-miR-370-3p gene" or "hsa-miR-370-3p" used herein includes the hsa-miR-370-3p gene (miRBase Accession No. MIMAT0000722) described in SEQ ID NO: 36, a homolog or an ortholog of a different organism species, and the like. The hsa-miR-370-3p gene can be obtained by a method described in Suh M R et al., 2004, Dev Biol., Vol. 270, 488-498. Also, "hsa-mir-370" (miRBase Accession No. MI0000778, SEQ ID NO: 372) having a hairpin-like structure is known as a precursor of "hsa-miR-370-3p".

The term "hsa-miR-373-5p gene" or "hsa-miR-373-5p" used herein includes the hsa-miR-373-5p gene (miRBase Accession No. MIMAT0000725) described in SEQ ID NO: 37, a homolog or an ortholog of a different organism species, and the like. The hsa-miR-373-5p gene can be obtained by a method described in Suh M R et al., 2004, Dev Biol, Vol. 270, p. 488-498. Also, "hsa-mir-373" (miRBase Accession No. MI0000781, SEQ ID NO: 373) having a hairpin-like structure is known as a precursor of "hsa-miR-373-5p".

The term "hsa-miR-3917 gene" or "hsa-miR-3917" used herein includes the hsa-miR-3917 gene (miRBase Accession No. MIMAT0018191) described in SEQ ID NO: 38, a homolog or an ortholog of a different organism species, and the like. The hsa-miR-3917 gene can be obtained by a method described in Creighton C J et al., 2010, PLoS One, Vol. 5, e9637. Also, "hsa-mir-3917" (miRBase Accession No. MI0016423, SEQ ID NO: 374) having a hairpin-like structure is known as a precursor of "hsa-miR-3917".

The term "hsa-miR-3937 gene" or "hsa-miR-3937" used herein includes the hsa-miR-3937 gene (miRBase Accession No. MIMAT0018352) described in SEQ ID NO: 39, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 375) having a hairpin-like structure is known as a precursor of "hsa-miR-3937".

The term "hsa-miR-4259 gene" or "hsa-miR-4259" used herein includes the hsa-miR-4259 gene (miRBase Accession No. MIMAT0016880) described in SEQ ID NO: 40, a homolog or an ortholog of a different organism species, and the like. The hsa-miR-4259 gene can be obtained by a method described in Goff L A et al., 2009, PLoS One, Vol. 4, e7192. Also, "hsa-mir-4259" (miRBase Accession No. MI0015858, SEQ ID NO: 376) having a hairpin-like structure is known as a precursor of "hsa-miR-4259".

The term "hsa-miR-4281 gene" or "hsa-miR-4281" used herein includes the hsa-miR-4281 gene (miRBase Accession No. MIMAT0016907) described in SEQ ID NO: 41, a homolog or an ortholog of a different organism species, and the like. The hsa-miR-4281 gene can be obtained by a method described in Goff L A et al., 2009, PLoS One, Vol. 4, e7192. Also, "hsa-mir-4281" (miRBase Accession No. MI0015885, SEQ ID NO: 377) having a hairpin-like structure is known as a precursor of "hsa-miR-4281".

The term "hsa-miR-4294 gene" or "hsa-miR-4294" used herein includes the hsa-miR-4294 gene (miRBase Accession No. MIMAT0016849) described in SEQ ID NO: 42, a homolog or an ortholog of a different organism species, and the like. The hsa-miR-4294 gene can be obtained by a method described in Goff L A et al., 2009, PLoS One, Vol. 4, e7192. Also, "hsa-mir-4294" (miRBase Accession No. MI0015827, SEQ ID NO: 378) having a hairpin-like structure is known as a precursor of "hsa-miR-4294".

The term "hsa-miR-4419b gene" or "hsa-miR-4419b" used herein includes the hsa-miR-4419b gene (miRBase Accession No. MIMAT0019034) described in SEQ ID NO: 43, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 379) having a hairpin-like structure is known as a precursor of "hsa-miR-4419b".

The term "hsa-miR-4428 gene" or "hsa-miR-4428" used herein includes the hsa-miR-4428 gene (miRBase Accession No. MIMAT0018943) described in SEQ ID NO: 44, a homolog or an ortholog of a different organism species, and the like. The hsa-miR-4428 gene can be obtained by a method described in Jima D D et al., 2010, Blood., Vol. 116, e118-e127. Also, "hsa-mir-4428" (miRBase Accession No. MI0016767, SEQ ID NO: 380) having a hairpin-like structure is known as a precursor of "hsa-miR-4428".

The term "hsa-miR-4429 gene" or "hsa-miR-4429" used herein includes the hsa-miR-4429 gene (miRBase Accession No. MIMAT0018944) described in SEQ ID NO: 45, a homolog or an ortholog of a different organism species, and the like. The hsa-miR-4429 gene can be obtained by a method described in Jima D D et al., 2010, Blood, Vol. 116, e118-e127. Also, "hsa-mir-4429" (miRBase Accession No. MI0016768, SEQ ID NO: 381) having a hairpin-like structure is known as a precursor of "hsa-miR-4429".

The term "hsa-miR-4433a-3p gene" or "hsa-miR-4433a-3p" used herein includes the hsa-miR-4433a-3p gene (miRBase Accession No. MIMAT0018949) described in SEQ ID NO: 46, a homolog or an ortholog of a different organism species, and the like. The hsa-miR-4433a-3p gene can be obtained by a method described in Jima D D et al., 2010, Blood, Vol. 116, e118-e127. Also, "hsa-mir-4433a" (miRBase Accession No. MI0016773, SEQ ID NO: 382) having a hairpin-like structure is known as a precursor of "hsa-miR-4433a-3p".

The term "hsa-miR-4447 gene" or "hsa-miR-4447" used herein includes the hsa-miR-4447 gene (miRBase Accession No. MIMAT0018966) described in SEQ ID NO: 47, a homolog or an ortholog of a different organism species, and the like. The hsa-miR-4447 gene can be obtained by a method described in Jima D D et al., 2010, Blood, Vol. 116, e118-e127. Also, "hsa-mir-4447" (miRBase Accession No. MI0016790, SEQ ID NO: 383) having a hairpin-like structure is known as a precursor of "hsa-miR-4447".

The term "hsa-miR-4449 gene" or "hsa-miR-4449" used herein includes the hsa-miR-4449 gene (miRBase Accession No. MIMAT0018968) described in SEQ ID NO: 48, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No. MI0016792, SEQ ID NO: 384) having a hairpin-like structure is known as a precursor of "hsa-miR-4449".

The term "hsa-miR-4459 gene" or "hsa-miR-4459" used herein includes the hsa-miR-4459 gene (miRBase Accession No. MIMAT0018981) described in SEQ ID NO: 49, a homolog or an ortholog of a different organism species, and the like. The hsa-miR-4459 gene can be obtained by a method described in Jima D D et al., 2010, Blood, Vol. 116, e118-e127. Also, "hsa-mir-4459" (miRBase Accession No. MI0016805, SEQ ID NO: 385) having a hairpin-like structure is known as a precursor of "hsa-miR-4459".

The term "hsa-miR-4480 gene" or "hsa-miR-4480" used herein includes the hsa-miR-4480 gene (miRBase Accession No. MIMAT0019014) described in SEQ ID NO: 50, a homolog or an ortholog of a different organism species, and the like. The hsa-miR-4480 gene can be obtained by a method described in Jima D D et al., 2010, Blood, Vol. 116, e118-e127. Also, "hsa-mir-4480" (miRBase Accession No. MI0016841, SEQ ID NO: 386) having a hairpin-like structure is known as a precursor of "hsa-miR-4480".

The term "hsa-miR-4485-5p gene" or "hsa-miR-4485-5p" used herein includes the hsa-miR-4485-5p gene (miRBase Accession No. MIMAT0032116) described in SEQ ID NO: 51, a homolog or an ortholog of a different organism species, and the like. The hsa-miR-4485-5p gene can be obtained by a method described in Jima D D et al., 2010, Blood., Vol. 116, e118-e127. Also, "hsa-mir-4485" (miRBase Accession No. MI0016846, SEQ ID NO: 387) having a hairpin-like structure is known as a precursor of "hsa-miR-4485-5p".

The term "hsa-miR-4486 gene" or "hsa-miR-4486" used herein includes the hsa-miR-4486 gene (miRBase Accession No. MIMAT0019020) described in SEQ ID NO: 52, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847, SEQ ID NO: 388) having a hairpin-like structure is known as a precursor of "hsa-miR-4486".

The term "hsa-miR-4488 gene" or "hsa-miR-4488" used herein includes the hsa-miR-4488 gene (miRBase Accession No. MIMAT0019022) described in SEQ ID NO: 53, a homolog or an ortholog of a different organism species, and the like. The hsa-miR-4488 gene can be obtained by a method described in Jima D D et al., 2010, Blood, Vol. 116, e118-e127. Also, "hsa-mir-4488" (miRBase Accession No. MI0016849, SEQ ID NO: 389) having a hairpin-like structure is known as a precursor of "hsa-miR-4488".

The term "hsa-miR-4489 gene" or "hsa-miR-4489" used herein includes the hsa-miR-4489 gene (miRBase Accession No. MIMAT0019023) described in SEQ ID NO: 54, a homolog or an ortholog of a different organism species, and the like. The hsa-miR-4489 gene can be obtained by a method described in Jima D D et al., 2010, Blood., Vol. 116, e118-e127. Also, "hsa-mir-4489" (miRBase Accession No. MI0016850, SEQ ID NO: 390) having a hairpin-like structure is known as a precursor of "hsa-miR-4489".

The term "hsa-miR-4505 gene" or "hsa-miR-4505" used herein includes the hsa-miR-4505 gene (miRBase Accession No. MIMAT0019041) described in SEQ ID NO: 55, a homolog or an ortholog of a different organism species, and the like. The hsa-miR-4505 gene can be obtained by a method described in Jima D D et al., 2010, Blood, Vol. 116, e118-e127. Also, "hsa-mir-4505" (miRBase Accession No. MI0016868, SEQ ID NO: 391) having a hairpin-like structure is known as a precursor of "hsa-miR-4505".

The term "hsa-miR-4513 gene" or "hsa-miR-4513" used herein includes the hsa-miR-4513 gene (miRBase Accession No. MIMAT0019050) described in SEQ ID NO: 56, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 392) having a hairpin-like structure is known as a precursor of "hsa-miR-4513".

The term "hsa-miR-4515 gene" or "hsa-miR-4515" used herein includes the hsa-miR-4515 gene (miRBase Accession No. MIMAT0019052) described in SEQ ID NO: 57, a homolog or an ortholog of a different organism species, and the like. The hsa-miR-4515 gene can be obtained by a method described in Jima D D et al., 2010, Blood, Vol. 116, e118-e127. Also, "hsa-mir-4515" (miRBase Accession No. MI0016881, SEQ ID NO: 393) having a hairpin-like structure is known as a precursor of "hsa-miR-4515".

The term "hsa-miR-4530 gene" or "hsa-miR-4530" used herein includes the hsa-miR-4530 gene (miRBase Accession No. MIMAT0019069) described in SEQ ID NO: 58, a homolog or an ortholog of a different organism species, and the like. The hsa-miR-4530 gene can be obtained by a method described in Jima D D et al., 2010, Blood, Vol. 116, e118-e127. Also, "hsa-mir-4530" (miRBase Accession No. MI0016897, SEQ ID NO: 394) having a hairpin-like structure is known as a precursor of "hsa-miR-4530".

The term "hsa-miR-4535 gene" or "hsa-miR-4535" used herein includes the hsa-miR-4535 gene (miRBase Accession No. MIMAT0019075) described in SEQ ID NO: 59, a homolog or an ortholog of a different organism species, and the like. The hsa-miR-4535 gene can be obtained by a method described in Jima D D et al., 2010, Blood., Vol. 116, e118-e127. Also, "hsa-mir-4535" (miRBase Accession No. MI0016903, SEQ ID NO: 395) having a hairpin-like structure is known as a precursor of "hsa-miR-4535".

The term "hsa-miR-4635 gene" or "hsa-miR-4635" used herein includes the hsa-miR-4635 gene (miRBase Accession No. MIMAT0019692) described in SEQ ID NO: 60, a homolog or an ortholog of a different organism species, and the like. The hsa-miR-4635 gene can be obtained by a method described in Persson H et al., 2011, Cancer Res., Vol. 71, p. 78-86. Also, "hsa-mir-4635" (miRBase Accession No. MI0017262, SEQ ID NO: 396) having a hairpin-like structure is known as a precursor of "hsa-miR-4635".

The term "hsa-miR-4640-5p gene" or "hsa-miR-4640-5p" used herein includes the hsa-miR-4640-5p gene (miRBase Accession No. MIMAT0019699) described in SEQ ID NO: 61, a homolog or an ortholog of a different organism species, and the like. The hsa-miR-4640-5p gene can be obtained by a method described in Persson H et al., 2011, Cancer Res, Vol. 71, p. 78-86. Also, "hsa-mir-4640" (miRBase Accession No. MI0017267, SEQ ID NO: 397) having a hairpin-like structure is known as a precursor of "hsa-miR-4640-5p".

The term "hsa-miR-4646-5p gene" or "hsa-miR-4646-5p" used herein includes the hsa-miR-4646-5p gene (miRBase Accession No. MIMAT0019707) described in SEQ ID NO: 62, a homolog or an ortholog of a different organism species, and the like. The hsa-miR-4646-5p gene can be obtained by a method described in Persson H et al., 2011, Cancer Res., Vol. 71, p. 78-86. Also, "hsa-mir-4646" (miRBase Accession No. MI0017273, SEQ ID NO: 398) having a hairpin-like structure is known as a precursor of "hsa-miR-4646-5p".

The term "hsa-miR-4656 gene" or "hsa-miR-4656" used herein includes the hsa-miR-4656 gene (miRBase Accession No. MIMAT0019723) described in SEQ ID NO: 63, a homolog or an ortholog of a different organism species, and the like. The hsa-miR-4656 gene can be obtained by a method described in Persson H et al., 2011, Cancer Res, Vol. 71, p. 78-86. Also, "hsa-mir-4656" (miRBase Accession No. MI0017284, SEQ ID NO: 399) having a hairpin-like structure is known as a precursor of "hsa-miR-4656".

The term "hsa-miR-4663 gene" or "hsa-miR-4663" used herein includes the hsa-miR-4663 gene (miRBase Accession No. MIMAT0019735) described in SEQ ID NO: 64, a homolog or an ortholog of a different organism species, and the like. The hsa-miR-4663 gene can be obtained by a method described in Persson H. et al., 2011, Cancer Research, Vol. 71, p. 78-86. Also, "hsa-mir-4663" (miRBase Accession No. MI0017292, SEQ ID NO: 400) having a hairpin-like structure is known as a precursor of "hsa-miR-4663".

The term "hsa-miR-4665-5p gene" or "hsa-miR-4665-5p" used herein includes the hsa-miR-4665-5p gene (miRBase Accession No. MIMAT0019739) described in SEQ ID NO: 65, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 401) having a hairpin-like structure is known as a precursor of "hsa-miR-4665-5p".

The term "hsa-miR-4706 gene" or "hsa-miR-4706" used herein includes the hsa-miR-4706 gene (miRBase Accession No. MIMAT0019806) described in SEQ ID NO: 66, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 402) having a hairpin-like structure is known as a precursor of "hsa-miR-4706".

The term "hsa-miR-4707-5p gene" or "hsa-miR-4707-5p" used herein includes the hsa-miR-4707-5p gene (miRBase Accession No. MIMAT0019807) described in SEQ ID NO: 67, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 403) having a hairpin-like structure is known as a precursor of "hsa-miR-4707-5p".

The term "hsa-miR-4708-3p gene" or "hsa-miR-4708-3p" used herein includes the hsa-miR-4708-3p gene (miRBase Accession No. MIMAT0019810) described in SEQ ID NO: 68, a homolog or an ortholog of a different organism species, and the like. The hsa-miR-4708-3p gene can be obtained by a method described in Persson H et al., 2011, Cancer Res, Vol. 71, p. 78-86. Also, "hsa-mir-4708" (miRBase Accession No. MI0017341, SEQ ID NO: 404) having a hairpin-like structure is known as a precursor of "hsa-miR-4708-3p".

The term "hsa-miR-4710 gene" or "hsa-miR-4710" used herein includes the hsa-miR-4710 gene (miRBase Accession No. MIMAT0019815) described in SEQ ID NO: 69, a homolog or an ortholog of a different organism species, and the like. The hsa-miR-4710 gene can be obtained by a method described in Persson H et al., 2011, Cancer Res, Vol. 71, p. 78-86. Also, "hsa-mir-4710" (miRBase Accession No. MI0017344, SEQ ID NO: 405) having a hairpin-like structure is known as a precursor of "hsa-miR-4710".

The term "hsa-miR-4718 gene" or "hsa-miR-4718" used herein includes the hsa-miR-4718 gene (miRBase Accession No. MIMAT0019831) described in SEQ ID NO: 70, a homolog or an ortholog of a different organism species, and the like. The hsa-miR-4718 gene can be obtained by a method described in Persson H et al., 2011, Cancer Res, Vol. 71, p. 78-86. Also, "hsa-mir-4718" (miRBase Accession No. MI0017353, SEQ ID NO: 406) having a hairpin-like structure is known as a precursor of "hsa-miR-4718".

The term "hsa-miR-4722-5p gene" or "hsa-miR-4722-5p" used herein includes the hsa-miR-4722-5p gene (miRBase Accession No. MIMAT0019836) described in SEQ ID NO: 71, a homolog or an ortholog of a different organism species, and the like. The hsa-miR-4722-5p gene can be obtained by a method described in Persson H et al., 2011, Cancer Res, Vol. 71, p. 78-86. Also, "hsa-mir-4722" (miRBase Accession No. MI0017357, SEQ ID NO: 407) having a hairpin-like structure is known as a precursor of "hsa-miR-4722-5p".

The term "hsa-miR-4727-3p gene" or "hsa-miR-4727-3p" used herein includes the hsa-miR-4727-3p gene (miRBase Accession No. MIMAT0019848) described in SEQ ID NO: 72, a homolog or an ortholog of a different organism species, and the like. The hsa-miR-4727-3p gene can be obtained by a method described in Persson H et al., 2011, Cancer Res, Vol. 71, p. 78-86. Also, "hsa-mir-4727" (miRBase Accession No. MI0017364, SEQ ID NO: 408) having a hairpin-like structure is known as a precursor of "hsa-miR-4727-3p".

The term "hsa-miR-4730 gene" or "hsa-miR-4730" used herein includes the hsa-miR-4730 gene (miRBase Accession No. MIMAT0019852) described in SEQ ID NO: 73, a homolog or an ortholog of a different organism species, and the like. The hsa-miR-4730 gene can be obtained by a method described in Persson H et al., 2011, Cancer Res, Vol. 71, p. 78-86. Also, "hsa-mir-4730" (miRBase Accession No.

MI0017367, SEQ ID NO: 409) having a hairpin-like structure is known as a precursor of "hsa-miR-4730".

The term "hsa-miR-4734 gene" or "hsa-miR-4734" used herein includes the hsa-miR-4734 gene (miRBase Accession No. MIMAT0019859) described in SEQ ID NO: 74, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 410) having a hairpin-like structure is known as a precursor of "hsa-miR-4734".

The term "hsa-miR-4740-5p gene" or "hsa-miR-4740-5p" used herein includes the hsa-miR-4740-5p gene (miRBase Accession No. MIMAT0019869) described in SEQ ID NO: 75, a homolog or an ortholog of a different organism species, and the like. The hsa-miR-4740-5p gene can be obtained by a method described in Persson H et al., 2011, Cancer Res, Vol. 71, p. 78-86. Also, "hsa-mir-4740" (miRBase Accession No. MI0017378, SEQ ID NO: 411) having a hairpin-like structure is known as a precursor of "hsa-miR-4740-5p".

The term "hsa-miR-4747-3p gene" or "hsa-miR-4747-3p" used herein includes the hsa-miR-4747-3p gene (miRBase Accession No. MIMAT0019883) described in SEQ ID NO: 76, a homolog or an ortholog of a different organism species, and the like. The hsa-miR-4747-3p gene can be obtained by a method described in Persson H et al., 2011, Cancer Res, Vol. 71, p. 78-86. Also, "hsa-mir-4747" (miRBase Accession No. MI0017386, SEQ ID NO: 412) having a hairpin-like structure is known as a precursor of "hsa-miR-4747-3p".

The term "hsa-miR-4749-5p gene" or "hsa-miR-4749-5p" used herein includes the hsa-miR-4749-5p gene (miRBase Accession No. MIMAT0019885) described in SEQ ID NO: 77, a homolog or an ortholog of a different organism species, and the like. The hsa-miR-4749-5p gene can be obtained by a method described in Persson H et al., 2011, Cancer Res, Vol. 71, p. 78-86. Also, "hsa-mir-4749" (miRBase Accession No. MI0017388, SEQ ID NO: 413) having a hairpin-like structure is known as a precursor of "hsa-miR-4749-5p".

The term "hsa-miR-4755-3p gene" or "hsa-miR-4755-3p" used herein includes the hsa-miR-4755-3p gene (miRBase Accession No. MIMAT0019896) described in SEQ ID NO: 78, a homolog or an ortholog of a different organism species, and the like. The hsa-miR-4755-3p gene can be obtained by a method described in Persson H. et al., 2011, Cancer Research, Vol. 71, p. 78-86. Also, "hsa-mir-4755" (miRBase Accession No. MI0017395, SEQ ID NO: 414) having a hairpin-like structure is known as a precursor of "hsa-miR-4755-3p".

The term "hsa-miR-4763-5p gene" or "hsa-miR-4763-5p" used herein includes the hsa-miR-4763-5p gene (miRBase Accession No. MIMAT0019912) described in SEQ ID NO: 79, a homolog or an ortholog of a different organism species, and the like. The hsa-miR-4763-5p gene can be obtained by a method described in Persson H et al., 2011, Cancer Res., Vol. 71, p. 78-86. Also, "hsa-mir-4763" (miRBase Accession No. MI0017404, SEQ ID NO: 415) having a hairpin-like structure is known as a precursor of "hsa-miR-4763-5p".

The term "hsa-miR-4787-3p gene" or "hsa-miR-4787-3p" used herein includes the hsa-miR-4787-3p gene (miRBase Accession No. MIMAT0019957) described in SEQ ID NO: 80, a homolog or an ortholog of a different organism species, and the like. The hsa-miR-4787-3p gene can be obtained by a method described in Persson H et al., 2011, Cancer Res, Vol. 71, p. 78-86. Also, "hsa-mir-4787" (miRBase Accession No. MI0017434, SEQ ID NO: 416) having a hairpin-like structure is known as a precursor of "hsa-miR-4787-3p".

The term "hsa-miR-5008-5p gene" or "hsa-miR-5008-5p" used herein includes the hsa-miR-5008-5p gene (miRBase Accession No. MIMAT0021039) described in SEQ ID NO: 81, a homolog or an ortholog of a different organism species, and the like. The hsa-miR-5008-5p gene can be obtained by a method described in Hansen T B et al., 2011, RNA Biol, Vol. 8, p. 378-383. Also, "hsa-mir-5008" (miRBase Accession No. MI0017876, SEQ ID NO: 417) having a hairpin-like structure is known as a precursor of "hsa-miR-5008-5p".

The term "hsa-miR-5010-5p gene" or "hsa-miR-5010-5p" used herein includes the hsa-miR-5010-5p gene (miRBase Accession No. MIMAT0021043) described in SEQ ID NO: 82, a homolog or an ortholog of a different organism species, and the like. The hsa-miR-5010-5p gene can be obtained by a method described in Hansen T B et al., 2011, RNA Biol, Vol. 8, p. 378-383. Also, "hsa-mir-5010" (miRBase Accession No. MI0017878, SEQ ID NO: 418) having a hairpin-like structure is known as a precursor of "hsa-miR-5010-5p".

The term "hsa-miR-504-3p gene" or "hsa-miR-504-3p" used herein includes the hsa-miR-504-3p gene (miRBase Accession No. MIMAT0026612) described in SEQ ID NO: 83, a homolog or an ortholog of a different organism species, and the like. The hsa-miR-504-3p gene can be obtained by a method described in Bentwich I et al., 2005, Nat Genet, Vol. 37, p. 766-770. Also, "hsa-mir-504" (miRBase Accession No. MI0003189, SEQ ID NO: 419) having a hairpin-like structure is known as a precursor of "hsa-miR-504-3p".

The term "hsa-miR-5090 gene" or "hsa-miR-5090" used herein includes the hsa-miR-5090 gene (miRBase Accession No. MIMAT0021082) described in SEQ ID NO: 84, a homolog or an ortholog of a different organism species, and the like. The hsa-miR-5090 gene can be obtained by a method described in Ding N et al., 2011, J Radiat Res, Vol. 52, p. 425-432. Also, "hsa-mir-5090" (miRBase Accession No. MI0017979, SEQ ID NO: 420) having a hairpin-like structure is known as a precursor of "hsa-miR-5090".

The term "hsa-miR-5100 gene" or "hsa-miR-5100" used herein includes the hsa-miR-5100 gene (miRBase Accession No. MIMAT0022259) described in SEQ ID NO: 85, a homolog or an ortholog of a different organism species, and the like. The hsa-miR-5100 gene can be obtained by a method described in Tandon M et al., 2012, Oral Dis, Vol. 18, p. 127-131. Also, "hsa-mir-5100" (miRBase Accession No. MI0019116, SEQ ID NO: 421) having a hairpin-like structure is known as a precursor of "hsa-miR-5100".

The term "hsa-miR-5196-5p gene" or "hsa-miR-5196-5p" used herein includes the hsa-miR-5196-5p gene (miRBase Accession No. MIMAT0021128) described in SEQ ID NO: 86, a homolog or an ortholog of a different organism species, and the like. The hsa-miR-5196-5p gene can be obtained by a method described in Schotte D et al., 2011, Leukemia, Vol. 25, p. 1389-1399. Also, "hsa-mir-5196" (miRBase Accession No. MI0018175, SEQ ID NO: 422) having a hairpin-like structure is known as a precursor of "hsa-miR-5196-5p".

The term "hsa-miR-551b-5p gene" or "hsa-miR-551b-5p" used herein includes the hsa-miR-551b-5p gene (miRBase Accession No. MIMAT0004794) described in SEQ ID NO: 87, a homolog or an ortholog of a different organism species, and the like. The hsa-miR-551b-5p gene can be obtained by a method described in Cummins J M et al., 2006, Proc Natl Acad Sci USA, Vol. 103, p. 3687-3692. Also, "hsa-mir-551b" (miRBase Accession No. MI0003575, SEQ ID NO: 423) having a hairpin-like structure is known as a precursor of "hsa-miR-551b-5p".

The term "hsa-miR-557 gene" or "hsa-miR-557" used herein includes the hsa-miR-557 gene (miRBase Accession No. MIMAT0003221) described in SEQ ID NO: 88, a homolog or an ortholog of a different organism species, and the like. The hsa-miR-557 gene can be obtained by a method described in Cummins J M et al., 2006, Proc Natl Acad Sci USA, Vol. 103, p. 3687-3692. Also, "hsa-mir-557" (miRBase Accession No. MI0003563, SEQ ID NO: 424) having a hairpin-like structure is known as a precursor of "hsa-miR-557".

The term "hsa-miR-5787 gene" or "hsa-miR-5787" used herein includes the hsa-miR-5787 gene (miRBase Accession No. MIMAT0023252) described in SEQ ID NO: 89, a homolog or an ortholog of a different organism species, and the like. The hsa-miR-5787 gene can be obtained by a method described in Yoo H et al., 2011, Biochem Biophys Res Commun, Vol. 415, p. 567-572. Also, "hsa-mir-5787" (miRBase Accession No. MI0019797, SEQ ID NO: 425) having a hairpin-like structure is known as a precursor of "hsa-miR-5787".

The term "hsa-miR-6090 gene" or "hsa-miR-6090" used herein includes the hsa-miR-6090 gene (miRBase Accession No. MIMAT0023715) described in SEQ ID NO: 90, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 426) having a hairpin-like structure is known as a precursor of "hsa-miR-6090".

The term "hsa-miR-6124 gene" or "hsa-miR-6124" used herein includes the hsa-miR-6124 gene (miRBase Accession No. MIMAT0024597) described in SEQ ID NO: 91, a homolog or an ortholog of a different organism species, and the like. The hsa-miR-6124 gene can be obtained by a method described in Smith J L et al., 2012, J Virol, Vol. 86, p. 5278-5287. Also, "hsa-mir-6124" (miRBase Accession No. MI0021258, SEQ ID NO: 427) having a hairpin-like structure is known as a precursor of "hsa-miR-6124".

The term "hsa-miR-6132 gene" or "hsa-miR-6132" used herein includes the hsa-miR-6132 gene (miRBase Accession No. MIMAT0024616) described in SEQ ID NO: 92, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 428) having a hairpin-like structure is known as a precursor of "hsa-miR-6132".

The term "hsa-miR-6510-5p gene" or "hsa-miR-6510-5p" used herein includes the hsa-miR-6510-5p gene (miRBase Accession No. MIMAT0025476) described in SEQ ID NO: 93, a homolog or an ortholog of a different organism species, and the like. The hsa-miR-6510-5p gene can be obtained by a method described in Joyce C E et al., 2011, Hum Mol Genet, Vol. 20, p. 4025-4040. Also, "hsa-mir-6510" (miRBase Accession No. MI0022222, SEQ ID NO: 429) having a hairpin-like structure is known as a precursor of "hsa-miR-6510-5p".

The term "hsa-miR-6511b-5p gene" or "hsa-miR-6511b-5p" used herein includes the hsa-miR-6511b-5p gene (miRBase Accession No. MIMAT0025847) described in SEQ ID NO: 94, a homolog or an ortholog of a different organism species, and the like. The hsa-miR-6511b-5p gene can be obtained by a method described in Li Y et al., 2012, Gene, Vol. 497, p. 330-335. Also, "hsa-mir-6511b-1 and hsa-mir-6511b-2" (miRBase Accession Nos. MI0022552 and MI0023431, SEQ ID NOs: 430 and 431) having a hairpin-like structure are known as precursors of "hsa-miR-6511b-5p".

The term "hsa-miR-6515-3p gene" or "hsa-miR-6515-3p" used herein includes the hsa-miR-6515-3p gene (miRBase Accession No. MIMAT0025487) described in SEQ ID NO: 95, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 432) having a hairpin-like structure is known as a precursor of "hsa-miR-6515-3p".

The term "hsa-miR-654-5p gene" or "hsa-miR-654-5p" used herein includes the hsa-miR-654-5p gene (miRBase Accession No. MIMAT0003330) described in SEQ ID NO: 96, a homolog or an ortholog of a different organism species, and the like. The hsa-miR-654-5p gene can be obtained by a method described in Cummins J M et al., 2006, Proc Natl Acad Sci USA., Vol. 103, p. 3687-3692. Also, "hsa-mir-654" (miRBase Accession No. MI0003676, SEQ ID NO: 433) having a hairpin-like structure is known as a precursor of "hsa-miR-654-5p".

The term "hsa-miR-658 gene" or "hsa-miR-658" used herein includes the hsa-miR-658 gene (miRBase Accession No. MIMAT0003336) described in SEQ ID NO: 97, a homolog or an ortholog of a different organism species, and the like. The hsa-miR-658 gene can be obtained by a method described in Cummins J M et al., 2006, Proc Natl Acad Sci USA, Vol. 103, p. 3687-3692. Also, "hsa-mir-658" (miRBase Accession No. MI0003682, SEQ ID NO: 434) having a hairpin-like structure is known as a precursor of "hsa-miR-658".

The term "hsa-miR-668-5p gene" or "hsa-miR-668-5p" used herein includes the hsa-miR-668-5p gene (miRBase Accession No. MIMAT0026636) described in SEQ ID NO: 98, a homolog or an ortholog of a different organism species, and the like. The hsa-miR-668-5p gene can be obtained by a method described in Berezikov E et al., 2006, Genome Res., Vol. 16, p. 1289-1298. Also, "hsa-mir-668" (miRBase Accession No. MI0003761, SEQ ID NO: 435) having a hairpin-like structure is known as a precursor of "hsa-miR-668-5p".

The term "hsa-miR-6722-5p gene" or "hsa-miR-6722-5p" used herein includes the hsa-miR-6722-5p gene (miRBase Accession No. MIMAT0025853) described in SEQ ID NO: 99, a homolog or an ortholog of a different organism species, and the like. The hsa-miR-6722-5p gene can be obtained by a method described in Li Y et al., 2012, Gene., Vol. 497, p. 330-335. Also, "hsa-mir-6722" (miRBase Accession No. MI0022557, SEQ ID NO: 436) having a hairpin-like structure is known as a precursor of "hsa-miR-6722-5p".

The term "hsa-miR-6724-5p gene" or "hsa-miR-6724-5p" used herein includes the hsa-miR-6724-5p gene (miRBase Accession No. MIMAT0025856) described in SEQ ID NO: 100, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 437) having a hairpin-like structure is known as a precursor of "hsa-miR-6724-5p".

The term "hsa-miR-6729-3p gene" or "hsa-miR-6729-3p" used herein includes the hsa-miR-6729-3p gene (miRBase Accession No. MIMAT0027360) described in SEQ ID NO: 101, a homolog or an ortholog of a different organism species, and the like. The hsa-miR-6729-3p gene can be obtained by a method described in Ladewig E et al., 2012, Genome Res, Vol. 22, p. 1634-1645. Also, "hsa-mir-6729" (miRBase Accession No. MI0022574, SEQ ID NO: 438) having a hairpin-like structure is known as a precursor of "hsa-miR-6729-3p".

The term "hsa-miR-6737-5p gene" or "hsa-miR-6737-5p" used herein includes the hsa-miR-6737-5p gene (miRBase Accession No. MIMAT0027375) described in SEQ ID NO: 102, a homolog or an ortholog of a different organism species, and the like. The hsa-miR-6737-5p gene can be obtained by a method described in Ladewig E et al., 2012, Genome Res, Vol. 22, p. 1634-1645. Also, "hsa-mir-6737" (miRBase Accession No. MI0022582, SEQ ID NO: 439) having a hairpin-like structure is known as a precursor of "hsa-miR-6737-5p".

The term "hsa-miR-6756-5p gene" or "hsa-miR-6756-5p" used herein includes the hsa-miR-6756-5p gene (miRBase Accession No. MIMAT0027412) described in SEQ ID NO: 103, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 440) having a hairpin-like structure is known as a precursor of "hsa-miR-6756-5p".

The term "hsa-miR-6762-5p gene" or "hsa-miR-6762-5p" used herein includes the hsa-miR-6762-5p gene (miRBase Accession No. MIMAT0027424) described in SEQ ID NO: 104, a homolog or an ortholog of a different organism species, and the like. The hsa-miR-6762-5p gene can be obtained by a method described in Ladewig E et al., 2012, Genome Res, Vol. 22, p. 1634-1645. Also, "hsa-mir-6762" (miRBase Accession No. MI0022607, SEQ ID NO: 441) having a hairpin-like structure is known as a precursor of "hsa-miR-6762-5p".

The term "hsa-miR-6763-3p gene" or "hsa-miR-6763-3p" used herein includes the hsa-miR-6763-3p gene (miRBase Accession No. MIMAT0027427) described in SEQ ID NO: 105, a homolog or an ortholog of a different organism species, and the like. The hsa-miR-6763-3p gene can be obtained by a method described in Ladewig E et al., 2012, Genome Res, Vol. 22, p. 1634-1645. Also, "hsa-mir-6763" (miRBase Accession No. MI0022608, SEQ ID NO: 442) having a hairpin-like structure is known as a precursor of "hsa-miR-6763-3p".

The term "hsa-miR-6766-5p gene" or "hsa-miR-6766-5p" used herein includes the hsa-miR-6766-5p gene (miRBase Accession No. MIMAT0027432) described in SEQ ID NO: 106, a homolog or an ortholog of a different organism species, and the like. The hsa-miR-6766-5p gene can be obtained by a method described in Ladewig E et al., 2012, Genome Res, Vol. 22, p. 1634-1645. Also, "hsa-mir-6766" (miRBase Accession No. MI0022611, SEQ ID NO: 443) having a hairpin-like structure is known as a precursor of "hsa-miR-6766-5p".

The term "hsa-miR-6769a-5p gene" or "hsa-miR-6769a-5p" used herein includes the hsa-miR-6769a-5p gene (miRBase Accession No. MIMAT0027438) described in SEQ ID NO: 107, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 444) having a hairpin-like structure is known as a precursor of "hsa-miR-6769a-5p".

The term "hsa-miR-6771-5p gene" or "hsa-miR-6771-5p" used herein includes the hsa-miR-6771-5p gene (miRBase Accession No. MIMAT0027442) described in SEQ ID NO: 108, a homolog or an ortholog of a different organism species, and the like. The hsa-miR-6771-5p gene can be obtained by a method described in Ladewig E et al., 2012, Genome Res, Vol. 22, p. 1634-1645. Also, "hsa-mir-6771" (miRBase Accession No. MI0022616, SEQ ID NO: 445) having a hairpin-like structure is known as a precursor of "hsa-miR-6771-5p".

The term "hsa-miR-6786-5p gene" or "hsa-miR-6786-5p" used herein includes the hsa-miR-6786-5p gene (miRBase Accession No. MIMAT0027472) described in SEQ ID NO: 109, a homolog or an ortholog of a different organism species, and the like. The hsa-miR-6786-5p gene can be obtained by a method described in Ladewig E et al., 2012, Genome Res, Vol. 22, p. 1634-1645. Also, "hsa-mir-6786" (miRBase Accession No. MI0022631, SEQ ID NO: 446) having a hairpin-like structure is known as a precursor of "hsa-miR-6786-5p".

The term "hsa-miR-6789-5p gene" or "hsa-miR-6789-5p" used herein includes the hsa-miR-6789-5p gene (miRBase Accession No. MIMAT0027478) described in SEQ ID NO: 110, a homolog or an ortholog of a different organism species, and the like. The hsa-miR-6789-5p gene can be obtained by a method described in Ladewig E et al., 2012, Genome Res., No. 22, p. 1634-1645. Also, "hsa-mir-6789" (miRBase Accession No. MI0022634, SEQ ID NO: 447) having a hairpin-like structure is known as a precursor of "hsa-miR-6789-5p".

The term "hsa-miR-6794-5p gene" or "hsa-miR-6794-5p" used herein includes the hsa-miR-6794-5p gene (miRBase Accession No. MIMAT0027488) described in SEQ ID NO: 111, a homolog or an ortholog of a different organism species, and the like. The hsa-miR-6794-5p gene can be obtained by a method described in Ladewig E et al., 2012, Genome Res, Vol. 22, p. 1634-1645. Also, "hsa-mir-6794" (miRBase Accession No. MI0022639, SEQ ID NO: 448) having a hairpin-like structure is known as a precursor of "hsa-miR-6794-5p".

The term "hsa-miR-6796-3p gene" or "hsa-miR-6796-3p" used herein includes the hsa-miR-6796-3p gene (miRBase Accession No. MIMAT0027493) described in SEQ ID NO: 112, a homolog or an ortholog of a different organism species, and the like. The hsa-miR-6796-3p gene can be obtained by a method described in Ladewig E et al., 2012, Genome Res, Vol. 22, p. 1634-1645. Also, "hsa-mir-6796" (miRBase Accession No. MI0022641, SEQ ID NO: 449) having a hairpin-like structure is known as a precursor of "hsa-miR-6796-3p".

The term "hsa-miR-6797-5p gene" or "hsa-miR-6797-5p" used herein includes the hsa-miR-6797-5p gene (miRBase Accession No. MIMAT0027494) described in SEQ ID NO: 113, a homolog or an ortholog of a different organism species, and the like. The hsa-miR-6797-5p gene can be obtained by a method described in Ladewig E et al., 2012, Genome Res, Vol. 22, p. 1634-1645. Also, "hsa-mir-6797" (miRBase Accession No. MI0022642, SEQ ID NO: 450) having a hairpin-like structure is known as a precursor of "hsa-miR-6797-5p".

The term "hsa-miR-6800-3p gene" or "hsa-miR-6800-3p" used herein includes the hsa-miR-6800-3p gene (miRBase Accession No. MIMAT0027501) described in SEQ ID NO: 114, a homolog or an ortholog of a different organism species, and the like. The hsa-miR-6800-3p gene can be obtained by a method described in Ladewig E et al., 2012, Genome Res, Vol. 22, p. 1634-1645. Also, "hsa-mir-6800"

(miRBase Accession No. MI0022645, SEQ ID NO: 451) having a hairpin-like structure is known as a precursor of "hsa-miR-6800-3p".

The term "hsa-miR-6802-5p gene" or "hsa-miR-6802-5p" used herein includes the hsa-miR-6802-5p gene (miRBase Accession No. MIMAT0027504) described in SEQ ID NO: 115, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802" (miRBase Accession No. MI0022647, SEQ ID NO: 452) having a hairpin-like structure is known as a precursor of "hsa-miR-6802-5p".

The term "hsa-miR-6803-5p gene" or "hsa-miR-6803-5p" used herein includes the hsa-miR-6803-5p gene (miRBase Accession No. MIMAT0027506) described in SEQ ID NO: 116, a homolog or an ortholog of a different organism species, and the like. The hsa-miR-6803-5p gene can be obtained by a method described in Ladewig E et al., 2012, Genome Res, Vol. 22, p. 1634-1645. Also, "hsa-mir-6803" (miRBase Accession No. MI0022648, SEQ ID NO: 453) having a hairpin-like structure is known as a precursor of "hsa-miR-6803-5p".

The term "hsa-miR-6805-3p gene" or "hsa-miR-6805-3p" used herein includes the hsa-miR-6805-3p gene (miRBase Accession No. MIMAT0027511) described in SEQ ID NO: 117, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 454) having a hairpin-like structure is known as a precursor of "hsa-miR-6805-3p".

The term "hsa-miR-6805-5p gene" or "hsa-miR-6805-5p" used herein includes the hsa-miR-6805-5p gene (miRBase Accession No. MIMAT0027510) described in SEQ ID NO: 118, a homolog or an ortholog of a different organism species, and the like. The hsa-miR-6805-5p gene can be obtained by a method described in Ladewig E et al., 2012, Genome Res, Vol. 22, p. 1634-1645. Also, "hsa-mir-6805" (miRBase Accession No. MI0022650, SEQ ID NO: 454) having a hairpin-like structure is known as a precursor of "hsa-miR-6805-5p".

The term "hsa-miR-6807-5p gene" or "hsa-miR-6807-5p" used herein includes the hsa-miR-6807-5p gene (miRBase Accession No. MIMAT0027514) described in SEQ ID NO: 119, a homolog or an ortholog of a different organism species, and the like. The hsa-miR-6807-5p gene can be obtained by a method described in Ladewig E et al., 2012, Genome Res, Vol. 22, p. 1634-1645. Also, "hsa-mir-6807" (miRBase Accession No. MI0022652, SEQ ID NO: 455) having a hairpin-like structure is known as a precursor of "hsa-miR-6807-5p".

The term "hsa-miR-6812-5p gene" or "hsa-miR-6812-5p" used herein includes the hsa-miR-6812-5p gene (miRBase Accession No. MIMAT0027524) described in SEQ ID NO: 120, a homolog or an ortholog of a different organism species, and the like. The hsa-miR-6812-5p gene can be obtained by a method described in Ladewig E et al., 2012, Genome Res, Vol. 22, p. 1634-1645. Also, "hsa-mir-6812" (miRBase Accession No. MI0022657, SEQ ID NO: 456) having a hairpin-like structure is known as a precursor of "hsa-miR-6812-5p".

The term "hsa-miR-6819-5p gene" or "hsa-miR-6819-5p" used herein includes the hsa-miR-6819-5p gene (miRBase Accession No. MIMAT0027538) described in SEQ ID NO: 121, a homolog or an ortholog of a different organism species, and the like. The hsa-miR-6819-5p gene can be obtained by a method described in Ladewig E et al., 2012, Genome Res, Vol. 22, p. 1634-1645. Also, "hsa-mir-6819" (miRBase Accession No. MI0022664, SEQ ID NO: 457) having a hairpin-like structure is known as a precursor of "hsa-miR-6819-5p".

The term "hsa-miR-6822-5p gene" or "hsa-miR-6822-5p" used herein includes the hsa-miR-6822-5p gene (miRBase Accession No. MIMAT0027544) described in SEQ ID NO: 122, a homolog or an ortholog of a different organism species, and the like. The hsa-miR-6822-5p gene can be obtained by a method described in Ladewig E et al., 2012, Genome Res, Vol. 22, p. 1634-1645. Also, "hsa-mir-6822" (miRBase Accession No. MI0022667, SEQ ID NO: 458) having a hairpin-like structure is known as a precursor of "hsa-miR-6822-5p".

The term "hsa-miR-6824-5p gene" or "hsa-miR-6824-5p" used herein includes the hsa-miR-6824-5p gene (miRBase Accession No. MIMAT0027548) described in SEQ ID NO: 123, a homolog or an ortholog of a different organism species, and the like. The hsa-miR-6824-5p gene can be obtained by a method described in Ladewig E et al., 2012, Genome Res, Vol. 22, p. 1634-1645. Also, "hsa-mir-6824" (miRBase Accession No. MI0022669, SEQ ID NO: 459) having a hairpin-like structure is known as a precursor of "hsa-miR-6824-5p".

The term "hsa-miR-6826-5p gene" or "hsa-miR-6826-5p" used herein includes the hsa-miR-6826-5p gene (miRBase Accession No. MIMAT0027552) described in SEQ ID NO: 124, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 460) having a hairpin-like structure is known as a precursor of "hsa-miR-6826-5p".

The term "hsa-miR-6850-5p gene" or "hsa-miR-6850-5p" used herein includes the hsa-miR-6850-5p gene (miRBase Accession No. MIMAT0027600) described in SEQ ID NO: 125, a homolog or an ortholog of a different organism species, and the like. The hsa-miR-6850-5p gene can be obtained by a method described in Ladewig E et al., 2012, Genome Res, Vol. 22, p. 1634-1645. Also, "hsa-mir-6850" (miRBase Accession No. MI0022696, SEQ ID NO: 461) having a hairpin-like structure is known as a precursor of "hsa-miR-6850-5p".

The term "hsa-miR-6858-5p gene" or "hsa-miR-6858-5p" used herein includes the hsa-miR-6858-5p gene (miRBase Accession No. MIMAT0027616) described in SEQ ID NO: 126, a homolog or an ortholog of a different organism species, and the like. The hsa-miR-6858-5p gene can be obtained by a method described in Ladewig E et al., 2012, Genome Res, Vol. 22, p. 1634-1645. Also, "hsa-mir-6858" (miRBase Accession No. MI0022704, SEQ ID NO: 462) having a hairpin-like structure is known as a precursor of "hsa-miR-6858-5p".

The term "hsa-miR-6861-5p gene" or "hsa-miR-6861-5p" used herein includes the hsa-miR-6861-5p gene (miRBase Accession No. MIMAT0027623) described in SEQ ID NO: 127, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 463) having a hairpin-like structure is known as a precursor of "hsa-miR-6861-5p".

The term "hsa-miR-6880-3p gene" or "hsa-miR-6880-3p" used herein includes the hsa-miR-6880-3p gene (miRBase Accession No. MIMAT0027661) described in SEQ ID NO: 128, a homolog or an ortholog of a different organism species, and the like. The hsa-miR-6880-3p gene can be obtained by a method described in Ladewig E et al., 2012, Genome Res, Vol. 22, p. 1634-1645. Also, "hsa-mir-6880" (miRBase Accession No. MI0022727, SEQ ID NO: 464) having a hairpin-like structure is known as a precursor of "hsa-miR-6880-3p".

The term "hsa-miR-7107-5p gene" or "hsa-miR-7107-5p" used herein includes the hsa-miR-7107-5p gene (miRBase Accession No. MIMAT0028111) described in SEQ ID NO: 129, a homolog or an ortholog of a different organism species, and the like. The hsa-miR-7107-5p gene can be obtained by a method described in Ladewig E et al., 2012, Genome Res, Vol. 22, p. 1634-1645. Also, "hsa-mir-7107" (miRBase Accession No. MI0022958, SEQ ID NO: 465) having a hairpin-like structure is known as a precursor of "hsa-miR-7107-5p".

The term "hsa-miR-7109-5p gene" or "hsa-miR-7109-5p" used herein includes the hsa-miR-7109-5p gene (miRBase Accession No. MIMAT0028115) described in SEQ ID NO: 130, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 466) having a hairpin-like structure is known as a precursor of "hsa-miR-7109-5p".

The term "hsa-miR-7114-5p gene" or "hsa-miR-7114-5p" used herein includes the hsa-miR-7114-5p gene (miRBase Accession No. MIMAT0028125) described in SEQ ID NO: 131, a homolog or an ortholog of a different organism species, and the like. The hsa-miR-7114-5p gene can be obtained by a method described in Ladewig E et al., 2012, Genome Res, Vol. 22, p. 1634-1645. Also, "hsa-mir-7114" (miRBase Accession No. MI0022965, SEQ ID NO: 467) having a hairpin-like structure is known as a precursor of "hsa-miR-7114-5p".

The term "hsa-miR-7704 gene" or "hsa-miR-7704" used herein includes the hsa-miR-7704 gene (miRBase Accession No. MIMAT0030019) described in SEQ ID NO: 132, a homolog or an ortholog of a different organism species, and the like. The hsa-miR-7704 gene can be obtained by a method described in Swaminathan S et al., 2013, Biochem Biophys Res Commun, Vol. 434, p. 228-234. Also, "hsa-mir-7704" (miRBase Accession No. MI0025240, SEQ ID NO: 468) having a hairpin-like structure is known as a precursor of "hsa-miR-7704".

The term "hsa-miR-7846-3p gene" or "hsa-miR-7846-3p" used herein includes the hsa-miR-7846-3p gene (miRBase Accession No. MIMAT0030421) described in SEQ ID NO: 133, a homolog or an ortholog of a different organism species, and the like. The hsa-miR-7846-3p gene can be obtained by a method described in Ple H et al., 2012, PLoS One., Vol. 7, e50746. Also, "hsa-mir-7846" (miRBase Accession No. MI0025516, SEQ ID NO: 469) having a hairpin-like structure is known as a precursor of "hsa-miR-7846-3p".

The term "hsa-miR-8052 gene" or "hsa-miR-8052" used herein includes the hsa-miR-8052 gene (miRBase Accession No. MIMAT0030979) described in SEQ ID NO: 134, a homolog or an ortholog of a different organism species, and the like. The hsa-miR-8052 gene can be obtained by a method described in Wang H J et al., 2013, Shock., Vol. 39, 480-487. Also, "hsa-mir-8052" (miRBase Accession No. MI0025888, SEQ ID NO: 470) having a hairpin-like structure is known as a precursor of "hsa-miR-8052".

The term "hsa-miR-8060 gene" or "hsa-miR-8060" used herein includes the hsa-miR-8060 gene (miRBase Accession No. MIMAT0030987) described in SEQ ID NO: 135, a homolog or an ortholog of a different organism species, and the like. The hsa-miR-8060 gene can be obtained by a method described in Wang H J et al., 2013, Shock., Vol. 39, 480-487. Also, "hsa-mir-8060" (miRBase Accession No. MI0025896, SEQ ID NO: 471) having a hairpin-like structure is known as a precursor of "hsa-miR-8060".

The term "hsa-miR-8071 gene" or "hsa-miR-8071" used herein includes the hsa-miR-8071 gene (miRBase Accession No. MIMAT0030998) described in SEQ ID NO: 136, a homolog or an ortholog of a different organism species, and the like. The hsa-miR-8071 gene can be obtained by a method described in Wang H J et al., 2013, Shock, Vol. 39, p. 480-487. Also, "hsa-mir-8071-1 and hsa-mir-8071-2" (miRBase Accession Nos. MI0025907 and MI0026417, SEQ ID NOs: 472 and 473) having a hairpin-like structure are known as precursors of "hsa-miR-8071".

The term "hsa-miR-8073 gene" or "hsa-miR-8073" used herein includes the hsa-miR-8073 gene (miRBase Accession No. MIMAT0031000) described in SEQ ID NO: 137, a homolog or an ortholog of a different organism species, and the like. The hsa-miR-8073 gene can be obtained by a method described in Wang H J et al., 2013, Shock, Vol. 39, p. 480-487. Also, "hsa-mir-8073" (miRBase Accession No. MI0025909, SEQ ID NO: 474) having a hairpin-like structure is known as a precursor of "hsa-miR-8073".

The term "hsa-miR-874-5p gene" or "hsa-miR-874-5p" used herein includes the hsa-miR-874-5p gene (miRBase Accession No. MIMAT0026718) described in SEQ ID NO: 138, a homolog or an ortholog of a different organism species, and the like. The hsa-miR-874-5p gene can be obtained by a method described in Landgraf P et al., 2007, Cell., Vol. 129, p. 1401-1414. Also, "hsa-mir-874" (miRBase Accession No. MI0005532, SEQ ID NO: 475) having a hairpin-like structure is known as a precursor of "hsa-miR-874-5p".

The term "hsa-miR-204-3p gene" or "hsa-miR-204-3p" used herein includes the hsa-miR-204-3p gene (miRBase Accession No. MIMAT0022693) described in SEQ ID NO: 139, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 476) having a hairpin-like structure is known as a precursor of "hsa-miR-204-3p".

The term "hsa-miR-3154 gene" or "hsa-miR-3154" used herein includes the hsa-miR-3154 gene (miRBase Accession No. MIMAT0015028) described in SEQ ID NO: 140, a homolog or an ortholog of a different organism species, and the like. The hsa-miR-3154 gene can be obtained by a method described in Berezikov E et al., 2006, Genome Res, Vol. 16, p. 1289-1298. Also, "hsa-mir-3154" (miRBase Accession No. MI0014182, SEQ ID NO: 477) having a hairpin-like structure is known as a precursor of "hsa-miR-3154".

The term "hsa-miR-3960 gene" or "hsa-miR-3960" used herein includes the hsa-miR-3960 gene (miRBase Accession No. MIMAT0019337) described in SEQ ID NO: 141, a homolog or an ortholog of a different organism species, and the like. The hsa-miR-3960 gene can be obtained by a method described in Hu R et al., 2011, J Biol Chem, Vol. 286, p. 12328-12339. Also, "hsa-mir-3960" (miRBase Accession No. MI0016964, SEQ ID NO: 478) having a hairpin-like structure is known as a precursor of "hsa-miR-3960".

The term "hsa-miR-4433a-5p gene" or "hsa-miR-4433a-5p" used herein includes the hsa-miR-4433a-5p gene (miRBase Accession No. MIMAT0020956) described in SEQ ID NO: 142, a homolog or an ortholog of a different organism species, and the like. The hsa-miR-4433a-5p gene can be obtained by a method described in Jima D D et al., 2010, Blood, Vol. 116, e118-e127. Also, "hsa-mir-4433a" (miRBase Accession No. MI0016773, SEQ ID NO: 382) having a hairpin-like structure is known as a precursor of "hsa-miR-4433a-5p".

The term "hsa-miR-4455 gene" or "hsa-miR-4455" used herein includes the hsa-miR-4455 gene (miRBase Accession No. MIMAT0018977) described in SEQ ID NO: 143, a homolog or an ortholog of a different organism species, and the like. The hsa-miR-4455 gene can be obtained by a method described in Jima D D et al., 2010, Blood., Vol. 116, e118-e127. Also, "hsa-mir-4455" (miRBase Accession No. MI0016801, SEQ ID NO: 479) having a hairpin-like structure is known as a precursor of "hsa-miR-4455".

The term "hsa-miR-4462 gene" or "hsa-miR-4462" used herein includes the hsa-miR-4462 gene (miRBase Accession No. MIMAT0018986) described in SEQ ID NO: 144, a homolog or an ortholog of a different organism species, and the like. The hsa-miR-4462 gene can be obtained by a method described in Jima D D et al., 2010, Blood., Vol. 116, e118-e127. Also, "hsa-mir-4462" (miRBase Accession No. MI0016810, SEQ ID NO: 480) having a hairpin-like structure is known as a precursor of "hsa-miR-4462".

The term "hsa-miR-4476 gene" or "hsa-miR-4476" used herein includes the hsa-miR-4476 gene (miRBase Accession No. MIMAT0019003) described in SEQ ID NO: 145, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 481) having a hairpin-like structure is known as a precursor of "hsa-miR-4476".

The term "hsa-miR-4508 gene" or "hsa-miR-4508" used herein includes the hsa-miR-4508 gene (miRBase Accession No. MIMAT0019045) described in SEQ ID NO: 146, a homolog or an ortholog of a different organism species, and the like. The hsa-miR-4508 gene can be obtained by a method described in Jima D D et al., 2010, Blood, Vol. 116, e118-e127. Also, "hsa-mir-4508" (miRBase Accession No. MI0016872, SEQ ID NO: 482) having a hairpin-like structure is known as a precursor of "hsa-miR-4508".

The term "hsa-miR-4687-3p gene" or "hsa-miR-4687-3p" used herein includes the hsa-miR-4687-3p gene (miRBase Accession No. MIMAT0019775) described in SEQ ID NO: 147, a homolog or an ortholog of a different organism species, and the like. The hsa-miR-4687-3p gene can be obtained by a method described in Persson H et al., 2011, Cancer Res, Vol. 71, p. 78-86. Also, "hsa-mir-4687" (miRBase Accession No. MI0017319, SEQ ID NO: 483) having a hairpin-like structure is known as a precursor of "hsa-miR-4687-3p".

The term "hsa-miR-4687-5p gene" or "hsa-miR-4687-5p" used herein includes the hsa-miR-4687-5p gene (miRBase Accession No. MIMAT0019774) described in SEQ ID NO: 148, a homolog or an ortholog of a different organism species, and the like. The hsa-miR-4687-5p gene can be obtained by a method described in Persson H et al., 2011, Cancer Res, Vol. 71, p. 78-86. Also, "hsa-mir-4687" (miRBase Accession No. MI0017319, SEQ ID NO: 483) having a hairpin-like structure is known as a precursor of "hsa-miR-4687-5p".

The term "hsa-miR-4732-5p gene" or "hsa-miR-4732-5p" used herein includes the hsa-miR-4732-5p gene (miRBase Accession No. MIMAT0019855) described in SEQ ID NO: 149, a homolog or an ortholog of a different organism species, and the like. The hsa-miR-4732-5p gene can be obtained by a method described in Persson H et al., 2011, Cancer Res, Vol. 71, p. 78-86. Also, "hsa-mir-4732" (miRBase Accession No. MI0017369, SEQ ID NO: 484) having a hairpin-like structure is known as a precursor of "hsa-miR-4732-5p".

The term "hsa-miR-4771 gene" or "hsa-miR-4771" used herein includes the hsa-miR-4771 gene (miRBase Accession No. MIMAT0019925) described in SEQ ID NO: 150, a homolog or an ortholog of a different organism species, and the like. The hsa-miR-4771 gene can be obtained by a method described in Persson H et al., 2011, Cancer Res, Vol. 71, p. 78-86. Also, "hsa-mir-4771-1 and hsa-mir-4771-2" (miRBase Accession Nos. MI0017412 and MI0017413, SEQ ID NOs: 485 and 486) having a hairpin-like structure are known as precursors of "hsa-miR-4771".

The term "hsa-miR-642a-3p gene" or "hsa-miR-642a-3p" used herein includes the hsa-miR-642a-3p gene (miRBase Accession No. MIMAT0020924) described in SEQ ID NO: 151, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 487) having a hairpin-like structure is known as a precursor of "hsa-miR-642a-3p".

The term "hsa-miR-6732-5p gene" or "hsa-miR-6732-5p" used herein includes the hsa-miR-6732-5p gene (miRBase Accession No. MIMAT0027365) described in SEQ ID NO: 152, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 488) having a hairpin-like structure is known as a precursor of "hsa-miR-6732-5p".

The term "hsa-miR-6760-5p gene" or "hsa-miR-6760-5p" used herein includes the hsa-miR-6760-5p gene (miRBase Accession No. MIMAT0027420) described in SEQ ID NO: 153, a homolog or an ortholog of a different organism species, and the like. The hsa-miR-6760-5p gene can be obtained by a method described in Ladewig E et al., 2012, Genome Res., Vol. 22, p. 1634-1645. Also, "hsa-mir-6760" (miRBase Accession No. MI0022605, SEQ ID NO: 489) having a hairpin-like structure is known as a precursor of "hsa-miR-6760-5p".

The term "hsa-miR-6799-5p gene" or "hsa-miR-6799-5p" used herein includes the hsa-miR-6799-5p gene (miRBase Accession No. MIMAT0027498) described in SEQ ID NO: 154, a homolog or an ortholog of a different organism species, and the like. The hsa-miR-6799-5p gene can be obtained by a method described in Ladewig E et al., 2012, Genome Res, Vol. 22, p. 1634-1645. Also, "hsa-mir-6799" (miRBase Accession No. MI0022644, SEQ ID NO: 490) having a hairpin-like structure is known as a precursor of "hsa-miR-6799-5p".

The term "hsa-miR-6820-5p gene" or "hsa-miR-6820-5p" used herein includes the hsa-miR-6820-5p gene (miRBase Accession No. MIMAT0027540) described in SEQ ID NO: 155, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 491) having a hairpin-like structure is known as a precursor of "hsa-miR-6820-5p".

The term "hsa-miR-6821-5p gene" or "hsa-miR-6821-5p" used herein includes the hsa-miR-6821-5p gene (miRBase Accession No. MIMAT0027542) described in SEQ ID NO: 156, a homolog or an ortholog of a different organism species, and the like. The hsa-miR-6821-5p gene can be obtained by a method described in Ladewig E et al., 2012, Genome Res, Vol. 22, p. 1634-1645. Also, "hsa-mir-6821" (miRBase Accession No. MI0022666, SEQ ID NO: 492) having a hairpin-like structure is known as a precursor of "hsa-miR-6821-5p".

The term "hsa-miR-6829-5p gene" or "hsa-miR-6829-5p" used herein includes the hsa-miR-6829-5p gene (miRBase Accession No. MIMAT0027558) described in SEQ ID NO: 157, a homolog or an ortholog of a different organism species, and the like. The hsa-miR-6829-5p gene can be obtained by a method described in Ladewig E et al., 2012, Genome Res, Vol. 22, p. 1634-1645. Also, "hsa-mir-6829" (miRBase Accession No. MI0022674, SEQ ID NO: 493) having a hairpin-like structure is known as a precursor of "hsa-miR-6829-5p".

The term "hsa-miR-6893-5p gene" or "hsa-miR-6893-5p" used herein includes the hsa-miR-6893-5p gene (miRBase Accession No. MIMAT0027686) described in SEQ ID NO: 158, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 494) having a hairpin-like structure is known as a precursor of "hsa-miR-6893-5p".

The term "hsa-miR-7108-3p gene" or "hsa-miR-7108-3p" used herein includes the hsa-miR-7108-3p gene (miRBase Accession No. MIMAT0028114) described in SEQ ID NO: 159, a homolog or an ortholog of a different organism species, and the like. The hsa-miR-7108-3p gene can be obtained by a method described in Ladewig E et al., 2012, Genome Res, Vol. 22, p. 1634-1645. Also, "hsa-mir-7108" (miRBase Accession No. MI0022959, SEQ ID NO: 495) having a hairpin-like structure is known as a precursor of "hsa-miR-7108-3p".

The term "hsa-miR-7111-5p gene" or "hsa-miR-7111-5p" used herein includes the hsa-miR-7111-5p gene (miRBase Accession No. MIMAT0028119) described in SEQ ID NO: 160, a homolog or an ortholog of a different organism species, and the like. The hsa-miR-7111-5p gene can be obtained by a method described in Ladewig E et al., 2012, Genome Res, Vol. 22, p. 1634-1645. Also, "hsa-mir-7111" (miRBase Accession No. MI0022962, SEQ ID NO: 496) having a hairpin-like structure is known as a precursor of "hsa-miR-7111-5p".

The term "hsa-miR-8089 gene" or "hsa-miR-8089" used herein includes the hsa-miR-8089 gene (miRBase Accession No. MIMAT0031016) described in SEQ ID NO: 161, a homolog or an ortholog of a different organism species, and the like. The hsa-miR-8089 gene can be obtained by a method described in Wang H J et al., 2013, Shock, Vol. 39, p. 480-487. Also, "hsa-miR-8089" (miRBase Accession No. MI0025925, SEQ ID NO: 497) having a hairpin-like structure is known as a precursor of "hsa-miR-8089".

The term "hsa-miR-885-3p gene" or "hsa-miR-885-3p" used herein includes the hsa-miR-885-3p gene (miRBase Accession No. MIMAT0004948) described in SEQ ID NO: 162, a homolog or an ortholog of a different organism species, and the like. The hsa-miR-885-3p gene can be obtained by a method described in Berezikov E et al., 2006, Genome Res, Vol. 16, p. 1289-1298. Also, "hsa-mir-885" (miRBase Accession No. MI0005560, SEQ ID NO: 498) having a hairpin-like structure is known as a precursor of "hsa-miR-885-3p".

The term "hsa-miR-92b-3p gene" or "hsa-miR-92b-3p" used herein includes the hsa-miR-92b-3p gene (miRBase Accession No. MIMAT0003218) described in SEQ ID NO: 163, a homolog or an ortholog of a different organism species, and the like. The hsa-miR-92b-3p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 499) having a hairpin-like structure is known as a precursor of "hsa-miR-92b-3p".

The term "hsa-miR-1343-3p gene" or "hsa-miR-1343-3p" used herein includes the hsa-miR-1343-3p gene (miRBase Accession No. MIMAT0019776) described in SEQ ID NO: 164, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 500) having a hairpin-like structure is known as a precursor of "hsa-miR-1343-3p".

The term "hsa-miR-6746-5p gene" or "hsa-miR-6746-5p" used herein includes the hsa-miR-6746-5p gene (miRBase Accession No. MIMAT0027392) described in SEQ ID NO: 165, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 501) having a hairpin-like structure is known as a precursor of "hsa-miR-6746-5p".

The term "hsa-miR-422a gene" or "hsa-miR-422a" used herein includes the hsa-miR-422a gene (miRBase Accession No. MIMAT0001339) described in SEQ ID NO: 166, a homolog or an ortholog of a different organism species, and the like. The hsa-miR-422a gene can be obtained by a method described in Kasashima K et al., 2004, Biochem Biophys Res Commun, Vol. 322, p. 403-410. Also, "hsa-mir-422a" (miRBase Accession No. MI0001444, SEQ ID NO: 502) having a hairpin-like structure is known as a precursor of "hsa-miR-422a".

The term "hsa-miR-187-5p gene" or "hsa-miR-187-5p" used herein includes the hsa-miR-187-5p gene (miRBase Accession No. MIMAT0004561) described in SEQ ID NO: 167, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 503) having a hairpin-like structure is known as a precursor of "hsa-miR-187-5p".

The term "hsa-miR-4632-5p gene" or "hsa-miR-4632-5p" used herein includes the hsa-miR-4632-5p gene (miRBase Accession No. MIMAT0022977) described in SEQ ID NO: 168, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miR- Base Accession No. MI0017259, SEQ ID NO: 504) having a hairpin-like structure is known as a precursor of "hsa-miR-4632-5p".

The term "hsa-miR-6791-5p gene" or "hsa-miR-6791-5p" used herein includes the hsa-miR-6791-5p gene (miRBase Accession No. MIMAT0027482) described in SEQ ID NO: 169, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 505) having a hairpin-like structure is known as a precursor of "hsa-miR-6791-5p".

The term "hsa-miR-103a-3p gene" or "hsa-miR-103a-3p" used herein includes the hsa-miR-103a-3p gene (miRBase Accession No. MIMAT0000101) described in SEQ ID NO: 170, a homolog or an ortholog of a different organism species, and the like. The hsa-miR-103a-3p gene can be obtained by a method described in Mourelatos Z et al., 2002, Genes Dev. Vol. 16: p. 720-728. Also, "hsa-mir-103a-2 and hsa-mir-103a-1" (miRBase Accession Nos. MI0000109 and MI0000108, SEQ ID NOs: 506 and 507) having a hairpin-like structure are known as precursors of "hsa-miR-103a-3p".

The term "hsa-miR-107 gene" or "hsa-miR-107" used herein includes the hsa-miR-107 gene (miRBase Accession No. MIMAT0000104) described in SEQ ID NO: 171, a homolog or an ortholog of a different organism species, and the like. The hsa-miR-107 gene can be obtained by a method described in Mourelatos Z et al., 2002, Genes Dev., Vol. 16, p. 720-728. Also, "hsa-mir-107" (miRBase Accession No. MI0000114, SEQ ID NO: 508) having a hairpin-like structure is known as a precursor of "hsa-miR-107".

The term "hsa-miR-1199-5p gene" or "hsa-miR-1199-5p" used herein includes the hsa-miR-1199-5p gene (miRBase Accession No. MIMAT0031119) described in SEQ ID NO: 172, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 509) having a hairpin-like structure is known as a precursor of "hsa-miR-1199-5p".

The term "hsa-miR-1225-3p gene" or "hsa-miR-1225-3p" used herein includes the hsa-miR-1225-3p gene (miRBase Accession No. MIMAT0005573) described in SEQ ID NO: 173, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 510) having a hairpin-like structure is known as a precursor of "hsa-miR-1225-3p".

The term "hsa-miR-1225-5p gene" or "hsa-miR-1225-5p" used herein includes the hsa-miR-1225-5p gene (miRBase Accession No. MIMAT0005572) described in SEQ ID NO: 174, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 510) having a hairpin-like structure is known as a precursor of "hsa-miR-1225-5p".

The term "hsa-miR-1228-5p gene" or "hsa-miR-1228-5p" used herein includes the hsa-miR-1228-5p gene (miRBase Accession No. MIMAT0005582) described in SEQ ID NO: 175, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 511) having a hairpin-like structure is known as a precursor of "hsa-miR-1228-5p".

The term "hsa-miR-1229-5p gene" or "hsa-miR-1229-5p" used herein includes the hsa-miR-1229-5p gene (miRBase Accession No. MIMAT0022942) described in SEQ ID NO: 176, a homolog or an ortholog of a different organism species, and the like. The hsa-miR-1229-5p gene can be obtained by a method described in Berezikov E et al., 2007, Mol Cell, Vol. 28, p. 328-336. Also, "hsa-mir-1229" (miRBase Accession No. MI0006319, SEQ ID NO: 512) having a hairpin-like structure is known as a precursor of "hsa-miR-1229-5p".

The term "hsa-miR-1233-5p gene" or "hsa-miR-1233-5p" used herein includes the hsa-miR-1233-5p gene (miRBase Accession No. MIMAT0022943) described in SEQ ID NO: 177, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 513 and 514) having a hairpin-like structure are known as precursors of "hsa-miR-1233-5p".

The term "hsa-miR-1237-5p gene" or "hsa-miR-1237-5p" used herein includes the hsa-miR-1237-5p gene (miRBase Accession No. MIMAT0022946) described in SEQ ID NO: 178, a homolog or an ortholog of a different organism species, and the like. The hsa-miR-1237-5p gene can be obtained by a method described in Berezikov E et al., 2007, Mol Cell, Vol. 28, p. 328-336. Also, "hsa-mir-1237" (miRBase Accession No. MI0006327, SEQ ID NO: 515) having a hairpin-like structure is known as a precursor of "hsa-miR-1237-5p".

The term "hsa-miR-1247-3p gene" or "hsa-miR-1247-3p" used herein includes the hsa-miR-1247-3p gene (miRBase Accession No. MIMAT0022721) described in SEQ ID NO: 179, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 516) having a hairpin-like structure is known as a precursor of "hsa-miR-1247-3p".

The term "hsa-miR-1249-3p gene" or "hsa-miR-1249-3p" used herein includes the hsa-miR-1249-3p gene (miRBase Accession No. MIMAT0005901) described in SEQ ID NO: 180, a homolog or an ortholog of a different organism species, and the like. The hsa-miR-1249-3p gene can be obtained by a method described in Morin R D et al., 2008, Genome Res, Vol. 18, p. 610-621. Also, "hsa-mir-1249" (miRBase Accession No. MI0006384, SEQ ID NO: 343) having a hairpin-like structure is known as a precursor of "hsa-miR-1249-3p".

The term "hsa-miR-1254 gene" or "hsa-miR-1254" used herein includes the hsa-miR-1254 gene (miRBase Accession No. MIMAT0005905) described in SEQ ID NO: 181, a homolog or an ortholog of a different organism species, and the like. The hsa-miR-1254 gene can be obtained by a method described in Morin R D et al., 2008, Genome Res, Vol. 18, p. 610-621. Also, "hsa-mir-1254-1 and hsa-mir-1254-2" (miRBase Accession Nos. MI0006388 and MI0016747, SEQ ID NOs: 517 and 518) having a hairpin-like structure are known as precursors of "hsa-miR-1254".

The term "hsa-miR-1260b gene" or "hsa-miR-1260b" used herein includes the hsa-miR-1260b gene (miRBase Accession No. MIMAT0015041) described in SEQ ID NO: 182, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 519) having a hairpin-like structure is known as a precursor of "hsa-miR-1260b".

The term "hsa-miR-1268a gene" or "hsa-miR-1268a" used herein includes the hsa-miR-1268a gene (miRBase Accession No. MIMAT0005922) described in SEQ ID NO: 183, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 520) having a hairpin-like structure is known as a precursor of "hsa-miR-1268a".

The term "hsa-miR-1268b gene" or "hsa-miR-1268b" used herein includes the hsa-miR-1268b gene (miRBase Accession No. MIMAT0018925) described in SEQ ID NO: 184, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 521) having a hairpin-like structure is known as a precursor of "hsa-miR-1268b".

The term "hsa-miR-1273g-3p gene" or "hsa-miR-1273g-3p" used herein includes the hsa-miR-1273g-3p gene (miRBase Accession No. MIMAT0022742) described in SEQ ID NO: 185, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. MI0018003, SEQ ID NO: 522) having a hairpin-like structure is known as a precursor of "hsa-miR-1273g-3p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 186, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 523) having a hairpin-like structure is known as a precursor of "hsa-miR-128-1-5p".

The term "hsa-miR-128-2-5p gene" or "hsa-miR-128-2-5p" used herein includes the hsa-miR-128-2-5p gene (miRBase Accession No. MIMAT0031095) described in SEQ ID NO: 187, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 524) having a hairpin-like structure is known as a precursor of "hsa-miR-128-2-5p".

The term "hsa-miR-1290 gene" or "hsa-miR-1290" used herein includes the hsa-miR-1290 gene (miRBase Accession No. MIMAT0005880) described in SEQ ID NO: 188, a homolog or an ortholog of a different organism species, and the like. The hsa-miR-1290 gene can be obtained by a method described in Morin R D et al., 2008, Genome Res, Vol. 18, p. 610-621. Also, "hsa-mir-1290" (miRBase Accession No. MI0006352, SEQ ID NO: 525) having a hairpin-like structure is known as a precursor of "hsa-miR-1290".

The term "hsa-miR-150-3p gene" or "hsa-miR-150-3p" used herein includes the hsa-miR-150-3p gene (miRBase Accession No. MIMAT0004610) described in SEQ ID NO: 189, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 526) having a hairpin-like structure is known as a precursor of "hsa-miR-150-3p".

The term "hsa-miR-17-3p gene" or "hsa-miR-17-3p" used herein includes the hsa-miR-17-3p gene (miRBase Accession No. MIMAT0000071) described in SEQ ID NO: 190, a homolog or an ortholog of a different organism species, and the like. The hsa-miR-17-3p gene can be obtained by a method described in Lagos-Quintana M et al., 2001, Science., Vol. 294, p. 853-858. Also, "hsa-mir-17" (miRBase Accession No. MI0000071, SEQ ID NO: 527) having a hairpin-like structure is known as a precursor of "hsa-miR-17-3p".

The term "hsa-miR-1908-5p gene" or "hsa-miR-1908-5p" used herein includes the hsa-miR-1908-5p gene (miRBase Accession No. MIMAT0007881) described in SEQ ID NO: 191, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 528) having a hairpin-like structure is known as a precursor of "hsa-miR-1908-5p".

The term "hsa-miR-1909-3p gene" or "hsa-miR-1909-3p" used herein includes the hsa-miR-1909-3p gene (miRBase Accession No. MIMAT0007883) described in SEQ ID NO: 192, a homolog or an ortholog of a different organism species, and the like. The hsa-miR-1909-3p gene can be obtained by a method described in Bar M et al., 2008, Stem Cells, Vol. 26, p. 2496-2505. Also, "hsa-mir-1909" (miRBase Accession No. MI0008330, SEQ ID NO: 529) having a hairpin-like structure is known as a precursor of "hsa-miR-1909-3p".

The term "hsa-miR-1914-3p gene" or "hsa-miR-1914-3p" used herein includes the hsa-miR-1914-3p gene (miRBase Accession No. MIMAT0007890) described in SEQ ID NO: 193, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 530) having a hairpin-like structure is known as a precursor of "hsa-miR-1914-3p".

The term "hsa-miR-1915-3p gene" or "hsa-miR-1915-3p" used herein includes the hsa-miR-1915-3p gene (miRBase Accession No. MIMAT0007892) described in SEQ ID NO: 194, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 531) having a hairpin-like structure is known as a precursor of "hsa-miR-1915-3p".

The term "hsa-miR-191-5p gene" or "hsa-miR-191-5p" used herein includes the hsa-miR-191-5p gene (miRBase Accession No. MIMAT0000440) described in SEQ ID NO: 195, a homolog or an ortholog of a different organism species, and the like. The hsa-miR-191-5p gene can be obtained by a method described in Lagos-Quintana M et al., 2003, RNA, Vol. 9, p. 175-179. Also, "hsa-mir-191" (miRBase Accession No. MI0000465, SEQ ID NO: 532) having a hairpin-like structure is known as a precursor of "hsa-miR-191-5p".

The term "hsa-miR-22-3p gene" or "hsa-miR-22-3p" used herein includes the hsa-miR-22-3p gene (miRBase Accession No. MIMAT0000077) described in SEQ ID NO: 196, a homolog or an ortholog of a different organism species, and the like. The hsa-miR-22-3p gene can be obtained by a method described in Lagos-Quintana M et al., 2001, Science, Vol. 294, p. 853-858. Also, "hsa-mir-22" (miRBase Accession No. MI0000078, SEQ ID NO: 533) having a hairpin-like structure is known as a precursor of "hsa-miR-22-3p".

The term "hsa-miR-23b-3p gene" or "hsa-miR-23b-3p" used herein includes the hsa-miR-23b-3p gene (miRBase Accession No. MIMAT0000418) described in SEQ ID NO: 197, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 534) having a hairpin-like structure is known as a precursor of "hsa-miR-23b-3p".

The term "hsa-miR-24-3p gene" or "hsa-miR-24-3p" used herein includes the hsa-miR-24-3p gene (miRBase Accession No. MIMAT0000080) described in SEQ ID NO: 198, a homolog or an ortholog of a different organism species, and the like. The hsa-miR-24-3p gene can be obtained by a method described in Lagos-Quintana M et al., 2001, Science, Vol. 294, p. 853-858. Also, "hsa-mir-24-1 and hsa-mir-24-2" (miRBase Accession Nos. MI0000080 and MI0000081, SEQ ID NOs: 535 and 536) having a hairpin-like structure are known as precursors of "hsa-miR-24-3p".

The term "hsa-miR-296-3p gene" or "hsa-miR-296-3p" used herein includes the hsa-miR-296-3p gene (miRBase Accession No. MIMAT0004679) described in SEQ ID NO: 199, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 537) having a hairpin-like structure is known as a precursor of "hsa-miR-296-3p".

The term "hsa-miR-296-5p gene" or "hsa-miR-296-5p" used herein includes the hsa-miR-296-5p gene (miRBase Accession No. MIMAT0000690) described in SEQ ID NO: 200, a homolog or an ortholog of a different organism species, and the like. The hsa-miR-296-5p gene can be obtained by a method described in Houbaviy H B et al., 2003, Dev Cell, Vol. 5, p. 351-358. Also, "hsa-mir-296" (miRBase Accession No. MI0000747, SEQ ID NO: 537) having a hairpin-like structure is known as a precursor of "hsa-miR-296-5p".

The term "hsa-miR-3131 gene" or "hsa-miR-3131" used herein includes the hsa-miR-3131 gene (miRBase Accession No. MIMAT0014996) described in SEQ ID NO: 201, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 538) having a hairpin-like structure is known as a precursor of "hsa-miR-3131".

The term "hsa-miR-3162-5p gene" or "hsa-miR-3162-5p" used herein includes the hsa-miR-3162-5p gene (miRBase Accession No. MIMAT0015036) described in SEQ ID NO: 202, a homolog or an ortholog of a different organism species, and the like. The hsa-miR-3162-5p gene can be obtained by a method described in Stark M S et al., 2010, PLoS One, Vol. 5, e9685. Also, "hsa-mir-3162" (miRBase Accession No. MI0014192, SEQ ID NO: 539) having a hairpin-like structure is known as a precursor of "hsa-miR-3162-5p".

The term "hsa-miR-3188 gene" or "hsa-miR-3188" used herein includes the hsa-miR-3188 gene (miRBase Accession No. MIMAT0015070) described in SEQ ID NO: 203, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 540) having a hairpin-like structure is known as a precursor of "hsa-miR-3188".

The term "hsa-miR-3196 gene" or "hsa-miR-3196" used herein includes the hsa-miR-3196 gene (miRBase Accession No. MIMAT0015080) described in SEQ ID NO: 204, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 541) having a hairpin-like structure is known as a precursor of "hsa-miR-3196".

The term "hsa-miR-3197 gene" or "hsa-miR-3197" used herein includes the hsa-miR-3197 gene (miRBase Accession No. MIMAT0015082) described in SEQ ID NO: 205, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 542) having a hairpin-like structure is known as a precursor of "hsa-miR-3197".

The term "hsa-miR-320a gene" or "hsa-miR-320a" used herein includes the hsa-miR-320a gene (miRBase Accession No. MIMAT0000510) described in SEQ ID NO: 206, a homolog or an ortholog of a different organism species, and the like. The hsa-miR-320a gene can be obtained by a method described in Michael M Z et al., 2003, Mol Cancer Res, Vol. 1, p. 882-891. Also, "hsa-mir-320a" (miRBase Accession No. MI0000542, SEQ ID NO: 543) having a hairpin-like structure is known as a precursor of "hsa-miR-320a".

The term "hsa-miR-342-5p gene" or "hsa-miR-342-5p" used herein includes the hsa-miR-342-5p gene (miRBase Accession No. MIMAT0004694) described in SEQ ID NO: 207, a homolog or an ortholog of a different organism species, and the like. The hsa-miR-342-5p gene can be obtained by a method described in Kim J et al., 2004, Proc Natl Acad Sci USA, Vol. 101, p. 360-365. Also, "hsa-mir-342" (miRBase Accession No. MI0000805, SEQ ID NO: 544) having a hairpin-like structure is known as a precursor of "hsa-miR-342-5p".

The term "hsa-miR-3621 gene" or "hsa-miR-3621" used herein includes the hsa-miR-3621 gene (miRBase Accession No. MIMAT0018002) described in SEQ ID NO: 208, a homolog or an ortholog of a different organism species, and the like. The hsa-miR-3621 gene can be obtained by a method described in Witten D et al., 2010, BMC Biol, Vol. 8, p. 58. Also, "hsa-mir-3621" (miRBase Accession No. MI0016012, SEQ ID NO: 545) having a hairpin-like structure is known as a precursor of "hsa-miR-3621".

The term "hsa-miR-3648 gene" or "hsa-miR-3648" used herein includes the hsa-miR-3648 gene (miRBase Accession No. MIMAT0018068) described in SEQ ID NO: 209, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648" (miRBase Accession No. MI0016048, SEQ ID NO: 546) having a hairpin-like structure is known as a precursor of "hsa-miR-3648".

The term "hsa-miR-3656 gene" or "hsa-miR-3656" used herein includes the hsa-miR-3656 gene (miRBase Accession No. MIMAT0018076) described in SEQ ID NO: 210, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 547) having a hairpin-like structure is known as a precursor of "hsa-miR-3656".

The term "hsa-miR-365a-5p gene" or "hsa-miR-365a-5p" used herein includes the hsa-miR-365a-5p gene (miRBase Accession No. MIMAT0009199) described in SEQ ID NO: 211, a homolog or an ortholog of a different organism species, and the like. The hsa-miR-365a-5p gene can be obtained by a method described in Xie X et al., 2005, Nature, Vol. 434, p. 338-345. Also, "hsa-mir-365a" (miRBase Accession No. MI0000767, SEQ ID NO: 548) having a hairpin-like structure is known as a precursor of "hsa-miR-365a-5p".

The term "hsa-miR-3665 gene" or "hsa-miR-3665" used herein includes the hsa-miR-3665 gene (miRBase Accession No. MIMAT0018087) described in SEQ ID NO: 212, a homolog or an ortholog of a different organism species, and the like. The hsa-miR-3665 gene can be obtained by a method described in 'Xie X et al., 2005, Nature, Vol. 434, p. 338-345'. Also, "hsa-mir-3665" (miRBase Accession No. MI0016066, SEQ ID NO: 549) having a hairpin-like structure is known as a precursor of "hsa-miR-3665".

The term "hsa-miR-3679-5p gene" or "hsa-miR-3679-5p" used herein includes the hsa-miR-3679-5p gene (miRBase Accession No. MIMAT0018104) described in SEQ ID NO: 213, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 550) having a hairpin-like structure is known as a precursor of "hsa-miR-3679-5p".

The term "hsa-miR-371a-5p gene" or "hsa-miR-371a-5p" used herein includes the hsa-miR-371a-5p gene (miRBase Accession No. MIMAT0004687) described in SEQ ID NO: 214, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 551) having a hairpin-like structure is known as a precursor of "hsa-miR-371a-5p".

The term "hsa-miR-3940-5p gene" or "hsa-miR-3940-5p" used herein includes the hsa-miR-3940-5p gene (miRBase Accession No. MIMAT0019229) described in SEQ ID NO: 215, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 552) having a hairpin-like structure is known as a precursor of "hsa-miR-3940-5p".

The term "hsa-miR-423-5p gene" or "hsa-miR-423-5p" used herein includes the hsa-miR-423-5p gene (miRBase Accession No. MIMAT0004748) described in SEQ ID NO: 216, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 553) having a hairpin-like structure is known as a precursor of "hsa-miR-423-5p".

The term "hsa-miR-4257 gene" or "hsa-miR-4257" used herein includes the hsa-miR-4257 gene (miRBase Accession No. MIMAT0016878) described in SEQ ID NO: 217, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 554) having a hairpin-like structure is known as a precursor of "hsa-miR-4257".

The term "hsa-miR-4270 gene" or "hsa-miR-4270" used herein includes the hsa-miR-4270 gene (miRBase Accession No. MIMAT0016900) described in SEQ ID NO: 218, a homolog or an ortholog of a different organism species, and the like. The hsa-miR-4270 gene can be obtained by a method described in Goff L A et al., 2009, PLoS One, Vol. 4, e7192. Also, "hsa-mir-4270" (miRBase Accession No. MI0015878, SEQ ID NO: 555) having a hairpin-like structure is known as a precursor of "hsa-miR-4270".

The term "hsa-miR-4271 gene" or "hsa-miR-4271" used herein includes the hsa-miR-4271 gene (miRBase Accession No. MIMAT0016901) described in SEQ ID NO: 219, a homolog or an ortholog of a different organism species, and the like. The hsa-miR-4271 gene can be obtained by a method described in Goff L A et al., 2009, PLoS One, Vol. 4, e7192. Also, "hsa-mir-4271" (miRBase Accession No. MI0015879, SEQ ID NO: 556) having a hairpin-like structure is known as a precursor of "hsa-miR-4271".

The term "hsa-miR-4286 gene" or "hsa-miR-4286" used herein includes the hsa-miR-4286 gene (miRBase Accession No. MIMAT0016916) described in SEQ ID NO: 220, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 557) having a hairpin-like structure is known as a precursor of "hsa-miR-4286".

The term "hsa-miR-4298 gene" or "hsa-miR-4298" used herein includes the hsa-miR-4298 gene (miRBase Accession No. MIMAT0016852) described in SEQ ID NO: 221, a homolog or an ortholog of a different organism species, and the like. The hsa-miR-4298 gene can be obtained by a method described in Goff L A et al., 2009, PLoS One, Vol. 4, e7192. Also, "hsa-mir-4298" (miRBase Accession No. MI0015830, SEQ ID NO: 558) having a hairpin-like structure is known as a precursor of "hsa-miR-4298".

The term "hsa-miR-4417 gene" or "hsa-miR-4417" used herein includes the hsa-miR-4417 gene (miRBase Accession No. MIMAT0018929) described in SEQ ID NO: 222, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 559) having a hairpin-like structure is known as a precursor of "hsa-miR-4417".

The term "hsa-miR-4442 gene" or "hsa-miR-4442" used herein includes the hsa-miR-4442 gene (miRBase Accession No. MIMAT0018960) described in SEQ ID NO: 223, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 560) having a hairpin-like structure is known as a precursor of "hsa-miR-4442".

The term "hsa-miR-4446-3p gene" or "hsa-miR-4446-3p" used herein includes the hsa-miR-4446-3p gene (miRBase Accession No. MIMAT0018965) described in SEQ ID NO: 224, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 561) having a hairpin-like structure is known as a precursor of "hsa-miR-4446-3p".

The term "hsa-miR-4448 gene" or "hsa-miR-4448" used herein includes the hsa-miR-4448 gene (miRBase Accession No. MIMAT0018967) described in SEQ ID NO: 225, a homolog or an ortholog of a different organism species, and the like. The hsa-miR-4448 gene can be obtained by a method described in Jima D D et al., 2010, Blood, Vol. 116, e118-e127. Also, "hsa-mir-4448" (miRBase Accession No. MI0016791, SEQ ID NO: 562) having a hairpin-like structure is known as a precursor of "hsa-miR-4448".

The term "hsa-miR-4454 gene" or "hsa-miR-4454" used herein includes the hsa-miR-4454 gene (miRBase Accession No. MIMAT0018976) described in SEQ ID NO: 226, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 563) having a hairpin-like structure is known as a precursor of "hsa-miR-4454".

The term "hsa-miR-4467 gene" or "hsa-miR-4467" used herein includes the hsa-miR-4467 gene (miRBase Accession No. MIMAT0018994) described in SEQ ID NO: 227, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 564) having a hairpin-like structure is known as a precursor of "hsa-miR-4467".

The term "hsa-miR-4472 gene" or "hsa-miR-4472" used herein includes the hsa-miR-4472 gene (miRBase Accession No. MIMAT0018999) described in SEQ ID NO: 228, a homolog or an ortholog of a different organism species, and the like. The hsa-miR-4472 gene can be obtained by a method described in Jima D D et al., 2010, Blood, Vol. 116, e118-e127. Also, "hsa-mir-4472-1 and hsa-mir-4472-2" (miRBase Accession Nos. MI0016823 and MI0016824, SEQ ID NOs: 565 and 566) having a hairpin-like structure are known as precursors of "hsa-miR-4472".

The term "hsa-miR-4507 gene" or "hsa-miR-4507" used herein includes the hsa-miR-4507 gene (miRBase Accession No. MIMAT0019044) described in SEQ ID NO: 229, a homolog or an ortholog of a different organism species, and the like. The hsa-miR-4507 gene can be obtained by a method described in Jima D D et al., 2010, Blood, Vol. 116, e118-e127. Also, "hsa-mir-4507" (miRBase Accession No. MI0016871, SEQ ID NO: 567) having a hairpin-like structure is known as a precursor of "hsa-miR-4507".

The term "hsa-miR-4516 gene" or "hsa-miR-4516" used herein includes the hsa-miR-4516 gene (miRBase Accession No. MIMAT0019053) described in SEQ ID NO: 230, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 568) having a hairpin-like structure is known as a precursor of "hsa-miR-4516".

The term "hsa-miR-451a gene" or "hsa-miR-451a" used herein includes the hsa-miR-451a gene (miRBase Accession No. MIMAT0001631) described in SEQ ID NO: 231, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 569) having a hairpin-like structure is known as a precursor of "hsa-miR-451a".

The term "hsa-miR-4649-5p gene" or "hsa-miR-4649-5p" used herein includes the hsa-miR-4649-5p gene (miRBase Accession No. MIMAT0019711) described in SEQ ID NO: 232, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 570) having a hairpin-like structure is known as a precursor of "hsa-miR-4649-5p".

The term "hsa-miR-4651 gene" or "hsa-miR-4651" used herein includes the hsa-miR-4651 gene (miRBase Accession No. MIMAT0019715) described in SEQ ID NO: 233, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 571) having a hairpin-like structure is known as a precursor of "hsa-miR-4651".

The term "hsa-miR-4665-3p gene" or "hsa-miR-4665-3p" used herein includes the hsa-miR-4665-3p gene (miRBase Accession No. MIMAT0019740) described in SEQ ID NO: 234, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 401) having a hairpin-like structure is known as a precursor of "hsa-miR-4665-3p".

The term "hsa-miR-4674 gene" or "hsa-miR-4674" used herein includes the hsa-miR-4674 gene (miRBase Accession No. MIMAT0019756) described in SEQ ID NO: 235, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 572) having a hairpin-like structure is known as a precursor of "hsa-miR-4674".

The term "hsa-miR-4675 gene" or "hsa-miR-4675" used herein includes the hsa-miR-4675 gene (miRBase Accession No. MIMAT0019757) described in SEQ ID NO: 236, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 573) having a hairpin-like structure is known as a precursor of "hsa-miR-4675".

The term "hsa-miR-4689 gene" or "hsa-miR-4689" used herein includes the hsa-miR-4689 gene (miRBase Accession No. MIMAT0019778) described in SEQ ID NO: 237, a homolog or an ortholog of a different organism species, and the like. The hsa-miR-4689 gene can be obtained by a method described in Persson H et al., 2011, Cancer Res, Vol.

71, p. 78-86. Also, "hsa-mir-4689" (miRBase Accession No. MI0017322, SEQ ID NO: 574) having a hairpin-like structure is known as a precursor of "hsa-miR-4689".

The term "hsa-miR-4695-5p gene" or "hsa-miR-4695-5p" used herein includes the hsa-miR-4695-5p gene (miRBase Accession No. MIMAT0019788) described in SEQ ID NO: 238, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 575) having a hairpin-like structure is known as a precursor of "hsa-miR-4695-5p".

The term "hsa-miR-4697-5p gene" or "hsa-miR-4697-5p" used herein includes the hsa-miR-4697-5p gene (miRBase Accession No. MIMAT0019791) described in SEQ ID NO: 239, a homolog or an ortholog of a different organism species, and the like. The hsa-miR-4697-5p gene can be obtained by a method described in Persson H et al., 2011, Cancer Res, Vol. 71, p. 78-86. Also, "hsa-mir-4697" (miRBase Accession No. MI0017330, SEQ ID NO: 576) having a hairpin-like structure is known as a precursor of "hsa-miR-4697-5p".

The term "hsa-miR-4725-3p gene" or "hsa-miR-4725-3p" used herein includes the hsa-miR-4725-3p gene (miRBase Accession No. MIMAT0019844) described in SEQ ID NO: 240, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 577) having a hairpin-like structure is known as a precursor of "hsa-miR-4725-3p".

The term "hsa-miR-4739 gene" or "hsa-miR-4739" used herein includes the hsa-miR-4739 gene (miRBase Accession No. MIMAT0019868) described in SEQ ID NO: 241, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 578) having a hairpin-like structure is known as a precursor of "hsa-miR-4739".

The term "hsa-miR-4745-5p gene" or "hsa-miR-4745-5p" used herein includes the hsa-miR-4745-5p gene (miRBase Accession No. MIMAT0019878) described in SEQ ID NO: 242, a homolog or an ortholog of a different organism species, and the like. The hsa-miR-4745-5p gene can be obtained by a method described in Persson H et al., 2011, Cancer Res, Vol. 71, p. 78-86. Also, "hsa-mir-4745" (miRBase Accession No. MI0017384, SEQ ID NO: 579) having a hairpin-like structure is known as a precursor of "hsa-miR-4745-5p".

The term "hsa-miR-4763-3p gene" or "hsa-miR-4763-3p" used herein includes the hsa-miR-4763-3p gene (miRBase Accession No. MIMAT0019913) described in SEQ ID NO: 243, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 415) having a hairpin-like structure is known as a precursor of "hsa-miR-4763-3p".

The term "hsa-miR-4792 gene" or "hsa-miR-4792" used herein includes the hsa-miR-4792 gene (miRBase Accession No. MIMAT0019964) described in SEQ ID NO: 244, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 580) having a hairpin-like structure is known as a precursor of "hsa-miR-4792".

The term "hsa-miR-486-3p gene" or "hsa-miR-486-3p" used herein includes the hsa-miR-486-3p gene (miRBase Accession No. MIMAT0004762) described in SEQ ID NO: 245, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 581 and 582) having a hairpin-like structure are known as precursors of "hsa-miR-486-3p".

The term "hsa-miR-5001-5p gene" or "hsa-miR-5001-5p" used herein includes the hsa-miR-5001-5p gene (miRBase Accession No. MIMAT0021021) described in SEQ ID NO: 246, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 583) having a hairpin-like structure is known as a precursor of "hsa-miR-5001-5p".

The term "hsa-miR-5195-3p gene" or "hsa-miR-5195-3p" used herein includes the hsa-miR-5195-3p gene (miRBase Accession No. MIMAT0021127) described in SEQ ID NO: 247, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 584) having a hairpin-like structure is known as a precursor of "hsa-miR-5195-3p".

The term "hsa-miR-550a-5p gene" or "hsa-miR-550a-5p" used herein includes the hsa-miR-550a-5p gene (miRBase Accession No. MIMAT0004800) described in SEQ ID NO: 248, a homolog or an ortholog of a different organism species, and the like. The hsa-miR-550a-5p gene can be obtained by a method described in Cummins J M, 2006, Proc Natl Acad Sci, Vol. 103, p. 3687-3692. Also, "hsa-mir-550a-1 and hsa-mir-550a-2" (miRBase Accession Nos. MI0003600 and MI0003601, SEQ ID NOs: 585 and 586) having a hairpin-like structure are known as precursors of "hsa-miR-550a-5p".

The term "hsa-miR-5698 gene" or "hsa-miR-5698" used herein includes the hsa-miR-5698 gene (miRBase Accession No. MIMAT0022491) described in SEQ ID NO: 249, a homolog or an ortholog of a different organism species, and the like. The hsa-miR-5698 gene can be obtained by a method described in Watahiki A et al., 2011, PLoS One, Vol. 6, e24950. Also, "hsa-mir-5698" (miRBase Accession No. MI0019305, SEQ ID NO: 587) having a hairpin-like structure is known as a precursor of "hsa-miR-5698".

The term "hsa-miR-6075 gene" or "hsa-miR-6075" used herein includes the hsa-miR-6075 gene (miRBase Accession No. MIMAT0023700) described in SEQ ID NO: 250, a homolog or an ortholog of a different organism species, and the like. The hsa-miR-6075 gene can be obtained by a method described in Voellenkle C et al., 2012, RNA, Vol. 18, p. 472-484. Also, "hsa-mir-6075" (miRBase Accession No. MI0020352, SEQ ID NO: 588) having a hairpin-like structure is known as a precursor of "hsa-miR-6075".

The term "hsa-miR-6088 gene" or "hsa-miR-6088" used herein includes the hsa-miR-6088 gene (miRBase Accession No. MIMAT0023713) described in SEQ ID NO: 251, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 589) having a hairpin-like structure is known as a precursor of "hsa-miR-6088".

The term "hsa-miR-6089 gene" or "hsa-miR-6089" used herein includes the hsa-miR-6089 gene (miRBase Accession No. MIMAT0023714) described in SEQ ID NO: 252, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. MI0020366 and MI0023563, SEQ ID NOs: 590 and 591) having a hairpin-like structure are known as precursors of "hsa-miR-6089".

The term "hsa-miR-6125 gene" or "hsa-miR-6125" used herein includes the hsa-miR-6125 gene (miRBase Accession No. MIMAT0024598) described in SEQ ID NO: 253, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 592) having a hairpin-like structure is known as a precursor of "hsa-miR-6125".

The term "hsa-miR-6126 gene" or "hsa-miR-6126" used herein includes the hsa-miR-6126 gene (miRBase Accession No. MIMAT0024599) described in SEQ ID NO: 254, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 593) having a hairpin-like structure is known as a precursor of "hsa-miR-6126".

The term "hsa-miR-614 gene" or "hsa-miR-614" used herein includes the hsa-miR-614 gene (miRBase Accession No. MIMAT0003282) described in SEQ ID NO: 255, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 594) having a hairpin-like structure is known as a precursor of "hsa-miR-614".

The term "hsa-miR-615-5p gene" or "hsa-miR-615-5p" used herein includes the hsa-miR-615-5p gene (miRBase Accession No. MIMAT0004804) described in SEQ ID NO: 256, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 595) having a hairpin-like structure is known as a precursor of "hsa-miR-615-5p".

The term "hsa-miR-619-5p gene" or "hsa-miR-619-5p" used herein includes the hsa-miR-619-5p gene (miRBase Accession No. MIMAT0026622) described in SEQ ID NO: 257, a homolog or an ortholog of a different organism species, and the like. The hsa-miR-619-5p gene can be obtained by a method described in Cummins J M et al., 2006, Proc Natl Acad Sci USA, Vol. 103, p. 3687-3692. Also, "hsa-mir-619" (miRBase Accession No. MI0003633, SEQ ID NO: 596) having a hairpin-like structure is known as a precursor of "hsa-miR-619-5p".

The term "hsa-miR-638 gene" or "hsa-miR-638" used herein includes the hsa-miR-638 gene (miRBase Accession No. MIMAT0003308) described in SEQ ID NO: 258, a homolog or an ortholog of a different organism species, and the like. The hsa-miR-638 gene can be obtained by a method described in Cummins J M et al., 2006, Proc Natl Acad Sci USA, Vol. 103, p. 3687-3692. Also, "hsa-mir-638" (miRBase Accession No. MI0003653, SEQ ID NO: 597) having a hairpin-like structure is known as a precursor of "hsa-miR-638".

The term "hsa-miR-642b-3p gene" or "hsa-miR-642b-3p" used herein includes the hsa-miR-642b-3p gene (miRBase Accession No. MIMAT0018444) described in SEQ ID NO: 259, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 598) having a hairpin-like structure is known as a precursor of "hsa-miR-642b-3p".

The term "hsa-miR-650 gene" or "hsa-miR-650" used herein includes the hsa-miR-650 gene (miRBase Accession No. MIMAT0003320) described in SEQ ID NO: 260, a homolog or an ortholog of a different organism species, and the like. The hsa-miR-650 gene can be obtained by a method described in Cummins J M et al., 2006, Proc Natl Acad Sci USA., Vol. 103, 3687-3692. Also, "hsa-mir-650" (miRBase Accession No. MI0003665, SEQ ID NO: 599) having a hairpin-like structure is known as a precursor of "hsa-miR-650".

The term "hsa-miR-663a gene" or "hsa-miR-663a" used herein includes the hsa-miR-663a gene (miRBase Accession No. MIMAT0003326) described in SEQ ID NO: 261, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 600) having a hairpin-like structure is known as a precursor of "hsa-miR-663a".

The term "hsa-miR-663b gene" or "hsa-miR-663b" used herein includes the hsa-miR-663b gene (miRBase Accession No. MIMAT0005867) described in SEQ ID NO: 262, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 601) having a hairpin-like structure is known as a precursor of "hsa-miR-663b".

The term "hsa-miR-6717-5p gene" or "hsa-miR-6717-5p" used herein includes the hsa-miR-6717-5p gene (miRBase Accession No. MIMAT0025846) described in SEQ ID NO: 263, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 602) having a hairpin-like structure is known as a precursor of "hsa-miR-6717-5p".

The term "hsa-miR-6721-5p gene" or "hsa-miR-6721-5p" used herein includes the hsa-miR-6721-5p gene (miRBase Accession No. MIMAT0025852) described in SEQ ID NO: 264, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 603) having a hairpin-like structure is known as a precursor of "hsa-miR-6721-5p".

The term "hsa-miR-6726-5p gene" or "hsa-miR-6726-5p" used herein includes the hsa-miR-6726-5p gene (miRBase Accession No. MIMAT0027353) described in SEQ ID NO: 265, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 604) having a hairpin-like structure is known as a precursor of "hsa-miR-6726-5p".

The term "hsa-miR-6727-5p gene" or "hsa-miR-6727-5p" used herein includes the hsa-miR-6727-5p gene (miRBase Accession No. MIMAT0027355) described in SEQ ID NO: 266, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 605) having a hairpin-like structure is known as a precursor of "hsa-miR-6727-5p".

The term "hsa-miR-6738-5p gene" or "hsa-miR-6738-5p" used herein includes the hsa-miR-6738-5p gene (miRBase Accession No. MIMAT0027377) described in SEQ ID NO: 267, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 606) having a hairpin-like structure is known as a precursor of "hsa-miR-6738-5p".

The term "hsa-miR-6741-5p gene" or "hsa-miR-6741-5p" used herein includes the hsa-miR-6741-5p gene (miRBase Accession No. MIMAT0027383) described in SEQ ID NO: 268, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 607) having a hairpin-like structure is known as a precursor of "hsa-miR-6741-5p".

The term "hsa-miR-6749-5p gene" or "hsa-miR-6749-5p" used herein includes the hsa-miR-6749-5p gene (miRBase Accession No. MIMAT0027398) described in SEQ ID NO: 269, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 608) having a hairpin-like structure is known as a precursor of "hsa-miR-6749-5p".

The term "hsa-miR-6752-5p gene" or "hsa-miR-6752-5p" used herein includes the hsa-miR-6752-5p gene (miRBase Accession No. MIMAT0027404) described in SEQ ID NO: 270, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 609) having a hairpin-like structure is known as a precursor of "hsa-miR-6752-5p".

The term "hsa-miR-675-5p gene" or "hsa-miR-675-5p" used herein includes the hsa-miR-675-5p gene (miRBase Accession No. MIMAT0004284) described in SEQ ID NO: 271, a homolog or an ortholog of a different organism species, and the like. The hsa-miR-675-5p gene can be obtained by a method described in Cai X et al., 2007, RNA, Vol. 13, p. 313-316. Also, "hsa-mir-675" (miRBase Accession No. MI0005416, SEQ ID NO: 610) having a hairpin-like structure is known as a precursor of "hsa-miR-675-5p".

The term "hsa-miR-6757-5p gene" or "hsa-miR-6757-5p" used herein includes the hsa-miR-6757-5p gene (miRBase Accession No. MIMAT0027414) described in SEQ ID NO: 272, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 611) having a hairpin-like structure is known as a precursor of "hsa-miR-6757-5p".

The term "hsa-miR-6763-5p gene" or "hsa-miR-6763-5p" used herein includes the hsa-miR-6763-5p gene (miRBase Accession No. MIMAT0027426) described in SEQ ID NO: 273, a homolog or an ortholog of a different organism species, and the like. The hsa-miR-6763-5p gene can be obtained by a method described in Ladewig E et al., 2012, Genome Res, Vol. 22, p. 1634-1645. Also, "hsa-mir-6763" (miRBase Accession No. MI0022608, SEQ ID NO: 442) having a hairpin-like structure is known as a precursor of "hsa-miR-6763-5p".

The term "hsa-miR-6765-5p gene" or "hsa-miR-6765-5p" used herein includes the hsa-miR-6765-5p gene (miRBase Accession No. MIMAT0027430) described in SEQ ID NO: 274, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 612) having a hairpin-like structure is known as a precursor of "hsa-miR-6765-5p".

The term "hsa-miR-6775-5p gene" or "hsa-miR-6775-5p" used herein includes the hsa-miR-6775-5p gene (miRBase Accession No. MIMAT0027450) described in SEQ ID NO: 275, a homolog or an ortholog of a different organism species, and the like. The hsa-miR-6775-5p gene can be obtained by a method described in Ladewig E et al., 2012, Genome Res, Vol. 22, p. 1634-1645. Also, "hsa-mir-6775" (miRBase Accession No. MI0022620, SEQ ID NO: 613) having a hairpin-like structure is known as a precursor of "hsa-miR-6775-5p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 276, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 614) having a hairpin-like structure is known as a precursor of "hsa-miR-6780b-5p".

The term "hsa-miR-6782-5p gene" or "hsa-miR-6782-5p" used herein includes the hsa-miR-6782-5p gene (miRBase Accession No. MIMAT0027464) described in SEQ ID NO: 277, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 615) having a hairpin-like structure is known as a precursor of "hsa-miR-6782-5p".

The term "hsa-miR-6784-5p gene" or "hsa-miR-6784-5p" used herein includes the hsa-miR-6784-5p gene (miRBase Accession No. MIMAT0027468) described in SEQ ID NO: 278, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 616) having a hairpin-like structure is known as a precursor of "hsa-miR-6784-5p".

The term "hsa-miR-6800-5p gene" or "hsa-miR-6800-5p" used herein includes the hsa-miR-6800-5p gene (miRBase Accession No. MIMAT0027500) described in SEQ ID NO: 279, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 451) having a hairpin-like structure is known as a precursor of "hsa-miR-6800-5p".

The term "hsa-miR-6806-5p gene" or "hsa-miR-6806-5p" used herein includes the hsa-miR-6806-5p gene (miRBase Accession No. MIMAT0027512) described in SEQ ID NO: 280, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 617) having a hairpin-like structure is known as a precursor of "hsa-miR-6806-5p".

The term "hsa-miR-6840-3p gene" or "hsa-miR-6840-3p" used herein includes the hsa-miR-6840-3p gene (miRBase Accession No. MIMAT0027583) described in SEQ ID NO: 281, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 618) having a hairpin-like structure is known as a precursor of "hsa-miR-6840-3p".

The term "hsa-miR-6848-5p gene" or "hsa-miR-6848-5p" used herein includes the hsa-miR-6848-5p gene (miRBase Accession No. MIMAT0027596) described in SEQ ID NO: 282, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 619) having a hairpin-like structure is known as a precursor of "hsa-miR-6848-5p".

The term "hsa-miR-6851-5p gene" or "hsa-miR-6851-5p" used herein includes the hsa-miR-6851-5p gene (miRBase Accession No. MIMAT0027602) described in SEQ ID NO: 283, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697, SEQ ID NO: 620) having a hairpin-like structure is known as a precursor of "hsa-miR-6851-5p".

The term "hsa-miR-6870-5p gene" or "hsa-miR-6870-5p" used herein includes the hsa-miR-6870-5p gene (miRBase Accession No. MIMAT0027640) described in SEQ ID NO: 284, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 621) having a hairpin-like structure is known as a precursor of "hsa-miR-6870-5p".

The term "hsa-miR-6872-3p gene" or "hsa-miR-6872-3p" used herein includes the hsa-miR-6872-3p gene (miRBase Accession No. MIMAT0027645) described in SEQ ID NO: 285, a homolog or an ortholog of a different organism species, and the like. The hsa-miR-6872-3p gene can be obtained by a method described in Ladewig E et al., 2012, Genome Res, Vol. 22, p. 1634-1645. Also, "hsa-mir-6872" (miRBase Accession No. MI0022719, SEQ ID NO: 622) having a hairpin-like structure is known as a precursor of "hsa-miR-6872-3p".

The term "hsa-miR-6875-5p gene" or "hsa-miR-6875-5p" used herein includes the hsa-miR-6875-5p gene (miRBase Accession No. MIMAT0027650) described in SEQ ID NO: 286, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 623) having a hairpin-like structure is known as a precursor of "hsa-miR-6875-5p".

The term "hsa-miR-6877-5p gene" or "hsa-miR-6877-5p" used herein includes the hsa-miR-6877-5p gene (miRBase Accession No. MIMAT0027654) described in SEQ ID NO: 287, a homolog or an ortholog of a different organism species, and the like. The hsa-miR-6877-5p gene can be obtained by a method described in Ladewig E et al., 2012, Genome Res, Vol. 22, p. 1634-1645. Also, "hsa-mir-6877" (miRBase Accession No. MI0022724, SEQ ID NO: 624) having a hairpin-like structure is known as a precursor of "hsa-miR-6877-5p".

The term "hsa-miR-6879-5p gene" or "hsa-miR-6879-5p" used herein includes the hsa-miR-6879-5p gene (miRBase Accession No. MIMAT0027658) described in SEQ ID NO: 288, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 625) having a hairpin-like structure is known as a precursor of "hsa-miR-6879-5p".

The term "hsa-miR-6880-5p gene" or "hsa-miR-6880-5p" used herein includes the hsa-miR-6880-5p gene (miRBase Accession No. MIMAT0027660) described in SEQ ID NO: 289, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 464) having a hairpin-like structure is known as a precursor of "hsa-miR-6880-5p".

The term "hsa-miR-6885-5p gene" or "hsa-miR-6885-5p" used herein includes the hsa-miR-6885-5p gene (miRBase Accession No. MIMAT0027670) described in SEQ ID NO: 290, a homolog or an ortholog of a different organism species, and the like. The hsa-miR-6885-5p gene can be obtained by a method described in Ladewig E et al., 2012, Genome Res, Vol. 22, p. 1634-1645. Also, "hsa-mir-6885" (miRBase Accession No. MI0022732, SEQ ID NO: 626) having a hairpin-like structure is known as a precursor of "hsa-miR-6885-5p".

The term "hsa-miR-6887-5p gene" or "hsa-miR-6887-5p" used herein includes the hsa-miR-6887-5p gene (miRBase Accession No. MIMAT0027674) described in SEQ ID NO: 291, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887"

(miRBase Accession No. MI0022734, SEQ ID NO: 627) having a hairpin-like structure is known as a precursor of "hsa-miR-6887-5p".

The term "hsa-miR-7108-5p gene" or "hsa-miR-7108-5p" used herein includes the hsa-miR-7108-5p gene (miRBase Accession No. MIMAT0028113) described in SEQ ID NO: 292, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 495) having a hairpin-like structure is known as a precursor of "hsa-miR-7108-5p".

The term "hsa-miR-711 gene" or "hsa-miR-711" used herein includes the hsa-miR-711 gene (miRBase Accession No. MIMAT0012734) described in SEQ ID NO: 293, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 628) having a hairpin-like structure is known as a precursor of "hsa-miR-711".

The term "hsa-miR-7113-3p gene" or "hsa-miR-7113-3p" used herein includes the hsa-miR-7113-3p gene (miRBase Accession No. MIMAT0028124) described in SEQ ID NO: 294, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 629) having a hairpin-like structure is known as a precursor of "hsa-miR-7113-3p".

The term "hsa-miR-744-5p gene" or "hsa-miR-744-5p" used herein includes the hsa-miR-744-5p gene (miRBase Accession No. MIMAT0004945) described in SEQ ID NO: 295, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 630) having a hairpin-like structure is known as a precursor of "hsa-miR-744-5p".

The term "hsa-miR-760 gene" or "hsa-miR-760" used herein includes the hsa-miR-760 gene (miRBase Accession No. MIMAT0004957) described in SEQ ID NO: 296, a homolog or an ortholog of a different organism species, and the like. The hsa-miR-760 gene can be obtained by a method described in Berezikov E et al., 2006, Genome Res, Vol. 16, p. 1289-1298. Also, "hsa-mir-760" (miRBase Accession No. MI0005567, SEQ ID NO: 631) having a hairpin-like structure is known as a precursor of "hsa-miR-760".

The term "hsa-miR-7845-5p gene" or "hsa-miR-7845-5p" used herein includes the hsa-miR-7845-5p gene (miRBase Accession No. MIMAT0030420) described in SEQ ID NO: 297, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 632) having a hairpin-like structure is known as a precursor of "hsa-miR-7845-5p".

The term "hsa-miR-7847-3p gene" or "hsa-miR-7847-3p" used herein includes the hsa-miR-7847-3p gene (miRBase Accession No. MIMAT0030422) described in SEQ ID NO: 298, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 633) having a hairpin-like structure is known as a precursor of "hsa-miR-7847-3p".

The term "hsa-miR-7977 gene" or "hsa-miR-7977" used herein includes the hsa-miR-7977 gene (miRBase Accession No. MIMAT0031180) described in SEQ ID NO: 299, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 634) having a hairpin-like structure is known as a precursor of "hsa-miR-7977".

The term "hsa-miR-8059 gene" or "hsa-miR-8059" used herein includes the hsa-miR-8059 gene (miRBase Accession No. MIMAT0030986) described in SEQ ID NO: 300, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 635) having a hairpin-like structure is known as a precursor of "hsa-miR-8059".

The term "hsa-miR-8063 gene" or "hsa-miR-8063" used herein includes the hsa-miR-8063 gene (miRBase Accession No. MIMAT0030990) described in SEQ ID NO: 301, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 636) having a hairpin-like structure is known as a precursor of "hsa-miR-8063".

The term "hsa-miR-8072 gene" or "hsa-miR-8072" used herein includes the hsa-miR-8072 gene (miRBase Accession No. MIMAT0030999) described in SEQ ID NO: 302, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 637) having a hairpin-like structure is known as a precursor of "hsa-miR-8072".

The term "hsa-miR-874-3p gene" or "hsa-miR-874-3p" used herein includes the hsa-miR-874-3p gene (miRBase Accession No. MIMAT0004911) described in SEQ ID NO: 303, a homolog or an ortholog of a different organism species, and the like. The hsa-miR-874-3p gene can be obtained by a method described in Landgraf P et al., 2007, Cell., Vol. 129, p. 1401-1414. Also, "hsa-mir-874" (miRBase Accession No. MI0005532, SEQ ID NO: 475) having a hairpin-like structure is known as a precursor of "hsa-miR-874-3p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 304, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 638) having a hairpin-like structure is known as a precursor of "hsa-miR-92a-2-5p".

The term "hsa-miR-92b-5p gene" or "hsa-miR-92b-5p" used herein includes the hsa-miR-92b-5p gene (miRBase Accession No. MIMAT0004792) described in SEQ ID NO: 305, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692.

Also, "hsa-mir-92b" (miRBase Accession No. MI0003560, SEQ ID NO: 499) having a hairpin-like structure is known as a precursor of "hsa-miR-92b-5p".

The term "hsa-miR-940 gene" or "hsa-miR-940" used herein includes the hsa-miR-940 gene (miRBase Accession No. MIMAT0004983) described in SEQ ID NO: 306, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No. MI0005762, SEQ ID NO: 639) having a hairpin-like structure is known as a precursor of "hsa-miR-940".

The term "hsa-miR-1228-3p gene" or "hsa-miR-1228-3p" used herein includes the hsa-miR-1228-3p gene (miRBase Accession No. MIMAT0005583) described in SEQ ID NO: 307, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 511) having a hairpin-like structure is known as a precursor of "hsa-miR-1228-3p".

The term "hsa-miR-1275 gene" or "hsa-miR-1275" used herein includes the hsa-miR-1275 gene (miRBase Accession No. MIMAT0005929) described in SEQ ID NO: 308, a homolog or an ortholog of a different organism species, and the like. The hsa-miR-1275 gene can be obtained by a method described in Morin R D et al., 2008, Genome Res, Vol. 18, p. 610-621. Also, "hsa-mir-1275" (miRBase Accession No. MI0006415, SEQ ID NO: 640) having a hairpin-like structure is known as a precursor of "hsa-miR-1275".

The term "hsa-miR-1307-3p gene" or "hsa-miR-1307-3p" used herein includes the hsa-miR-1307-3p gene (miRBase Accession No. MIMAT0005951) described in SEQ ID NO: 309, a homolog or an ortholog of a different organism species, and the like. The hsa-miR-1307-3p gene can be obtained by a method described in Morin R D et al., 2008, Genome Res, Vol. 18, p. 610-621. Also, "hsa-mir-1307" (miRBase Accession No. MI0006444, SEQ ID NO: 641) having a hairpin-like structure is known as a precursor of "hsa-miR-1307-3p".

The term "hsa-miR-1343-5p gene" or "hsa-miR-1343-5p" used herein includes the hsa-miR-1343-5p gene (miRBase Accession No. MIMAT0027038) described in SEQ ID NO: 310, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 500) having a hairpin-like structure is known as a precursor of "hsa-miR-1343-5p".

The term "hsa-miR-23a-3p gene" or "hsa-miR-23a-3p" used herein includes the hsa-miR-23a-3p gene (miRBase Accession No. MIMAT0000078) described in SEQ ID NO: 311, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 642) having a hairpin-like structure is known as a precursor of "hsa-miR-23a-3p".

The term "hsa-miR-29b-3p gene" or "hsa-miR-29b-3p" used herein includes the hsa-miR-29b-3p gene (miRBase Accession No. MIMAT0000100) described in SEQ ID NO: 312, a homolog or an ortholog of a different organism species, and the like. The hsa-miR-29b-3p gene can be obtained by a method described in Mourelatos Z et al., 2002, Genes Dev., Vol. 16, p. 720-728. Also, "hsa-mir-29b-1 and hsa-mir-29b-2" (miRBase Accession Nos. MI0000105 and MI0000107, SEQ ID NOs: 643 and 644) having a hairpin-like structure are known as precursors of "hsa-miR-29b-3p".

The term "hsa-miR-3135b gene" or "hsa-miR-3135b" used herein includes the hsa-miR-3135b gene (miRBase Accession No. MIMAT0018985) described in SEQ ID NO: 313, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 645) having a hairpin-like structure is known as a precursor of "hsa-miR-3135b".

The term "hsa-miR-3185 gene" or "hsa-miR-3185" used herein includes the hsa-miR-3185 gene (miRBase Accession No. MIMAT0015065) described in SEQ ID NO: 314, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 646) having a hairpin-like structure is known as a precursor of "hsa-miR-3185".

The term "hsa-miR-4532 gene" or "hsa-miR-4532" used herein includes the hsa-miR-4532 gene (miRBase Accession No. MIMAT0019071) described in SEQ ID NO: 315, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 647) having a hairpin-like structure is known as a precursor of "hsa-miR-4532".

The term "hsa-miR-4690-5p gene" or "hsa-miR-4690-5p" used herein includes the hsa-miR-4690-5p gene (miRBase Accession No. MIMAT0019779) described in SEQ ID NO: 316, a homolog or an ortholog of a different organism species, and the like. The hsa-miR-4690-5p gene can be obtained by a method described in Persson H et al., 2011, Cancer Res, Vol. 71, p. 78-86. Also, "hsa-mir-4690" (miRBase Accession No. MI0017323, SEQ ID NO: 648) having a hairpin-like structure is known as a precursor of "hsa-miR-4690-5p".

The term "hsa-miR-4758-5p gene" or "hsa-miR-4758-5p" used herein includes the hsa-miR-4758-5p gene (miRBase Accession No. MIMAT0019903) described in SEQ ID NO: 317, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 649) having a hairpin-like structure is known as a precursor of "hsa-miR-4758-5p".

The term "hsa-miR-4783-3p gene" or "hsa-miR-4783-3p" used herein includes the hsa-miR-4783-3p gene (miRBase Accession No. MIMAT0019947) described in SEQ ID NO: 318, a homolog or an ortholog of a different organism species, and the like. The hsa-miR-4783-3p gene can be obtained by a method described in Persson H et al., 2011, Cancer Res, Vol. 71, p. 78-86. Also, "hsa-mir-4783" (miRBase Accession No. MI0017428, SEQ ID NO: 650) having a hairpin-like structure is known as a precursor of "hsa-miR-4783-3p".

The term "hsa-miR-6131 gene" or "hsa-miR-6131" used herein includes the hsa-miR-6131 gene (miRBase Accession No. MIMAT0024615) described in SEQ ID NO: 319, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 651) having a hairpin-like structure is known as a precursor of "hsa-miR-6131".

The term "hsa-miR-625-3p gene" or "hsa-miR-625-3p" used herein includes the hsa-miR-625-3p gene (miRBase Accession No. MIMAT0004808) described in SEQ ID NO: 320, a homolog or an ortholog of a different organism species, and the like. The hsa-miR-625-3p gene can be obtained by a method described in Cummins J M et al., 2006, Proc Natl Acad Sci USA, Vol. 103, p. 3687-3692. Also, "hsa-mir-625" (miRBase Accession No. MI0003639, SEQ ID NO: 652) having a hairpin-like structure is known as a precursor of "hsa-miR-625-3p".

The term "hsa-miR-6511a-5p gene" or "hsa-miR-6511a-5p" used herein includes the hsa-miR-6511a-5p gene (miRBase Accession No. MIMAT0025478) described in SEQ ID NO: 321, a homolog or an ortholog of a different organism species, and the like. The hsa-miR-6511a-5p gene can be obtained by a method described in Joyce C E et al., 2011, Hum Mol Genet, Vol. 20, p. 4025-4040. Also, "hsa-mir-6511a-1, hsa-mir-6511a-2, hsa-mir-6511a-3, and hsa-mir-6511a-4" (miRBase Accession Nos. MI0022223, MI0023564, MI0023565, and MI0023566, SEQ ID NOs: 653, 654, 655, and 656) having a hairpin-like structure are known as precursors of "hsa-miR-6511a-5p".

The term "hsa-miR-6765-3p gene" or "hsa-miR-6765-3p" used herein includes the hsa-miR-6765-3p gene (miRBase Accession No. MIMAT0027431) described in SEQ ID NO: 322, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 612) having a hairpin-like structure is known as a precursor of "hsa-miR-6765-3p".

The term "hsa-miR-6816-5p gene" or "hsa-miR-6816-5p" used herein includes the hsa-miR-6816-5p gene (miRBase Accession No. MIMAT0027532) described in SEQ ID NO: 323, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 657) having a hairpin-like structure is known as a precursor of "hsa-miR-6816-5p".

The term "hsa-miR-6825-5p gene" or "hsa-miR-6825-5p" used herein includes the hsa-miR-6825-5p gene (miRBase Accession No. MIMAT0027550) described in SEQ ID NO: 324, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 658) having a hairpin-like structure is known as a precursor of "hsa-miR-6825-5p".

The term "hsa-miR-6845-5p gene" or "hsa-miR-6845-5p" used herein includes the hsa-miR-6845-5p gene (miRBase Accession No. MIMAT0027590) described in SEQ ID NO: 325, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 659) having a hairpin-like structure is known as a precursor of "hsa-miR-6845-5p".

The term "hsa-miR-7150 gene" or "hsa-miR-7150" used herein includes the hsa-miR-7150 gene (miRBase Accession No. MIMAT0028211) described in SEQ ID NO: 326, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 660) having a hairpin-like structure is known as a precursor of "hsa-miR-7150".

The term "hsa-miR-7641 gene" or "hsa-miR-7641" used herein includes the hsa-miR-7641 gene (miRBase Accession No. MIMAT0029782) described in SEQ ID NO: 327, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NOs: 661 and 662) having a hairpin-like structure are known as precursors of "hsa-miR-7641".

The term "hsa-miR-7975 gene" or "hsa-miR-7975" used herein includes the hsa-miR-7975 gene (miRBase Accession No. MIMAT0031178) described in SEQ ID NO: 328, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 663) having a hairpin-like structure is known as a precursor of "hsa-miR-7975".

The term "hsa-miR-92a-3p gene" or "hsa-miR-92a-3p" used herein includes the hsa-miR-92a-3p gene (miRBase Accession No. MIMAT0000092) described in SEQ ID NO: 329, a homolog or an ortholog of a different organism species, and the like. The hsa-miR-92a-3p gene can be obtained by a method described in Mourelatos Z et al., 2002, Genes Dev, Vol. 16, p. 720-728. Also, "hsa-mir-92a-1 and hsa-mir-92a-2" (miRBase Accession Nos. MI0000093 and MI0000094, SEQ ID NOs: 664 and 638) having a hairpin-like structure are known as precursors of "hsa-miR-92a-3p".

A mature miRNA may become a variant shorter or longer by one to several flanking nucleotides due to the sequence cleavage, or due to substitution of nucleotides, when cut out as the mature miRNA from its RNA precursor having a hairpin-like structure. This variant is called isomiR (Morin R D. et al., 2008, Genome Res., Vol. 18, p. 610-621). The miRBase Release 21 shows the nucleotide sequences represented by SEQ ID NOs: 1 to 329 as well as a large number of the nucleotide sequence variants and fragments represented by SEQ ID NOs: 665 to 1000, called isomiRs. These variants can also be obtained as miRNAs having a nucleotide sequence represented by any of SEQ ID NOs: 1 to 329. Specifically, according to the present invention, among the variants of polynucleotides consisting of the nucleotide sequence represented by any of SEQ ID NOs: 4, 7, 8, 9, 13, 14, 18, 20, 21, 22, 23, 26, 28, 31, 32, 33, 35, 36, 38, 41, 44, 45, 46, 48, 49, 51, 52, 53, 54, 55, 56, 57, 58, 61, 62, 68, 73, 74, 77, 78, 82, 83, 84, 85, 86, 87, 91, 92, 93, 94, 95, 96, 97, 100, 101, 138, 139, 141, 145, 146, 147, 150, 151, 163, 164, 167, 170, 171, 175, 177, 179, 180, 181, 182, 183, 184, 185, 188, 189, 190, 191, 192, 193, 195, 196, 197, 198, 200, 201, 202, 203, 204, 206, 207, 209, 210, 211, 212, 214, 216, 220, 223, 224, 226, 227, 229, 230, 231, 233, 235, 237, 240, 241, 244, 245, 246, 249, 252, 253, 254, 256, 257, 258, 259, 260, 261, 262, 263, 264, 295, 296, 303, 304, 305, 306, 307, 308, 309, 311, 312, 313, 315, 316, 317, 318, 319, 320, 321, and 329, or the nucleotide sequence in which the nucleic acid u is replaced with t, examples of the longest variants registered in miRBase Release 21 include polynucleotides represented by SEQ ID NOs: 666, 668, 669, 671, 674, 676, 679, 681, 683, 685, 687, 691, 693, 697, 699, 701, 703, 705, 707, 709, 712, 713, 715, 717, 719, 721, 723, 724, 726, 728, 730, 732, 734, 736, 738, 743, 748, 750, 752, 754, 757, 759, 761, 763, 765, 767, 770, 772, 774, 776, 778, 779, 781, 783, 785, 787, 789, 792, 795, 797, 799, 803, 805, 808, 810, 812, 815, 817, 819, 821, 824, 826, 828, 830, 832, 834, 836, 840, 842, 844, 846, 848, 850, 853, 855, 857, 859, 862, 864, 866, 868, 870, 873, 875, 877, 879, 881, 883, 886, 889, 892, 896, 898, 901, 903, 904, 906, 908, 911, 912, 914, 917, 919, 923, 925, 927, 930, 933, 935, 937, 940, 942, 944, 946, 948, 950, 952, 954, 956, 960, 962, 964, 966, 968, 970, 972, 974, 976, 978, 980, 982, 985, 987, 989, 991, 993, 994, 996, and 999, respectively. Also, according to the present invention, among the variants of polynucleotides consisting of the nucleotide sequence represented by any of SEQ ID NOs: 3, 4, 8, 9, 10, 13, 14, 17, 18, 20, 21, 22, 23, 24, 25, 26, 28, 29, 30, 31, 32, 33, 35, 36, 38, 41, 43, 45, 46, 48, 49, 51, 53, 54, 55, 56, 57, 58, 61, 62, 65, 66, 67, 68, 69, 71, 72, 73, 74, 77, 78, 80, 82, 83, 84, 85, 86, 87, 89, 91, 92, 93, 94, 96, 97, 100, 114, 138, 139, 140, 141, 142, 145, 146, 147, 148, 149, 150, 151, 162, 163, 164, 167, 168, 170, 171, 175, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 209, 210, 211, 212, 213, 214, 215, 216, 219, 220, 221, 222, 223, 224, 225, 226, 229, 230, 231, 232, 235, 237, 238, 240, 241, 242, 243, 244, 245, 246, 248, 249, 251, 252, 253, 254, 255, 256, 257, 258, 259, 260, 261, 262, 263, 264, 271, 293, 295, 296, 303, 304, 305, 306, 307, 308, 309, 311, 312, 313, 314, 315, 316, 317, 318, 320, 321, 328, and 329, or the nucleotide sequence in which the nucleic acid u is replaced with t, examples of the shortest variants registered in the miRBase Release 21 include polynucleotides having sequences represented by SEQ ID NOs: 665, 667, 670, 672, 673, 675, 677, 678, 680, 682, 684, 686, 688, 689, 690, 692, 694, 695, 696, 698, 700, 702, 704, 706, 708, 710, 711, 714, 716, 718, 720, 722, 725, 727, 729, 731, 733, 735, 737, 739, 740, 741, 742, 744, 745, 746, 747, 749, 751, 753, 755, 756, 758, 760, 762, 764, 766, 768, 769, 771, 773, 775, 777, 780, 782, 784, 786, 788, 790, 791, 793, 794, 796, 798, 800, 801, 802, 804, 806, 807, 809, 811, 813, 814, 816, 818, 820, 822, 823, 825, 827, 829, 831, 833, 835, 837, 838, 839, 841, 843, 845, 847, 849, 851, 852, 854, 856, 858, 860, 861, 863, 865, 867, 869, 871, 872, 874, 876, 878, 880, 882, 884, 885, 887, 888, 890, 891, 893, 894, 895, 897, 899, 900, 902, 905, 907, 909, 910, 913, 915, 916, 918, 920, 921, 922, 924, 926, 928, 929, 931, 932, 934, 936, 938, 939, 941, 943, 945, 947, 949, 951, 953, 955, 957, 958, 959, 961, 963, 965, 967, 969, 971, 973, 975, 977, 979, 981, 983, 984, 986, 988, 990, 992, 995, 997, 998, and 1000, respectively. In addition to these variants and fragments, examples thereof include a large number of isomiR polynucleotides of SEQ ID NOs: 1 to 329 registered in the miRBase. Examples of the polynucleotide comprising a nucleotide sequence represented by any of SEQ ID NOs: 1 to 329 include a polynucleotide represented by any of SEQ ID NOs: 330 to 664, which are their respective precursors.

The names and miRBase Accession Nos. (registration numbers) of the genes represented by SEQ ID NOs: 1 to 1000 are shown in Table 1.

As used herein, the term "capable of specifically binding" means that nucleic acids such as the nucleic acid probe or the primer used in the present invention binds to a particular target nucleic acid and cannot substantially bind to other nucleic acids.

TABLE 1

| SEQ ID NO: | Name of gene | Accession No. of miRBase |
|---|---|---|
| 1 | hsa-miR-6787-5p | MIMAT0027474 |
| 2 | hsa-miR-920 | MIMAT0004970 |
| 3 | hsa-miR-3622a-5p | MIMAT0018003 |
| 4 | hsa-miR-1185-1-3p | MIMAT0022838 |
| 5 | hsa-miR-4327 | MIMAT0016889 |
| 6 | hsa-miR-5739 | MIMAT0023116 |
| 7 | hsa-miR-937-5p | MIMAT0022938 |
| 8 | hsa-miR-1181 | MIMAT0005826 |
| 9 | hsa-miR-1185-2-3p | MIMAT0022713 |
| 10 | hsa-miR-1193 | MIMAT0015049 |
| 11 | hsa-miR-1207-5p | MIMAT0005871 |
| 12 | hsa-miR-1238-5p | MIMAT0022947 |
| 13 | hsa-miR-1246 | MIMAT0005898 |
| 14 | hsa-miR-1249-5p | MIMAT0032029 |
| 15 | hsa-miR-1292-3p | MIMAT0022948 |
| 16 | hsa-miR-1469 | MIMAT0007347 |
| 17 | hsa-miR-1470 | MIMAT0007348 |
| 18 | hsa-miR-197-5p | MIMAT0022691 |
| 19 | hsa-miR-208a-5p | MIMAT0026474 |
| 20 | hsa-miR-2110 | MIMAT0010133 |
| 21 | hsa-miR-211-3p | MIMAT0022694 |
| 22 | hsa-miR-2467-3p | MIMAT0019953 |
| 23 | hsa-miR-3122 | MIMAT0014984 |
| 24 | hsa-miR-3141 | MIMAT0015010 |
| 25 | hsa-miR-3156-5p | MIMAT0015030 |
| 26 | hsa-miR-3158-5p | MIMAT0019211 |
| 27 | hsa-miR-3160-5p | MIMAT0019212 |
| 28 | hsa-miR-3180-3p | MIMAT0015058 |
| 29 | hsa-miR-3191-3p | MIMAT0015075 |
| 30 | hsa-miR-3194-3p | MIMAT0019218 |
| 31 | hsa-miR-320b | MIMAT0005792 |
| 32 | hsa-miR-328-5p | MIMAT0026486 |
| 33 | hsa-miR-3610 | MIMAT0017987 |
| 34 | hsa-miR-3619-3p | MIMAT0019219 |
| 35 | hsa-miR-3620-5p | MIMAT0022967 |
| 36 | hsa-miR-370-3p | MIMAT0000722 |
| 37 | hsa-miR-373-5p | MIMAT0000725 |
| 38 | hsa-miR-3917 | MIMAT0018191 |
| 39 | hsa-miR-3937 | MIMAT0018352 |
| 40 | hsa-miR-4259 | MIMAT0016880 |
| 41 | hsa-miR-4281 | MIMAT0016907 |
| 42 | hsa-miR-4294 | MIMAT0016849 |
| 43 | hsa-miR-4419b | MIMAT0019034 |
| 44 | hsa-miR-4428 | MIMAT0018943 |
| 45 | hsa-miR-4429 | MIMAT0018944 |
| 46 | hsa-miR-4433a-3p | MIMAT0018949 |
| 47 | hsa-miR-4447 | MIMAT0018966 |
| 48 | hsa-miR-4449 | MIMAT0018968 |
| 49 | hsa-miR-4459 | MIMAT0018981 |
| 50 | hsa-miR-4480 | MIMAT0019014 |
| 51 | hsa-miR-4485-5p | MIMAT0032116 |
| 52 | hsa-miR-4486 | MIMAT0019020 |
| 53 | hsa-miR-4488 | MIMAT0019022 |
| 54 | hsa-miR-4489 | MIMAT0019023 |
| 55 | hsa-miR-4505 | MIMAT0019041 |
| 56 | hsa-miR-4513 | MIMAT0019050 |
| 57 | hsa-miR-4515 | MIMAT0019052 |
| 58 | hsa-miR-4530 | MIMAT0019069 |
| 59 | hsa-miR-4535 | MIMAT0019075 |
| 60 | hsa-miR-4635 | MIMAT0019692 |
| 61 | hsa-miR-4640-5p | MIMAT0019699 |
| 62 | hsa-miR-4646-5p | MIMAT0019707 |
| 63 | hsa-miR-4656 | MIMAT0019723 |
| 64 | hsa-miR-4663 | MIMAT0019735 |
| 65 | hsa-miR-4665-5p | MIMAT0019739 |
| 66 | hsa-miR-4706 | MIMAT0019806 |
| 67 | hsa-miR-4707-5p | MIMAT0019807 |
| 68 | hsa-miR-4708-3p | MIMAT0019810 |
| 69 | hsa-miR-4710 | MIMAT0019815 |
| 70 | hsa-miR-4718 | MIMAT0019831 |
| 71 | hsa-miR-4722-5p | MIMAT0019836 |
| 72 | hsa-miR-4727-3p | MIMAT0019848 |
| 73 | hsa-miR-4730 | MIMAT0019852 |
| 74 | hsa-miR-4734 | MIMAT0019859 |
| 75 | hsa-miR-4740-5p | MIMAT0019869 |
| 76 | hsa-miR-4747-3p | MIMAT0019883 |
| 77 | hsa-miR-4749-5p | MIMAT0019885 |

TABLE 1-continued

| SEQ ID NO: | Name of gene | Accession No. of miRBase |
|---|---|---|
| 78 | hsa-miR-4755-3p | MIMAT0019896 |
| 79 | hsa-miR-4763-5p | MIMAT0019912 |
| 80 | hsa-miR-4787-3p | MIMAT0019957 |
| 81 | hsa-miR-5008-5p | MIMAT0021039 |
| 82 | hsa-miR-5010-5p | MIMAT0021043 |
| 83 | hsa-miR-504-3p | MIMAT0026612 |
| 84 | hsa-miR-5090 | MIMAT0021082 |
| 85 | hsa-miR-5100 | MIMAT0022259 |
| 86 | hsa-miR-5196-5p | MIMAT0021128 |
| 87 | hsa-miR-551b-5p | MIMAT0004794 |
| 88 | hsa-miR-557 | MIMAT0003221 |
| 89 | hsa-miR-5787 | MIMAT0023252 |
| 90 | hsa-miR-6090 | MIMAT0023715 |
| 91 | hsa-miR-6124 | MIMAT0024597 |
| 92 | hsa-miR-6132 | MIMAT0024616 |
| 93 | hsa-miR-6510-5p | MIMAT0025476 |
| 94 | hsa-miR-6511b-5p | MIMAT0025847 |
| 95 | hsa-miR-6515-3p | MIMAT0025487 |
| 96 | hsa-miR-654-5p | MIMAT0003330 |
| 97 | hsa-miR-658 | MIMAT0003336 |
| 98 | hsa-miR-668-5p | MIMAT0026636 |
| 99 | hsa-miR-6722-5p | MIMAT0025853 |
| 100 | hsa-miR-6724-5p | MIMAT0025856 |
| 101 | hsa-miR-6729-3p | MIMAT0027360 |
| 102 | hsa-miR-6737-5p | MIMAT0027375 |
| 103 | hsa-miR-6756-5p | MIMAT0027412 |
| 104 | hsa-miR-6762-5p | MIMAT0027424 |
| 105 | hsa-miR-6763-3p | MIMAT0027427 |
| 106 | hsa-miR-6766-5p | MIMAT0027432 |
| 107 | hsa-miR-6769a-5p | MIMAT0027438 |
| 108 | hsa-miR-6771-5p | MIMAT0027442 |
| 109 | hsa-miR-6786-5p | MIMAT0027472 |
| 110 | hsa-miR-6789-5p | MIMAT0027478 |
| 111 | hsa-miR-6794-5p | MIMAT0027488 |
| 112 | hsa-miR-6796-3p | MIMAT0027493 |
| 113 | hsa-miR-6797-5p | MIMAT0027494 |
| 114 | hsa-miR-6800-3p | MIMAT0027501 |
| 115 | hsa-miR-6802-5p | MIMAT0027504 |
| 116 | hsa-miR-6803-5p | MIMAT0027506 |
| 117 | hsa-miR-6805-3p | MIMAT0027511 |
| 118 | hsa-miR-6805-5p | MIMAT0027510 |
| 119 | hsa-miR-6807-5p | MIMAT0027514 |
| 120 | hsa-miR-6812-5p | MIMAT0027524 |
| 121 | hsa-miR-6819-5p | MIMAT0027538 |
| 122 | hsa-miR-6822-5p | MIMAT0027544 |
| 123 | hsa-miR-6824-5p | MIMAT0027548 |
| 124 | hsa-miR-6826-5p | MIMAT0027552 |
| 125 | hsa-miR-6850-5p | MIMAT0027600 |
| 126 | hsa-miR-6858-5p | MIMAT0027616 |
| 127 | hsa-miR-6861-5p | MIMAT0027623 |
| 128 | hsa-miR-6880-3p | MIMAT0027661 |
| 129 | hsa-miR-7107-5p | MIMAT0028111 |
| 130 | hsa-miR-7109-5p | MIMAT0028115 |
| 131 | hsa-miR-7114-5p | MIMAT0028125 |
| 132 | hsa-miR-7704 | MIMAT0030019 |
| 133 | hsa-miR-7846-3p | MIMAT0030421 |
| 134 | hsa-miR-8052 | MIMAT0030979 |
| 135 | hsa-miR-8060 | MIMAT0030987 |
| 136 | hsa-miR-8071 | MIMAT0030998 |
| 137 | hsa-miR-8073 | MIMAT0031000 |
| 138 | hsa-miR-874-5p | MIMAT0026718 |
| 139 | hsa-miR-204-3p | MIMAT0022693 |
| 140 | hsa-miR-3154 | MIMAT0015028 |
| 141 | hsa-miR-3960 | MIMAT0019337 |
| 142 | hsa-miR-4433a-5p | MIMAT0020956 |
| 143 | hsa-miR-4455 | MIMAT0018977 |
| 144 | hsa-miR-4462 | MIMAT0018986 |
| 145 | hsa-miR-4476 | MIMAT0019003 |
| 146 | hsa-miR-4508 | MIMAT0019045 |
| 147 | hsa-miR-4687-3p | MIMAT0019775 |
| 148 | hsa-miR-4687-5p | MIMAT0019774 |
| 149 | hsa-miR-4732-5p | MIMAT0019855 |
| 150 | hsa-miR-4771 | MIMAT0019925 |
| 151 | hsa-miR-642a-3p | MIMAT0020924 |
| 152 | hsa-miR-6732-5p | MIMAT0027365 |
| 153 | hsa-miR-6760-5p | MIMAT0027420 |
| 154 | hsa-miR-6799-5p | MIMAT0027498 |
| 155 | hsa-miR-6820-5p | MIMAT0027540 |
| 156 | hsa-miR-6821-5p | MIMAT0027542 |
| 157 | hsa-miR-6829-5p | MIMAT0027558 |
| 158 | hsa-miR-6893-5p | MIMAT0027686 |
| 159 | hsa-miR-7108-5p | MIMAT0028114 |
| 160 | hsa-miR-7111-5p | MIMAT0028119 |
| 161 | hsa-miR-8089 | MIMAT0031016 |
| 162 | hsa-miR-885-3p | MIMAT0004948 |
| 163 | hsa-miR-92b-3p | MIMAT0003218 |
| 164 | hsa-miR-1343-3p | MIMAT0019776 |
| 165 | hsa-miR-6746-5p | MIMAT0027392 |
| 166 | hsa-miR-422a | MIMAT0001339 |
| 167 | hsa-miR-187-5p | MIMAT0004561 |
| 168 | hsa-miR-4632-5p | MIMAT0022977 |
| 169 | hsa-miR-6791-5p | MIMAT0027482 |
| 170 | hsa-miR-103a-3p | MIMAT0000101 |
| 171 | hsa-miR-107 | MIMAT0000104 |
| 172 | hsa-miR-1199-5p | MIMAT0031119 |
| 173 | hsa-miR-1225-3p | MIMAT0005573 |
| 174 | hsa-miR-1225-5p | MIMAT0005572 |
| 175 | hsa-miR-1228-5p | MIMAT0005582 |
| 176 | hsa-miR-1229-5p | MIMAT0022942 |
| 177 | hsa-miR-1233-5p | MIMAT0022943 |
| 178 | hsa-miR-1237-5p | MIMAT0022946 |
| 179 | hsa-miR-1247-3p | MIMAT0022721 |
| 180 | hsa-miR-1249-3p | MIMAT0005901 |
| 181 | hsa-miR-1254 | MIMAT0005905 |
| 182 | hsa-miR-1260b | MIMAT0015041 |
| 183 | hsa-miR-1268a | MIMAT0005922 |
| 184 | hsa-miR-1268b | MIMAT0018925 |
| 185 | hsa-miR-1273g-3p | MIMAT0022742 |
| 186 | hsa-miR-128-1-5p | MIMAT0026477 |
| 187 | hsa-miR-128-2-5p | MIMAT0031095 |
| 188 | hsa-miR-1290 | MIMAT0005880 |
| 189 | hsa-miR-150-3p | MIMAT0004610 |
| 190 | hsa-miR-17-3p | MIMAT0000071 |
| 191 | hsa-miR-1908-5p | MIMAT0007881 |
| 192 | hsa-miR-1909-3p | MIMAT0007883 |
| 193 | hsa-miR-1914-3p | MIMAT0007890 |
| 194 | hsa-miR-1915-3p | MIMAT0007892 |
| 195 | hsa-miR-191-5p | MIMAT0000440 |
| 196 | hsa-miR-22-3p | MIMAT0000077 |
| 197 | hsa-miR-23b-3p | MIMAT0000418 |
| 198 | hsa-miR-24-3p | MIMAT0000080 |
| 199 | hsa-miR-296-3p | MIMAT0004679 |
| 200 | hsa-miR-296-5p | MIMAT0000690 |
| 201 | hsa-miR-3131 | MIMAT0014996 |
| 202 | hsa-miR-3162-5p | MIMAT0015036 |
| 203 | hsa-miR-3188 | MIMAT0015070 |
| 204 | hsa-miR-3196 | MIMAT0015080 |
| 205 | hsa-miR-3197 | MIMAT0015082 |
| 206 | hsa-miR-320a | MIMAT0000510 |
| 207 | hsa-miR-342-5p | MIMAT0004694 |
| 208 | hsa-miR-3621 | MIMAT0018002 |
| 209 | hsa-miR-3648 | MIMAT0018068 |
| 210 | hsa-miR-3656 | MIMAT0018076 |
| 211 | hsa-miR-365a-5p | MIMAT0009199 |
| 212 | hsa-miR-3665 | MIMAT0018087 |
| 213 | hsa-miR-3679-5p | MIMAT0018104 |
| 214 | hsa-miR-371a-5p | MIMAT0004687 |
| 215 | hsa-miR-3940-5p | MIMAT0019229 |
| 216 | hsa-miR-423-5p | MIMAT0004748 |
| 217 | hsa-miR-4257 | MIMAT0016878 |
| 218 | hsa-miR-4270 | MIMAT0016900 |
| 219 | hsa-miR-4271 | MIMAT0016901 |
| 220 | hsa-miR-4286 | MIMAT0016916 |
| 221 | hsa-miR-4298 | MIMAT0016852 |
| 222 | hsa-miR-4417 | MIMAT0018929 |
| 223 | hsa-miR-4442 | MIMAT0018960 |
| 224 | hsa-miR-4446-3p | MIMAT0018965 |
| 225 | hsa-miR-4448 | MIMAT0018967 |
| 226 | hsa-miR-4454 | MIMAT0018976 |
| 227 | hsa-miR-4467 | MIMAT0018994 |
| 228 | hsa-miR-4472 | MIMAT0018999 |
| 229 | hsa-miR-4507 | MIMAT0019044 |
| 230 | hsa-miR-4516 | MIMAT0019053 |
| 231 | hsa-miR-451a | MIMAT0001631 |

TABLE 1-continued

| SEQ ID NO: | Name of gene | Accession No. of miRBase |
|---|---|---|
| 232 | hsa-miR-4649-5p | MIMAT0019711 |
| 233 | hsa-miR-4651 | MIMAT0019715 |
| 234 | hsa-miR-4665-3p | MIMAT0019740 |
| 235 | hsa-miR-4674 | MIMAT0019756 |
| 236 | hsa-miR-4675 | MIMAT0019757 |
| 237 | hsa-miR-4689 | MIMAT0019778 |
| 238 | hsa-miR-4695-5p | MIMAT0019788 |
| 239 | hsa-miR-4697-5p | MIMAT0019791 |
| 240 | hsa-miR-4725-3p | MIMAT0019844 |
| 241 | hsa-miR-4739 | MIMAT0019868 |
| 242 | hsa-miR-4745-5p | MIMAT0019878 |
| 243 | hsa-miR-4763-3p | MIMAT0019913 |
| 244 | hsa-miR-4792 | MIMAT0019964 |
| 245 | hsa-miR-486-3p | MIMAT0004762 |
| 246 | hsa-miR-5001-5p | MIMAT0021021 |
| 247 | hsa-miR-5195-3p | MIMAT0021127 |
| 248 | hsa-miR-550a-5p | MIMAT0004800 |
| 249 | hsa-miR-5698 | MIMAT0022491 |
| 250 | hsa-miR-6075 | MIMAT0023700 |
| 251 | hsa-miR-6088 | MIMAT0023713 |
| 252 | hsa-miR-6089 | MIMAT0023714 |
| 253 | hsa-miR-6125 | MIMAT0024598 |
| 254 | hsa-miR-6126 | MIMAT0024599 |
| 255 | hsa-miR-614 | MIMAT0003282 |
| 256 | hsa-miR-615-5p | MIMAT0004804 |
| 257 | hsa-miR-619-5p | MIMAT0026622 |
| 258 | hsa-miR-638 | MIMAT0003308 |
| 259 | hsa-miR-642b-3p | MIMAT0018444 |
| 260 | hsa-miR-650 | MIMAT0003320 |
| 261 | hsa-miR-663a | MIMAT0003326 |
| 262 | hsa-miR-663b | MIMAT0005867 |
| 263 | hsa-miR-6717-5p | MIMAT0025846 |
| 264 | hsa-miR-6721-5p | MIMAT0025852 |
| 265 | hsa-miR-6726-5p | MIMAT0027353 |
| 266 | hsa-miR-6727-5p | MIMAT0027355 |
| 267 | hsa-miR-6738-5p | MIMAT0027377 |
| 268 | hsa-miR-6741-5p | MIMAT0027383 |
| 269 | hsa-miR-6749-5p | MIMAT0027398 |
| 270 | hsa-miR-6752-5p | MIMAT0027404 |
| 271 | hsa-miR-675-5p | MIMAT0004284 |
| 272 | hsa-miR-6757-5p | MIMAT0027414 |
| 273 | hsa-miR-6763-5p | MIMAT0027426 |
| 274 | hsa-miR-6765-5p | MIMAT0027430 |
| 275 | hsa-miR-6775-5p | MIMAT0027450 |
| 276 | hsa-miR-6780b-5p | MIMAT0027572 |
| 277 | hsa-miR-6782-5p | MIMAT0027464 |
| 278 | hsa-miR-6784-5p | MIMAT0027468 |
| 279 | hsa-miR-6800-5p | MIMAT0027500 |
| 280 | hsa-miR-6806-5p | MIMAT0027512 |
| 281 | hsa-miR-6840-3p | MIMAT0027583 |
| 282 | hsa-miR-6848-5p | MIMAT0027596 |
| 283 | hsa-miR-6851-5p | MIMAT0027602 |
| 284 | hsa-miR-6870-5p | MIMAT0027640 |
| 285 | hsa-miR-6872-3p | MIMAT0027645 |
| 286 | hsa-miR-6875-5p | MIMAT0027650 |
| 287 | hsa-miR-6877-5p | MIMAT0027654 |
| 288 | hsa-miR-6879-5p | MIMAT0027658 |
| 289 | hsa-miR-6880-5p | MIMAT0027660 |
| 290 | hsa-miR-6885-5p | MIMAT0027670 |
| 291 | hsa-miR-6887-5p | MIMAT0027674 |
| 292 | hsa-miR-7108-5p | MIMAT0028113 |
| 293 | hsa-miR-711 | MIMAT0012734 |
| 294 | hsa-miR-7113-3p | MIMAT0028124 |
| 295 | hsa-miR-744-5p | MIMAT0004945 |
| 296 | hsa-miR-760 | MIMAT0004957 |
| 297 | hsa-miR-7845-5p | MIMAT0030420 |
| 298 | hsa-miR-7847-3p | MIMAT0030422 |
| 299 | hsa-miR-7977 | MIMAT0031180 |
| 300 | hsa-miR-8059 | MIMAT0030986 |
| 301 | hsa-miR-8063 | MIMAT0030990 |
| 302 | hsa-miR-8072 | MIMAT0030999 |
| 303 | hsa-miR-874-3p | MIMAT0004911 |
| 304 | hsa-miR-92a-2-5p | MIMAT0004508 |
| 305 | hsa-miR-92b-5p | MIMAT0004792 |
| 306 | hsa-miR-940 | MIMAT0004983 |
| 307 | hsa-miR-1228-3p | MIMAT0005583 |
| 308 | hsa-miR-1275 | MIMAT0005929 |
| 309 | hsa-miR-1307-3p | MIMAT0005951 |
| 310 | hsa-miR-1343-5p | MIMAT0027038 |
| 311 | hsa-miR-23a-3p | MIMAT0000078 |
| 312 | hsa-miR-29b-3p | MIMAT0000100 |
| 313 | hsa-miR-3135b | MIMAT0018985 |
| 314 | hsa-miR-3185 | MIMAT0015065 |
| 315 | hsa-miR-4532 | MIMAT0019071 |
| 316 | hsa-miR-4690-5p | MIMAT0019779 |
| 317 | hsa-miR-4758-5p | MIMAT0019903 |
| 318 | hsa-miR-4783-3p | MIMAT0019947 |
| 319 | hsa-miR-6131 | MIMAT0024615 |
| 320 | hsa-miR-625-3p | MIMAT0004808 |
| 321 | hsa-miR-6511a-5p | MIMAT0025478 |
| 322 | hsa-miR-6765-3p | MIMAT0027431 |
| 323 | hsa-miR-6816-5p | MIMAT0027532 |
| 324 | hsa-miR-6825-5p | MIMAT0027550 |
| 325 | hsa-miR-6845-5p | MIMAT0027590 |
| 326 | hsa-miR-7150 | MIMAT0028211 |
| 327 | hsa-miR-7641 | MIMAT0029782 |
| 328 | hsa-miR-7975 | MIMAT0031178 |
| 329 | hsa-miR-92a-3p | MIMAT0000092 |
| 330 | hsa-mir-6787 | MI0022632 |
| 331 | hsa-mir-920 | MI0005712 |
| 332 | hsa-mir-3622a | MI0016013 |
| 333 | hsa-mir-1185-1 | MI0003844 |
| 334 | hsa-mir-4327 | MI0015867 |
| 335 | hsa-mir-5739 | MI0019412 |
| 336 | hsa-mir-937 | MI0005759 |
| 337 | hsa-mir-1181 | MI0006274 |
| 338 | hsa-mir-1185-2 | MI0003821 |
| 339 | hsa-mir-1193 | MI0014205 |
| 340 | hsa-mir-1207 | MI0006340 |
| 341 | hsa-mir-1238 | MI0006328 |
| 342 | hsa-mir-1246 | MI0006381 |
| 343 | hsa-mir-1249 | MI0006384 |
| 344 | hsa-mir-1292 | MI0006433 |
| 345 | hsa-mir-1469 | MI0007074 |
| 346 | hsa-mir-1470 | MI0007075 |
| 347 | hsa-mir-197 | MI0000239 |
| 348 | hsa-mir-208a | MI0000251 |
| 349 | hsa-mir-2110 | MI0010629 |
| 350 | hsa-mir-211 | MI0000287 |
| 351 | hsa-mir-2467 | MI0017432 |
| 352 | hsa-mir-3122 | MI0014138 |
| 353 | hsa-mir-3141 | MI0014165 |
| 354 | hsa-mir-3156-1 | MI0014184 |
| 355 | hsa-mir-3156-2 | MI0014230 |
| 356 | hsa-mir-3156-3 | MI0014242 |
| 357 | hsa-mir-3158-1 | MI0014186 |
| 358 | hsa-mir-3158-2 | MI0014187 |
| 359 | hsa-mir-3160-1 | MI0014189 |
| 360 | hsa-mir-3160-2 | MI0014190 |
| 361 | hsa-mir-3180-1 | MI0014214 |
| 362 | hsa-mir-3180-2 | MI0014215 |
| 363 | hsa-mir-3180-3 | MI0014217 |
| 364 | hsa-mir-3191 | MI0014236 |
| 365 | hsa-mir-3194 | MI0014239 |
| 366 | hsa-mir-320b-1 | MI0003776 |
| 367 | hsa-mir-320b-2 | MI0003839 |
| 368 | hsa-mir-328 | MI0000804 |
| 369 | hsa-mir-3610 | MI0016000 |
| 370 | hsa-mir-3619 | MI0016009 |
| 371 | hsa-mir-3620 | MI0016011 |
| 372 | hsa-mir-370 | MI0000778 |
| 373 | hsa-mir-373 | MI0000781 |
| 374 | hsa-mir-3917 | MI0016423 |
| 375 | hsa-mir-3937 | MI0016593 |
| 376 | hsa-mir-4259 | MI0015858 |
| 377 | hsa-mir-4281 | MI0015885 |
| 378 | hsa-mir-4294 | MI0015827 |
| 379 | hsa-mir-4419b | MI0016861 |
| 380 | hsa-mir-4428 | MI0016767 |
| 381 | hsa-mir-4429 | MI0016768 |
| 382 | hsa-mir-4433a | MI0016773 |
| 383 | hsa-mir-4447 | MI0016790 |
| 384 | hsa-mir-4449 | MI0016792 |
| 385 | hsa-mir-4459 | MI0016805 |

TABLE 1-continued

| SEQ ID NO: | Name of gene | Accession No. of miRBase |
|---|---|---|
| 386 | hsa-mir-4480 | MI0016841 |
| 387 | hsa-mir-4485 | MI0016846 |
| 388 | hsa-mir-4486 | MI0016847 |
| 389 | hsa-mir-4488 | MI0016849 |
| 390 | hsa-mir-4489 | MI0016850 |
| 391 | hsa-mir-4505 | MI0016868 |
| 392 | hsa-mir-4513 | MI0016879 |
| 393 | hsa-mir-4515 | MI0016881 |
| 394 | hsa-mir-4530 | MI0016897 |
| 395 | hsa-mir-4535 | MI0016903 |
| 396 | hsa-mir-4635 | MI0017262 |
| 397 | hsa-mir-4640 | MI0017267 |
| 398 | hsa-mir-4646 | MI0017273 |
| 399 | hsa-mir-4656 | MI0017284 |
| 400 | hsa-mir-4663 | MI0017292 |
| 401 | hsa-mir-4665 | MI0017295 |
| 402 | hsa-mir-4706 | MI0017339 |
| 403 | hsa-mir-4707 | MI0017340 |
| 404 | hsa-mir-4708 | MI0017341 |
| 405 | hsa-mir-4710 | MI0017344 |
| 406 | hsa-mir-4718 | MI0017353 |
| 407 | hsa-mir-4722 | MI0017357 |
| 408 | hsa-mir-4727 | MI0017364 |
| 409 | hsa-mir-4730 | MI0017367 |
| 410 | hsa-mir-4734 | MI0017371 |
| 411 | hsa-mir-4740 | MI0017378 |
| 412 | hsa-mir-4747 | MI0017386 |
| 413 | hsa-mir-4749 | MI0017388 |
| 414 | hsa-mir-4755 | MI0017395 |
| 415 | hsa-mir-4763 | MI0017404 |
| 416 | hsa-mir-4787 | MI0017434 |
| 417 | hsa-mir-5008 | MI0017876 |
| 418 | hsa-mir-5010 | MI0017878 |
| 419 | hsa-mir-504 | MI0003189 |
| 420 | hsa-mir-5090 | MI0017979 |
| 421 | hsa-mir-5100 | MI0019116 |
| 422 | hsa-mir-5196 | MI0018175 |
| 423 | hsa-mir-551b | MI0003575 |
| 424 | hsa-mir-557 | MI0003563 |
| 425 | hsa-mir-5787 | MI0019797 |
| 426 | hsa-mir-6090 | MI0020367 |
| 427 | hsa-mir-6124 | MI0021258 |
| 428 | hsa-mir-6132 | MI0021277 |
| 429 | hsa-mir-6510 | MI0022222 |
| 430 | hsa-mir-6511b-1 | MI0022552 |
| 431 | hsa-mir-6511b-2 | MI0023431 |
| 432 | hsa-mir-6515 | MI0022227 |
| 433 | hsa-mir-654 | MI0003676 |
| 434 | hsa-mir-658 | MI0003682 |
| 435 | hsa-mir-668 | MI0003761 |
| 436 | hsa-mir-6722 | MI0022557 |
| 437 | hsa-mir-6724 | MI0022559 |
| 438 | hsa-mir-6729 | MI0022574 |
| 439 | hsa-mir-6737 | MI0022582 |
| 440 | hsa-mir-6756 | MI0022601 |
| 441 | hsa-mir-6762 | MI0022607 |
| 442 | hsa-mir-6763 | MI0022608 |
| 443 | hsa-mir-6766 | MI0022611 |
| 444 | hsa-mir-6769a | MI0022614 |
| 445 | hsa-mir-6771 | MI0022616 |
| 446 | hsa-mir-6786 | MI0022631 |
| 447 | hsa-mir-6789 | MI0022634 |
| 448 | hsa-mir-6794 | MI0022639 |
| 449 | hsa-mir-6796 | MI0022641 |
| 450 | hsa-mir-6797 | MI0022642 |
| 451 | hsa-mir-6800 | MI0022645 |
| 452 | hsa-mir-6802 | MI0022647 |
| 453 | hsa-mir-6803 | MI0022648 |
| 454 | hsa-mir-6805 | MI0022650 |
| 455 | hsa-mir-6807 | MI0022652 |
| 456 | hsa-mir-6812 | MI0022657 |
| 457 | hsa-mir-6819 | MI0022664 |
| 458 | hsa-mir-6822 | MI0022667 |
| 459 | hsa-mir-6824 | MI0022669 |
| 460 | hsa-mir-6826 | MI0022671 |
| 461 | hsa-mir-6850 | MI0022696 |
| 462 | hsa-mir-6858 | MI0022704 |
| 463 | hsa-mir-6861 | MI0022708 |
| 464 | hsa-mir-6880 | MI0022727 |
| 465 | hsa-mir-7107 | MI0022958 |
| 466 | hsa-mir-7109 | MI0022960 |
| 467 | hsa-mir-7114 | MI0022965 |
| 468 | hsa-mir-7704 | MI0025240 |
| 469 | hsa-mir-7846 | MI0025516 |
| 470 | hsa-mir-8052 | MI0025888 |
| 471 | hsa-mir-8060 | MI0025896 |
| 472 | hsa-mir-8071-1 | MI0025907 |
| 473 | hsa-mir-8071-2 | MI0026417 |
| 474 | hsa-mir-8073 | MI0025909 |
| 475 | hsa-mir-874 | MI0005532 |
| 476 | hsa-mir-204 | MI0000284 |
| 477 | hsa-mir-3154 | MI0014182 |
| 478 | hsa-mir-3960 | MI0016964 |
| 479 | hsa-mir-4455 | MI0016801 |
| 480 | hsa-mir-4462 | MI0016810 |
| 481 | hsa-mir-4476 | MI0016828 |
| 482 | hsa-mir-4508 | MI0016872 |
| 483 | hsa-mir-4687 | MI0017319 |
| 484 | hsa-mir-4732 | MI0017369 |
| 485 | hsa-mir-4771-1 | MI0017412 |
| 486 | hsa-mir-4771-2 | MI0017413 |
| 487 | hsa-mir-642a | MI0003657 |
| 488 | hsa-mir-6732 | MI0022577 |
| 489 | hsa-mir-6760 | MI0022605 |
| 490 | hsa-mir-6799 | MI0022644 |
| 491 | hsa-mir-6820 | MI0022665 |
| 492 | hsa-mir-6821 | MI0022666 |
| 493 | hsa-mir-6829 | MI0022674 |
| 494 | hsa-mir-6893 | MI0022740 |
| 495 | hsa-mir-7108 | MI0022959 |
| 496 | hsa-mir-7111 | MI0022962 |
| 497 | hsa-mir-8089 | MI0025925 |
| 498 | hsa-mir-885 | MI0005560 |
| 499 | hsa-mir-92b | MI0003560 |
| 500 | hsa-mir-1343 | MI0017320 |
| 501 | hsa-mir-6746 | MI0022591 |
| 502 | hsa-mir-422a | MI0001444 |
| 503 | hsa-mir-187 | MI0000274 |
| 504 | hsa-mir-4632 | MI0017259 |
| 505 | hsa-mir-6791 | MI0022636 |
| 506 | hsa-mir-103a-2 | MI0000109 |
| 507 | hsa-mir-103a-1 | MI0000108 |
| 508 | hsa-mir-107 | MI0000114 |
| 509 | hsa-mir-1199 | MI0020340 |
| 510 | hsa-mir-1225 | MI0006311 |
| 511 | hsa-mir-1228 | MI0006318 |
| 512 | hsa-mir-1229 | MI0006319 |
| 513 | hsa-mir-1233-1 | MI0006323 |
| 514 | hsa-mir-1233-2 | MI0015973 |
| 515 | hsa-mir-1237 | MI0006327 |
| 516 | hsa-mir-1247 | MI0006382 |
| 517 | hsa-mir-1254-1 | MI0006388 |
| 518 | hsa-mir-1254-2 | MI0016747 |
| 519 | hsa-mir-1260b | MI0014197 |
| 520 | hsa-mir-1268a | MI0006405 |
| 521 | hsa-mir-1268b | MI0016748 |
| 522 | hsa-mir-1273g | MI0018003 |
| 523 | hsa-mir-128-1 | MI0000447 |
| 524 | hsa-mir-128-2 | MI0000727 |
| 525 | hsa-mir-1290 | MI0006352 |
| 526 | hsa-mir-150 | MI0000479 |
| 527 | hsa-mir-17 | MI0000071 |
| 528 | hsa-mir-1908 | MI0008329 |
| 529 | hsa-mir-1909 | MI0008330 |
| 530 | hsa-mir-1914 | MI0008335 |
| 531 | hsa-mir-1915 | MI0008336 |
| 532 | hsa-mir-191 | MI0000465 |
| 533 | hsa-mir-22 | MI0000078 |
| 534 | hsa-mir-23b | MI0000439 |
| 535 | hsa-mir-24-1 | MI0000080 |
| 536 | hsa-mir-24-2 | MI0000081 |
| 537 | hsa-mir-296 | MI0000747 |
| 538 | hsa-mir-3131 | MI0014151 |
| 539 | hsa-mir-3162 | MI0014192 |

TABLE 1-continued

| SEQ ID NO: | Name of gene | Accession No. of miRBase |
|---|---|---|
| 540 | hsa-mir-3188 | MI0014232 |
| 541 | hsa-mir-3196 | MI0014241 |
| 542 | hsa-mir-3197 | MI0014245 |
| 543 | hsa-mir-320a | MI0000542 |
| 544 | hsa-mir-342 | MI0000805 |
| 545 | hsa-mir-3621 | MI0016012 |
| 546 | hsa-mir-3648 | MI0016048 |
| 547 | hsa-mir-3656 | MI0016056 |
| 548 | hsa-mir-365a | MI0000767 |
| 549 | hsa-mir-3665 | MI0016066 |
| 550 | hsa-mir-3679 | MI0016080 |
| 551 | hsa-mir-371a | MI0000779 |
| 552 | hsa-mir-3940 | MI0016597 |
| 553 | hsa-mir-423 | MI0001445 |
| 554 | hsa-mir-4257 | MI0015856 |
| 555 | hsa-mir-4270 | MI0015878 |
| 556 | hsa-mir-4271 | MI0015879 |
| 557 | hsa-mir-4286 | MI0015894 |
| 558 | hsa-mir-4298 | MI0015830 |
| 559 | hsa-mir-4417 | MI0016753 |
| 560 | hsa-mir-4442 | MI0016785 |
| 561 | hsa-mir-4446 | MI0016789 |
| 562 | hsa-mir-4448 | MI0016791 |
| 563 | hsa-mir-4454 | MI0016800 |
| 564 | hsa-mir-4467 | MI0016818 |
| 565 | hsa-mir-4472-1 | MI0016823 |
| 566 | hsa-mir-4472-2 | MI0016824 |
| 567 | hsa-mir-4507 | MI0016871 |
| 568 | hsa-mir-4516 | MI0016882 |
| 569 | hsa-mir-451a | MI0001729 |
| 570 | hsa-mir-4649 | MI0017276 |
| 571 | hsa-mir-4651 | MI0017279 |
| 572 | hsa-mir-4674 | MI0017305 |
| 573 | hsa-mir-4675 | MI0017306 |
| 574 | hsa-mir-4689 | MI0017322 |
| 575 | hsa-mir-4695 | MI0017328 |
| 576 | hsa-mir-4697 | MI0017330 |
| 577 | hsa-mir-4725 | MI0017362 |
| 578 | hsa-mir-4739 | MI0017377 |
| 579 | hsa-mir-4745 | MI0017384 |
| 580 | hsa-mir-4792 | MI0017439 |
| 581 | hsa-mir-486 | MI0002470 |
| 582 | hsa-mir-486-2 | MI0023622 |
| 583 | hsa-mir-5001 | MI0017867 |
| 584 | hsa-mir-5195 | MI0018174 |
| 585 | hsa-mir-550a-1 | MI0003600 |
| 586 | hsa-mir-550a-2 | MI0003601 |
| 587 | hsa-mir-5698 | MI0019305 |
| 588 | hsa-mir-6075 | MI0020352 |
| 589 | hsa-mir-6088 | MI0020365 |
| 590 | hsa-mir-6089-1 | MI0020366 |
| 591 | hsa-mir-6089-2 | MI0023563 |
| 592 | hsa-mir-6125 | MI0021259 |
| 593 | hsa-mir-6126 | MI0021260 |
| 594 | hsa-mir-614 | MI0003627 |
| 595 | hsa-mir-615 | MI0003628 |
| 596 | hsa-mir-619 | MI0003633 |
| 597 | hsa-mir-638 | MI0003653 |
| 598 | hsa-mir-642b | MI0016685 |
| 599 | hsa-mir-650 | MI0003665 |
| 600 | hsa-mir-663a | MI0003672 |
| 601 | hsa-mir-663b | MI0006336 |
| 602 | hsa-mir-6717 | MI0022551 |
| 603 | hsa-mir-6721 | MI0022556 |
| 604 | hsa-mir-6726 | MI0022571 |
| 605 | hsa-mir-6727 | MI0022572 |
| 606 | hsa-mir-6738 | MI0022583 |
| 607 | hsa-mir-6741 | MI0022586 |
| 608 | hsa-mir-6749 | MI0022594 |
| 609 | hsa-mir-6752 | MI0022597 |
| 610 | hsa-mir-675 | MI0005416 |
| 611 | hsa-mir-6757 | MI0022602 |
| 612 | hsa-mir-6765 | MI0022610 |
| 613 | hsa-mir-6775 | MI0022620 |
| 614 | hsa-mir-6780b | MI0022681 |
| 615 | hsa-mir-6782 | MI0022627 |
| 616 | hsa-mir-6784 | MI0022629 |
| 617 | hsa-mir-6806 | MI0022651 |
| 618 | hsa-mir-6840 | MI0022686 |
| 619 | hsa-mir-6848 | MI0022694 |
| 620 | hsa-mir-6851 | MI0022697 |
| 621 | hsa-mir-6870 | MI0022717 |
| 622 | hsa-mir-6872 | MI0022719 |
| 623 | hsa-mir-6875 | MI0022722 |
| 624 | hsa-mir-6877 | MI0022724 |
| 625 | hsa-mir-6879 | MI0022726 |
| 626 | hsa-mir-6885 | MI0022732 |
| 627 | hsa-mir-6887 | MI0022734 |
| 628 | hsa-mir-711 | MI0012488 |
| 629 | hsa-mir-7113 | MI0022964 |
| 630 | hsa-mir-744 | MI0005559 |
| 631 | hsa-mir-760 | MI0005567 |
| 632 | hsa-mir-7845 | MI0025515 |
| 633 | hsa-mir-7847 | MI0025517 |
| 634 | hsa-mir-7977 | MI0025753 |
| 635 | hsa-mir-8059 | MI0025895 |
| 636 | hsa-mir-8063 | MI0025899 |
| 637 | hsa-mir-8072 | MI0025908 |
| 638 | hsa-mir-92a-2 | MI0000094 |
| 639 | hsa-mir-940 | MI0005762 |
| 640 | hsa-mir-1275 | MI0006415 |
| 641 | hsa-mir-1307 | MI0006444 |
| 642 | hsa-mir-23a | MI0000079 |
| 643 | hsa-mir-29b-1 | MI0000105 |
| 644 | hsa-mir-29b-2 | MI0000107 |
| 645 | hsa-mir-3135b | MI0016809 |
| 646 | hsa-mir-3185 | MI0014227 |
| 647 | hsa-mir-4532 | MI0016899 |
| 648 | hsa-mir-4690 | MI0017323 |
| 649 | hsa-mir-4758 | MI0017399 |
| 650 | hsa-mir-4783 | MI0017428 |
| 651 | hsa-mir-6131 | MI0021276 |
| 652 | hsa-mir-625 | MI0003639 |
| 653 | hsa-mir-6511a-1 | MI0022223 |
| 654 | hsa-mir-6511a-2 | MI0023564 |
| 655 | hsa-mir-6511a-3 | MI0023565 |
| 656 | hsa-mir-6511a-4 | MI0023566 |
| 657 | hsa-mir-6816 | MI0022661 |
| 658 | hsa-mir-6825 | MI0022670 |
| 659 | hsa-mir-6845 | MI0022691 |
| 660 | hsa-mir-7150 | MI0023610 |
| 661 | hsa-mir-7641-1 | MI0024975 |
| 662 | hsa-mir-7641-2 | MI0024976 |
| 663 | hsa-mir-7975 | MI0025751 |
| 664 | hsa-mir-92a-1 | MI0000093 |
| 665 | isomiR Example 1 of SEQ ID NO: 3 | — |
| 666 | isomiR Example 1 of SEQ ID NO: 4 | — |
| 667 | isomiR Example 1 of SEQ ID NO: 4 | — |
| 668 | isomiR Example 1 of SEQ ID NO: 7 | — |
| 669 | isomiR Example 1 of SEQ ID NO: 8 | — |
| 670 | isomiR Example 2 of SEQ ID NO: 8 | — |
| 671 | isomiR Example 1 of SEQ ID NO: 9 | — |
| 672 | isomiR Example 2 of SEQ ID NO: 9 | — |
| 673 | isomiR Example 1 of SEQ ID NO: 10 | — |
| 674 | isomiR Example 1 of SEQ ID NO: 13 | — |
| 675 | isomiR Example 2 of SEQ ID NO: 13 | — |
| 676 | isomiR Example 1 of SEQ ID NO: 14 | — |
| 677 | isomiR Example 2 of SEQ ID NO: 14 | — |
| 678 | isomiR Example 1 of SEQ ID NO: 17 | — |
| 679 | isomiR Example 1 of SEQ ID NO: 18 | — |
| 680 | isomiR Example 2 of SEQ ID NO: 18 | — |
| 681 | isomiR Example 1 of SEQ ID NO: 20 | — |
| 682 | isomiR Example 2 of SEQ ID NO: 20 | — |
| 683 | isomiR Example 1 of SEQ ID NO: 21 | — |
| 684 | isomiR Example 2 of SEQ ID NO: 21 | — |
| 685 | isomiR Example 1 of SEQ ID NO: 22 | — |
| 686 | isomiR Example 2 of SEQ ID NO: 22 | — |
| 687 | isomiR Example 1 of SEQ ID NO: 23 | — |
| 688 | isomiR Example 2 of SEQ ID NO: 23 | — |
| 689 | isomiR Example 1 of SEQ ID NO: 24 | — |
| 690 | isomiR Example 1 of SEQ ID NO: 25 | — |
| 691 | isomiR Example 1 of SEQ ID NO: 26 | — |
| 692 | isomiR Example 2 of SEQ ID NO: 26 | — |
| 693 | isomiR Example 1 of SEQ ID NO: 28 | — |

TABLE 1-continued

| SEQ ID NO: | Name of gene | Accession No. of miRBase |
|---|---|---|
| 694 | isomiR Example 2 of SEQ ID NO: 28 | — |
| 695 | isomiR Example 1 of SEQ ID NO: 29 | — |
| 696 | isomiR Example 1 of SEQ ID NO: 30 | — |
| 697 | isomiR Example 1 of SEQ ID NO: 31 | — |
| 698 | isomiR Example 2 of SEQ ID NO: 31 | — |
| 699 | isomiR Example 1 of SEQ ID NO: 32 | — |
| 700 | isomiR Example 2 of SEQ ID NO: 32 | — |
| 701 | isomiR Example 1 of SEQ ID NO: 33 | — |
| 702 | isomiR Example 2 of SEQ ID NO: 33 | — |
| 703 | isomiR Example 1 of SEQ ID NO: 35 | — |
| 704 | isomiR Example 2 of SEQ ID NO: 35 | — |
| 705 | isomiR Example 1 of SEQ ID NO: 36 | — |
| 706 | isomiR Example 2 of SEQ ID NO: 36 | — |
| 707 | isomiR Example 1 of SEQ ID NO: 38 | — |
| 708 | isomiR Example 2 of SEQ ID NO: 38 | — |
| 709 | isomiR Example 1 of SEQ ID NO: 41 | — |
| 710 | isomiR Example 2 of SEQ ID NO: 41 | — |
| 711 | isomiR Example 1 of SEQ ID NO: 43 | — |
| 712 | isomiR Example 1 of SEQ ID NO: 44 | — |
| 713 | isomiR Example 1 of SEQ ID NO: 45 | — |
| 714 | isomiR Example 2 of SEQ ID NO: 45 | — |
| 715 | isomiR Example 1 of SEQ ID NO: 46 | — |
| 716 | isomiR Example 2 of SEQ ID NO: 46 | — |
| 717 | isomiR Example 1 of SEQ ID NO: 48 | — |
| 718 | isomiR Example 2 of SEQ ID NO: 48 | — |
| 719 | isomiR Example 1 of SEQ ID NO: 49 | — |
| 720 | isomiR Example 2 of SEQ ID NO: 49 | — |
| 721 | isomiR Example 1 of SEQ ID NO: 51 | — |
| 722 | isomiR Example 2 of SEQ ID NO: 51 | — |
| 723 | isomiR Example 1 of SEQ ID NO: 52 | — |
| 724 | isomiR Example 1 of SEQ ID NO: 53 | — |
| 725 | isomiR Example 2 of SEQ ID NO: 53 | — |
| 726 | isomiR Example 1 of SEQ ID NO: 54 | — |
| 727 | isomiR Example 2 of SEQ ID NO: 54 | — |
| 728 | isomiR Example 1 of SEQ ID NO: 55 | — |
| 729 | isomiR Example 2 of SEQ ID NO: 55 | — |
| 730 | isomiR Example 1 of SEQ ID NO: 56 | — |
| 731 | isomiR Example 2 of SEQ ID NO: 56 | — |
| 732 | isomiR Example 1 of SEQ ID NO: 57 | — |
| 733 | isomiR Example 2 of SEQ ID NO: 57 | — |
| 734 | isomiR Example 1 of SEQ ID NO: 58 | — |
| 735 | isomiR Example 2 of SEQ ID NO: 58 | — |
| 736 | isomiR Example 1 of SEQ ID NO: 61 | — |
| 737 | isomiR Example 2 of SEQ ID NO: 61 | — |
| 738 | isomiR Example 1 of SEQ ID NO: 62 | — |
| 739 | isomiR Example 2 of SEQ ID NO: 62 | — |
| 740 | isomiR Example 1 of SEQ ID NO: 65 | — |
| 741 | isomiR Example 1 of SEQ ID NO: 66 | — |
| 742 | isomiR Example 1 of SEQ ID NO: 67 | — |
| 743 | isomiR Example 1 of SEQ ID NO: 68 | — |
| 744 | isomiR Example 2 of SEQ ID NO: 68 | — |
| 745 | isomiR Example 1 of SEQ ID NO: 69 | — |
| 746 | isomiR Example 1 of SEQ ID NO: 71 | — |
| 747 | isomiR Example 1 of SEQ ID NO: 72 | — |
| 748 | isomiR Example 1 of SEQ ID NO: 73 | — |
| 749 | isomiR Example 2 of SEQ ID NO: 73 | — |
| 750 | isomiR Example 1 of SEQ ID NO: 74 | — |
| 751 | isomiR Example 2 of SEQ ID NO: 74 | — |
| 752 | isomiR Example 1 of SEQ ID NO: 77 | — |
| 753 | isomiR Example 2 of SEQ ID NO: 77 | — |
| 754 | isomiR Example 1 of SEQ ID NO: 78 | — |
| 755 | isomiR Example 2 of SEQ ID NO: 78 | — |
| 756 | isomiR Example 1 of SEQ ID NO: 80 | — |
| 757 | isomiR Example 1 of SEQ ID NO: 82 | — |
| 758 | isomiR Example 2 of SEQ ID NO: 82 | — |
| 759 | isomiR Example 1 of SEQ ID NO: 83 | — |
| 760 | isomiR Example 2 of SEQ ID NO: 83 | — |
| 761 | isomiR Example 1 of SEQ ID NO: 84 | — |
| 762 | isomiR Example 2 of SEQ ID NO: 84 | — |
| 763 | isomiR Example 1 of SEQ ID NO: 85 | — |
| 764 | isomiR Example 2 of SEQ ID NO: 85 | — |
| 765 | isomiR Example 1 of SEQ ID NO: 86 | — |
| 766 | isomiR Example 2 of SEQ ID NO: 86 | — |
| 767 | isomiR Example 1 of SEQ ID NO: 87 | — |
| 768 | isomiR Example 2 of SEQ ID NO: 87 | — |
| 769 | isomiR Example 1 of SEQ ID NO: 89 | — |
| 770 | isomiR Example 1 of SEQ ID NO: 91 | — |
| 771 | isomiR Example 2 of SEQ ID NO: 91 | — |
| 772 | isomiR Example 1 of SEQ ID NO: 92 | — |
| 773 | isomiR Example 2 of SEQ ID NO: 92 | — |
| 774 | isomiR Example 1 of SEQ ID NO: 93 | — |
| 775 | isomiR Example 2 of SEQ ID NO: 93 | — |
| 776 | isomiR Example 1 of SEQ ID NO: 94 | — |
| 777 | isomiR Example 2 of SEQ ID NO: 94 | — |
| 778 | isomiR Example 1 of SEQ ID NO: 95 | — |
| 779 | isomiR Example 1 of SEQ ID NO: 96 | — |
| 780 | isomiR Example 2 of SEQ ID NO: 96 | — |
| 781 | isomiR Example 1 of SEQ ID NO: 97 | — |
| 782 | isomiR Example 2 of SEQ ID NO: 97 | — |
| 783 | isomiR Example 1 of SEQ ID NO: 100 | — |
| 784 | isomiR Example 2 of SEQ ID NO: 100 | — |
| 785 | isomiR Example 1 of SEQ ID NO: 101 | — |
| 786 | isomiR Example 1 of SEQ ID NO: 114 | — |
| 787 | isomiR Example 1 of SEQ ID NO: 138 | — |
| 788 | isomiR Example 2 of SEQ ID NO: 138 | — |
| 789 | isomiR Example 1 of SEQ ID NO: 139 | — |
| 790 | isomiR Example 2 of SEQ ID NO: 139 | — |
| 791 | isomiR Example 1 of SEQ ID NO: 140 | — |
| 792 | isomiR Example 1 of SEQ ID NO: 141 | — |
| 793 | isomiR Example 2 of SEQ ID NO: 141 | — |
| 794 | isomiR Example 1 of SEQ ID NO: 142 | — |
| 795 | isomiR Example 1 of SEQ ID NO: 145 | — |
| 796 | isomiR Example 2 of SEQ ID NO: 145 | — |
| 797 | isomiR Example 1 of SEQ ID NO: 146 | — |
| 798 | isomiR Example 2 of SEQ ID NO: 146 | — |
| 799 | isomiR Example 1 of SEQ ID NO: 147 | — |
| 800 | isomiR Example 2 of SEQ ID NO: 147 | — |
| 801 | isomiR Example 1 of SEQ ID NO: 148 | — |
| 802 | isomiR Example 1 of SEQ ID NO: 149 | — |
| 803 | isomiR Example 1 of SEQ ID NO: 150 | — |
| 804 | isomiR Example 2 of SEQ ID NO: 150 | — |
| 805 | isomiR Example 1 of SEQ ID NO: 151 | — |
| 806 | isomiR Example 2 of SEQ ID NO: 151 | — |
| 807 | isomiR Example 1 of SEQ ID NO: 162 | — |
| 808 | isomiR Example 1 of SEQ ID NO: 163 | — |
| 809 | isomiR Example 2 of SEQ ID NO: 163 | — |
| 810 | isomiR Example 1 of SEQ ID NO: 164 | — |
| 811 | isomiR Example 2 of SEQ ID NO: 164 | — |
| 812 | isomiR Example 1 of SEQ ID NO: 167 | — |
| 813 | isomiR Example 2 of SEQ ID NO: 167 | — |
| 814 | isomiR Example 1 of SEQ ID NO: 168 | — |
| 815 | isomiR Example 1 of SEQ ID NO: 170 | — |
| 816 | isomiR Example 2 of SEQ ID NO: 170 | — |
| 817 | isomiR Example 1 of SEQ ID NO: 171 | — |
| 818 | isomiR Example 2 of SEQ ID NO: 171 | — |
| 819 | isomiR Example 1 of SEQ ID NO: 175 | — |
| 820 | isomiR Example 2 of SEQ ID NO: 175 | — |
| 821 | isomiR Example 1 of SEQ ID NO: 177 | — |
| 822 | isomiR Example 2 of SEQ ID NO: 177 | — |
| 823 | isomiR Example 1 of SEQ ID NO: 178 | — |
| 824 | isomiR Example 1 of SEQ ID NO: 179 | — |
| 825 | isomiR Example 2 of SEQ ID NO: 179 | — |
| 826 | isomiR Example 1 of SEQ ID NO: 180 | — |
| 827 | isomiR Example 2 of SEQ ID NO: 180 | — |
| 828 | isomiR Example 1 of SEQ ID NO: 181 | — |
| 829 | isomiR Example 2 of SEQ ID NO: 181 | — |
| 830 | isomiR Example 1 of SEQ ID NO: 182 | — |
| 831 | isomiR Example 2 of SEQ ID NO: 182 | — |
| 832 | isomiR Example 1 of SEQ ID NO: 183 | — |
| 833 | isomiR Example 2 of SEQ ID NO: 183 | — |
| 834 | isomiR Example 1 of SEQ ID NO: 184 | — |
| 835 | isomiR Example 2 of SEQ ID NO: 184 | — |
| 836 | isomiR Example 1 of SEQ ID NO: 185 | — |
| 837 | isomiR Example 2 of SEQ ID NO: 185 | — |
| 838 | isomiR Example 1 of SEQ ID NO: 186 | — |
| 839 | isomiR Example 1 of SEQ ID NO: 187 | — |
| 840 | isomiR Example 1 of SEQ ID NO: 188 | — |
| 841 | isomiR Example 2 of SEQ ID NO: 188 | — |
| 842 | isomiR Example 1 of SEQ ID NO: 189 | — |
| 843 | isomiR Example 2 of SEQ ID NO: 189 | — |
| 844 | isomiR Example 1 of SEQ ID NO: 190 | — |
| 845 | isomiR Example 2 of SEQ ID NO: 190 | — |
| 846 | isomiR Example 1 of SEQ ID NO: 191 | — |
| 847 | isomiR Example 2 of SEQ ID NO: 191 | — |

TABLE 1-continued

| SEQ ID NO: | Name of gene | Accession No. of miRBase |
|---|---|---|
| 848 | isomiR Example 1 of SEQ ID NO: 192 | — |
| 849 | isomiR Example 2 of SEQ ID NO: 192 | — |
| 850 | isomiR Example 1 of SEQ ID NO: 193 | — |
| 851 | isomiR Example 2 of SEQ ID NO: 193 | — |
| 852 | isomiR Example 1 of SEQ ID NO: 194 | — |
| 853 | isomiR Example 1 of SEQ ID NO: 195 | — |
| 854 | isomiR Example 2 of SEQ ID NO: 195 | — |
| 855 | isomiR Example 1 of SEQ ID NO: 196 | — |
| 856 | isomiR Example 2 of SEQ ID NO: 196 | — |
| 857 | isomiR Example 1 of SEQ ID NO: 197 | — |
| 858 | isomiR Example 2 of SEQ ID NO: 197 | — |
| 859 | isomiR Example 1 of SEQ ID NO: 198 | — |
| 860 | isomiR Example 2 of SEQ ID NO: 198 | — |
| 861 | isomiR Example 1 of SEQ ID NO: 199 | — |
| 862 | isomiR Example 1 of SEQ ID NO: 200 | — |
| 863 | isomiR Example 2 of SEQ ID NO: 200 | — |
| 864 | isomiR Example 1 of SEQ ID NO: 201 | — |
| 865 | isomiR Example 2 of SEQ ID NO: 201 | — |
| 866 | isomiR Example 1 of SEQ ID NO: 202 | — |
| 867 | isomiR Example 2 of SEQ ID NO: 202 | — |
| 868 | isomiR Example 1 of SEQ ID NO: 203 | — |
| 869 | isomiR Example 2 of SEQ ID NO: 203 | — |
| 870 | isomiR Example 1 of SEQ ID NO: 204 | — |
| 871 | isomiR Example 2 of SEQ ID NO: 204 | — |
| 872 | isomiR Example 1 of SEQ ID NO: 205 | — |
| 873 | isomiR Example 1 of SEQ ID NO: 206 | — |
| 874 | isomiR Example 2 of SEQ ID NO: 206 | — |
| 875 | isomiR Example 1 of SEQ ID NO: 207 | — |
| 876 | isomiR Example 2 of SEQ ID NO: 207 | — |
| 877 | isomiR Example 1 of SEQ ID NO: 209 | — |
| 878 | isomiR Example 2 of SEQ ID NO: 209 | — |
| 879 | isomiR Example 1 of SEQ ID NO: 210 | — |
| 880 | isomiR Example 2 of SEQ ID NO: 210 | — |
| 881 | isomiR Example 1 of SEQ ID NO: 211 | — |
| 882 | isomiR Example 2 of SEQ ID NO: 211 | — |
| 883 | isomiR Example 1 of SEQ ID NO: 212 | — |
| 884 | isomiR Example 2 of SEQ ID NO: 212 | — |
| 885 | isomiR Example 1 of SEQ ID NO: 213 | — |
| 886 | isomiR Example 1 of SEQ ID NO: 214 | — |
| 887 | isomiR Example 2 of SEQ ID NO: 214 | — |
| 888 | isomiR Example 1 of SEQ ID NO: 215 | — |
| 889 | isomiR Example 1 of SEQ ID NO: 216 | — |
| 890 | isomiR Example 2 of SEQ ID NO: 216 | — |
| 891 | isomiR Example 1 of SEQ ID NO: 219 | — |
| 892 | isomiR Example 1 of SEQ ID NO: 220 | — |
| 893 | isomiR Example 2 of SEQ ID NO: 220 | — |
| 894 | isomiR Example 1 of SEQ ID NO: 221 | — |
| 895 | isomiR Example 1 of SEQ ID NO: 222 | — |
| 896 | isomiR Example 1 of SEQ ID NO: 223 | — |
| 897 | isomiR Example 2 of SEQ ID NO: 223 | — |
| 898 | isomiR Example 1 of SEQ ID NO: 224 | — |
| 899 | isomiR Example 2 of SEQ ID NO: 224 | — |
| 900 | isomiR Example 1 of SEQ ID NO: 225 | — |
| 901 | isomiR Example 1 of SEQ ID NO: 226 | — |
| 902 | isomiR Example 2 of SEQ ID NO: 226 | — |
| 903 | isomiR Example 1 of SEQ ID NO: 227 | — |
| 904 | isomiR Example 1 of SEQ ID NO: 229 | — |
| 905 | isomiR Example 2 of SEQ ID NO: 229 | — |
| 906 | isomiR Example 1 of SEQ ID NO: 230 | — |
| 907 | isomiR Example 2 of SEQ ID NO: 230 | — |
| 908 | isomiR Example 1 of SEQ ID NO: 231 | — |
| 909 | isomiR Example 2 of SEQ ID NO: 231 | — |
| 910 | isomiR Example 1 of SEQ ID NO: 232 | — |
| 911 | isomiR Example 1 of SEQ ID NO: 233 | — |
| 912 | isomiR Example 1 of SEQ ID NO: 235 | — |
| 913 | isomiR Example 2 of SEQ ID NO: 235 | — |
| 914 | isomiR Example 1 of SEQ ID NO: 237 | — |
| 915 | isomiR Example 2 of SEQ ID NO: 237 | — |
| 916 | isomiR Example 1 of SEQ ID NO: 238 | — |
| 917 | isomiR Example 1 of SEQ ID NO: 240 | — |
| 918 | isomiR Example 2 of SEQ ID NO: 240 | — |
| 919 | isomiR Example 1 of SEQ ID NO: 241 | — |
| 920 | isomiR Example 2 of SEQ ID NO: 241 | — |
| 921 | isomiR Example 1 of SEQ ID NO: 242 | — |
| 922 | isomiR Example 1 of SEQ ID NO: 243 | — |
| 923 | isomiR Example 1 of SEQ ID NO: 244 | — |
| 924 | isomiR Example 2 of SEQ ID NO: 244 | — |
| 925 | isomiR Example 1 of SEQ ID NO: 245 | — |
| 926 | isomiR Example 2 of SEQ ID NO: 245 | — |
| 927 | isomiR Example 1 of SEQ ID NO: 246 | — |
| 928 | isomiR Example 2 of SEQ ID NO: 246 | — |
| 929 | isomiR Example 1 of SEQ ID NO: 248 | — |
| 930 | isomiR Example 1 of SEQ ID NO: 249 | — |
| 931 | isomiR Example 2 of SEQ ID NO: 249 | — |
| 932 | isomiR Example 1 of SEQ ID NO: 251 | — |
| 933 | isomiR Example 1 of SEQ ID NO: 252 | — |
| 934 | isomiR Example 2 of SEQ ID NO: 252 | — |
| 935 | isomiR Example 1 of SEQ ID NO: 253 | — |
| 936 | isomiR Example 2 of SEQ ID NO: 253 | — |
| 937 | isomiR Example 1 of SEQ ID NO: 254 | — |
| 938 | isomiR Example 2 of SEQ ID NO: 254 | — |
| 939 | isomiR Example 1 of SEQ ID NO: 255 | — |
| 940 | isomiR Example 1 of SEQ ID NO: 256 | — |
| 941 | isomiR Example 2 of SEQ ID NO: 256 | — |
| 942 | isomiR Example 1 of SEQ ID NO: 257 | — |
| 943 | isomiR Example 2 of SEQ ID NO: 257 | — |
| 944 | isomiR Example 1 of SEQ ID NO: 258 | — |
| 945 | isomiR Example 2 of SEQ ID NO: 258 | — |
| 946 | isomiR Example 1 of SEQ ID NO: 259 | — |
| 947 | isomiR Example 2 of SEQ ID NO: 259 | — |
| 948 | isomiR Example 1 of SEQ ID NO: 260 | — |
| 949 | isomiR Example 2 of SEQ ID NO: 260 | — |
| 950 | isomiR Example 1 of SEQ ID NO: 261 | — |
| 951 | isomiR Example 2 of SEQ ID NO: 261 | — |
| 952 | isomiR Example 1 of SEQ ID NO: 262 | — |
| 953 | isomiR Example 2 of SEQ ID NO: 262 | — |
| 954 | isomiR Example 1 of SEQ ID NO: 263 | — |
| 955 | isomiR Example 2 of SEQ ID NO: 263 | — |
| 956 | isomiR Example 1 of SEQ ID NO: 264 | — |
| 957 | isomiR Example 2 of SEQ ID NO: 264 | — |
| 958 | isomiR Example 1 of SEQ ID NO: 271 | — |
| 959 | isomiR Example 1 of SEQ ID NO: 293 | — |
| 960 | isomiR Example 1 of SEQ ID NO: 295 | — |
| 961 | isomiR Example 2 of SEQ ID NO: 295 | — |
| 962 | isomiR Example 1 of SEQ ID NO: 296 | — |
| 963 | isomiR Example 2 of SEQ ID NO: 296 | — |
| 964 | isomiR Example 1 of SEQ ID NO: 303 | — |
| 965 | isomiR Example 2 of SEQ ID NO: 303 | — |
| 966 | isomiR Example 1 of SEQ ID NO: 304 | — |
| 967 | isomiR Example 2 of SEQ ID NO: 304 | — |
| 968 | isomiR Example 1 of SEQ ID NO: 305 | — |
| 969 | isomiR Example 2 of SEQ ID NO: 305 | — |
| 970 | isomiR Example 1 of SEQ ID NO: 306 | — |
| 971 | isomiR Example 2 of SEQ ID NO: 306 | — |
| 972 | isomiR Example 1 of SEQ ID NO: 307 | — |
| 973 | isomiR Example 2 of SEQ ID NO: 307 | — |
| 974 | isomiR Example 1 of SEQ ID NO: 308 | — |
| 975 | isomiR Example 2 of SEQ ID NO: 308 | — |
| 976 | isomiR Example 1 of SEQ ID NO: 309 | — |
| 977 | isomiR Example 2 of SEQ ID NO: 309 | — |
| 978 | isomiR Example 1 of SEQ ID NO: 311 | — |
| 979 | isomiR Example 2 of SEQ ID NO: 311 | — |
| 980 | isomiR Example 1 of SEQ ID NO: 312 | — |
| 981 | isomiR Example 2 of SEQ ID NO: 312 | — |
| 982 | isomiR Example 1 of SEQ ID NO: 313 | — |
| 983 | isomiR Example 2 of SEQ ID NO: 313 | — |
| 984 | isomiR Example 1 of SEQ ID NO: 314 | — |
| 985 | isomiR Example 1 of SEQ ID NO: 315 | — |
| 986 | isomiR Example 2 of SEQ ID NO: 315 | — |
| 987 | isomiR Example 1 of SEQ ID NO: 316 | — |
| 988 | isomiR Example 2 of SEQ ID NO: 316 | — |
| 989 | isomiR Example 1 of SEQ ID NO: 317 | — |
| 990 | isomiR Example 2 of SEQ ID NO: 317 | — |
| 991 | isomiR Example 1 of SEQ ID NO: 318 | — |
| 992 | isomiR Example 2 of SEQ ID NO: 318 | — |
| 993 | isomiR Example 1 of SEQ ID NO: 319 | — |
| 994 | isomiR Example 1 of SEQ ID NO: 320 | — |
| 995 | isomiR Example 2 of SEQ ID NO: 320 | — |
| 996 | isomiR Example 1 of SEQ ID NO: 321 | — |
| 997 | isomiR Example 2 of SEQ ID NO: 321 | — |
| 998 | isomiR Example 1 of SEQ ID NO: 328 | — |
| 999 | isomiR Example 1 of SEQ ID NO: 329 | — |
| 1000 | isomiR Example 2 of SEQ ID NO: 329 | — |

Effect of Invention

According to the present invention, lung cancer can be detected easily and in high accuracy. For example, the presence or absence of lung cancer in patients can be easily detected by using, as indicators, the determined expression levels of one to several miRNAs in blood, serum, and/or plasma of the patients, which can be collected with limited invasiveness.

The present specification encompasses the contents disclosed in Japanese Patent Application No. 2017-126933 from which the present application claims priority.

MODES FOR CARRYING OUT THE INVENTION

Figure 1:
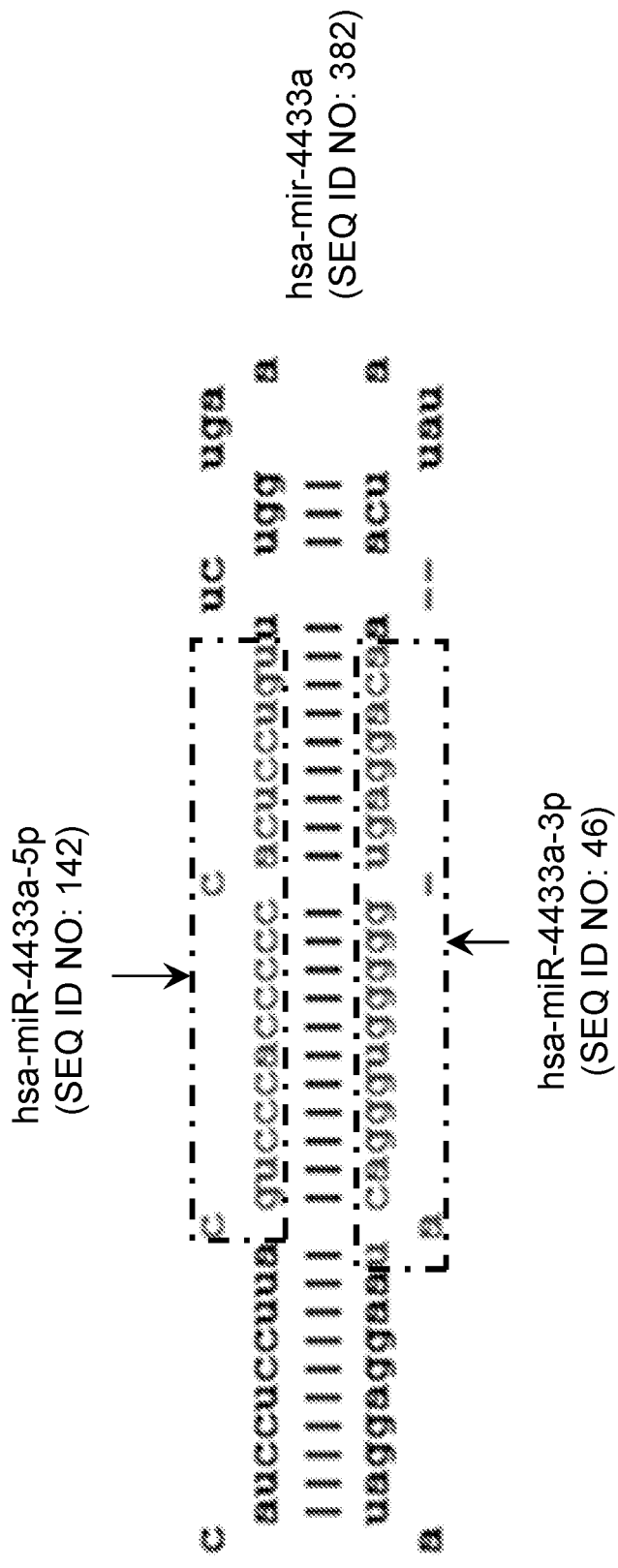
FIG. 1 This figure shows the relationship between the nucleotide sequences of hsa-miR-4433a-5p represented by SEQ ID NO: 142 and hsa-miR-4433a-3p represented by SEQ ID NO: 46, which are produced from the precursor hsa-mir-4433a represented by SEQ ID NO: 382.

Hereinafter, the present invention will be further described in detail.

1. Target Nucleic Acid for Lung Cancer

Primary target nucleic acids, as lung cancer markers, for detecting the presence and/or absence of lung cancer or lung cancer cells using the nucleic acids such as the nucleic acid probes or the primers for detection of lung cancer defined above according to the present invention comprise at least one miRNA selected from the group consisting of the following miRNAs: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p, or a polynucleotide complementary to the miRNA. Furthermore, at least one miRNA selected from the group consisting of the following other lung cancer markers that can be combined with these miRNAs, i.e., miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-5p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, or a polynucleotide complementary to the miRNA can also be preferably used as target nucleic acids.

These miRNAs include, for example, a human gene comprising a nucleotide sequence represented by any of SEQ ID NOs: 1 to 329 (i.e., miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, miR-92b-3p, miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, respectively), a congener thereof, a transcript thereof, or/and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 329 or a transcript thereof, more preferably the transcript, i.e., a miRNA or its precursor RNA, pri-miRNA or pre-miRNA, or a polynucleotide complementary thereto.

The first target gene is the hsa-miR-6787-5p gene, a congener thereof, a transcript thereof, or a variant or a derivative thereof. None of the previously known report shows that change in the expression of the gene or the transcript thereof can serve as a marker for lung cancer.

The second target gene is the hsa-miR-920 gene, a congener thereof, a transcript thereof, or a variant or a derivative thereof. None of the previously known report shows that change in the expression of the gene or the transcript thereof can serve as a marker for lung cancer.

The third target gene is the hsa-miR-3622a-5p gene, a congener thereof, a transcript thereof, or a variant or a derivative thereof. None of the previously known report shows that change in the expression of the gene or the transcript thereof can serve as a marker for lung cancer.

The fourth target gene is the hsa-miR-1185-1-3p gene, a congener thereof, a transcript thereof, or a variant or a derivative thereof. None of the previously known report shows that change in the expression of the gene or the transcript thereof can serve as a marker for lung cancer.

The fifth target gene is the hsa-miR-4327 gene, a congener thereof, a transcript thereof, or a variant or a derivative thereof. None of the previously known report shows that change in the expression of the gene or the transcript thereof can serve as a marker for lung cancer.

The sixth target gene is the hsa-miR-5739 gene, a congener thereof, a transcript thereof, or a variant or a derivative thereof. None of the previously known report shows that change in the expression of the gene or the transcript thereof can serve as a marker for lung cancer.

The seventh target gene is the hsa-miR-937-5p gene, a congener thereof, a transcript thereof, or a variant or a derivative thereof. None of the previously known report shows that change in the expression of the gene or the transcript thereof can serve as a marker for lung cancer.

The eighth target gene is the hsa-miR-1181 gene, a congener thereof, a transcript thereof, or a variant or a derivative thereof. None of the previously known report shows that change in the expression of the gene or the transcript thereof can serve as a marker for lung cancer.

The ninth target gene is the hsa-miR-1185-2-3p gene, a congener thereof, a transcript thereof, or a variant or a derivative thereof. None of the previously known report shows that change in the expression of the gene or the transcript thereof can serve as a marker for lung cancer.

The 10th target gene is the hsa-miR-1193 gene, a congener thereof, a transcript thereof, or a variant or a derivative thereof. None of the previously known report shows that change in the expression of the gene or the transcript thereof can serve as a marker for lung cancer.

The 11th target gene is the hsa-miR-1207-5p gene, a congener thereof, a transcript thereof, or a variant or a derivative thereof. None of the previously known report shows that change in the expression of the gene or the transcript thereof can serve as a marker for lung cancer.

The 12th target gene is the hsa-miR-1238-5p gene, a congener thereof, a transcript thereof, or a variant or a derivative thereof. None of the previously known report shows that change in the expression of the gene or the transcript thereof can serve as a marker for lung cancer.

The 13th target gene is the hsa-miR-1246 gene, a congener thereof, a transcript thereof, or a variant or a derivative thereof. None of the previously known report shows that change in the expression of the gene or the transcript thereof can serve as a marker for lung cancer.

The 14th target gene is the hsa-miR-1249-5p gene, a congener thereof, a transcript thereof, or a variant or a derivative thereof. None of the previously known report shows that change in the expression of the gene or the transcript thereof can serve as a marker for lung cancer.

The 15th target gene is the hsa-miR-1292-3p gene, a congener thereof, a transcript thereof, or a variant or a derivative thereof. None of the previously known report shows that change in the expression of the gene or the transcript thereof can serve as a marker for lung cancer.

The 16th target gene is the hsa-miR-1469 gene, a congener thereof, a transcript thereof, or a variant or a derivative thereof. None of the previously known report shows that change in the expression of the gene or the transcript thereof can serve as a marker for lung cancer.

The 17th target gene is the hsa-miR-1470 gene, a congener thereof, a transcript thereof, or a variant or a derivative thereof. None of the previously known report shows that change in the expression of the gene or the transcript thereof can serve as a marker for lung cancer.

The 18th target gene is the hsa-miR-197-5p gene, a congener thereof, a transcript thereof, or a variant or a derivative thereof. None of the previously known report shows that change in the expression of the gene or the transcript thereof can serve as a marker for lung cancer.

The 19th target gene is the hsa-miR-208a-5p gene, a congener thereof, a transcript thereof, or a variant or a derivative thereof. None of the previously known report shows that change in the expression of the gene or the transcript thereof can serve as a marker for lung cancer.

The 20th target gene is the hsa-miR-2110 gene, a congener thereof, a transcript thereof, or a variant or a derivative thereof. None of the previously known report shows that change in the expression of the gene or the transcript thereof can serve as a marker for lung cancer.

The 21st target gene is the hsa-miR-211-3p gene, a congener thereof, a transcript thereof, or a variant or a derivative thereof. None of the previously known report shows that change in the expression of the gene or the transcript thereof can serve as a marker for lung cancer.

The 22nd target gene is the hsa-miR-2467-3p gene, a congener thereof, a transcript thereof, or a variant or a derivative thereof. None of the previously known report shows that change in the expression of the gene or the transcript thereof can serve as a marker for lung cancer.

The 23rd target gene is the hsa-miR-3122 gene, a congener thereof, a transcript thereof, or a variant or a derivative thereof. None of the previously known report shows that change in the expression of the gene or the transcript thereof can serve as a marker for lung cancer.

The 24th target gene is the hsa-miR-3141 gene, a congener thereof, a transcript thereof, or a variant or a derivative thereof. None of the previously known report shows that change in the expression of the gene or the transcript thereof can serve as a marker for lung cancer.

The 25th target gene is the hsa-miR-3156-5p gene, a congener thereof, a transcript thereof, or a variant or a derivative thereof. None of the previously known report shows that change in the expression of the gene or the transcript thereof can serve as a marker for lung cancer.

The 26th target gene is the hsa-miR-3158-5p gene, a congener thereof, a transcript thereof, or a variant or a derivative thereof. None of the previously known report shows that change in the expression of the gene or the transcript thereof can serve as a marker for lung cancer.

The 27th target gene is the hsa-miR-3160-5p gene, a congener thereof, a transcript thereof, or a variant or a derivative thereof. None of the previously known report shows that change in the expression of the gene or the transcript thereof can serve as a marker for lung cancer.

The 28th target gene is the hsa-miR-3180-3p gene, a congener thereof, a transcript thereof, or a variant or a derivative thereof. None of the previously known report shows that change in the expression of the gene or the transcript thereof can serve as a marker for lung cancer.

The 29th target gene is the hsa-miR-3191-3p gene, a congener thereof, a transcript thereof, or a variant or a The 30th target gene is the hsa-miR-3194-3p gene, a congener thereof, a transcript thereof, or a variant or a derivative thereof. None of the previously known report shows that change in the expression of the gene or the transcript thereof can serve as a marker for lung cancer.

The 31st target gene is the hsa-miR-320b gene, a congener thereof, a transcript thereof, or a variant or a derivative thereof. None of the previously known report shows that change in the expression of the gene or the transcript thereof can serve as a marker for lung cancer.

The 32nd target gene is the hsa-miR-328-5p gene, a congener thereof, a transcript thereof, or a variant or a derivative thereof. None of the previously known report shows that change in the expression of the gene or the transcript thereof can serve as a marker for lung cancer.

The 33rd target gene is the hsa-miR-3610 gene, a congener thereof, a transcript thereof, or a variant or a derivative thereof. None of the previously known report shows that change in the expression of the gene or the transcript thereof can serve as a marker for lung cancer.

The 34th target gene is the hsa-miR-3619-3p gene, a congener thereof, a transcript thereof, or a variant or a derivative thereof. None of the previously known report shows that change in the expression of the gene or the transcript thereof can serve as a marker for lung cancer.

The 35th target gene is the hsa-miR-3620-5p gene, a congener thereof, a transcript thereof, or a variant or a derivative thereof. None of the previously known report shows that change in the expression of the gene or the transcript thereof can serve as a marker for lung cancer.

The 36th target gene is the hsa-miR-370-3p gene, a congener thereof, a transcript thereof, or a variant or a derivative thereof. None of the previously known report shows that change in the expression of the gene or the transcript thereof can serve as a marker for lung cancer.

The 37th target gene is the hsa-miR-373-5p gene, a congener thereof, a transcript thereof, or a variant or a derivative thereof. None of the previously known report shows that change in the expression of the gene or the transcript thereof can serve as a marker for lung cancer.

The 38th target gene is the hsa-miR-3917 gene, a congener thereof, a transcript thereof, or a variant or a derivative thereof. None of the previously known report shows that change in the expression of the gene or the transcript thereof can serve as a marker for lung cancer.

The 39th target gene is the hsa-miR-3937 gene, a congener thereof, a transcript thereof, or a variant or a derivative thereof. None of the previously known report shows that change in the expression of the gene or the transcript thereof can serve as a marker for lung cancer.

The 40th target gene is the hsa-miR-4259 gene, a congener thereof, a transcript thereof, or a variant or a derivative thereof. None of the previously known report shows that change in the expression of the gene or the transcript thereof can serve as a marker for lung cancer.

The 41st target gene is the hsa-miR-4281 gene, a congener thereof, a transcript thereof, or a variant or a derivative thereof. None of the previously known report shows that change in the expression of the gene or the transcript thereof can serve as a marker for lung cancer.

The 42nd target gene is the hsa-miR-4294 gene, a congener thereof, a transcript thereof, or a variant or a derivative thereof. None of the previously known report shows that change in the expression of the gene or the transcript thereof can serve as a marker for lung cancer.

The 43rd target gene is the hsa-miR-4419b gene, a congener thereof, a transcript thereof, or a variant or a derivative thereof. None of the previously known report shows that change in the expression of the gene or the transcript thereof can serve as a marker for lung cancer.

The 44th target gene is the hsa-miR-4428 gene, a congener thereof, a transcript thereof, or a variant or a derivative thereof. None of the previously known report shows that change in the expression of the gene or the transcript thereof can serve as a marker for lung cancer.

The 45th target gene is the hsa-miR-4429 gene, a congener thereof, a transcript thereof, or a variant or a derivative thereof. None of the previously known report shows that change in the expression of the gene or the transcript thereof can serve as a marker for lung cancer.

The 46th target gene is the hsa-miR-4433a-3p gene, a congener thereof, a transcript thereof, or a variant or a derivative thereof. None of the previously known report shows that change in the expression of the gene or the transcript thereof can serve as a marker for lung cancer.

The 47th target gene is the hsa-miR-4447 gene, a congener thereof, a transcript thereof, or a variant or a derivative thereof. None of the previously known report shows that change in the expression of the gene or the transcript thereof can serve as a marker for lung cancer.

The 48th target gene is the hsa-miR-4449 gene, a congener thereof, a transcript thereof, or a variant or a derivative thereof. None of the previously known report shows that change in the expression of the gene or the transcript thereof can serve as a marker for lung cancer.

The 49th target gene is the hsa-miR-4459 gene, a congener thereof, a transcript thereof, or a variant or a derivative thereof. None of the previously known report shows that change in the expression of the gene or the transcript thereof can serve as a marker for lung cancer.

The 50th target gene is the hsa-miR-4480 gene, a congener thereof, a transcript thereof, or a variant or a derivative thereof. None of the previously known report shows that change in the expression of the gene or the transcript thereof can serve as a marker for lung cancer.

The 51st target gene is the hsa-miR-4485-5p gene, a congener thereof, a transcript thereof, or a variant or a derivative thereof. None of the previously known report shows that change in the expression of the gene or the transcript thereof can serve as a marker for lung cancer.

The 52nd target gene is the hsa-miR-4486 gene, a congener thereof, a transcript thereof, or a variant or a derivative thereof. None of the previously known report shows that change in the expression of the gene or the transcript thereof can serve as a marker for lung cancer.

The 53rd target gene is the hsa-miR-4488 gene, a congener thereof, a transcript thereof, or a variant or a derivative thereof. None of the previously known report shows that change in the expression of the gene or the transcript thereof can serve as a marker for lung cancer.

The 54th target gene is the hsa-miR-4489 gene, a congener thereof, a transcript thereof, or a variant or a derivative thereof. None of the previously known report shows that change in the expression of the gene or the transcript thereof can serve as a marker for lung cancer.

The 55th target gene is the hsa-miR-4505 gene, a congener thereof, a transcript thereof, or a variant or a derivative thereof. None of the previously known report shows that change in the expression of the gene or the transcript thereof can serve as a marker for lung cancer.

The 56th target gene is the hsa-miR-4513 gene, a congener thereof, a transcript thereof, or a variant or a derivative thereof. None of the previously known report shows that change in the expression of the gene or the transcript thereof can serve as a marker for lung cancer.

The 57th target gene is the hsa-miR-4515 gene, a congener thereof, a transcript thereof, or a variant or a derivative thereof. None of the previously known report shows that change in the expression of the gene or the transcript thereof can serve as a marker for lung cancer.

The 58th target gene is the hsa-miR-4530 gene, a congener thereof, a transcript thereof, or a variant or a derivative thereof. None of the previously known report shows that change in the expression of the gene or the transcript thereof can serve as a marker for lung cancer.

The 59th target gene is the hsa-miR-4535 gene, a congener thereof, a transcript thereof, or a variant or a derivative thereof. None of the previously known report shows that change in the expression of the gene or the transcript thereof can serve as a marker for lung cancer.

The 60th target gene is the hsa-miR-4635 gene, a congener thereof, a transcript thereof, or a variant or a derivative thereof. None of the previously known report shows that change in the expression of the gene or the transcript thereof can serve as a marker for lung cancer.

The 61st target gene is the hsa-miR-4640-5p gene, a congener thereof, a transcript thereof, or a variant or a derivative thereof. None of the previously known report shows that change in the expression of the gene or the transcript thereof can serve as a marker for lung cancer.

The 62nd target gene is the hsa-miR-4646-5p gene, a congener thereof, a transcript thereof, or a variant or a derivative thereof. None of the previously known report shows that change in the expression of the gene or the transcript thereof can serve as a marker for lung cancer.

The 63rd target gene is the hsa-miR-4656 gene, a congener thereof, a transcript thereof, or a variant or a derivative thereof. None of the previously known report shows that change in the expression of the gene or the transcript thereof can serve as a marker for lung cancer.

The 64th target gene is the hsa-miR-4663 gene, a congener thereof, a transcript thereof, or a variant or a derivative thereof. None of the previously known report shows that change in the expression of the gene or the transcript thereof can serve as a marker for lung cancer.

The 65th target gene is the hsa-miR-4665-5p gene, a congener thereof, a transcript thereof, or a variant or a derivative thereof. None of the previously known report shows that change in the expression of the gene or the transcript thereof can serve as a marker for lung cancer.

The 66th target gene is the hsa-miR-4706 gene, a congener thereof, a transcript thereof, or a variant or a derivative thereof. None of the previously known report shows that change in the expression of the gene or the transcript thereof can serve as a marker for lung cancer.

The 67th target gene is the hsa-miR-4707-5p gene, a congener thereof, a transcript thereof, or a variant or a derivative thereof. None of the previously known report shows that change in the expression of the gene or the transcript thereof can serve as a marker for lung cancer.

The 68th target gene is the hsa-miR-4708-3p gene, a congener thereof, a transcript thereof, or a variant or a derivative thereof. None of the previously known report shows that change in the expression of the gene or the transcript thereof can serve as a marker for lung cancer.

The 69th target gene is the hsa-miR-4710 gene, a congener thereof, a transcript thereof, or a variant or a derivative thereof. None of the previously known report shows that change in the expression of the gene or the transcript thereof can serve as a marker for lung cancer.

The 70th target gene is the hsa-miR-4718 gene, a congener thereof, a transcript thereof, or a variant or a derivative thereof. None of the previously known report shows that change in the expression of the gene or the transcript thereof can serve as a marker for lung cancer.

The 71st target gene is the hsa-miR-4722-5p gene, a congener thereof, a transcript thereof, or a variant or a derivative thereof. None of the previously known report shows that change in the expression of the gene or the transcript thereof can serve as a marker for lung cancer.

The 72nd target gene is the hsa-miR-4727-3p gene, a congener thereof, a transcript thereof, or a variant or a derivative thereof. None of the previously known report shows that change in the expression of the gene or the transcript thereof can serve as a marker for lung cancer.

The 73rd target gene is the hsa-miR-4730 gene, a congener thereof, a transcript thereof, or a variant or a derivative thereof. None of the previously known report shows that change in the expression of the gene or the transcript thereof can serve as a marker for lung cancer.

The 74th target gene is the hsa-miR-4734 gene, a congener thereof, a transcript thereof, or a variant or a derivative thereof. None of the previously known report shows that change in the expression of the gene or the transcript thereof can serve as a marker for lung cancer.

The 75th target gene is the hsa-miR-4740-5p gene, a congener thereof, a transcript thereof, or a variant or a derivative thereof. None of the previously known report shows that change in the expression of the gene or the transcript thereof can serve as a marker for lung cancer.

The 76th target gene is the hsa-miR-4747-3p gene, a congener thereof, a transcript thereof, or a variant or a derivative thereof. None of the previously known report shows that change in the expression of the gene or the transcript thereof can serve as a marker for lung cancer.

The 77th target gene is the hsa-miR-4749-5p gene, a congener thereof, a transcript thereof, or a variant or a derivative thereof. None of the previously known report shows that change in the expression of the gene or the transcript thereof can serve as a marker for lung cancer.

The 78th target gene is the hsa-miR-4755-3p gene, a congener thereof, a transcript thereof, or a variant or a derivative thereof. None of the previously known report shows that change in the expression of the gene or the transcript thereof can serve as a marker for lung cancer.

The 79th target gene is the hsa-miR-4763-5p gene, a congener thereof, a transcript thereof, or a variant or a derivative thereof. None of the previously known report shows that change in the expression of the gene or the transcript thereof can serve as a marker for lung cancer.

The 80th target gene is the hsa-miR-4787-3p gene, a congener thereof, a transcript thereof, or a variant or a derivative thereof. None of the previously known report shows that change in the expression of the gene or the transcript thereof can serve as a marker for lung cancer.

The 81st target gene is the hsa-miR-5008-5p gene, a congener thereof, a transcript thereof, or a variant or a derivative thereof. None of the previously known report shows that change in the expression of the gene or the transcript thereof can serve as a marker for lung cancer.

The 82nd target gene is the hsa-miR-5010-5p gene, a congener thereof, a transcript thereof, or a variant or a derivative thereof. None of the previously known report shows that change in the expression of the gene or the transcript thereof can serve as a marker for lung cancer.

The 83rd target gene is the hsa-miR-504-3p gene, a congener thereof, a transcript thereof, or a variant or a derivative thereof. None of the previously known report shows that change in the expression of the gene or the transcript thereof can serve as a marker for lung cancer.

The 84th target gene is the hsa-miR-5090 gene, a congener thereof, a transcript thereof, or a variant or a derivative thereof. None of the previously known report shows that change in the expression of the gene or the transcript thereof can serve as a marker for lung cancer.

The 85th target gene is the hsa-miR-5100 gene, a congener thereof, a transcript thereof, or a variant or a derivative thereof. None of the previously known report shows that change in the expression of the gene or the transcript thereof can serve as a marker for lung cancer.

The 86th target gene is the hsa-miR-5196-5p gene, a congener thereof, a transcript thereof, or a variant or a derivative thereof. None of the previously known report shows that change in the expression of the gene or the transcript thereof can serve as a marker for lung cancer.

The 87th target gene is the hsa-miR-551b-5p gene, a congener thereof, a transcript thereof, or a variant or a derivative thereof. None of the previously known report shows that change in the expression of the gene or the transcript thereof can serve as a marker for lung cancer.

The 88th target gene is the hsa-miR-557 gene, a congener thereof, a transcript thereof, or a variant or a derivative thereof. None of the previously known report shows that change in the expression of the gene or the transcript thereof can serve as a marker for lung cancer.

The 89th target gene is the hsa-miR-5787 gene, a congener thereof, a transcript thereof, or a variant or a derivative thereof. None of the previously known report shows that change in the expression of the gene or the transcript thereof can serve as a marker for lung cancer.

The 90th target gene is the hsa-miR-6090 gene, a congener thereof, a transcript thereof, or a variant or a derivative thereof. None of the previously known report shows that change in the expression of the gene or the transcript thereof can serve as a marker for lung cancer.

The 91st target gene is the hsa-miR-6124 gene, a congener thereof, a transcript thereof, or a variant or a derivative thereof. None of the previously known report shows that change in the expression of the gene or the transcript thereof can serve as a marker for lung cancer.

The 92nd target gene is the hsa-miR-6132 gene, a congener thereof, a transcript thereof, or a variant or a derivative thereof. None of the previously known report shows that change in the expression of the gene or the transcript thereof can serve as a marker for lung cancer.

The 93rd target gene is the hsa-miR-6510-5p gene, a congener thereof, a transcript thereof, or a variant or a derivative thereof. None of the previously known report shows that change in the expression of the gene or the transcript thereof can serve as a marker for lung cancer.

The 94th target gene is the hsa-miR-6511b-5p gene, a congener thereof, a transcript thereof, or a variant or a derivative thereof. None of the previously known report shows that change in the expression of the gene or the transcript thereof can serve as a marker for lung cancer.

The 95th target gene is the hsa-miR-6515-3p gene, a congener thereof, a transcript thereof, or a variant or a derivative thereof. None of the previously known report shows that change in the expression of the gene or the transcript thereof can serve as a marker for lung cancer.

The 96th target gene is the hsa-miR-654-5p gene, a congener thereof, a transcript thereof, or a variant or a derivative thereof. None of the previously known report shows that change in the expression of the gene or the transcript thereof can serve as a marker for lung cancer.

The 97th target gene is the hsa-miR-658 gene, a congener thereof, a transcript thereof, or a variant or a derivative thereof. None of the previously known report shows that change in the expression of the gene or the transcript thereof can serve as a marker for lung cancer.

The 98th target gene is the hsa-miR-668-5p gene, a congener thereof, a transcript thereof, or a variant or a derivative thereof. None of the previously known report shows that change in the expression of the gene or the transcript thereof can serve as a marker for lung cancer.

The 99th target gene is the hsa-miR-6722-5p gene, a congener thereof, a transcript thereof, or a variant or a derivative thereof. None of the previously known report shows that change in the expression of the gene or the transcript thereof can serve as a marker for lung cancer.

The 100th target gene is the hsa-miR-6724-5p gene, a congener thereof, a transcript thereof, or a variant or a derivative thereof. None of the previously known report shows that change in the expression of the gene or the transcript thereof can serve as a marker for lung cancer.

The 101st target gene is the hsa-miR-6729-3p gene, a congener thereof, a transcript thereof, or a variant or a derivative thereof. None of the previously known report shows that change in the expression of the gene or the transcript thereof can serve as a marker for lung cancer.

The 102nd target gene is the hsa-miR-6737-5p gene, a congener thereof, a transcript thereof, or a variant or a derivative thereof. None of the previously known report shows that change in the expression of the gene or the transcript thereof can serve as a marker for lung cancer.

The 103rd target gene is the hsa-miR-6756-5p gene, a congener thereof, a transcript thereof, or a variant or a derivative thereof. None of the previously known report shows that change in the expression of the gene or the transcript thereof can serve as a marker for lung cancer.

The 104th target gene is the hsa-miR-6762-5p gene, a congener thereof, a transcript thereof, or a variant or a derivative thereof. None of the previously known report shows that change in the expression of the gene or the transcript thereof can serve as a marker for lung cancer.

The 105th target gene is the hsa-miR-6763-3p gene, a congener thereof, a transcript thereof, or a variant or a derivative thereof. None of the previously known report shows that change in the expression of the gene or the transcript thereof can serve as a marker for lung cancer.

The 106th target gene is the hsa-miR-6766-5p gene, a congener thereof, a transcript thereof, or a variant or a derivative thereof. None of the previously known report shows that change in the expression of the gene or the transcript thereof can serve as a marker for lung cancer.

The 107th target gene is the hsa-miR-6769a-5p gene, a congener thereof, a transcript thereof, or a variant or a derivative thereof. None of the previously known report shows that change in the expression of the gene or the transcript thereof can serve as a marker for lung cancer.

The 108th target gene is the hsa-miR-6771-5p gene, a congener thereof, a transcript thereof, or a variant or a derivative thereof. None of the previously known report shows that change in the expression of the gene or the transcript thereof can serve as a marker for lung cancer.

The 109th target gene is the hsa-miR-6786-5p gene, a congener thereof, a transcript thereof, or a variant or a derivative thereof. None of the previously known report shows that change in the expression of the gene or the transcript thereof can serve as a marker for lung cancer.

The 110th target gene is the hsa-miR-6789-5p gene, a congener thereof, a transcript thereof, or a variant or a derivative thereof. None of the previously known report shows that change in the expression of the gene or the transcript thereof can serve as a marker for lung cancer.

The 111th target gene is the hsa-miR-6794-5p gene, a congener thereof, a transcript thereof, or a variant or a derivative thereof. None of the previously known report shows that change in the expression of the gene or the transcript thereof can serve as a marker for lung cancer.

The 112th target gene is the hsa-miR-6796-3p gene, a congener thereof, a transcript thereof, or a variant or a derivative thereof. None of the previously known report shows that change in the expression of the gene or the transcript thereof can serve as a marker for lung cancer.

The 113th target gene is the hsa-miR-6797-5p gene, a congener thereof, a transcript thereof, or a variant or a derivative thereof. None of the previously known report shows that change in the expression of the gene or the transcript thereof can serve as a marker for lung cancer.

The 114th target gene is the hsa-miR-6800-3p gene, a congener thereof, a transcript thereof, or a variant or a derivative thereof. None of the previously known report shows that change in the expression of the gene or the transcript thereof can serve as a marker for lung cancer.

The 115th target gene is the hsa-miR-6802-5p gene, a congener thereof, a transcript thereof, or a variant or a derivative thereof. None of the previously known report shows that change in the expression of the gene or the transcript thereof can serve as a marker for lung cancer.

The 116th target gene is the hsa-miR-6803-5p gene, a congener thereof, a transcript thereof, or a variant or a derivative thereof. None of the previously known report shows that change in the expression of the gene or the transcript thereof can serve as a marker for lung cancer.

The 117th target gene is the hsa-miR-6805-3p gene, a congener thereof, a transcript thereof, or a variant or a derivative thereof. None of the previously known report shows that change in the expression of the gene or the transcript thereof can serve as a marker for lung cancer.

The 118th target gene is the hsa-miR-6805-5p gene, a congener thereof, a transcript thereof, or a variant or a derivative thereof. None of the previously known report shows that change in the expression of the gene or the transcript thereof can serve as a marker for lung cancer.

The 119th target gene is the hsa-miR-6807-5p gene, a congener thereof, a transcript thereof, or a variant or a derivative thereof. None of the previously known report shows that change in the expression of the gene or the transcript thereof can serve as a marker for lung cancer.

The 120th target gene is the hsa-miR-6812-5p gene, a congener thereof, a transcript thereof, or a variant or a derivative thereof. None of the previously known report shows that change in the expression of the gene or the transcript thereof can serve as a marker for lung cancer.

The 121st target gene is the hsa-miR-6819-5p gene, a congener thereof, a transcript thereof, or a variant or a derivative thereof. None of the previously known report shows that change in the expression of the gene or the transcript thereof can serve as a marker for lung cancer.

The 122nd target gene is the hsa-miR-6822-5p gene, a congener thereof, a transcript thereof, or a variant or a derivative thereof. None of the previously known report shows that change in the expression of the gene or the transcript thereof can serve as a marker for lung cancer.

The 123rd target gene is the hsa-miR-6824-5p gene, a congener thereof, a transcript thereof, or a variant or a derivative thereof. None of the previously known report shows that change in the expression of the gene or the transcript thereof can serve as a marker for lung cancer.

The 124th target gene is the hsa-miR-6826-5p gene, a congener thereof, a transcript thereof, or a variant or a derivative thereof. None of the previously known report shows that change in the expression of the gene or the transcript thereof can serve as a marker for lung cancer.

The 125th target gene is the hsa-miR-6850-5p gene, a congener thereof, a transcript thereof, or a variant or a derivative thereof. None of the previously known report shows that change in the expression of the gene or the transcript thereof can serve as a marker for lung cancer.

The 126th target gene is the hsa-miR-6858-5p gene, a congener thereof, a transcript thereof, or a variant or a derivative thereof. None of the previously known report shows that change in the expression of the gene or the transcript thereof can serve as a marker for lung cancer.

The 127th target gene is the hsa-miR-6861-5p gene, a congener thereof, a transcript thereof, or a variant or a derivative thereof. None of the previously known report shows that change in the expression of the gene or the transcript thereof can serve as a marker for lung cancer.

The 128th target gene is the hsa-miR-6880-3p gene, a congener thereof, a transcript thereof, or a variant or a derivative thereof. None of the previously known report shows that change in the expression of the gene or the transcript thereof can serve as a marker for lung cancer.

The 129th target gene is the hsa-miR-7107-5p gene, a congener thereof, a transcript thereof, or a variant or a derivative thereof. None of the previously known report shows that change in the expression of the gene or the transcript thereof can serve as a marker for lung cancer.

The 130th target gene is the hsa-miR-7109-5p gene, a congener thereof, a transcript thereof, or a variant or a derivative thereof. None of the previously known report shows that change in the expression of the gene or the transcript thereof can serve as a marker for lung cancer.

The 131st target gene is the hsa-miR-7114-5p gene, a congener thereof, a transcript thereof, or a variant or a derivative thereof. None of the previously known report shows that change in the expression of the gene or the transcript thereof can serve as a marker for lung cancer.

The 132nd target gene is the hsa-miR-7704 gene, a congener thereof, a transcript thereof, or a variant or a derivative thereof. None of the previously known report shows that change in the expression of the gene or the transcript thereof can serve as a marker for lung cancer.

The 133rd target gene is the hsa-miR-7846-3p gene, a congener thereof, a transcript thereof, or a variant or a derivative thereof. None of the previously known report shows that change in the expression of the gene or the transcript thereof can serve as a marker for lung cancer.

The 134th target gene is the hsa-miR-8052 gene, a congener thereof, a transcript thereof, or a variant or a derivative thereof. None of the previously known report shows that change in the expression of the gene or the transcript thereof can serve as a marker for lung cancer.

The 135th target gene is the hsa-miR-8060 gene, a congener thereof, a transcript thereof, or a variant or a derivative thereof. None of the previously known report shows that change in the expression of the gene or the transcript thereof can serve as a marker for lung cancer.

The 136th target gene is the hsa-miR-8071 gene, a congener thereof, a transcript thereof, or a variant or a derivative thereof. None of the previously known report shows that change in the expression of the gene or the transcript thereof can serve as a marker for lung cancer.

The 137th target gene is the hsa-miR-8073 gene, a congener thereof, a transcript thereof, or a variant or a derivative thereof. None of the previously known report shows that change in the expression of the gene or the transcript thereof can serve as a marker for lung cancer.

The 138th target gene is the hsa-miR-874-5p gene, a congener thereof, a transcript thereof, or a variant or a derivative thereof. None of the previously known report shows that change in the expression of the gene or the transcript thereof can serve as a marker for lung cancer.

The 139th target gene is the hsa-miR-204-3p gene, a congener thereof, a transcript thereof, or a variant or a derivative thereof. None of the previously known report shows that change in the expression of the gene or the transcript thereof can serve as a marker for lung cancer.

The 140th target gene is the hsa-miR-3154 gene, a congener thereof, a transcript thereof, or a variant or a derivative thereof. None of the previously known report shows that change in the expression of the gene or the transcript thereof can serve as a marker for lung cancer.

The 141st target gene is the hsa-miR-3960 gene, a congener thereof, a transcript thereof, or a variant or a derivative thereof. None of the previously known report shows that change in the expression of the gene or the transcript thereof can serve as a marker for lung cancer.

The 142nd target gene is the hsa-miR-4433a-5p gene, a congener thereof, a transcript thereof, or a variant or a derivative thereof. None of the previously known report shows that change in the expression of the gene or the transcript thereof can serve as a marker for lung cancer.

The 143rd target gene is the hsa-miR-4455 gene, a congener thereof, a transcript thereof, or a variant or a derivative thereof. None of the previously known report shows that change in the expression of the gene or the transcript thereof can serve as a marker for lung cancer.

The 144th target gene is the hsa-miR-4462 gene, a congener thereof, a transcript thereof, or a variant or a derivative thereof. None of the previously known report shows that change in the expression of the gene or the transcript thereof can serve as a marker for lung cancer.

The 145th target gene is the hsa-miR-4476 gene, a congener thereof, a transcript thereof, or a variant or a derivative thereof. None of the previously known report shows that change in the expression of the gene or the transcript thereof can serve as a marker for lung cancer.

The 146th target gene is the hsa-miR-4508 gene, a congener thereof, a transcript thereof, or a variant or a derivative thereof. None of the previously known report shows that change in the expression of the gene or the transcript thereof can serve as a marker for lung cancer.

The 147th target gene is the hsa-miR-4687-3p gene, a congener thereof, a transcript thereof, or a variant or a derivative thereof. None of the previously known report shows that change in the expression of the gene or the transcript thereof can serve as a marker for lung cancer.

The 148th target gene is the hsa-miR-4687-5p gene, a congener thereof, a transcript thereof, or a variant or a derivative thereof. None of the previously known report shows that change in the expression of the gene or the transcript thereof can serve as a marker for lung cancer.

The 149th target gene is the hsa-miR-4732-5p gene, a congener thereof, a transcript thereof, or a variant or a derivative thereof. None of the previously known report shows that change in the expression of the gene or the transcript thereof can serve as a marker for lung cancer.

The 150th target gene is the hsa-miR-4771 gene, a congener thereof, a transcript thereof, or a variant or a derivative thereof. None of the previously known report shows that change in the expression of the gene or the transcript thereof can serve as a marker for lung cancer.

The 151st target gene is the hsa-miR-642a-3p gene, a congener thereof, a transcript thereof, or a variant or a derivative thereof. None of the previously known report shows that change in the expression of the gene or the transcript thereof can serve as a marker for lung cancer.

The 152nd target gene is the hsa-miR-6732-5p gene, a congener thereof, a transcript thereof, or a variant or a derivative thereof. None of the previously known report shows that change in the expression of the gene or the transcript thereof can serve as a marker for lung cancer.

The 153rd target gene is the hsa-miR-6760-5p gene, a congener thereof, a transcript thereof, or a variant or a derivative thereof. None of the previously known report shows that change in the expression of the gene or the transcript thereof can serve as a marker for lung cancer.

The 154th target gene is the hsa-miR-6799-5p gene, a congener thereof, a transcript thereof, or a variant or a derivative thereof. None of the previously known report shows that change in the expression of the gene or the transcript thereof can serve as a marker for lung cancer.

The 155th target gene is the hsa-miR-6820-5p gene, a congener thereof, a transcript thereof, or a variant or a derivative thereof. None of the previously known report shows that change in the expression of the gene or the transcript thereof can serve as a marker for lung cancer.

The 156th target gene is the hsa-miR-6821-5p gene, a congener thereof, a transcript thereof, or a variant or a derivative thereof. None of the previously known report shows that change in the expression of the gene or the transcript thereof can serve as a marker for lung cancer.

The 157th target gene is the hsa-miR-6829-5p gene, a congener thereof, a transcript thereof, or a variant or a derivative thereof. None of the previously known report shows that change in the expression of the gene or the transcript thereof can serve as a marker for lung cancer.

The 158th target gene is the hsa-miR-6893-5p gene, a congener thereof, a transcript thereof, or a variant or a derivative thereof. None of the previously known report shows that change in the expression of the gene or the transcript thereof can serve as a marker for lung cancer.

The 159th target gene is the hsa-miR-7108-3p gene, a congener thereof, a transcript thereof, or a variant or a derivative thereof. None of the previously known report shows that change in the expression of the gene or the transcript thereof can serve as a marker for lung cancer.

The 160th target gene is the hsa-miR-7111-5p gene, a congener thereof, a transcript thereof, or a variant or a derivative thereof. None of the previously known report shows that change in the expression of the gene or the transcript thereof can serve as a marker for lung cancer.

The 161st target gene is the hsa-miR-8089 gene, a congener thereof, a transcript thereof, or a variant or a derivative thereof. None of the previously known report shows that change in the expression of the gene or the transcript thereof can serve as a marker for lung cancer.

The 162nd target gene is the hsa-miR-885-3p gene, a congener thereof, a transcript thereof, or a variant or a derivative thereof. None of the previously known report shows that change in the expression of the gene or the transcript thereof can serve as a marker for lung cancer.

The 163rd target gene is the hsa-miR-92b-3p gene, a congener thereof, a transcript thereof, or a variant or a derivative thereof. None of the previously known report shows that change in the expression of the gene or the transcript thereof can serve as a marker for lung cancer.

The 164th target gene is the hsa-miR-1343-3p gene, a congener thereof, a transcript thereof, or a variant or a derivative thereof. The previously known report shows that change in the expression of the gene or the transcript thereof can serve as a marker for lung cancer (Patent Literature 1).

The 165th target gene is the hsa-miR-6746-5p gene, a congener thereof, a transcript thereof, or a variant or a derivative thereof. The previously known report shows that change in the expression of the gene or the transcript thereof can serve as a marker for lung cancer (Patent Literature 1).

The 166th target gene is the hsa-miR-422a gene, a congener thereof, a transcript thereof, or a variant or a derivative thereof. The previously known report shows that change in the expression of the gene or the transcript thereof can serve as a marker for lung cancer (Patent Literature 2).

The 167th target gene is the hsa-miR-187-5p gene, a congener thereof, a transcript thereof, or a variant or a derivative thereof. The previously known report shows that change in the expression of the gene or the transcript thereof can serve as a marker for lung cancer (Patent Literature 1).

The 168th target gene is the hsa-miR-4632-5p gene, a congener thereof, a transcript thereof, or a variant or a derivative thereof. The previously known report shows that change in the expression of the gene or the transcript thereof can serve as a marker for lung cancer (Patent Literature 1).

The 169th target gene is the hsa-miR-6791-5p gene, a congener thereof, a transcript thereof, or a variant or a derivative thereof. The previously known report shows that change in the expression of the gene or the transcript thereof can serve as a marker for lung cancer (Patent Literature 1).

The 170th target gene is the hsa-miR-103a-3p gene, a congener thereof, a transcript thereof, or a variant or a derivative thereof. The previously known report shows that change in the expression of the gene or the transcript thereof can serve as a marker for lung cancer (Patent Literature 3).

The 171st target gene is the hsa-miR-107 gene, a congener thereof, a transcript thereof, or a variant or a derivative thereof. The previously known report shows that change in the expression of the gene or the transcript thereof can serve as a marker for lung cancer (Patent Literature 3).

The 172nd target gene is the hsa-miR-1199-5p gene, a congener thereof, a transcript thereof, or a variant or a derivative thereof. The previously known report shows that change in the expression of the gene or the transcript thereof can serve as a marker for lung cancer (Patent Literature 1).

The 173rd target gene is the hsa-miR-1225-3p gene, a congener thereof, a transcript thereof, or a variant or a derivative thereof. The previously known report shows that change in the expression of the gene or the transcript thereof can serve as a marker for lung cancer (Patent Literature 1).

The 174th target gene is the hsa-miR-1225-5p gene, a congener thereof, a transcript thereof, or a variant or a derivative thereof. The previously known report shows that change in the expression of the gene or the transcript thereof can serve as a marker for lung cancer (Patent Literature 1).

The 175th target gene is the hsa-miR-1228-5p gene, a congener thereof, a transcript thereof, or a variant or a derivative thereof. The previously known report shows that change in the expression of the gene or the transcript thereof can serve as a marker for lung cancer (Patent Literature 1).

The 176th target gene is the hsa-miR-1229-5p gene, a congener thereof, a transcript thereof, or a variant or a derivative thereof. The previously known report shows that change in the expression of the gene or the transcript thereof can serve as a marker for lung cancer (Non-Patent Literature 5).

The 177th target gene is the hsa-miR-1233-5p gene, a congener thereof, a transcript thereof, or a variant or a derivative thereof. The previously known report shows that change in the expression of the gene or the transcript thereof can serve as a marker for lung cancer (Patent Literature 1).

The 178th target gene is the hsa-miR-1237-5p gene, a congener thereof, a transcript thereof, or a variant or a derivative thereof. The previously known report shows that change in the expression of the gene or the transcript thereof can serve as a marker for lung cancer (Patent Literature 1).

The 179th target gene is the hsa-miR-1247-3p gene, a congener thereof, a transcript thereof, or a variant or a derivative thereof. The previously known report shows that change in the expression of the gene or the transcript thereof can serve as a marker for lung cancer (Patent Literature 1).

The 180th target gene is the hsa-miR-1249-3p gene, a congener thereof, a transcript thereof, or a variant or a derivative thereof. The previously known report shows that change in the expression of the gene or the transcript thereof can serve as a marker for lung cancer (Patent Literature 5).

The 181st target gene is the hsa-miR-1254 gene, a congener thereof, a transcript thereof, or a variant or a derivative thereof. The previously known report shows that change in the expression of the gene or the transcript thereof can serve as a marker for lung cancer (Non-Patent Literature 6).

The 182nd target gene is the hsa-miR-1260b gene, a congener thereof, a transcript thereof, or a variant or a derivative thereof. The previously known report shows that change in the expression of the gene or the transcript thereof can serve as a marker for lung cancer (Patent Literature 1).

The 183rd target gene is the hsa-miR-1268a gene, a congener thereof, a transcript thereof, or a variant or a derivative thereof. The previously known report shows that change in the expression of the gene or the transcript thereof can serve as a marker for lung cancer (Patent Literature 1).

The 184th target gene is the hsa-miR-1268b gene, a congener thereof, a transcript thereof, or a variant or a derivative thereof. The previously known report shows that change in the expression of the gene or the transcript thereof can serve as a marker for lung cancer (Patent Literature 1).

The 185th target gene is the hsa-miR-1273g-3p gene, a congener thereof, a transcript thereof, or a variant or a derivative thereof. The previously known report shows that change in the expression of the gene or the transcript thereof can serve as a marker for lung cancer (Patent Literature 1).

The 186th target gene is the hsa-miR-128-1-5p gene, a congener thereof, a transcript thereof, or a variant or a derivative thereof. The previously known report shows that change in the expression of the gene or the transcript thereof can serve as a marker for lung cancer (Patent Literature 1).

The 187th target gene is the hsa-miR-128-2-5p gene, a congener thereof, a transcript thereof, or a variant or a derivative thereof. The previously known report shows that change in the expression of the gene or the transcript thereof can serve as a marker for lung cancer (Patent Literature 1).

The 188th target gene is the hsa-miR-1290 gene, a congener thereof, a transcript thereof, or a variant or a derivative thereof. The previously known report shows that change in the expression of the gene or the transcript thereof can serve as a marker for lung cancer (Non-Patent Literature 1).

The 189th target gene is the hsa-miR-150-3p gene, a congener thereof, a transcript thereof, or a variant or a derivative thereof. The previously known report shows that change in the expression of the gene or the transcript thereof can serve as a marker for lung cancer (Patent Literature 3).

The 190th target gene is the hsa-miR-17-3p gene, a congener thereof, a transcript thereof, or a variant or a derivative thereof. The previously known report shows that change in the expression of the gene or the transcript thereof can serve as a marker for lung cancer (Patent Literature 1).

The 191st target gene is the hsa-miR-1908-5p gene, a congener thereof, a transcript thereof, or a variant or a derivative thereof. The previously known report shows that change in the expression of the gene or the transcript thereof can serve as a marker for lung cancer (Patent Literature 1).

The 192nd target gene is the hsa-miR-1909-3p gene, a congener thereof, a transcript thereof, or a variant or a derivative thereof. The previously known report shows that change in the expression of the gene or the transcript thereof can serve as a marker for lung cancer (Patent Literature 4).

The 193rd target gene is the hsa-miR-1914-3p gene, a congener thereof, a transcript thereof, or a variant or a derivative thereof. The previously known report shows that change in the expression of the gene or the transcript thereof can serve as a marker for lung cancer (Patent Literature 1).

The 194th target gene is the hsa-miR-1915-3p gene, a congener thereof, a transcript thereof, or a variant or a derivative thereof. The previously known report shows that change in the expression of the gene or the transcript thereof can serve as a marker for lung cancer (Patent Literature 1).

The 195th target gene is the hsa-miR-191-5p gene, a congener thereof, a transcript thereof, or a variant or a derivative thereof. The previously known report shows that change in the expression of the gene or the transcript thereof can serve as a marker for lung cancer (Patent Literature 1).

The 196th target gene is the hsa-miR-22-3p gene, a congener thereof, a transcript thereof, or a variant or a derivative thereof. The previously known report shows that change in the expression of the gene or the transcript thereof can serve as a marker for lung cancer (Patent Literature 1).

The 197th target gene is the hsa-miR-23b-3p gene, a congener thereof, a transcript thereof, or a variant or a derivative thereof. The previously known report shows that change in the expression of the gene or the transcript thereof can serve as a marker for lung cancer (Patent Literature 4).

The 198th target gene is the hsa-miR-24-3p gene, a congener thereof, a transcript thereof, or a variant or a derivative thereof. The previously known report shows that change in the expression of the gene or the transcript thereof can serve as a marker for lung cancer (Patent Literature 2).

The 199th target gene is the hsa-miR-296-3p gene, a congener thereof, a transcript thereof, or a variant or a derivative thereof. The previously known report shows that change in the expression of the gene or the transcript thereof can serve as a marker for lung cancer (Patent Literature 1).

The 200th target gene is the hsa-miR-296-5p gene, a congener thereof, a transcript thereof, or a variant or a derivative thereof. The previously known report shows that change in the expression of the gene or the transcript thereof can serve as a marker for lung cancer (Patent Literature 2).

The 201st target gene is the hsa-miR-3131 gene, a congener thereof, a transcript thereof, or a variant or a derivative thereof. The previously known report shows that change in the expression of the gene or the transcript thereof can serve as a marker for lung cancer (Patent Literature 1).

The 202nd target gene is the hsa-miR-3162-5p gene, a congener thereof, a transcript thereof, or a variant or a derivative thereof. The previously known report shows that change in the expression of the gene or the transcript thereof can serve as a marker for lung cancer (Patent Literature 1).

The 203rd target gene is the hsa-miR-3188 gene, a congener thereof, a transcript thereof, or a variant or a derivative thereof. The previously known report shows that change in the expression of the gene or the transcript thereof can serve as a marker for lung cancer (Patent Literature 1).

The 204th target gene is the hsa-miR-3196 gene, a congener thereof, a transcript thereof, or a variant or a derivative thereof. The previously known report shows that change in the expression of the gene or the transcript thereof can serve as a marker for lung cancer (Patent Literature 1).

The 205th target gene is the hsa-miR-3197 gene, a congener thereof, a transcript thereof, or a variant or a derivative thereof. The previously known report shows that change in the expression of the gene or the transcript thereof can serve as a marker for lung cancer (Patent Literature 1).

The 206th target gene is the hsa-miR-320a gene, a congener thereof, a transcript thereof, or a variant or a derivative thereof. The previously known report shows that change in the expression of the gene or the transcript thereof can serve as a marker for lung cancer (Patent Literature 2).

The 207th target gene is the hsa-miR-342-5p gene, a congener thereof, a transcript thereof, or a variant or a derivative thereof. The previously known report shows that change in the expression of the gene or the transcript thereof can serve as a marker for lung cancer (Non-Patent Literature 3).

The 208th target gene is the hsa-miR-3621 gene, a congener thereof, a transcript thereof, or a variant or a derivative thereof. The previously known report shows that change in the expression of the gene or the transcript thereof can serve as a marker for lung cancer (Patent Literature 1).

The 209th target gene is the hsa-miR-3648 gene, a congener thereof, a transcript thereof, or a variant or a derivative thereof. The previously known report shows that change in the expression of the gene or the transcript thereof can serve as a marker for lung cancer (Patent Literature 1).

The 210th target gene is the hsa-miR-3656 gene, a congener thereof, a transcript thereof, or a variant or a derivative thereof. The previously known report shows that change in the expression of the gene or the transcript thereof can serve as a marker for lung cancer (Patent Literature 1).

The 211th target gene is the hsa-miR-365a-5p gene, a congener thereof, a transcript thereof, or a variant or a derivative thereof. The previously known report shows that change in the expression of the gene or the transcript thereof can serve as a marker for lung cancer (Patent Literature 1).

The 212th target gene is the hsa-miR-3665 gene, a congener thereof, a transcript thereof, or a variant or a derivative thereof. The previously known report shows that change in the expression of the gene or the transcript thereof can serve as a marker for lung cancer (Patent Literature 1).

The 213th target gene is the hsa-miR-3679-5p gene, a congener thereof, a transcript thereof, or a variant or a derivative thereof. The previously known report shows that change in the expression of the gene or the transcript thereof can serve as a marker for lung cancer (Patent Literature 1).

The 214th target gene is the hsa-miR-371a-5p gene, a congener thereof, a transcript thereof, or a variant or a derivative thereof. The previously known report shows that change in the expression of the gene or the transcript thereof can serve as a marker for lung cancer (Patent Literature 1).

The 215th target gene is the hsa-miR-3940-5p gene, a congener thereof, a transcript thereof, or a variant or a derivative thereof. The previously known report shows that change in the expression of the gene or the transcript thereof can serve as a marker for lung cancer (Patent Literature 1).

The 216th target gene is the hsa-miR-423-5p gene, a congener thereof, a transcript thereof, or a variant or a derivative thereof. The previously known report shows that change in the expression of the gene or the transcript thereof can serve as a marker for lung cancer (Patent Literature 4).

The 217th target gene is the hsa-miR-4257 gene, a congener thereof, a transcript thereof, or a variant or a derivative thereof. The previously known report shows that change in the expression of the gene or the transcript thereof can serve as a marker for lung cancer (Patent Literature 1).

The 218th target gene is the hsa-miR-4270 gene, a congener thereof, a transcript thereof, or a variant or a derivative thereof. The previously known report shows that change in the expression of the gene or the transcript thereof can serve as a marker for lung cancer (Patent Literature 1).

The 219th target gene is the hsa-miR-4271 gene, a congener thereof, a transcript thereof, or a variant or a derivative thereof. The previously known report shows that change in the expression of the gene or the transcript thereof can serve as a marker for lung cancer (Patent Literature 1).

The 220th target gene is the hsa-miR-4286 gene, a congener thereof, a transcript thereof, or a variant or a derivative thereof. The previously known report shows that change in the expression of the gene or the transcript thereof can serve as a marker for lung cancer (Patent Literature 1).

The 221st target gene is the hsa-miR-4298 gene, a congener thereof, a transcript thereof, or a variant or a derivative thereof. The previously known report shows that change in the expression of the gene or the transcript thereof can serve as a marker for lung cancer (Patent Literature 1).

The 222nd target gene is the hsa-miR-4417 gene, a congener thereof, a transcript thereof, or a variant or a derivative thereof. The previously known report shows that change in the expression of the gene or the transcript thereof can serve as a marker for lung cancer (Patent Literature 1).

The 223rd target gene is the hsa-miR-4442 gene, a congener thereof, a transcript thereof, or a variant or a derivative thereof. The previously known report shows that change in the expression of the gene or the transcript thereof can serve as a marker for lung cancer (Patent Literature 1).

The 224th target gene is the hsa-miR-4446-3p gene, a congener thereof, a transcript thereof, or a variant or a derivative thereof. The previously known report shows that change in the expression of the gene or the transcript thereof can serve as a marker for lung cancer (Patent Literature 1).

The 225th target gene is the hsa-miR-4448 gene, a congener thereof, a transcript thereof, or a variant or a derivative thereof. The previously known report shows that change in the expression of the gene or the transcript thereof can serve as a marker for lung cancer (Patent Literature 1).

The 226th target gene is the hsa-miR-4454 gene, a congener thereof, a transcript thereof, or a variant or a derivative thereof. The previously known report shows that change in the expression of the gene or the transcript thereof can serve as a marker for lung cancer (Patent Literature 1).

The 227th target gene is the hsa-miR-4467 gene, a congener thereof, a transcript thereof, or a variant or a derivative thereof. The previously known report shows that change in the expression of the gene or the transcript thereof can serve as a marker for lung cancer (Patent Literature 1).

The 228th target gene is the hsa-miR-4472 gene, a congener thereof, a transcript thereof, or a variant or a derivative thereof. The previously known report shows that change in the expression of the gene or the transcript thereof can serve as a marker for lung cancer (Patent Literature 1).

The 229th target gene is the hsa-miR-4507 gene, a congener thereof, a transcript thereof, or a variant or a derivative thereof. The previously known report shows that change in the expression of the gene or the transcript thereof can serve as a marker for lung cancer (Patent Literature 1).

The 230th target gene is the hsa-miR-4516 gene, a congener thereof, a transcript thereof, or a variant or a derivative thereof. The previously known report shows that change in the expression of the gene or the transcript thereof can serve as a marker for lung cancer (Patent Literature 1).

The 231st target gene is the hsa-miR-451a gene, a congener thereof, a transcript thereof, or a variant or a derivative thereof. The previously known report shows that change in the expression of the gene or the transcript thereof can serve as a marker for lung cancer (Patent Literature 1).

The 232nd target gene is the hsa-miR-4649-5p gene, a congener thereof, a transcript thereof, or a variant or a derivative thereof. The previously known report shows that change in the expression of the gene or the transcript thereof can serve as a marker for lung cancer (Patent Literature 1).

The 233rd target gene is the hsa-miR-4651 gene, a congener thereof, a transcript thereof, or a variant or a derivative thereof. The previously known report shows that change in the expression of the gene or the transcript thereof can serve as a marker for lung cancer (Patent Literature 1).

The 234th target gene is the hsa-miR-4665-3p gene, a congener thereof, a transcript thereof, or a variant or a derivative thereof. The previously known report shows that change in the expression of the gene or the transcript thereof can serve as a marker for lung cancer (Patent Literature 1).

The 235th target gene is the hsa-miR-4674 gene, a congener thereof, a transcript thereof, or a variant or a derivative thereof. The previously known report shows that change in the expression of the gene or the transcript thereof can serve as a marker for lung cancer (Patent Literature 1).

The 236th target gene is the hsa-miR-4675 gene, a congener thereof, a transcript thereof, or a variant or a derivative thereof. The previously known report shows that change in the expression of the gene or the transcript thereof can serve as a marker for lung cancer (Patent Literature 1).

The 237th target gene is the hsa-miR-4689 gene, a congener thereof, a transcript thereof, or a variant or a derivative thereof. The previously known report shows that change in the expression of the gene or the transcript thereof can serve as a marker for lung cancer (Patent Literature 1).

The 238th target gene is the hsa-miR-4695-5p gene, a congener thereof, a transcript thereof, or a variant or a derivative thereof. The previously known report shows that change in the expression of the gene or the transcript thereof can serve as a marker for lung cancer (Patent Literature 1).

The 239th target gene is the hsa-miR-4697-5p gene, a congener thereof, a transcript thereof, or a variant or a derivative thereof. The previously known report shows that change in the expression of the gene or the transcript thereof can serve as a marker for lung cancer (Patent Literature 1).

The 240th target gene is the hsa-miR-4725-3p gene, a congener thereof, a transcript thereof, or a variant or a derivative thereof. The previously known report shows that change in the expression of the gene or the transcript thereof can serve as a marker for lung cancer (Patent Literature 1).

The 241st target gene is the hsa-miR-4739 gene, a congener thereof, a transcript thereof, or a variant or a derivative thereof. The previously known report shows that change in the expression of the gene or the transcript thereof can serve as a marker for lung cancer (Patent Literature 1).

The 242nd target gene is the hsa-miR-4745-5p gene, a congener thereof, a transcript thereof, or a variant or a derivative thereof. The previously known report shows that change in the expression of the gene or the transcript thereof can serve as a marker for lung cancer (Patent Literature 1).

The 243rd target gene is the hsa-miR-4763-3p gene, a congener thereof, a transcript thereof, or a variant or a derivative thereof. The previously known report shows that change in the expression of the gene or the transcript thereof can serve as a marker for lung cancer (Patent Literature 1).

The 244th target gene is the hsa-miR-4792 gene, a congener thereof, a transcript thereof, or a variant or a derivative thereof. The previously known report shows that change in the expression of the gene or the transcript thereof can serve as a marker for lung cancer (Patent Literature 1).

The 245th target gene is the hsa-miR-486-3p gene, a congener thereof, a transcript thereof, or a variant or a derivative thereof. The previously known report shows that change in the expression of the gene or the transcript thereof can serve as a marker for lung cancer (Patent Literature 1).

The 246th target gene is the hsa-miR-5001-5p gene, a congener thereof, a transcript thereof, or a variant or a derivative thereof. The previously known report shows that change in the expression of the gene or the transcript thereof can serve as a marker for lung cancer (Patent Literature 1).

The 247th target gene is the hsa-miR-5195-3p gene, a congener thereof, a transcript thereof, or a variant or a derivative thereof. The previously known report shows that change in the expression of the gene or the transcript thereof can serve as a marker for lung cancer (Patent Literature 1).

The 248th target gene is the hsa-miR-550a-5p gene, a congener thereof, a transcript thereof, or a variant or a derivative thereof. The previously known report shows that change in the expression of the gene or the transcript thereof can serve as a marker for lung cancer (Non-Patent Literature 4).

The 249th target gene is the hsa-miR-5698 gene, a congener thereof, a transcript thereof, or a variant or a derivative thereof. The previously known report shows that change in the expression of the gene or the transcript thereof can serve as a marker for lung cancer (Patent Literature 1).

The 250th target gene is the hsa-miR-6075 gene, a congener thereof, a transcript thereof, or a variant or a derivative thereof. The previously known report shows that change in the expression of the gene or the transcript thereof can serve as a marker for lung cancer (Patent Literature 1).

The 251st target gene is the hsa-miR-6088 gene, a congener thereof, a transcript thereof, or a variant or a derivative thereof. The previously known report shows that change in the expression of the gene or the transcript thereof can serve as a marker for lung cancer (Patent Literature 1).

The 252nd target gene is the hsa-miR-6089 gene, a congener thereof, a transcript thereof, or a variant or a derivative thereof. The previously known report shows that change in the expression of the gene or the transcript thereof can serve as a marker for lung cancer (Patent Literature 1).

The 253rd target gene is the hsa-miR-6125 gene, a congener thereof, a transcript thereof, or a variant or a derivative thereof. The previously known report shows that change in the expression of the gene or the transcript thereof can serve as a marker for lung cancer (Patent Literature 1).

The 254th target gene is the hsa-miR-6126 gene, a congener thereof, a transcript thereof, or a variant or a derivative thereof. The previously known report shows that change in the expression of the gene or the transcript thereof can serve as a marker for lung cancer (Patent Literature 1).

The 255th target gene is the hsa-miR-614 gene, a congener thereof, a transcript thereof, or a variant or a derivative thereof. The previously known report shows that change in the expression of the gene or the transcript thereof can serve as a marker for lung cancer (Patent Literature 1).

The 256th target gene is the hsa-miR-615-5p gene, a congener thereof, a transcript thereof, or a variant or a derivative thereof. The previously known report shows that change in the expression of the gene or the transcript thereof can serve as a marker for lung cancer (Patent Literature 1).

The 257th target gene is the hsa-miR-619-5p gene, a congener thereof, a transcript thereof, or a variant or a derivative thereof. The previously known report shows that change in the expression of the gene or the transcript thereof can serve as a marker for lung cancer (Patent Literature 1).

The 258th target gene is the hsa-miR-638 gene, a congener thereof, a transcript thereof, or a variant or a derivative thereof. The previously known report shows that change in the expression of the gene or the transcript thereof can serve as a marker for lung cancer (Patent Literature 2).

The 259th target gene is the hsa-miR-642b-3p gene, a congener thereof, a transcript thereof, or a variant or a derivative thereof. The previously known report shows that change in the expression of the gene or the transcript thereof can serve as a marker for lung cancer (Patent Literature 1).

The 260th target gene is the hsa-miR-650 gene, a congener thereof, a transcript thereof, or a variant or a derivative thereof. The previously known report shows that change in the expression of the gene or the transcript thereof can serve as a marker for lung cancer (Non-Patent Literature 2).

The 261st target gene is the hsa-miR-663a gene, a congener thereof, a transcript thereof, or a variant or a derivative thereof. The previously known report shows that change in the expression of the gene or the transcript thereof can serve as a marker for lung cancer (Patent Literature 1).

The 262nd target gene is the hsa-miR-663b gene, a congener thereof, a transcript thereof, or a variant or a derivative thereof. The previously known report shows that change in the expression of the gene or the transcript thereof can serve as a marker for lung cancer (Patent Literature 1).

The 263rd target gene is the hsa-miR-6717-5p gene, a congener thereof, a transcript thereof, or a variant or a derivative thereof. The previously known report shows that change in the expression of the gene or the transcript thereof can serve as a marker for lung cancer (Patent Literature 1).

The 264th target gene is the hsa-miR-6721-5p gene, a congener thereof, a transcript thereof, or a variant or a derivative thereof. The previously known report shows that change in the expression of the gene or the transcript thereof can serve as a marker for lung cancer (Patent Literature 1).

The 265th target gene is the hsa-miR-6726-5p gene, a congener thereof, a transcript thereof, or a variant or a derivative thereof. The previously known report shows that change in the expression of the gene or the transcript thereof can serve as a marker for lung cancer (Patent Literature 1).

The 266th target gene is the hsa-miR-6727-5p gene, a congener thereof, a transcript thereof, or a variant or a derivative thereof. The previously known report shows that change in the expression of the gene or the transcript thereof can serve as a marker for lung cancer (Patent Literature 1).

The 267th target gene is the hsa-miR-6738-5p gene, a congener thereof, a transcript thereof, or a variant or a derivative thereof. The previously known report shows that change in the expression of the gene or the transcript thereof can serve as a marker for lung cancer (Patent Literature 1).

The 268th target gene is the hsa-miR-6741-5p gene, a congener thereof, a transcript thereof, or a variant or a derivative thereof. The previously known report shows that change in the expression of the gene or the transcript thereof can serve as a marker for lung cancer (Patent Literature 1).

The 269th target gene is the hsa-miR-6749-5p gene, a congener thereof, a transcript thereof, or a variant or a derivative thereof. The previously known report shows that change in the expression of the gene or the transcript thereof can serve as a marker for lung cancer (Patent Literature 1).

The 270th target gene is the hsa-miR-6752-5p gene, a congener thereof, a transcript thereof, or a variant or a derivative thereof. The previously known report shows that change in the expression of the gene or the transcript thereof can serve as a marker for lung cancer (Patent Literature 1).

The 271st target gene is the hsa-miR-675-5p gene, a congener thereof, a transcript thereof, or a variant or a derivative thereof. The previously known report shows that change in the expression of the gene or the transcript thereof can serve as a marker for lung cancer (Patent Literature 1).

The 272nd target gene is the hsa-miR-6757-5p gene, a congener thereof, a transcript thereof, or a variant or a derivative thereof. The previously known report shows that change in the expression of the gene or the transcript thereof can serve as a marker for lung cancer (Patent Literature 1).

The 273rd target gene is the hsa-miR-6763-5p gene, a congener thereof, a transcript thereof, or a variant or a derivative thereof. The previously known report shows that change in the expression of the gene or the transcript thereof can serve as a marker for lung cancer (Patent Literature 1).

The 274th target gene is the hsa-miR-6765-5p gene, a congener thereof, a transcript thereof, or a variant or a derivative thereof. The previously known report shows that change in the expression of the gene or the transcript thereof can serve as a marker for lung cancer (Patent Literature 1).

The 275th target gene is the hsa-miR-6775-5p gene, a congener thereof, a transcript thereof, or a variant or a derivative thereof. The previously known report shows that change in the expression of the gene or the transcript thereof can serve as a marker for lung cancer (Patent Literature 1).

The 276th target gene is the hsa-miR-6780b-5p gene, a congener thereof, a transcript thereof, or a variant or a derivative thereof. The previously known report shows that change in the expression of the gene or the transcript thereof can serve as a marker for lung cancer (Patent Literature 1).

The 277th target gene is the hsa-miR-6782-5p gene, a congener thereof, a transcript thereof, or a variant or a derivative thereof. The previously known report shows that change in the expression of the gene or the transcript thereof can serve as a marker for lung cancer (Patent Literature 1).

The 278th target gene is the hsa-miR-6784-5p gene, a congener thereof, a transcript thereof, or a variant or a derivative thereof. The previously known report shows that change in the expression of the gene or the transcript thereof can serve as a marker for lung cancer (Patent Literature 1).

The 279th target gene is the hsa-miR-6800-5p gene, a congener thereof, a transcript thereof, or a variant or a derivative thereof. The previously known report shows that change in the expression of the gene or the transcript thereof can serve as a marker for lung cancer (Patent Literature 1).

The 280th target gene is the hsa-miR-6806-5p gene, a congener thereof, a transcript thereof, or a variant or a derivative thereof. The previously known report shows that change in the expression of the gene or the transcript thereof can serve as a marker for lung cancer (Patent Literature 1).

The 281st target gene is the hsa-miR-6840-3p gene, a congener thereof, a transcript thereof, or a variant or a derivative thereof. The previously known report shows that change in the expression of the gene or the transcript thereof can serve as a marker for lung cancer (Patent Literature 1).

The 282nd target gene is the hsa-miR-6848-5p gene, a congener thereof, a transcript thereof, or a variant or a derivative thereof. The previously known report shows that change in the expression of the gene or the transcript thereof can serve as a marker for lung cancer (Patent Literature 1).

The 283rd target gene is the hsa-miR-6851-5p gene, a congener thereof, a transcript thereof, or a variant or a derivative thereof. The previously known report shows that change in the expression of the gene or the transcript thereof can serve as a marker for lung cancer (Patent Literature 1).

The 284th target gene is the hsa-miR-6870-5p gene, a congener thereof, a transcript thereof, or a variant or a derivative thereof. The previously known report shows that change in the expression of the gene or the transcript thereof can serve as a marker for lung cancer (Patent Literature 1).

The 285th target gene is the hsa-miR-6872-3p gene, a congener thereof, a transcript thereof, or a variant or a derivative thereof. The previously known report shows that change in the expression of the gene or the transcript thereof can serve as a marker for lung cancer (Patent Literature 1).

The 286th target gene is the hsa-miR-6875-5p gene, a congener thereof, a transcript thereof, or a variant or a derivative thereof. The previously known report shows that change in the expression of the gene or the transcript thereof can serve as a marker for lung cancer (Patent Literature 1).

The 287th target gene is the hsa-miR-6877-5p gene, a congener thereof, a transcript thereof, or a variant or a derivative thereof. The previously known report shows that change in the expression of the gene or the transcript thereof can serve as a marker for lung cancer (Patent Literature 1).

The 288th target gene is the hsa-miR-6879-5p gene, a congener thereof, a transcript thereof, or a variant or a derivative thereof. The previously known report shows that change in the expression of the gene or the transcript thereof can serve as a marker for lung cancer (Patent Literature 1).

The 289th target gene is the hsa-miR-6880-5p gene, a congener thereof, a transcript thereof, or a variant or a derivative thereof. The previously known report shows that change in the expression of the gene or the transcript thereof can serve as a marker for lung cancer (Patent Literature 1).

The 290th target gene is the hsa-miR-6885-5p gene, a congener thereof, a transcript thereof, or a variant or a derivative thereof. The previously known report shows that change in the expression of the gene or the transcript thereof can serve as a marker for lung cancer (Patent Literature 1).

The 291st target gene is the hsa-miR-6887-5p gene, a congener thereof, a transcript thereof, or a variant or a derivative thereof. The previously known report shows that change in the expression of the gene or the transcript thereof can serve as a marker for lung cancer (Patent Literature 1).

The 292nd target gene is the hsa-miR-7108-5p gene, a congener thereof, a transcript thereof, or a variant or a derivative thereof. The previously known report shows that change in the expression of the gene or the transcript thereof can serve as a marker for lung cancer (Patent Literature 1).

The 293rd target gene is the hsa-miR-711 gene, a congener thereof, a transcript thereof, or a variant or a derivative thereof. The previously known report shows that change in the expression of the gene or the transcript thereof can serve as a marker for lung cancer (Patent Literature 1).

The 294th target gene is the hsa-miR-7113-3p gene, a congener thereof, a transcript thereof, or a variant or a derivative thereof. The previously known report shows that change in the expression of the gene or the transcript thereof can serve as a marker for lung cancer (Patent Literature 1).

The 295th target gene is the hsa-miR-744-5p gene, a congener thereof, a transcript thereof, or a variant or a derivative thereof. The previously known report shows that change in the expression of the gene or the transcript thereof can serve as a marker for lung cancer (Patent Literature 5).

The 296th target gene is the hsa-miR-760 gene, a congener thereof, a transcript thereof, or a variant or a derivative thereof. The previously known report shows that change in the expression of the gene or the transcript thereof can serve as a marker for lung cancer (Patent Literature 1).

The 297th target gene is the hsa-miR-7845-5p gene, a congener thereof, a transcript thereof, or a variant or a derivative thereof. The previously known report shows that change in the expression of the gene or the transcript thereof can serve as a marker for lung cancer (Patent Literature 1).

The 298th target gene is the hsa-miR-7847-3p gene, a congener thereof, a transcript thereof, or a variant or a derivative thereof. The previously known report shows that change in the expression of the gene or the transcript thereof can serve as a marker for lung cancer (Patent Literature 1).

The 299th target gene is the hsa-miR-7977 gene, a congener thereof, a transcript thereof, or a variant or a derivative thereof. The previously known report shows that change in the expression of the gene or the transcript thereof can serve as a marker for lung cancer (Patent Literature 1).

The 300th target gene is the hsa-miR-8059 gene, a congener thereof, a transcript thereof, or a variant or a derivative thereof. The previously known report shows that change in the expression of the gene or the transcript thereof can serve as a marker for lung cancer (Patent Literature 1).

The 301st target gene is the hsa-miR-8063 gene, a congener thereof, a transcript thereof, or a variant or a derivative thereof. The previously known report shows that change in the expression of the gene or the transcript thereof can serve as a marker for lung cancer (Patent Literature 1).

The 302nd target gene is the hsa-miR-8072 gene, a congener thereof, a transcript thereof, or a variant or a derivative thereof. The previously known report shows that change in the expression of the gene or the transcript thereof can serve as a marker for lung cancer (Patent Literature 1).

The 303rd target gene is the hsa-miR-874-3p gene, a congener thereof, a transcript thereof, or a variant or a derivative thereof. The previously known report shows that change in the expression of the gene or the transcript thereof can serve as a marker for lung cancer (Patent Literature 5).

The 304th target gene is the hsa-miR-92a-2-5p gene, a congener thereof, a transcript thereof, or a variant or a derivative thereof. The previously known report shows that change in the expression of the gene or the transcript thereof can serve as a marker for lung cancer (Patent Literature 1).

The 305th target gene is the hsa-miR-92b-5p gene, a congener thereof, a transcript thereof, or a variant or a derivative thereof. The previously known report shows that change in the expression of the gene or the transcript thereof can serve as a marker for lung cancer (Patent Literature 1).

The 306th target gene is the hsa-miR-940 gene, a congener thereof, a transcript thereof, or a variant or a derivative thereof. The previously known report shows that change in the expression of the gene or the transcript thereof can serve as a marker for lung cancer (Patent Literature 1).

The 307th target gene is the hsa-miR-1228-3p gene, a congener thereof, a transcript thereof, or a variant or a derivative thereof. The previously known report shows that change in the expression of the gene or the transcript thereof can serve as a marker for lung cancer (Patent Literature 1).

The 308th target gene is the hsa-miR-1275 gene, a congener thereof, a transcript thereof, or a variant or a derivative thereof. The previously known report shows that change in the expression of the gene or the transcript thereof can serve as a marker for lung cancer (Patent Literature 5).

The 309th target gene is the hsa-miR-1307-3p gene, a congener thereof, a transcript thereof, or a variant or a derivative thereof. The previously known report shows that change in the expression of the gene or the transcript thereof can serve as a marker for lung cancer (Patent Literature 1).

The 310th target gene is the hsa-miR-1343-5p gene, a congener thereof, a transcript thereof, or a variant or a derivative thereof. The previously known report shows that change in the expression of the gene or the transcript thereof can serve as a marker for lung cancer (Patent Literature 1).

The 311th target gene is the hsa-miR-23a-3p gene, a congener thereof, a transcript thereof, or a variant or a derivative thereof. The previously known report shows that change in the expression of the gene or the transcript thereof can serve as a marker for lung cancer (Patent Literature 2).

The 312th target gene is the hsa-miR-29b-3p gene, a congener thereof, a transcript thereof, or a variant or a derivative thereof. The previously known report shows that change in the expression of the gene or the transcript thereof can serve as a marker for lung cancer (Patent Literature 2).

The 313th target gene is the hsa-miR-3135b gene, a congener thereof, a transcript thereof, or a variant or a derivative thereof. The previously known report shows that change in the expression of the gene or the transcript thereof can serve as a marker for lung cancer (Patent Literature 1).

The 314th target gene is the hsa-miR-3185 gene, a congener thereof, a transcript thereof, or a variant or a derivative thereof. The previously known report shows that change in the expression of the gene or the transcript thereof can serve as a marker for lung cancer (Patent Literature 1).

The 315th target gene is the hsa-miR-4532 gene, a congener thereof, a transcript thereof, or a variant or a derivative thereof. The previously known report shows that change in the expression of the gene or the transcript thereof can serve as a marker for lung cancer (Patent Literature 1).

The 316th target gene is the hsa-miR-4690-5p gene, a congener thereof, a transcript thereof, or a variant or a derivative thereof. The previously known report shows that change in the expression of the gene or the transcript thereof can serve as a marker for lung cancer (Patent Literature 1).

The 317th target gene is the hsa-miR-4758-5p gene, a congener thereof, a transcript thereof, or a variant or a derivative thereof. The previously known report shows that change in the expression of the gene or the transcript thereof can serve as a marker for lung cancer (Patent Literature 1).

The 318th target gene is the hsa-miR-4783-3p gene, a congener thereof, a transcript thereof, or a variant or a derivative thereof. The previously known report shows that change in the expression of the gene or the transcript thereof can serve as a marker for lung cancer (Patent Literature 1).

The 319th target gene is the hsa-miR-6131 gene, a congener thereof, a transcript thereof, or a variant or a derivative thereof. The previously known report shows that change in the expression of the gene or the transcript thereof can serve as a marker for lung cancer (Patent Literature 1).

The 320th target gene is the hsa-miR-625-3p gene, a congener thereof, a transcript thereof, or a variant or a derivative thereof. The previously known report shows that change in the expression of the gene or the transcript thereof can serve as a marker for lung cancer (Patent Literature 4).

The 321st target gene is the hsa-miR-6511a-5p gene, a congener thereof, a transcript thereof, or a variant or a derivative thereof. The previously known report shows that change in the expression of the gene or the transcript thereof can serve as a marker for lung cancer (Patent Literature 1).

The 322nd target gene is the hsa-miR-6765-3p gene, a congener thereof, a transcript thereof, or a variant or a derivative thereof. The previously known report shows that change in the expression of the gene or the transcript thereof can serve as a marker for lung cancer (Patent Literature 1).

The 323rd target gene is the hsa-miR-6816-5p gene, a congener thereof, a transcript thereof, or a variant or a derivative thereof. The previously known report shows that change in the expression of the gene or the transcript thereof can serve as a marker for lung cancer (Patent Literature 1).

The 324th target gene is the hsa-miR-6825-5p gene, a congener thereof, a transcript thereof, or a variant or a derivative thereof. The previously known report shows that change in the expression of the gene or the transcript thereof can serve as a marker for lung cancer (Patent Literature 1).

The 325th target gene is the hsa-miR-6845-5p gene, a congener thereof, a transcript thereof, or a variant or a derivative thereof. The previously known report shows that change in the expression of the gene or the transcript thereof can serve as a marker for lung cancer (Patent Literature 1).

The 326th target gene is the hsa-miR-7150 gene, a congener thereof, a transcript thereof, or a variant or a derivative thereof. The previously known report shows that change in the expression of the gene or the transcript thereof can serve as a marker for lung cancer (Patent Literature 1).

The 327th target gene is the hsa-miR-7641 gene, a congener thereof, a transcript thereof, or a variant or a derivative thereof. The previously known report shows that change in the expression of the gene or the transcript thereof can serve as a marker for lung cancer (Patent Literature 1).

The 328th target gene is the hsa-miR-7975 gene, a congener thereof, a transcript thereof, or a variant or a derivative thereof. The previously known report shows that change in the expression of the gene or the transcript thereof can serve as a marker for lung cancer (Patent Literature 1).

The 329th target gene is the hsa-miR-92a-3p gene, a congener thereof, a transcript thereof, or a variant or a derivative thereof. The previously known report shows that change in the expression of the gene or the transcript thereof can serve as a marker for lung cancer (Patent Literature 1).

In one aspect, the present invention relates to a marker containing at least one of the target nucleic acids described above for detecting lung cancer or for diagnosing lung cancer.

In one aspect, the present invention relates to use of at least one of the target nucleic acids described above for detecting lung cancer or for diagnosing lung cancer.

2. Nucleic Acid for Detection of Lung Cancer

In the present invention, the nucleic acids for detecting lung cancer, e.g., nucleic acid probes or primers that can be used for diagnosing lung cancer enable qualitative and/or quantitative measurement of the presence, expression levels, or existing amounts (abundance) of: human-derived miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, miR-92b-3p, miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, as target nucleic acids for lung cancer, or combinations thereof, congeners thereof, transcripts thereof, or variants or derivatives thereof.

The expression levels of the target nucleic acids described above are increased or decreased (hereinafter, referred to as "increased/decreased") depending on the types of the target nucleic acids in subjects having lung cancer as compared with healthy subjects, benign bone and soft tissue tumor patients and benign breast disease patients, and subjects having a cancer other than lung cancer. Hence, the kit or device of the present invention can be effectively used for measuring expression levels of the target nucleic acids in body fluids from subjects (e.g., humans) suspected of having lung cancer and body fluids from healthy subjects, benign bone and soft tissue tumor patients and benign breast disease patients (or diseased animals), and patients (or cancer animals) having a cancer other than lung cancer, and thereby detecting lung cancer through the comparison thereof.

The nucleic acid probe or primer(s) that can be used in the present invention is, for example, a nucleic acid probe capable of specifically binding to a polynucleotide consisting of a nucleotide sequence represented by at least one of SEQ ID NOs: 1 to 163; or a primer(s) for amplifying a polynucleotide consisting of a nucleotide sequence represented by at least one of SEQ ID NOs: 1 to 163.

The nucleic acid probe or primer(s) that can be used in the present invention may further comprise, for example, a nucleic acid probe capable of specifically binding to a polynucleotide consisting of a nucleotide sequence represented by at least one of SEQ ID NOs: 164 to 329; or a primer(s) for amplifying a polynucleotide consisting of a nucleotide sequence represented by at least one of SEQ ID NOs: 164 to 329.

In a preferred embodiment of the present invention, specifically, these nucleic acid probes or primers comprise a combination of one or more polynucleotides selected from: a group of polynucleotides comprising nucleotide sequences represented by any of SEQ ID NOs: 1 to 1000, or the nucleotide sequences in which the nucleic acid u is replaced with t, and a group of complementary polynucleotides thereof; a group of polynucleotides respectively hybridizing under stringent conditions (mentioned later) to DNAs consisting of nucleotide sequences complementary to these nucleotide sequences, and a group of complementary polynucleotides thereof; and a group of polynucleotides comprising 15 or more, preferably 17 or more consecutive nucleotides and being from the nucleotide sequences of these polynucleotide groups. These polynucleotides can be used as nucleic acid probes and primers for detecting the lung cancer markers as target nucleic acids.

More specifically, examples of the nucleic acid probes or the primers that can be used in the present invention include one or more polynucleotides selected from the group consisting of the following polynucleotides (a) to (e):

(a) a polynucleotide consisting of a nucleotide sequence represented by any of SEQ ID NOs: 1 to 163 or a nucleotide sequence derived from the nucleotide sequence in which the nucleic acid u is replaced with t, a variant thereof, a derivative thereof, or a fragment thereof comprising 15 or more consecutive nucleotides;

(b) a polynucleotide comprising a nucleotide sequence represented by any of SEQ ID NOs: 1 to 163;

(c) a polynucleotide consisting of a nucleotide sequence complementary to a nucleotide sequence represented by any of SEQ ID NOs: 1 to 163, or a nucleotide sequence derived from the nucleotide sequence in which the nucleic acid u is replaced with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 163, or a nucleotide sequence derived from the nucleotide sequence in which the nucleic acid u is replaced with t; and (e) a polynucleotide hybridizing under stringent conditions to any of the polynucleotides (a) to (d).

In addition to at least one polynucleotide selected from any of the polynucleotides (a) to (e), the nucleic acid probes or the primers that can be used in the present invention may further comprise any of the following polynucleotides (f) to (j):

(f) a polynucleotide consisting of a nucleotide sequence represented by any of SEQ ID NOs: 164 to 329, or a nucleotide sequence derived from the nucleotide sequence in which the nucleic acid u is replaced with t, a variant thereof, a derivative thereof, or a fragment thereof comprising 15 or more consecutive nucleotides;

(g) a polynucleotide comprising a nucleotide sequence represented by any of SEQ ID NOs: 164 to 329;

(h) a polynucleotide consisting of a nucleotide sequence complementary to a nucleotide sequence represented by any of SEQ ID NOs: 164 to 329, or a nucleotide sequence derived from the nucleotide sequence in which the nucleic acid u is replaced with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 164 to 329, or a nucleotide sequence derived from the nucleotide sequence in which the nucleic acid u is replaced with t; and (j) a polynucleotide hybridizing under stringent conditions to any of the polynucleotides (f) to (i).

These polynucleotides or fragments thereof used in the present invention may each be DNA or may each be RNA.

The polynucleotides that can be used in the present invention can be prepared by use of a general technique such as a DNA recombination technique, a PCR method, or a method using an automatic DNA/RNA synthesizer.

The DNA recombination technique and the PCR method may employ techniques described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR- 6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, miR-92b-3p, miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p represented by SEQ ID NOs: 1 to 329 are known, and methods to obtain them are also known as mentioned above. Therefore, each polynucleotide that can be used as a nucleic acid probe or a primer in the present invention can be prepared by cloning the gene.

Such nucleic acid probes or primers can be chemically synthesized using an automatic DNA synthesizer. In general, the phosphoramidite method is used in this synthesis, and single-stranded DNA in length of up to approximately 100 nucleotides can be automatically synthesized by this method. The automatic DNA synthesizer is commercially available from, for example, Polygen GmbH, ABI, or Applied Biosystems, Inc.

Alternatively, the polynucleotides of the present invention can also be prepared by cDNA cloning methods. The cDNA cloning technique may employ, for example, microRNA Cloning Kit Wako.

In this context, the sequences of the nucleic acid probes and the primers for detecting the polynucleotide consisting of a nucleotide sequence represented by any of SEQ ID NOs: 1 to 329 do not exist as miRNAs or precursors thereof in the living body or in vivo. For example, the nucleotide sequences represented by SEQ ID NO: 142 and SEQ ID NO: 46 are produced from the precursor represented by SEQ ID NO: 382. This precursor has a hairpin-like structure as shown in FIG. 1, and the nucleotide sequences represented by SEQ ID NO: 142 and SEQ ID NO: 46 have mismatch sequences with each other. As such, a nucleotide sequence completely complementary to the nucleotide sequence represented by SEQ ID NO: 142 or SEQ ID NO: 46 does not naturally occur in vivo. Therefore, the nucleic acid probes and the primers for detecting the nucleotide sequence represented by any of SEQ ID NOs: 1 to 329 can have artificial nucleotide sequences that do not exist in the living body or in vivo.

3. Kit or Device for Detection of Lung Cancer

The present invention also provides a kit or a device for detecting lung cancer, comprising one or more polynucleotides (which may include a variant, a fragment, or a derivative thereof) that can be used as nucleic acid probes or primers in the present invention for measuring target nucleic acids as lung cancer markers.

The target nucleic acids as lung cancer markers according to the present invention are preferably selected from the following group A:

Group A:
miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p.

Additional target nucleic acids that may be optionally used in the measurement are preferably selected from the following group B:

Group B:
miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p.

The kit or the device of the present invention comprises one or more nucleic acids capable of specifically binding to any of the target nucleic acids as the lung cancer markers described above or nucleic acids for detecting the target nucleic acids, preferably one or more polynucleotides selected from the polynucleotides described in the preceding Section 2, or variants thereof.

Specifically, the kit or the device of the present invention can comprise at least one polynucleotide comprising (or consisting of), for example, a nucleotide sequence represented by any of SEQ ID NOs: 1 to 163, or a nucleotide sequence derived from the nucleotide sequence in which the nucleic acid u is replaced with t, polynucleotide(s) comprising (or consisting of) a complementary sequence thereof, a polynucleotide(s) hybridizing under stringent conditions to any of these polynucleotides, or a variant(s) or a fragment(s) comprising 15 or more consecutive nucleotides of any of these polynucleotide sequences.

The kit or the device of the present invention can further comprise one or more polynucleotides comprising (or consisting of), for example, a nucleotide sequence represented by any of SEQ ID NOs: 164 to 329, or a nucleotide sequence derived from the nucleotide sequence in which the nucleic acid u is replaced with t, a polynucleotide(s) comprising (or consisting of) a complementary sequence thereof, a polynucleotide(s) hybridizing under stringent conditions to any of these polynucleotides, a variant(s) or a fragment(s) comprising 15 or more consecutive nucleotides of any of these polynucleotide sequences.

The fragment or fragments that can be comprised in the kit or the device of the present invention is/are, for example, one or more polynucleotides, preferably two or more polynucleotides, selected from the group consisting of the following polynucleotides (1) and (2):

(1) a polynucleotide comprising 15 or more consecutive nucleotides derived from a nucleotide sequence represented by any of SEQ ID NOs: 1 to 163 in which the nucleic acid u is replaced with t, or a complementary sequence thereof; and (2) a polynucleotide comprising 15 or more consecutive nucleotides derived from a nucleotide sequence represented by any of SEQ ID NOs: 164 to 329 in which the nucleic acid u is replaced with t, or a complementary sequence thereof.

In a preferred embodiment, the polynucleotide is a polynucleotide consisting of a nucleotide sequence represented by any of SEQ ID NOs: 1 to 163, or a nucleotide sequence derived from the nucleotide sequence in which the nucleic acid u is replaced with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 164 to 329, or a nucleotide sequence derived from the nucleotide sequence in which the nucleic acid u is replaced with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

Examples of the combination of the above-mentioned polynucleotides as target nucleic acids in the kit or the device of the present invention can include a single (one) polynucleotide or combinations of 2, 3, 4, 5, 6, 7, 8, 9, 10 or more of the above-mentioned polynucleotides consisting of the nucleotide sequences represented by SEQ ID NOs: 1 to 329 as shown in Table 1 above. However, these are given merely for illustrative purposes, and all of various other possible combinations are included in the present invention.

Examples of the combinations of target nucleic acids in the kit or the device for discriminating lung cancer patients from test subjects without lung cancer, such as healthy subjects, benign bone and soft tissue tumor patients and benign breast disease patients, or patients having a cancer other than lung cancer, according to the present invention can include combinations of two or more of the above-mentioned polynucleotides consisting of the nucleotide sequences represented by SEQ ID NOs as shown in Table 1. For example, any two or more of the above-mentioned polynucleotides consisting of nucleotide sequences represented by SEQ ID NOs: 1 to 329 can be combined. Among them, at least one polynucleotide of the newly found polynucleotides consisting of the nucleotide sequences represented by SEQ ID NOs: 1 to 163 is preferably selected. Among them, particularly, a combination comprising at least one polynucleotide selected from the group consisting of the polynucleotides of SEQ ID NOs: 18, 4, 130, 2, 9, 17, and 121 (hereinafter, this group is referred to as "cancer type-specific polynucleotide group") is more preferred.

Non-limiting examples of the combination comprising the polynucleotide consisting of the nucleotide sequence represented by SEQ ID NO: 18 or a complementary sequence thereof are listed below as combinations of target nucleic acids:

(1) a combination of SEQ ID NOs: 18, and 164;
(2) a combination of SEQ ID NOs: 18, 164, and 255;
(3) a combination of SEQ ID NOs: 18, 164, and 300;
(4) a combination of SEQ ID NOs: 18, 164, and 190;
(5) a combination of SEQ ID NOs: 18, 85, and 164;
(6) a combination of SEQ ID NOs: 18, 147, and 164;
(7) a combination of SEQ ID NOs: 18, 22, and 164;
(8) a combination of SEQ ID NOs: 18, 164, and 312;
(9) a combination of SEQ ID NOs: 18, 66, and 164;
(10) a combination of SEQ ID NOs: 18, 78, and 164;
(11) a combination of SEQ ID NOs: 18, 27, and 164;
(12) a combination of SEQ ID NOs: 18, 164, and 207;
(13) a combination of SEQ ID NOs: 18, 82, and 164;
(14) a combination of SEQ ID NOs: 18, 164, and 263;
(15) a combination of SEQ ID NOs: 18, 164, and 168;
(16) a combination of SEQ ID NOs: 18, 34, and 164;
(17) a combination of SEQ ID NOs: 18, 39, and 164;
(18) a combination of SEQ ID NOs: 18, 57, and 164;
(19) a combination of SEQ ID NOs: 18, 121, and 164;
(20) a combination of SEQ ID NOs: 18, 107, and 164;
(21) a combination of SEQ ID NOs: 18, 70, and 164;
(22) a combination of SEQ ID NOs: 18, 50, and 164;
(23) a combination of SEQ ID NOs: 18, 164, and 250;
(24) a combination of SEQ ID NOs: 18, 164, and 315;
(25) a combination of SEQ ID NOs: 18, 164, and 211;
(26) a combination of SEQ ID NOs: 18, 164, and 326;
(27) a combination of SEQ ID NOs: 18, 164, and 308;
(28) a combination of SEQ ID NOs: 18, 164, and 268;
(29) a combination of SEQ ID NOs: 18, 164, and 191;
(30) a combination of SEQ ID NOs: 18, 149, and 165;
(31) a combination of SEQ ID NOs: 18, 121, 130, and 164;
(32) a combination of SEQ ID NOs: 18, 164, 255, and 316;
(33) a combination of SEQ ID NOs: 18, 121, 164, and 255;
(34) a combination of SEQ ID NOs: 18, 147, 164, and 255;
(35) a combination of SEQ ID NOs: 18, 27, 164, and 255;
(36) a combination of SEQ ID NOs: 18, 34, 164, and 255;
(37) a combination of SEQ ID NOs: 18, 47, 164, and 255;
(38) a combination of SEQ ID NOs: 18, 158, 164, and 255;
(39) a combination of SEQ ID NOs: 18, 164, 220, and 255;
(40) a combination of SEQ ID NOs: 18, 88, 164, and 255;
(41) a combination of SEQ ID NOs: 18, 130, 164, and 268;
(42) a combination of SEQ ID NOs: 18, 164, 255, and 321;
(43) a combination of SEQ ID NOs: 18, 164, 184, and 255;
(44) a combination of SEQ ID NOs: 18, 152, 164, and 255;
(45) a combination of SEQ ID NOs: 18, 164, 185, and 255;
(46) a combination of SEQ ID NOs: 18, 164, 238, and 255;
(47) a combination of SEQ ID NOs: 18, 164, 255, and 256;
(48) a combination of SEQ ID NOs: 18, 127, 164, and 255;
(49) a combination of SEQ ID NOs: 18, 164, 222, and 255;
(50) a combination of SEQ ID NOs: 18, 139, 164, and 255;
(51) a combination of SEQ ID NOs: 18, 39, 164, and 255;
(52) a combination of SEQ ID NOs: 18, 164, 255, and 295;
(53) a combination of SEQ ID NOs: 18, 146, 164, and 255;
(54) a combination of SEQ ID NOs: 18, 164, 211, and 255;
(55) a combination of SEQ ID NOs: 18, 164, 255, and 322;
(56) a combination of SEQ ID NOs: 18, 164, 255, and 318;
(57) a combination of SEQ ID NOs: 18, 121, 164, and 201;
(58) a combination of SEQ ID NOs: 18, 147, 164, and 300;
(59) a combination of SEQ ID NOs: 18, 121, 151, and 164;
(60) a combination of SEQ ID NOs: 18, 164, 211, and 300;
(61) a combination of SEQ ID NOs: 18, 95, 164, and 268;
(62) a combination of SEQ ID NOs: 18, 164, 231, and 268;
(63) a combination of SEQ ID NOs: 18, 147, 164, and 268;
(64) a combination of SEQ ID NOs: 18, 164, 188, and 268;
(65) a combination of SEQ ID NOs: 18, 164, 268, and 312;
(66) a combination of SEQ ID NOs: 18, 39, 164, and 300;
(67) a combination of SEQ ID NOs: 18, 95, 121, and 164;
(68) a combination of SEQ ID NOs: 18, 93, 164, and 268;
(69) a combination of SEQ ID NOs: 18, 164, 268, and 308;
(70) a combination of SEQ ID NOs: 18, 107, 121, and 164;
(71) a combination of SEQ ID NOs: 18, 164, 218, and 268;
(72) a combination of SEQ ID NOs: 18, 164, 202, and 268;
(73) a combination of SEQ ID NOs: 13, 18, 130, and 165;
(74) a combination of SEQ ID NOs: 18, 149, 165, and 168;
(75) a combination of SEQ ID NOs: 18, 164, 242, and 268;
(76) a combination of SEQ ID NOs: 18, 164, 214, and 268;
(77) a combination of SEQ ID NOs: 18, 164, 268, and 313;
(78) a combination of SEQ ID NOs: 18, 162, 164, and 268;

(79) a combination of SEQ ID NOs: 18, 150, 164, and 268;
(80) a combination of SEQ ID NOs: 18, 164, 268, and 315;
(81) a combination of SEQ ID NOs: 18, 152, 164, and 268;
(82) a combination of SEQ ID NOs: 18, 164, 268, and 325;
(83) a combination of SEQ ID NOs: 18, 121, 149, and 165;
(84) a combination of SEQ ID NOs: 13, 18, 165, and 260;
(85) a combination of SEQ ID NOs: 13, 18, 165, and 268;
(86) a combination of SEQ ID NOs: 13, 18, 121, and 165;
(87) a combination of SEQ ID NOs: 13, 18, 165, and 168;
(88) a combination of SEQ ID NOs: 18, 149, 165, and 268;
(89) a combination of SEQ ID NOs: 13, 18, 83, and 165;
(90) a combination of SEQ ID NOs: 13, 18, 165, and 263;
(91) a combination of SEQ ID NOs: 2, 18, 165, and 268;
(92) a combination of SEQ ID NOs: 13, 18, 165, and 211;
(93) a combination of SEQ ID NOs: 13, 18, 165, and 256;
(94) a combination of SEQ ID NOs: 13, 18, 165, and 276;
(95) a combination of SEQ ID NOs: 13, 18, 165, and 302;
(96) a combination of SEQ ID NOs: 13, 18, 165, and 190;
(97) a combination of SEQ ID NOs: 18, 121, 130, 136, and 164;
(98) a combination of SEQ ID NOs: 18, 121, 130, 164, and 314;
(99) a combination of SEQ ID NOs: 18, 114, 121, 130, and 164;
(100) a combination of SEQ ID NOs: 18, 121, 130, 164, and 214;
(101) a combination of SEQ ID NOs: 18, 121, 130, 164, and 193;
(102) a combination of SEQ ID NOs: 18, 130, 164, 255, and 268;
(103) a combination of SEQ ID NOs: 18, 121, 130, 164, and 320;
(104) a combination of SEQ ID NOs: 18, 121, 130, 164, and 301;
(105) a combination of SEQ ID NOs: 18, 121, 130, 144, and 164;
(106) a combination of SEQ ID NOs: 18, 121, 130, 164, and 168;
(107) a combination of SEQ ID NOs: 18, 121, 130, 164, and 205;
(108) a combination of SEQ ID NOs: 18, 121, 130, 158, and 164;
(109) a combination of SEQ ID NOs: 18, 121, 130, 164, and 260;
(110) a combination of SEQ ID NOs: 18, 106, 121, 130, and 164;
(111) a combination of SEQ ID NOs: 18, 121, 130, 164, and 318;
(112) a combination of SEQ ID NOs: 18, 121, 130, 164, and 286;
(113) a combination of SEQ ID NOs: 18, 121, 130, 164, and 315;
(114) a combination of SEQ ID NOs: 18, 121, 130, 164, and 237;
(115) a combination of SEQ ID NOs: 18, 121, 130, 164, and 184;
(116) a combination of SEQ ID NOs: 18, 121, 130, 164, and 270;
(117) a combination of SEQ ID NOs: 18, 121, 130, 164, and 309;
(118) a combination of SEQ ID NOs: 18, 121, 130, 164, and 278;
(119) a combination of SEQ ID NOs: 18, 82, 121, 130, and 164;
(120) a combination of SEQ ID NOs: 18, 23, 121, 130, and 164;
(121) a combination of SEQ ID NOs: 18, 121, 130, 164, and 189;
(122) a combination of SEQ ID NOs: 18, 121, 130, 152, and 164;
(123) a combination of SEQ ID NOs: 18, 121, 130, 164, and 213;
(124) a combination of SEQ ID NOs: 18, 121, 130, 164, and 229;
(125) a combination of SEQ ID NOs: 18, 57, 121, 130, and 164;
(126) a combination of SEQ ID NOs: 18, 121, 130, 142, and 164;
(127) a combination of SEQ ID NOs: 18, 121, 130, 155, and 164;
(128) a combination of SEQ ID NOs: 18, 39, 121, 130, and 164;
(129) a combination of SEQ ID NOs: 18, 27, 130, 164, and 268;
(130) a combination of SEQ ID NOs: 18, 33, 121, 130, and 164;
(131) a combination of SEQ ID NOs: 18, 121, 126, 130, and 164;
(132) a combination of SEQ ID NOs: 18, 121, 130, 164, and 319;
(133) a combination of SEQ ID NOs: 18, 22, 121, 130, and 164;
(134) a combination of SEQ ID NOs: 18, 59, 121, 130, and 164;
(135) a combination of SEQ ID NOs: 18, 27, 121, 130, and 164;
(136) a combination of SEQ ID NOs: 18, 130, 164, 268, and 317;
(137) a combination of SEQ ID NOs: 18, 121, 130, 164, and 201;
(138) a combination of SEQ ID NOs: 18, 34, 164, 211, and 255;
(139) a combination of SEQ ID NOs: 18, 19, 121, 130, and 164;
(140) a combination of SEQ ID NOs: 18, 74, 130, 164, and 268;
(141) a combination of SEQ ID NOs: 18, 130, 164, 264, and 268;
(142) a combination of SEQ ID NOs: 18, 39, 164, 255, and 328;
(143) a combination of SEQ ID NOs: 18, 39, 164, 226, and 255;
(144) a combination of SEQ ID NOs: 18, 95, 121, 164, and 188;
(145) a combination of SEQ ID NOs: 13, 18, 121, 130, and 165;
(146) a combination of SEQ ID NOs: 13, 18, 130, 165, and 268;
(147) a combination of SEQ ID NOs: 18, 151, 164, 268, and 315;
(148) a combination of SEQ ID NOs: 18, 147, 164, 184, and 268;
(149) a combination of SEQ ID NOs: 18, 149, 165, 168, and 268;
(150) a combination of SEQ ID NOs: 13, 18, 165, 268, and 276;

(151) a combination of SEQ ID NOs: 2, 18, 165, 268, and 301;
(152) a combination of SEQ ID NOs: 2, 18, 165, 268, and 315;
(153) a combination of SEQ ID NOs: 13, 18, 165, 183, and 268; and
(154) a combination of SEQ ID NOs: 13, 18, 165, 184, and 268.

Non-limiting examples of the combination comprising the polynucleotide consisting of the nucleotide sequence represented by SEQ ID NO: 4 or a complementary sequence thereof are further listed below as combinations of target nucleic acids:

(1) a combination of SEQ ID NOs: 4, and 164;
(2) a combination of SEQ ID NOs: 4, 165, and 168;
(3) a combination of SEQ ID NOs: 4, 165, 168, and 246;
(4) a combination of SEQ ID NOs: 4, 128, 165, and 168;
(5) a combination of SEQ ID NOs: 4, 117, 165, and 168;
(6) a combination of SEQ ID NOs: 4, 159, 165, and 168;
(7) a combination of SEQ ID NOs: 4, 165, 168, and 260;
(8) a combination of SEQ ID NOs: 4, 17, 165, and 168;
(9) a combination of SEQ ID NOs: 4, 165, 168, and 173;
(10) a combination of SEQ ID NOs: 4, 80, 165, and 168;
(11) a combination of SEQ ID NOs: 4, 99, 165, and 168;
(12) a combination of SEQ ID NOs: 2, 4, 168, and 246;
(13) a combination of SEQ ID NOs: 4, 17, 115, and 168;
(14) a combination of SEQ ID NOs: 4, 17, 115, and 302;
(15) a combination of SEQ ID NOs: 4, 94, 173, and 183;
(16) a combination of SEQ ID NOs: 2, 4, 173, and 183;
(17) a combination of SEQ ID NOs: 2, 4, 115, and 168;
(18) a combination of SEQ ID NOs: 4, 17, 115, and 184;
(19) a combination of SEQ ID NOs: 4, 17, 165, 168, and 173;
(20) a combination of SEQ ID NOs: 4, 17, 165, 168, and 223;
(21) a combination of SEQ ID NOs: 4, 128, 129, 165, and 168;
(22) a combination of SEQ ID NOs: 2, 4, 130, 168, and 246;
(23) a combination of SEQ ID NOs: 4, 17, 128, 165, and 168;
(24) a combination of SEQ ID NOs: 4, 17, 165, 168, and 169;
(25) a combination of SEQ ID NOs: 4, 17, 117, 165, and 168;
(26) a combination of SEQ ID NOs: 4, 17, 165, 168, and 323;
(27) a combination of SEQ ID NOs: 4, 17, 81, 165, and 168;
(28) a combination of SEQ ID NOs: 4, 17, 165, 168, and 253;
(29) a combination of SEQ ID NOs: 4, 17, 162, 165, and 168;
(30) a combination of SEQ ID NOs: 2, 4, 168, 201, and 246;
(31) a combination of SEQ ID NOs: 4, 17, 141, 165, and 168;
(32) a combination of SEQ ID NOs: 4, 17, 129, 165, and 168;
(33) a combination of SEQ ID NOs: 4, 17, 165, 168, and 258;
(34) a combination of SEQ ID NOs: 4, 17, 165, 168, and 190;
(35) a combination of SEQ ID NOs: 4, 17, 115, 168, and 177;
(36) a combination of SEQ ID NOs: 4, 17, 165, 168, and 191;
(37) a combination of SEQ ID NOs: 4, 17, 158, 165, and 168;
(38) a combination of SEQ ID NOs: 4, 17, 165, 168, and 184;
(39) a combination of SEQ ID NOs: 4, 17, 94, 165, and 168;
(40) a combination of SEQ ID NOs: 4, 17, 165, 168, and 296;
(41) a combination of SEQ ID NOs: 4, 17, 165, 168, and 307;
(42) a combination of SEQ ID NOs: 4, 17, 123, 165, and 168;
(43) a combination of SEQ ID NOs: 4, 17, 39, 165, and 168;
(44) a combination of SEQ ID NOs: 4, 17, 145, 165, and 168;
(45) a combination of SEQ ID NOs: 4, 17, 165, 168, and 286;
(46) a combination of SEQ ID NOs: 4, 17, 73, 165, and 168;
(47) a combination of SEQ ID NOs: 4, 17, 115, 165, and 168;
(48) a combination of SEQ ID NOs: 4, 17, 108, 165, and 168;
(49) a combination of SEQ ID NOs: 4, 17, 156, 165, and 168;
(50) a combination of SEQ ID NOs: 4, 17, 165, 168, and 249;
(51) a combination of SEQ ID NOs: 4, 17, 131, 165, and 168;
(52) a combination of SEQ ID NOs: 4, 17, 165, 168, and 304;
(53) a combination of SEQ ID NOs: 4, 17, 157, 165, and 168;
(54) a combination of SEQ ID NOs: 4, 17, 165, 168, and 318;
(55) a combination of SEQ ID NOs: 4, 17, 74, 165, and 168;
(56) a combination of SEQ ID NOs: 4, 17, 165, 168, and 216;
(57) a combination of SEQ ID NOs: 4, 17, 165, 168, and 309;
(58) a combination of SEQ ID NOs: 4, 17, 165, 168, and 236;
(59) a combination of SEQ ID NOs: 4, 17, 165, 168, and 324;
(60) a combination of SEQ ID NOs: 2, 4, 111, 168, and 173;
(61) a combination of SEQ ID NOs: 4, 17, 115, 130, and 168;
(62) a combination of SEQ ID NOs: 2, 4, 130, 168, and 173;
(63) a combination of SEQ ID NOs: 4, 17, 111, 115, and 168;
(64) a combination of SEQ ID NOs: 2, 4, 168, 173, and 201;
(65) a combination of SEQ ID NOs: 4, 17, 115, 160, and 168;
(66) a combination of SEQ ID NOs: 4, 17, 115, 168, and 246;
(67) a combination of SEQ ID NOs: 2, 4, 115, 168, and 173;
(68) a combination of SEQ ID NOs: 4, 17, 115, 168, and 201;
(69) a combination of SEQ ID NOs: 4, 17, 115, 168, and 217;

(70) a combination of SEQ ID NOs: 2, 4, 17, 115, and 168;
(71) a combination of SEQ ID NOs: 4, 17, 115, 140, and 168; and
(72) a combination of SEQ ID NOs: 4, 17, 102, 115, and 168.

Non-limiting examples of the combination comprising the polynucleotide consisting of the nucleotide sequence represented by SEQ ID NO: 130 or a complementary sequence thereof are further listed below as combinations of target nucleic acids:

(1) a combination of SEQ ID NOs: 121, 130, and 164;
(2) a combination of SEQ ID NOs: 18, 121, 130, and 164;
(3) a combination of SEQ ID NOs: 18, 130, 164, and 268;
(4) a combination of SEQ ID NOs: 13, 18, 130, and 165;
(5) a combination of SEQ ID NOs: 18, 121, 130, 136, and 164;
(6) a combination of SEQ ID NOs: 18, 121, 130, 164, and 314;
(7) a combination of SEQ ID NOs: 18, 114, 121, 130, and 164;
(8) a combination of SEQ ID NOs: 18, 121, 130, 164, and 214;
(9) a combination of SEQ ID NOs: 18, 121, 130, 164, and 193;
(10) a combination of SEQ ID NOs: 18, 130, 164, 255, and 268;
(11) a combination of SEQ ID NOs: 18, 121, 130, 164, and 320;
(12) a combination of SEQ ID NOs: 18, 121, 130, 164, and 301;
(13) a combination of SEQ ID NOs: 18, 121, 130, 144, and 164;
(14) a combination of SEQ ID NOs: 18, 121, 130, 164, and 168;
(15) a combination of SEQ ID NOs: 18, 121, 130, 164, and 205;
(16) a combination of SEQ ID NOs: 18, 121, 130, 158, and 164;
(17) a combination of SEQ ID NOs: 18, 121, 130, 164, and 260;
(18) a combination of SEQ ID NOs: 18, 106, 121, 130, and 164;
(19) a combination of SEQ ID NOs: 18, 121, 130, 164, and 318;
(20) a combination of SEQ ID NOs: 18, 121, 130, 164, and 286;
(21) a combination of SEQ ID NOs: 18, 121, 130, 164, and 315;
(22) a combination of SEQ ID NOs: 18, 121, 130, 164, and 237;
(23) a combination of SEQ ID NOs: 18, 121, 130, 164, and 184;
(24) a combination of SEQ ID NOs: 18, 121, 130, 164, and 270;
(25) a combination of SEQ ID NOs: 18, 121, 130, 164, and 309;
(26) a combination of SEQ ID NOs: 18, 121, 130, 164, and 278;
(27) a combination of SEQ ID NOs: 18, 82, 121, 130, and 164;
(28) a combination of SEQ ID NOs: 18, 23, 121, 130, and 164;
(29) a combination of SEQ ID NOs: 18, 121, 130, 164, and 189;
(30) a combination of SEQ ID NOs: 18, 121, 130, 152, and 164;
(31) a combination of SEQ ID NOs: 18, 121, 130, 164, and 213;
(32) a combination of SEQ ID NOs: 18, 121, 130, 164, and 229;
(33) a combination of SEQ ID NOs: 18, 57, 121, 130, and 164;
(34) a combination of SEQ ID NOs: 18, 121, 130, 142, and 164;
(35) a combination of SEQ ID NOs: 18, 121, 130, 155, and 164;
(36) a combination of SEQ ID NOs: 18, 39, 121, 130, and 164;
(37) a combination of SEQ ID NOs: 18, 27, 130, 164, and 268;
(38) a combination of SEQ ID NOs: 18, 33, 121, 130, and 164;
(39) a combination of SEQ ID NOs: 18, 121, 126, 130, and 164;
(40) a combination of SEQ ID NOs: 18, 121, 130, 164, and 319;
(41) a combination of SEQ ID NOs: 18, 22, 121, 130, and 164;
(42) a combination of SEQ ID NOs: 18, 59, 121, 130, and 164;
(43) a combination of SEQ ID NOs: 18, 27, 121, 130, and 164;
(44) a combination of SEQ ID NOs: 18, 130, 164, 268, and 317;
(45) a combination of SEQ ID NOs: 18, 121, 130, 164, and 201;
(46) a combination of SEQ ID NOs: 18, 19, 121, 130, and 164;
(47) a combination of SEQ ID NOs: 18, 74, 130, 164, and 268;
(48) a combination of SEQ ID NOs: 18, 130, 164, 264, and 268;
(49) a combination of SEQ ID NOs: 2, 4, 130, 168, and 246;
(50) a combination of SEQ ID NOs: 2, 9, 130, 168, and 246;
(51) a combination of SEQ ID NOs: 13, 18, 121, 130, and 165;
(52) a combination of SEQ ID NOs: 13, 18, 130, 165, and 268;
(53) a combination of SEQ ID NOs: 4, 17, 115, 130, and 168;
(54) a combination of SEQ ID NOs: 2, 4, 130, 168, and 173;
(55) a combination of SEQ ID NOs: 2, 9, 130, 168, and 173;
(56) a combination of SEQ ID NOs: 2, 111, 130, 168, and 173;
(57) a combination of SEQ ID NOs: 2, 83, 130, 168, and 173;
(58) a combination of SEQ ID NOs: 2, 6, 130, 168, and 173;
(59) a combination of SEQ ID NOs: 2, 6, 130, 173, and 184;
(60) a combination of SEQ ID NOs: 2, 130, 168, 173, and 213;
(61) a combination of SEQ ID NOs: 2, 5, 130, 168, and 173; and
(62) a combination of SEQ ID NOs: 2, 130, 168, 173, and 249.

Non-limiting examples of the combination comprising the polynucleotide consisting of the nucleotide sequence represented by SEQ ID NO: 2 or a complementary sequence thereof are further listed below as combinations of target nucleic acids:
(1) a combination of SEQ ID NOs: 2, 121, 165, and 168;
(2) a combination of SEQ ID NOs: 2, 165, 168, and 268;
(3) a combination of SEQ ID NOs: 2, 4, 168, and 246;
(4) a combination of SEQ ID NOs: 2, 18, 165, and 268;
(5) a combination of SEQ ID NOs: 2, 4, 173, and 183;
(6) a combination of SEQ ID NOs: 2, 4, 115, and 168;
(7) a combination of SEQ ID NOs: 2, 9, 168, and 246;
(8) a combination of SEQ ID NOs: 2, 111, 168, and 246;
(9) a combination of SEQ ID NOs: 2, 111, 168, and 173;
(10) a combination of SEQ ID NOs: 2, 102, 168, and 246;
(11) a combination of SEQ ID NOs: 2, 4, 130, 168, and 246;
(12) a combination of SEQ ID NOs: 2, 4, 168, 201, and 246;
(13) a combination of SEQ ID NOs: 2, 9, 130, 168, and 246;
(14) a combination of SEQ ID NOs: 2, 4, 111, 168, and 173;
(15) a combination of SEQ ID NOs: 2, 4, 130, 168, and 173;
(16) a combination of SEQ ID NOs: 2, 4, 168, 173, and 201;
(17) a combination of SEQ ID NOs: 2, 4, 115, 168, and 173;
(18) a combination of SEQ ID NOs: 2, 9, 130, 168, and 173;
(19) a combination of SEQ ID NOs: 2, 4, 17, 115, and 168;
(20) a combination of SEQ ID NOs: 2, 111, 168, 173, and 268;
(21) a combination of SEQ ID NOs: 2, 18, 165, 268, and 301;
(22) a combination of SEQ ID NOs: 2, 18, 165, 268, and 315;
(23) a combination of SEQ ID NOs: 2, 111, 130, 168, and 173;
(24) a combination of SEQ ID NOs: 2, 83, 130, 168, and 173;
(25) a combination of SEQ ID NOs: 2, 6, 130, 168, and 173;
(26) a combination of SEQ ID NOs: 2, 111, 168, 173, and 223;
(27) a combination of SEQ ID NOs: 2, 5, 111, 168, and 173;
(28) a combination of SEQ ID NOs: 2, 6, 130, 173, and 184;
(29) a combination of SEQ ID NOs: 2, 39, 111, 168, and 173;
(30) a combination of SEQ ID NOs: 2, 111, 168, 173, and 222;
(31) a combination of SEQ ID NOs: 2, 111, 152, 168, and 173;
(32) a combination of SEQ ID NOs: 2, 111, 168, 173, and 241;
(33) a combination of SEQ ID NOs: 2, 130, 168, 173, and 213;
(34) a combination of SEQ ID NOs: 2, 111, 168, 173, and 184;
(35) a combination of SEQ ID NOs: 2, 102, 111, 168, and 173;
(36) a combination of SEQ ID NOs: 2, 5, 130, 168, and 173;
(37) a combination of SEQ ID NOs: 2, 111, 168, 173, and 234;
(38) a combination of SEQ ID NOs: 2, 111, 168, 173, and 230;
(39) a combination of SEQ ID NOs: 2, 111, 168, 173, and 307;
(40) a combination of SEQ ID NOs: 2, 130, 168, 173, and 249;
(41) a combination of SEQ ID NOs: 2, 111, 158, 168, and 173; and
(42) a combination of SEQ ID NOs: 2, 39, 168, 169, and 173.

Non-limiting examples of the combination comprising the polynucleotide consisting of the nucleotide sequence represented by SEQ ID NO: 9 or a complementary sequence thereof are further listed below as combinations of target nucleic acids:
(1) a combination of SEQ ID NOs: 9, 165, and 168;
(2) a combination of SEQ ID NOs: 9, 165, 168, and 173;
(3) a combination of SEQ ID NOs: 9, 128, 165, and 168;
(4) a combination of SEQ ID NOs: 9, 17, 165, and 168;
(5) a combination of SEQ ID NOs: 9, 80, 165, and 168;
(6) a combination of SEQ ID NOs: 2, 9, 168, and 246;
(7) a combination of SEQ ID NOs: 5, 9, 165, 168, and 173;
(8) a combination of SEQ ID NOs: 9, 128, 129, 165, and 168;
(9) a combination of SEQ ID NOs: 2, 9, 130, 168, and 246;
(10) a combination of SEQ ID NOs: 9, 17, 159, 165, and 168;
(11) a combination of SEQ ID NOs: 9, 17, 165, 168, and 173; and
(12) a combination of SEQ ID NOs: 2, 9, 130, 168, and 173.

Non-limiting examples of the combination comprising the polynucleotide consisting of the nucleotide sequence represented by SEQ ID NO: 17 or a complementary sequence thereof are further listed below as combinations of target nucleic acids:
(1) a combination of SEQ ID NOs: 17, 164, and 168;
(2) a combination of SEQ ID NOs: 4, 17, 165, and 168;
(3) a combination of SEQ ID NOs: 9, 17, 165, and 168;
(4) a combination of SEQ ID NOs: 4, 17, 115, and 168;
(5) a combination of SEQ ID NOs: 4, 17, 115, and 302;
(6) a combination of SEQ ID NOs: 4, 17, 115, and 184;
(7) a combination of SEQ ID NOs: 4, 17, 165, 168, and 173;
(8) a combination of SEQ ID NOs: 4, 17, 165, 168, and 223;
(9) a combination of SEQ ID NOs: 4, 17, 128, 165, and 168;
(10) a combination of SEQ ID NOs: 4, 17, 165, 168, and 169;
(11) a combination of SEQ ID NOs: 4, 17, 117, 165, and 168;
(12) a combination of SEQ ID NOs: 4, 17, 165, 168, and 323;
(13) a combination of SEQ ID NOs: 4, 17, 81, 165, and 168;
(14) a combination of SEQ ID NOs: 4, 17, 165, 168, and 253;
(15) a combination of SEQ ID NOs: 4, 17, 162, 165, and 168;
(16) a combination of SEQ ID NOs: 4, 17, 141, 165, and 168;
(17) a combination of SEQ ID NOs: 4, 17, 129, 165, and 168;

(18) a combination of SEQ ID NOs: 4, 17, 165, 168, and 258;
(19) a combination of SEQ ID NOs: 4, 17, 165, 168, and 190;
(20) a combination of SEQ ID NOs: 4, 17, 115, 168, and 177;
(21) a combination of SEQ ID NOs: 4, 17, 165, 168, and 191;
(22) a combination of SEQ ID NOs: 4, 17, 158, 165, and 168;
(23) a combination of SEQ ID NOs: 4, 17, 165, 168, and 184;
(24) a combination of SEQ ID NOs: 4, 17, 94, 165, and 168;
(25) a combination of SEQ ID NOs: 4, 17, 165, 168, and 296;
(26) a combination of SEQ ID NOs: 4, 17, 165, 168, and 307;
(27) a combination of SEQ ID NOs: 4, 17, 123, 165, and 168;
(28) a combination of SEQ ID NOs: 4, 17, 39, 165, and 168;
(29) a combination of SEQ ID NOs: 4, 17, 145, 165, and 168;
(30) a combination of SEQ ID NOs: 4, 17, 165, 168, and 286;
(31) a combination of SEQ ID NOs: 4, 17, 73, 165, and 168;
(32) a combination of SEQ ID NOs: 4, 17, 115, 165, and 168;
(33) a combination of SEQ ID NOs: 4, 17, 108, 165, and 168;
(34) a combination of SEQ ID NOs: 4, 17, 156, 165, and 168;
(35) a combination of SEQ ID NOs: 4, 17, 165, 168, and 249;
(36) a combination of SEQ ID NOs: 4, 17, 131, 165, and 168;
(37) a combination of SEQ ID NOs: 4, 17, 165, 168, and 304;
(38) a combination of SEQ ID NOs: 4, 17, 157, 165, and 168;
(39) a combination of SEQ ID NOs: 4, 17, 165, 168, and 318;
(40) a combination of SEQ ID NOs: 4, 17, 74, 165, and 168;
(41) a combination of SEQ ID NOs: 4, 17, 165, 168, and 216;
(42) a combination of SEQ ID NOs: 4, 17, 165, 168, and 309;
(43) a combination of SEQ ID NOs: 4, 17, 165, 168, and 236;
(44) a combination of SEQ ID NOs: 4, 17, 165, 168, and 324;
(45) a combination of SEQ ID NOs: 9, 17, 159, 165, and 168;
(46) a combination of SEQ ID NOs: 4, 17, 115, 130, and 168;
(47) a combination of SEQ ID NOs: 4, 17, 111, 115, and 168;
(48) a combination of SEQ ID NOs: 9, 17, 165, 168, and 173;
(49) a combination of SEQ ID NOs: 4, 17, 115, 160, and 168;
(50) a combination of SEQ ID NOs: 4, 17, 115, 168, and 246;
(51) a combination of SEQ ID NOs: 4, 17, 115, 168, and 201;
(52) a combination of SEQ ID NOs: 4, 17, 115, 168, and 217;
(53) a combination of SEQ ID NOs: 2, 4, 17, 115, and 168;
(54) a combination of SEQ ID NOs: 4, 17, 115, 140, and 168; and
(55) a combination of SEQ ID NOs: 4, 17, 102, 115, and 168.

Non-limiting examples of the combination comprising the polynucleotide consisting of the nucleotide sequence represented by SEQ ID NO: 121 or a complementary sequence thereof are further listed below as combinations of target nucleic acids:

(1) a combination of SEQ ID NOs: 121, 130, and 164;
(2) a combination of SEQ ID NOs: 18, 121, and 164;
(3) a combination of SEQ ID NOs: 121, 164, and 168;
(4) a combination of SEQ ID NOs: 121, 164, and 328;
(5) a combination of SEQ ID NOs: 121, 164, and 211;
(6) a combination of SEQ ID NOs: 95, 121, and 164;
(7) a combination of SEQ ID NOs: 6, 121, and 165;
(8) a combination of SEQ ID NOs: 18, 121, 130, and 164;
(9) a combination of SEQ ID NOs: 18, 121, 164, and 255;
(10) a combination of SEQ ID NOs: 18, 121, 164, and 201;
(11) a combination of SEQ ID NOs: 18, 121, 151, and 164;
(12) a combination of SEQ ID NOs: 18, 95, 121, and 164;
(13) a combination of SEQ ID NOs: 18, 107, 121, and 164;
(14) a combination of SEQ ID NOs: 2, 121, 165, and 168;
(15) a combination of SEQ ID NOs: 18, 121, 149, and 165;
(16) a combination of SEQ ID NOs: 13, 18, 121, and 165;
(17) a combination of SEQ ID NOs: 18, 121, 130, 136, and 164;
(18) a combination of SEQ ID NOs: 18, 121, 130, 164, and 314;
(19) a combination of SEQ ID NOs: 18, 114, 121, 130, and 164;
(20) a combination of SEQ ID NOs: 18, 121, 130, 164, and 214;
(21) a combination of SEQ ID NOs: 18, 121, 130, 164, and 193;
(22) a combination of SEQ ID NOs: 18, 121, 130, 164, and 320;
(23) a combination of SEQ ID NOs: 18, 121, 130, 164, and 301;
(24) a combination of SEQ ID NOs: 18, 121, 130, 144, and 164;
(25) a combination of SEQ ID NOs: 18, 121, 130, 164, and 168;
(26) a combination of SEQ ID NOs: 18, 121, 130, 164, and 205;
(27) a combination of SEQ ID NOs: 18, 121, 130, 158, and 164;
(28) a combination of SEQ ID NOs: 18, 121, 130, 164, and 260;
(29) a combination of SEQ ID NOs: 18, 106, 121, 130, and 164;
(30) a combination of SEQ ID NOs: 18, 121, 130, 164, and 318;
(31) a combination of SEQ ID NOs: 18, 121, 130, 164, and 286;
(32) a combination of SEQ ID NOs: 18, 121, 130, 164, and 315;

(33) a combination of SEQ ID NOs: 18, 121, 130, 164, and 237;
(34) a combination of SEQ ID NOs: 18, 121, 130, 164, and 184;
(35) a combination of SEQ ID NOs: 18, 121, 130, 164, and 270;
(36) a combination of SEQ ID NOs: 18, 121, 130, 164, and 309;
(37) a combination of SEQ ID NOs: 18, 121, 130, 164, and 278;
(38) a combination of SEQ ID NOs: 18, 82, 121, 130, and 164;
(39) a combination of SEQ ID NOs: 18, 23, 121, 130, and 164;
(40) a combination of SEQ ID NOs: 18, 121, 130, 164, and 189;
(41) a combination of SEQ ID NOs: 18, 121, 130, 152, and 164;
(42) a combination of SEQ ID NOs: 18, 121, 130, 164, and 213;
(43) a combination of SEQ ID NOs: 18, 121, 130, 164, and 229;
(44) a combination of SEQ ID NOs: 18, 57, 121, 130, and 164;
(45) a combination of SEQ ID NOs: 18, 121, 130, 142, and 164;
(46) a combination of SEQ ID NOs: 18, 121, 130, 155, and 164;
(47) a combination of SEQ ID NOs: 18, 39, 121, 130, and 164;
(48) a combination of SEQ ID NOs: 18, 33, 121, 130, and 164;
(49) a combination of SEQ ID NOs: 18, 121, 126, 130, and 164;
(50) a combination of SEQ ID NOs: 18, 121, 130, 164, and 319;
(51) a combination of SEQ ID NOs: 18, 22, 121, 130, and 164;
(52) a combination of SEQ ID NOs: 18, 59, 121, 130, and 164;
(53) a combination of SEQ ID NOs: 18, 27, 121, 130, and 164;
(54) a combination of SEQ ID NOs: 18, 121, 130, 164, and 201;
(55) a combination of SEQ ID NOs: 18, 19, 121, 130, and 164;
(56) a combination of SEQ ID NOs: 18, 95, 121, 164, and 188; and
(57) a combination of SEQ ID NOs: 13, 18, 121, 130, and 165.

Examples of the combinations of target nucleic acids in the kit or the device for discriminating lung adenocarcinoma patients from test subjects without lung cancer, such as healthy subjects, benign bone and soft tissue tumor patients and benign breast disease patients, or patients having a cancer other than lung cancer, according to the present invention can include combinations of two or more of the above-mentioned polynucleotides consisting of the nucleotide sequences represented by SEQ ID NOs as shown in Table 1. For example, any two or more of the above-mentioned polynucleotides consisting of nucleotide sequences represented by SEQ ID NOs: 1 to 329 can be combined. Among them, at least one polynucleotide of the newly found polynucleotides consisting of the nucleotide sequences represented by SEQ ID NOs: 1 to 163 is preferably selected.

Examples of the combinations of target nucleic acids in the kit or the device for discriminating squamous cell carcinoma patients from test subjects without lung cancer, such as healthy subjects, benign bone and soft tissue tumor patients and benign breast disease patients, or patients having a cancer other than lung cancer, according to the present invention can include combinations of two or more of the above-mentioned polynucleotides consisting of the nucleotide sequences represented by SEQ ID NOs as shown in Table 1. For example, any two or more of the above-mentioned polynucleotides consisting of nucleotide sequences represented by SEQ ID NOs: 1 to 329 can be combined. Among them, at least one polynucleotide of the newly found polynucleotides consisting of the nucleotide sequences represented by SEQ ID NOs: 1 to 163 is preferably selected.

Examples of the combinations of target nucleic acids in the kit or the device for discriminating large cell carcinoma patients from test subjects without lung cancer, such as healthy subjects, benign bone and soft tissue tumor patients and benign breast disease patients, or patients having a cancer other than lung cancer, according to the present invention can include combinations of two or more of the above-mentioned polynucleotides consisting of the nucleotide sequences represented by SEQ ID NOs as shown in Table 1. For example, any two or more of the above-mentioned polynucleotides consisting of nucleotide sequences represented by SEQ ID NOs: 1 to 329 can be combined. Among them, at least one polynucleotide of the newly found polynucleotides consisting of the nucleotide sequences represented by SEQ ID NOs: 1 to 163 is preferably selected.

Examples of the combinations of target nucleic acids in the kit or the device for discriminating small cell carcinoma patients from test subjects without lung cancer, such as healthy subjects, benign bone and soft tissue tumor patients and benign breast disease patients, or patients having a cancer other than lung cancer, according to the present invention can include combinations of two or more of the above-mentioned polynucleotides consisting of the nucleotide sequences represented by SEQ ID NOs as shown in Table 1. For example, any two or more of the above-mentioned polynucleotides consisting of nucleotide sequences represented by SEQ ID NOs: 1 to 329 can be combined. Among them, at least one polynucleotide of the newly found polynucleotides consisting of the nucleotide sequences represented by SEQ ID NOs: 1 to 163 is preferably selected.

The kit or device of the present invention can also comprise polynucleotide(s) which can detect lung cancer and are known in the art or will be found in the future in addition to the polynucleotide(s) (that can comprise variant(s), fragments, or derivative(s)) according to the present invention as described above.

The kit or device of the present invention can also comprise an antibody for measuring a marker or markers for lung cancer examination known in the art, such as CEA and CYFRA21-1, in addition to the polynucleotide(s) according to the present invention as described above.

These polynucleotides and variants thereof or fragments thereof contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention is a device for measurement of cancer markers in which nucleic acids such as the polynucleotides according to the present invention described above, variants thereof, derivatives thereof, or fragments thereof are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one, preferably at least two, more preferably at least three, most preferably at least five to all of the lung cancer marker miRNAs, respectively, of the group A described above, or to a polynucleotide(s) consisting of a nucleotide sequence(s) complementary to that of the polynucleotide(s). The kit or the device of the present invention can optionally further comprise nucleic acids capable of specifically binding to the polynucleotides of at least one, preferably at least two, more preferably at least three, most preferably at least five to all of the lung cancer marker miRNAs, respectively, of the group B described above, or to a polynucleotide(s) consisting of a nucleotide sequence(s) complementary to that of the polynucleotide(s).

The kit or the device of the present invention can be used for detecting lung cancer as described in Section 4 below.

4. Method for Detecting Lung Cancer

The present invention further provides a method for detecting lung cancer, using the above-mentioned nucleic acid(s) that can be used in the present invention (alternatively, e.g., the kit or the device of the present invention as described in Section 3 above) to measure one or more expression levels of lung cancer-derived genes represented by: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p; and optionally an expression level(s) of lung cancer-derived gene(s) represented by: miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, in a sample, and evaluating in vitro whether or not the subject has lung cancer, based on the expression levels measured (and control expression levels of healthy subjects optionally measured in the same way as above). In the method, for example, using samples, such as blood, serum, or plasma, collected from a subject suspected of having lung cancer and a subject without lung cancer, the expression levels of the above mentioned genes obtained from these subjects are compared, and if the expression level(s) of the target nucleic acid(s) is different between these samples, the subject is evaluated to have lung cancer.

This method of the present invention enables a limitedly invasive, early diagnosis of lung adenocarcinoma, lung squamous cell carcinoma, large cell lung carcinoma, small cell lung carcinoma and other lung cancers with high sensitivity and high specificity and thereby brings about early treatment and improved prognosis. In addition, the disease progression or the effectiveness of surgical, radiotherapeutic, and chemotherapeutic treatments can be monitored by the present invention.

According to the present invention, the method for extracting the lung cancer-derived gene(s) from the sample such as blood, serum, or plasma prepared by the addition of a reagent for RNA extraction in 3D-Gene™ RNA extraction reagent from liquid sample kit (Toray Industries, Inc., Japan) is particularly preferable. A general acidic phenol method (acid guanidinium-phenol-chloroform (AGPC)) or Trizol™ (Life Technologies Corp.) may be used. The lung cancer-derived gene(s) may be also prepared by the addition of a reagent for RNA extraction containing acidic phenol, such as Trizol (Life Technologies Corp.) or Isogen (Nippon Gene Co., Ltd., Japan). Alternatively, a kit such as miRNeasy™ Mini Kit (Qiagen N.V.) may be used, although the method is not limited thereto.

The present invention also provides use of the kit or the device of the present invention for detecting in vitro an expression product(s) of a lung cancer-derived miRNA gene(s) in a sample from a subject.

In the method of the present invention, the kit or the device described above comprises a single polynucleotide or any possible combination of polynucleotides that can be used in the present invention as described above.

In the detection or (genetic) diagnosis of lung cancer according to the present invention, each polynucleotide contained in the kit or the device of the present invention can be used as a probe or a primer. In the case of using the polynucleotides as primers, TaqMan™ MicroRNA Assays from Life Technologies Corp., miScript PCR System from Qiagen N.V., or the like can be used, although the method is not limited thereto.

In the method of the present invention, measurement of the gene expression levels can be performed using the above-mentioned primers or probes according to a routine method in a method known in the art specifically for detecting particular genes, for example, a hybridization technique such as Northern blot, Southern blot, in situ hybridization, Northern hybridization, or Southern hybridization, a quantitative amplification technique such as quantitative RT-PCR, or a method with a next-generation sequencer. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The method, the kit or the device of the present invention is useful for diagnosis of lung cancer or the detection of the presence or absence of lung cancer. Specifically, the detection of lung cancer using the method, the kit or the device can be performed by detecting in vitro an expression level(s) of a gene(s) which is detected by the method or detected using the nucleic acid probe(s) or the primer(s) contained in the kit or the device, in a sample such as blood, serum, plasma, or urine from a subject suspected of having lung cancer. The subject suspected of having lung cancer can be evaluated as having lung cancer when the expression level(s) of a polynucleotide(s) consisting of a nucleotide sequence(s) represented by at least one of, for example, SEQ ID NOs: 1 to 163 and optionally a nucleotide sequence(s) represented by one or more of, for example, SEQ ID NOs: 164 to 329, as target nucleic acids, in the sample such as blood, serum, plasma, or urine of the subject, is significantly high in statistic compared to an expression level(s) of the nucleotide sequences in the sample such as blood, serum, or plasma, or urine of a subject without lung cancer (i.e., also referred to as a control animal).

In the method of the present invention, or the method using the kit or the device of the present invention, the method for detecting the presence or the absence of lung cancer in a sample from a subject comprises collecting a body fluid such as blood, serum, plasma, or urine of a subject, and measuring the expression level(s) of the target gene(s) (or target nucleic acid(s)) contained therein using one or more polynucleotides (including a variant(s), a fragment(s), or a derivative(s)) selected from the groups of polynucleotides of the present invention, to evaluate the presence or absence of lung cancer or to detect lung cancer.

The method for detecting lung cancer according to the present invention can be used in combination with an imaging test method such as chest X-ray examination, CT examination, MRI examination, or PET examination. The method for detecting lung cancer according to the present invention can also be used in combination with sputum cytology, pleural fluid analysis, bronchoscopy, percutaneous needle biopsy or the like, which is a pathological examination method involving the microscopic examination of collected cells or tissues. The method for detecting lung cancer according to the present invention is capable of specifically detecting lung cancer and therefore, can substantially discriminate lung cancer from cancer other than lung cancer and can determine lung cancer with higher reliability by combination with another examination method such as the imaging test method or the pathological examination method described above. Furthermore, the method of the present invention can also be utilized to confirm the necessaity of carrying out another examination method such an imaging test or a pathological examination.

The method for detecting lung cancer according to the present invention can also be used to evaluate or diagnose, for example, the presence or absence of amelioration of the disease or the degree of amelioration thereof in a lung cancer patient in the case that a lung cancer-related therapeutic drug which is known or on a development stage (including cisplatin, gefitinib, docetaxel, etoposide, carboplatin, paclitaxel, and combination drugs thereof as non-limiting examples) is administered to the patient for treatment or amelioration of the disease.

The method of the present invention can comprise, for example, the following steps (a), (b), and (c):

(a) a step of contacting in vitro a sample from a subject with a polynucleotide(s) contained in the kit or the device of the present invention;

(b) a step of measuring an expression level(s) of the target nucleic acid(s) in the sample using the polynucleotide(s) as a nucleic acid probe(s) or primer(s); and (c) a step of evaluating the presence or absence of lung cancer (cells) in the subject on the basis of the measurement results in the step (b).

In one embodiment, the present invention provides a method for detecting lung cancer, comprising: measuring an expression level(s) of a target nucleic acid(s) in a sample of a subject using a nucleic acid(s) capable of specifically binding to at least one, preferably at least two polynucleotides selected from the group consisting of the following miRNAs: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, and miR-92b-3p, or to a polynucleotide(s) consisting of a nucleotide sequence(s) complementary to that of the polynucleotide(s); or a nucleic acid(s) for detecting the polynucleotide(s); and evaluating in vitro whether or not the subject has lung cancer using the above-measured expression levels and control expression levels of a subject(s) without lung cancer measured in the same way as above.

As used herein, the term "evaluating" is evaluation support based on results of in vitro examination, not physician's judgment.

As described above, in the method of the present invention, specifically, miR-6787-5p is hsa-miR-6787-5p, miR-920 is hsa-miR-920, miR-3622a-5p is hsa-miR-3622a-5p, miR-1185-1-3p is hsa-miR-1185-1-3p, miR-4327 is hsa-miR-4327, miR-5739 is hsa-miR-5739, miR-937-5p is hsa-miR-937-5p, miR-1181 is hsa-miR-1181, miR-1185-2-3p is hsa-miR-1185-2-3p, miR-1193 is hsa-miR-1193, miR-1207-5p is hsa-miR-1207-5p, miR-1238-5p is hsa-miR-1238-5p, miR-1246 is hsa-miR-1246, miR-1249-5p is hsa-miR-1249-5p, miR-1292-3p is hsa-miR-1292-3p, miR-1469 is hsa-miR-1469, miR-1470 is hsa-miR-1470, miR-197-5p is hsa-miR-197-5p, miR-208a-5p is hsa-miR-208a-5p, miR-2110 is hsa-miR-2110, miR-211-3p is hsa-miR-211-3p, miR-2467-3p is hsa-miR-2467-3p, miR-3122 is hsa-miR-3122, miR-3141 is hsa-miR-3141, miR-3156-5p is hsa-miR-3156-5p, miR-3158-5p is hsa-miR-3158-5p, miR-3160-5p is hsa-miR-3160-5p, miR-3180-3p is hsa-miR-3180-3p, miR-3191-3p is hsa-miR-3191-3p, miR-3194-3p is hsa-miR-3194-3p, miR-320b is hsa-miR-320b, miR-328-5p is hsa-miR-328-5p, miR-3610 is hsa-miR-3610, miR-3619-3p is hsa-miR-3619-3p, miR-3620-5p is hsa-miR-3620-5p, miR-370-3p is hsa-miR-370-3p, miR-373-5p is hsa-miR-373-5p, miR-3917 is hsa-miR-3917, miR-3937 is hsa-miR-3937, miR-4259 is hsa-miR-4259, miR-4281 is hsa-miR-4281, miR-4294 is hsa-miR-4294, miR-4419b is hsa-miR-4419b, miR-4428 is hsa-miR-4428, miR-4429 is hsa-miR-4429, miR-4433a-3p is hsa-miR-4433a-3p, miR-4447 is hsa-miR-4447, miR-4449 is hsa-miR-4449, miR-4459 is hsa-miR-4459, miR-4480 is hsa-miR-4480, miR-4485-5p is hsa-miR-4485-5p, miR-4486 is hsa-miR-4486, miR-4488 is hsa-miR-4488, miR-4489 is hsa-miR-4489, miR-4505 is hsa-miR-4505, miR-4513 is hsa-miR-4513, miR-4515 is hsa-miR-4515, miR-4530 is hsa-miR-4530, miR-4535 is hsa-miR-4535, miR-4635 is hsa-miR-4635, miR-4640-5p is hsa-miR-4640-5p, miR-4646-5p is hsa-miR-4646-5p, miR-4656 is hsa-miR-4656, miR-4663 is hsa-miR-4663, miR-4665-5p is hsa-miR-4665-5p, miR-4706 is hsa-miR-4706, miR-4707-5p is hsa-miR-4707-5p, miR-4708-3p is hsa-miR-4708-3p, miR-4710 is hsa-miR-4710, miR-4718 is hsa-miR-4718, miR-4722-5p is hsa-miR-4722-5p, miR-4727-3p is hsa-miR-4727-3p, miR-4730 is hsa-miR-4730, miR-4734 is hsa-miR-4734, miR-4740-5p is hsa-miR-4740-5p, miR-4747-3p is hsa-miR-4747-3p, miR-4749-5p is hsa-miR-4749-5p, miR-4755-3p is hsa-miR-4755-3p, miR-4763-5p is hsa-miR-4763-5p, miR-4787-3p is hsa-miR-4787-3p, miR-5008-5p is hsa-miR-5008-5p, miR-5010-5p is hsa-miR-5010-5p, miR-504-3p is hsa-miR-504-3p, miR-5090 is hsa-miR-5090, miR-5100 is hsa-miR-5100, miR-5196-5p is hsa-miR-5196-5p, miR-551b-5p is hsa-miR-551b-5p, miR-557 is hsa-miR-557, miR-5787 is hsa-miR-5787, miR-6090 is hsa-miR-6090, miR-6124 is hsa-miR-6124, miR-6132 is hsa-miR-6132, miR-6510-5p is hsa-miR-6510-5p, miR-6511b-5p is hsa-miR-6511b-5p, miR-6515-3p is hsa-miR-6515-3p, miR-654-5p is hsa-miR-654-5p, miR-658 is hsa-miR-658, miR-668-5p is hsa-miR-668-5p, miR-6722-5p is hsa-miR-6722-5p, miR-6724-5p is hsa-miR-6724-5p, miR-6729-3p is hsa-miR-6729-3p, miR-6737-5p is hsa-miR-6737-5p, miR-6756-5p is hsa-miR-6756-5p, miR-6762-5p is hsa-miR-6762-5p, miR-6763-3p is hsa-miR-6763-3p, miR-6766-5p is hsa-miR-6766-5p, miR-6769a-5p is hsa-miR-6769a-5p, miR-6771-5p is hsa-miR-6771-5p, miR-6786-5p is hsa-miR-6786-5p, miR-6789-5p is hsa-miR-6789-5p, miR-6794-5p is hsa-miR-6794-5p, miR-6796-3p is hsa-miR-6796-3p, miR-6797-5p is hsa-miR-6797-5p, miR-6800-3p is hsa-miR-6800-3p, miR-6802-5p is hsa-miR-6802-5p, miR-6803-5p is hsa-miR-6803-5p, miR-6805-3p is hsa-miR-6805-3p, miR-6805-5p is hsa-miR-6805-5p, miR-6807-5p is hsa-miR-6807-5p, miR-6812-5p is hsa-miR-6812-5p, miR-6819-5p is hsa-miR-6819-5p, miR-6822-5p is hsa-miR-6822-5p, miR-6824-5p is hsa-miR-6824-5p, miR-6826-5p is hsa-miR-6826-5p, miR-6850-5p is hsa-miR-6850-5p, miR-6858-5p is hsa-miR-6858-5p, miR-6861-5p is hsa-miR-6861-5p, miR-6880-3p is hsa-miR-6880-3p, miR-7107-5p is hsa-miR-7107-5p, miR-7109-5p is hsa-miR-7109-5p, miR-7114-5p is hsa-miR-7114-5p, miR-7704 is hsa-miR-7704, miR-7846-3p is hsa-miR-7846-3p, miR-8052 is hsa-miR-8052, miR-8060 is hsa-miR-8060, miR- 8071 is hsa-miR-8071, miR-8073 is hsa-miR-8073, miR-874-5p is hsa-miR-874-5p, miR-204-3p is hsa-miR-204-3p, miR-3154 is hsa-miR-3154, miR-3960 is hsa-miR-3960, miR-4433a-5p is hsa-miR-4433a-5p, miR-4455 is hsa-miR-4455, miR-4462 is hsa-miR-4462, miR-4476 is hsa-miR-4476, miR-4508 is hsa-miR-4508, miR-4687-3p is hsa-miR-4687-3p, miR-4687-5p is hsa-miR-4687-5p, miR-4732-5p is hsa-miR-4732-5p, miR-4771 is hsa-miR-4771, miR-642a-3p is hsa-miR-642a-3p, miR-6732-5p is hsa-miR-6732-5p, miR-6760-5p is hsa-miR-6760-5p, miR-6799-5p is hsa-miR-6799-5p, miR-6820-5p is hsa-miR-6820-5p, miR-6821-5p is hsa-miR-6821-5p, miR-6829-5p is hsa-miR-6829-5p, miR-6893-5p is hsa-miR-6893-5p, miR-7108-3p is hsa-miR-7108-3p, miR-7111-5p is hsa-miR-7111-5p, miR-8089 is hsa-miR-8089, miR-885-3p is hsa-miR-885-3p, and miR-92b-3p is hsa-miR-92b-3p.

Additionally, in one embodiment, the nucleic acid(s) (e.g., a probe(s) or a primer(s)) in the method of the present invention is selected from the group consisting of, for example, the following polynucleotides (a) to (e):

(a) a polynucleotide consisting of a nucleotide sequence represented by any of SEQ ID NOs: 1 to 163, or a nucleotide sequence derived from the nucleotide sequence in which the nucleic acid u is replaced with t, a variant thereof, a derivative thereof, or a fragment thereof comprising 15 or more consecutive nucleotides;

(b) a polynucleotide comprising a nucleotide sequence represented by any of SEQ ID NOs: 1 to 163;

(c) a polynucleotide consisting of a nucleotide sequence complementary to a nucleotide sequence represented by any of SEQ ID NOs: 1 to 163, or a nucleotide sequence derived from the nucleotide sequence in which the nucleic acid u is replaced with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 163, or a nucleotide sequence derived from the nucleotide sequence in which the nucleic acid u is replaced with t; and (e) a polynucleotide hybridizing under stringent conditions to any of the polynucleotides (a) to (d).

The nucleic acid(s) used in the method of the present invention can further comprise a nucleic acid(s) capable of specifically binding to at least one polynucleotide selected from the group consisting of the following miRNAs: miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, or to a polynucleotide consisting of a nucleotide sequence complementary to that of the polynucleotide.

Specifically, miR-1343-3p is hsa-miR-1343-3p, miR-6746-5p is hsa-miR-6746-5p, miR-422a is hsa-miR-422a, miR-187-5p is hsa-miR-187-5p, miR-4632-5p is hsa-miR-4632-5p, miR-6791-5p is hsa-miR-6791-5p, miR-103a-3p is hsa-miR-103a-3p, miR-107 is hsa-miR-107, miR-1199-5p is hsa-miR-1199-5p, miR-1225-3p is hsa-miR-1225-3p, miR-1225-5p is hsa-miR-1225-5p, miR-1228-5p is hsa-miR-1228-5p, miR-1229-5p is hsa-miR-1229-5p, miR-1233-5p is hsa-miR-1233-5p, miR-1237-5p is hsa-miR-1237-5p, miR-1247-3p is hsa-miR-1247-3p, miR-1249-3p is hsa-miR-1249-3p, miR-1254 is hsa-miR-1254, miR-1260b is hsa-miR-1260b, miR-1268a is hsa-miR-1268a, miR-1268b is hsa-miR-1268b, miR-1273g-3p is hsa-miR-1273g-3p, miR-128-1-5p is hsa-miR-128-1-5p, miR-128-2-5p is hsa-miR-128-2-5p, miR-1290 is hsa-miR-1290, miR-150-3p is hsa-miR-150-3p, miR-17-3p is hsa-miR-17-3p, miR-1908-5p is hsa-miR-1908-5p, miR-1909-3p is hsa-miR-1909-3p, miR-1914-3p is hsa-miR-1914-3p, miR-1915-3p is hsa-miR-1915-3p, miR-191-5p is hsa-miR-191-5p, miR-22-3p is hsa-miR-22-3p, miR-23b-3p is hsa-miR-23b-3p, miR-24-3p is hsa-miR-24-3p, miR-296-3p is hsa-miR-296-3p, miR-296-5p is hsa-miR-296-5p, miR-3131 is hsa-miR-3131, miR-3162-5p is hsa-miR-3162-5p, miR-3188 is hsa-miR-3188, miR-3196 is hsa-miR-3196, miR-3197 is hsa-miR-3197, miR-320a is hsa-miR-320a, miR-342-5p is hsa-miR-342-5p, miR-3621 is hsa-miR-3621, miR-3648 is hsa-miR-3648, miR-3656 is hsa-miR-3656, miR-365a-5p is hsa-miR-365a-5p, miR-3665 is hsa-miR-3665, miR-3679-5p is hsa-miR-3679-5p, miR-371a-5p is hsa-miR-371a-5p, miR-3940-5p is hsa-miR-3940-5p, miR-423-5p is hsa-miR-423-5p, miR-4257 is hsa-miR-4257, miR-4270 is hsa-miR-4270, miR-4271 is hsa-miR-4271, miR-4286 is hsa-miR-4286, miR-4298 is hsa-miR-4298, miR-4417 is hsa-miR-4417, miR-4442 is hsa-miR-4442, miR-4446-3p is hsa-miR-4446-3p, miR-4448 is hsa-miR-4448, miR-4454 is hsa-miR-4454, miR-4467 is hsa-miR-4467, miR-4472 is hsa-miR-4472, miR-4507 is hsa-miR-4507, miR-4516 is hsa-miR-4516, miR-451a is hsa-miR-451a, miR-4649-5p is hsa-miR-4649-5p, miR-4651 is hsa-miR-4651, miR-4665-3p is hsa-miR-4665-3p, miR-4674 is hsa-miR-4674, miR-4675 is hsa-miR-4675, miR-4689 is hsa-miR-4689, miR-4695-5p is hsa-miR-4695-5p, miR-4697-5p is hsa-miR-4697-5p, miR-4725-3p is hsa-miR-4725-3p, miR-4739 is hsa-miR-4739, miR-4745-5p is hsa-miR-4745-5p, miR-4763-3p is hsa-miR-4763-3p, miR-4792 is hsa-miR-4792, miR-486-3p is hsa-miR-486-3p, miR-5001-5p is hsa-miR-5001-5p, miR-5195-3p is hsa-miR-5195-3p, miR-550a-5p is hsa-miR-550a-5p, miR-5698 is hsa-miR-5698, miR-6075 is hsa-miR-6075, miR-6088 is hsa-miR-6088, miR-6089 is hsa-miR-6089, miR-6125 is hsa-miR-6125, miR-6126 is hsa-miR-6126, miR-614 is hsa-miR-614, miR-615-5p is hsa-miR-615-5p, miR-619-5p is hsa-miR-619-5p, miR-638 is hsa-miR-638, miR-642b-3p is hsa-miR-642b-3p, miR-650 is hsa-miR-650, miR-663a is hsa-miR-663a, miR-663b is hsa-miR-663b, miR-6717-5p is hsa-miR-6717-5p, miR-6721-5p is hsa-miR-6721-5p, miR-6726-5p is hsa-miR-6726-5p, miR-6727-5p is hsa-miR-6727-5p, miR-6738-5p is hsa-miR-6738-5p, miR-6741-5p is hsa-miR-6741-5p, miR-6749-5p is hsa-miR-6749-5p, miR-6752-5p is hsa-miR-6752-5p, miR-675-5p is hsa-miR-675-5p, miR-6757-5p is hsa-miR-6757-5p, miR-6763-5p is hsa-miR-6763-5p, miR-6765-5p is hsa-miR-6765-5p, miR-6775-5p is hsa-miR-6775-5p, miR-6780b-5p is hsa-miR-6780b-5p, miR-6782-5p is hsa-miR-6782-5p, miR-6784-5p is hsa-miR-6784-5p, miR-6800-5p is hsa-miR-6800-5p, miR-6806-5p is hsa-miR-6806-5p, miR-6840-3p is hsa-miR-6840-3p, miR-6848-5p is hsa-miR-6848-5p, miR-6851-5p is hsa-miR-6851-5p, miR-6870-5p is hsa-miR-6870-5p, miR-6872-3p is hsa-miR-6872-3p, miR-6875-5p is hsa-miR-6875-5p, miR-6877-5p is hsa-miR-6877-5p, miR-6879-5p is hsa-miR-6879-5p, miR-6880-5p is hsa-miR-6880-5p, miR-6885-5p is hsa-miR-6885-5p, miR-6887-5p is hsa-miR-6887-5p, miR-7108-5p is hsa-miR-7108-5p, miR-711 is hsa-miR-711, miR-7113-3p is hsa-miR-7113-3p, miR-744-5p is hsa-miR-744-5p, miR-760 is hsa-miR-760, miR-7845-5p is hsa-miR-7845-5p, miR-7847-3p is hsa-miR-7847-3p, miR-7977 is hsa-miR-7977, miR-8059 is hsa-miR-8059, miR-8063 is hsa-miR-8063, miR-8072 is hsa-miR-8072, miR-874-3p is hsa-miR-874-3p, miR-92a-2-5p is hsa-miR-92a-2-5p, miR-92b-5p is hsa-miR-92b-5p, miR-940 is hsa-miR-940, miR-1228-3p is hsa-miR-1228-3p, miR-1275 is hsa-miR-1275, miR-1307-3p is hsa-miR-1307-3p, miR-1343-5p is hsa-miR-1343-5p, miR-23a-3p is hsa-miR-23a-3p, miR-29b-3p is hsa-miR-29b-3p, miR-3135b is hsa-miR-3135b, miR-3185 is hsa-miR-3185, miR-4532 is hsa-miR-4532, miR-4690-5p is hsa-miR-4690-5p, miR-4758-5p is hsa-miR-4758-5p, miR-4783-3p is hsa-miR-4783-3p, miR-6131 is hsa-miR-6131, miR-625-3p is hsa-miR-625-3p, miR-6511a-5p is hsa-miR-6511a-5p, miR-6765-3p is hsa-miR-6765-3p, miR-6816-5p is hsa-miR-6816-5p, miR-6825-5p is hsa-miR-6825-5p, miR-6845-5p is hsa-miR-6845-5p, miR-7150 is hsa-miR-7150, miR-7641 is hsa-miR-7641, miR-7975 is hsa-miR-7975, and miR-92a-3p is hsa-miR-92a-3p.

In one embodiment, the nucleic acid(s) may further be selected from, for example, the group consisting of the following polynucleotides (f) to (j):

(f) a polynucleotide consisting of a nucleotide sequence represented by any of SEQ ID NOs: 164 to 329, or a nucleotide sequence derived from the nucleotide sequence in which the nucleic acid u is replaced with t, a variant thereof, a derivative thereof, or a fragment thereof comprising 15 or more consecutive nucleotides;

(g) a polynucleotide comprising a nucleotide sequence represented by any of SEQ ID NOs: 164 to 329;

(h) a polynucleotide consisting of a nucleotide sequence complementary to a nucleotide sequence represented by any of SEQ ID NOs: 164 to 329, or a nucleotide sequence derived from the nucleotide sequence in which the nucleic acid u is replaced with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 164 to 329, or a nucleotide sequence derived from the nucleotide sequence in which the nucleic acid u is replaced with t; and (j) a polynucleotide hybridizing under stringent conditions to any of the polynucleotides (f) to (i).

Examples of the sample used in the method of the present invention can include samples prepared from living tissues (preferably lung tissues) or body fluids such as blood, serum, plasma, and urine from subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a human, a monkey, a mouse, or a rat, without any limitation, and is preferably a human.

The steps of the method of the present invention can be changed according to the type of the sample to be measured.

In the case of using RNA as an analyte, the method for detecting lung cancer (cells) can comprise, for example, the following steps (a), (b), and (c):

(a) a step of binding RNA prepared from a sample from a subject (wherein, for example, the 3' end of the RNA may be polyadenylated for quantitative RT-PCR in step (b)) or complementary polynucleotides (cDNAs) transcribed from the RNA to a polynucleotide(s) in the kit of the present invention;

(b) a step of measuring the sample-derived RNA or the cDNAs synthesized from the RNA, which is/are bound to the polynucleotide(s), by hybridization using the polynucleotide(s) as a nucleic acid probe(s) or by quantitative RT-PCR using the polynucleotide(s) as a primer(s); and (c) a step of evaluating the presence or absence of lung cancer (or lung cancer-derived gene) on the basis of the measurement results of the step (b).

For example, various hybridization methods can be used for measuring the expression level(s) of a target gene(s), or detecting, examining, evaluating, or diagnosing lung cancer (or lung cancer-derived gene) in vitro according to the present invention. For example, Northern blot, Southern blot, DNA chip analysis, in situ hybridization, Northern hybridization, or Southern hybridization can be used as such a hybridization method. PCR such as quantitative RT-PCR can also be used in combination with hybridization method, or as an alternative thereof.

In the case of using the Northern blot, the presence or absence of expression of each gene or the expression level thereof in the RNA can be detected or measured by use of, for example, the nucleic acid probe(s) that can be used in the present invention. Specific examples thereof can include a method which comprises labeling the nucleic acid probe (or a complementary strand) with a radioisotope (32P, 33P, 35S, etc.), a fluorescent material, or the like, hybridizing the labeled product with the tissue-derived RNA from a subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of, for example, the primer that can be used in the present invention. Specific examples thereof can include a method which comprises recovering the tissue-derived RNA from a subject, preparing cDNAs according to reverse transcription using 3'-end polyadenylation treatment, specific primers, and the like, hybridizing a pair of primers (consisting of a plus strand and a reverse strand binding to the cDNA) prepared from the kit for detection of the present invention with the cDNA such that the region of each target gene marker can be amplified with the cDNA as a template, and performing PCR according to a routine method to detect the obtained single-stranded or double-stranded DNA. The method for detecting the single-stranded or double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced single-stranded or double-stranded DNA to a nylon membrane or the like according to a routine method and hybridizing the single-stranded or double-stranded DNA to a labeled nucleic acid probe for detection.

In the case of using the nucleic acid array analysis, an RNA chip or a DNA chip in which the kit or device for detection of the present invention is attached as nucleic acid probes (single-stranded or double-stranded) to a substrate (solid phase), for example, is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. In the present specification, the term "chip" includes these arrays. 3D-Gene™ Human miRNA Oligo chip (Toray Industries, Inc., Japan) can be used as the DNA chip, though the DNA chip is not limited thereto.

Examples of the measurement using the DNA chip can include, but are not limited to, a method of detecting and measuring a signal derived from the label on the kit or device for detection using an image detector (examples thereof can include Typhoon 9410 (GE Healthcare) and 3D-Gene™ scanner (Toray Industries, Inc., Japan)).

The "stringent conditions" used herein are, as mentioned above, conditions under which a nucleic acid probe hybridizes to its target sequence to a detectably larger extent (e.g., a measurement value equal to or larger than "(a mean of background measurement values)+(a standard error of the background measurement values)×2") than that for other sequences.

The stringent conditions are defined by hybridization and subsequent washing. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.), LNA™-based MicroRNA PCR (Exiqon), or Ncode™ miRNA qRT-PCT kit (Invitrogen Corp.) may be used.

In the method of the present invention, measurement of the gene expression level(s) may be performed with a sequencer, in addition to hybridization methods described above. hi use of a sequencer, any of DNA sequencers of the first generation based on Sanger method, the second generation with shorter read size, and the third generation with longer read size can be used (herein referred to as "next-generation sequencer", including sequencers of the second generation and the third generation). For example, a commercially available measurement kit specifically designed for measuring miRNA using Miseq, Hiseq, or NexSeq (Illumina, Inc.); Ion Proton, Ion PGM, or Ion S5/S5 XL (Thermo Fisher Scientific Inc.); PacBio RS II or Sequel (Pacific Biosciences of California, Inc.); MinION (Oxford Nanopore Technologies Ltd.) exemplified in use of a Nanopore sequencer; or the like may be used.

Next-generation sequencing is a method of obtaining sequence information using a next-generation sequencer, and characterized by being capable of simultaneously performing a huge number of sequencing reactions compared to Sanger method (e.g., Rick Kamps et al., Int. J. Mol. Sci., 2017, 18(2), p.308 and Int. Neurourol. J., 2016, 20 (Suppl.2), S76-83). Examples of next-generation sequencing steps for miRNA include, but not limited to, the following steps: at first, adaptor sequences having predetermined nucleotide sequences are attached, and all RNAs are reverse-transcribed into cDNAs before or after attachment of the sequences. After the reverse transcription, cDNAs derived from specific target miRNAs may be enriched or concentrated by PCR or the like or with a probe or the like, for analyzing the target miRNA before sequencing steps. Subsequent sequencing steps varies in detail depending on the type of a next-generation sequencer, but typically, a sequencing reaction is performed by linking to a substrate via an adaptor sequence and further using the adaptor sequence as a priming site. See details of the sequencing reaction, for example, in Rick Kamps et al. (see supra). Finally, the data are outputted. This step provides a collection of sequence information (reads) obtained by the sequencing reaction. For example, next-generation sequencing can identify a target miRNA(s) based on the sequence information, and measure the expression level thereof based on the number of reads having the sequences of the target miRNA(s).

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably three times, more preferably six times the standard deviation of the measurement values of the blank spots are added to the average measurement value of the blank spots on the DNA chip, and probe spots having a signal value equal to or larger than the resulting value can be regarded as detected spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only genes that show gene expression levels of $2^6$, preferably $2^8$, more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method of detecting a lung cancer (or assisting detection thereof) in a subject, comprising measuring target genes or gene expression levels in a sample from the subject using the gene markers (or target nucleic acids) of the present invention, the nucleic acids (or polynucleotides for detection or diagnosis), the kit, or the device (e.g., chip) for detecting the gene marker or a combination thereof; and assigning the expression levels of the target genes in a sample from the subject to a discriminant (discriminant function), which is prepared using gene expression levels of a sample(s) from a subject(s) (for example, a patient(s)) known to have a lung cancer and a sample(s) from a subject(s) (also referred to as control animal) having no lung cancer, as a training sample(s), and which can distinguishably discriminate the presence or absence of a lung cancer, thereby evaluating the presence or absence of the lung cancer, for example.

Specifically, the present invention further provides the method comprising a first step of measuring in vitro expression levels of target genes, which are known to determine or evaluate that a subject has a lung cancer and/or not, in multiple samples, using the gene marker (or target nucleic acid) of the present invention, the nucleic acids (or polynucleotides for detection or diagnosis), the kit, the device (e.g., chip) for detecting the gene marker or a combination thereof; a second step of preparing a discriminant with the measurement values of the expression levels of the target genes obtained in the first step as training samples; a third step of measuring in vitro the expression levels of the target genes in a sample from the subject in the same manner as in the first step; and a fourth step of assigning the measurement values of the expression levels of the target genes obtained in the third step to the discriminant obtained in the second step, and determining or evaluating whether the subject has a lung cancer or not on the basis of the results obtained from the discriminant, for example. The above target genes are those that can be detected, for example, by the polynucleotides for detection or diagnosis, the polynucleotides contained in the kit or device, and variants thereof or fragments thereof.

The discriminant herein can be prepared by use of any discriminant analysis method that can create a discriminant that distinguishably discriminate the presence or absence of a lung cancer, such as Fisher's discriminant analysis, non-linear discriminant analysis based on the Mahalanobis' distance, neural network or Support Vector Machine (SVM), although the analysis method is not limited to these specific examples.

When a clustering boundary is a straight line or a hyperplane, the linear discriminant analysis is a method for determining the belonging of a cluster using Formula 1 as a discriminant. In Formula 1, x represents an explanatory variable, w represents a coefficient of the explanatory variable, and wo represents a constant term.

[Expression 1]

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, a type of linear discriminant analysis, is a dimension-reducing method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer, 2002). In the Fisher's discriminant analysis, direction w of projection is determined so as to maximize Formula 2. In this formula, µ represents an average input, ng represents the number of data belonging to class g, and µg represents an average input of the data belonging to class g. The numerator and the denominator are the interclass variance and the intraclass variance, respectively, when each of data is projected in the direction of the vector w. Discriminant coefficient $w_i$ is determined by maximizing this ratio (Takafumi Kanamori et al., "Pattern Recognition", KYORITSU SHUPPAN CO., LTD. (Tokyo, Japan) (2009); Richard O. et al., Pattern Classification, Second Edition., Wiley-Interscience, 2000).

[Expression 2]

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)}$$

$$\text{subject to } \mu = \sum_{i=1}^{n} \frac{x_i}{n}, \mu_g = \sum_{i:u_i=g}^{n} \frac{x_i}{n_g}$$

Formula 2

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, $\mu$ represents a central vector of each cluster, and $S^{-1}$ represents an inverse matrix of the variance-covariance matrix of the cluster. The central vector is calculated from explanatory variable x, and an average vector, a median value vector, or the like can be used.

[Expression 3]

$$D(x, \mu) = \{(x - \mu)^t S^{-1}(x - \mu)\}^{\frac{1}{2}}$$

Formula 3

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of being classified into correct classes, or may be a distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (Tokyo, Japan) (2004); Nello Cristianini et al., Introduction to SVM, Kyoritsu Shuppan Co., Ltd. (Tokyo, Japan) (2008)).

C-support vector classification (C-SVC), a type of SVM, comprises preparing a hyperplane by training a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a group of lung cancer patients and a group of test subjects having no lung cancer. For example, lung tissue examination can be used for a reference under which each subject is confirmed to have a lung cancer or not.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

[Expression 4]

$$\min_a \frac{1}{2} a^T Q a - e^T a$$

subject to $y^T a = 0, 0 \le a_i \le C. i = 1, \ldots, l,$

Formula 4

Formula 5 is a finally obtained discriminant, and a group in which the data point belongs to can be determined on the basis of the sign of a value obtained according to the discriminant. In this formula, x represents a support vector, y represents a label indicating the belonging of a group, a represents the corresponding coefficient, b represents a constant term, and K represents a kernel function.

[Expression 5]

$$f(x) = \text{sgn}\left(\sum_{i=1}^{l} y_i a_i K(x_i, x) + b\right)$$

Formula 5

For example, a RBF kernel defined by Formula 6 can be used as the kernel function. In this formula, x represents a support vector, and y represents a kernel parameter for adjusting the complexity of the hyperplane.

[Expression 6]

$$K(x_i, x_j) = \exp(-r\|x_i - x_j\|^2) r < 0$$

Formula 6

In addition, an approach such as neural network, k-nearest neighbor algorithms, decision trees, or logistic regression analysis can be selected as a method for determining or evaluating the presence or absence of lung cancer in a sample from a subject.

In an embodiment, the method of the present invention can comprise, for example, the following steps (a), (b) and (c):

(a) a step of measuring an expression level(s) of a target gene(s) in samples from subjects who are already known to have lung cancer or known to have no lung cancer, using the polynucleotide(s), the kit, or the device (e.g., DNA chip) for detection or diagnosis according to the present invention;

(b) a step of preparing the discriminants of Formulas 1 to 3, 5 and 6 described above from the measurement values of the expression level determined in the step (a), and (c) a step of measuring an expression level(s) of the target gene(s) in a sample from a subject using the polynucleotide(s), the kit, or the device (e.g., DNA chip) for detection or diagnosis according to the present invention, and assigning the obtained measurement value(s) to the discriminants prepared in the step (b), and determining or evaluating that the subject has a lung cancer or not on the basis of the obtained results, or evaluating the expression level derived from a lung cancer patient by comparison with a control from a subject having no lung cancer (including, e.g., a healthy subject). In this context, in the discriminants of Formulas 1 to 3, 5 and 6, x represents an explanatory variable and includes a value obtained by measuring a polynucleotide(s) or a fragment(s) thereof selected from the polynucleotides serving as target nucleic acids described in Section 2 above. Specifically, the explanatory variable of the present invention for discriminating a lung cancer patient and a subject having no lung cancer is a gene expression level(s) selected from, for example, the following expression level (1) or (2).

(1) a gene expression level(s) in the serum of a lung cancer patient and a subject having no lung cancer measured by any nucleic acid (e.g., DNA or RNA) comprising 15 or more consecutive nucleotides in the nucleotide sequence represented by any of SEQ ID NOs: 1 to 163 or a complementary sequence thereof; and (2) a gene expression level(s) in the serum of a lung cancer patient and a subject having no lung cancer measured by any nucleic acid (e.g., DNA or RNA) comprising 15 or more consecutive nucleotides in the nucleotide sequence represented by any of SEQ ID NOs: 164 to 329 or a complementary sequence thereof.

As described above, as the method for determining or evaluating whether a subject has a lung cancer or not in a sample from the subject, it is necessary to use a discriminant employing one or more gene expression levels as an explanatory variable(s). In particular, for enhancing the discrimination accuracy of the discriminant using a single gene expression level alone, it is necessary to use a gene having a clear difference in expression level between two groups consisting of a group of lung cancer patients and a group of healthy subjects, in a discriminant.

Specifically, the gene that is used for an explanatory variable of a discriminant is preferably determined as follows. First, using comprehensive gene expression levels of a group of lung cancer patients and comprehensive gene expression levels of a group of test subjects having no lung cancer, both of which are in a training cohort, as a data set, the degree of difference in the expression level of each gene between the two groups is obtained by use of, for example, the P value of a parametric analysis such as t-test, the P value of a nonparametric analysis such as the Mann-Whitney's U test or the P value of the Wilcoxon test.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (Tokyo, Japan) (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of statistical tests, the absolute value of an expression ratio of a median value of each gene expression level (fold change) between gene expression levels of a group of patients having lung cancer and gene expression levels of a group of test subjects having no lung cancer may be calculated to select a gene that is used for an explanatory variable in a discriminant. Alternatively, ROC curves may be prepared using gene expression levels of a group of patients having lung cancer and a group of test subjects having no lung cancer, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discrimination accuracy include a method of constructing a discriminant in every combination of genes that satisfy the significance level being P value, and a method of repetitively evaluating the genes for use in the preparation of a discriminant while increasing the number of genes one by one in a descending order of difference in gene expression level (Furey T S. et al., 2000, Bioinformatics., Vol. 16, p. 906-14). To the discriminant, the gene expression level of another independent patient having a lung cancer or a test subject having no lung cancer is assigned as an explanatory variable to calculate discrimination results of the group to which the independent patient having a lung cancer or the test subject having no lung cancer belongs. Specifically, the gene set for diagnosis found and the discriminant constructed using the gene set for diagnosis can be evaluated in an independent sample cohort to find more universal gene set for diagnosis that can detect a lung cancer and a more universal method for discriminating a lung cancer.

In preparing a discriminant using expression levels of multiple genes as an explanatory variable, it is not necessary to select a gene having a clear difference in expression level between the group of lung cancer patients and the group of test subjects having no lung cancer as described above. Specifically, if expression levels of multiple genes are used in combination even though the expression levels of individual genes do not clearly differ, a discriminant having high discriminant performance can be obtained, as the case may be. Because of this, a method of directly searching a discriminant having high discriminant performance without prior selection of the gene to be employed in the discriminant can also be used.

Split-sample method is preferably used for evaluating the performance (generality) of the discriminant. Specifically, a data set is divided into a training cohort and a validation cohort, and gene selection by a statistical test and discriminant preparation are performed using the training cohort. Accuracy, sensitivity, and specificity are calculated using a result of discriminating a validation cohort according to the discriminant, and a true group to which the validation cohort belongs, to evaluate the performance of the discriminant. On the other hand, instead of dividing a data set, the gene selection by a statistical test and discriminant preparation may be performed using all of samples, and accuracy, sensitivity, and specificity can be calculated by the discriminant using a newly prepared sample cohort for evaluation of the performance of the discriminant.

The present invention provides a polynucleotide(s) for detection or diagnosis of a disease useful for diagnosing and treating a lung cancer, a method for detecting a lung cancer using the polynucleotide(s), and a kit and device for detecting or diagnosing a lung cancer, comprising the polynucleotide(s). Particularly, in order to select a gene(s) for diagnosis and prepare a discriminant so as to exhibit accuracy beyond the lung cancer diagnosis method using the existing tumor marker CEA, a gene set for diagnosis and a discriminant for the method of present invention can be constructed, which exhibit accuracy beyond CEA, for example, by comparing expressed genes in serum from a patient confirmed to be negative using CEA but finally found to have a lung cancer by detailed examination such as computed tomography using a contrast medium, with genes expressed in serum from a patient having no lung cancer.

For example, the gene set for diagnosis is set to any combination selected from: one or two or more of the polynucleotides based on a nucleotide sequence(s) represented by any of SEQ ID NOs: 1 to 163 as described above; and optionally one or two or more of the polynucleotides based on a nucleotide sequence(s) represented by any of SEQ ID NOs: 164 to 329. Further, a discriminant is constructed using the expression levels of the gene set for diagnosis in samples from a lung cancer patient as a result of tissue diagnosis and samples from a test subject having no lung cancer as a result of tissue diagnosis. As a result, whether a subject, from which a sample with unknown lung cancer status is provided, has a lung cancer or not can be determined with 100% accuracy at the maximum by measuring expression levels of the gene set for diagnosis in the sample.

EXAMPLES

The present invention will be described further specifically with reference to Examples below. However, the scope of the present invention is not intended to be limited by these Examples.

Reference Example

<Collection of Samples>

Sera were collected using VENOJECT II vacuum blood collecting tube VP-AS109K60 (Terumo Corp. (Japan)) from total 10,869 people (Table 11a) including 4,660 healthy subjects, 327 benign bone and soft tissue tumor patients, 41 benign breast disease patients, 1,694 lung cancer patients, 1,417 stomach cancer patients, 595 esophagus cancer patients, 355 liver cancer patients, 862 pancreatic cancer patients, 406 biliary cancer patients, and 512 bladder cancer patients, after receiving their informed consents. The histological types of the lung cancer patients were adenocarcinoma in 1,308 people, squamous cell carcinoma in 243 people, large cell carcinoma in 23 people, small cell carcinoma in 25 people, adenosquamous carcinoma in 18 people, polymorphic cell cancer in 33 people, salivary gland-type cancer in 2 people, carcinoid tumor in 13 people, preinvasive lesion in 1 person, and other lung cancers in 28 people. Also, the stages of the lung cancer patients were stage IA in 1,068 people, stage IB in 337 people, stage IIA in 97 people, stage IIB in 89 people, stage IIIA in 46 people, stage IIIB in 29 people, stage IV in 4 people, unknown stages in 24 people (Table 2).

<Extraction of Total RNA>

Total RNA was obtained using a reagent for "RNA extraction in 3D-Gene™ RNA extraction reagent from liquid sample kit" (Toray Industries, Inc. (Japan)) according to the protocol provided by the manufacturer, from 300 µL of the serum sample obtained from each of 10,869 people in total.

<Measurement of Gene Expression Level>

MicroRNA in the total RNA that was obtained from the serum samples of a total of 10,869 people was fluorescently labeled by use of 3D-Gene™ miRNA Labeling kit (Toray Industries, Inc.) according to the protocol provided by the manufacturer. The oligo DNA chip used was 3D-Gene™ Human miRNA Oligo chip (Toray Industries, Inc.) with attached probes having sequences complementary to 2,565 miRNAs among the miRNAs registered in miRBase Release 21. Hybridization under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value having a base of 2 and used as a gene expression level, from which a blank value was subtracted. A missing value was replaced with a signal value 0.1. As a result, the comprehensive gene expression levels of the miRNAs in the sera were obtained for the 10,869 people described above.

Subsequently, the samples were extracted for use in the discriminant analysis of lung cancer. In the description below, healthy subjects, benign bone and soft tissue tumor patients and benign breast disease patients, and patients having a cancer other than lung cancer will be collectively referred to as "test subjects without lung cancer". Also, stomach cancer, esophagus cancer, liver cancer, pancreatic cancer, biliary cancer and bladder cancer patients will be collectively referred to as "patients having a cancer other than lung cancer". Firstly, 1,694 lung cancer patients were used as a positive sample group. Secondly, 1,800 people from the healthy subjects described above, and a total of 1,800 people including 300 people having each cancer other than lung cancer were extracted at random, and combined with 368 benign bone and soft tissue tumor patients and benign breast disease patients to select a total of 3,968 people as a negative sample group (Table 11b). Thirdly, 70% of each sample group was used as a training cohort and the remaining 30% thereof as a validation cohort. Specifically, the training cohort consisted of 1,233 healthy subjects, 263 benign bone and soft tissue tumor patients and benign breast disease patients, 1,186 lung cancer patients and 1,281 patients having a cancer other than lung cancer; while the validation cohort consisted of 567 healthy subjects, 105 benign bone and soft tissue tumor patients and benign breast disease patients, 508 lung cancer patients and 519 patients having a cancer other than lung cancer. Calculation and statistical analysis using the digitized gene expression levels of the miRNAs were carried out using R language 3.3.1 (R Core Team (2016). R: A language and environment for statistical computing. R Foundation for Statistical Computing, Vienna, Austria. URL https://www.R-project.org/.) and MASS package 7.3.45 (Venables, W. N. & Ripley, B. D. (2002) Modern Applied Statistics with S. Fourth Edition. Springer, New York. ISBN 0-387-95457-0).

TABLE 2

|  |  | Stage | | | | | | | | |
| --- | --- | --- | --- | --- | --- | --- | --- | --- | --- | --- |
|  |  | IA | IB | IIA | IIB | IIIA | IIIB | IV | Unknown | Total |
| Histological type | Adenocarcinoma | 917 | 250 | 57 | 36 | 19 | 20 | 2 | 7 | 1308 |
|  | Squamous cell carcinoma | 95 | 54 | 30 | 39 | 18 | 6 | 0 | 1 | 243 |
|  | Large cell carcinoma | 11 | 5 | 2 | 2 | 2 | 0 | 0 | 1 | 23 |
|  | Small cell carcinoma | 7 | 2 | 1 | 0 | 0 | 0 | 0 | 1 | 11 |
|  | Combined small cell carcinoma | 8 | 3 | 2 | 0 | 0 | 0 | 1 | 0 | 14 |
|  | Adenosquamous carcinoma | 10 | 5 | 0 | 3 | 0 | 0 | 0 | 0 | 18 |
|  | Polymorphic cell cancer | 6 | 11 | 4 | 6 | 4 | 0 | 1 | 1 | 33 |
|  | Salivary gland-type cancer | 0 | 0 | 0 | 0 | 0 | 1 | 0 | 1 | 2 |
|  | Carcinoid tumor | 3 | 1 | 0 | 0 | 1 | 0 | 0 | 8 | 13 |
|  | Preinvasive lesion | 1 | 0 | 0 | 0 | 0 | 0 | 0 | 0 | 1 |
|  | Others | 10 | 6 | 1 | 3 | 2 | 2 | 0 | 4 | 28 |
|  | Total | 1068 | 337 | 97 | 89 | 46 | 29 | 4 | 24 | 1694 |

TABLE 11

| Subject | a. All samples | b. All samples used in discriminant analysis | b1. Training cohort used in discriminant analysis | b2. Validation cohort used in discriminant analysis |
| --- | --- | --- | --- | --- |
| Healthy | 4660 | 1800 | 1233 | 567 |
| Benign bone and soft tissue tumor | 327 | 368 | 263 | 105 |
| Benign breast disease | 41 |  |  |  |
| Lung cancer | 1694 | 1694 | 1186 | 508 |
| Stomach cancer | 1417 | 1800 | 1281 | 519 |
| Esophagus cancer | 595 |  |  |  |
| Liver cancer | 355 |  |  |  |
| Pancreatic cancer | 862 |  |  |  |
| Biliary cancer | 406 |  |  |  |
| Bladder cancer | 512 |  |  |  |

Example 1

<Discriminant Analysis Using Up to Two miRNAs in Combination>

In this Example, a discriminant(s) was prepared using one or two gene markers in the training cohort including the lung cancer patients and the test subjects without lung cancer (Table 11 b1), and then, the discriminant performance was evaluated in the validation cohort (Table 11b2). Based on the evaluation, gene(s) used in discriminant(s) with high performance were extracted to obtain gene marker(s) that was able to detect lung cancer.

To be more specific, firstly the miRNA expression levels of the training cohort and the validation cohort obtained in the preceding Reference Examples were combined and normalized by global normalization. Secondly, in order to acquire diagnostic markers with higher reliability, only 396 genes having the expression level of $2^6$ or higher in 50% or more of the samples in either of the group of the lung cancer patients or the group of the test subjects without lung cancer were selected as analytes.

Thirdly, one and two in combination of the 396 gene expression level measurement values described above were subjected to the Fisher's discriminant analysis to construct discriminants to discriminate the presence or absence of lung cancer. Accuracy, sensitivity, and specificity in the validation cohort were further calculated using the discriminants prepared above and the discriminant performance was validated using the independent samples. As a result, 645 discriminants with 80% or more discrimination accuracy in the validation cohort were obtained. Among these discriminants, for the discriminants that used a combination of two gene expression levels, only those whose discrimination accuracy is better than the discriminant that used any single one of the gene expression levels were selected, which led to 490 discriminants with 80% or more discrimination accuracy. The 281 genes used in these discriminants were selected as diagnostic markers for the lung cancer patients and the test subjects without lung cancer. In this way, miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-2467-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4730, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, and miR-940, and the relevant polynucleotides consisting of nucleotide sequences of SEQ ID NOs: 1 to 138 and 164 to 306, were found. Among them, the genes newly found as the markers for examining the presence or absence of lung cancer are polynucleotides consisting of the nucleotide sequences represented by SEQ ID NOs: 1 to 138.

The sensitivities in the validation cohort determined by the discriminants obtained using any single one of the polynucleotides consisting of the nucleotide sequences represented by SEQ ID NOs: 188, 164, 85, 13, 175, 137, 231, 195, 263, 165, 226, 94, 45, 190, 274, 80, 220, 198, 98, 43, 2, 115, 299, 50, 196, 31, 182, 72, 96, 70, 40, 127, 183, 68, 3, 60, 66, 25, 75, 12, 255, 7, 1, 291, 87, 199, 120, 222, 278, 260, 246, 197, 103, 22, 106, 57, 29, 184, 206, 135, 179, 287, 56, 207, 261, 201, 217, 172, 300, 102, 285, 20, 21, 73, 78, 15, 30, 134, 76, 107, 97, 23, 33, 215, 122, 38, 54, 225, 26, 298, 114, 185, 128, 109, 104, 277, 303, 181, 59, 209, 236, 214, 51, 99, 105, 294, 58, 272, 101, 42, 180, 170, 47, 44, 16, 124, 241, 46, 130, 79, 247, 262, 95, 267, 69, 259, 118, 234, 138, 286, 110, 173, 200, 257, 167, 8, 111, 27, 64, 304, 177, 74, 34, 17, 36, 171, 251, 211, 193, and 256 among the polynucleotides described above, are shown in Table 3. Also, discriminant coefficients and constant terms are shown in Table 4. In this context, the general sensitivity of the existing marker CEA has been reported as being 69%. Accordingly, it was demonstrated that the polynucleotides represented by these SEQ ID NOs singly detect lung cancer with sensitivity beyond CEA.

Discriminants that were all able to discriminate lung cancer with 80% or more accuracy were also able to be prepared by combining each of the expression levels of the 281 genes represented by the nucleotide sequences of SEQ ID NOs: 1 to 138 and 164 to 306 with another gene expression level (Table 5). In this respect, discriminant coefficients and constant terms are shown in Table 6. The performance of all the discriminants using these combinations exceeded the discriminant performance of the existing marker CEA. Note that, in the tables, in the column of "SEQ ID NO or Gene", the combinations of multiple polynucleotides used are described by SEQ ID NOs. (the same applies to tables described later).

From the above, it was demonstrated that all polynucleotides consisting of the nucleotide sequences represented by SEQ ID NOs: 1 to 138 and 164 to 306 are genes capable of discriminating a lung cancer patient from a test subject without lung cancer with high accuracy if these are used alone or in combination of two or more.

TABLE 3

| SEQ ID NO: | Training cohort | | | Validation cohort | | |
|---|---|---|---|---|---|---|
| | Accuracy | Sensitivity | Specificity | Accuracy | Sensitivity | Specificity |
| 188 | 71.9 | 98.1 | 60.8 | 72.7 | 97.0 | 62.3 |
| 164 | 83.4 | 97.0 | 77.7 | 83.8 | 95.9 | 78.6 |
| 85 | 73.2 | 95.3 | 63.8 | 74.0 | 94.3 | 65.4 |
| 13 | 73.4 | 93.4 | 64.9 | 73.0 | 91.7 | 65.1 |
| 175 | 71.3 | 91.4 | 62.7 | 71.5 | 91.5 | 62.9 |
| 137 | 74.9 | 93.9 | 66.8 | 74.4 | 91.1 | 67.3 |
| 231 | 74.4 | 91.8 | 66.9 | 75.8 | 90.2 | 69.6 |
| 319 | 72.2 | 92.6 | 63.5 | 72.7 | 90.2 | 65.2 |
| 195 | 71.1 | 92.2 | 62.0 | 71.9 | 90.2 | 64.1 |
| 263 | 71.5 | 91.0 | 63.2 | 73.0 | 90.0 | 65.7 |
| 165 | 78.4 | 89.7 | 73.6 | 79.7 | 89.8 | 75.4 |
| 226 | 72.0 | 89.5 | 64.5 | 74.5 | 89.6 | 68.0 |
| 94 | 77.3 | 87.6 | 72.9 | 77.3 | 88.8 | 72.5 |
| 45 | 73.3 | 88.9 | 66.6 | 75.0 | 88.8 | 69.1 |
| 190 | 68.7 | 89.0 | 60.0 | 70.3 | 88.4 | 62.6 |
| 274 | 74.2 | 85.7 | 69.2 | 75.0 | 88.2 | 69.4 |
| 328 | 72.1 | 89.4 | 64.7 | 74.4 | 87.2 | 68.9 |
| 80 | 68.9 | 86.8 | 61.2 | 70.6 | 87.0 | 63.6 |
| 220 | 74.1 | 87.9 | 68.2 | 75.5 | 86.8 | 70.7 |
| 198 | 73.1 | 87.5 | 67.0 | 73.7 | 86.6 | 68.2 |
| 98 | 76.2 | 86.6 | 71.7 | 77.6 | 86.4 | 73.8 |
| 43 | 72.0 | 84.2 | 66.7 | 73.7 | 86.4 | 68.3 |
| 316 | 69.2 | 86.0 | 62.1 | 71.5 | 86.4 | 65.2 |
| 2 | 79.7 | 87.4 | 76.4 | 78.3 | 86.2 | 75.0 |
| 115 | 73.4 | 88.0 | 67.2 | 74.5 | 86.0 | 69.5 |
| 299 | 71.7 | 88.0 | 64.7 | 73.2 | 85.8 | 67.8 |
| 50 | 70.4 | 87.4 | 63.2 | 70.9 | 85.8 | 64.6 |
| 150 | 71.6 | 88.5 | 64.4 | 71.0 | 85.6 | 64.8 |
| 196 | 73.0 | 86.9 | 67.1 | 72.8 | 85.2 | 67.5 |
| 31 | 64.1 | 83.6 | 55.7 | 67.3 | 85.2 | 59.7 |
| 182 | 70.0 | 86.0 | 63.2 | 71.8 | 85.0 | 66.2 |
| 72 | 74.0 | 87.0 | 68.5 | 75.5 | 84.8 | 71.5 |
| 318 | 67.8 | 84.7 | 60.5 | 69.3 | 84.8 | 62.6 |
| 149 | 75.5 | 85.8 | 71.2 | 75.0 | 84.6 | 70.9 |
| 312 | 73.1 | 87.4 | 67.0 | 73.8 | 84.6 | 69.2 |
| 96 | 71.4 | 84.3 | 65.9 | 72.7 | 84.3 | 67.8 |
| 329 | 73.7 | 84.1 | 69.3 | 74.7 | 84.1 | 70.7 |
| 70 | 71.4 | 86.5 | 64.9 | 72.1 | 84.1 | 67.0 |
| 40 | 76.4 | 88.7 | 71.2 | 76.4 | 83.7 | 73.3 |
| 127 | 68.7 | 84.5 | 62.0 | 71.3 | 83.3 | 66.2 |
| 153 | 76.4 | 86.1 | 72.3 | 76.8 | 83.1 | 74.1 |
| 183 | 72.9 | 81.8 | 69.1 | 73.9 | 83.1 | 69.9 |
| 148 | 70.6 | 83.5 | 65.1 | 71.7 | 83.1 | 66.9 |
| 68 | 73.3 | 86.4 | 67.7 | 73.8 | 82.9 | 69.2 |
| 3 | 79.2 | 85.7 | 76.4 | 79.7 | 82.7 | 78.4 |
| 60 | 77.8 | 84.4 | 75.0 | 78.2 | 82.5 | 76.4 |
| 66 | 74.8 | 85.5 | 70.2 | 76.3 | 82.5 | 73.7 |
| 25 | 66.3 | 81.6 | 59.8 | 68.6 | 82.5 | 62.6 |
| 75 | 70.7 | 83.8 | 65.1 | 71.8 | 82.3 | 67.3 |
| 12 | 69.2 | 84.7 | 62.6 | 70.5 | 82.3 | 65.4 |
| 255 | 68.9 | 86.3 | 61.5 | 69.6 | 82.3 | 64.2 |
| 7 | 75.4 | 81.6 | 72.8 | 76.7 | 82.1 | 74.4 |
| 1 | 79.4 | 84.7 | 77.1 | 79.4 | 81.9 | 78.3 |
| 291 | 73.3 | 81.6 | 69.7 | 73.9 | 81.9 | 70.4 |
| 162 | 64.6 | 81.5 | 57.4 | 66.3 | 81.9 | 59.6 |
| 163 | 75.3 | 83.0 | 72.1 | 74.7 | 81.7 | 71.8 |
| 87 | 72.6 | 84.2 | 67.6 | 73.3 | 81.7 | 69.7 |

TABLE 3-continued

| SEQ ID NO: | Training cohort | | | Validation cohort | | |
|---|---|---|---|---|---|---|
| | Accuracy | Sensitivity | Specificity | Accuracy | Sensitivity | Specificity |
| 199 | 68.4 | 81.3 | 62.9 | 70.9 | 81.7 | 66.2 |
| 120 | 73.7 | 80.9 | 70.6 | 73.3 | 81.5 | 69.9 |
| 222 | 70.2 | 77.2 | 67.3 | 71.3 | 81.5 | 67.0 |
| 311 | 74.5 | 82.6 | 71.0 | 75.2 | 81.3 | 72.5 |
| 278 | 64.5 | 83.7 | 56.4 | 65.7 | 81.3 | 59.1 |
| 260 | 76.7 | 84.3 | 73.4 | 76.5 | 81.1 | 74.6 |
| 246 | 71.6 | 85.2 | 65.8 | 72.1 | 81.1 | 68.3 |
| 197 | 73.7 | 84.1 | 69.3 | 73.9 | 80.9 | 70.9 |
| 103 | 68.4 | 80.9 | 63.1 | 70.1 | 80.9 | 65.5 |
| 22 | 70.3 | 82.6 | 65.1 | 71.4 | 80.7 | 67.4 |
| 106 | 70.9 | 83.2 | 65.7 | 71.6 | 80.5 | 67.8 |
| 322 | 69.4 | 81.3 | 64.3 | 71.5 | 80.5 | 67.7 |
| 57 | 69.1 | 83.5 | 63.0 | 70.9 | 80.5 | 66.8 |
| 309 | 68.2 | 80.9 | 62.7 | 69.6 | 80.5 | 64.9 |
| 29 | 78.1 | 82.6 | 76.2 | 78.2 | 80.1 | 77.4 |
| 184 | 71.5 | 78.2 | 68.8 | 72.2 | 80.1 | 68.8 |
| 206 | 63.7 | 81.3 | 56.2 | 65.0 | 80.1 | 58.5 |
| 135 | 78.9 | 83.3 | 77.0 | 77.9 | 79.9 | 77.1 |
| 179 | 73.5 | 81.5 | 70.0 | 75.0 | 79.9 | 72.9 |
| 287 | 75.9 | 82.5 | 73.1 | 77.1 | 79.5 | 76.1 |
| 56 | 71.9 | 79.9 | 68.5 | 73.9 | 79.5 | 71.5 |
| 207 | 67.0 | 81.8 | 60.7 | 68.9 | 79.5 | 64.3 |
| 261 | 64.4 | 78.8 | 58.3 | 66.2 | 79.5 | 60.5 |
| 201 | 71.8 | 80.4 | 68.1 | 71.6 | 79.1 | 68.3 |
| 217 | 74.7 | 80.6 | 72.2 | 76.3 | 78.9 | 75.1 |
| 317 | 71.9 | 79.0 | 68.9 | 72.7 | 78.9 | 70.0 |
| 172 | 69.4 | 78.4 | 65.6 | 71.3 | 78.9 | 68.1 |
| 300 | 69.6 | 82.7 | 64.1 | 70.7 | 78.7 | 67.3 |
| 102 | 77.1 | 78.6 | 76.5 | 76.0 | 78.5 | 75.0 |
| 285 | 69.5 | 81.0 | 64.6 | 69.9 | 78.5 | 66.2 |
| 20 | 73.8 | 80.1 | 71.2 | 74.3 | 78.3 | 72.5 |
| 159 | 70.9 | 80.7 | 66.8 | 70.6 | 78.3 | 67.3 |
| 21 | 68.4 | 80.2 | 63.4 | 70.5 | 78.1 | 67.2 |
| 73 | 61.6 | 79.0 | 54.2 | 64.0 | 78.1 | 57.9 |
| 78 | 70.5 | 80.9 | 66.1 | 70.9 | 78.0 | 67.8 |
| 15 | 68.6 | 76.5 | 65.2 | 70.5 | 78.0 | 67.3 |
| 30 | 70.3 | 79.8 | 66.3 | 71.3 | 77.8 | 68.5 |
| 134 | 70.6 | 78.7 | 67.2 | 72.9 | 77.6 | 70.9 |
| 315 | 67.4 | 73.5 | 64.8 | 70.6 | 77.6 | 67.6 |
| 76 | 66.5 | 76.5 | 62.2 | 67.3 | 77.6 | 63.0 |
| 107 | 71.3 | 80.2 | 67.5 | 72.5 | 77.2 | 70.4 |
| 97 | 61.8 | 75.8 | 55.8 | 63.0 | 77.0 | 57.0 |
| 23 | 74.8 | 81.2 | 72.0 | 74.7 | 76.8 | 73.9 |
| 33 | 71.7 | 78.5 | 68.7 | 72.0 | 76.4 | 70.2 |
| 307 | 67.9 | 76.0 | 64.4 | 69.7 | 76.2 | 67.0 |
| 215 | 63.0 | 78.6 | 56.4 | 64.4 | 76.2 | 59.4 |
| 122 | 71.9 | 79.0 | 68.8 | 71.3 | 76.0 | 69.4 |
| 38 | 66.4 | 77.9 | 61.5 | 68.1 | 76.0 | 64.7 |
| 54 | 71.4 | 78.5 | 68.3 | 70.8 | 75.8 | 68.7 |
| 225 | 71.0 | 78.1 | 68.0 | 70.6 | 75.6 | 68.5 |
| 26 | 65.7 | 76.6 | 61.0 | 65.8 | 75.6 | 61.6 |
| 298 | 66.3 | 76.8 | 61.8 | 66.5 | 75.4 | 62.6 |
| 114 | 64.7 | 74.2 | 60.6 | 66.3 | 75.4 | 62.4 |
| 185 | 69.0 | 76.4 | 65.8 | 70.6 | 75.2 | 68.6 |
| 128 | 68.6 | 77.7 | 64.7 | 69.6 | 75.2 | 67.2 |
| 109 | 68.2 | 75.0 | 65.3 | 69.4 | 75.2 | 66.9 |
| 104 | 67.4 | 71.8 | 65.6 | 66.0 | 75.2 | 62.1 |
| 277 | 65.8 | 74.5 | 62.2 | 64.6 | 75.2 | 60.0 |
| 327 | 65.0 | 76.4 | 60.1 | 64.6 | 75.2 | 60.0 |
| 303 | 68.3 | 76.1 | 65.0 | 68.9 | 75.0 | 66.3 |
| 181 | 69.1 | 76.3 | 66.0 | 69.8 | 74.8 | 67.7 |
| 59 | 66.8 | 74.9 | 63.4 | 67.7 | 74.8 | 64.7 |
| 209 | 63.2 | 73.2 | 58.9 | 65.3 | 74.8 | 61.2 |
| 236 | 61.7 | 76.1 | 55.6 | 63.2 | 74.8 | 58.3 |
| 214 | 66.6 | 74.7 | 63.2 | 67.9 | 74.4 | 65.1 |
| 51 | 65.1 | 76.6 | 60.1 | 65.0 | 74.2 | 61.0 |
| 140 | 65.9 | 75.5 | 61.8 | 64.7 | 74.2 | 60.7 |
| 99 | 69.2 | 75.5 | 66.5 | 69.1 | 74.0 | 67.0 |
| 105 | 66.8 | 75.6 | 63.0 | 67.3 | 74.0 | 64.4 |
| 294 | 63.2 | 74.6 | 58.4 | 64.4 | 74.0 | 60.4 |
| 58 | 59.4 | 75.0 | 52.8 | 59.7 | 73.8 | 53.7 |
| 143 | 70.1 | 75.9 | 67.6 | 71.2 | 73.6 | 70.2 |
| 272 | 65.6 | 78.1 | 60.2 | 65.8 | 73.6 | 62.5 |
| 101 | 65.1 | 74.5 | 61.1 | 65.7 | 73.4 | 62.4 |
| 144 | 68.3 | 75.4 | 65.3 | 68.2 | 73.0 | 66.1 |
| 42 | 68.3 | 77.5 | 64.4 | 67.6 | 73.0 | 65.3 |
| 180 | 68.3 | 76.6 | 64.8 | 67.7 | 72.8 | 65.5 |
| 170 | 72.0 | 74.7 | 70.9 | 72.7 | 72.6 | 72.7 |
| 47 | 68.5 | 71.0 | 67.4 | 69.7 | 72.6 | 68.4 |
| 44 | 68.7 | 77.6 | 64.9 | 68.5 | 72.6 | 66.8 |
| 16 | 65.2 | 71.8 | 62.4 | 67.8 | 72.4 | 65.8 |
| 124 | 65.1 | 74.7 | 61.0 | 66.5 | 72.4 | 63.9 |
| 241 | 64.8 | 72.1 | 61.7 | 66.0 | 72.4 | 63.3 |
| 46 | 68.2 | 73.0 | 66.2 | 67.4 | 72.2 | 65.3 |
| 321 | 65.7 | 75.6 | 61.4 | 66.5 | 72.2 | 64.1 |
| 130 | 69.1 | 72.4 | 67.7 | 69.9 | 72.0 | 68.9 |
| 79 | 64.3 | 71.8 | 61.1 | 66.3 | 72.0 | 63.8 |
| 247 | 62.1 | 71.2 | 58.2 | 64.4 | 72.0 | 61.2 |
| 262 | 65.3 | 70.0 | 63.2 | 68.0 | 71.7 | 66.4 |
| 95 | 66.6 | 72.4 | 64.1 | 67.0 | 71.7 | 65.0 |
| 142 | 65.5 | 71.2 | 63.0 | 65.0 | 71.7 | 62.1 |
| 267 | 64.0 | 73.4 | 60.0 | 64.3 | 71.7 | 61.2 |
| 69 | 67.8 | 71.4 | 66.2 | 68.9 | 71.5 | 67.8 |
| 259 | 62.7 | 69.6 | 59.8 | 65.5 | 71.5 | 63.0 |
| 118 | 65.4 | 72.6 | 62.3 | 67.2 | 71.3 | 65.4 |
| 234 | 65.5 | 71.1 | 63.1 | 65.0 | 71.3 | 62.3 |
| 138 | 65.3 | 71.8 | 62.5 | 64.0 | 71.3 | 60.9 |
| 286 | 69.0 | 68.8 | 69.1 | 69.7 | 71.1 | 69.1 |
| 110 | 67.2 | 68.0 | 66.9 | 69.1 | 71.1 | 68.3 |
| 173 | 70.2 | 78.0 | 66.9 | 68.6 | 71.1 | 67.6 |
| 320 | 65.1 | 69.9 | 63.1 | 65.9 | 71.1 | 63.6 |
| 200 | 64.6 | 72.3 | 61.3 | 64.9 | 71.1 | 62.2 |
| 257 | 67.4 | 69.6 | 66.5 | 69.6 | 70.9 | 69.1 |
| 167 | 67.1 | 72.7 | 64.7 | 66.9 | 70.9 | 65.2 |
| 314 | 68.0 | 74.3 | 65.3 | 65.4 | 70.9 | 63.1 |
| 8 | 62.7 | 76.5 | 56.8 | 60.0 | 70.9 | 55.3 |
| 111 | 78.3 | 74.3 | 80.0 | 76.2 | 70.7 | 78.5 |
| 27 | 68.2 | 72.8 | 66.2 | 69.2 | 70.5 | 68.7 |
| 64 | 68.0 | 75.0 | 65.0 | 68.5 | 70.1 | 67.8 |
| 304 | 64.1 | 69.5 | 61.9 | 65.1 | 70.1 | 63.0 |
| 177 | 59.3 | 67.5 | 55.9 | 63.5 | 70.1 | 60.7 |
| 74 | 68.2 | 67.5 | 68.6 | 70.9 | 69.7 | 71.4 |
| 34 | 66.3 | 69.8 | 64.8 | 66.9 | 69.7 | 65.7 |
| 17 | 66.3 | 72.9 | 63.4 | 65.1 | 69.7 | 63.1 |
| 36 | 64.3 | 73.6 | 60.4 | 64.4 | 69.7 | 62.1 |
| 171 | 72.0 | 73.4 | 71.3 | 72.3 | 69.5 | 73.6 |
| 251 | 62.8 | 70.9 | 59.3 | 64.0 | 69.5 | 61.7 |
| 211 | 65.2 | 71.9 | 62.3 | 65.5 | 69.3 | 63.9 |
| 193 | 69.5 | 71.7 | 68.6 | 69.7 | 69.1 | 69.9 |
| 256 | 62.4 | 69.0 | 59.6 | 65.2 | 69.1 | 63.6 |

TABLE 4

| SEQ ID NO: | Coefficient | Constant term |
|---|---|---|
| 188 | 0.46 | −3.96 |
| 164 | 1.52 | −12.87 |
| 85 | 0.76 | −9.89 |
| 13 | 0.44 | −3.44 |
| 175 | −2.56 | 28.63 |
| 137 | 1.19 | −9.35 |
| 231 | 0.52 | −3.92 |
| 319 | 0.50 | −5.37 |
| 195 | 0.52 | −2.98 |
| 263 | 0.74 | −5.56 |
| 165 | 1.72 | −13.28 |
| 226 | 0.90 | −9.97 |
| 94 | 1.04 | −6.31 |
| 45 | 1.09 | −7.88 |
| 190 | 0.52 | −2.78 |
| 274 | −3.35 | 34.66 |
| 328 | 0.90 | −8.02 |
| 80 | 1.00 | −7.29 |
| 220 | 1.16 | −8.43 |
| 198 | 0.71 | −4.51 |
| 98 | 0.90 | −4.61 |
| 43 | 1.05 | −7.31 |

TABLE 4-continued

| SEQ ID NO: | Coefficient | Constant term |
|---|---|---|
| 316 | 1.29 | −8.88 |
| 2 | 1.01 | −6.10 |
| 115 | 2.20 | −20.21 |
| 299 | 1.00 | −9.37 |
| 50 | 0.47 | −2.72 |
| 150 | 0.56 | −3.02 |
| 196 | 0.56 | −3.19 |
| 31 | 0.53 | −3.07 |
| 182 | 1.11 | −10.40 |
| 72 | 0.75 | −4.45 |
| 318 | 0.74 | −5.73 |
| 149 | 0.81 | −5.37 |
| 312 | 0.61 | −2.91 |
| 96 | 0.70 | −3.37 |
| 329 | 0.81 | −5.51 |
| 70 | 0.53 | −4.19 |
| 40 | 0.86 | −4.96 |
| 127 | 1.53 | −12.09 |
| 153 | 0.76 | −4.05 |
| 183 | −3.32 | 35.60 |
| 148 | 1.25 | −8.23 |
| 68 | 0.68 | −5.43 |
| 3 | 1.39 | −9.03 |
| 60 | 0.86 | −4.09 |
| 66 | 1.97 | −16.60 |
| 25 | 0.56 | −3.00 |
| 75 | 0.61 | −3.65 |
| 12 | 0.98 | −7.25 |
| 255 | 0.72 | −7.17 |
| 7 | 2.37 | −19.98 |
| 1 | 2.02 | −19.02 |
| 291 | 1.25 | −8.99 |
| 162 | 0.63 | −3.74 |
| 163 | 0.81 | −4.70 |
| 87 | 0.73 | −3.97 |
| 199 | 0.90 | −6.60 |
| 120 | 1.00 | −6.11 |
| 222 | 3.07 | −26.17 |
| 311 | 0.59 | −3.50 |
| 278 | −1.45 | 16.91 |
| 260 | 0.90 | −4.36 |
| 246 | 1.85 | −16.38 |
| 197 | 0.57 | −3.42 |
| 103 | 2.01 | −17.60 |
| 22 | 0.53 | −4.56 |
| 106 | 1.05 | −6.86 |
| 322 | 0.95 | −7.58 |
| 57 | 0.56 | −3.59 |
| 309 | 0.71 | −5.45 |
| 29 | 1.18 | −6.74 |
| 184 | −3.26 | 31.56 |
| 206 | 0.66 | −4.32 |
| 135 | 0.89 | −4.22 |
| 179 | 1.56 | −11.11 |
| 287 | 1.88 | −15.11 |
| 56 | 1.31 | −8.81 |
| 207 | 0.63 | −3.95 |
| 261 | 1.04 | −12.53 |
| 201 | 1.27 | −10.31 |
| 217 | 1.58 | −12.07 |
| 317 | 2.32 | −21.17 |
| 172 | 0.85 | −5.07 |
| 300 | 0.91 | −9.12 |
| 102 | 1.40 | −9.99 |
| 285 | 0.94 | −5.62 |
| 20 | 1.03 | −6.33 |
| 159 | 1.19 | −7.36 |
| 21 | 1.16 | −8.70 |
| 73 | −0.53 | 4.41 |
| 78 | 0.48 | −2.44 |
| 15 | 0.87 | −5.39 |
| 30 | 0.43 | −3.27 |
| 134 | 1.00 | −6.04 |
| 315 | 0.74 | −9.76 |
| 76 | 0.75 | −4.45 |
| 107 | 1.18 | −8.80 |
| 97 | 0.57 | −3.71 |
| 23 | 0.91 | −4.91 |
| 33 | 0.86 | −4.72 |
| 307 | 1.66 | −11.62 |
| 215 | −1.63 | 18.47 |
| 122 | 0.80 | −4.37 |
| 38 | 0.83 | −5.46 |
| 54 | 0.67 | −3.37 |
| 225 | 0.63 | −5.27 |
| 26 | 0.52 | −3.11 |
| 298 | 0.87 | −6.15 |
| 114 | 0.64 | −3.71 |
| 185 | 0.81 | −6.70 |
| 128 | 1.01 | −6.33 |
| 109 | −2.71 | 33.33 |
| 104 | 1.28 | −10.29 |
| 277 | 0.63 | −3.80 |
| 327 | 0.52 | −3.47 |
| 303 | 0.78 | −4.47 |
| 181 | 0.87 | −5.65 |
| 59 | 0.67 | −3.76 |
| 209 | 1.09 | −14.30 |
| 236 | 0.88 | −7.04 |
| 214 | 1.28 | −9.55 |
| 51 | 0.64 | −3.99 |
| 140 | 0.81 | −5.16 |
| 99 | 0.73 | −3.95 |
| 105 | 0.77 | −4.44 |
| 294 | 0.62 | −3.83 |
| 58 | −1.09 | 10.55 |
| 143 | 0.62 | −3.40 |
| 272 | 0.96 | −7.96 |
| 101 | 0.93 | −5.82 |
| 144 | 0.67 | −3.81 |
| 42 | −1.55 | 15.71 |
| 180 | 1.31 | −9.04 |
| 170 | 0.57 | −2.49 |
| 47 | 1.03 | −7.03 |
| 44 | 0.64 | −3.54 |
| 16 | 1.18 | −13.90 |
| 124 | 0.97 | −7.04 |
| 241 | −2.20 | 24.78 |
| 46 | 1.29 | −9.94 |
| 321 | 1.00 | −7.64 |
| 130 | 1.67 | −13.02 |
| 79 | 0.65 | −3.61 |
| 247 | 0.69 | −4.92 |
| 262 | 0.84 | −7.44 |
| 95 | 1.45 | −10.46 |
| 142 | 0.65 | −3.63 |
| 267 | 0.69 | −4.79 |
| 69 | 0.55 | −4.42 |
| 259 | 0.64 | −6.21 |
| 118 | −1.78 | 19.05 |
| 234 | 0.72 | −4.36 |
| 138 | 0.57 | −3.21 |
| 286 | −1.05 | 8.89 |
| 110 | 1.63 | −16.52 |
| 173 | 1.60 | −11.35 |
| 320 | 0.62 | −3.53 |
| 200 | 1.40 | −10.95 |
| 257 | 0.51 | −3.87 |
| 167 | 1.29 | −11.15 |
| 314 | 1.59 | −12.95 |
| 8 | 0.66 | −4.07 |
| 111 | 2.44 | −20.94 |
| 27 | 0.38 | −2.72 |
| 64 | 0.45 | −2.24 |
| 304 | −0.61 | 4.99 |
| 177 | 0.59 | −7.14 |
| 74 | 0.86 | −10.97 |
| 34 | 0.84 | −6.99 |
| 17 | 0.77 | −4.63 |
| 36 | 0.69 | −4.14 |
| 171 | 0.57 | −2.50 |
| 251 | 0.85 | −9.59 |
| 211 | 1.02 | −7.34 |
| 193 | 1.57 | −12.18 |
| 256 | 0.47 | −3.00 |

TABLE 5

| Gene | Training cohort Accuracy | Training cohort Sensitivity | Training cohort Specificity | Validation cohort Accuracy | Validation cohort Sensitivity | Validation cohort Specificity |
|---|---|---|---|---|---|---|
| 18_164 | 86.4 | 98.0 | 81.4 | 86.7 | 98.2 | 81.8 |
| 255_164 | 86.9 | 96.1 | 83.0 | 86.6 | 96.1 | 82.5 |
| 177_164 | 86.1 | 94.6 | 82.5 | 86.3 | 94.5 | 82.9 |
| 4_164 | 85.8 | 91.1 | 83.5 | 86.0 | 91.3 | 83.7 |
| 164_9 | 85.4 | 92.0 | 82.6 | 85.9 | 91.5 | 83.5 |
| 300_164 | 85.8 | 96.1 | 81.5 | 85.7 | 96.1 | 81.3 |
| 272_164 | 84.8 | 97.6 | 79.4 | 85.7 | 97.0 | 80.9 |
| 206_164 | 86.0 | 95.3 | 82.0 | 85.6 | 93.9 | 82.0 |
| 12_164 | 85.6 | 96.0 | 81.2 | 85.6 | 95.5 | 81.4 |
| 166_164 | 85.6 | 92.8 | 82.5 | 85.6 | 91.7 | 83.0 |
| 168_164 | 85.3 | 97.6 | 80.1 | 85.6 | 97.4 | 80.6 |
| 6_164 | 85.0 | 97.1 | 79.8 | 85.6 | 97.0 | 80.8 |
| 259_164 | 85.0 | 94.7 | 80.8 | 85.5 | 93.9 | 81.9 |
| 115_164 | 84.8 | 96.4 | 79.8 | 85.5 | 96.1 | 81.0 |
| 164_129 | 84.5 | 95.8 | 79.7 | 85.4 | 95.3 | 81.2 |
| 190_164 | 85.5 | 95.4 | 81.3 | 85.3 | 95.1 | 81.2 |
| 199_164 | 85.4 | 95.9 | 81.0 | 85.3 | 95.9 | 80.8 |
| 66_164 | 85.4 | 96.3 | 80.7 | 85.3 | 96.5 | 80.5 |
| 164_107 | 85.4 | 97.1 | 80.4 | 85.3 | 97.2 | 80.3 |
| 207_164 | 85.3 | 96.8 | 80.4 | 85.3 | 95.3 | 81.0 |
| 263_164 | 85.1 | 97.5 | 79.8 | 85.3 | 97.0 | 80.4 |
| 16_164 | 85.0 | 95.3 | 80.6 | 85.3 | 95.1 | 81.2 |
| 37_164 | 84.9 | 94.9 | 80.6 | 85.3 | 94.1 | 81.5 |
| 38_164 | 84.9 | 96.9 | 79.8 | 85.3 | 96.3 | 80.7 |
| 261_164 | 85.5 | 94.8 | 81.6 | 85.2 | 93.9 | 81.5 |
| 305_164 | 85.2 | 94.7 | 81.2 | 85.2 | 93.7 | 81.6 |
| 55_164 | 85.1 | 94.2 | 81.2 | 85.2 | 93.1 | 81.9 |
| 127_164 | 84.6 | 95.6 | 79.9 | 85.2 | 95.1 | 80.9 |
| 104_164 | 84.2 | 96.2 | 79.1 | 85.2 | 96.1 | 80.5 |
| 31_164 | 85.2 | 95.9 | 80.6 | 85.1 | 94.3 | 81.2 |
| 121_164 | 84.7 | 97.8 | 79.0 | 85.1 | 97.4 | 79.8 |
| 81_164 | 84.6 | 95.4 | 79.9 | 85.1 | 95.5 | 80.7 |
| 295_164 | 84.6 | 93.8 | 80.7 | 85.1 | 93.1 | 81.6 |
| 6_165 | 84.5 | 95.3 | 79.9 | 85.1 | 95.9 | 80.5 |
| 25_164 | 84.5 | 96.1 | 79.5 | 85.1 | 95.5 | 80.6 |
| 83_164 | 84.4 | 97.1 | 79.0 | 85.1 | 96.7 | 80.2 |
| 32_164 | 85.1 | 94.7 | 81.0 | 85.0 | 94.1 | 81.1 |
| 247_164 | 84.5 | 95.8 | 79.7 | 85.0 | 95.1 | 80.7 |
| 26_164 | 84.1 | 96.2 | 78.9 | 85.0 | 96.3 | 80.2 |
| 302_164 | 84.5 | 95.4 | 79.8 | 84.9 | 94.7 | 80.7 |
| 268_164 | 84.5 | 97.3 | 79.0 | 84.9 | 96.9 | 79.8 |
| 90_164 | 84.4 | 95.8 | 79.5 | 84.9 | 95.9 | 80.2 |
| 287_164 | 84.2 | 96.9 | 78.8 | 84.9 | 96.7 | 79.9 |
| 278_164 | 84.9 | 96.0 | 80.1 | 84.8 | 94.7 | 80.5 |
| 5_164 | 84.7 | 93.6 | 80.9 | 84.8 | 93.7 | 81.0 |
| 137_164 | 84.5 | 95.9 | 79.7 | 84.8 | 95.5 | 80.3 |
| 276_164 | 84.5 | 94.9 | 80.0 | 84.8 | 94.9 | 80.5 |
| 164_271 | 84.1 | 96.6 | 78.8 | 84.8 | 95.9 | 80.0 |
| 167_164 | 83.8 | 97.4 | 78.0 | 84.8 | 97.2 | 79.4 |
| 126_164 | 84.7 | 96.8 | 79.5 | 84.7 | 96.1 | 79.8 |
| 211_164 | 84.3 | 96.6 | 79.0 | 84.7 | 96.7 | 79.6 |
| 67_164 | 84.2 | 95.2 | 79.4 | 84.7 | 93.7 | 80.9 |
| 39_164 | 83.9 | 95.9 | 78.8 | 84.7 | 96.1 | 79.8 |
| 186_164 | 85.1 | 95.7 | 80.6 | 84.6 | 94.3 | 80.5 |
| 182_164 | 85.0 | 96.0 | 80.3 | 84.6 | 94.7 | 80.4 |
| 226_164 | 85.0 | 96.0 | 80.3 | 84.6 | 95.1 | 80.1 |
| 27_164 | 84.7 | 96.3 | 79.7 | 84.6 | 95.3 | 80.0 |
| 275_164 | 84.6 | 95.7 | 79.8 | 84.6 | 94.1 | 80.5 |
| 185_164 | 84.3 | 95.8 | 79.3 | 84.6 | 95.1 | 80.2 |
| 92_164 | 84.2 | 93.8 | 80.1 | 84.6 | 93.3 | 80.9 |
| 10_164 | 85.0 | 95.9 | 80.4 | 84.5 | 94.7 | 80.1 |
| 279_164 | 84.7 | 93.3 | 81.1 | 84.5 | 92.7 | 80.9 |
| 256_164 | 84.7 | 96.5 | 79.6 | 84.5 | 96.1 | 79.5 |
| 80_164 | 84.6 | 94.8 | 80.2 | 84.5 | 93.3 | 80.8 |
| 164_195 | 84.6 | 95.6 | 79.9 | 84.5 | 94.9 | 80.1 |
| 243_164 | 84.5 | 96.9 | 79.2 | 84.5 | 96.5 | 79.3 |
| 22_164 | 84.5 | 95.4 | 79.8 | 84.5 | 94.7 | 80.1 |
| 164_97 | 84.4 | 96.4 | 79.2 | 84.5 | 95.9 | 79.6 |
| 34_164 | 84.2 | 97.6 | 78.4 | 84.5 | 96.9 | 79.3 |
| 215_164 | 84.2 | 95.1 | 79.5 | 84.5 | 94.1 | 80.4 |
| 187_164 | 84.0 | 95.1 | 79.3 | 84.5 | 93.7 | 80.6 |
| 164_174 | 84.0 | 96.5 | 78.6 | 84.5 | 96.3 | 79.4 |
| 50_164 | 83.9 | 95.8 | 78.8 | 84.5 | 94.9 | 80.0 |
| 62_164 | 83.8 | 96.9 | 78.2 | 84.5 | 96.7 | 79.3 |
| 75_164 | 83.8 | 96.0 | 78.6 | 84.5 | 95.9 | 79.7 |
| 61_164 | 83.8 | 95.4 | 78.9 | 84.5 | 95.9 | 79.6 |
| 89_164 | 83.7 | 96.6 | 78.2 | 84.5 | 96.1 | 79.6 |
| 306_164 | 83.6 | 95.5 | 78.5 | 84.5 | 94.1 | 80.4 |
| 164_286 | 83.5 | 97.5 | 77.6 | 84.5 | 96.9 | 79.3 |
| 85_164 | 84.6 | 95.6 | 79.8 | 84.4 | 94.9 | 79.9 |
| 192_164 | 83.9 | 97.0 | 78.3 | 84.4 | 96.1 | 79.4 |
| 223_164 | 85.1 | 95.6 | 80.6 | 84.3 | 94.3 | 80.1 |
| 299_164 | 84.8 | 96.4 | 79.8 | 84.3 | 95.1 | 79.8 |
| 73_164 | 84.5 | 96.0 | 79.7 | 84.3 | 95.1 | 79.7 |
| 241_164 | 84.2 | 96.5 | 78.9 | 84.3 | 95.9 | 79.4 |
| 118_164 | 84.1 | 97.0 | 78.6 | 84.3 | 95.9 | 79.4 |
| 283_164 | 84.1 | 96.8 | 78.7 | 84.3 | 95.1 | 79.8 |
| 164_77 | 84.0 | 96.5 | 78.6 | 84.3 | 95.9 | 79.3 |
| 175_164 | 83.9 | 95.2 | 79.1 | 84.3 | 93.5 | 80.4 |
| 164_65 | 83.8 | 95.9 | 78.6 | 84.3 | 95.3 | 79.6 |
| 7_164 | 83.6 | 96.4 | 78.2 | 84.3 | 95.3 | 79.6 |
| 205_164 | 83.3 | 97.3 | 77.3 | 84.3 | 96.5 | 79.2 |
| 188_164 | 84.2 | 96.5 | 78.9 | 84.2 | 95.1 | 79.6 |
| 100_164 | 84.1 | 94.8 | 79.5 | 84.2 | 94.1 | 79.9 |
| 13_164 | 84.0 | 96.2 | 78.8 | 84.2 | 95.7 | 79.3 |
| 106_164 | 84.0 | 97.3 | 78.4 | 84.2 | 96.3 | 79.1 |
| 53_164 | 84.0 | 95.6 | 79.0 | 84.2 | 93.5 | 80.3 |
| 64_164 | 83.9 | 96.1 | 78.7 | 84.2 | 96.1 | 79.2 |
| 210_164 | 83.9 | 93.6 | 79.7 | 84.2 | 91.3 | 81.2 |
| 290_164 | 83.9 | 95.4 | 78.9 | 84.2 | 94.1 | 79.9 |
| 164_43 | 83.9 | 98.1 | 77.9 | 84.2 | 96.3 | 79.1 |
| 164_44 | 83.9 | 97.0 | 78.3 | 84.2 | 96.3 | 79.0 |
| 30_164 | 83.8 | 95.9 | 78.7 | 84.2 | 95.1 | 79.6 |
| 21_164 | 83.8 | 96.4 | 78.4 | 84.2 | 95.9 | 79.3 |
| 301_164 | 83.8 | 97.6 | 77.9 | 84.2 | 96.3 | 79.1 |
| 24_164 | 83.7 | 97.2 | 77.9 | 84.2 | 96.5 | 78.9 |
| 45_164 | 83.7 | 96.9 | 78.0 | 84.2 | 96.7 | 78.9 |
| 200_164 | 83.7 | 96.0 | 78.5 | 84.2 | 95.1 | 79.6 |
| 214_164 | 83.6 | 96.8 | 78.0 | 84.2 | 95.7 | 79.3 |
| 170_164 | 83.5 | 97.0 | 77.7 | 84.2 | 96.3 | 79.0 |
| 213_164 | 83.5 | 97.0 | 77.7 | 84.2 | 96.1 | 79.1 |
| 184_164 | 83.5 | 97.6 | 77.5 | 84.2 | 97.0 | 78.8 |
| 292_164 | 83.4 | 95.4 | 78.3 | 84.2 | 93.7 | 80.2 |
| 171_164 | 83.3 | 96.5 | 77.7 | 84.2 | 96.5 | 79.0 |
| 172_164 | 83.3 | 97.6 | 77.3 | 84.2 | 97.0 | 78.8 |
| 264_164 | 84.7 | 95.4 | 80.2 | 84.1 | 94.3 | 79.8 |
| 70_164 | 84.2 | 95.9 | 79.2 | 84.1 | 95.1 | 79.4 |
| 269_164 | 84.1 | 95.3 | 79.3 | 84.1 | 94.1 | 79.8 |
| 239_164 | 84.0 | 96.9 | 78.5 | 84.1 | 95.9 | 79.1 |
| 71_164 | 84.0 | 97.0 | 78.4 | 84.1 | 96.7 | 78.8 |
| 234_164 | 83.7 | 97.4 | 77.9 | 84.1 | 96.7 | 78.8 |
| 78_164 | 83.6 | 96.1 | 78.3 | 84.1 | 95.3 | 79.3 |
| 96_164 | 83.6 | 96.3 | 78.1 | 84.1 | 95.7 | 79.2 |
| 19_164 | 83.6 | 97.6 | 77.7 | 84.1 | 96.7 | 78.8 |
| 138_164 | 83.6 | 97.0 | 77.9 | 84.1 | 95.7 | 79.2 |
| 245_164 | 83.3 | 97.0 | 77.5 | 84.1 | 96.3 | 78.9 |
| 111_164 | 84.1 | 94.7 | 79.6 | 84.0 | 94.1 | 79.7 |
| 304_164 | 84.1 | 96.2 | 78.9 | 84.0 | 94.9 | 79.4 |
| 250_164 | 83.9 | 95.0 | 79.2 | 84.0 | 94.9 | 79.4 |
| 178_164 | 83.9 | 96.2 | 78.6 | 84.0 | 94.9 | 79.4 |
| 289_164 | 83.9 | 94.9 | 79.3 | 84.0 | 93.7 | 79.9 |
| 84_164 | 83.9 | 95.9 | 78.8 | 84.0 | 94.9 | 79.3 |
| 116_164 | 83.9 | 95.8 | 78.8 | 84.0 | 94.9 | 79.3 |
| 180_164 | 83.7 | 96.7 | 78.1 | 84.0 | 96.1 | 78.8 |
| 94_164 | 83.7 | 96.5 | 78.2 | 84.0 | 95.1 | 79.3 |
| 164_253 | 83.7 | 96.5 | 78.3 | 84.0 | 95.3 | 79.3 |
| 82_164 | 83.6 | 97.0 | 77.9 | 84.0 | 95.9 | 78.9 |
| 132_164 | 83.6 | 96.7 | 78.0 | 84.0 | 96.1 | 78.8 |
| 265_164 | 83.6 | 94.8 | 78.8 | 84.0 | 93.7 | 79.8 |
| 274_164 | 83.6 | 97.4 | 77.8 | 84.0 | 96.1 | 78.9 |
| 164_252 | 83.6 | 97.0 | 78.0 | 84.0 | 96.1 | 78.9 |
| 41_164 | 83.5 | 96.5 | 78.0 | 84.0 | 95.7 | 79.1 |
| 230_164 | 83.5 | 97.0 | 77.7 | 84.0 | 96.5 | 78.7 |
| 191_164 | 83.5 | 96.1 | 78.1 | 84.0 | 95.1 | 79.3 |
| 196_164 | 83.5 | 96.5 | 77.9 | 84.0 | 96.3 | 78.8 |
| 112_164 | 83.5 | 96.9 | 77.8 | 84.0 | 96.3 | 78.8 |
| 280_164 | 83.4 | 96.6 | 77.7 | 84.0 | 96.3 | 78.8 |
| 99_164 | 83.4 | 97.0 | 77.6 | 84.0 | 96.1 | 78.8 |
| 224_164 | 83.4 | 96.3 | 78.0 | 84.0 | 95.7 | 79.0 |
| 193_164 | 83.4 | 97.5 | 77.4 | 84.0 | 96.5 | 78.7 |

TABLE 5-continued

| Gene | Training cohort | | | Validation cohort | | |
|---|---|---|---|---|---|---|
| | Accuracy | Sensitivity | Specificity | Accuracy | Sensitivity | Specificity |
| 17_164 | 83.4 | 97.7 | 77.3 | 84.0 | 96.7 | 78.6 |
| 20_164 | 83.4 | 96.5 | 77.8 | 84.0 | 95.5 | 79.1 |
| 164_108 | 83.4 | 97.1 | 77.5 | 84.0 | 96.1 | 78.8 |
| 28_164 | 83.3 | 96.7 | 77.6 | 84.0 | 95.7 | 79.1 |
| 298_164 | 83.3 | 97.3 | 77.3 | 84.0 | 96.5 | 78.7 |
| 240_164 | 83.3 | 95.3 | 78.2 | 84.0 | 94.9 | 79.4 |
| 198_164 | 83.2 | 97.0 | 77.3 | 84.0 | 96.3 | 78.8 |
| 220_164 | 84.2 | 96.7 | 78.9 | 83.9 | 95.7 | 78.8 |
| 124_164 | 84.1 | 97.4 | 78.4 | 83.9 | 96.1 | 78.8 |
| 236_164 | 84.0 | 94.7 | 79.5 | 83.9 | 93.9 | 79.7 |
| 282_164 | 83.9 | 96.0 | 78.8 | 83.9 | 94.9 | 79.2 |
| 235_164 | 83.9 | 96.6 | 78.4 | 83.9 | 96.1 | 78.8 |
| 232_164 | 83.9 | 95.1 | 79.2 | 83.9 | 93.1 | 80.0 |
| 57_164 | 83.8 | 95.5 | 78.8 | 83.9 | 94.3 | 79.4 |
| 277_164 | 83.8 | 96.8 | 78.2 | 83.9 | 95.5 | 78.9 |
| 173_164 | 83.7 | 96.8 | 78.1 | 83.9 | 95.5 | 78.9 |
| 227_164 | 83.7 | 96.0 | 78.4 | 83.9 | 94.9 | 79.2 |
| 69_164 | 83.7 | 97.0 | 78.1 | 83.9 | 95.9 | 78.8 |
| 47_164 | 83.7 | 97.0 | 78.0 | 83.9 | 95.9 | 78.8 |
| 122_164 | 83.6 | 96.5 | 78.1 | 83.9 | 95.5 | 79.0 |
| 242_164 | 83.6 | 97.2 | 77.8 | 83.9 | 96.1 | 78.8 |
| 176_164 | 83.6 | 97.2 | 77.7 | 83.9 | 96.3 | 78.6 |
| 202_164 | 83.6 | 97.3 | 77.7 | 83.9 | 96.1 | 78.7 |
| 197_164 | 83.6 | 97.1 | 77.8 | 83.9 | 96.3 | 78.7 |
| 218_164 | 83.6 | 97.1 | 77.9 | 83.9 | 96.1 | 78.8 |
| 46_164 | 83.5 | 97.0 | 77.7 | 83.9 | 96.3 | 78.7 |
| 86_164 | 83.5 | 97.4 | 77.6 | 83.9 | 96.5 | 78.5 |
| 93_164 | 83.5 | 97.0 | 77.8 | 83.9 | 96.3 | 78.6 |
| 63_164 | 83.5 | 96.5 | 78.0 | 83.9 | 96.1 | 78.7 |
| 109_164 | 83.5 | 96.9 | 77.9 | 83.9 | 95.7 | 78.9 |
| 204_164 | 83.5 | 96.9 | 77.8 | 83.9 | 95.7 | 78.8 |
| 216_164 | 83.5 | 97.1 | 77.7 | 83.9 | 96.3 | 78.6 |
| 169_164 | 83.5 | 96.7 | 77.9 | 83.9 | 95.7 | 78.8 |
| 164_254 | 83.5 | 96.6 | 77.9 | 83.9 | 95.9 | 78.8 |
| 164_203 | 83.5 | 97.0 | 77.7 | 83.9 | 96.3 | 78.7 |
| 98_164 | 83.4 | 97.0 | 77.7 | 83.9 | 96.1 | 78.7 |
| 221_164 | 83.4 | 97.3 | 77.5 | 83.9 | 96.7 | 78.4 |
| 233_164 | 83.4 | 96.0 | 78.0 | 83.9 | 95.1 | 79.1 |
| 284_164 | 83.4 | 96.9 | 77.6 | 83.9 | 96.5 | 78.6 |
| 42_164 | 83.4 | 97.1 | 77.6 | 83.9 | 96.1 | 78.8 |
| 56_164 | 83.4 | 97.2 | 77.6 | 83.9 | 95.9 | 78.8 |
| 296_164 | 83.4 | 97.1 | 77.5 | 83.9 | 96.3 | 78.6 |
| 36_164 | 83.4 | 97.0 | 77.6 | 83.9 | 96.1 | 78.8 |
| 164_229 | 83.4 | 97.1 | 77.5 | 83.9 | 96.7 | 78.4 |
| 134_164 | 83.3 | 97.0 | 77.4 | 83.9 | 96.7 | 78.4 |
| 294_164 | 83.3 | 97.1 | 77.3 | 83.9 | 96.5 | 78.5 |
| 113_164 | 83.3 | 97.3 | 77.3 | 83.9 | 96.5 | 78.5 |
| 164_273 | 83.3 | 97.6 | 77.2 | 83.9 | 96.5 | 78.6 |
| 164_238 | 83.2 | 97.6 | 77.1 | 83.9 | 97.2 | 78.3 |
| 74_164 | 83.0 | 96.9 | 77.1 | 83.9 | 95.9 | 78.8 |
| 102_164 | 84.5 | 95.9 | 79.6 | 83.8 | 93.5 | 79.7 |
| 270_164 | 84.3 | 95.8 | 79.4 | 83.8 | 93.5 | 79.6 |
| 189_164 | 84.0 | 95.5 | 79.0 | 83.8 | 95.1 | 79.0 |
| 262_164 | 84.0 | 95.5 | 79.0 | 83.8 | 94.5 | 79.2 |
| 164_58 | 83.9 | 94.2 | 79.5 | 83.8 | 92.7 | 79.9 |
| 164_251 | 83.9 | 96.0 | 78.7 | 83.8 | 94.1 | 79.4 |
| 103_164 | 83.8 | 96.5 | 78.3 | 83.8 | 95.7 | 78.8 |
| 208_164 | 83.8 | 97.1 | 78.1 | 83.8 | 96.5 | 78.4 |
| 110_164 | 83.8 | 95.5 | 78.8 | 83.8 | 94.5 | 79.2 |
| 281_164 | 83.7 | 96.0 | 78.4 | 83.8 | 95.3 | 78.9 |
| 68_164 | 83.7 | 96.6 | 78.1 | 83.8 | 95.3 | 78.8 |
| 249_164 | 83.7 | 97.0 | 78.1 | 83.8 | 96.5 | 78.3 |
| 219_164 | 83.6 | 97.2 | 77.9 | 83.8 | 95.7 | 78.8 |
| 120_164 | 83.6 | 96.8 | 77.9 | 83.8 | 95.9 | 78.7 |
| 225_164 | 83.6 | 96.5 | 78.1 | 83.8 | 95.3 | 78.9 |
| 52_164 | 83.6 | 97.0 | 77.9 | 83.8 | 96.1 | 78.6 |
| 297_164 | 83.6 | 97.0 | 77.9 | 83.8 | 95.7 | 78.7 |
| 212_164 | 83.6 | 97.0 | 77.8 | 83.8 | 95.9 | 78.6 |
| 248_164 | 83.6 | 97.0 | 77.8 | 83.8 | 95.9 | 78.6 |
| 88_164 | 83.6 | 97.3 | 77.8 | 83.8 | 96.1 | 78.6 |
| 257_164 | 83.6 | 96.8 | 78.0 | 83.8 | 96.1 | 78.5 |
| 244_164 | 83.6 | 97.4 | 77.7 | 83.8 | 96.1 | 78.6 |
| 258_164 | 83.6 | 97.0 | 77.9 | 83.8 | 95.9 | 78.7 |
| 164_79 | 83.6 | 97.3 | 77.7 | 83.8 | 96.3 | 78.5 |
| 181_164 | 83.5 | 97.0 | 77.7 | 83.8 | 96.1 | 78.6 |
| 117_164 | 83.5 | 97.0 | 77.7 | 83.8 | 96.1 | 78.5 |
| 51_164 | 83.5 | 96.7 | 77.9 | 83.8 | 96.1 | 78.5 |
| 209_164 | 83.5 | 97.0 | 77.7 | 83.8 | 95.9 | 78.6 |
| 72_164 | 83.5 | 96.8 | 77.9 | 83.8 | 96.1 | 78.6 |
| 101_164 | 83.5 | 96.8 | 77.9 | 83.8 | 95.7 | 78.7 |
| 59_164 | 83.5 | 97.0 | 77.7 | 83.8 | 96.1 | 78.5 |
| 222_164 | 83.5 | 96.5 | 77.9 | 83.8 | 95.9 | 78.6 |
| 123_164 | 83.5 | 96.8 | 77.9 | 83.8 | 95.7 | 78.7 |
| 266_164 | 83.5 | 96.9 | 77.8 | 83.8 | 95.9 | 78.7 |
| 133_164 | 83.5 | 97.0 | 77.7 | 83.8 | 95.9 | 78.6 |
| 91_164 | 83.5 | 96.7 | 77.9 | 83.8 | 96.1 | 78.6 |
| 35_164 | 83.5 | 97.1 | 77.6 | 83.8 | 96.3 | 78.5 |
| 54_164 | 83.5 | 97.1 | 77.7 | 83.8 | 96.3 | 78.5 |
| 293_164 | 83.5 | 96.9 | 77.9 | 83.8 | 95.9 | 78.7 |
| 291_164 | 83.5 | 97.4 | 77.6 | 83.8 | 96.1 | 78.5 |
| 164_267 | 83.5 | 97.0 | 77.8 | 83.8 | 96.1 | 78.6 |
| 164_285 | 83.5 | 96.4 | 78.0 | 83.8 | 95.9 | 78.6 |
| 164 | 83.4 | 97.0 | 77.7 | 83.8 | 95.9 | 78.6 |
| 167_1 | 81.9 | 89.1 | 78.8 | 82.6 | 86.0 | 81.1 |
| 166_217 | 82.3 | 82.4 | 82.3 | 82.3 | 80.7 | 83.0 |
| 183_169 | 81.9 | 89.3 | 78.7 | 82.3 | 89.0 | 79.4 |
| 246_5 | 81.0 | 86.8 | 78.6 | 82.2 | 87.6 | 79.9 |
| 3_168 | 81.3 | 89.0 | 78.1 | 82.0 | 86.8 | 80.0 |
| 165_2 | 81.2 | 90.1 | 77.4 | 81.8 | 90.2 | 78.3 |
| 166_87 | 82.9 | 88.5 | 80.5 | 81.5 | 86.6 | 79.3 |
| 60_166 | 81.3 | 84.3 | 80.0 | 81.5 | 83.9 | 80.5 |
| 165_136 | 80.0 | 94.4 | 73.9 | 81.5 | 94.9 | 75.7 |
| 7_29 | 80.5 | 84.8 | 78.7 | 81.3 | 84.1 | 80.1 |
| 49_165 | 80.4 | 93.5 | 74.8 | 81.3 | 93.9 | 75.9 |
| 231_165 | 80.2 | 92.7 | 74.8 | 81.2 | 92.9 | 76.2 |
| 165_237 | 80.1 | 90.4 | 75.7 | 81.2 | 92.3 | 76.5 |
| 2_260 | 81.0 | 88.6 | 77.7 | 81.0 | 87.4 | 78.3 |
| 165_288 | 80.4 | 93.6 | 74.8 | 81.0 | 94.7 | 75.1 |
| 165_131 | 80.3 | 95.7 | 73.7 | 81.0 | 96.1 | 74.6 |
| 303_1 | 80.2 | 86.7 | 77.5 | 80.8 | 84.4 | 79.3 |
| 1_15 | 80.0 | 86.2 | 77.4 | 80.7 | 83.3 | 79.6 |
| 119_2 | 80.8 | 88.6 | 77.4 | 80.6 | 86.8 | 77.9 |
| 135_167 | 80.6 | 85.9 | 78.3 | 80.6 | 85.2 | 78.7 |
| 3_228 | 80.1 | 83.0 | 78.8 | 80.6 | 81.9 | 80.1 |
| 3_130 | 80.7 | 85.0 | 78.8 | 80.5 | 83.3 | 79.3 |
| 2_128 | 80.6 | 87.3 | 77.8 | 80.5 | 87.4 | 77.5 |
| 23_2 | 80.7 | 87.9 | 77.6 | 80.4 | 86.2 | 77.9 |
| 33_1 | 80.6 | 85.8 | 78.5 | 80.4 | 83.5 | 79.1 |
| 194_1 | 80.5 | 85.4 | 78.5 | 80.4 | 81.9 | 79.8 |
| 8_1 | 80.9 | 87.4 | 78.1 | 80.3 | 82.5 | 79.4 |
| 201_1 | 80.4 | 86.1 | 78.0 | 80.3 | 83.3 | 79.0 |
| 125_1 | 80.0 | 84.7 | 78.1 | 80.3 | 81.7 | 79.8 |
| 48_1 | 81.2 | 88.3 | 78.2 | 80.1 | 82.9 | 78.9 |
| 3_11 | 80.1 | 85.2 | 77.9 | 80.1 | 82.1 | 79.3 |
| 105_2 | 80.1 | 86.9 | 77.1 | 80.1 | 88.4 | 76.6 |
| 4_179 | 80.8 | 81.7 | 80.4 | 80.0 | 82.3 | 79.1 |
| 14_2 | 80.5 | 87.8 | 77.4 | 80.0 | 87.4 | 76.8 |
| 2_40 | 80.4 | 87.8 | 77.3 | 80.0 | 87.2 | 77.0 |
| 95_2 | 80.1 | 87.9 | 76.8 | 80.0 | 86.6 | 77.2 |
| 76_1 | 80.0 | 87.0 | 77.1 | 80.0 | 82.7 | 78.8 |
| 114_1 | 80.0 | 85.9 | 77.4 | 80.0 | 82.7 | 78.9 |

TABLE 6

| SEQ ID NO: | Coefficient 1 | Coefficient 2 | Constant term |
|---|---|---|---|
| 18_164 | −1.60 | 2.07 | −4.82 |
| 255_164 | −0.98 | 2.48 | −11.23 |
| 177_164 | −1.10 | 2.10 | −4.44 |
| 4_164 | −0.85 | 1.78 | −8.30 |
| 164_9 | 1.73 | −0.66 | −9.70 |
| 300_164 | −1.00 | 2.32 | −9.50 |
| 272_164 | −0.85 | 1.91 | −9.04 |
| 206_164 | −0.91 | 2.23 | −12.83 |
| 12_164 | −0.92 | 2.10 | −10.95 |
| 166_164 | −0.55 | 1.58 | −9.95 |
| 168_164 | −1.98 | 1.65 | 3.77 |

TABLE 6-continued

| SEQ ID NO: | Coefficient 1 | Coefficient 2 | Constant term |
|---|---|---|---|
| 6_164 | −1.20 | 1.67 | −5.70 |
| 259_164 | −0.82 | 1.95 | −8.42 |
| 115_164 | −1.79 | 2.29 | −2.81 |
| 164_129 | 1.72 | −1.15 | −5.57 |
| 190_164 | −0.48 | 2.13 | −15.45 |
| 199_164 | −1.10 | 2.33 | −11.65 |
| 66_164 | −1.88 | 2.44 | −4.75 |
| 164_107 | 2.03 | −0.94 | −10.10 |
| 207_164 | −0.64 | 2.08 | −13.57 |
| 263_164 | −0.56 | 2.11 | −13.68 |
| 16_164 | −0.88 | 1.86 | −5.46 |
| 37_164 | −1.04 | 1.96 | −9.42 |
| 38_164 | −1.07 | 2.09 | −10.66 |
| 261_164 | −1.03 | 2.07 | −5.02 |
| 305_164 | −1.09 | 1.82 | −5.02 |
| 55_164 | −1.62 | 1.94 | −0.70 |
| 127_164 | −1.50 | 2.16 | −6.33 |
| 104_164 | 0.60 | 1.44 | −17.01 |
| 31_164 | −0.56 | 2.05 | −14.07 |
| 121_164 | −1.11 | 1.74 | −5.58 |
| 81_164 | −0.53 | 1.74 | −11.39 |
| 295_164 | −1.02 | 1.89 | −7.03 |
| 6_165 | −1.66 | 2.22 | −5.42 |
| 25_164 | −0.40 | 1.88 | −13.73 |
| 83_164 | −0.57 | 1.59 | −9.82 |
| 32_164 | −2.50 | 1.64 | 14.46 |
| 247_164 | −0.67 | 1.75 | −9.95 |
| 26_164 | −0.32 | 1.70 | −12.40 |
| 302_164 | −1.77 | 1.59 | 9.32 |
| 268_164 | −0.92 | 1.75 | −7.57 |
| 90_164 | −0.98 | 1.71 | −1.22 |
| 287_164 | −0.85 | 1.89 | −9.10 |
| 278_164 | 1.28 | 2.03 | −32.12 |
| 5_164 | −1.83 | 1.84 | 1.34 |
| 137_164 | −0.56 | 1.98 | −12.35 |
| 276_164 | −1.05 | 1.76 | −3.97 |
| 164_271 | 1.61 | −0.44 | −10.57 |
| 167_164 | 0.63 | 1.44 | −17.66 |
| 126_164 | −1.58 | 1.79 | −1.86 |
| 211_164 | −0.88 | 1.83 | −9.18 |
| 67_164 | −1.06 | 1.72 | −5.62 |
| 39_164 | −1.38 | 1.62 | −2.09 |
| 186_164 | 0.55 | 1.66 | −17.66 |
| 182_164 | −0.93 | 2.15 | −9.42 |
| 226_164 | −0.68 | 2.13 | −10.43 |
| 27_164 | −0.27 | 1.80 | −13.29 |
| 275_164 | −1.38 | 1.65 | −1.88 |
| 185_164 | −0.40 | 1.75 | −11.50 |
| 92_164 | −0.97 | 1.81 | −6.28 |
| 10_164 | −0.86 | 1.79 | −9.84 |
| 279_164 | 0.87 | 1.72 | −21.61 |
| 256_164 | −0.69 | 1.70 | −10.03 |
| 80_164 | −0.65 | 2.02 | −12.33 |
| 164_195 | 1.96 | −0.27 | −15.00 |
| 243_164 | −1.46 | 1.66 | −0.44 |
| 22_164 | −0.39 | 1.97 | −13.31 |
| 164_97 | 1.69 | −0.48 | −11.18 |
| 34_164 | −0.46 | 1.67 | −10.31 |
| 215_164 | 1.34 | 1.94 | −31.62 |
| 187_164 | −0.51 | 1.68 | −8.56 |
| 164_174 | 1.59 | 0.59 | −17.66 |
| 50_164 | −0.24 | 1.85 | −14.26 |
| 62_164 | −0.22 | 1.65 | −12.75 |
| 75_164 | −0.23 | 1.77 | −13.59 |
| 61_164 | 0.79 | 1.52 | −18.90 |
| 89_164 | −0.43 | 1.57 | −7.48 |
| 306_164 | −0.59 | 1.72 | −10.12 |
| 164_286 | 1.45 | −0.32 | −9.57 |
| 85_164 | −0.39 | 1.98 | −11.58 |
| 192_164 | 0.78 | 1.60 | −20.45 |
| 223_164 | −1.58 | 1.66 | 0.62 |
| 299_164 | −0.75 | 2.07 | −10.44 |
| 73_164 | 0.45 | 1.81 | −19.02 |
| 241_164 | −1.09 | 1.46 | −0.04 |
| 118_164 | 0.71 | 1.67 | −21.70 |
| 283_164 | 0.29 | 1.54 | −14.75 |
| 164_77 | 1.74 | −1.41 | −2.70 |
| 175_164 | 1.39 | 1.98 | −32.32 |
| 164_65 | 1.68 | −0.74 | −7.18 |
| 7_164 | 0.43 | 1.43 | −15.72 |
| 205_164 | −0.92 | 1.57 | −3.72 |
| 188_164 | −0.14 | 1.73 | −13.43 |
| 100_164 | −1.13 | 1.66 | −2.07 |
| 13_164 | −0.12 | 1.76 | −13.99 |
| 106_164 | −0.71 | 1.92 | −11.57 |
| 53_164 | −1.10 | 1.61 | 0.96 |
| 64_164 | −0.15 | 1.69 | −13.55 |
| 210_164 | −1.94 | 1.61 | 8.98 |
| 290_164 | −0.45 | 1.65 | −8.84 |
| 164_43 | 1.88 | −0.56 | −12.03 |
| 164_44 | 1.66 | −0.22 | −12.81 |
| 30_164 | −0.17 | 1.76 | −13.60 |
| 21_164 | −0.44 | 1.74 | −11.46 |
| 301_164 | 0.22 | 1.50 | −14.48 |
| 24_164 | −0.37 | 1.51 | −10.00 |
| 45_164 | −0.46 | 1.84 | −12.20 |
| 200_164 | −0.47 | 1.62 | −10.00 |
| 214_164 | −0.45 | 1.66 | −10.68 |
| 170_164 | −0.15 | 1.72 | −13.87 |
| 213_164 | −0.41 | 1.52 | −9.71 |
| 184_164 | −1.04 | 1.39 | −1.69 |
| 292_164 | −1.29 | 1.60 | −1.13 |
| 171_164 | −0.13 | 1.68 | −13.66 |
| 172_164 | 0.26 | 1.46 | −13.87 |
| 264_164 | 0.70 | 1.63 | −18.75 |
| 70_164 | −0.24 | 1.83 | −13.58 |
| 269_164 | −0.78 | 1.69 | −6.52 |
| 239_164 | −0.35 | 1.61 | −10.55 |
| 71_164 | −0.45 | 1.65 | −10.96 |
| 234_164 | 0.38 | 1.49 | −14.91 |
| 78_164 | −0.19 | 1.76 | −13.93 |
| 96_164 | −0.14 | 1.66 | −13.34 |
| 19_164 | 0.27 | 1.52 | −14.36 |
| 138_164 | 0.11 | 1.51 | −13.33 |
| 245_164 | 0.34 | 1.54 | −15.75 |
| 111_164 | 0.71 | 1.38 | −17.76 |
| 304_164 | 0.35 | 1.67 | −16.93 |
| 250_164 | −1.07 | 1.82 | −5.84 |
| 178_164 | −0.65 | 1.54 | −4.79 |
| 289_164 | 0.36 | 1.54 | −15.62 |
| 84_164 | 0.51 | 1.64 | −17.49 |
| 116_164 | −1.61 | 1.54 | 4.66 |
| 180_164 | −0.16 | 1.56 | −12.08 |
| 94_164 | 0.22 | 1.39 | −13.09 |
| 164_253 | 1.50 | −1.23 | 2.24 |
| 82_164 | −0.25 | 1.57 | −11.81 |
| 132_164 | 0.52 | 1.56 | −20.15 |
| 265_164 | −0.76 | 1.67 | −6.92 |
| 274_164 | −0.87 | 1.35 | −2.46 |
| 164_252 | 1.51 | −0.40 | −7.36 |
| 41_164 | −0.28 | 1.55 | −9.93 |
| 230_164 | 0.39 | 1.52 | −17.97 |
| 191_164 | −0.96 | 1.49 | −1.36 |
| 196_164 | −0.13 | 1.70 | −13.61 |
| 112_164 | −0.12 | 1.54 | −12.28 |
| 280_164 | 0.17 | 1.50 | −13.80 |
| 99_164 | 0.05 | 1.51 | −13.01 |
| 224_164 | 0.33 | 1.58 | −15.79 |
| 193_164 | −0.38 | 1.61 | −10.63 |
| 17_164 | 0.27 | 1.48 | −14.10 |
| 20_164 | 0.15 | 1.47 | −13.35 |
| 164_108 | 1.51 | −0.31 | −10.06 |
| 28_164 | −0.59 | 1.54 | −7.68 |
| 298_164 | −0.13 | 1.56 | −12.24 |
| 240_164 | −0.80 | 1.61 | −6.09 |
| 198_164 | −0.14 | 1.65 | −13.04 |
| 220_164 | −0.50 | 1.90 | −12.49 |
| 124_164 | −0.50 | 1.72 | −10.87 |
| 236_164 | −0.51 | 1.71 | −10.38 |
| 282_164 | 0.37 | 1.57 | −15.84 |
| 235_164 | 0.45 | 1.60 | −17.95 |
| 232_164 | −0.54 | 1.69 | −8.55 |
| 57_164 | −0.35 | 1.91 | −13.90 |
| 277_164 | 0.21 | 1.49 | −13.91 |
| 173_164 | −0.09 | 1.55 | −12.45 |
| 227_164 | −0.70 | 1.57 | −5.93 |

TABLE 6-continued

| SEQ ID NO: | Coefficient 1 | Coefficient 2 | Constant term |
|---|---|---|---|
| 69_164 | −0.08 | 1.59 | −12.80 |
| 47_164 | −0.15 | 1.58 | −12.28 |
| 122_164 | 0.10 | 1.46 | −12.92 |
| 242_164 | −0.07 | 1.53 | −12.07 |
| 176_164 | −0.29 | 1.55 | −10.76 |
| 202_164 | −0.36 | 1.61 | −10.87 |
| 197_164 | −0.08 | 1.64 | −13.36 |
| 218_164 | −0.51 | 1.52 | −8.70 |
| 46_164 | 0.31 | 1.49 | −14.95 |
| 86_164 | −0.13 | 1.55 | −12.25 |
| 93_164 | −0.13 | 1.52 | −11.99 |
| 63_164 | −0.49 | 1.60 | −9.70 |
| 109_164 | 0.38 | 1.58 | −17.95 |
| 204_164 | −0.20 | 1.51 | −10.38 |
| 216_164 | −0.28 | 1.53 | −10.91 |
| 169_164 | 0.20 | 1.50 | −14.62 |
| 164_254 | 1.53 | −0.24 | −10.19 |
| 164_203 | 1.53 | 0.17 | −14.06 |
| 98_164 | 0.04 | 1.48 | −12.76 |
| 221_164 | −0.15 | 1.56 | −12.18 |
| 233_164 | −0.71 | 1.54 | −5.44 |
| 284_164 | −0.08 | 1.51 | −12.23 |
| 42_164 | −0.10 | 1.50 | −11.66 |
| 56_164 | −0.14 | 1.57 | −12.32 |
| 296_164 | −0.03 | 1.52 | −12.58 |
| 36_164 | −0.02 | 1.53 | −12.80 |
| 164_229 | 1.51 | −0.10 | −12.23 |
| 134_164 | −0.31 | 1.66 | −12.15 |
| 294_164 | 0.11 | 1.51 | −13.40 |
| 113_164 | −0.24 | 1.57 | −11.89 |
| 164_273 | 1.55 | −0.12 | −12.21 |
| 164_238 | 1.60 | −0.63 | −8.26 |
| 74_164 | 0.43 | 1.47 | −17.92 |
| 102_164 | 0.68 | 1.42 | −16.82 |
| 270_164 | 2.03 | 1.83 | −37.88 |
| 189_164 | 0.34 | 1.52 | −15.01 |
| 262_164 | −0.26 | 1.62 | −11.37 |
| 164_58 | 1.71 | 0.83 | −22.48 |
| 164_251 | 1.63 | −0.46 | −8.53 |
| 103_164 | −1.28 | 1.84 | −4.36 |
| 208_164 | 0.68 | 1.60 | −21.40 |
| 110_164 | −0.50 | 1.64 | −8.76 |
| 281_164 | −0.36 | 1.62 | −10.57 |
| 68_164 | −0.12 | 1.66 | −13.02 |
| 249_164 | −0.44 | 1.52 | −10.19 |
| 219_164 | −0.30 | 1.53 | −10.58 |
| 120_164 | 0.14 | 1.46 | −13.23 |
| 225_164 | −0.16 | 1.67 | −12.79 |
| 52_164 | 0.06 | 1.52 | −13.28 |
| 297_164 | 0.05 | 1.53 | −13.21 |
| 212_164 | 0.06 | 1.52 | −13.64 |
| 248_164 | −0.16 | 1.54 | −11.99 |
| 88_164 | 0.27 | 1.52 | −14.70 |
| 257_164 | −0.08 | 1.57 | −12.63 |
| 244_164 | 0.25 | 1.55 | −14.58 |
| 258_164 | −0.30 | 1.50 | −8.85 |
| 164_79 | 1.50 | 0.13 | −13.38 |
| 181_164 | −0.03 | 1.53 | −12.75 |
| 117_164 | 0.04 | 1.52 | −13.21 |
| 51_164 | −0.12 | 1.56 | −12.44 |
| 209_164 | −0.01 | 1.53 | −12.74 |
| 72_164 | −0.07 | 1.59 | −13.05 |
| 101_164 | −0.14 | 1.55 | −12.27 |
| 59_164 | −0.01 | 1.53 | −12.84 |
| 222_164 | −0.23 | 1.56 | −11.22 |
| 123_164 | 0.07 | 1.52 | −13.33 |
| 266_164 | 0.21 | 1.54 | −15.65 |
| 133_164 | 0.01 | 1.52 | −12.92 |
| 91_164 | −0.20 | 1.51 | −11.31 |
| 35_164 | −0.30 | 1.49 | −10.30 |
| 54_164 | −0.11 | 1.61 | −13.01 |
| 293_164 | 0.06 | 1.53 | −13.43 |
| 291_164 | −0.15 | 1.59 | −12.36 |
| 164_267 | 1.61 | −0.32 | −11.40 |
| 164_285 | 1.61 | −0.19 | −12.48 |
| 164 | 1.52 | NA | −12.87 |
| 167_1 | 1.12 | 1.96 | −28.15 |
| 166_217 | −0.69 | 1.95 | −10.62 |
| 183_169 | −4.31 | 3.31 | 14.07 |
| 246_5 | 3.66 | −3.20 | −2.97 |
| 3_168 | 1.58 | −1.82 | 6.03 |
| 165_2 | 1.07 | 0.64 | −12.10 |
| 166_87 | −0.74 | 0.95 | −0.57 |
| 60_166 | 0.88 | −0.48 | −1.19 |
| 165_136 | 1.72 | −0.72 | −8.51 |
| 7_29 | 1.53 | 0.90 | −18.05 |
| 49_165 | −1.32 | 1.80 | −1.73 |
| 231_165 | 0.32 | 1.27 | −12.22 |
| 165_237 | 1.91 | −0.81 | −7.22 |
| 2_260 | 0.72 | 0.50 | −6.78 |
| 165_288 | 2.06 | −1.38 | −3.16 |
| 165_131 | 1.75 | −0.84 | −7.21 |
| 303_1 | 0.47 | 1.93 | −20.83 |
| 1_15 | 1.91 | 0.36 | −20.23 |
| 119_2 | −0.51 | 1.19 | −4.27 |
| 135_167 | 0.83 | 0.98 | −12.50 |
| 3_228 | 1.32 | 0.32 | −10.30 |
| 3_130 | 1.22 | 0.90 | −14.91 |
| 2_128 | 0.95 | 0.77 | −10.55 |
| 23_2 | 0.39 | 0.88 | −7.42 |
| 33_1 | 0.44 | 1.82 | −19.51 |
| 194_1 | 0.96 | 2.15 | −30.54 |
| 8_1 | 0.69 | 2.03 | −23.35 |
| 201_1 | 0.56 | 1.75 | −20.94 |
| 125_1 | 0.73 | 2.11 | −28.03 |
| 48_1 | 0.61 | 2.08 | −23.93 |
| 3_11 | 1.45 | −0.64 | −4.99 |
| 105_2 | 0.51 | 0.97 | −8.76 |
| 4_179 | −0.78 | 2.02 | −8.19 |
| 14_2 | −0.38 | 1.01 | −3.29 |
| 2_40 | 0.74 | 0.42 | −6.86 |
| 95_2 | 0.94 | 0.94 | −12.41 |
| 76_1 | 0.40 | 1.90 | −20.30 |
| 114_1 | 0.42 | 1.97 | −20.95 |

Example 2

<Discriminant Analysis Using Up to Five miRNAs in Combination>

In this Example, discriminants were prepared using one to five gene markers in the training cohort including the lung cancer patients and the test subjects without lung cancer (Table 11b1), and then, the discriminant performance was evaluated in the validation cohort (Table 11b2). Based on the evaluation, genes used in discriminants with high performance were extracted to obtain gene markers that were able to detect lung cancer.

To be more specific, firstly, the miRNA expression levels of the training cohort and the validation cohort obtained in the preceding Reference Examples were combined and normalized by global normalization. Secondly, in order to acquire diagnostic markers with higher reliability, only 396 genes having the gene expression level of $2^6$ or higher in 50% or more of the samples in either of the positive sample group (lung cancer patients) or the negative sample group (healthy subjects, benign bone and soft tissue tumor patients and benign breast disease patients and patients having a cancer other than lung cancer), were selected as analytes.

Thirdly, combinations of one to five genes of the 396 gene above were subjected to the Fisher's discriminant analysis using the 396 gene expression level measurement values described above to construct discriminants for discriminating the presence or absence of lung cancer. In this relation, discriminants with high discriminant performance were searched for using a modified greedy algorithm. Accuracy, sensitivity, and specificity in the validation cohort were further calculated using the discriminants prepared above, and the discriminant performance was validated using independent samples. As a result, total 750 discriminants including top 150 discriminants having higher performance as to the combinations of one to five genes were obtained. The genes contained in these discriminants were selected as other diagnostic markers for the lung cancer patients and the test subjects without lung cancer. In this way, miR-920, miR-1185-1-3p, miR-4327, miR-5739, miR-1185-2-3p, miR-1238-5p, miR-1246, miR-1470, miR-197-5p, miR-208a-5p, miR-2467-3p, miR-3122, miR-3160-5p, miR-320b, miR-3610, miR-3619-3p, miR-3937, miR-4447, miR-4480, miR-4505, miR-4515, miR-4535, miR-4706, miR-4718, miR-4730, miR-4734, miR-4755-3p, miR-4787-3p, miR-5008-5p, miR-5010-5p, miR-504-3p, miR-5100, miR-557, miR-6510-5p, miR-6511b-5p, miR-6515-3p, miR-6722-5p, miR-6737-5p, miR-6766-5p, miR-6769a-5p, miR-6771-5p, miR-6786-5p, miR-6794-5p, miR-6800-3p, miR-6802-5p, miR-6805-3p, miR-6819-5p, miR-6824-5p, miR-6858-5p, miR-6861-5p, miR-6880-3p, miR-7107-5p, miR-7109-5p, miR-7114-5p, miR-8071, miR-204-3p, miR-3154, miR-3960, miR-4433a-5p, miR-4462, miR-4476, miR-4508, miR-4687-3p, miR-4732-5p, miR-4771, miR-642a-3p, miR-6732-5p, miR-6820-5p, miR-6821-5p, miR-6829-5p, miR-6893-5p, miR-7108-3p, miR-7111-5p, miR-885-3p, miR-1343-3p, miR-6746-5p, miR-422a, miR-4632-5p, miR-6791-5p, miR-1225-3p, miR-1233-5p, miR-1268a, miR-1268b, miR-1273g-3p, miR-1290, miR-150-3p, miR-17-3p, miR-1908-5p, miR-1914-3p, miR-296-3p, miR-3131, miR-3162-5p, miR-3197, miR-320a, miR-342-5p, miR-365a-5p, miR-3679-5p, miR-371a-5p, miR-423-5p, miR-4257, miR-4270, miR-4286, miR-4417, miR-4442, miR-4454, miR-4507, miR-4516, miR-451a, miR-4665-3p, miR-4675, miR-4689, miR-4695-5p, miR-4739, miR-4745-5p, miR-5001-5p, miR-5698, miR-6075, miR-6125, miR-614, miR-615-5p, miR-638, miR-650, miR-6717-5p, miR-6721-5p, miR-6741-5p, miR-6752-5p, miR-6780b-5p, miR-6784-5p, miR-6875-5p, miR-744-5p, miR-760, miR-7977, miR-8059, miR-8063, miR-8072, miR-92a-2-5p, miR-1228-3p, miR-1275, miR-1307-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, and miR-7975, and the relevant polynucleotides consisting of nucleotide sequences of SEQ ID NOs: 2, 4, 5, 6, 9, 12, 13, 17, 18, 19, 22, 23, 27, 31, 33, 34, 39, 47, 50, 55, 57, 59, 66, 70, 73, 74, 78, 80, 81, 82, 83, 85, 88, 93, 94, 95, 99, 102, 106, 107, 108, 109, 111, 114, 115, 117, 121, 123, 126 to 131, 136, 139 to 142, 144, 145, 146, 147, 149 to 152,155 to 160, 162, 164, 165, 166, 168, 169, 173, 177, 183, 184, 185, 188 to 191, 193, 199, 201, 202, 205, 206, 207, 211, 213, 214, 216, 217, 218, 220, 222, 223, 226, 229, 230, 231, 234, 236, 237, 238, 241, 242, 246, 249, 250, 253, 255, 256, 258, 260, 263, 264, 268, 270, 276, 278, 286, 295, 296, 299 to 302, 304, 307, 308, 309, 312 to 326, and 328, were found. Among them, the genes newly found as the marker for examining the presence or absence of lung cancer are polynucleotides consisting of the nucleotide sequences represented by SEQ ID NOs: 164, 165, 166, 168, 169, 173, 177, 183, 184, 185, 188 to 191, 193, 199, 201, 202, 205, 206, 207, 211, 213, 214, 216, 217, 218, 220, 222, 223, 226, 229, 230, 231, 234, 236, 237, 238, 241, 242, 246, 249, 250, 253, 255, 256, 258, 260, 263, 264, 268, 270, 276, 278, 286, 295, 296, 299 to 302, 304, 307, 308, 309, 312 to 326, and 328.

The sensitivities in the validation cohort determined by the discriminants obtained using any single one of the 88 polynucleotides consisting of the nucleotide sequences represented by SEQ ID NOs: 188, 164, 85, 13, 231, 319, 263, 165, 226, 94, 190, 328, 80, 220, 316, 2, 115, 299, 50, 150, 31, 318, 149, 312, 70, 127, 183, 66, 12, 255, 162, 199, 222, 278, 260, 246, 22, 106, 322, 57, 309, 184, 206, 207, 201, 217, 317, 300, 102, 159, 73, 78, 315, 107, 23, 33, 307, 114, 185, 128, 109, 59, 236, 214, 140, 99, 144, 47, 241, 321, 130, 95, 142, 234, 286, 173, 320, 314, 111, 27, 304, 177, 74, 34, 17, 211, 193, and 256 among the polynucleotides described above are shown in Table 3. Also, discriminant coefficients and constant terms are shown in Table 4. In this context, the general sensitivity of the existing marker CEA has been reported as being 69%. Accordingly, it was demonstrated that the polynucleotides represented by these SEQ ID NOs singly detect lung cancer with sensitivity beyond CEA.

The genes represented by SEQ ID NOs: 2, 4, 5, 6, 9, 12, 13, 17, 18, 19, 22, 23, 27, 31, 33, 34, 39, 47, 50, 55, 57, 59, 66, 70, 73, 74, 78, 80, 81, 82, 83, 85, 88, 93, 94, 95, 99, 102, 106, 107, 108, 109, 111, 114, 115, 117, 121, 123, 126 to 131, 136, 139 to 142, 144, 145, 146, 147, 149 to 152, 155 to 160, 162, 164, 165, 166, 168, 169, 173, 177, 183, 184, 185, 188 to 191, 193, 199, 201, 202, 205, 206, 207, 211, 213, 214, 216, 217, 218, 220, 222, 223, 226, 229, 230, 231, 234, 236, 237, 238, 241, 242, 246, 249, 250, 253, 255, 256, 258, 260, 263, 264, 268, 270, 276, 278, 286, 295, 296, 299 to 302, 304, 307, 308, 309, 312 to 326, and 328 provide excellent lung cancer discriminant performance, when the genes are used not only alone but also in combinations of, for example, 2, 3, 4, 5, 6, 7, 8, 9, 10 or more genes. For example, when a discriminant was prepared using gene expression level of the nucleotide sequence represented by SEQ ID NO: 18 alone, the discrimination accuracy in the validation cohort was 61.6%; however, when a discriminant was prepared using two genes (SEQ ID NOs: 18 and 164) in combination, the discrimination accuracy in the validation cohort was 86.7%, if a discriminant was prepared using three genes (SEQ ID NOs: 18, 164 and 255), the discrimination accuracy in the validation cohort was 88.2%, when a discriminant was prepared using four genes (SEQ ID NOs: 18, 121, 130 and 164), the discrimination accuracy in the validation cohort was 88.6%, and when a discriminant was prepared using five genes (SEQ ID NOs: 18, 121, 130, 136 and 164), the discrimination accuracy in the validation cohort was 88.8%.

Figure 2:
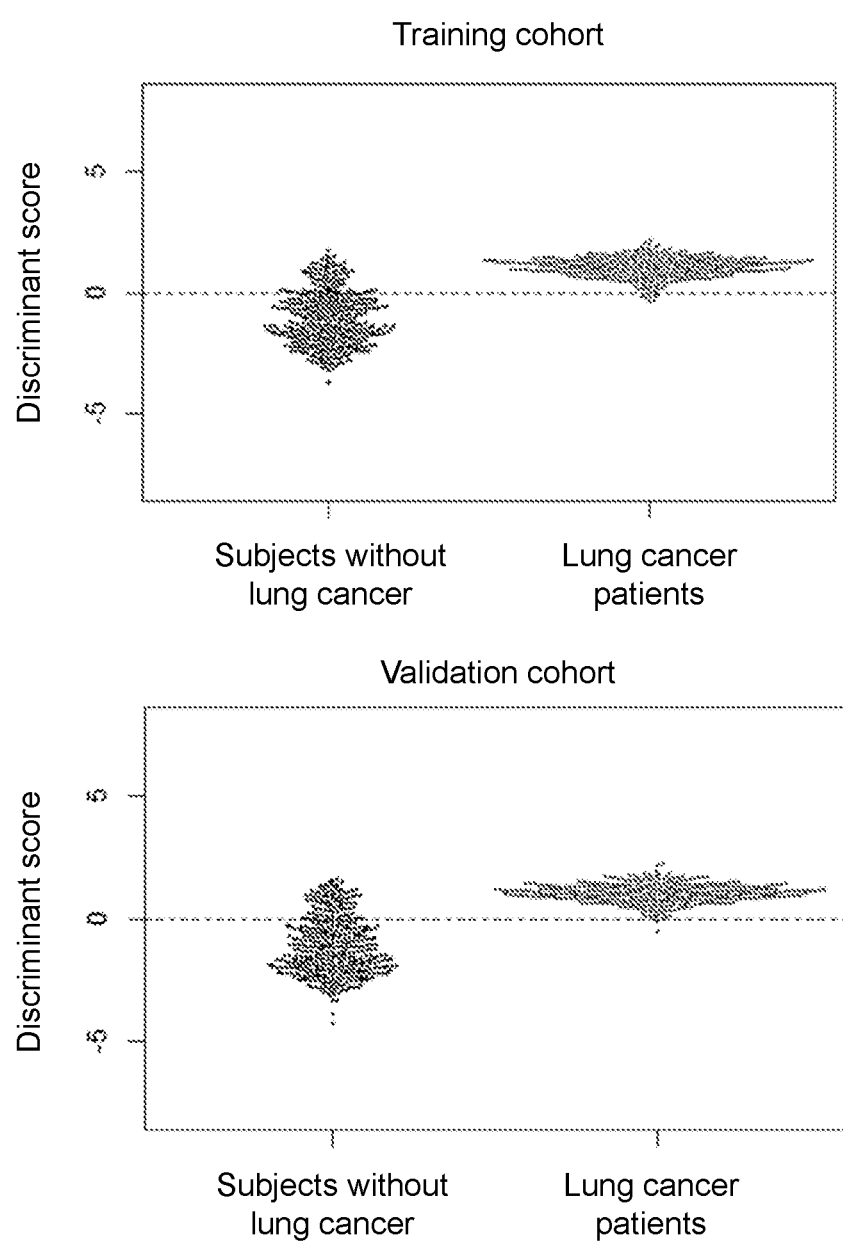
FIG. 2 Upper panel: a discriminant (0.960×hsa-miR-1343-3p−0.703×hsa-miR-197-5p−0.184×hsa-miR-6741-5p+0.506×hsa-miR-4687-3p−0.471×hsa-miR-1268b−1.273) was prepared by use of Fisher's discriminant analysis from the measured expression level values of hsa-miR-1343-3p (SEQ ID NO: 164), hsa-miR-197-5p (SEQ ID NO: 18), hsa-miR-6741-5p (SEQ ID NO: 268), hsa-miR-4687-3p (SEQ ID NO: 147), and hsa-miR-1268b (SEQ ID NO: 184) in sera of test subjects without lung cancer (total 2,777 people including 1,233 healthy subjects, 263 benign bone and soft tissue tumor patients and benign breast disease patients, 1,281 patients having a cancer other than lung cancer) and lung cancer patients (1,186 people) selected as a training cohort, and discriminant scores obtained from the discriminant were plotted on the ordinate against the sample groups on the abscissa. In consideration of easy viewability of the figure, the discriminant scores are shown as to 400 people each extracted at random from the test subjects without lung cancer and the patients with lung cancer. The dotted line in the panel depicts a discriminant boundary that offered a discriminant score of 0 and discriminated between the two groups. Lower panel: discriminant scores obtained from assignment to the discriminant (0.960×hsa-miR-1343-3p−0.703×hsa-miR-197-5p−0.184×hsa-miR-6741-5p+0.506×hsa-miR-4687-3p−0.471×hsa-miR-1268b−1.273) prepared from the training cohort as to the measured expression level values of hsa-miR-1343-3p (SEQ ID NO: 164), hsa-miR-197-5p (SEQ ID NO: 18), hsa-miR-6741-5p (SEQ ID NO: 268), hsa-miR-4687-3p (SEQ ID NO: 147), and hsa-miR-1268b (SEQ ID NO: 184) in sera of test subjects without lung cancer (total 1,191 people including 567 healthy subjects, 105 benign bone and soft tissue tumor patients and benign breast disease patients, 519 patients having a cancer other than lung cancer) and lung cancer patients (508 people) selected as a validation cohort were plotted on the ordinate against the sample groups on the abscissa. In consideration of easy viewability of the figure, the discriminant scores are shown as to 400 people each extracted at random from the test subjects without lung cancer and the patients with lung cancer. The dotted line in the panel depicts the discriminant boundary that offered a discriminant score of 0 and discriminated between the two groups.

As to the discriminant prepared using measurement values of nucleotide sequences represented by SEQ ID NOs: 164, 18, 268, 147 and 184 in combination, discriminant scores of 1,186 lung cancer patients and 2,777 test subjects without lung cancer in the training cohort were significantly separated, as shown in the upper panel of FIG. 2.

The same results were able to be reproduced also in the validation cohort (FIG. 2, lower panel).

Figure 3:
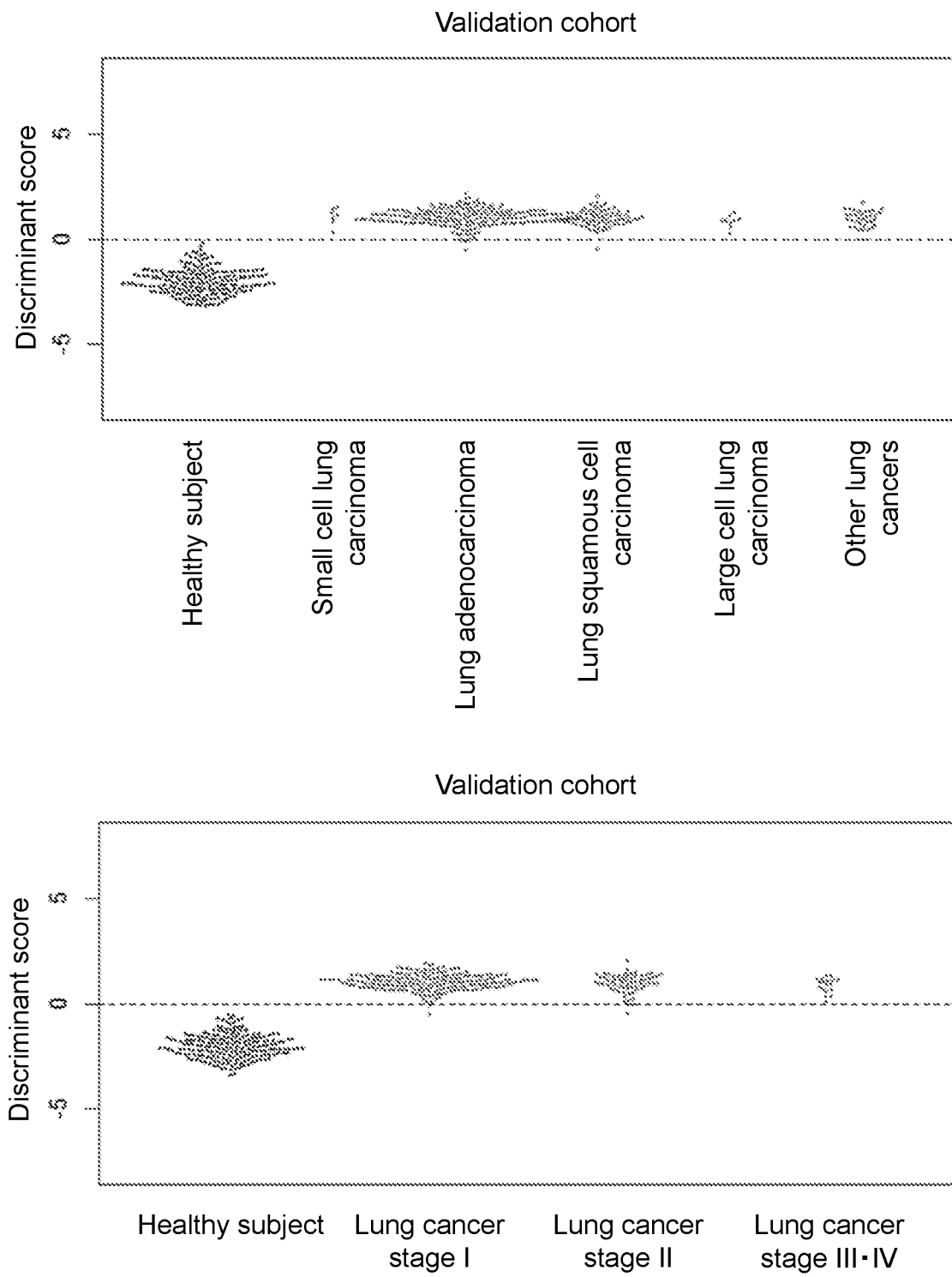
FIG. 3 Upper panel: the discriminant scores of the validation cohort described above are categorized on the basis of the healthy subjects and each histological type of lung cancer (small cell carcinoma, adenocarcinoma, squamous cell carcinoma, large cell carcinoma, and other lung cancers). The dotted line in the panel depicts the discriminant boundary that offered a discriminant score of 0 and discriminated between the two groups. Lower panel: the discriminant scores of the validation cohort described above are categorized on the basis of the healthy subjects and the progressive stages of lung cancer (stage I, stage II, and stage III/IV (stage III and stage IV)). The dotted line in the panel depicts the discriminant boundary that offered a discriminant score of 0 and discriminated between the two groups.

The discriminant scores were categorized on the basis of the histological types and stages of the lung cancer patients. As a result, it was confirmed that lung cancer in all of the categories was able to be detected with high sensitivity (FIG. 3).

Of the 750 discriminants obtained above, the number of discriminants exhibiting a discrimination accuracy of 85% or more both in the training cohort and the validation cohort was 305. These discriminants having particularly high discriminant performance contained at least one of the genes represented by SEQ ID NOs: 18, 4, 130, 2, 9, 17, and 121. These seven genes are referred to as "cancer type-specific polynucleotide group".

Specifically, when measurement was carried out using a polynucleotide consisting of the nucleotide sequence represented by SEQ ID NO: 18 or a complementary sequence thereof as a target nucleic acid, discrimination accuracy is shown in Table 7-1. The measurement using a combination of 2, 3, 4 or 5 genes comprising the polynucleotide consisting of the nucleotide sequence represented by SEQ ID NO: 18 or a complementary sequence thereof exhibited the highest accuracy of 86.7%, 88.2%, 88.6% and 88.8%, respectively, in the validation cohort.

Further, when measurement was carried out using a polynucleotide consisting of the nucleotide sequence represented by SEQ ID NO: 4 or a complementary sequence thereof as a target nucleic acid, discrimination accuracy is shown in Table 7-2. The measurement using a combination of 2, 3, 4 or 5 genes comprising the polynucleotide consisting of the nucleotide sequence represented by SEQ ID NO: 4 or a complementary sequence thereof exhibited the highest accuracy of 86.0%, 87.1%, 87.8% and 87.8%, respectively, in the validation cohort.

Further, when measurement was carried out using a polynucleotide consisting of the nucleotide sequence represented by SEQ ID NO: 130 or a complementary sequence thereof as a target nucleic acid, discrimination accuracy is shown in Table 7-3. The measurement using a combination of 3, 4 or 5 genes comprising the polynucleotide consisting of the nucleotide sequence represented by SEQ ID NO: 130 or a complementary sequence thereof exhibited the highest accuracy of 86.9%, 88.6% and 88.8%, respectively, in the validation cohort.

Further, when measurement was carried out using a polynucleotide consisting of the nucleotide sequence represented by SEQ ID NO: 2 or a complementary sequence thereof as a target nucleic acid, discrimination accuracy is shown in Table 7-4. The measurement using a combination of 4 or 5 genes comprising the polynucleotide consisting of the nucleotide sequence represented by SEQ ID NO: 2 or a complementary sequence thereof exhibited the highest accuracy of 86.3% and 87.8%, respectively, in the validation cohort.

Further, when measurement was carried out using a polynucleotide consisting of the nucleotide sequence represented by SEQ ID NO: 9 or a complementary sequence thereof as a target nucleic acid, discrimination accuracy is shown in Table 7-5. The measurement using a combination of 3, 4 or 5 genes comprising the polynucleotide consisting of the nucleotide sequence represented by SEQ ID NO: 9 or a complementary sequence thereof exhibited the highest accuracy of 86.9%, 87.2% and 87.6%, respectively, in the validation cohort.

Further, when measurement was carried out using a polynucleotide consisting of the nucleotide sequence represented by SEQ ID NO: 17 or a complementary sequence thereof as a target nucleic acid, discrimination accuracy is shown in Table 7-6. The measurement using a combination of 3, 4 or 5 genes comprising the polynucleotide consisting of the nucleotide sequence represented by SEQ ID NO: 17 or a complementary sequence thereof exhibited the highest accuracy of 85.6%, 87.5% and 87.8%, respectively, in the validation cohort.

Further, when measurement was carried out using a polynucleotide consisting of the nucleotide sequence represented by SEQ ID NO: 121 or a complementary sequence thereof as a target nucleic acid, discrimination accuracy is shown in Table 7-7. The measurement using a combination of 3, 4 or 5 genes comprising the polynucleotide consisting of the nucleotide sequence represented by SEQ ID NO: 121 or a complementary sequence thereof exhibited the highest accuracy of 86.9%, 88.6% and 88.8%, respectively, in the validation cohort.

Further, lung adenocarcinoma, lung squamous cell carcinoma, small cell lung carcinoma and large cell lung carcinoma were able to be detected with average sensitivities of 96.4%, 97.1%, 97.8% and 97.6%, respectively, determined by the 305 discriminants obtained using the polynucleotides consisting of SEQ ID NOs described in Tables 7-1 to 7-7 in combination. In addition, stage I (IA and IIA), stage II (IIA and IIB), and stage III/IV (IIIA, IIIB and IV) of lung cancer were able to be detected with average sensitivities of 96.9%, 94.0% and 94.6%, respectively, determined by the 305 discriminants obtained using the polynucleotides consisting of SEQ ID NOs described in Tables 7-1 to 7-7 in combination. Accordingly, the polynucleotides obtained in this Example exerted a high detection ability without missing a particular histological type or stage of progression of lung cancer.

From the above-mentioned results, the polynucleotides consisting of the nucleotide sequences of SEQ ID NOs: 2, 4, 5, 6, 9, 12, 13, 17, 18, 19, 22, 23, 27, 31, 33, 34, 39, 47, 50, 55, 57, 59, 66, 70, 73, 74, 78, 80, 81, 82, 83, 85, 88, 93, 94, 95, 99, 102, 106, 107, 108, 109, 111, 114, 115, 117, 121, 123, 126 to 131, 136, 139 to 142, 144, 145, 146, 147, 149 to 152, 155 to 160, 162, 164, 165, 166, 168, 169, 173, 177, 183, 184, 185, 188 to 191, 193, 199, 201, 202, 205, 206, 207, 211, 213, 214, 216, 217, 218, 220, 222, 223, 226, 229, 230, 231, 234, 236, 237, 238, 241, 242, 246, 249, 250, 253, 255, 256, 258, 260, 263, 264, 268, 270, 276, 278, 286, 295, 296, 299 to 302, 304, 307, 308, 309, 312 to 326, and 328, obtained in this Example, are deemed to be gene groups that lung cancer patients can be specifically discriminated from any of healthy subjects, benign bone and soft tissue tumor patients and benign breast disease patients, and patients having a cancer other than lung cancer. It was further demonstrated that high lung cancer discriminant performance can be obtained by using multiple polynucleotides in combination as target nucleic acids rather than using a single polynucleotide or fewer polynucleotides in combination. In this relation, particularly high discriminant performance can be obtained by using the polynucleotides contained in the cancer type-specific polynucleotide group in combination, wherein the combination of the multiple polynucleotides is not limited to those mentioned above. Even if the polynucleotides are used in any combination, lung cancer can be detected.

Specifically, as shown in the preceding Examples 1 or 2, it is concluded that in all of the polynucleotides consisting of the nucleotide sequences represented by SEQ ID NOs: 1 to 329 or complementary sequences thereof as the target nucleic acids, there exist combinations of 1, 2, 3, 4 or 5 genes that exhibit discriminant performance beyond the existing lung cancer markers, thus indicating that the polynucleotides are excellent diagnostic markers for lung cancer that can detect any histological type or stage of progression of lung cancer described in the preceding Reference Example.

TABLE 7-1

| Combined gene number | SEQ ID NO: | Validation cohort | | |
|---|---|---|---|---|
| | | Sensitivity | Specificity | Accuracy |
| 2 | 18_164 | 98.2 | 81.8 | 86.7 |
| 3 | 18_164_255 | 98.2 | 83.9 | 88.2 |
| 3 | 18_164_300 | 97.8 | 83.0 | 87.5 |
| 3 | 18_164_190 | 97.6 | 83.0 | 87.4 |
| 3 | 18_85_164 | 97.2 | 83.2 | 87.4 |
| 3 | 18_147_164 | 98.2 | 82.5 | 87.2 |
| 3 | 18_22_164 | 97.4 | 82.8 | 87.2 |
| 3 | 18_164_312 | 98.2 | 82.3 | 87.1 |

TABLE 7-1-continued

| Combined gene number | SEQ ID NO: | Validation cohort Sensitivity | Specificity | Accuracy |
|---|---|---|---|---|
| 3 | 18_66_164 | 97.8 | 82.5 | 87.1 |
| 3 | 18_78_164 | 97.8 | 82.4 | 87.0 |
| 3 | 18_27_164 | 97.4 | 82.5 | 87.0 |
| 3 | 18_164_207 | 98.2 | 82.0 | 86.9 |
| 3 | 18_82_164 | 98.0 | 82.1 | 86.9 |
| 3 | 18_164_263 | 98.4 | 81.9 | 86.8 |
| 3 | 18_164_168 | 98.2 | 82.0 | 86.8 |
| 3 | 18_34_164 | 98.0 | 82.0 | 86.8 |
| 3 | 18_39_164 | 97.6 | 82.1 | 86.8 |
| 3 | 18_57_164 | 97.6 | 82.2 | 86.8 |
| 3 | 18_121_164 | 98.6 | 81.6 | 86.7 |
| 3 | 18_107_164 | 98.2 | 81.8 | 86.7 |
| 3 | 18_70_164 | 97.6 | 82.0 | 86.7 |
| 3 | 18_50_164 | 97.6 | 82.0 | 86.7 |
| 3 | 18_164_250 | 96.9 | 82.4 | 86.7 |
| 3 | 18_164_315 | 98.2 | 81.6 | 86.6 |
| 3 | 18_164_211 | 98.0 | 81.8 | 86.6 |
| 3 | 18_164_326 | 97.2 | 82.1 | 86.6 |
| 3 | 18_164_308 | 98.4 | 81.3 | 86.4 |
| 3 | 18_164_268 | 98.2 | 81.4 | 86.4 |
| 3 | 18_164_191 | 97.8 | 81.4 | 86.3 |
| 3 | 18_149_165 | 95.5 | 81.2 | 85.5 |
| 4 | 18_121_130_164 | 98.6 | 84.4 | 88.6 |
| 4 | 18_164_255_316 | 98.4 | 84.3 | 88.5 |
| 4 | 18_121_164_255 | 98.0 | 84.2 | 88.4 |
| 4 | 18_147_164_255 | 98.0 | 84.3 | 88.4 |
| 4 | 18_27_164_255 | 97.8 | 84.3 | 88.4 |
| 4 | 18_34_164_255 | 98.0 | 84.1 | 88.3 |
| 4 | 18_47_164_255 | 98.2 | 84.0 | 88.2 |
| 4 | 18_158_164_255 | 98.0 | 84.1 | 88.2 |
| 4 | 18_164_220_255 | 98.0 | 84.0 | 88.2 |
| 4 | 18_88_164_255 | 97.8 | 84.1 | 88.2 |
| 4 | 18_130_164_268 | 98.4 | 83.7 | 88.1 |
| 4 | 18_164_255_321 | 98.2 | 83.8 | 88.1 |
| 4 | 18_164_184_255 | 98.2 | 83.7 | 88.1 |
| 4 | 18_152_164_255 | 98.0 | 83.8 | 88.1 |
| 4 | 18_164_185_255 | 98.0 | 83.9 | 88.1 |
| 4 | 18_164_238_255 | 98.0 | 83.8 | 88.1 |
| 4 | 18_164_255_256 | 97.8 | 83.9 | 88.1 |
| 4 | 18_127_164_255 | 97.6 | 84.1 | 88.1 |
| 4 | 18_164_222_255 | 98.2 | 83.6 | 88.0 |
| 4 | 18_139_164_255 | 98.0 | 83.7 | 88.0 |
| 4 | 18_39_164_255 | 97.6 | 83.9 | 88.0 |
| 4 | 18_164_255_295 | 96.9 | 84.2 | 88.0 |
| 4 | 18_146_164_255 | 97.6 | 83.7 | 87.9 |
| 4 | 18_164_211_255 | 97.4 | 83.7 | 87.8 |
| 4 | 18_164_255_322 | 97.4 | 83.7 | 87.8 |
| 4 | 18_164_255_318 | 98.0 | 83.3 | 87.7 |
| 4 | 18_121_164_201 | 98.2 | 83.0 | 87.6 |
| 4 | 18_147_164_300 | 98.2 | 83.1 | 87.6 |
| 4 | 18_121_151_164 | 98.2 | 83.1 | 87.6 |
| 4 | 18_164_211_300 | 97.2 | 83.0 | 87.3 |
| 4 | 18_95_164_268 | 98.8 | 82.0 | 87.1 |
| 4 | 18_164_231_268 | 98.4 | 82.2 | 87.1 |
| 4 | 18_147_164_268 | 98.4 | 82.2 | 87.1 |
| 4 | 18_164_188_268 | 98.2 | 82.4 | 87.1 |
| 4 | 18_164_268_312 | 98.0 | 82.5 | 87.1 |
| 4 | 18_39_164_300 | 97.4 | 82.6 | 87.1 |
| 4 | 18_95_121_164 | 99.0 | 81.5 | 86.8 |
| 4 | 18_93_164_268 | 98.6 | 81.7 | 86.8 |
| 4 | 18_164_268_308 | 98.6 | 81.6 | 86.7 |
| 4 | 18_107_121_164 | 98.6 | 81.6 | 86.7 |
| 4 | 18_164_218_268 | 98.4 | 81.5 | 86.6 |
| 4 | 18_164_202_268 | 98.2 | 81.6 | 86.6 |
| 4 | 13_18_130_165 | 98.2 | 81.5 | 86.5 |
| 4 | 18_149_165_168 | 96.7 | 82.1 | 86.5 |
| 4 | 18_164_242_268 | 98.2 | 81.5 | 86.5 |
| 4 | 18_164_214_268 | 98.2 | 81.5 | 86.5 |
| 4 | 18_164_268_313 | 98.2 | 81.4 | 86.5 |
| 4 | 18_162_164_268 | 98.0 | 81.5 | 86.5 |
| 4 | 18_150_164_268 | 98.0 | 81.6 | 86.5 |
| 4 | 18_164_268_315 | 98.6 | 81.2 | 86.4 |
| 4 | 18_152_164_268 | 98.6 | 81.2 | 86.4 |
| 4 | 18_164_268_325 | 98.2 | 81.4 | 86.4 |
| 4 | 18_121_149_165 | 97.1 | 81.7 | 86.3 |
| 4 | 13_18_165_260 | 98.6 | 80.8 | 86.1 |
| 4 | 13_18_165_268 | 98.8 | 80.6 | 86.1 |
| 4 | 13_18_121_165 | 99.2 | 80.4 | 86.1 |
| 4 | 13_18_165_168 | 98.2 | 80.9 | 86.1 |
| 4 | 18_149_165_268 | 96.1 | 81.7 | 86.0 |
| 4 | 13_18_83_165 | 98.0 | 80.9 | 86.0 |
| 4 | 13_18_165_263 | 98.6 | 80.5 | 85.9 |
| 4 | 2_18_165_268 | 95.5 | 81.7 | 85.8 |
| 4 | 13_18_165_211 | 98.2 | 80.4 | 85.8 |
| 4 | 13_18_165_256 | 98.2 | 80.4 | 85.7 |
| 4 | 13_18_165_276 | 98.0 | 80.2 | 85.5 |
| 4 | 13_18_165_302 | 98.0 | 80.1 | 85.5 |
| 4 | 13_18_165_190 | 98.2 | 79.9 | 85.3 |
| 5 | 18_121_130_136_164 | 98.6 | 84.6 | 88.8 |
| 5 | 18_121_130_164_314 | 98.4 | 84.6 | 88.8 |
| 5 | 18_114_121_130_164 | 99.0 | 84.3 | 88.7 |
| 5 | 18_121_130_164_214 | 98.6 | 84.5 | 88.7 |
| 5 | 18_121_130_164_193 | 98.8 | 84.3 | 88.6 |
| 5 | 18_130_164_255_268 | 98.6 | 84.4 | 88.6 |
| 5 | 18_121_130_164_320 | 98.6 | 84.4 | 88.6 |
| 5 | 18_121_130_164_301 | 98.6 | 84.3 | 88.6 |
| 5 | 18_121_130_144_164 | 98.6 | 84.4 | 88.6 |
| 5 | 18_121_130_164_168 | 98.4 | 84.5 | 88.6 |
| 5 | 18_121_130_164_205 | 98.4 | 84.4 | 88.6 |
| 5 | 18_121_130_158_164 | 98.8 | 84.1 | 88.5 |
| 5 | 18_121_130_164_260 | 98.8 | 84.1 | 88.5 |
| 5 | 18_106_121_130_164 | 98.8 | 84.1 | 88.5 |
| 5 | 18_121_130_164_318 | 98.6 | 84.2 | 88.5 |
| 5 | 18_121_130_164_286 | 98.6 | 84.1 | 88.5 |
| 5 | 18_121_130_164_315 | 98.6 | 84.2 | 88.5 |
| 5 | 18_121_130_164_237 | 98.6 | 84.2 | 88.5 |
| 5 | 18_121_130_164_184 | 98.6 | 84.2 | 88.5 |
| 5 | 18_121_130_164_270 | 98.4 | 84.2 | 88.5 |
| 5 | 18_121_130_164_309 | 98.4 | 84.2 | 88.5 |
| 5 | 18_121_130_164_278 | 98.4 | 84.3 | 88.5 |
| 5 | 18_82_121_130_164 | 98.4 | 84.2 | 88.5 |
| 5 | 18_23_121_130_164 | 98.4 | 84.2 | 88.5 |
| 5 | 18_121_130_164_189 | 98.4 | 84.3 | 88.5 |
| 5 | 18_121_130_152_164 | 98.2 | 84.3 | 88.5 |
| 5 | 18_121_130_164_213 | 98.2 | 84.3 | 88.5 |
| 5 | 18_121_130_164_229 | 98.2 | 84.3 | 88.5 |
| 5 | 18_57_121_130_164 | 98.2 | 84.4 | 88.5 |
| 5 | 18_121_130_142_164 | 98.8 | 83.9 | 88.4 |
| 5 | 18_121_130_155_164 | 98.6 | 84.0 | 88.4 |
| 5 | 18_39_121_130_164 | 98.4 | 84.1 | 88.4 |
| 5 | 18_27_130_164_268 | 98.4 | 84.1 | 88.4 |
| 5 | 18_33_121_130_164 | 98.4 | 84.1 | 88.4 |
| 5 | 18_121_126_130_164 | 98.4 | 84.1 | 88.4 |
| 5 | 18_121_130_164_319 | 98.4 | 84.1 | 88.4 |
| 5 | 18_22_121_130_164 | 98.2 | 84.1 | 88.4 |
| 5 | 18_59_121_130_164 | 98.2 | 84.1 | 88.4 |
| 5 | 18_27_121_130_164 | 97.8 | 84.4 | 88.4 |
| 5 | 18_130_164_268_317 | 98.2 | 84.1 | 88.3 |
| 5 | 18_121_130_164_201 | 98.2 | 84.1 | 88.3 |
| 5 | 18_34_164_211_255 | 97.6 | 84.3 | 88.3 |
| 5 | 18_19_121_130_164 | 98.4 | 83.9 | 88.2 |
| 5 | 18_74_130_164_268 | 98.4 | 83.7 | 88.1 |
| 5 | 18_130_164_264_268 | 97.2 | 84.1 | 88.0 |
| 5 | 18_39_164_255_328 | 97.4 | 83.9 | 87.9 |
| 5 | 18_39_164_226_255 | 97.4 | 83.9 | 87.9 |
| 5 | 18_95_121_164_188 | 99.0 | 83.0 | 87.8 |
| 5 | 13_18_121_130_165 | 98.4 | 82.5 | 87.2 |
| 5 | 13_18_130_165_268 | 98.6 | 82.3 | 87.2 |
| 5 | 18_151_164_268_315 | 98.0 | 82.3 | 87.0 |
| 5 | 18_147_164_184_268 | 98.8 | 81.9 | 86.9 |
| 5 | 18_149_165_168_268 | 96.7 | 82.6 | 86.8 |
| 5 | 13_18_165_268_276 | 98.0 | 81.3 | 86.3 |
| 5 | 2_18_165_268_301 | 95.3 | 82.2 | 86.1 |
| 5 | 2_18_165_268_315 | 96.3 | 81.8 | 86.1 |
| 5 | 13_18_165_183_268 | 99.0 | 80.2 | 85.8 |
| 5 | 13_18_165_184_268 | 99.0 | 80.1 | 85.8 |

TABLE 7-2

| Combined gene number | SEQ ID NO: | Validation cohort Sensitivity | Specificity | Accuracy |
|---|---|---|---|---|
| 2 | 4_164 | 91.3 | 83.7 | 86.0 |
| 3 | 4_165_168 | 95.3 | 83.5 | 87.1 |
| 4 | 4_165_168_246 | 97.4 | 83.7 | 87.8 |
| 4 | 4_128_165_168 | 96.3 | 84.0 | 87.6 |
| 4 | 4_117_165_168 | 96.5 | 83.8 | 87.6 |
| 4 | 4_159_165_168 | 95.5 | 84.1 | 87.5 |
| 4 | 4_165_168_260 | 95.3 | 84.2 | 87.5 |
| 4 | 4_17_165_168 | 95.1 | 84.2 | 87.5 |
| 4 | 4_165_168_173 | 96.3 | 83.6 | 87.4 |
| 4 | 4_80_165_168 | 96.5 | 82.6 | 86.8 |
| 4 | 4_99_165_168 | 94.5 | 83.4 | 86.7 |
| 4 | 2_4_168_246 | 93.3 | 82.8 | 85.9 |
| 4 | 4_17_115_168 | 92.1 | 83.3 | 85.9 |
| 4 | 4_17_115_302 | 89.8 | 84.1 | 85.8 |
| 4 | 4_94_173_183 | 93.9 | 82.2 | 85.7 |
| 4 | 2_4_173_183 | 93.3 | 82.2 | 85.5 |
| 4 | 2_4_115_168 | 90.8 | 83.3 | 85.5 |
| 4 | 4_17_115_184 | 91.5 | 82.7 | 85.3 |
| 5 | 4_17_165_168_173 | 96.5 | 84.1 | 87.8 |
| 5 | 4_17_165_168_223 | 95.7 | 84.5 | 87.8 |
| 5 | 4_128_129_165_168 | 94.5 | 84.9 | 87.8 |
| 5 | 2_4_130_168_246 | 95.9 | 84.3 | 87.8 |
| 5 | 4_17_128_165_168 | 95.5 | 84.4 | 87.7 |
| 5 | 4_17_165_168_169 | 95.3 | 84.5 | 87.7 |
| 5 | 4_17_117_165_168 | 95.3 | 84.4 | 87.6 |
| 5 | 4_17_165_168_323 | 95.3 | 84.3 | 87.6 |
| 5 | 4_17_81_165_168 | 94.7 | 84.6 | 87.6 |
| 5 | 4_17_165_168_253 | 95.1 | 84.4 | 87.6 |
| 5 | 4_17_162_165_168 | 95.5 | 84.2 | 87.6 |
| 5 | 2_4_168_201_246 | 94.5 | 84.7 | 87.6 |
| 5 | 4_17_141_165_168 | 94.7 | 84.5 | 87.5 |
| 5 | 4_17_129_165_168 | 94.3 | 84.6 | 87.5 |
| 5 | 4_17_165_168_258 | 94.7 | 84.4 | 87.5 |
| 5 | 4_17_165_168_190 | 95.7 | 84.0 | 87.5 |
| 5 | 4_17_115_168_177 | 92.7 | 85.3 | 87.5 |
| 5 | 4_17_165_168_191 | 94.9 | 84.2 | 87.4 |
| 5 | 4_17_158_165_168 | 95.3 | 84.1 | 87.4 |
| 5 | 4_17_165_168_184 | 95.7 | 83.9 | 87.4 |
| 5 | 4_17_94_165_168 | 95.3 | 84.1 | 87.4 |
| 5 | 4_17_165_168_296 | 95.5 | 83.9 | 87.4 |
| 5 | 4_17_165_168_307 | 95.1 | 84.1 | 87.4 |
| 5 | 4_17_123_165_168 | 95.5 | 83.9 | 87.4 |
| 5 | 4_17_39_165_168 | 94.9 | 84.1 | 87.4 |
| 5 | 4_17_145_165_168 | 95.3 | 83.9 | 87.3 |
| 5 | 4_17_165_168_286 | 94.9 | 84.1 | 87.3 |
| 5 | 4_17_73_165_168 | 95.3 | 83.8 | 87.2 |
| 5 | 4_17_115_165_168 | 94.9 | 84.0 | 87.2 |
| 5 | 4_17_108_165_168 | 94.7 | 84.1 | 87.2 |
| 5 | 4_17_156_165_168 | 94.9 | 84.0 | 87.2 |
| 5 | 4_17_165_168_249 | 95.5 | 83.6 | 87.2 |
| 5 | 4_17_131_165_168 | 95.3 | 83.7 | 87.2 |
| 5 | 4_17_165_168_304 | 94.9 | 83.9 | 87.2 |
| 5 | 4_17_157_165_168 | 95.1 | 83.8 | 87.2 |
| 5 | 4_17_165_168_318 | 94.9 | 83.8 | 87.1 |
| 5 | 4_17_74_165_168 | 94.3 | 84.1 | 87.1 |
| 5 | 4_17_165_168_216 | 94.9 | 83.6 | 87.0 |
| 5 | 4_17_165_168_309 | 94.5 | 83.8 | 87.0 |
| 5 | 4_17_165_168_236 | 94.7 | 83.7 | 87.0 |
| 5 | 4_17_165_168_324 | 95.3 | 83.5 | 87.0 |
| 5 | 2_4_111_168_173 | 92.7 | 84.5 | 86.9 |
| 5 | 4_17_115_130_168 | 92.7 | 84.3 | 86.8 |
| 5 | 2_4_130_168_173 | 93.7 | 83.9 | 86.8 |
| 5 | 4_17_111_115_168 | 91.9 | 84.6 | 86.8 |
| 5 | 2_4_168_173_201 | 93.5 | 83.7 | 86.6 |
| 5 | 4_17_115_160_168 | 92.1 | 84.3 | 86.6 |
| 5 | 4_17_115_168_246 | 94.1 | 83.5 | 86.6 |
| 5 | 2_4_115_168_173 | 94.3 | 83.3 | 86.6 |
| 5 | 4_17_115_168_201 | 92.3 | 84.1 | 86.5 |
| 5 | 4_17_115_168_217 | 92.9 | 83.8 | 86.5 |
| 5 | 2_4_17_115_168 | 92.5 | 83.6 | 86.3 |
| 5 | 4_17_115_140_168 | 90.9 | 84.1 | 86.1 |
| 5 | 4_17_102_115_168 | 92.1 | 83.3 | 85.9 |

TABLE 7-3

| Combined gene number | SEQ ID NO: | Validation cohort Sensitivity | Specificity | Accuracy |
|---|---|---|---|---|
| 3 | 121_130_164 | 97.6 | 82.3 | 86.9 |
| 4 | 18_121_130_164 | 98.6 | 84.4 | 88.6 |
| 4 | 18_130_164_268 | 98.4 | 83.7 | 88.1 |
| 4 | 13_18_130_165 | 98.2 | 81.5 | 86.5 |
| 5 | 18_121_130_136_164 | 98.6 | 84.6 | 88.8 |
| 5 | 18_121_130_164_314 | 98.4 | 84.6 | 88.8 |
| 5 | 18_114_121_130_164 | 99.0 | 84.3 | 88.7 |
| 5 | 18_121_130_164_214 | 98.6 | 84.5 | 88.7 |
| 5 | 18_121_130_164_193 | 98.8 | 84.3 | 88.6 |
| 5 | 18_130_164_255_268 | 98.6 | 84.4 | 88.6 |
| 5 | 18_121_130_164_320 | 98.6 | 84.4 | 88.6 |
| 5 | 18_121_130_164_301 | 98.6 | 84.3 | 88.6 |
| 5 | 18_121_130_144_164 | 98.6 | 84.4 | 88.6 |
| 5 | 18_121_130_164_168 | 98.4 | 84.5 | 88.6 |
| 5 | 18_121_130_164_205 | 98.4 | 84.4 | 88.6 |
| 5 | 18_121_130_158_164 | 98.8 | 84.1 | 88.5 |
| 5 | 18_121_130_164_260 | 98.8 | 84.1 | 88.5 |
| 5 | 18_106_121_130_164 | 98.8 | 84.1 | 88.5 |
| 5 | 18_121_130_164_318 | 98.6 | 84.2 | 88.5 |
| 5 | 18_121_130_164_286 | 98.6 | 84.1 | 88.5 |
| 5 | 18_121_130_164_315 | 98.6 | 84.2 | 88.5 |
| 5 | 18_121_130_164_237 | 98.6 | 84.2 | 88.5 |
| 5 | 18_121_130_164_184 | 98.6 | 84.2 | 88.5 |
| 5 | 18_121_130_164_270 | 98.4 | 84.2 | 88.5 |
| 5 | 18_121_130_164_309 | 98.4 | 84.2 | 88.5 |
| 5 | 18_121_130_164_278 | 98.4 | 84.3 | 88.5 |
| 5 | 18_82_121_130_164 | 98.4 | 84.2 | 88.5 |
| 5 | 18_23_121_130_164 | 98.4 | 84.2 | 88.5 |
| 5 | 18_121_130_164_189 | 98.4 | 84.3 | 88.5 |
| 5 | 18_121_130_152_164 | 98.2 | 84.3 | 88.5 |
| 5 | 18_121_130_164_213 | 98.2 | 84.3 | 88.5 |
| 5 | 18_121_130_164_229 | 98.2 | 84.3 | 88.5 |
| 5 | 18_57_121_130_164 | 98.2 | 84.4 | 88.5 |
| 5 | 18_121_130_142_164 | 98.8 | 83.9 | 88.4 |
| 5 | 18_121_130_155_164 | 98.6 | 84.0 | 88.4 |
| 5 | 18_39_121_130_164 | 98.4 | 84.1 | 88.4 |
| 5 | 18_27_130_164_268 | 98.4 | 84.1 | 88.4 |
| 5 | 18_33_121_130_164 | 98.4 | 84.1 | 88.4 |
| 5 | 18_121_126_130_164 | 98.4 | 84.1 | 88.4 |
| 5 | 18_121_130_164_319 | 98.4 | 84.1 | 88.4 |
| 5 | 18_22_121_130_164 | 98.2 | 84.1 | 88.4 |
| 5 | 18_59_121_130_164 | 98.2 | 84.1 | 88.4 |
| 5 | 18_27_121_130_164 | 97.8 | 84.4 | 88.4 |
| 5 | 18_130_164_268_317 | 98.2 | 84.1 | 88.3 |
| 5 | 18_121_130_164_201 | 98.2 | 84.1 | 88.3 |
| 5 | 18_19_121_130_164 | 98.4 | 83.9 | 88.2 |
| 5 | 18_74_130_164_268 | 98.4 | 83.7 | 88.1 |
| 5 | 18_130_164_264_268 | 97.2 | 84.1 | 88.0 |
| 5 | 2_4_130_168_246 | 95.9 | 84.3 | 87.8 |
| 5 | 2_9_130_168_246 | 95.9 | 84.0 | 87.5 |
| 5 | 13_18_121_130_165 | 98.4 | 82.5 | 87.2 |
| 5 | 13_18_130_165_268 | 98.6 | 82.3 | 87.2 |
| 5 | 4_17_115_130_168 | 92.7 | 84.3 | 86.8 |
| 5 | 2_4_130_168_173 | 93.7 | 83.9 | 86.8 |
| 5 | 2_9_130_168_173 | 93.7 | 83.2 | 86.3 |
| 5 | 2_111_130_168_173 | 93.3 | 83.0 | 86.1 |
| 5 | 2_83_130_168_173 | 94.5 | 82.2 | 85.9 |
| 5 | 2_6_130_168_173 | 94.5 | 82.0 | 85.7 |
| 5 | 2_6_130_173_184 | 95.9 | 81.3 | 85.6 |
| 5 | 2_130_168_173_213 | 94.9 | 81.4 | 85.4 |
| 5 | 2_5_130_168_173 | 92.9 | 82.1 | 85.3 |
| 5 | 2_130_168_173_249 | 93.9 | 81.5 | 85.2 |

TABLE 7-4

| Combined gene number | SEQ ID NO: | Validation cohort Sensitivity | Specificity | Accuracy |
|---|---|---|---|---|
| 4 | 2_121_165_168 | 95.3 | 82.5 | 86.3 |
| 4 | 2_165_168_268 | 94.9 | 82.0 | 85.9 |
| 4 | 2_4_168_246 | 93.3 | 82.8 | 85.9 |
| 4 | 2_18_165_268 | 95.5 | 81.7 | 85.8 |

TABLE 7-4-continued

| Combined gene number | SEQ ID NO: | Sensitivity | Specificity | Accuracy |
|---|---|---|---|---|
| 4 | 2_4_173_183 | 93.3 | 82.2 | 85.5 |
| 4 | 2_4_115_168 | 90.8 | 83.3 | 85.5 |
| 4 | 2_9_168_246 | 93.3 | 82.1 | 85.5 |
| 4 | 2_111_168_246 | 92.7 | 82.3 | 85.4 |
| 4 | 2_111_168_173 | 92.9 | 82.1 | 85.3 |
| 4 | 2_102_168_246 | 93.1 | 81.7 | 85.1 |
| 5 | 2_4_130_168_246 | 95.9 | 84.3 | 87.8 |
| 5 | 2_4_168_201_246 | 94.5 | 84.7 | 87.6 |
| 5 | 2_9_130_168_246 | 95.9 | 84.0 | 87.5 |
| 5 | 2_4_111_168_173 | 92.7 | 84.5 | 86.9 |
| 5 | 2_4_130_168_173 | 93.7 | 83.9 | 86.8 |
| 5 | 2_4_168_173_201 | 93.5 | 83.7 | 86.6 |
| 5 | 2_4_115_168_173 | 94.3 | 83.3 | 86.6 |
| 5 | 2_9_130_168_173 | 93.7 | 83.2 | 86.3 |
| 5 | 2_4_17_115_168 | 92.5 | 83.6 | 86.3 |
| 5 | 2_111_168_173_268 | 93.7 | 83.1 | 86.3 |
| 5 | 2_18_165_268_301 | 95.3 | 82.2 | 86.1 |
| 5 | 2_18_165_268_315 | 96.3 | 81.8 | 86.1 |
| 5 | 2_111_130_168_173 | 93.3 | 83.0 | 86.1 |
| 5 | 2_83_130_168_173 | 94.5 | 82.2 | 85.9 |
| 5 | 2_6_130_168_173 | 94.5 | 82.0 | 85.7 |
| 5 | 2_111_168_173_223 | 92.7 | 82.7 | 85.7 |
| 5 | 2_5_111_168_173 | 92.1 | 83.0 | 85.7 |
| 5 | 2_6_130_173_184 | 95.9 | 81.3 | 85.6 |
| 5 | 2_39_111_168_173 | 93.3 | 82.3 | 85.6 |
| 5 | 2_111_168_173_222 | 93.9 | 82.0 | 85.5 |
| 5 | 2_111_152_168_173 | 93.5 | 82.0 | 85.5 |
| 5 | 2_111_168_173_241 | 93.1 | 82.2 | 85.5 |
| 5 | 2_130_168_173_213 | 94.9 | 81.4 | 85.4 |
| 5 | 2_111_168_173_184 | 94.1 | 81.7 | 85.4 |
| 5 | 2_102_111_168_173 | 92.3 | 82.5 | 85.4 |
| 5 | 2_5_130_168_173 | 92.9 | 82.1 | 85.3 |
| 5 | 2_111_168_173_234 | 92.3 | 82.4 | 85.3 |
| 5 | 2_111_168_173_230 | 93.1 | 82.0 | 85.3 |
| 5 | 2_111_168_173_307 | 93.3 | 81.9 | 85.3 |
| 5 | 2_130_168_173_249 | 93.9 | 81.5 | 85.2 |
| 5 | 2_111_158_168_173 | 92.9 | 81.8 | 85.1 |
| 5 | 2_39_168_169_173 | 93.3 | 81.5 | 85.1 |

TABLE 7-5

| Combined gene number | SEQ ID NO: | Sensitivity | Specificity | Accuracy |
|---|---|---|---|---|
| 3 | 9_165_168 | 95.9 | 83.0 | 86.9 |
| 4 | 9_165_168_173 | 96.5 | 83.2 | 87.2 |
| 4 | 9_128_165_168 | 95.3 | 83.6 | 87.1 |
| 4 | 9_17_165_168 | 94.7 | 83.5 | 86.9 |
| 4 | 9_80_165_168 | 97.4 | 82.2 | 86.8 |
| 4 | 2_9_168_246 | 93.3 | 82.1 | 85.5 |
| 5 | 5_9_165_168_173 | 96.5 | 83.9 | 87.6 |
| 5 | 9_128_129_165_168 | 94.5 | 84.6 | 87.5 |
| 5 | 2_9_130_168_246 | 95.9 | 84.0 | 87.5 |
| 5 | 9_17_159_165_168 | 94.7 | 83.4 | 86.8 |
| 5 | 9_17_165_168_173 | 95.1 | 83.1 | 86.7 |
| 5 | 2_9_130_168_173 | 93.7 | 83.2 | 86.3 |

TABLE 7-6

| Combined gene number | SEQ ID NO: | Sensitivity | Specificity | Accuracy |
|---|---|---|---|---|
| 3 | 17_164_168 | 97.8 | 80.4 | 85.6 |
| 4 | 4_17_165_168 | 95.1 | 84.2 | 87.5 |
| 4 | 9_17_165_168 | 94.7 | 83.5 | 86.9 |
| 4 | 4_17_115_168 | 92.1 | 83.3 | 85.9 |
| 4 | 4_17_115_302 | 89.8 | 84.1 | 85.8 |
| 4 | 4_17_115_184 | 91.5 | 82.7 | 85.3 |
| 5 | 4_17_165_168_173 | 96.5 | 84.1 | 87.8 |

TABLE 7-6-continued

| Combined gene number | SEQ ID NO: | Sensitivity | Specificity | Accuracy |
|---|---|---|---|---|
| 5 | 4_17_165_168_223 | 95.7 | 84.5 | 87.8 |
| 5 | 4_17_128_165_168 | 95.5 | 84.4 | 87.7 |
| 5 | 4_17_165_168_169 | 95.3 | 84.5 | 87.7 |
| 5 | 4_17_117_165_168 | 95.3 | 84.4 | 87.6 |
| 5 | 4_17_165_168_323 | 95.3 | 84.3 | 87.6 |
| 5 | 4_17_81_165_168 | 94.7 | 84.6 | 87.6 |
| 5 | 4_17_165_168_253 | 95.1 | 84.4 | 87.6 |
| 5 | 4_17_162_165_168 | 95.5 | 84.2 | 87.6 |
| 5 | 4_17_141_165_168 | 94.7 | 84.5 | 87.5 |
| 5 | 4_17_129_165_168 | 94.3 | 84.6 | 87.5 |
| 5 | 4_17_165_168_258 | 94.7 | 84.4 | 87.5 |
| 5 | 4_17_165_168_190 | 95.7 | 84.0 | 87.5 |
| 5 | 4_17_115_168_177 | 92.7 | 85.3 | 87.5 |
| 5 | 4_17_165_168_191 | 94.9 | 84.2 | 87.4 |
| 5 | 4_17_158_165_168 | 95.3 | 84.1 | 87.4 |
| 5 | 4_17_165_168_184 | 95.7 | 83.9 | 87.4 |
| 5 | 4_17_94_165_168 | 95.3 | 84.1 | 87.4 |
| 5 | 4_17_165_168_296 | 95.5 | 83.9 | 87.4 |
| 5 | 4_17_165_168_307 | 95.1 | 84.1 | 87.4 |
| 5 | 4_17_123_165_168 | 95.5 | 83.9 | 87.4 |
| 5 | 4_17_39_165_168 | 94.9 | 84.1 | 87.4 |
| 5 | 4_17_145_165_168 | 95.3 | 83.9 | 87.3 |
| 5 | 4_17_165_168_286 | 94.9 | 84.1 | 87.3 |
| 5 | 4_17_73_165_168 | 95.3 | 83.8 | 87.2 |
| 5 | 4_17_115_165_168 | 94.9 | 84.0 | 87.2 |
| 5 | 4_17_108_165_168 | 94.7 | 84.1 | 87.2 |
| 5 | 4_17_156_165_168 | 94.9 | 84.0 | 87.2 |
| 5 | 4_17_165_168_249 | 95.5 | 83.6 | 87.2 |
| 5 | 4_17_131_165_168 | 95.3 | 83.7 | 87.2 |
| 5 | 4_17_165_168_304 | 94.9 | 83.9 | 87.2 |
| 5 | 4_17_157_165_168 | 95.1 | 83.8 | 87.2 |
| 5 | 4_17_165_168_318 | 94.9 | 83.8 | 87.1 |
| 5 | 4_17_74_165_168 | 94.3 | 84.1 | 87.1 |
| 5 | 4_17_165_168_216 | 94.9 | 83.6 | 87.0 |
| 5 | 4_17_165_168_309 | 94.5 | 83.8 | 87.0 |
| 5 | 4_17_165_168_236 | 94.7 | 83.7 | 87.0 |
| 5 | 4_17_165_168_324 | 95.3 | 83.5 | 87.0 |
| 5 | 9_17_159_165_168 | 94.7 | 83.4 | 86.8 |
| 5 | 4_17_115_130_168 | 92.7 | 84.3 | 86.8 |
| 5 | 4_17_111_115_168 | 91.9 | 84.6 | 86.8 |
| 5 | 9_17_165_168_173 | 95.1 | 83.1 | 86.7 |
| 5 | 4_17_115_160_168 | 92.1 | 84.3 | 86.6 |
| 5 | 4_17_115_168_246 | 94.1 | 83.5 | 86.6 |
| 5 | 4_17_115_168_201 | 92.3 | 84.1 | 86.5 |
| 5 | 4_17_115_168_217 | 92.9 | 83.8 | 86.5 |
| 5 | 2_4_17_115_168 | 92.5 | 83.6 | 86.3 |
| 5 | 4_17_115_140_168 | 90.9 | 84.1 | 86.1 |
| 5 | 4_17_102_115_168 | 92.1 | 83.3 | 85.9 |

TABLE 7-7

| Combined gene number | SEQ ID NO: | Sensitivity | Specificity | Accuracy |
|---|---|---|---|---|
| 3 | 121_130_164 | 97.6 | 82.3 | 86.9 |
| 3 | 18_121_164 | 98.6 | 81.6 | 86.7 |
| 3 | 121_164_168 | 97.8 | 80.9 | 85.9 |
| 3 | 121_164_328 | 96.3 | 81.1 | 85.6 |
| 3 | 121_164_211 | 97.6 | 80.2 | 85.4 |
| 3 | 95_121_164 | 98.4 | 79.7 | 85.3 |
| 3 | 6_121_165 | 96.3 | 80.3 | 85.1 |
| 4 | 18_121_130_164 | 98.6 | 84.4 | 88.6 |
| 4 | 18_121_164_255 | 98.0 | 84.2 | 88.4 |
| 4 | 18_121_164_201 | 98.2 | 83.0 | 87.6 |
| 4 | 18_121_151_164 | 98.2 | 83.1 | 87.6 |
| 4 | 18_95_121_164 | 99.0 | 81.5 | 86.8 |
| 4 | 18_107_121_164 | 98.6 | 81.6 | 86.7 |
| 4 | 2_121_165_168 | 95.3 | 82.5 | 86.3 |
| 4 | 18_121_149_165 | 97.1 | 81.7 | 86.3 |
| 4 | 13_18_121_165 | 99.2 | 80.4 | 86.1 |
| 5 | 18_121_130_136_164 | 98.6 | 84.6 | 88.8 |
| 5 | 18_121_130_164_314 | 98.4 | 84.6 | 88.8 |

TABLE 7-7-continued

| Combined gene number | SEQ ID NO: | Validation cohort | | |
|---|---|---|---|---|
| | | Sensitivity | Specificity | Accuracy |
| 5 | 18_114_121_130_164 | 99.0 | 84.3 | 88.7 |
| 5 | 18_121_130_164_214 | 98.6 | 84.5 | 88.7 |
| 5 | 18_121_130_164_193 | 98.8 | 84.3 | 88.6 |
| 5 | 18_121_130_164_320 | 98.6 | 84.4 | 88.6 |
| 5 | 18_121_130_164_301 | 98.6 | 84.3 | 88.6 |
| 5 | 18_121_130_144_164 | 98.6 | 84.4 | 88.6 |
| 5 | 18_121_130_164_168 | 98.4 | 84.5 | 88.6 |
| 5 | 18_121_130_164_205 | 98.4 | 84.4 | 88.6 |
| 5 | 18_121_130_158_164 | 98.8 | 84.1 | 88.5 |
| 5 | 18_121_130_164_260 | 98.8 | 84.1 | 88.5 |
| 5 | 18_106_121_130_164 | 98.8 | 84.1 | 88.5 |
| 5 | 18_121_130_164_318 | 98.6 | 84.2 | 88.5 |
| 5 | 18_121_130_164_286 | 98.6 | 84.1 | 88.5 |
| 5 | 18_121_130_164_315 | 98.6 | 84.2 | 88.5 |
| 5 | 18_121_130_164_237 | 98.6 | 84.2 | 88.5 |
| 5 | 18_121_130_164_184 | 98.6 | 84.2 | 88.5 |
| 5 | 18_121_130_164_270 | 98.4 | 84.2 | 88.5 |
| 5 | 18_121_130_164_309 | 98.4 | 84.2 | 88.5 |
| 5 | 18_121_130_164_278 | 98.4 | 84.3 | 88.5 |
| 5 | 18_82_121_130_164 | 98.4 | 84.2 | 88.5 |
| 5 | 18_23_121_130_164 | 98.4 | 84.2 | 88.5 |
| 5 | 18_121_130_164_189 | 98.4 | 84.3 | 88.5 |
| 5 | 18_121_130_152_164 | 98.2 | 84.3 | 88.5 |
| 5 | 18_121_130_164_213 | 98.2 | 84.3 | 88.5 |
| 5 | 18_121_130_164_229 | 98.2 | 84.3 | 88.5 |
| 5 | 18_57_121_130_164 | 98.2 | 84.4 | 88.5 |
| 5 | 18_121_130_142_164 | 98.8 | 83.9 | 88.4 |
| 5 | 18_121_130_155_164 | 98.6 | 84.0 | 88.4 |
| 5 | 18_39_121_130_164 | 98.4 | 84.1 | 88.4 |
| 5 | 18_33_121_130_164 | 98.4 | 84.1 | 88.4 |
| 5 | 18_121_126_130_164 | 98.4 | 84.1 | 88.4 |
| 5 | 18_121_130_164_319 | 98.4 | 84.1 | 88.4 |
| 5 | 18_22_121_130_164 | 98.2 | 84.1 | 88.4 |
| 5 | 18_59_121_130_164 | 98.2 | 84.1 | 88.4 |
| 5 | 18_27_121_130_164 | 97.8 | 84.4 | 88.4 |
| 5 | 18_121_130_164_201 | 98.2 | 84.1 | 88.3 |
| 5 | 18_19_121_130_164 | 98.4 | 83.9 | 88.2 |
| 5 | 18_95_121_164_188 | 99.0 | 83.0 | 87.8 |
| 5 | 13_18_121_130_165 | 98.4 | 82.5 | 87.2 |

Example 3

<Comparison of miRNA Expression Levels in Serum Between Lung Cancer Patient and Healthy Subject>

In this Example, miRNA expression levels in sera were compared between lung cancer patients and healthy subjects in order to verify the reliability of the gene markers obtained in Examples 1 and 2. In this experiment, because higher statistical reliability regarding gene expression levels could be obtained when a larger number of samples is used, all the samples in which the gene expression levels were measured in the preceding Reference Examples were used (Table 11a). To be more specific, firstly, the miRNA expression levels of 1,694 lung cancer patients and 4,660 healthy subjects obtained in the preceding Reference Examples were combined and normalized by global normalization. Secondly, in order to evaluate diagnostic markers with higher reliability, only genes having the expression level of $2^6$ or higher in 50% or more of the samples in either of the lung cancer patient group or the healthy subject group, were selected. Thirdly, in order to evaluate a gene whose expression level significantly differs in statistics between a lung cancer patient group and the healthy subject group, a two-sided t-test assuming equal variance was carried out, and then, a P value after the Bonferroni correction was calculated. Forthly, in order to evaluate whether to be easily affected by noise at the time of measurement, an absolute value of the difference (fold change) in gene expression level, which is obtained by logarithmic conversion between the lung cancer patient group and the healthy subject group, was calculated. Genes having a P value after the correction which was 0.05 or less and having an absolute value of fold change which was 0.5 or more, were extracted as genes varying in expression. The results are shown in Table 8.

TABLE 8

| SEQ ID NO: | P value after Bonferroni correction | Fold change of lung cancer patient to healthy subject |
|---|---|---|
| 1 | <1E-308 | 2.02 |
| 2 | <1E-308 | 2.95 |
| 3 | <1E-308 | 1.63 |
| 7 | <1E-308 | 0.81 |
| 10 | 5.30E-284 | 0.67 |
| 12 | <1E-308 | 2.04 |
| 13 | <1E-308 | 7.81 |
| 14 | 4.44E-148 | -0.52 |
| 15 | <1E-308 | 1.00 |
| 16 | <1E-308 | 1.41 |
| 17 | <1E-308 | 0.86 |
| 18 | <1E-308 | 0.85 |
| 19 | 4.47E-85 | 0.65 |
| 20 | <1E-308 | 1.29 |
| 21 | <1E-308 | 1.85 |
| 22 | <1E-308 | 3.64 |
| 23 | <1E-308 | 1.60 |
| 25 | <1E-308 | 3.01 |
| 26 | <1E-308 | 1.87 |
| 27 | <1E-308 | 3.01 |
| 29 | <1E-308 | 1.91 |
| 30 | <1E-308 | 4.83 |
| 31 | <1E-308 | 3.23 |
| 33 | <1E-308 | 1.53 |
| 34 | 3.29E-303 | 0.82 |
| 35 | <1E-308 | -0.54 |
| 36 | 2.02E-291 | 0.99 |
| 37 | <1E-308 | 1.21 |
| 38 | <1E-308 | 1.53 |
| 40 | <1E-308 | 3.15 |
| 42 | <1E-308 | -0.94 |
| 43 | <1E-308 | 2.13 |
| 44 | <1E-308 | 1.95 |
| 45 | <1E-308 | 2.38 |
| 46 | <1E-308 | 0.58 |
| 47 | <1E-308 | 1.30 |
| 50 | <1E-308 | 4.63 |
| 51 | <1E-308 | 1.09 |
| 55 | <1E-308 | 0.68 |
| 56 | <1E-308 | 1.19 |
| 57 | <1E-308 | 3.71 |
| 58 | <1E-308 | -0.92 |
| 59 | <1E-308 | 1.27 |
| 60 | <1E-308 | 3.87 |
| 64 | <1E-308 | 4.03 |
| 65 | <1E-308 | 0.58 |
| 66 | <1E-308 | 1.62 |
| 67 | <1E-308 | 0.60 |
| 68 | <1E-308 | 3.95 |
| 69 | <1E-308 | 3.20 |
| 70 | <1E-308 | 4.36 |
| 71 | <1E-308 | 0.81 |
| 72 | <1E-308 | 3.83 |
| 73 | <1E-308 | -2.42 |
| 74 | <1E-308 | 0.97 |
| 75 | <1E-308 | 3.76 |
| 76 | <1E-308 | 1.16 |
| 78 | <1E-308 | 4.29 |
| 79 | 7.77E-294 | 0.77 |
| 80 | <1E-308 | 2.72 |
| 81 | <1E-308 | 1.08 |
| 84 | <1E-308 | -0.80 |
| 85 | <1E-308 | 3.89 |
| 86 | 4.63E-209 | 0.57 |
| 87 | <1E-308 | 3.01 |
| 90 | <1E-308 | 0.67 |
| 92 | <1E-308 | 0.86 |

TABLE 8-continued

| SEQ ID NO: | P value after Bonferroni correction | Fold change of lung cancer patient to healthy subject |
|---|---|---|
| 94 | <1E−308 | 2.29 |
| 95 | <1E−308 | 0.75 |
| 96 | <1E−308 | 3.61 |
| 97 | <1E−308 | 1.15 |
| 98 | <1E−308 | 3.35 |
| 99 | <1E−308 | 1.22 |
| 101 | <1E−308 | 0.87 |
| 102 | <1E−308 | 0.58 |
| 103 | <1E−308 | 0.85 |
| 104 | <1E−308 | 0.78 |
| 105 | <1E−308 | 0.75 |
| 106 | <1E−308 | 1.77 |
| 107 | <1E−308 | 1.61 |
| 109 | <1E−308 | −0.58 |
| 110 | <1E−308 | 0.89 |
| 111 | <1E−308 | 0.72 |
| 113 | 8.52E−107 | 0.52 |
| 114 | 3.97E−267 | 0.63 |
| 115 | <1E−308 | 1.51 |
| 118 | <1E−308 | −0.80 |
| 120 | <1E−308 | 1.56 |
| 122 | <1E−308 | 2.26 |
| 124 | <1E−308 | 1.24 |
| 127 | <1E−308 | 1.40 |
| 128 | <1E−308 | 1.05 |
| 130 | <1E−308 | 0.55 |
| 131 | <1E−308 | −1.09 |
| 134 | <1E−308 | 1.38 |
| 135 | <1E−308 | 3.67 |
| 136 | <1E−308 | −1.41 |
| 137 | <1E−308 | 2.98 |
| 138 | 9.35E−164 | 0.54 |
| 140 | 8.27E−232 | 0.63 |
| 142 | 7.60E−293 | 0.73 |
| 143 | <1E−308 | 2.39 |
| 144 | <1E−308 | 1.12 |
| 145 | <1E−308 | −1.21 |
| 148 | <1E−308 | 1.55 |
| 149 | <1E−308 | 3.33 |
| 150 | <1E−308 | 4.64 |
| 153 | <1E−308 | 2.85 |
| 159 | <1E−308 | 1.19 |
| 162 | <1E−308 | 2.23 |
| 163 | <1E−308 | 3.49 |
| 164 | <1E−308 | 3.66 |
| 165 | <1E−308 | 1.98 |
| 166 | 3.76E−62 | −0.65 |
| 167 | 2.34E−248 | 0.61 |
| 170 | <1E−308 | 4.76 |
| 172 | <1E−308 | 1.30 |
| 173 | <1E−308 | 1.13 |
| 175 | <1E−308 | −1.26 |
| 177 | <1E−308 | 1.68 |
| 179 | <1E−308 | 1.49 |
| 180 | <1E−308 | 0.90 |
| 181 | <1E−308 | 1.16 |
| 182 | <1E−308 | 2.32 |
| 183 | <1E−308 | −0.85 |
| 184 | <1E−308 | −0.69 |
| 185 | <1E−308 | 1.96 |
| 186 | <1E−308 | −0.95 |
| 187 | <1E−308 | 1.14 |
| 188 | <1E−308 | 4.99 |
| 190 | <1E−308 | 4.22 |
| 193 | <1E−308 | 0.65 |
| 195 | <1E−308 | 5.97 |
| 196 | <1E−308 | 4.90 |
| 197 | <1E−308 | 5.16 |
| 198 | <1E−308 | 3.04 |
| 199 | <1E−308 | 2.28 |
| 200 | <1E−308 | 0.74 |
| 201 | <1E−308 | 1.42 |
| 202 | <1E−308 | 0.72 |
| 206 | <1E−308 | 2.54 |
| 207 | <1E−308 | 2.68 |
| 209 | <1E−308 | 1.03 |
| 211 | <1E−308 | 1.06 |
| 214 | <1E−308 | 1.09 |
| 215 | <1E−308 | −1.12 |
| 217 | <1E−308 | 1.32 |
| 220 | <1E−308 | 2.71 |
| 221 | <1E−308 | 0.79 |
| 222 | <1E−308 | 0.64 |
| 225 | <1E−308 | 3.19 |
| 226 | <1E−308 | 3.05 |
| 229 | 4.55E−203 | −0.63 |
| 231 | <1E−308 | 5.80 |
| 232 | <1E−308 | 1.10 |
| 235 | 7.77E−196 | −0.55 |
| 236 | <1E−308 | 1.52 |
| 239 | <1E−308 | 0.95 |
| 246 | <1E−308 | 1.36 |
| 247 | <1E−308 | 1.17 |
| 249 | 3.06E−90 | −0.65 |
| 250 | <1E−308 | 0.81 |
| 251 | <1E−308 | 1.01 |
| 255 | <1E−308 | 3.10 |
| 256 | 3.79E−269 | 0.56 |
| 257 | <1E−308 | 1.99 |
| 259 | <1E−308 | 1.72 |
| 260 | <1E−308 | 3.26 |
| 261 | <1E−308 | 1.88 |
| 262 | <1E−308 | 1.54 |
| 263 | <1E−308 | 3.49 |
| 265 | 2.97E−266 | 0.55 |
| 267 | <1E−308 | 0.91 |
| 268 | 1.19E−234 | 0.55 |
| 269 | <1E−308 | 0.77 |
| 272 | <1E−308 | 1.43 |
| 273 | 1.04E−304 | 0.57 |
| 274 | <1E−308 | −0.92 |
| 276 | <1E−308 | 0.73 |
| 277 | 6.62E−218 | 0.64 |
| 278 | <1E−308 | −1.41 |
| 279 | <1E−308 | −0.83 |
| 280 | 1.54E−225 | 0.57 |
| 281 | <1E−308 | 1.05 |
| 282 | <1E−308 | −0.50 |
| 284 | 2.35E−278 | −0.60 |
| 285 | <1E−308 | 1.67 |
| 286 | <1E−308 | −1.27 |
| 287 | <1E−308 | 1.31 |
| 290 | <1E−308 | 1.08 |
| 291 | <1E−308 | 1.57 |
| 293 | <1E−308 | −0.51 |
| 294 | 2.90E−300 | 0.64 |
| 295 | <1E−308 | 1.12 |
| 296 | 5.92E−276 | −0.64 |
| 297 | 6.60E−269 | −0.60 |
| 298 | <1E−308 | 0.87 |
| 299 | <1E−308 | 2.46 |
| 300 | <1E−308 | 2.52 |
| 301 | <1E−308 | 0.87 |
| 303 | <1E−308 | 0.88 |
| 304 | <1E−308 | −1.68 |
| 305 | <1E−308 | 0.87 |
| 306 | <1E−308 | 1.06 |
| 307 | <1E−308 | 0.79 |
| 309 | <1E−308 | 3.01 |
| 311 | <1E−308 | 5.07 |
| 312 | <1E−308 | 4.83 |
| 313 | <1E−308 | 1.14 |
| 314 | <1E−308 | 0.75 |
| 315 | <1E−308 | 2.69 |
| 316 | <1E−308 | 1.63 |
| 317 | <1E−308 | 0.97 |
| 318 | <1E−308 | 3.19 |
| 319 | <1E−308 | 5.62 |
| 320 | <1E−308 | 1.02 |
| 321 | <1E−308 | 1.24 |
| 322 | <1E−308 | 2.07 |
| 324 | <1E−308 | −1.84 |

TABLE 8-continued

| SEQ ID NO: | P value after Bonferroni correction | Fold change of lung cancer patient to healthy subject |
|---|---|---|
| 327 | 5.87E−261 | 1.52 |
| 328 | <1E−308 | 2.66 |
| 329 | <1E−308 | 3.30 |

Example 4

<Comparison of miRNA Expression Levels in Serum Between Lung Cancer Patient and Benign Bone and Soft Tissue Tumor Patients and Benign Breast Disease Patients>

In this Example, miRNA expression levels in sera were compared between lung cancer patients and benign bone and soft tissue tumor patients and benign breast disease patients in order to verify the reliability of the gene markers obtained in Examples 1 and 2. In this experiment, because higher statistical reliability regarding gene expression levels could be obtained when a larger number of samples is used, all the samples in which the gene expression levels were measured in the preceding Reference Examples were used (Table 11a). To be more specific, firstly, the miRNA expression levels of 1,694 lung cancer patients and 368 benign bone and soft tissue tumor patients and benign breast disease patients obtained in the preceding Reference Examples were combined and normalized by global normalization.

Secondly, in order to evaluate diagnostic markers with higher reliability, only genes having the expression level of $2^6$ or higher in 50% or more of the samples in either of the group of lung cancer patients or the group of benign bone and soft tissue tumor patients and benign breast disease patients, were selected. Thirdly, in order to evaluate a gene whose expression level significantly differs in statistics between the group of lung cancer patients and the group of benign bone and soft tissue tumor patients and benign breast disease patients, a two-sided t-test assuming equal variance was carried out, and then, a P value after the Bonferroni correction was calculated. Forthly, in order to evaluate whether to be easily affected by noise at the time of measurement, an absolute value of the difference (fold change) in gene expression level, which is obtained by logarithmic conversion between the group of lung cancer patients and the group of benign bone and soft tissue tumor patients and benign breast disease patients, was calculated. A gene having a P value after the correction which was 0.05 or less and having an absolute value of fold change which was 0.5 or more, was extracted as a gene varying in expression. The results are shown in Table 9.

TABLE 9

| SEQ ID NO: | P value after Bonferroni correction | Fold change of lung cancer patient to benign bone and soft tissue tumor patients and benign breast disease patients |
|---|---|---|
| 1 | 2.39E−129 | 0.94 |
| 2 | 1.31E−199 | 2.34 |
| 3 | 7.47E−167 | 1.49 |
| 4 | 3.64E−68 | −1.48 |
| 8 | 2.49E−75 | 1.03 |
| 9 | 9.04E−40 | −1.17 |
| 11 | 8.51E−43 | −0.55 |
| 12 | 7.12E−163 | 1.24 |
| 13 | 1.57E−149 | 2.56 |
| 15 | 1.26E−108 | 1.26 |
| 20 | 5.02E−73 | 1.03 |
| 22 | 2.96E−67 | 1.33 |
| 23 | 2.55E−128 | 1.57 |
| 24 | 7.59E−83 | −0.55 |
| 25 | 1.04E−58 | 1.12 |
| 27 | 1.98E−75 | 1.76 |
| 29 | 2.82E−175 | 1.91 |
| 30 | 2.35E−57 | 1.78 |
| 31 | 9.31E−74 | 1.14 |
| 32 | 3.51E−288 | −0.51 |
| 33 | 2.39E−102 | 1.50 |
| 34 | 1.65E−117 | 0.87 |
| 36 | 2.38E−48 | 0.85 |
| 40 | 7.11E−197 | 2.24 |
| 43 | 4.45E−73 | 0.88 |
| 44 | 6.93E−34 | 0.88 |
| 45 | 1.20E−84 | 0.83 |
| 47 | 2.20E−55 | 0.84 |
| 48 | 7.93E−64 | 0.79 |
| 50 | 4.47E−86 | 1.69 |
| 56 | 6.73E−93 | 0.90 |
| 57 | 6.51E−65 | 1.24 |
| 59 | 1.22E−39 | 0.85 |
| 60 | 6.33E−158 | 2.26 |
| 64 | 8.48E−18 | 1.00 |
| 66 | 1.35E−144 | 0.77 |
| 68 | 4.04E−101 | 1.61 |
| 69 | 1.85E−27 | 1.00 |
| 70 | 5.91E−114 | 1.85 |
| 72 | 1.62E−91 | 1.67 |
| 73 | 2.55E−32 | 0.62 |
| 75 | 2.81E−85 | 1.55 |
| 76 | 4.11E−23 | 0.59 |
| 78 | 2.75E−73 | 1.79 |
| 79 | 1.95E−45 | 0.85 |
| 80 | 1.21E−150 | 1.33 |
| 85 | <1E−308 | 4.19 |
| 87 | 2.13E−115 | 1.66 |
| 94 | 7.34E−131 | 1.46 |
| 96 | 8.87E−95 | 1.42 |
| 98 | 4.83E−171 | 2.02 |
| 99 | 1.02E−39 | 0.84 |
| 102 | 6.67E−165 | 1.11 |
| 106 | 5.24E−29 | 0.50 |
| 107 | 7.47E−61 | 0.67 |
| 110 | 5.98E−82 | 0.53 |
| 114 | 2.73E−20 | 0.52 |
| 115 | 8.65E−115 | 0.54 |
| 120 | 3.91E−46 | 0.81 |
| 122 | 4.73E−52 | 1.17 |
| 126 | 1.19E−154 | −0.53 |
| 128 | 9.40E−33 | 0.64 |
| 134 | 1.36E−41 | 0.72 |
| 135 | 5.46E−172 | 2.32 |
| 136 | 4.38E−35 | −0.70 |
| 137 | <1E−308 | 1.71 |
| 138 | 9.15E−27 | 0.64 |
| 139 | 9.22E−34 | 0.62 |
| 140 | 1.08E−44 | 0.74 |
| 143 | 2.03E−70 | 1.52 |
| 144 | 3.76E−22 | 0.62 |
| 148 | 1.34E−47 | 0.66 |
| 149 | 8.40E−110 | 1.76 |
| 150 | 1.98E−89 | 1.68 |
| 153 | 1.39E−161 | 2.04 |
| 159 | 1.11E−50 | 0.74 |
| 163 | 1.05E−120 | 1.98 |
| 164 | <1E−308 | 2.51 |
| 165 | 9.44E−220 | 1.28 |
| 166 | 5.85E−66 | −1.73 |
| 167 | 6.22E−235 | 1.31 |

TABLE 9-continued

| SEQ ID NO: | P value after Bonferroni correction | Fold change of lung cancer patient to benign bone and soft tissue tumor patients and benign breast disease patients |
|---|---|---|
| 170 | 7.90E−67 | 1.84 |
| 172 | 2.04E−94 | 1.31 |
| 173 | 9.00E−61 | 0.60 |
| 179 | 5.55E−45 | 0.55 |
| 181 | 7.23E−54 | 0.81 |
| 182 | 1.03E−104 | 0.81 |
| 185 | 1.24E−82 | 1.06 |
| 186 | 8.97E−59 | 0.86 |
| 188 | <1E−308 | 6.00 |
| 189 | 6.66E−102 | 1.18 |
| 190 | 2.48E−177 | 2.08 |
| 194 | 3.50E−122 | 0.67 |
| 195 | 6.34E−123 | 1.89 |
| 196 | 1.24E−104 | 2.05 |
| 197 | 5.84E−97 | 2.35 |
| 198 | 1.14E−114 | 1.54 |
| 199 | 8.95E−90 | 0.93 |
| 201 | 1.58E−195 | 1.24 |
| 202 | 6.22E−55 | 0.58 |
| 206 | 2.35E−30 | 0.56 |
| 209 | 2.52E−75 | 0.52 |
| 213 | 1.88E−68 | −0.66 |
| 217 | 3.25E−133 | 0.94 |
| 220 | 2.19E−173 | 1.30 |
| 225 | 4.62E−84 | 1.58 |
| 226 | 8.00E−184 | 1.32 |
| 228 | 1.25E−59 | 1.42 |
| 231 | <1E−308 | 4.03 |
| 235 | 2.68E−20 | 0.52 |
| 241 | 2.57E−182 | −0.57 |
| 244 | 1.26E−14 | 0.53 |
| 249 | 2.46E−25 | −0.78 |
| 250 | 2.66E−89 | 0.58 |
| 255 | 8.95E−34 | 0.58 |
| 257 | 5.57E−54 | 1.34 |
| 260 | 4.52E−157 | 1.97 |
| 262 | 3.71E−31 | 0.53 |
| 263 | 4.51E−89 | 1.03 |
| 285 | 6.31E−83 | 1.16 |
| 287 | 2.36E−295 | 1.36 |
| 289 | 5.59E−114 | 1.04 |
| 291 | 4.37E−44 | 0.55 |
| 294 | 2.77E−20 | 0.51 |
| 299 | 6.64E−135 | 1.05 |
| 303 | 7.57E−59 | 0.95 |
| 311 | 2.95E−83 | 2.16 |
| 312 | 3.35E−238 | 2.89 |
| 313 | 1.44E−53 | 0.76 |
| 315 | 1.73E−20 | 0.68 |
| 319 | 7.52E−85 | 1.75 |
| 320 | 3.60E−29 | 0.71 |
| 322 | 9.40E−116 | 1.07 |
| 325 | 3.44E−130 | −0.55 |
| 327 | 2.41E−29 | 0.90 |
| 328 | 2.19E−125 | 1.08 |
| 329 | 2.60E−73 | 1.31 |

Example 5

<Comparison of miRNA Expression Levels in Serum Between Lung Cancer Patient and Patient Having a Cancer Other than Lung Cancer>

In this Example, miRNA expression levels in sera were compared between lung cancer patients and other cancer patients in order to verify the reliability of the gene markers obtained in Examples 1 and 2. In this experiment, because higher statistical reliability regarding gene expression levels could be obtained when a larger number of samples is used, all the samples in which the gene expression levels were measured in the preceding Reference Examples, were used (Table 11a). To be specific, firstly, the miRNA expression levels of 1,694 lung cancer patients and 4,147 other cancer patients obtained in the preceding Reference Examples were combined and normalized by global normalization. Secondly, in order to evaluate diagnostic markers with higher reliability, only genes having the expression level of $2^6$ or higher in 50% or more of the samples in either of the group of lung cancer patients or the group of other cancer patients, were selected. Thirdly, in order to evaluate a gene whose gene expression level significantly differs in statistics between the group of lung cancer patients and the group of other cancer patients, a two-sided t-test assuming equal variance was carried out, and then, a P value after the Bonferroni correction was calculated. Forthly, in order to evaluate whether to be easily affected by noise at the time of measurement, an absolute value of the difference (fold change) in gene expression level, which is obtained by logarithmic conversion between the group of lung cancer patients and the group of patients having a cancer other than lung cancer, was calculated. A gene having a P value after the correction which was 0.05 or less and having an absolute value of fold change which was 0.5 or more, was extracted as a gene varying in expression. The results are shown in Table 10.

TABLE 10

| SEQ ID NO: | P value after Bonferroni correction | Fold change of lung cancer patient to patient having cancer other than lung cancer |
|---|---|---|
| 1 | 4.58E−123 | 0.55 |
| 2 | 1.88E−145 | 1.27 |
| 3 | 6.31E−96 | 0.66 |
| 4 | 1.76E−150 | −1.08 |
| 9 | 8.54E−95 | −0.93 |
| 13 | 1.21E−114 | 1.38 |
| 20 | 1.20E−69 | 0.57 |
| 23 | 2.52E−48 | 0.53 |
| 29 | 3.77E−99 | 0.77 |
| 30 | 3.12E−43 | 0.83 |
| 33 | 1.61E−53 | 0.57 |
| 40 | 8.43E−82 | 0.78 |
| 50 | 2.76E−40 | 0.67 |
| 60 | 7.34E−122 | 1.10 |
| 64 | 4.67E−30 | 0.64 |
| 68 | 4.99E−91 | 0.92 |
| 69 | 9.36E−39 | 0.58 |
| 70 | 8.65E−59 | 0.77 |
| 72 | 5.35E−106 | 0.91 |
| 75 | 2.31E−52 | 0.67 |
| 78 | 3.67E−39 | 0.73 |
| 87 | 6.09E−57 | 0.66 |
| 94 | 1.00E−113 | 0.90 |
| 96 | 3.83E−68 | 0.65 |
| 98 | 6.51E−115 | 0.93 |
| 102 | 4.09E−92 | 0.51 |
| 120 | 2.93E−63 | 0.61 |
| 122 | 5.74E−73 | 0.76 |
| 135 | 2.97E−118 | 1.08 |
| 140 | 1.69E−67 | 0.56 |
| 143 | 1.34E−60 | 0.74 |
| 149 | 8.83E−80 | 0.88 |
| 150 | 2.47E−76 | 0.89 |
| 153 | 3.64E−76 | 0.80 |
| 163 | 1.53E−95 | 0.91 |
| 164 | 5.78E−212 | 0.92 |
| 165 | 2.37E−104 | 0.56 |
| 166 | 2.06E−83 | −1.03 |
| 170 | 9.80E−60 | 0.85 |
| 188 | 1.53E−44 | 0.57 |
| 195 | 1.39E−75 | 0.83 |
| 196 | 5.59E−82 | 1.00 |

TABLE 10-continued

| SEQ ID NO: | P value after Bonferroni correction | Fold change of lung cancer patient to patient having cancer other than lung cancer |
| --- | --- | --- |
| 197 | 1.10E−77 | 1.09 |
| 198 | 1.49E−75 | 0.74 |
| 220 | 6.63E−89 | 0.56 |
| 225 | 3.64E−51 | 0.67 |
| 228 | 1.25E−100 | 0.86 |
| 231 | 2.36E−114 | 1.27 |
| 260 | 8.14E−106 | 0.92 |
| 263 | 6.10E−65 | 0.66 |
| 311 | 6.14E−102 | 1.34 |
| 312 | 9.19E−63 | 0.80 |
| 319 | 4.08E−58 | 0.97 |
| 327 | 4.54E−51 | 0.69 |
| 329 | 4.55E−101 | 0.92 |

As shown in the above Examples, the kit, device and method of the present invention can detect lung adenocarcinoma, lung squamous cell carcinoma, large cell lung carcinoma, small cell lung carcinoma and other lung cancers with higher sensitivity than the existing tumor markers and therefore permit early detection of lung cancer. As a result, a treatment such as a chemotherapy, a radiotherapy, an immunotherapy, a molecular targeted therapy, or surgery with a high degree of probability for complete therapy can be applied early, thereby significantly improving a survival rate.

INDUSTRIAL APPLICABILITY

According to the present invention, various histological types or stages of progression of lung cancer can be effectively detected by a simple and inexpensive method. This enables early detection, diagnosis and treatment of lung cancer. Also, the method of the present invention enables less-invasive detection of lung cancer using patient's blood and therefore lung cancer can be simply and quickly detected.

All publications, patents, and patent applications cited herein are incorporated herein by reference in their entirety.

The invention claimed is:

1. A method for detecting and treating or performing a diagnostic procedure for lung cancer, comprising: determining an expression level of hsa-miR-4730 in a sample from a human subject using a nucleic acid(s) capable of specifically binding to hsa-miR-4730, or using a kit or device comprising a nucleic acid(s) capable of specifically binding to hsa-miR-4730, wherein the determining comprises the following steps of:
(a) isolating a sample from a human subject comprising has-miR-4730
(b) contacting has-miR-4730 in the sample or complementary polynucleotide(s) thereof prepared from has-miR04730 with the nucleic acids;
(c) measuring an expression level of hsa-miR-4730;
(d) comparing the expression level of hsa-miR-4730 measured in the step (c) to a control expression level of hsa-miR-4730 in a control sample from a healthy human subject measured in the same way as in the step (c) to allow for diagnosis of lung cancer;
(e) detecting a decreased level of hsa-miR-4730 in the sample from the human subject as compared to the control expression level of hsa-miR-4730 from the sample from the human subject that does not have lung cancer, wherein the decreased level of hsa-miR-4730 indicates that the human subject has lung cancer; and (f) treating the human subject having lung cancer or performing a diagnostic procedure on the human subject having lung cancer;

wherein the sample is blood, serum, or plasma;

wherein the treatment comprises chemotherapy, radiotherapy, immunotherapy, molecular targeted therapy, surgery or a combination thereof; and wherein the diagnostic procedure comprises an imaging test method selected from the group consisting of a chest X-ray examination, CT examination, MRI examination, and PET examination; a pathological examination method selected from the group consisting of sputum cytology, pleural fluid analysis, bronchoscopy, and percutaneous needle biopsy; or a combination thereof.

2. The method according to claim 1, wherein the nucleic acid(s) is a polynucleotide(s) selected from the group consisting of the following polynucleotides (a) to (e):
(a) a polynucleotide consisting of a nucleotide sequence of SEQ ID NO: 73, or a nucleotide sequence derived from the nucleotide sequence in which the nucleic acid u is replaced with t, a variant thereof, a derivative thereof, or a fragment thereof comprising 15 or more consecutive nucleotides;
(b) a polynucleotide comprising a nucleotide sequence of SEQ ID NO: 73;
(c) a polynucleotide consisting of a nucleotide sequence complementary to a nucleotide sequence of SEQ ID NO: 73, or a nucleotide sequence derived from the nucleotide sequence in which the nucleic acid u is replaced with t, a variant thereof, a derivative thereof, or a fragment thereof comprising 15 or more consecutive nucleotides;

(d) a polynucleotide comprising a nucleotide sequence complementary to a nucleotide sequence of SEQ ID NO: 73, or a nucleotide sequence derived from the nucleotide sequence in which the nucleic acid u is replaced with t; and (e) a polynucleotide hybridizing under stringent conditions to any of the polynucleotides (a) to (d).

3. The method according to claim 1, wherein the method further comprises:

determining an expression level(s) of one or more other miRNA(s) selected from the following other lung cancer markers: miR-6787-5p, miR-920, miR-3622a-5p, miR-1185-1-3p, miR-4327, miR-5739, miR-937-5p, miR-1181, miR-1185-2-3p, miR-1193, miR-1207-5p, miR-1238-5p, miR-1246, miR-1249-5p, miR-1292-3p, miR-1469, miR-1470, miR-197-5p, miR-208a-5p, miR-2110, miR-211-3p, miR-3122, miR-3141, miR-3156-5p, miR-3158-5p, miR-3160-5p, miR-3180-3p, miR-3191-3p, miR-3194-3p, miR-320b, miR-328-5p, miR-3610, miR-3619-3p, miR-3620-5p, miR-370-3p, miR-373-5p, miR-3917, miR-3937, miR-4259, miR-4281, miR-4294, miR-4419b, miR-4428, miR-4429, miR-4433a-3p, miR-4447, miR-4449, miR-4459, miR-4480, miR-4485-5p, miR-4486, miR-4488, miR-4489, miR-4505, miR-4513, miR-4515, miR-4530, miR-4535, miR-4635, miR-4640-5p, miR-4646-5p, miR-4656, miR-4663, miR-4665-5p, miR-4706, miR-4707-5p, miR-4708-3p, miR-4710, miR-4718, miR-4722-5p, miR-4727-3p, miR-4734, miR-4740-5p, miR-4747-3p, miR-4749-5p, miR-4755-3p, miR-4763-5p, miR-4787-3p, miR-5008-5p, miR-5010-5p, miR-504-3p, miR-5090, miR-5100, miR-5196-5p, miR-551b-5p, miR-557, miR-5787, miR-6090, miR-6124, miR-6132, miR-6510-5p, miR-6511b-5p, miR-6515-3p, miR-654-5p, miR-658, miR-668-5p, miR-6722-5p, miR-6724-5p, miR-6729-3p, miR-6737-5p, miR-6756-5p, miR-6762-5p, miR-6763-3p, miR-6766-5p, miR-6769a-5p, miR-6771-5p, miR-6786-5p, miR-6789-5p, miR-6794-5p, miR-6796-3p, miR-6797-5p, miR-6800-3p, miR-6802-5p, miR-6803-5p, miR-6805-3p, miR-6805-5p, miR-6807-5p, miR-6812-5p, miR-6819-5p, miR-6822-5p, miR-6824-5p, miR-6826-5p, miR-6850-5p, miR-6858-5p, miR-6861-5p, miR-6880-3p, miR-7107-5p, miR-7109-5p, miR-7114-5p, miR-7704, miR-7846-3p, miR-8052, miR-8060, miR-8071, miR-8073, miR-874-5p, miR-204-3p, miR-3154, miR-3960, miR-4433a-5p, miR-4455, miR-4462, miR-4476, miR-4508, miR-4687-3p, miR-4687-5p, miR-4732-5p, miR-4771, miR-642a-3p, miR-6732-5p, miR-6760-5p, miR-6799-5p, miR-6820-5p, miR-6821-5p, miR-6829-5p, miR-6893-5p, miR-7108-3p, miR-7111-5p, miR-8089, miR-885-3p, miR-92b-3p, miR-1343-3p, miR-6746-5p, miR-422a, miR-187-5p, miR-4632-5p, miR-6791-5p, miR-103a-3p, miR-107, miR-1199-5p, miR-1225-3p, miR-1225-5p, miR-1228-5p, miR-1229-5p, miR-1233-5p, miR-1237-5p, miR-1247-3p, miR-1249-3p, miR-1254, miR-1260b, miR-1268a, miR-1268b, miR-1273g-3p, miR-128-1-5p, miR-128-2-5p, miR-1290, miR-150-3p, miR-17-3p, miR-1908-5p, miR-1909-3p, miR-1914-3p, miR-1915-3p, miR-191-5p, miR-22-3p, miR-23b-3p, miR-24-3p, miR-296-3p, miR-296-5p, miR-3131, miR-3162-5p, miR-3188, miR-3196, miR-3197, miR-320a, miR-342-5p, miR-3621, miR-3648, miR-3656, miR-365a-5p, miR-3665, miR-3679-5p, miR-371a-5p, miR-3940-5p, miR-423-5p, miR-4257, miR-4270, miR-4271, miR-4286, miR-4298, miR-4417, miR-4442, miR-4446-3p, miR-4448, miR-4454, miR-4467, miR-4472, miR-4507, miR-4516, miR-451a, miR-4649-5p, miR-4651, miR-4665-3p, miR-4674, miR-4675, miR-4689, miR-4695-5p, miR-4697-5p, miR-4725-3p, miR-4739, miR-4745-5p, miR-4763-3p, miR-4792, miR-486-3p, miR-5001-5p, miR-5195-3p, miR-550a-5p, miR-5698, miR-6075, miR-6088, miR-6089, miR-6125, miR-6126, miR-614, miR-615-5p, miR-619-5p, miR-638, miR-642b-3p, miR-650, miR-663a, miR-663b, miR-6717-5p, miR-6721-5p, miR-6726-5p, miR-6727-5p, miR-6738-5p, miR-6741-5p, miR-6749-5p, miR-6752-5p, miR-675-5p, miR-6757-5p, miR-6763-5p, miR-6765-5p, miR-6775-5p, miR-6780b-5p, miR-6782-5p, miR-6784-5p, miR-6800-5p, miR-6806-5p, miR-6840-3p, miR-6848-5p, miR-6851-5p, miR-6870-5p, miR-6872-3p, miR-6875-5p, miR-6877-5p, miR-6879-5p, miR-6880-5p, miR-6885-5p, miR-6887-5p, miR-7108-5p, miR-711, miR-7113-3p, miR-744-5p, miR-760, miR-7845-5p, miR-7847-3p, miR-7977, miR-8059, miR-8063, miR-8072, miR-874-3p, miR-92a-2-5p, miR-92b-5p, miR-940, miR-1228-3p, miR-1275, miR-1307-3p, miR-1343-5p, miR-23a-3p, miR-29b-3p, miR-3135b, miR-3185, miR-4532, miR-4690-5p, miR-4758-5p, miR-4783-3p, miR-6131, miR-625-3p, miR-6511a-5p, miR-6765-3p, miR-6816-5p, miR-6825-5p, miR-6845-5p, miR-7150, miR-7641, miR-7975, and miR-92a-3p, or to a complementary strand of the polynucleotide, in the sample from the human subject by the same way as in the steps (a) and (b) using a nucleic acid(s) capable of specifically binding to the miRNA(s), or using a kit or device comprising a nucleic acid(s) capable of specifically binding to the miRNA(s).

4. The method according to claim 1, wherein the measuring in the step (b) is performed by quantitative RT-PCR using the nucleic acid(s) as primer(s).

5. The method according to claim 1, wherein the measuring in the step (b) is performed by hybridization using the nucleic acid(s) as probe(s).

6. The method according to claim 3, wherein the measuring in the step (b) is performed by quantitative RT-PCR using the nucleic acid(s) as primer(s).

7. The method according to claim 3, wherein the measuring in the step (b) is performed by hybridization using the nucleic acid(s) as probe(s).

* * * * *

```
                        SEQUENCE LISTING

Sequence total quantity: 1000
SEQ ID NO: 1            moltype = RNA   length = 22
FEATURE                 Location/Qualifiers
source                  1..22
                        mol_type = transcribed RNA
                        organism = Homo sapiens
SEQUENCE: 1
tggcgggggt agagctggct gc                                                22

SEQ ID NO: 2            moltype = RNA   length = 20
FEATURE                 Location/Qualifiers
source                  1..20
                        mol_type = transcribed RNA
                        organism = Homo sapiens
SEQUENCE: 2
ggggagctgt ggaagcagta                                                   20

SEQ ID NO: 3            moltype = RNA   length = 22
FEATURE                 Location/Qualifiers
source                  1..22
                        mol_type = transcribed RNA
                        organism = Homo sapiens
SEQUENCE: 3
caggcacggg agctcaggtg ag                                                22

SEQ ID NO: 4            moltype = RNA   length = 22
FEATURE                 Location/Qualifiers
source                  1..22
                        mol_type = transcribed RNA
                        organism = Homo sapiens
SEQUENCE: 4
atatacaggg ggagactctt at                                                22

SEQ ID NO: 5            moltype = RNA   length = 19
FEATURE                 Location/Qualifiers
source                  1..19
                        mol_type = transcribed RNA
                        organism = Homo sapiens
SEQUENCE: 5
ggcttgcatg ggggactgg                                                    19

SEQ ID NO: 6            moltype = RNA   length = 20
FEATURE                 Location/Qualifiers
source                  1..20
                        mol_type = transcribed RNA
                        organism = Homo sapiens
SEQUENCE: 6
gcggagagag aatggggagc                                                   20

SEQ ID NO: 7            moltype = RNA   length = 20
FEATURE                 Location/Qualifiers
```

```
                          -continued source                    1..20
                          mol_type = transcribed RNA
                          organism = Homo sapiens
SEQUENCE: 7
gtgagtcagg gtggggctgg                                              20

SEQ ID NO: 8              moltype = RNA   length = 21
FEATURE                   Location/Qualifiers
source                    1..21
                          mol_type = transcribed RNA
                          organism = Homo sapiens
SEQUENCE: 8
ccgtcgccgc cacccgagcc g                                            21

SEQ ID NO: 9              moltype = RNA   length = 22
FEATURE                   Location/Qualifiers
source                    1..22
                          mol_type = transcribed RNA
                          organism = Homo sapiens
SEQUENCE: 9
atatacaggg ggagactctc at                                           22

SEQ ID NO: 10             moltype = RNA   length = 23
FEATURE                   Location/Qualifiers
source                    1..23
                          mol_type = transcribed RNA
                          organism = Homo sapiens
SEQUENCE: 10
gggatggtag accggtgacg tgc                                          23

SEQ ID NO: 11             moltype = RNA   length = 21
FEATURE                   Location/Qualifiers
source                    1..21
                          mol_type = transcribed RNA
                          organism = Homo sapiens
SEQUENCE: 11
tggcagggag gctgggaggg g                                            21

SEQ ID NO: 12             moltype = RNA   length = 23
FEATURE                   Location/Qualifiers
source                    1..23
                          mol_type = transcribed RNA
                          organism = Homo sapiens
SEQUENCE: 12
gtgagtggga gccccagtgt gtg                                          23

SEQ ID NO: 13             moltype = RNA   length = 19
FEATURE                   Location/Qualifiers
source                    1..19
                          mol_type = transcribed RNA
                          organism = Homo sapiens
SEQUENCE: 13
aatggatttt tggagcagg                                               19

SEQ ID NO: 14             moltype = RNA   length = 24
FEATURE                   Location/Qualifiers
source                    1..24
                          mol_type = transcribed RNA
                          organism = Homo sapiens
SEQUENCE: 14
aggagggagg agatgggcca agtt                                         24

SEQ ID NO: 15             moltype = RNA   length = 20
FEATURE                   Location/Qualifiers
source                    1..20
                          mol_type = transcribed RNA
                          organism = Homo sapiens
SEQUENCE: 15
tcgcgccccg gctcccgttc                                              20

SEQ ID NO: 16             moltype = RNA   length = 22
FEATURE                   Location/Qualifiers
source                    1..22
                          mol_type = transcribed RNA
                          organism = Homo sapiens
SEQUENCE: 16
ctcggcgcgg ggcgcgggct cc                                           22

SEQ ID NO: 17             moltype = RNA   length = 21
```

```
FEATURE              Location/Qualifiers
source               1..21
                     mol_type = transcribed RNA
                     organism = Homo sapiens
SEQUENCE: 17
gccctccgcc cgtgcacccc g                                              21

SEQ ID NO: 18        moltype = RNA   length = 23
FEATURE              Location/Qualifiers
source               1..23
                     mol_type = transcribed RNA
                     organism = Homo sapiens
SEQUENCE: 18
cgggtagaga gggcagtggg agg                                            23

SEQ ID NO: 19        moltype = RNA   length = 22
FEATURE              Location/Qualifiers
source               1..22
                     mol_type = transcribed RNA
                     organism = Homo sapiens
SEQUENCE: 19
gagcttttgg cccgggttat ac                                             22

SEQ ID NO: 20        moltype = RNA   length = 22
FEATURE              Location/Qualifiers
source               1..22
                     mol_type = transcribed RNA
                     organism = Homo sapiens
SEQUENCE: 20
ttggggaaac ggccgctgag tg                                             22

SEQ ID NO: 21        moltype = RNA   length = 21
FEATURE              Location/Qualifiers
source               1..21
                     mol_type = transcribed RNA
                     organism = Homo sapiens
SEQUENCE: 21
gcagggacag caaagggtg c                                               21

SEQ ID NO: 22        moltype = RNA   length = 22
FEATURE              Location/Qualifiers
source               1..22
                     mol_type = transcribed RNA
                     organism = Homo sapiens
SEQUENCE: 22
agcagaggca gagaggctca gg                                             22

SEQ ID NO: 23        moltype = RNA   length = 22
FEATURE              Location/Qualifiers
source               1..22
                     mol_type = transcribed RNA
                     organism = Homo sapiens
SEQUENCE: 23
gttgggacaa gaggacggtc tt                                             22

SEQ ID NO: 24        moltype = RNA   length = 19
FEATURE              Location/Qualifiers
source               1..19
                     mol_type = transcribed RNA
                     organism = Homo sapiens
SEQUENCE: 24
gagggcgggt ggaggagga                                                 19

SEQ ID NO: 25        moltype = RNA   length = 22
FEATURE              Location/Qualifiers
source               1..22
                     mol_type = transcribed RNA
                     organism = Homo sapiens
SEQUENCE: 25
aaagatctgg aagtgggaga ca                                             22

SEQ ID NO: 26        moltype = RNA   length = 21
FEATURE              Location/Qualifiers
source               1..21
                     mol_type = transcribed RNA
                     organism = Homo sapiens
SEQUENCE: 26
cctgcagaga ggaagccctt c                                              21
```

```
SEQ ID NO: 27           moltype = RNA   length = 22
FEATURE                 Location/Qualifiers
source                  1..22
                        mol_type = transcribed RNA
                        organism = Homo sapiens
SEQUENCE: 27
ggctttctag tctcagctct cc                                                  22

SEQ ID NO: 28           moltype = RNA   length = 22
FEATURE                 Location/Qualifiers
source                  1..22
                        mol_type = transcribed RNA
                        organism = Homo sapiens
SEQUENCE: 28
tggggcggag cttccggagg cc                                                  22

SEQ ID NO: 29           moltype = RNA   length = 23
FEATURE                 Location/Qualifiers
source                  1..23
                        mol_type = transcribed RNA
                        organism = Homo sapiens
SEQUENCE: 29
tggggacgta gctggccaga cag                                                 23

SEQ ID NO: 30           moltype = RNA   length = 22
FEATURE                 Location/Qualifiers
source                  1..22
                        mol_type = transcribed RNA
                        organism = Homo sapiens
SEQUENCE: 30
agctctgctg ctcactggca gt                                                  22

SEQ ID NO: 31           moltype = RNA   length = 22
FEATURE                 Location/Qualifiers
source                  1..22
                        mol_type = transcribed RNA
                        organism = Homo sapiens
SEQUENCE: 31
aaaagctggg ttgagagggc aa                                                  22

SEQ ID NO: 32           moltype = RNA   length = 23
FEATURE                 Location/Qualifiers
source                  1..23
                        mol_type = transcribed RNA
                        organism = Homo sapiens
SEQUENCE: 32
gggggggcag gaggggctca ggg                                                 23

SEQ ID NO: 33           moltype = RNA   length = 20
FEATURE                 Location/Qualifiers
source                  1..20
                        mol_type = transcribed RNA
                        organism = Homo sapiens
SEQUENCE: 33
gaatcggaaa ggaggcgccg                                                     20

SEQ ID NO: 34           moltype = RNA   length = 22
FEATURE                 Location/Qualifiers
source                  1..22
                        mol_type = transcribed RNA
                        organism = Homo sapiens
SEQUENCE: 34
gggaccatcc tgcctgctgt gg                                                  22

SEQ ID NO: 35           moltype = RNA   length = 22
FEATURE                 Location/Qualifiers
source                  1..22
                        mol_type = transcribed RNA
                        organism = Homo sapiens
SEQUENCE: 35
gtgggctggg ctgggctggg cc                                                  22

SEQ ID NO: 36           moltype = RNA   length = 22
FEATURE                 Location/Qualifiers
source                  1..22
                        mol_type = transcribed RNA
                        organism = Homo sapiens
SEQUENCE: 36
gcctgctggg gtggaacctg gt                                                  22
```

```
SEQ ID NO: 37              moltype = RNA   length = 22
FEATURE                    Location/Qualifiers
source                     1..22
                           mol_type = transcribed RNA
                           organism = Homo sapiens
SEQUENCE: 37
actcaaaatg ggggcgcttt cc                                                  22

SEQ ID NO: 38              moltype = RNA   length = 20
FEATURE                    Location/Qualifiers
source                     1..20
                           mol_type = transcribed RNA
                           organism = Homo sapiens
SEQUENCE: 38
gctcggactg agcaggtggg                                                     20

SEQ ID NO: 39              moltype = RNA   length = 23
FEATURE                    Location/Qualifiers
source                     1..23
                           mol_type = transcribed RNA
                           organism = Homo sapiens
SEQUENCE: 39
acaggcggct gtagcaatgg ggg                                                 23

SEQ ID NO: 40              moltype = RNA   length = 22
FEATURE                    Location/Qualifiers
source                     1..22
                           mol_type = transcribed RNA
                           organism = Homo sapiens
SEQUENCE: 40
cagttgggtc tagggtcag ga                                                   22

SEQ ID NO: 41              moltype = RNA   length = 18
FEATURE                    Location/Qualifiers
source                     1..18
                           mol_type = transcribed RNA
                           organism = Homo sapiens
SEQUENCE: 41
gggtcccggg gaggggg                                                        18

SEQ ID NO: 42              moltype = RNA   length = 17
FEATURE                    Location/Qualifiers
source                     1..17
                           mol_type = transcribed RNA
                           organism = Homo sapiens
SEQUENCE: 42
gggagtctac agcaggg                                                        17

SEQ ID NO: 43              moltype = RNA   length = 18
FEATURE                    Location/Qualifiers
source                     1..18
                           mol_type = transcribed RNA
                           organism = Homo sapiens
SEQUENCE: 43
gaggctgaag gaagatgg                                                       18

SEQ ID NO: 44              moltype = RNA   length = 22
FEATURE                    Location/Qualifiers
source                     1..22
                           mol_type = transcribed RNA
                           organism = Homo sapiens
SEQUENCE: 44
caaggagacg ggaacatgga gc                                                  22

SEQ ID NO: 45              moltype = RNA   length = 20
FEATURE                    Location/Qualifiers
source                     1..20
                           mol_type = transcribed RNA
                           organism = Homo sapiens
SEQUENCE: 45
aaaagctggg ctgagaggcg                                                     20

SEQ ID NO: 46              moltype = RNA   length = 21
FEATURE                    Location/Qualifiers
source                     1..21
                           mol_type = transcribed RNA
                           organism = Homo sapiens
SEQUENCE: 46
```

```
acaggagtgg gggtgggaca t                                         21

SEQ ID NO: 47           moltype = RNA  length = 17
FEATURE                 Location/Qualifiers
source                  1..17
                        mol_type = transcribed RNA
                        organism = Homo sapiens
SEQUENCE: 47
ggtggggct gttgttt                                               17

SEQ ID NO: 48           moltype = RNA  length = 22
FEATURE                 Location/Qualifiers
source                  1..22
                        mol_type = transcribed RNA
                        organism = Homo sapiens
SEQUENCE: 48
cgtcccgggg ctgcgcgagg ca                                        22

SEQ ID NO: 49           moltype = RNA  length = 22
FEATURE                 Location/Qualifiers
source                  1..22
                        mol_type = transcribed RNA
                        organism = Homo sapiens
SEQUENCE: 49
ccaggaggcg gaggaggtgg ag                                        22

SEQ ID NO: 50           moltype = RNA  length = 21
FEATURE                 Location/Qualifiers
source                  1..21
                        mol_type = transcribed RNA
                        organism = Homo sapiens
SEQUENCE: 50
agccaagtgg aagttacttt a                                         21

SEQ ID NO: 51           moltype = RNA  length = 16
FEATURE                 Location/Qualifiers
source                  1..16
                        mol_type = transcribed RNA
                        organism = Homo sapiens
SEQUENCE: 51
accgcctgcc cagtga                                               16

SEQ ID NO: 52           moltype = RNA  length = 17
FEATURE                 Location/Qualifiers
source                  1..17
                        mol_type = transcribed RNA
                        organism = Homo sapiens
SEQUENCE: 52
gctgggcgag gctggca                                              17

SEQ ID NO: 53           moltype = RNA  length = 18
FEATURE                 Location/Qualifiers
source                  1..18
                        mol_type = transcribed RNA
                        organism = Homo sapiens
SEQUENCE: 53
aggggggcggg ctccggcg                                            18

SEQ ID NO: 54           moltype = RNA  length = 21
FEATURE                 Location/Qualifiers
source                  1..21
                        mol_type = transcribed RNA
                        organism = Homo sapiens
SEQUENCE: 54
tggggctagt gatgcaggac g                                         21

SEQ ID NO: 55           moltype = RNA  length = 18
FEATURE                 Location/Qualifiers
source                  1..18
                        mol_type = transcribed RNA
                        organism = Homo sapiens
SEQUENCE: 55
aggctgggct gggacgga                                             18

SEQ ID NO: 56           moltype = RNA  length = 22
FEATURE                 Location/Qualifiers
source                  1..22
                        mol_type = transcribed RNA
                        organism = Homo sapiens
```

```
SEQUENCE: 56
agactgacgg ctggaggccc at                                                22

SEQ ID NO: 57           moltype = RNA   length = 22
FEATURE                 Location/Qualifiers
source                  1..22
                        mol_type = transcribed RNA
                        organism = Homo sapiens
SEQUENCE: 57
aggactggac tcccggcagc cc                                                22

SEQ ID NO: 58           moltype = RNA   length = 18
FEATURE                 Location/Qualifiers
source                  1..18
                        mol_type = transcribed RNA
                        organism = Homo sapiens
SEQUENCE: 58
cccagcagga cgggagcg                                                     18

SEQ ID NO: 59           moltype = RNA   length = 17
FEATURE                 Location/Qualifiers
source                  1..17
                        mol_type = transcribed RNA
                        organism = Homo sapiens
SEQUENCE: 59
gtggacctgg ctgggac                                                      17

SEQ ID NO: 60           moltype = RNA   length = 21
FEATURE                 Location/Qualifiers
source                  1..21
                        mol_type = transcribed RNA
                        organism = Homo sapiens
SEQUENCE: 60
tcttgaagtc agaacccgca a                                                 21

SEQ ID NO: 61           moltype = RNA   length = 23
FEATURE                 Location/Qualifiers
source                  1..23
                        mol_type = transcribed RNA
                        organism = Homo sapiens
SEQUENCE: 61
tgggccaggg agcagctggt ggg                                               23

SEQ ID NO: 62           moltype = RNA   length = 22
FEATURE                 Location/Qualifiers
source                  1..22
                        mol_type = transcribed RNA
                        organism = Homo sapiens
SEQUENCE: 62
actgggaaga ggagctgagg ga                                                22

SEQ ID NO: 63           moltype = RNA   length = 23
FEATURE                 Location/Qualifiers
source                  1..23
                        mol_type = transcribed RNA
                        organism = Homo sapiens
SEQUENCE: 63
tgggctgagg gcaggaggcc tgt                                               23

SEQ ID NO: 64           moltype = RNA   length = 24
FEATURE                 Location/Qualifiers
source                  1..24
                        mol_type = transcribed RNA
                        organism = Homo sapiens
SEQUENCE: 64
agctgagctc catggacgtg cagt                                              24

SEQ ID NO: 65           moltype = RNA   length = 23
FEATURE                 Location/Qualifiers
source                  1..23
                        mol_type = transcribed RNA
                        organism = Homo sapiens
SEQUENCE: 65
ctgggggacg cgtgagcgcg agc                                               23

SEQ ID NO: 66           moltype = RNA   length = 25
FEATURE                 Location/Qualifiers
source                  1..25
                        mol_type = transcribed RNA
```

```
                                organism = Homo sapiens
SEQUENCE: 66
agcggggagg aagtgggcgc tgctt                                              25

SEQ ID NO: 67              moltype = RNA    length = 23
FEATURE                    Location/Qualifiers
source                     1..23
                           mol_type = transcribed RNA
                           organism = Homo sapiens
SEQUENCE: 67
gccccggcgc gggcgggttc tgg                                                23

SEQ ID NO: 68              moltype = RNA    length = 22
FEATURE                    Location/Qualifiers
source                     1..22
                           mol_type = transcribed RNA
                           organism = Homo sapiens
SEQUENCE: 68
agcaaggcgg catctctctg at                                                 22

SEQ ID NO: 69              moltype = RNA    length = 18
FEATURE                    Location/Qualifiers
source                     1..18
                           mol_type = transcribed RNA
                           organism = Homo sapiens
SEQUENCE: 69
gggtgagggc aggtggtt                                                      18

SEQ ID NO: 70              moltype = RNA    length = 21
FEATURE                    Location/Qualifiers
source                     1..21
                           mol_type = transcribed RNA
                           organism = Homo sapiens
SEQUENCE: 70
agctgtacct gaaaccaagc a                                                  21

SEQ ID NO: 71              moltype = RNA    length = 23
FEATURE                    Location/Qualifiers
source                     1..23
                           mol_type = transcribed RNA
                           organism = Homo sapiens
SEQUENCE: 71
ggcaggaggg ctgtgccagg ttg                                                23

SEQ ID NO: 72              moltype = RNA    length = 22
FEATURE                    Location/Qualifiers
source                     1..22
                           mol_type = transcribed RNA
                           organism = Homo sapiens
SEQUENCE: 72
atagtgggaa gctggcagat tc                                                 22

SEQ ID NO: 73              moltype = RNA    length = 23
FEATURE                    Location/Qualifiers
source                     1..23
                           mol_type = transcribed RNA
                           organism = Homo sapiens
SEQUENCE: 73
ctggcggagc ccattccatg cca                                                23

SEQ ID NO: 74              moltype = RNA    length = 22
FEATURE                    Location/Qualifiers
source                     1..22
                           mol_type = transcribed RNA
                           organism = Homo sapiens
SEQUENCE: 74
gctgcgggct gcggtcaggg cg                                                 22

SEQ ID NO: 75              moltype = RNA    length = 22
FEATURE                    Location/Qualifiers
source                     1..22
                           mol_type = transcribed RNA
                           organism = Homo sapiens
SEQUENCE: 75
aggactgatc ctctcgggca gg                                                 22

SEQ ID NO: 76              moltype = RNA    length = 22
FEATURE                    Location/Qualifiers
source                     1..22
```

```
                        mol_type = transcribed RNA
                        organism = Homo sapiens
SEQUENCE: 76
aaggcccggg ctttcctccc ag                                                22

SEQ ID NO: 77           moltype = RNA  length = 22
FEATURE                 Location/Qualifiers
source                  1..22
                        mol_type = transcribed RNA
                        organism = Homo sapiens
SEQUENCE: 77
tgcggggaca ggccagggca tc                                                22

SEQ ID NO: 78           moltype = RNA  length = 22
FEATURE                 Location/Qualifiers
source                  1..22
                        mol_type = transcribed RNA
                        organism = Homo sapiens
SEQUENCE: 78
agccaggctc tgaagggaaa gt                                                22

SEQ ID NO: 79           moltype = RNA  length = 21
FEATURE                 Location/Qualifiers
source                  1..21
                        mol_type = transcribed RNA
                        organism = Homo sapiens
SEQUENCE: 79
cgcctgccca gccctcctgc t                                                 21

SEQ ID NO: 80           moltype = RNA  length = 24
FEATURE                 Location/Qualifiers
source                  1..24
                        mol_type = transcribed RNA
                        organism = Homo sapiens
SEQUENCE: 80
gatgcgccgc ccactgcccc gcgc                                              24

SEQ ID NO: 81           moltype = RNA  length = 22
FEATURE                 Location/Qualifiers
source                  1..22
                        mol_type = transcribed RNA
                        organism = Homo sapiens
SEQUENCE: 81
tgaggccctt ggggcacagt gg                                                22

SEQ ID NO: 82           moltype = RNA  length = 22
FEATURE                 Location/Qualifiers
source                  1..22
                        mol_type = transcribed RNA
                        organism = Homo sapiens
SEQUENCE: 82
aggggatgg cagagcaaaa tt                                                 22

SEQ ID NO: 83           moltype = RNA  length = 21
FEATURE                 Location/Qualifiers
source                  1..21
                        mol_type = transcribed RNA
                        organism = Homo sapiens
SEQUENCE: 83
gggagtgcag ggcagggttt c                                                 21

SEQ ID NO: 84           moltype = RNA  length = 23
FEATURE                 Location/Qualifiers
source                  1..23
                        mol_type = transcribed RNA
                        organism = Homo sapiens
SEQUENCE: 84
ccggggcaga ttggtgtagg gtg                                               23

SEQ ID NO: 85           moltype = RNA  length = 22
FEATURE                 Location/Qualifiers
source                  1..22
                        mol_type = transcribed RNA
                        organism = Homo sapiens
SEQUENCE: 85
ttcagatccc agcggtgcct ct                                                22

SEQ ID NO: 86           moltype = RNA  length = 22
FEATURE                 Location/Qualifiers
```

```
                        source                  1..22
                                                mol_type = transcribed RNA
                                                organism = Homo sapiens
                        SEQUENCE: 86
                        agggaagggg acgagggttg gg                                        22

SEQ ID NO: 87           moltype = RNA   length = 22
                        FEATURE                 Location/Qualifiers
                        source                  1..22
                                                mol_type = transcribed RNA
                                                organism = Homo sapiens
                        SEQUENCE: 87
                        gaaatcaagc gtgggtgaga cc                                        22

SEQ ID NO: 88           moltype = RNA   length = 23
                        FEATURE                 Location/Qualifiers
                        source                  1..23
                                                mol_type = transcribed RNA
                                                organism = Homo sapiens
                        SEQUENCE: 88
                        gtttgcacgg gtgggccttg tct                                       23

SEQ ID NO: 89           moltype = RNA   length = 20
                        FEATURE                 Location/Qualifiers
                        source                  1..20
                                                mol_type = transcribed RNA
                                                organism = Homo sapiens
                        SEQUENCE: 89
                        gggctggggc gcggggaggt                                           20

SEQ ID NO: 90           moltype = RNA   length = 19
                        FEATURE                 Location/Qualifiers
                        source                  1..19
                                                mol_type = transcribed RNA
                                                organism = Homo sapiens
                        SEQUENCE: 90
                        ggggagcgag gggcggggc                                            19

SEQ ID NO: 91           moltype = RNA   length = 20
                        FEATURE                 Location/Qualifiers
                        source                  1..20
                                                mol_type = transcribed RNA
                                                organism = Homo sapiens
                        SEQUENCE: 91
                        gggaaaagga aggggagga                                            20

SEQ ID NO: 92           moltype = RNA   length = 19
                        FEATURE                 Location/Qualifiers
                        source                  1..19
                                                mol_type = transcribed RNA
                                                organism = Homo sapiens
                        SEQUENCE: 92
                        agcagggctg gggattgca                                            19

SEQ ID NO: 93           moltype = RNA   length = 22
                        FEATURE                 Location/Qualifiers
                        source                  1..22
                                                mol_type = transcribed RNA
                                                organism = Homo sapiens
                        SEQUENCE: 93
                        cagcagggga gagagaggag tc                                        22

SEQ ID NO: 94           moltype = RNA   length = 24
                        FEATURE                 Location/Qualifiers
                        source                  1..24
                                                mol_type = transcribed RNA
                                                organism = Homo sapiens
                        SEQUENCE: 94
                        ctgcaggcag aagtggggct gaca                                      24

SEQ ID NO: 95           moltype = RNA   length = 20
                        FEATURE                 Location/Qualifiers
                        source                  1..20
                                                mol_type = transcribed RNA
                                                organism = Homo sapiens
                        SEQUENCE: 95
                        tctcttcatc tacccccag                                            20

SEQ ID NO: 96           moltype = RNA   length = 22
```

```
FEATURE                 Location/Qualifiers
source                  1..22
                        mol_type = transcribed RNA
                        organism = Homo sapiens
SEQUENCE: 96
tggtgggccg cagaacatgt gc                                              22

SEQ ID NO: 97           moltype = RNA   length = 25
FEATURE                 Location/Qualifiers
source                  1..25
                        mol_type = transcribed RNA
                        organism = Homo sapiens
SEQUENCE: 97
ggcggaggga agtaggtccg ttggt                                           25

SEQ ID NO: 98           moltype = RNA   length = 19
FEATURE                 Location/Qualifiers
source                  1..19
                        mol_type = transcribed RNA
                        organism = Homo sapiens
SEQUENCE: 98
tgcgcctcgg gtgagcatg                                                  19

SEQ ID NO: 99           moltype = RNA   length = 20
FEATURE                 Location/Qualifiers
source                  1..20
                        mol_type = transcribed RNA
                        organism = Homo sapiens
SEQUENCE: 99
aggcgcaccc gaccacatgc                                                 20

SEQ ID NO: 100          moltype = RNA   length = 23
FEATURE                 Location/Qualifiers
source                  1..23
                        mol_type = transcribed RNA
                        organism = Homo sapiens
SEQUENCE: 100
ctgggcccgc ggcgggcgtg ggg                                             23

SEQ ID NO: 101          moltype = RNA   length = 21
FEATURE                 Location/Qualifiers
source                  1..21
                        mol_type = transcribed RNA
                        organism = Homo sapiens
SEQUENCE: 101
tcatcccccT cgccctctca g                                               21

SEQ ID NO: 102          moltype = RNA   length = 21
FEATURE                 Location/Qualifiers
source                  1..21
                        mol_type = transcribed RNA
                        organism = Homo sapiens
SEQUENCE: 102
ttggggtggt cggccctgga g                                               21

SEQ ID NO: 103          moltype = RNA   length = 23
FEATURE                 Location/Qualifiers
source                  1..23
                        mol_type = transcribed RNA
                        organism = Homo sapiens
SEQUENCE: 103
agggtggggc tggaggtggg gct                                             23

SEQ ID NO: 104          moltype = RNA   length = 23
FEATURE                 Location/Qualifiers
source                  1..23
                        mol_type = transcribed RNA
                        organism = Homo sapiens
SEQUENCE: 104
cggggccatg gagcagcctg tgt                                             23

SEQ ID NO: 105          moltype = RNA   length = 21
FEATURE                 Location/Qualifiers
source                  1..21
                        mol_type = transcribed RNA
                        organism = Homo sapiens
SEQUENCE: 105
ctccccggcc tctgccccca g                                               21
```

```
SEQ ID NO: 106            moltype = RNA   length = 24
FEATURE                   Location/Qualifiers
source                    1..24
                          mol_type = transcribed RNA
                          organism = Homo sapiens
SEQUENCE: 106
cgggtgggag cagatcttat tgag                                               24

SEQ ID NO: 107            moltype = RNA   length = 21
FEATURE                   Location/Qualifiers
source                    1..21
                          mol_type = transcribed RNA
                          organism = Homo sapiens
SEQUENCE: 107
aggtgggtat ggaggagccc t                                                  21

SEQ ID NO: 108            moltype = RNA   length = 22
FEATURE                   Location/Qualifiers
source                    1..22
                          mol_type = transcribed RNA
                          organism = Homo sapiens
SEQUENCE: 108
ctcgggaggg catgggccag gc                                                 22

SEQ ID NO: 109            moltype = RNA   length = 21
FEATURE                   Location/Qualifiers
source                    1..21
                          mol_type = transcribed RNA
                          organism = Homo sapiens
SEQUENCE: 109
gcggtggggc cggaggggcg t                                                  21

SEQ ID NO: 110            moltype = RNA   length = 24
FEATURE                   Location/Qualifiers
source                    1..24
                          mol_type = transcribed RNA
                          organism = Homo sapiens
SEQUENCE: 110
gtagggggcgt cccgggcgcg cggg                                              24

SEQ ID NO: 111            moltype = RNA   length = 20
FEATURE                   Location/Qualifiers
source                    1..20
                          mol_type = transcribed RNA
                          organism = Homo sapiens
SEQUENCE: 111
caggggggact gggggtgagc                                                   20

SEQ ID NO: 112            moltype = RNA   length = 21
FEATURE                   Location/Qualifiers
source                    1..21
                          mol_type = transcribed RNA
                          organism = Homo sapiens
SEQUENCE: 112
gaagctctcc cctccccgca g                                                  21

SEQ ID NO: 113            moltype = RNA   length = 25
FEATURE                   Location/Qualifiers
source                    1..25
                          mol_type = transcribed RNA
                          organism = Homo sapiens
SEQUENCE: 113
aggagggaag gggctgagaa cagga                                              25

SEQ ID NO: 114            moltype = RNA   length = 21
FEATURE                   Location/Qualifiers
source                    1..21
                          mol_type = transcribed RNA
                          organism = Homo sapiens
SEQUENCE: 114
cacctctcct ggcatcgccc c                                                  21

SEQ ID NO: 115            moltype = RNA   length = 20
FEATURE                   Location/Qualifiers
source                    1..20
                          mol_type = transcribed RNA
                          organism = Homo sapiens
SEQUENCE: 115
ctaggtgggg ggcttgaagc                                                    20
```

```
SEQ ID NO: 116            moltype = RNA   length = 22
FEATURE                   Location/Qualifiers
source                    1..22
                          mol_type = transcribed RNA
                          organism = Homo sapiens
SEQUENCE: 116
ctgggggtgg ggggctgggc gt                                                   22

SEQ ID NO: 117            moltype = RNA   length = 23
FEATURE                   Location/Qualifiers
source                    1..23
                          mol_type = transcribed RNA
                          organism = Homo sapiens
SEQUENCE: 117
ttgctctgct cccccgcccc cag                                                  23

SEQ ID NO: 118            moltype = RNA   length = 22
FEATURE                   Location/Qualifiers
source                    1..22
                          mol_type = transcribed RNA
                          organism = Homo sapiens
SEQUENCE: 118
taggggcgg cttgtggagt gt                                                    22

SEQ ID NO: 119            moltype = RNA   length = 22
FEATURE                   Location/Qualifiers
source                    1..22
                          mol_type = transcribed RNA
                          organism = Homo sapiens
SEQUENCE: 119
gtgagccagt ggaatggaga gg                                                   22

SEQ ID NO: 120            moltype = RNA   length = 25
FEATURE                   Location/Qualifiers
source                    1..25
                          mol_type = transcribed RNA
                          organism = Homo sapiens
SEQUENCE: 120
atggggtgag atgggagga gcagc                                                 25

SEQ ID NO: 121            moltype = RNA   length = 22
FEATURE                   Location/Qualifiers
source                    1..22
                          mol_type = transcribed RNA
                          organism = Homo sapiens
SEQUENCE: 121
ttggggtgga gggccaagga gc                                                   22

SEQ ID NO: 122            moltype = RNA   length = 20
FEATURE                   Location/Qualifiers
source                    1..20
                          mol_type = transcribed RNA
                          organism = Homo sapiens
SEQUENCE: 122
cagggaacca gttggggctt                                                      20

SEQ ID NO: 123            moltype = RNA   length = 22
FEATURE                   Location/Qualifiers
source                    1..22
                          mol_type = transcribed RNA
                          organism = Homo sapiens
SEQUENCE: 123
gtaggggagg ttgggccagg ga                                                   22

SEQ ID NO: 124            moltype = RNA   length = 23
FEATURE                   Location/Qualifiers
source                    1..23
                          mol_type = transcribed RNA
                          organism = Homo sapiens
SEQUENCE: 124
tcaataggaa agaggtggga cct                                                  23

SEQ ID NO: 125            moltype = RNA   length = 22
FEATURE                   Location/Qualifiers
source                    1..22
                          mol_type = transcribed RNA
                          organism = Homo sapiens
SEQUENCE: 125
```

```
gtgcggaacg ctggccgggg cg                                               22

SEQ ID NO: 127         moltype = RNA   length = 22
FEATURE                Location/Qualifiers
source                 1..22
                       mol_type = transcribed RNA
                       organism = Homo sapiens
SEQUENCE: 126
gtgaggaggg gctggcaggg ac                                               22

SEQ ID NO: 127         moltype = RNA   length = 22
FEATURE                Location/Qualifiers
source                 1..22
                       mol_type = transcribed RNA
                       organism = Homo sapiens
SEQUENCE: 127
actgggtagg tggggctcca gg                                               22

SEQ ID NO: 128         moltype = RNA   length = 21
FEATURE                Location/Qualifiers
source                 1..21
                       mol_type = transcribed RNA
                       organism = Homo sapiens
SEQUENCE: 128
ccgccttctc tcctcccca g                                                 21

SEQ ID NO: 129         moltype = RNA   length = 22
FEATURE                Location/Qualifiers
source                 1..22
                       mol_type = transcribed RNA
                       organism = Homo sapiens
SEQUENCE: 129
tcggcctggg gaggaggaag gg                                               22

SEQ ID NO: 130         moltype = RNA   length = 21
FEATURE                Location/Qualifiers
source                 1..21
                       mol_type = transcribed RNA
                       organism = Homo sapiens
SEQUENCE: 130
ctgggggggag gagaccctgc t                                               21

SEQ ID NO: 131         moltype = RNA   length = 21
FEATURE                Location/Qualifiers
source                 1..21
                       mol_type = transcribed RNA
                       organism = Homo sapiens
SEQUENCE: 131
tctgtggagt ggggtgcctg t                                                21

SEQ ID NO: 132         moltype = RNA   length = 19
FEATURE                Location/Qualifiers
source                 1..19
                       mol_type = transcribed RNA
                       organism = Homo sapiens
SEQUENCE: 132
cggggtcggc ggcgacgtg                                                   19

SEQ ID NO: 133         moltype = RNA   length = 21
FEATURE                Location/Qualifiers
source                 1..21
                       mol_type = transcribed RNA
                       organism = Homo sapiens
SEQUENCE: 133
cagcggagcc tggagagaag g                                                21

SEQ ID NO: 134         moltype = RNA   length = 22
FEATURE                Location/Qualifiers
source                 1..22
                       mol_type = transcribed RNA
                       organism = Homo sapiens
SEQUENCE: 134
cgggactgta gagggcatga gc                                               22

SEQ ID NO: 135         moltype = RNA   length = 24
FEATURE                Location/Qualifiers
source                 1..24
                       mol_type = transcribed RNA
                       organism = Homo sapiens
```

```
SEQUENCE: 135
ccatgaagca gtgggtagga ggac                                                   24

SEQ ID NO: 136          moltype = RNA  length = 20
FEATURE                 Location/Qualifiers
source                  1..20
                        mol_type = transcribed RNA
                        organism = Homo sapiens
SEQUENCE: 136
cggtggactg gagtgggtgg                                                        20

SEQ ID NO: 137          moltype = RNA  length = 22
FEATURE                 Location/Qualifiers
source                  1..22
                        mol_type = transcribed RNA
                        organism = Homo sapiens
SEQUENCE: 137
acctggcagc agggagcgtc gt                                                     22

SEQ ID NO: 138          moltype = RNA  length = 23
FEATURE                 Location/Qualifiers
source                  1..23
                        mol_type = transcribed RNA
                        organism = Homo sapiens
SEQUENCE: 138
cggccccacg caccagggta aga                                                    23

SEQ ID NO: 139          moltype = RNA  length = 21
FEATURE                 Location/Qualifiers
source                  1..21
                        mol_type = transcribed RNA
                        organism = Homo sapiens
SEQUENCE: 139
gctgggaagg caaagggacg t                                                      21

SEQ ID NO: 140          moltype = RNA  length = 22
FEATURE                 Location/Qualifiers
source                  1..22
                        mol_type = transcribed RNA
                        organism = Homo sapiens
SEQUENCE: 140
cagaagggga gttgggagca ga                                                     22

SEQ ID NO: 141          moltype = RNA  length = 20
FEATURE                 Location/Qualifiers
source                  1..20
                        mol_type = transcribed RNA
                        organism = Homo sapiens
SEQUENCE: 141
ggcggcggcg gaggcggggg                                                        20

SEQ ID NO: 142          moltype = RNA  length = 21
FEATURE                 Location/Qualifiers
source                  1..21
                        mol_type = transcribed RNA
                        organism = Homo sapiens
SEQUENCE: 142
cgtcccaccc cccactcctg t                                                      21

SEQ ID NO: 143          moltype = RNA  length = 17
FEATURE                 Location/Qualifiers
source                  1..17
                        mol_type = transcribed RNA
                        organism = Homo sapiens
SEQUENCE: 143
agggtgtgtg tgtttttt                                                          17

SEQ ID NO: 144          moltype = RNA  length = 23
FEATURE                 Location/Qualifiers
source                  1..23
                        mol_type = transcribed RNA
                        organism = Homo sapiens
SEQUENCE: 144
tgacacggag ggtggcttgg gaa                                                    23

SEQ ID NO: 145          moltype = RNA  length = 22
FEATURE                 Location/Qualifiers
source                  1..22
                        mol_type = transcribed RNA
```

```
                              -continued
                           organism = Homo sapiens
SEQUENCE: 145
caggaaggat ttagggacag gc                                          22

SEQ ID NO: 146          moltype = RNA   length = 17
FEATURE                 Location/Qualifiers
source                  1..17
                        mol_type = transcribed RNA
                        organism = Homo sapiens
SEQUENCE: 146
gcggggctgg gcgcgcg                                                17

SEQ ID NO: 147          moltype = RNA   length = 21
FEATURE                 Location/Qualifiers
source                  1..21
                        mol_type = transcribed RNA
                        organism = Homo sapiens
SEQUENCE: 147
tggctgttgg aggggcagg c                                            21

SEQ ID NO: 148          moltype = RNA   length = 22
FEATURE                 Location/Qualifiers
source                  1..22
                        mol_type = transcribed RNA
                        organism = Homo sapiens
SEQUENCE: 148
cagccctcct cccgcaccca aa                                          22

SEQ ID NO: 149          moltype = RNA   length = 23
FEATURE                 Location/Qualifiers
source                  1..23
                        mol_type = transcribed RNA
                        organism = Homo sapiens
SEQUENCE: 149
tgtagagcag ggagcaggaa gct                                         23

SEQ ID NO: 150          moltype = RNA   length = 21
FEATURE                 Location/Qualifiers
source                  1..21
                        mol_type = transcribed RNA
                        organism = Homo sapiens
SEQUENCE: 150
agcagacttg acctacaatt a                                           21

SEQ ID NO: 151          moltype = RNA   length = 22
FEATURE                 Location/Qualifiers
source                  1..22
                        mol_type = transcribed RNA
                        organism = Homo sapiens
SEQUENCE: 151
agacacattt ggagagggaa cc                                          22

SEQ ID NO: 152          moltype = RNA   length = 20
FEATURE                 Location/Qualifiers
source                  1..20
                        mol_type = transcribed RNA
                        organism = Homo sapiens
SEQUENCE: 152
tagggggtgg caggctggcc                                             20

SEQ ID NO: 153          moltype = RNA   length = 23
FEATURE                 Location/Qualifiers
source                  1..23
                        mol_type = transcribed RNA
                        organism = Homo sapiens
SEQUENCE: 153
cagggagaag gtggaagtgc aga                                         23

SEQ ID NO: 154          moltype = RNA   length = 20
FEATURE                 Location/Qualifiers
source                  1..20
                        mol_type = transcribed RNA
                        organism = Homo sapiens
SEQUENCE: 154
ggggaggtgt gcagggctgg                                             20

SEQ ID NO: 155          moltype = RNA   length = 19
FEATURE                 Location/Qualifiers
source                  1..19
```

-continued

```
                            mol_type = transcribed RNA
                            organism = Homo sapiens
SEQUENCE: 155
tgcggcagag ctgggtca                                                  19

SEQ ID NO: 156              moltype = RNA   length = 23
FEATURE                     Location/Qualifiers
source                      1..23
                            mol_type = transcribed RNA
                            organism = Homo sapiens
SEQUENCE: 156
gtgcgtggtg gctcgaggcg ggg                                            23

SEQ ID NO: 157              moltype = RNA   length = 20
FEATURE                     Location/Qualifiers
source                      1..20
                            mol_type = transcribed RNA
                            organism = Homo sapiens
SEQUENCE: 157
tgggctgctg agaaggggca                                                20

SEQ ID NO: 158              moltype = RNA   length = 21
FEATURE                     Location/Qualifiers
source                      1..21
                            mol_type = transcribed RNA
                            organism = Homo sapiens
SEQUENCE: 158
caggcaggtg tagggtggag c                                              21

SEQ ID NO: 159              moltype = RNA   length = 20
FEATURE                     Location/Qualifiers
source                      1..20
                            mol_type = transcribed RNA
                            organism = Homo sapiens
SEQUENCE: 159
acccgcccgt ctccccacag                                                20

SEQ ID NO: 160              moltype = RNA   length = 22
FEATURE                     Location/Qualifiers
source                      1..22
                            mol_type = transcribed RNA
                            organism = Homo sapiens
SEQUENCE: 160
tgggggagga aggacaggcc at                                             22

SEQ ID NO: 161              moltype = RNA   length = 24
FEATURE                     Location/Qualifiers
source                      1..24
                            mol_type = transcribed RNA
                            organism = Homo sapiens
SEQUENCE: 161
cctggggaca ggggattggg gcag                                           24

SEQ ID NO: 162              moltype = RNA   length = 22
FEATURE                     Location/Qualifiers
source                      1..22
                            mol_type = transcribed RNA
                            organism = Homo sapiens
SEQUENCE: 162
aggcagcggg gtgtagtgga ta                                             22

SEQ ID NO: 163              moltype = RNA   length = 22
FEATURE                     Location/Qualifiers
source                      1..22
                            mol_type = transcribed RNA
                            organism = Homo sapiens
SEQUENCE: 163
tattgcactc gtcccggcct cc                                             22

SEQ ID NO: 164              moltype = RNA   length = 22
FEATURE                     Location/Qualifiers
source                      1..22
                            mol_type = transcribed RNA
                            organism = Homo sapiens
SEQUENCE: 164
ctcctggggc ccgcactctc gc                                             22

SEQ ID NO: 165              moltype = RNA   length = 22
FEATURE                     Location/Qualifiers
```

```
source                  1..22
                        mol_type = transcribed RNA
                        organism = Homo sapiens
SEQUENCE: 165
ccgggagaag gaggtggcct gg                                              22

SEQ ID NO: 166          moltype = RNA   length = 22
FEATURE                 Location/Qualifiers
source                  1..22
                        mol_type = transcribed RNA
                        organism = Homo sapiens
SEQUENCE: 166
actggactta gggtcagaag gc                                              22

SEQ ID NO: 167          moltype = RNA   length = 22
FEATURE                 Location/Qualifiers
source                  1..22
                        mol_type = transcribed RNA
                        organism = Homo sapiens
SEQUENCE: 167
ggctacaaca caggacccgg gc                                              22

SEQ ID NO: 168          moltype = RNA   length = 23
FEATURE                 Location/Qualifiers
source                  1..23
                        mol_type = transcribed RNA
                        organism = Homo sapiens
SEQUENCE: 168
gagggcagcg tgggtgtggc gga                                             23

SEQ ID NO: 169          moltype = RNA   length = 22
FEATURE                 Location/Qualifiers
source                  1..22
                        mol_type = transcribed RNA
                        organism = Homo sapiens
SEQUENCE: 169
cccctggggc tgggcaggcg ga                                              22

SEQ ID NO: 170          moltype = RNA   length = 23
FEATURE                 Location/Qualifiers
source                  1..23
                        mol_type = transcribed RNA
                        organism = Homo sapiens
SEQUENCE: 170
agcagcattg tacagggcta tga                                             23

SEQ ID NO: 171          moltype = RNA   length = 23
FEATURE                 Location/Qualifiers
source                  1..23
                        mol_type = transcribed RNA
                        organism = Homo sapiens
SEQUENCE: 171
agcagcattg tacagggcta tca                                             23

SEQ ID NO: 172          moltype = RNA   length = 20
FEATURE                 Location/Qualifiers
source                  1..20
                        mol_type = transcribed RNA
                        organism = Homo sapiens
SEQUENCE: 172
cctgagcccg ggccgcgcag                                                 20

SEQ ID NO: 173          moltype = RNA   length = 22
FEATURE                 Location/Qualifiers
source                  1..22
                        mol_type = transcribed RNA
                        organism = Homo sapiens
SEQUENCE: 173
tgagcccctg tgccgccccc ag                                              22

SEQ ID NO: 174          moltype = RNA   length = 22
FEATURE                 Location/Qualifiers
source                  1..22
                        mol_type = transcribed RNA
                        organism = Homo sapiens
SEQUENCE: 174
gtgggtacgg cccagtgggg gg                                              22

SEQ ID NO: 175          moltype = RNA   length = 21
```

```
FEATURE             Location/Qualifiers
source              1..21
                    mol_type = transcribed RNA
                    organism = Homo sapiens
SEQUENCE: 175
gtgggcgggg gcaggtgtgt g                                     21

SEQ ID NO: 176      moltype = RNA   length = 24
FEATURE             Location/Qualifiers
source              1..24
                    mol_type = transcribed RNA
                    organism = Homo sapiens
SEQUENCE: 176
gtgggtaggg tttgggggag agcg                                  24

SEQ ID NO: 177      moltype = RNA   length = 22
FEATURE             Location/Qualifiers
source              1..22
                    mol_type = transcribed RNA
                    organism = Homo sapiens
SEQUENCE: 177
agtgggaggc cagggcacgg ca                                    22

SEQ ID NO: 178      moltype = RNA   length = 21
FEATURE             Location/Qualifiers
source              1..21
                    mol_type = transcribed RNA
                    organism = Homo sapiens
SEQUENCE: 178
cgggggcggg gccgaagcgc g                                     21

SEQ ID NO: 179      moltype = RNA   length = 24
FEATURE             Location/Qualifiers
source              1..24
                    mol_type = transcribed RNA
                    organism = Homo sapiens
SEQUENCE: 179
ccccgggaac gtcgagactg gagc                                  24

SEQ ID NO: 180      moltype = RNA   length = 22
FEATURE             Location/Qualifiers
source              1..22
                    mol_type = transcribed RNA
                    organism = Homo sapiens
SEQUENCE: 180
acgcccttcc ccccttcttt ca                                    22

SEQ ID NO: 181      moltype = RNA   length = 24
FEATURE             Location/Qualifiers
source              1..24
                    mol_type = transcribed RNA
                    organism = Homo sapiens
SEQUENCE: 181
agcctggaag ctggagcctg cagt                                  24

SEQ ID NO: 182      moltype = RNA   length = 19
FEATURE             Location/Qualifiers
source              1..19
                    mol_type = transcribed RNA
                    organism = Homo sapiens
SEQUENCE: 182
atcccaccac tgccaccat                                        19

SEQ ID NO: 183      moltype = RNA   length = 18
FEATURE             Location/Qualifiers
source              1..18
                    mol_type = transcribed RNA
                    organism = Homo sapiens
SEQUENCE: 183
cgggcgtggt ggtggggg                                         18

SEQ ID NO: 184      moltype = RNA   length = 20
FEATURE             Location/Qualifiers
source              1..20
                    mol_type = transcribed RNA
                    organism = Homo sapiens
SEQUENCE: 184
cgggcgtggt ggtgggggtg                                       20
```

```
SEQ ID NO: 185          moltype = RNA   length = 21
FEATURE                 Location/Qualifiers
source                  1..21
                        mol_type = transcribed RNA
                        organism = Homo sapiens
SEQUENCE: 185
accactgcac tccagcctga g                                                   21

SEQ ID NO: 186          moltype = RNA   length = 23
FEATURE                 Location/Qualifiers
source                  1..23
                        mol_type = transcribed RNA
                        organism = Homo sapiens
SEQUENCE: 186
cggggccgta gcactgtctg aga                                                 23

SEQ ID NO: 187          moltype = RNA   length = 23
FEATURE                 Location/Qualifiers
source                  1..23
                        mol_type = transcribed RNA
                        organism = Homo sapiens
SEQUENCE: 187
gggggccgat acactgtacg aga                                                 23

SEQ ID NO: 188          moltype = RNA   length = 19
FEATURE                 Location/Qualifiers
source                  1..19
                        mol_type = transcribed RNA
                        organism = Homo sapiens
SEQUENCE: 188
tggatttttg gatcaggga                                                      19

SEQ ID NO: 189          moltype = RNA   length = 22
FEATURE                 Location/Qualifiers
source                  1..22
                        mol_type = transcribed RNA
                        organism = Homo sapiens
SEQUENCE: 189
ctggtacagg cctgggggac ag                                                  22

SEQ ID NO: 190          moltype = RNA   length = 22
FEATURE                 Location/Qualifiers
source                  1..22
                        mol_type = transcribed RNA
                        organism = Homo sapiens
SEQUENCE: 190
actgcagtga aggcacttgt ag                                                  22

SEQ ID NO: 191          moltype = RNA   length = 21
FEATURE                 Location/Qualifiers
source                  1..21
                        mol_type = transcribed RNA
                        organism = Homo sapiens
SEQUENCE: 191
cggcggggac ggcgattggt c                                                   21

SEQ ID NO: 192          moltype = RNA   length = 22
FEATURE                 Location/Qualifiers
source                  1..22
                        mol_type = transcribed RNA
                        organism = Homo sapiens
SEQUENCE: 192
cgcaggggcc gggtgctcac cg                                                  22

SEQ ID NO: 193          moltype = RNA   length = 22
FEATURE                 Location/Qualifiers
source                  1..22
                        mol_type = transcribed RNA
                        organism = Homo sapiens
SEQUENCE: 193
ggaggggtcc cgcactggga gg                                                  22

SEQ ID NO: 194          moltype = RNA   length = 20
FEATURE                 Location/Qualifiers
source                  1..20
                        mol_type = transcribed RNA
                        organism = Homo sapiens
SEQUENCE: 194
ccccagggcg acgcggcggg                                                     20
```

```
SEQ ID NO: 195          moltype = RNA   length = 23
FEATURE                 Location/Qualifiers
source                  1..23
                        mol_type = transcribed RNA
                        organism = Homo sapiens
SEQUENCE: 195
caacggaatc ccaaaagcag ctg                                                 23

SEQ ID NO: 196          moltype = RNA   length = 22
FEATURE                 Location/Qualifiers
source                  1..22
                        mol_type = transcribed RNA
                        organism = Homo sapiens
SEQUENCE: 196
aagctgccag ttgaagaact gt                                                  22

SEQ ID NO: 197          moltype = RNA   length = 21
FEATURE                 Location/Qualifiers
source                  1..21
                        mol_type = transcribed RNA
                        organism = Homo sapiens
SEQUENCE: 197
atcacattgc cagggattac c                                                   21

SEQ ID NO: 198          moltype = RNA   length = 22
FEATURE                 Location/Qualifiers
source                  1..22
                        mol_type = transcribed RNA
                        organism = Homo sapiens
SEQUENCE: 198
tggctcagtt cagcaggaac ag                                                  22

SEQ ID NO: 199          moltype = RNA   length = 22
FEATURE                 Location/Qualifiers
source                  1..22
                        mol_type = transcribed RNA
                        organism = Homo sapiens
SEQUENCE: 199
gagggttggg tggaggctct cc                                                  22

SEQ ID NO: 200          moltype = RNA   length = 21
FEATURE                 Location/Qualifiers
source                  1..21
                        mol_type = transcribed RNA
                        organism = Homo sapiens
SEQUENCE: 200
agggccccccc ctcaatcctg t                                                  21

SEQ ID NO: 201          moltype = RNA   length = 23
FEATURE                 Location/Qualifiers
source                  1..23
                        mol_type = transcribed RNA
                        organism = Homo sapiens
SEQUENCE: 201
tcgaggactg gtggaagggc ctt                                                 23

SEQ ID NO: 202          moltype = RNA   length = 23
FEATURE                 Location/Qualifiers
source                  1..23
                        mol_type = transcribed RNA
                        organism = Homo sapiens
SEQUENCE: 202
ttagggagta gaagggtggg gag                                                 23

SEQ ID NO: 203          moltype = RNA   length = 23
FEATURE                 Location/Qualifiers
source                  1..23
                        mol_type = transcribed RNA
                        organism = Homo sapiens
SEQUENCE: 203
agaggctttg tgcggatacg ggg                                                 23

SEQ ID NO: 204          moltype = RNA   length = 18
FEATURE                 Location/Qualifiers
source                  1..18
                        mol_type = transcribed RNA
                        organism = Homo sapiens
SEQUENCE: 204
```

```
cggggcggca ggggcctc                                                    18

SEQ ID NO: 205          moltype = RNA   length = 23
FEATURE                 Location/Qualifiers
source                  1..23
                        mol_type = transcribed RNA
                        organism = Homo sapiens
SEQUENCE: 205
ggaggcgcag gctcggaaag gcg                                              23

SEQ ID NO: 206          moltype = RNA   length = 22
FEATURE                 Location/Qualifiers
source                  1..22
                        mol_type = transcribed RNA
                        organism = Homo sapiens
SEQUENCE: 206
aaaagctggg ttgagagggc ga                                               22

SEQ ID NO: 207          moltype = RNA   length = 21
FEATURE                 Location/Qualifiers
source                  1..21
                        mol_type = transcribed RNA
                        organism = Homo sapiens
SEQUENCE: 207
agggtgcta tctgtgattg a                                                 21

SEQ ID NO: 208          moltype = RNA   length = 20
FEATURE                 Location/Qualifiers
source                  1..20
                        mol_type = transcribed RNA
                        organism = Homo sapiens
SEQUENCE: 208
cgcgggtcgg ggtctgcagg                                                  20

SEQ ID NO: 209          moltype = RNA   length = 21
FEATURE                 Location/Qualifiers
source                  1..21
                        mol_type = transcribed RNA
                        organism = Homo sapiens
SEQUENCE: 209
agccgcgggg atcgccgagg g                                                21

SEQ ID NO: 210          moltype = RNA   length = 17
FEATURE                 Location/Qualifiers
source                  1..17
                        mol_type = transcribed RNA
                        organism = Homo sapiens
SEQUENCE: 210
ggcgggtgcg ggggtgg                                                     17

SEQ ID NO: 211          moltype = RNA   length = 23
FEATURE                 Location/Qualifiers
source                  1..23
                        mol_type = transcribed RNA
                        organism = Homo sapiens
SEQUENCE: 211
agggactttt gggggcagat gtg                                              23

SEQ ID NO: 212          moltype = RNA   length = 18
FEATURE                 Location/Qualifiers
source                  1..18
                        mol_type = transcribed RNA
                        organism = Homo sapiens
SEQUENCE: 212
agcaggtgcg gggcggcg                                                    18

SEQ ID NO: 213          moltype = RNA   length = 23
FEATURE                 Location/Qualifiers
source                  1..23
                        mol_type = transcribed RNA
                        organism = Homo sapiens
SEQUENCE: 213
tgaggatatg gcagggaagg gga                                              23

SEQ ID NO: 214          moltype = RNA   length = 20
FEATURE                 Location/Qualifiers
source                  1..20
                        mol_type = transcribed RNA
                        organism = Homo sapiens
```

```
SEQUENCE: 214
actcaaactg tggggcact                                                       20

SEQ ID NO: 215         moltype = RNA  length = 20
FEATURE                Location/Qualifiers
source                 1..20
                       mol_type = transcribed RNA
                       organism = Homo sapiens
SEQUENCE: 215
gtgggttggg gcgggctctg                                                      20

SEQ ID NO: 216         moltype = RNA  length = 23
FEATURE                Location/Qualifiers
source                 1..23
                       mol_type = transcribed RNA
                       organism = Homo sapiens
SEQUENCE: 216
tgaggggcag agagcgagac ttt                                                  23

SEQ ID NO: 217         moltype = RNA  length = 18
FEATURE                Location/Qualifiers
source                 1..18
                       mol_type = transcribed RNA
                       organism = Homo sapiens
SEQUENCE: 217
ccagaggtgg ggactgag                                                        18

SEQ ID NO: 218         moltype = RNA  length = 20
FEATURE                Location/Qualifiers
source                 1..20
                       mol_type = transcribed RNA
                       organism = Homo sapiens
SEQUENCE: 218
tcagggagtc aggggagggc                                                      20

SEQ ID NO: 219         moltype = RNA  length = 19
FEATURE                Location/Qualifiers
source                 1..19
                       mol_type = transcribed RNA
                       organism = Homo sapiens
SEQUENCE: 219
gggggaagaa aaggtgggg                                                       19

SEQ ID NO: 220         moltype = RNA  length = 17
FEATURE                Location/Qualifiers
source                 1..17
                       mol_type = transcribed RNA
                       organism = Homo sapiens
SEQUENCE: 220
accccactcc tggtacc                                                         17

SEQ ID NO: 221         moltype = RNA  length = 22
FEATURE                Location/Qualifiers
source                 1..22
                       mol_type = transcribed RNA
                       organism = Homo sapiens
SEQUENCE: 221
ctgggacagg aggaggaggc ag                                                   22

SEQ ID NO: 222         moltype = RNA  length = 18
FEATURE                Location/Qualifiers
source                 1..18
                       mol_type = transcribed RNA
                       organism = Homo sapiens
SEQUENCE: 222
ggtgggcttc ccggaggg                                                        18

SEQ ID NO: 223         moltype = RNA  length = 17
FEATURE                Location/Qualifiers
source                 1..17
                       mol_type = transcribed RNA
                       organism = Homo sapiens
SEQUENCE: 223
gccggacaag agggagg                                                         17

SEQ ID NO: 224         moltype = RNA  length = 22
FEATURE                Location/Qualifiers
source                 1..22
                       mol_type = transcribed RNA
```

```
                        organism = Homo sapiens
SEQUENCE: 224
cagggctggc agtgacatgg gt                                                  22

SEQ ID NO: 225          moltype = RNA   length = 20
FEATURE                 Location/Qualifiers
source                  1..20
                        mol_type = transcribed RNA
                        organism = Homo sapiens
SEQUENCE: 225
ggctccttgg tctagggta                                                      20

SEQ ID NO: 226          moltype = RNA   length = 20
FEATURE                 Location/Qualifiers
source                  1..20
                        mol_type = transcribed RNA
                        organism = Homo sapiens
SEQUENCE: 226
ggatccgagt cacggcacca                                                     20

SEQ ID NO: 227          moltype = RNA   length = 22
FEATURE                 Location/Qualifiers
source                  1..22
                        mol_type = transcribed RNA
                        organism = Homo sapiens
SEQUENCE: 227
tggcggcggt agttatgggc tt                                                  22

SEQ ID NO: 228          moltype = RNA   length = 18
FEATURE                 Location/Qualifiers
source                  1..18
                        mol_type = transcribed RNA
                        organism = Homo sapiens
SEQUENCE: 228
ggtgggggt gttgtttt                                                        18

SEQ ID NO: 229          moltype = RNA   length = 20
FEATURE                 Location/Qualifiers
source                  1..20
                        mol_type = transcribed RNA
                        organism = Homo sapiens
SEQUENCE: 229
ctgggttggg ctgggctggg                                                     20

SEQ ID NO: 230          moltype = RNA   length = 17
FEATURE                 Location/Qualifiers
source                  1..17
                        mol_type = transcribed RNA
                        organism = Homo sapiens
SEQUENCE: 230
gggagaaggg tcgggc                                                         17

SEQ ID NO: 231          moltype = RNA   length = 22
FEATURE                 Location/Qualifiers
source                  1..22
                        mol_type = transcribed RNA
                        organism = Homo sapiens
SEQUENCE: 231
aaaccgttac cattactgag tt                                                  22

SEQ ID NO: 232          moltype = RNA   length = 24
FEATURE                 Location/Qualifiers
source                  1..24
                        mol_type = transcribed RNA
                        organism = Homo sapiens
SEQUENCE: 232
tgggcgaggg gtgggctctc agag                                                24

SEQ ID NO: 233          moltype = RNA   length = 20
FEATURE                 Location/Qualifiers
source                  1..20
                        mol_type = transcribed RNA
                        organism = Homo sapiens
SEQUENCE: 233
cggggtgggt gaggtcgggc                                                     20

SEQ ID NO: 234          moltype = RNA   length = 26
FEATURE                 Location/Qualifiers
source                  1..26
```

```
                        mol_type = transcribed RNA
                        organism = Homo sapiens
SEQUENCE: 234
ctcggccgcg gcgcgtagcc cccgcc                                          26

SEQ ID NO: 235          moltype = RNA   length = 21
FEATURE                 Location/Qualifiers
source                  1..21
                        mol_type = transcribed RNA
                        organism = Homo sapiens
SEQUENCE: 235
ctgggctcgg gacgcgcggc t                                               21

SEQ ID NO: 236          moltype = RNA   length = 22
FEATURE                 Location/Qualifiers
source                  1..22
                        mol_type = transcribed RNA
                        organism = Homo sapiens
SEQUENCE: 236
ggggctgtga ttgaccagca gg                                              22

SEQ ID NO: 237          moltype = RNA   length = 22
FEATURE                 Location/Qualifiers
source                  1..22
                        mol_type = transcribed RNA
                        organism = Homo sapiens
SEQUENCE: 237
ttgaggagac atggtggggg cc                                              22

SEQ ID NO: 238          moltype = RNA   length = 22
FEATURE                 Location/Qualifiers
source                  1..22
                        mol_type = transcribed RNA
                        organism = Homo sapiens
SEQUENCE: 238
caggaggcag tgggcgagca gg                                              22

SEQ ID NO: 239          moltype = RNA   length = 22
FEATURE                 Location/Qualifiers
source                  1..22
                        mol_type = transcribed RNA
                        organism = Homo sapiens
SEQUENCE: 239
aggggcgca gtcactgacg tg                                               22

SEQ ID NO: 240          moltype = RNA   length = 22
FEATURE                 Location/Qualifiers
source                  1..22
                        mol_type = transcribed RNA
                        organism = Homo sapiens
SEQUENCE: 240
tggggaaggc gtcagtgtcg gg                                              22

SEQ ID NO: 241          moltype = RNA   length = 25
FEATURE                 Location/Qualifiers
source                  1..25
                        mol_type = transcribed RNA
                        organism = Homo sapiens
SEQUENCE: 241
aagggaggag gagcggaggg gccct                                           25

SEQ ID NO: 242          moltype = RNA   length = 23
FEATURE                 Location/Qualifiers
source                  1..23
                        mol_type = transcribed RNA
                        organism = Homo sapiens
SEQUENCE: 242
tgagtggggc tcccgggacg gcg                                             23

SEQ ID NO: 243          moltype = RNA   length = 24
FEATURE                 Location/Qualifiers
source                  1..24
                        mol_type = transcribed RNA
                        organism = Homo sapiens
SEQUENCE: 243
aggcaggggc tggtgctggg cggg                                            24

SEQ ID NO: 244          moltype = RNA   length = 18
FEATURE                 Location/Qualifiers
```

```
source                  1..18
                        mol_type = transcribed RNA
                        organism = Homo sapiens
SEQUENCE: 244
cggtgagcgc tcgctggc                                                     18

SEQ ID NO: 245          moltype = RNA   length = 21
FEATURE                 Location/Qualifiers
source                  1..21
                        mol_type = transcribed RNA
                        organism = Homo sapiens
SEQUENCE: 245
cggggcagct cagtacagga t                                                 21

SEQ ID NO: 246          moltype = RNA   length = 24
FEATURE                 Location/Qualifiers
source                  1..24
                        mol_type = transcribed RNA
                        organism = Homo sapiens
SEQUENCE: 246
agggctggac tcagcggcgg agct                                              24

SEQ ID NO: 247          moltype = RNA   length = 21
FEATURE                 Location/Qualifiers
source                  1..21
                        mol_type = transcribed RNA
                        organism = Homo sapiens
SEQUENCE: 247
atccagttct ctgaggggc t                                                  21

SEQ ID NO: 248          moltype = RNA   length = 23
FEATURE                 Location/Qualifiers
source                  1..23
                        mol_type = transcribed RNA
                        organism = Homo sapiens
SEQUENCE: 248
agtgcctgag ggagtaagag ccc                                               23

SEQ ID NO: 249          moltype = RNA   length = 22
FEATURE                 Location/Qualifiers
source                  1..22
                        mol_type = transcribed RNA
                        organism = Homo sapiens
SEQUENCE: 249
tgggggagtg cagtgattgt gg                                                22

SEQ ID NO: 250          moltype = RNA   length = 21
FEATURE                 Location/Qualifiers
source                  1..21
                        mol_type = transcribed RNA
                        organism = Homo sapiens
SEQUENCE: 250
acggcccagg cggcattggt g                                                 21

SEQ ID NO: 251          moltype = RNA   length = 20
FEATURE                 Location/Qualifiers
source                  1..20
                        mol_type = transcribed RNA
                        organism = Homo sapiens
SEQUENCE: 251
agagatgaag cgggggggcg                                                   20

SEQ ID NO: 252          moltype = RNA   length = 24
FEATURE                 Location/Qualifiers
source                  1..24
                        mol_type = transcribed RNA
                        organism = Homo sapiens
SEQUENCE: 252
ggaggccggg gtggggcggg gcgg                                              24

SEQ ID NO: 253          moltype = RNA   length = 20
FEATURE                 Location/Qualifiers
source                  1..20
                        mol_type = transcribed RNA
                        organism = Homo sapiens
SEQUENCE: 253
gcggaaggcg gagcggcgga                                                   20

SEQ ID NO: 254          moltype = RNA   length = 18
```

```
FEATURE             Location/Qualifiers
source              1..18
                    mol_type = transcribed RNA
                    organism = Homo sapiens
SEQUENCE: 254
gtgaaggccc ggcggaga                                                 18

SEQ ID NO: 255      moltype = RNA   length = 23
FEATURE             Location/Qualifiers
source              1..23
                    mol_type = transcribed RNA
                    organism = Homo sapiens
SEQUENCE: 255
gaacgcctgt tcttgccagg tgg                                           23

SEQ ID NO: 256      moltype = RNA   length = 22
FEATURE             Location/Qualifiers
source              1..22
                    mol_type = transcribed RNA
                    organism = Homo sapiens
SEQUENCE: 256
gggggtcccc ggtgctcgga tc                                            22

SEQ ID NO: 257      moltype = RNA   length = 22
FEATURE             Location/Qualifiers
source              1..22
                    mol_type = transcribed RNA
                    organism = Homo sapiens
SEQUENCE: 257
gctgggatta caggcatgag cc                                            22

SEQ ID NO: 258      moltype = RNA   length = 25
FEATURE             Location/Qualifiers
source              1..25
                    mol_type = transcribed RNA
                    organism = Homo sapiens
SEQUENCE: 258
agggatcgcg ggcgggtggc ggcct                                         25

SEQ ID NO: 259      moltype = RNA   length = 22
FEATURE             Location/Qualifiers
source              1..22
                    mol_type = transcribed RNA
                    organism = Homo sapiens
SEQUENCE: 259
agacacattt ggagagggac cc                                            22

SEQ ID NO: 260      moltype = RNA   length = 21
FEATURE             Location/Qualifiers
source              1..21
                    mol_type = transcribed RNA
                    organism = Homo sapiens
SEQUENCE: 260
aggaggcagc gctctcagga c                                             21

SEQ ID NO: 261      moltype = RNA   length = 22
FEATURE             Location/Qualifiers
source              1..22
                    mol_type = transcribed RNA
                    organism = Homo sapiens
SEQUENCE: 261
aggcggggcg ccgcgggacc gc                                            22

SEQ ID NO: 262      moltype = RNA   length = 22
FEATURE             Location/Qualifiers
source              1..22
                    mol_type = transcribed RNA
                    organism = Homo sapiens
SEQUENCE: 262
ggtggcccgg ccgtgcctga gg                                            22

SEQ ID NO: 263      moltype = RNA   length = 22
FEATURE             Location/Qualifiers
source              1..22
                    mol_type = transcribed RNA
                    organism = Homo sapiens
SEQUENCE: 263
aggcgatgtg gggatgtaga ga                                            22
```

| | | |
|---|---|---|
| SEQ ID NO: 264<br>FEATURE<br>source | moltype = RNA length = 23<br>Location/Qualifiers<br>1..23<br>mol_type = transcribed RNA<br>organism = Homo sapiens | |
| SEQUENCE: 264<br>tgggcagggg cttattgtag gag | | 23 |
| SEQ ID NO: 265<br>FEATURE<br>source | moltype = RNA length = 21<br>Location/Qualifiers<br>1..21<br>mol_type = transcribed RNA<br>organism = Homo sapiens | |
| SEQUENCE: 265<br>cgggagctgg ggtctgcagg t | | 21 |
| SEQ ID NO: 266<br>FEATURE<br>source | moltype = RNA length = 23<br>Location/Qualifiers<br>1..23<br>mol_type = transcribed RNA<br>organism = Homo sapiens | |
| SEQUENCE: 266<br>ctcggggcag gcggctggga gcg | | 23 |
| SEQ ID NO: 267<br>FEATURE<br>source | moltype = RNA length = 23<br>Location/Qualifiers<br>1..23<br>mol_type = transcribed RNA<br>organism = Homo sapiens | |
| SEQUENCE: 267<br>cgagggtag aagagcacag ggg | | 23 |
| SEQ ID NO: 268<br>FEATURE<br>source | moltype = RNA length = 22<br>Location/Qualifiers<br>1..22<br>mol_type = transcribed RNA<br>organism = Homo sapiens | |
| SEQUENCE: 268<br>gtgggtgctg gtgggagccg tg | | 22 |
| SEQ ID NO: 269<br>FEATURE<br>source | moltype = RNA length = 22<br>Location/Qualifiers<br>1..22<br>mol_type = transcribed RNA<br>organism = Homo sapiens | |
| SEQUENCE: 269<br>tcgggcctgg ggttggggga gc | | 22 |
| SEQ ID NO: 270<br>FEATURE<br>source | moltype = RNA length = 22<br>Location/Qualifiers<br>1..22<br>mol_type = transcribed RNA<br>organism = Homo sapiens | |
| SEQUENCE: 270<br>gggggtgtg gagccagggg gc | | 22 |
| SEQ ID NO: 271<br>FEATURE<br>source | moltype = RNA length = 23<br>Location/Qualifiers<br>1..23<br>mol_type = transcribed RNA<br>organism = Homo sapiens | |
| SEQUENCE: 271<br>tggtgcggag agggcccaca gtg | | 23 |
| SEQ ID NO: 272<br>FEATURE<br>source | moltype = RNA length = 22<br>Location/Qualifiers<br>1..22<br>mol_type = transcribed RNA<br>organism = Homo sapiens | |
| SEQUENCE: 272<br>tagggatggg aggccaggat ga | | 22 |
| SEQ ID NO: 273<br>FEATURE<br>source | moltype = RNA length = 19<br>Location/Qualifiers<br>1..19<br>mol_type = transcribed RNA<br>organism = Homo sapiens | |
| SEQUENCE: 273<br>ctggggagtg gctgggag | | 19 |

```
SEQ ID NO: 274          moltype = RNA   length = 25
FEATURE                 Location/Qualifiers
source                  1..25
                        mol_type = transcribed RNA
                        organism = Homo sapiens
SEQUENCE: 274
gtgaggcggg gccaggaggg tgtgt                                              25

SEQ ID NO: 275          moltype = RNA   length = 25
FEATURE                 Location/Qualifiers
source                  1..25
                        mol_type = transcribed RNA
                        organism = Homo sapiens
SEQUENCE: 275
tcggggcatg ggggagggag gctgg                                              25

SEQ ID NO: 276          moltype = RNA   length = 23
FEATURE                 Location/Qualifiers
source                  1..23
                        mol_type = transcribed RNA
                        organism = Homo sapiens
SEQUENCE: 276
tggggaaggc ttggcaggga aga                                                23

SEQ ID NO: 277          moltype = RNA   length = 25
FEATURE                 Location/Qualifiers
source                  1..25
                        mol_type = transcribed RNA
                        organism = Homo sapiens
SEQUENCE: 277
tagggtggg ggaattcagg ggtgt                                               25

SEQ ID NO: 278          moltype = RNA   length = 20
FEATURE                 Location/Qualifiers
source                  1..20
                        mol_type = transcribed RNA
                        organism = Homo sapiens
SEQUENCE: 278
gccggggctt tgggtgaggg                                                    20

SEQ ID NO: 279          moltype = RNA   length = 21
FEATURE                 Location/Qualifiers
source                  1..21
                        mol_type = transcribed RNA
                        organism = Homo sapiens
SEQUENCE: 279
gtaggtgaca gtcaggggcg g                                                  21

SEQ ID NO: 280          moltype = RNA   length = 24
FEATURE                 Location/Qualifiers
source                  1..24
                        mol_type = transcribed RNA
                        organism = Homo sapiens
SEQUENCE: 280
tgtaggcatg aggcagggcc cagg                                               24

SEQ ID NO: 281          moltype = RNA   length = 22
FEATURE                 Location/Qualifiers
source                  1..22
                        mol_type = transcribed RNA
                        organism = Homo sapiens
SEQUENCE: 281
gcccaggact ttgtgcgggg tg                                                 22

SEQ ID NO: 282          moltype = RNA   length = 23
FEATURE                 Location/Qualifiers
source                  1..23
                        mol_type = transcribed RNA
                        organism = Homo sapiens
SEQUENCE: 282
tgggggctgg gatgggccat ggt                                                23

SEQ ID NO: 283          moltype = RNA   length = 23
FEATURE                 Location/Qualifiers
source                  1..23
                        mol_type = transcribed RNA
                        organism = Homo sapiens
SEQUENCE: 283
```

```
aggaggtggt actaggggcc agc                                          23

SEQ ID NO: 284          moltype = RNA   length = 19
FEATURE                 Location/Qualifiers
source                  1..19
                        mol_type = transcribed RNA
                        organism = Homo sapiens
SEQUENCE: 284
tgggggagat gggggttga                                               19

SEQ ID NO: 285          moltype = RNA   length = 21
FEATURE                 Location/Qualifiers
source                  1..21
                        mol_type = transcribed RNA
                        organism = Homo sapiens
SEQUENCE: 285
cccatgcctc ctgccgcggt c                                            21

SEQ ID NO: 286          moltype = RNA   length = 21
FEATURE                 Location/Qualifiers
source                  1..21
                        mol_type = transcribed RNA
                        organism = Homo sapiens
SEQUENCE: 286
tgagggaccc aggacaggag a                                            21

SEQ ID NO: 287          moltype = RNA   length = 22
FEATURE                 Location/Qualifiers
source                  1..22
                        mol_type = transcribed RNA
                        organism = Homo sapiens
SEQUENCE: 287
agggccgaag ggtggaagct gc                                           22

SEQ ID NO: 288          moltype = RNA   length = 22
FEATURE                 Location/Qualifiers
source                  1..22
                        mol_type = transcribed RNA
                        organism = Homo sapiens
SEQUENCE: 288
cagggcaggg aaggtgggag ag                                           22

SEQ ID NO: 289          moltype = RNA   length = 22
FEATURE                 Location/Qualifiers
source                  1..22
                        mol_type = transcribed RNA
                        organism = Homo sapiens
SEQUENCE: 289
tggtggagga agagggcagc tc                                           22

SEQ ID NO: 290          moltype = RNA   length = 25
FEATURE                 Location/Qualifiers
source                  1..25
                        mol_type = transcribed RNA
                        organism = Homo sapiens
SEQUENCE: 290
aggggggcac tgcgcaagca aagcc                                        25

SEQ ID NO: 291          moltype = RNA   length = 23
FEATURE                 Location/Qualifiers
source                  1..23
                        mol_type = transcribed RNA
                        organism = Homo sapiens
SEQUENCE: 291
tgggggaca gatggagagg aca                                           23

SEQ ID NO: 292          moltype = RNA   length = 21
FEATURE                 Location/Qualifiers
source                  1..21
                        mol_type = transcribed RNA
                        organism = Homo sapiens
SEQUENCE: 292
gtgtggccgg caggcgggtg g                                            21

SEQ ID NO: 293          moltype = RNA   length = 22
FEATURE                 Location/Qualifiers
source                  1..22
                        mol_type = transcribed RNA
                        organism = Homo sapiens
```

```
SEQUENCE: 293
gggacccagg gagagacgta ag                                                  22

SEQ ID NO: 294          moltype = RNA  length = 23
FEATURE                 Location/Qualifiers
source                  1..23
                        mol_type = transcribed RNA
                        organism = Homo sapiens
SEQUENCE: 294
cctccctgcc cgcctctctg cag                                                 23

SEQ ID NO: 295          moltype = RNA  length = 22
FEATURE                 Location/Qualifiers
source                  1..22
                        mol_type = transcribed RNA
                        organism = Homo sapiens
SEQUENCE: 295
tgcggggcta gggctaacag ca                                                  22

SEQ ID NO: 296          moltype = RNA  length = 20
FEATURE                 Location/Qualifiers
source                  1..20
                        mol_type = transcribed RNA
                        organism = Homo sapiens
SEQUENCE: 296
cggctctggg tctgtggga                                                      20

SEQ ID NO: 297          moltype = RNA  length = 21
FEATURE                 Location/Qualifiers
source                  1..21
                        mol_type = transcribed RNA
                        organism = Homo sapiens
SEQUENCE: 297
aagggacagg gagggtcgtg g                                                   21

SEQ ID NO: 298          moltype = RNA  length = 21
FEATURE                 Location/Qualifiers
source                  1..21
                        mol_type = transcribed RNA
                        organism = Homo sapiens
SEQUENCE: 298
cgtggaggac gaggaggagg c                                                   21

SEQ ID NO: 299          moltype = RNA  length = 18
FEATURE                 Location/Qualifiers
source                  1..18
                        mol_type = transcribed RNA
                        organism = Homo sapiens
SEQUENCE: 299
ttcccagcca acgcacca                                                       18

SEQ ID NO: 300          moltype = RNA  length = 22
FEATURE                 Location/Qualifiers
source                  1..22
                        mol_type = transcribed RNA
                        organism = Homo sapiens
SEQUENCE: 300
ggggaactgt agatgaaaag gc                                                  22

SEQ ID NO: 301          moltype = RNA  length = 22
FEATURE                 Location/Qualifiers
source                  1..22
                        mol_type = transcribed RNA
                        organism = Homo sapiens
SEQUENCE: 301
tcaaaatcag gagtcggggc tt                                                  22

SEQ ID NO: 302          moltype = RNA  length = 20
FEATURE                 Location/Qualifiers
source                  1..20
                        mol_type = transcribed RNA
                        organism = Homo sapiens
SEQUENCE: 302
ggcggcgggg aggtaggcag                                                     20

SEQ ID NO: 303          moltype = RNA  length = 22
FEATURE                 Location/Qualifiers
source                  1..22
                        mol_type = transcribed RNA
```

```
                        organism = Homo sapiens
SEQUENCE: 303
ctgccctggc ccgagggacc ga                                            22

SEQ ID NO: 304          moltype = RNA   length = 22
FEATURE                 Location/Qualifiers
source                  1..22
                        mol_type = transcribed RNA
                        organism = Homo sapiens
SEQUENCE: 304
gggtgggat ttgttgcatt ac                                             22

SEQ ID NO: 305          moltype = RNA   length = 22
FEATURE                 Location/Qualifiers
source                  1..22
                        mol_type = transcribed RNA
                        organism = Homo sapiens
SEQUENCE: 305
agggacggga cgcggtgcag tg                                            22

SEQ ID NO: 306          moltype = RNA   length = 21
FEATURE                 Location/Qualifiers
source                  1..21
                        mol_type = transcribed RNA
                        organism = Homo sapiens
SEQUENCE: 306
aaggcagggc ccccgctccc c                                             21

SEQ ID NO: 307          moltype = RNA   length = 20
FEATURE                 Location/Qualifiers
source                  1..20
                        mol_type = transcribed RNA
                        organism = Homo sapiens
SEQUENCE: 307
tcacacctgc ctcgccccccc                                              20

SEQ ID NO: 308          moltype = RNA   length = 17
FEATURE                 Location/Qualifiers
source                  1..17
                        mol_type = transcribed RNA
                        organism = Homo sapiens
SEQUENCE: 308
gtgggggaga ggctgtc                                                  17

SEQ ID NO: 309          moltype = RNA   length = 22
FEATURE                 Location/Qualifiers
source                  1..22
                        mol_type = transcribed RNA
                        organism = Homo sapiens
SEQUENCE: 309
actcggcgtg gcgtcggtcg tg                                            22

SEQ ID NO: 310          moltype = RNA   length = 22
FEATURE                 Location/Qualifiers
source                  1..22
                        mol_type = transcribed RNA
                        organism = Homo sapiens
SEQUENCE: 310
tggggagcgg ccccgggtg gg                                             22

SEQ ID NO: 311          moltype = RNA   length = 21
FEATURE                 Location/Qualifiers
source                  1..21
                        mol_type = transcribed RNA
                        organism = Homo sapiens
SEQUENCE: 311
atcacattgc cagggatttc c                                             21

SEQ ID NO: 312          moltype = RNA   length = 23
FEATURE                 Location/Qualifiers
source                  1..23
                        mol_type = transcribed RNA
                        organism = Homo sapiens
SEQUENCE: 312
tagcaccatt tgaaatcagt gtt                                           23

SEQ ID NO: 313          moltype = RNA   length = 22
FEATURE                 Location/Qualifiers
source                  1..22
```

```
                           mol_type = transcribed RNA
                           organism = Homo sapiens
SEQUENCE: 313
ggctggagcg agtgcagtgg tg                                             22

SEQ ID NO: 314             moltype = RNA  length = 23
FEATURE                    Location/Qualifiers
source                     1..23
                           mol_type = transcribed RNA
                           organism = Homo sapiens
SEQUENCE: 314
agaagaaggc ggtcggtctg cgg                                            23

SEQ ID NO: 315             moltype = RNA  length = 17
FEATURE                    Location/Qualifiers
source                     1..17
                           mol_type = transcribed RNA
                           organism = Homo sapiens
SEQUENCE: 315
ccccggggag cccggcg                                                   17

SEQ ID NO: 316             moltype = RNA  length = 22
FEATURE                    Location/Qualifiers
source                     1..22
                           mol_type = transcribed RNA
                           organism = Homo sapiens
SEQUENCE: 316
gagcaggcga ggctgggctg aa                                             22

SEQ ID NO: 317             moltype = RNA  length = 23
FEATURE                    Location/Qualifiers
source                     1..23
                           mol_type = transcribed RNA
                           organism = Homo sapiens
SEQUENCE: 317
gtgagtggga gccggtgggg ctg                                            23

SEQ ID NO: 318             moltype = RNA  length = 23
FEATURE                    Location/Qualifiers
source                     1..23
                           mol_type = transcribed RNA
                           organism = Homo sapiens
SEQUENCE: 318
ccccggtgtt ggggcgcgtc tgc                                            23

SEQ ID NO: 319             moltype = RNA  length = 19
FEATURE                    Location/Qualifiers
source                     1..19
                           mol_type = transcribed RNA
                           organism = Homo sapiens
SEQUENCE: 319
ggctggtcag atgggagtg                                                 19

SEQ ID NO: 320             moltype = RNA  length = 22
FEATURE                    Location/Qualifiers
source                     1..22
                           mol_type = transcribed RNA
                           organism = Homo sapiens
SEQUENCE: 320
gactatagaa ctttcccccct ca                                            22

SEQ ID NO: 321             moltype = RNA  length = 23
FEATURE                    Location/Qualifiers
source                     1..23
                           mol_type = transcribed RNA
                           organism = Homo sapiens
SEQUENCE: 321
caggcagaag tggggctgac agg                                            23

SEQ ID NO: 322             moltype = RNA  length = 21
FEATURE                    Location/Qualifiers
source                     1..21
                           mol_type = transcribed RNA
                           organism = Homo sapiens
SEQUENCE: 322
tcacctggct ggcccgccca g                                              21

SEQ ID NO: 323             moltype = RNA  length = 21
FEATURE                    Location/Qualifiers
```

```
source                  1..21
                        mol_type = transcribed RNA
                        organism = Homo sapiens
SEQUENCE: 323
tggggcgggg caggtccctg c                                           21

SEQ ID NO: 324          moltype = RNA   length = 22
FEATURE                 Location/Qualifiers
source                  1..22
                        mol_type = transcribed RNA
                        organism = Homo sapiens
SEQUENCE: 324
tggggaggtg tggagtcagc at                                          22

SEQ ID NO: 325          moltype = RNA   length = 19
FEATURE                 Location/Qualifiers
source                  1..19
                        mol_type = transcribed RNA
                        organism = Homo sapiens
SEQUENCE: 325
cggggccaga gcagagagc                                              19

SEQ ID NO: 326          moltype = RNA   length = 18
FEATURE                 Location/Qualifiers
source                  1..18
                        mol_type = transcribed RNA
                        organism = Homo sapiens
SEQUENCE: 326
ctggcagggg gagaggta                                               18

SEQ ID NO: 327          moltype = RNA   length = 19
FEATURE                 Location/Qualifiers
source                  1..19
                        mol_type = transcribed RNA
                        organism = Homo sapiens
SEQUENCE: 327
ttgatctcgg aagctaagc                                              19

SEQ ID NO: 328          moltype = RNA   length = 18
FEATURE                 Location/Qualifiers
source                  1..18
                        mol_type = transcribed RNA
                        organism = Homo sapiens
SEQUENCE: 328
atcctagtca cggcacca                                               18

SEQ ID NO: 329          moltype = RNA   length = 22
FEATURE                 Location/Qualifiers
source                  1..22
                        mol_type = transcribed RNA
                        organism = Homo sapiens
SEQUENCE: 329
tattgcactt gtcccggcct gt                                          22

SEQ ID NO: 330          moltype = RNA   length = 61
FEATURE                 Location/Qualifiers
source                  1..61
                        mol_type = transcribed RNA
                        organism = Homo sapiens
SEQUENCE: 330
tcggctggcg ggggtagagc tggctgcagg cccggcccct ctcagctgct gccctctcca  60
g                                                                 61

SEQ ID NO: 331          moltype = RNA   length = 75
FEATURE                 Location/Qualifiers
source                  1..75
                        mol_type = transcribed RNA
                        organism = Homo sapiens
SEQUENCE: 331
gtagttgttc tacagaagac ctggatgtgt aggagctaag acacactcca gggagctgt   60
ggaagcagta acacg                                                  75

SEQ ID NO: 332          moltype = RNA   length = 83
FEATURE                 Location/Qualifiers
source                  1..83
                        mol_type = transcribed RNA
                        organism = Homo sapiens
SEQUENCE: 332
aatagagggt gcacaggcac gggagctcag gtgaggcagg gagctgagct cacctgacct  60
```

```
cccatgcctg tgcaccctct att                                              83

SEQ ID NO: 333          moltype = RNA    length = 86
FEATURE                 Location/Qualifiers
source                  1..86
                        mol_type = transcribed RNA
                        organism = Homo sapiens
SEQUENCE: 333
tttggtactt gaagagagga tacccttgt atgttcactt gattaatggc gaatatacag       60
ggggagactc ttatttgcgt atcaaa                                           86

SEQ ID NO: 334          moltype = RNA    length = 85
FEATURE                 Location/Qualifiers
source                  1..85
                        mol_type = transcribed RNA
                        organism = Homo sapiens
SEQUENCE: 334
ggcctgggta ggcttgcatg ggggactggg aagagaccat gaacaggtta gtccagggag      60
ttctcatcaa gcctttactc agtag                                            85

SEQ ID NO: 335          moltype = RNA    length = 80
FEATURE                 Location/Qualifiers
source                  1..80
                        mol_type = transcribed RNA
                        organism = Homo sapiens
SEQUENCE: 335
ggttggctat aactatcatt tccaaggttg tgcttttagg aaatgttggc tgtcctgcgg      60
agagagaatg gggagccagg                                                  80

SEQ ID NO: 336          moltype = RNA    length = 86
FEATURE                 Location/Qualifiers
source                  1..86
                        mol_type = transcribed RNA
                        organism = Homo sapiens
SEQUENCE: 336
agcactgccc ccggtgagtc agggtggggc tggcccctg cttcgtgccc atccgcgctc       60
tgactctctg cccacctgca ggagct                                           86

SEQ ID NO: 337          moltype = RNA    length = 81
FEATURE                 Location/Qualifiers
source                  1..81
                        mol_type = transcribed RNA
                        organism = Homo sapiens
SEQUENCE: 337
tccactgctg ccgccgtcgc cgccacccga gccggagcgg gctgggccgc caaggcaaga     60
tggtggacta cagcgtgtgg g                                                81

SEQ ID NO: 338          moltype = RNA    length = 86
FEATURE                 Location/Qualifiers
source                  1..86
                        mol_type = transcribed RNA
                        organism = Homo sapiens
SEQUENCE: 338
tttggtactt aaagagagga tacccttgt atgttcactt gattaatggc gaatatacag       60
ggggagactc tcatttgcgt atcaaa                                           86

SEQ ID NO: 339          moltype = RNA    length = 78
FEATURE                 Location/Qualifiers
source                  1..78
                        mol_type = transcribed RNA
                        organism = Homo sapiens
SEQUENCE: 339
gtagctgagg ggatggtaga ccggtgacgt gcacttcatt tacgatgtag gtcacccgtt     60
tgactatcca ccagcgcc                                                    78

SEQ ID NO: 340          moltype = RNA    length = 87
FEATURE                 Location/Qualifiers
source                  1..87
                        mol_type = transcribed RNA
                        organism = Homo sapiens
SEQUENCE: 340
gcagggctgg cagggaggct gggagggggct ggctgggtct ggtagtgggc atcagctggc    60
cctcatttct taagacagca cttctgt                                          87

SEQ ID NO: 341          moltype = RNA    length = 83
FEATURE                 Location/Qualifiers
source                  1..83
                        mol_type = transcribed RNA
                        organism = Homo sapiens
```

```
SEQUENCE: 341
gtgagtggga gccccagtgt gtggttgggg ccatggcggg tgggcagccc agcctctgag   60
ccttcctcgt ctgtctgccc cag                                           83

SEQ ID NO: 342          moltype = RNA   length = 73
FEATURE                 Location/Qualifiers
source                  1..73
                        mol_type = transcribed RNA
                        organism = Homo sapiens
SEQUENCE: 342
tgtatccttg aatggatttt tggagcagga gtggacacct gacccaaagg aaatcaatcc   60
ataggctagc aat                                                      73

SEQ ID NO: 343          moltype = RNA   length = 66
FEATURE                 Location/Qualifiers
source                  1..66
                        mol_type = transcribed RNA
                        organism = Homo sapiens
SEQUENCE: 343
gggaggaggg aggagatggg ccaagttccc tctggctgga acgcccttcc ccccttctt   60
cacctg                                                              66

SEQ ID NO: 344          moltype = RNA   length = 66
FEATURE                 Location/Qualifiers
source                  1..66
                        mol_type = transcribed RNA
                        organism = Homo sapiens
SEQUENCE: 344
cctgggaacg ggttccggca gacgctgagg ttgcgttgac gctcgcgccc cggctcccgt   60
tccagg                                                              66

SEQ ID NO: 345          moltype = RNA   length = 47
FEATURE                 Location/Qualifiers
source                  1..47
                        mol_type = transcribed RNA
                        organism = Homo sapiens
SEQUENCE: 345
ctcggcgcgg ggcgcgggct ccggttggg gcgagccaac gccgggg                  47

SEQ ID NO: 346          moltype = RNA   length = 61
FEATURE                 Location/Qualifiers
source                  1..61
                        mol_type = transcribed RNA
                        organism = Homo sapiens
SEQUENCE: 346
gccctccgcc cgtgcacccc ggggcaggag accccgcggg acgcgccgag gtaggggga   60
c                                                                   61

SEQ ID NO: 347          moltype = RNA   length = 75
FEATURE                 Location/Qualifiers
source                  1..75
                        mol_type = transcribed RNA
                        organism = Homo sapiens
SEQUENCE: 347
ggctgtgccg ggtagagagg gcagtgggag gtaagagctc ttcacccttc accaccttct   60
ccacccagca tggcc                                                    75

SEQ ID NO: 348          moltype = RNA   length = 71
FEATURE                 Location/Qualifiers
source                  1..71
                        mol_type = transcribed RNA
                        organism = Homo sapiens
SEQUENCE: 348
tgacgggcga gcttttggcc cgggttatac ctgatgctca cgtataagac gagcaaaaag   60
cttgttggtc a                                                        71

SEQ ID NO: 349          moltype = RNA   length = 75
FEATURE                 Location/Qualifiers
source                  1..75
                        mol_type = transcribed RNA
                        organism = Homo sapiens
SEQUENCE: 349
caggggtttg gggaaacggc cgctgagtga ggcgtcggct gtgtttctca ccgcggtctt   60
ttcctcccac tcttg                                                    75

SEQ ID NO: 350          moltype = RNA   length = 110
FEATURE                 Location/Qualifiers
source                  1..110
                        mol_type = transcribed RNA
```

```
                          organism = Homo sapiens
SEQUENCE: 350
tcacctggcc atgtgacttg tgggcttccc tttgtcatcc ttcgcctagg gctctgagca    60
gggcagggac agcaaagggg tgctcagttg tcacttccca cagcacggag              110

SEQ ID NO: 351          moltype = RNA   length = 81
FEATURE                 Location/Qualifiers
source                  1..81
                        mol_type = transcribed RNA
                        organism = Homo sapiens
SEQUENCE: 351
ggacaggcac ctgaggctct gttagccttg gctctgggtc ctgctcctta gagcagaggc    60
agagaggctc agggtctgtc t                                              81

SEQ ID NO: 352          moltype = RNA   length = 73
FEATURE                 Location/Qualifiers
source                  1..73
                        mol_type = transcribed RNA
                        organism = Homo sapiens
SEQUENCE: 352
accagctctg ttgggacaag aggacggtct tcttttggaa ggaagaccat catcttgtcc    60
gaagagagct ggt                                                       73

SEQ ID NO: 353          moltype = RNA   length = 61
FEATURE                 Location/Qualifiers
source                  1..61
                        mol_type = transcribed RNA
                        organism = Homo sapiens
SEQUENCE: 353
tcaccCggtg agggcgggtg gaggaggagg gtccccacca tcagccttca ctgggacggg    60
a                                                                    61

SEQ ID NO: 354          moltype = RNA   length = 75
FEATURE                 Location/Qualifiers
source                  1..75
                        mol_type = transcribed RNA
                        organism = Homo sapiens
SEQUENCE: 354
gcagaagaaa gatctggaag tgggagacac ttttactata tatagtggct cccacttcca    60
gatctttctc tctgt                                                     75

SEQ ID NO: 355          moltype = RNA   length = 77
FEATURE                 Location/Qualifiers
source                  1..77
                        mol_type = transcribed RNA
                        organism = Homo sapiens
SEQUENCE: 355
tgcagaagaa agatctggaa gtgggagaca cttccactat atatagtggc tcccacttcc    60
agatctttct ctctgta                                                   77

SEQ ID NO: 356          moltype = RNA   length = 77
FEATURE                 Location/Qualifiers
source                  1..77
                        mol_type = transcribed RNA
                        organism = Homo sapiens
SEQUENCE: 356
tgcagaagaa agatctggaa gtgggagaca cttccactat atatagtggc tcccacttcc    60
tgatctttct ctctgta                                                   77

SEQ ID NO: 357          moltype = RNA   length = 81
FEATURE                 Location/Qualifiers
source                  1..81
                        mol_type = transcribed RNA
                        organism = Homo sapiens
SEQUENCE: 357
attcaggccg gtcctgcaga gaggaagccc ttctgcttac aggtattgga agggcttcct    60
ctctgcagga ccggcctgaa t                                              81

SEQ ID NO: 358          moltype = RNA   length = 81
FEATURE                 Location/Qualifiers
source                  1..81
                        mol_type = transcribed RNA
                        organism = Homo sapiens
SEQUENCE: 358
attcaggccg gtcctgcaga gaggaagccc ttccaatacc tgtaagcaga agggcttcct    60
ctctgcagga ccggcctgaa t                                              81

SEQ ID NO: 359          moltype = RNA   length = 85
FEATURE                 Location/Qualifiers
```

```
                    source          1..85
                                    mol_type = transcribed RNA
                                    organism = Homo sapiens
SEQUENCE: 359
ggacctgccc tgggctttct agtctcagct ctcctccagc tcagctggtc aggagagctg         60
agactagaaa gcccagggca ggttc                                               85

SEQ ID NO: 361          moltype = RNA   length = 81
FEATURE                 Location/Qualifiers
source                  1..81
                        mol_type = transcribed RNA
                        organism = Homo sapiens
SEQUENCE: 360
acctgccctg ggctttctag tctcagctct cctgaccagc tgagctggag gagagctgag         60
actagaaagc ccagggcagg t                                                   81

SEQ ID NO: 361          moltype = RNA   length = 94
FEATURE                 Location/Qualifiers
source                  1..94
                        mol_type = transcribed RNA
                        organism = Homo sapiens
SEQUENCE: 361
cagtgcgacg ggcggagctt ccagacgctc cgccccacgt cgcatgcgcc ccgggaaagc         60
gtggggcgga gcttccggag gccccgccct gctg                                     94

SEQ ID NO: 362          moltype = RNA   length = 88
FEATURE                 Location/Qualifiers
source                  1..88
                        mol_type = transcribed RNA
                        organism = Homo sapiens
SEQUENCE: 362
gcgacgggcg gagcttccag acgctccgcc ccacgtcgca tgcgccccgg gaaagcgtgg         60
ggcggagctt ccggaggccc cgccctgc                                            88

SEQ ID NO: 363          moltype = RNA   length = 94
FEATURE                 Location/Qualifiers
source                  1..94
                        mol_type = transcribed RNA
                        organism = Homo sapiens
SEQUENCE: 363
cagtgcgacg ggcggagctt ccagacgctc cgccccacgt cgcatgcgcc ccgggaaagc         60
gtggggcgga gcttccggag gccccgccct gctg                                     94

SEQ ID NO: 364          moltype = RNA   length = 76
FEATURE                 Location/Qualifiers
source                  1..76
                        mol_type = transcribed RNA
                        organism = Homo sapiens
SEQUENCE: 364
ggggtcacct ctctggccgt ctaccttcca cactgacaag ggccgtgggg acgtagctgg         60
ccagacaggt gacccc                                                         76

SEQ ID NO: 365          moltype = RNA   length = 73
FEATURE                 Location/Qualifiers
source                  1..73
                        mol_type = transcribed RNA
                        organism = Homo sapiens
SEQUENCE: 365
aggtggcagg gccagccacc aggagggctg cgtgccaccc gggcagctct gctgctcact         60
ggcagtgtca cct                                                            73

SEQ ID NO: 366          moltype = RNA   length = 79
FEATURE                 Location/Qualifiers
source                  1..79
                        mol_type = transcribed RNA
                        organism = Homo sapiens
SEQUENCE: 366
aattaatccc tctctttcta gttcttccta gagtgaggaa aagctgggtt gagagggcaa         60
acaaattaac taattaatt                                                      79

SEQ ID NO: 367          moltype = RNA   length = 138
FEATURE                 Location/Qualifiers
source                  1..138
                        mol_type = transcribed RNA
                        organism = Homo sapiens
SEQUENCE: 367
tgttattttt tgtcttctac ctaagaattc tgtctcttag gctttctctt cccagatttc         60
ccaaagttgg gaaagctggg gttgagaggg caaaaggaaa aaaaaagaat tctgtctctg        120
acataattag ataggggaa                                                     138
```

```
SEQ ID NO: 368          moltype = RNA   length = 75
FEATURE                 Location/Qualifiers
source                  1..75
                        mol_type = transcribed RNA
                        organism = Homo sapiens
SEQUENCE: 368
tggagtgggg gggcaggagg ggctcaggga gaaagtgcat acagccctg gccctctctg    60
ccttccgtc ccctg                                                     75

SEQ ID NO: 369          moltype = RNA   length = 73
FEATURE                 Location/Qualifiers
source                  1..73
                        mol_type = transcribed RNA
                        organism = Homo sapiens
SEQUENCE: 369
aagagccgcg gcgtaacggc agccatcttg tttgtttgag tgaatcggaa aggaggcgcc    60
ggctgtggcg gcg                                                      73

SEQ ID NO: 370          moltype = RNA   length = 83
FEATURE                 Location/Qualifiers
source                  1..83
                        mol_type = transcribed RNA
                        organism = Homo sapiens
SEQUENCE: 370
acggcatctt tgcactcagc aggcaggctg gtgcagcccg tggtggggga ccatcctgcc    60
tgctgtgggg taaggacggc tgt                                           83

SEQ ID NO: 371          moltype = RNA   length = 79
FEATURE                 Location/Qualifiers
source                  1..79
                        mol_type = transcribed RNA
                        organism = Homo sapiens
SEQUENCE: 371
gtgaggtggg ggccagcagg gagtgggctg ggctgggctg gccaaggta caaggcctca    60
ccctgcatcc cgcacccag                                                79

SEQ ID NO: 372          moltype = RNA   length = 75
FEATURE                 Location/Qualifiers
source                  1..75
                        mol_type = transcribed RNA
                        organism = Homo sapiens
SEQUENCE: 372
agacagagaa gccaggtcac gtctctgcag ttacacagct cacgagtgcc tgctggggtg    60
gaacctggtc tgtct                                                    75

SEQ ID NO: 373          moltype = RNA   length = 69
FEATURE                 Location/Qualifiers
source                  1..69
                        mol_type = transcribed RNA
                        organism = Homo sapiens
SEQUENCE: 373
gggatactca aaatgggggc gctttccttt ttgtctgtac tgggaagtgc ttcgattttg    60
gggtgtccc                                                           69

SEQ ID NO: 374          moltype = RNA   length = 93
FEATURE                 Location/Qualifiers
source                  1..93
                        mol_type = transcribed RNA
                        organism = Homo sapiens
SEQUENCE: 374
ggcgcttttg tgcgcgcccg ggtctgttgg tgctcagagt gtggtcaggc ggctcggact    60
gagcaggtgg gtgcggggct cggaggaggc ggc                                93

SEQ ID NO: 375          moltype = RNA   length = 106
FEATURE                 Location/Qualifiers
source                  1..106
                        mol_type = transcribed RNA
                        organism = Homo sapiens
SEQUENCE: 375
agaagaatgc ccaaccagcc ctcagttgct acagttccct gttgtttcag ctcgacaaca    60
acaggcggct gtagcaatgg ggggctggat gggcatctca atgtgc                  106

SEQ ID NO: 376          moltype = RNA   length = 101
FEATURE                 Location/Qualifiers
source                  1..101
                        mol_type = transcribed RNA
                        organism = Homo sapiens
SEQUENCE: 376
```

```
gatgggcccc ttgtgtcctg aattgggtgg gggctctgag tggggaaagt gggggcctag    60
gggaggtcac agttgggtct aggggtcagg agggcccagg a                       101

SEQ ID NO: 377          moltype = RNA   length = 62
FEATURE                 Location/Qualifiers
source                  1..62
                        mol_type = transcribed RNA
                        organism = Homo sapiens
SEQUENCE: 377
gctggggtc ccccgacagt gtggagctgg ggccgggtcc cggggagggg ggttctgggc    60
ag                                                                  62

SEQ ID NO: 378          moltype = RNA   length = 76
FEATURE                 Location/Qualifiers
source                  1..76
                        mol_type = transcribed RNA
                        organism = Homo sapiens
SEQUENCE: 378
ccgatgcctc gggagtctac agcagggcca tgtctgtgag gcccaaggg tgcatgtgtc    60
tcccaggttt cggtgc                                                   76

SEQ ID NO: 379          moltype = RNA   length = 68
FEATURE                 Location/Qualifiers
source                  1..68
                        mol_type = transcribed RNA
                        organism = Homo sapiens
SEQUENCE: 379
ctcaggctca gtggtgcatg cttatagtcc cagccactct ggaggctgaa ggaagatggc    60
ttgagcct                                                            68

SEQ ID NO: 380          moltype = RNA   length = 73
FEATURE                 Location/Qualifiers
source                  1..73
                        mol_type = transcribed RNA
                        organism = Homo sapiens
SEQUENCE: 380
ttggcaggtg ccatgttgcc tgctccttac tgtacacgtg gctggcaagg agacgggaac    60
atggagccgc cat                                                      73

SEQ ID NO: 381          moltype = RNA   length = 73
FEATURE                 Location/Qualifiers
source                  1..73
                        mol_type = transcribed RNA
                        organism = Homo sapiens
SEQUENCE: 381
agggagaaaa gctgggctga gaggcgactg gtgtctaatt tgtttgtctc tccaactcag    60
actgcctggc cca                                                      73

SEQ ID NO: 382          moltype = RNA   length = 81
FEATURE                 Location/Qualifiers
source                  1..81
                        mol_type = transcribed RNA
                        organism = Homo sapiens
SEQUENCE: 382
catcctcctt acgtcccacc ccccactcct gtttctggtg aaatattcaa acaggagtgg    60
gggtgggaca taaggaggat a                                             81

SEQ ID NO: 383          moltype = RNA   length = 91
FEATURE                 Location/Qualifiers
source                  1..91
                        mol_type = transcribed RNA
                        organism = Homo sapiens
SEQUENCE: 383
gttctagagc atggtttctc atcatttgca ctactgatac ttggggtcag ataattgttt    60
gtggtggggg ctgttgtttg cattgtagga t                                  91

SEQ ID NO: 384          moltype = RNA   length = 66
FEATURE                 Location/Qualifiers
source                  1..66
                        mol_type = transcribed RNA
                        organism = Homo sapiens
SEQUENCE: 384
agcagccctc ggcggcccgg ggggcgggcg gcggtgcccg tcccggggct gcgcgaggca    60
caggcg                                                              66

SEQ ID NO: 385          moltype = RNA   length = 66
FEATURE                 Location/Qualifiers
source                  1..66
                        mol_type = transcribed RNA
```

```
                        organism = Homo sapiens
SEQUENCE: 385
acccaggagg cggaggaggt ggaggttgca gtgagccaag atcgtggcac tgactccagc    60
ctgggg                                                               66

SEQ ID NO: 386          moltype = RNA   length = 71
FEATURE                 Location/Qualifiers
source                  1..71
                        mol_type = transcribed RNA
                        organism = Homo sapiens
SEQUENCE: 386
gcagaggtga gttgacctcc acagggccac ccagggagta agtagccaag tggaagttac    60
tttacctctg t                                                         71

SEQ ID NO: 387          moltype = RNA   length = 57
FEATURE                 Location/Qualifiers
source                  1..57
                        mol_type = transcribed RNA
                        organism = Homo sapiens
SEQUENCE: 387
agaggcaccg cctgcccagt gacatgcgtt taacggccgc ggtaccctaa ctgtgca       57

SEQ ID NO: 388          moltype = RNA   length = 63
FEATURE                 Location/Qualifiers
source                  1..63
                        mol_type = transcribed RNA
                        organism = Homo sapiens
SEQUENCE: 388
gcatgctggg cgaggctggc atctagcaca ggcggtagat gcttgctctt gccattgcaa    60
tga                                                                  63

SEQ ID NO: 389          moltype = RNA   length = 62
FEATURE                 Location/Qualifiers
source                  1..62
                        mol_type = transcribed RNA
                        organism = Homo sapiens
SEQUENCE: 389
ggtaggggc gggctccggc gctgggaccc cactaggtg gcgccttggc cccgccccgc      60
cc                                                                   62

SEQ ID NO: 390          moltype = RNA   length = 62
FEATURE                 Location/Qualifiers
source                  1..62
                        mol_type = transcribed RNA
                        organism = Homo sapiens
SEQUENCE: 390
gggggtgggg ctagtgatgc aggacgctgg ggactggaga agtcctgcct gaccctgtcc    60
ca                                                                   62

SEQ ID NO: 391          moltype = RNA   length = 73
FEATURE                 Location/Qualifiers
source                  1..73
                        mol_type = transcribed RNA
                        organism = Homo sapiens
SEQUENCE: 391
ggaggctggg ctgggacgga cacccggcct ccactttctg tggcaggtac ctcctccatg    60
tcggcccgcc ttg                                                       73

SEQ ID NO: 392          moltype = RNA   length = 86
FEATURE                 Location/Qualifiers
source                  1..86
                        mol_type = transcribed RNA
                        organism = Homo sapiens
SEQUENCE: 392
attctaggtg gggagactga cggctggagg cccataagct gtctaaaact tcggccccca    60
gatttctggt ctcccacttt cagaac                                         86

SEQ ID NO: 393          moltype = RNA   length = 81
FEATURE                 Location/Qualifiers
source                  1..81
                        mol_type = transcribed RNA
                        organism = Homo sapiens
SEQUENCE: 393
gcgggaggtg taacaggact ggactcccgg cagccccagg gcaggggcgt ggggagctgg    60
tcctagctca gcgctcccgg a                                              81

SEQ ID NO: 394          moltype = RNA   length = 56
FEATURE                 Location/Qualifiers
source                  1..56
```

```
                        mol_type = transcribed RNA
                        organism = Homo sapiens
SEQUENCE: 394
cgaccgcacc cgcccgaagc tgggtcaagg agcccagcag gacgggagcg cggcgc          56

SEQ ID NO: 395          moltype = RNA   length = 59
FEATURE                 Location/Qualifiers
source                  1..59
                        mol_type = transcribed RNA
                        organism = Homo sapiens
SEQUENCE: 395
aactgggtcc cagtcttcac agttggtttc tgacacgtgg acctggctgg gacgatgtg       59

SEQ ID NO: 396          moltype = RNA   length = 79
FEATURE                 Location/Qualifiers
source                  1..79
                        mol_type = transcribed RNA
                        organism = Homo sapiens
SEQUENCE: 396
ccgggacttt gtgggttctg accccacttg gatcacgccg acaacactgg tcttgaagtc      60
agaacccgca aagtcctgg                                                   79

SEQ ID NO: 397          moltype = RNA   length = 90
FEATURE                 Location/Qualifiers
source                  1..90
                        mol_type = transcribed RNA
                        organism = Homo sapiens
SEQUENCE: 397
ctgtgggctg ggccagggag cagctggtgg gtgggaagta agatctgacc tggactccat      60
cccacccacc ccctgtttcc tggcccacag                                       90

SEQ ID NO: 398          moltype = RNA   length = 63
FEATURE                 Location/Qualifiers
source                  1..63
                        mol_type = transcribed RNA
                        organism = Homo sapiens
SEQUENCE: 398
actgggaaga ggagctgagg gacattgcgg agagggtctc acattgtccc tctcccttcc      60
cag                                                                    63

SEQ ID NO: 399          moltype = RNA   length = 75
FEATURE                 Location/Qualifiers
source                  1..75
                        mol_type = transcribed RNA
                        organism = Homo sapiens
SEQUENCE: 399
aggctggcgt gggctgaggg caggaggcct gtggccggtc ccaggcctcc tgcttcctgg      60
gctcaggctc ggttt                                                       75

SEQ ID NO: 400          moltype = RNA   length = 76
FEATURE                 Location/Qualifiers
source                  1..76
                        mol_type = transcribed RNA
                        organism = Homo sapiens
SEQUENCE: 400
ctgtggtgga gctgagctcc atggacgtgc agtggcatct gtcattgctg ccttcctgga     60
gctcaggccc ttgcag                                                      76

SEQ ID NO: 401          moltype = RNA   length = 79
FEATURE                 Location/Qualifiers
source                  1..79
                        mol_type = transcribed RNA
                        organism = Homo sapiens
SEQUENCE: 401
ctcgaggtgc tgggggacgc gtgagcgcga gccgcttcct cacggctcgg ccgcggcgcg      60
tagcccccgc cacatcggg                                                   79

SEQ ID NO: 402          moltype = RNA   length = 82
FEATURE                 Location/Qualifiers
source                  1..82
                        mol_type = transcribed RNA
                        organism = Homo sapiens
SEQUENCE: 402
gctacgggga gcggggagga agtgggcgct gcttctgcgt tatctggaag gagcagccca      60
ctcctgtcct gggctctgtg gt                                               82

SEQ ID NO: 403          moltype = RNA   length = 80
FEATURE                 Location/Qualifiers
source                  1..80
```

```
                        mol_type = transcribed RNA
                        organism = Homo sapiens
SEQUENCE: 403
ggttccggag ccccggcgcg ggcgggttct ggggtgtaga cgctgctggc cagcccgccc    60
cagccgaggt tctcggcacc                                                80

SEQ ID NO: 404          moltype = RNA   length = 67
FEATURE                 Location/Qualifiers
source                  1..67
                        mol_type = transcribed RNA
                        organism = Homo sapiens
SEQUENCE: 404
tttaggagag agatgccgcc ttgctccttg aacaggagga gcaaggcggc atctctctga    60
tactaaa                                                              67

SEQ ID NO: 405          moltype = RNA   length = 56
FEATURE                 Location/Qualifiers
source                  1..56
                        mol_type = transcribed RNA
                        organism = Homo sapiens
SEQUENCE: 405
gaccgagtgg ggtgagggca ggtggttctt cccgaagcag ctctcgcctc ttcgtc        56

SEQ ID NO: 406          moltype = RNA   length = 51
FEATURE                 Location/Qualifiers
source                  1..51
                        mol_type = transcribed RNA
                        organism = Homo sapiens
SEQUENCE: 406
agctgtacct gaaaccaagc acctgtttgt gacttggctt cagttactag c             51

SEQ ID NO: 407          moltype = RNA   length = 60
FEATURE                 Location/Qualifiers
source                  1..60
                        mol_type = transcribed RNA
                        organism = Homo sapiens
SEQUENCE: 407
ggcaggaggg ctgtgccagg ttggctgggc caggcctgac ctgccagcac ctccctgcag    60

SEQ ID NO: 408          moltype = RNA   length = 55
FEATURE                 Location/Qualifiers
source                  1..55
                        mol_type = transcribed RNA
                        organism = Homo sapiens
SEQUENCE: 408
aatctgccag cttccacagt ggcagatttt cccatagtgg gaagctggca gattc         55

SEQ ID NO: 409          moltype = RNA   length = 76
FEATURE                 Location/Qualifiers
source                  1..76
                        mol_type = transcribed RNA
                        organism = Homo sapiens
SEQUENCE: 409
cgcaggcctc tggcggagcc cattccatgc cagatgctga gcgatggctg gtgtgtgctg    60
ctccacaggc ctggtg                                                    76

SEQ ID NO: 410          moltype = RNA   length = 70
FEATURE                 Location/Qualifiers
source                  1..70
                        mol_type = transcribed RNA
                        organism = Homo sapiens
SEQUENCE: 410
ctcgggcccg accgcgccgg cccgcacctc ccggcccgga gctgcgggct gcggtcaggg    60
cgatcccggg                                                           70

SEQ ID NO: 411          moltype = RNA   length = 63
FEATURE                 Location/Qualifiers
source                  1..63
                        mol_type = transcribed RNA
                        organism = Homo sapiens
SEQUENCE: 411
gccaaggact gatcctctcg ggcagggagt cagaggggac cgcccgagag gatccgtccc    60
tgc                                                                  63

SEQ ID NO: 412          moltype = RNA   length = 54
FEATURE                 Location/Qualifiers
source                  1..54
                        mol_type = transcribed RNA
                        organism = Homo sapiens
```

```
SEQUENCE: 412
agggaaggag gcttggtctt agcacggggt ctaaggcccg ggctttcctc ccag          54

SEQ ID NO: 413          moltype = RNA   length = 61
FEATURE                 Location/Qualifiers
source                  1..61
                        mol_type = transcribed RNA
                        organism = Homo sapiens
SEQUENCE: 413
cctgcgggga caggccaggg catctaggct gtgcacagtg acgcccctcc tgccccaca    60
g                                                                   61

SEQ ID NO: 414          moltype = RNA   length = 72
FEATURE                 Location/Qualifiers
source                  1..72
                        mol_type = transcribed RNA
                        organism = Homo sapiens
SEQUENCE: 414
agattcagct ttcccttcag agcctggctt tggcatctat gaaagccagg ctctgaaggg    60
aaagttgaat ct                                                       72

SEQ ID NO: 415          moltype = RNA   length = 92
FEATURE                 Location/Qualifiers
source                  1..92
                        mol_type = transcribed RNA
                        organism = Homo sapiens
SEQUENCE: 415
cctgtccctc ctgccctgcg cctgccagc cctcctgctc tggtgactga ggaccgccag     60
gcagggctg gtgctgggcg gggggcggcg gg                                  92

SEQ ID NO: 416          moltype = RNA   length = 84
FEATURE                 Location/Qualifiers
source                  1..84
                        mol_type = transcribed RNA
                        organism = Homo sapiens
SEQUENCE: 416
cggtccagac gtggcggggg tggcggcggc atcccggacg gcctgtgagg gatgcgccgc    60
ccactgcccc gcgccgcctg accg                                          84

SEQ ID NO: 417          moltype = RNA   length = 94
FEATURE                 Location/Qualifiers
source                  1..94
                        mol_type = transcribed RNA
                        organism = Homo sapiens
SEQUENCE: 417
gggctgaccc ctagggtcag gtgaggccct tggggcacag tggtgccatc tccctgtgc    60
tcccagggcc tcgcctgtcc cttgaggtcg gccc                               94

SEQ ID NO: 418          moltype = RNA   length = 120
FEATURE                 Location/Qualifiers
source                  1..120
                        mol_type = transcribed RNA
                        organism = Homo sapiens
SEQUENCE: 418
gatccaggga accctagagc aggggatgg cagagcaaaa ttcatggcct acagctgcct     60
cttgccaaac tgcactggat tttgtgtctc ccattcccca gagctgtctg aggtgctttg   120

SEQ ID NO: 419          moltype = RNA   length = 83
FEATURE                 Location/Qualifiers
source                  1..83
                        mol_type = transcribed RNA
                        organism = Homo sapiens
SEQUENCE: 419
gctgctgttg ggagaccctg gtctgcactc tatctgtatt cttactgaag ggagtgcagg    60
gcagggtttc ccatacagag ggc                                           83

SEQ ID NO: 420          moltype = RNA   length = 85
FEATURE                 Location/Qualifiers
source                  1..85
                        mol_type = transcribed RNA
                        organism = Homo sapiens
SEQUENCE: 420
tctgaggtac ccggggcaga ttggtgtagg gtgcaaagcc tgcccgcccc ctaagccttc    60
tgcccccaac tccagcctgt cagga                                         85

SEQ ID NO: 421          moltype = RNA   length = 119
FEATURE                 Location/Qualifiers
source                  1..119
                        mol_type = transcribed RNA
```

-continued

```
                         organism = Homo sapiens
SEQUENCE: 421
ccatgaggag ctggcagtgg gatggcctgg gggtaggagc gtggcttctg gagctagacc   60
acatggttc agatcccagc ggtgcctcta actggccaca ggaccttggg cagtcagct   119

SEQ ID NO: 422           moltype = RNA   length = 115
FEATURE                  Location/Qualifiers
source                   1..115
                         mol_type = transcribed RNA
                         organism = Homo sapiens
SEQUENCE: 422
tctgaggaga cctgggctgt cagaggccag ggaaggggac gagggttggg gaacaggtgg   60
ttagcacttc atcctcgtct ccctcccagg ttagaagggc ccccctctct gaagg       115

SEQ ID NO: 423           moltype = RNA   length = 96
FEATURE                  Location/Qualifiers
source                   1..96
                         mol_type = transcribed RNA
                         organism = Homo sapiens
SEQUENCE: 423
agatgtgctc tcctggccca tgaaatcaag cgtgggtgag acctggtgca gaacgggaag   60
gcgacccata cttggtttca gaggctgtga gaataa                             96

SEQ ID NO: 424           moltype = RNA   length = 98
FEATURE                  Location/Qualifiers
source                   1..98
                         mol_type = transcribed RNA
                         organism = Homo sapiens
SEQUENCE: 424
agaatgggca aatgaacagt aaatttggag gcctggggcc ctccctgctg ctggagaagt   60
gtttgcacgg gtgggccttg tctttgaaag gaggtgga                           98

SEQ ID NO: 425           moltype = RNA   length = 55
FEATURE                  Location/Qualifiers
source                   1..55
                         mol_type = transcribed RNA
                         organism = Homo sapiens
SEQUENCE: 425
gggggctggg gcgcggggag gtgctaggtc ggcctcggct cccgcgccgc acccc        55

SEQ ID NO: 426           moltype = RNA   length = 60
FEATURE                  Location/Qualifiers
source                   1..60
                         mol_type = transcribed RNA
                         organism = Homo sapiens
SEQUENCE: 426
cgctgggtcc gcgcgccctg ggccgggcga tgtccgcttg ggggagcgag gggcggggcg   60

SEQ ID NO: 427           moltype = RNA   length = 85
FEATURE                  Location/Qualifiers
source                   1..85
                         mol_type = transcribed RNA
                         organism = Homo sapiens
SEQUENCE: 427
ggggaggtag ggaaaaggaa gggggaggag aaggtgagac caatgtcctg ggtgccactc   60
ctgcccagtg cctcccttcc tcgtt                                         85

SEQ ID NO: 428           moltype = RNA   length = 109
FEATURE                  Location/Qualifiers
source                   1..109
                         mol_type = transcribed RNA
                         organism = Homo sapiens
SEQUENCE: 428
tgctattgtc ttactgctac agcagggctg gggattgcag tatccgctgt tgctgctgct   60
cccagtcctg ccctgctgc tacctagtcc agcctcaccg catcccaga              109

SEQ ID NO: 429           moltype = RNA   length = 54
FEATURE                  Location/Qualifiers
source                   1..54
                         mol_type = transcribed RNA
                         organism = Homo sapiens
SEQUENCE: 429
agcagcaggg gagagagagg agtcctctag acaccgactc tgtctcctgc agat         54

SEQ ID NO: 430           moltype = RNA   length = 85
FEATURE                  Location/Qualifiers
source                   1..85
                         mol_type = transcribed RNA
                         organism = Homo sapiens
```

```
SEQUENCE: 430
gggacggggc ctgcaggcag aagtggggct gacagggcag agggttgcgc cccctcacca    60
cccttctgc ctgcagcggt gggct                                           85

SEQ ID NO: 431          moltype = RNA   length = 71
FEATURE                 Location/Qualifiers
source                  1..71
                        mol_type = transcribed RNA
                        organism = Homo sapiens
SEQUENCE: 431
ggggcctgca ggcagaagtg gggctgacag ggcagagggt tgcgcccct caccacccct     60
tctgcctgca g                                                         71

SEQ ID NO: 432          moltype = RNA   length = 57
FEATURE                 Location/Qualifiers
source                  1..57
                        mol_type = transcribed RNA
                        organism = Homo sapiens
SEQUENCE: 432
cattggaggg tgtggaagac atctgggcca actctgatct cttcatctac cccccag       57

SEQ ID NO: 433          moltype = RNA   length = 81
FEATURE                 Location/Qualifiers
source                  1..81
                        mol_type = transcribed RNA
                        organism = Homo sapiens
SEQUENCE: 433
gggtaagtgg aaagatggtg ggccgcagaa catgtgctga gttcgtgcca tatgtctgct    60
gaccatcacc tttagaagcc c                                              81

SEQ ID NO: 434          moltype = RNA   length = 100
FEATURE                 Location/Qualifiers
source                  1..100
                        mol_type = transcribed RNA
                        organism = Homo sapiens
SEQUENCE: 434
gctcggttgc cgtggttgcg ggccctgccc gcccgccagc tcgctgacag cacgactcag    60
ggcggaggga agtaggtccg ttggtcggtc gggaacgagg                          100

SEQ ID NO: 435          moltype = RNA   length = 66
FEATURE                 Location/Qualifiers
source                  1..66
                        mol_type = transcribed RNA
                        organism = Homo sapiens
SEQUENCE: 435
ggtaagtgcg cctcgggtga gcatgcactt aatgtgggtg tatgtcactc ggctcggccc    60
actacc                                                               66

SEQ ID NO: 436          moltype = RNA   length = 78
FEATURE                 Location/Qualifiers
source                  1..78
                        mol_type = transcribed RNA
                        organism = Homo sapiens
SEQUENCE: 436
ggcctcaggc aggcgcaccc gaccacatgc atggctggtg gcggcgtgca ggggtcgggt    60
gggccaggct gtggggcg                                                  78

SEQ ID NO: 437          moltype = RNA   length = 92
FEATURE                 Location/Qualifiers
source                  1..92
                        mol_type = transcribed RNA
                        organism = Homo sapiens
SEQUENCE: 437
cgctgcgctt ctgggcccgc ggcgggcgtg gggctgcccg ggccggtcga ccagcgcgcc    60
gtagctcccg aggcccgagc cgcgaccgc gg                                   92

SEQ ID NO: 438          moltype = RNA   length = 65
FEATURE                 Location/Qualifiers
source                  1..65
                        mol_type = transcribed RNA
                        organism = Homo sapiens
SEQUENCE: 438
gagggtgggc gagggcggct gagcggctcc atccccggc ctgctcatcc ccctcgccct     60
ctcag                                                                65

SEQ ID NO: 439          moltype = RNA   length = 70
FEATURE                 Location/Qualifiers
source                  1..70
                        mol_type = transcribed RNA
```

```
                          organism = Homo sapiens
SEQUENCE: 439
ttgggttggg gtggtcggcc ctggaggggg tttgtttgct tattcccctc tgtgcttcac    60
ccctacccag                                                           70

SEQ ID NO: 440        moltype = RNA   length = 63
FEATURE               Location/Qualifiers
source                1..63
                      mol_type = transcribed RNA
                      organism = Homo sapiens
SEQUENCE: 440
accctagggt ggggctggag gtggggctga ggctgagtct tcctcccctt cctccctgcc    60
cag                                                                  63

SEQ ID NO: 441        moltype = RNA   length = 86
FEATURE               Location/Qualifiers
source                1..86
                      mol_type = transcribed RNA
                      organism = Homo sapiens
SEQUENCE: 441
agagccgggg ccatggagca gcctgtgtag acggggacct gccctgcatg ggcaccccct    60
cactggctgc ttccttggt ctccag                                          86

SEQ ID NO: 442        moltype = RNA   length = 65
FEATURE               Location/Qualifiers
source                1..65
                      mol_type = transcribed RNA
                      organism = Homo sapiens
SEQUENCE: 442
ttctcctggg gagtggctgg ggagcagaca gacccaacct catgctcccc ggcctctgcc    60
cccag                                                                65

SEQ ID NO: 443        moltype = RNA   length = 72
FEATURE               Location/Qualifiers
source                1..72
                      mol_type = transcribed RNA
                      organism = Homo sapiens
SEQUENCE: 443
atgagcgggt gggagcagat cttattgaga gttccttctc ctgctcctga ttgtcttccc    60
ccaccctcac ag                                                        72

SEQ ID NO: 444        moltype = RNA   length = 73
FEATURE               Location/Qualifiers
source                1..73
                      mol_type = transcribed RNA
                      organism = Homo sapiens
SEQUENCE: 444
aggccaggtg ggtatggagg agccctcata tggcagttgg cgagggccca gtgagcccct    60
ctctgctctc cag                                                       73

SEQ ID NO: 445        moltype = RNA   length = 60
FEATURE               Location/Qualifiers
source                1..60
                      mol_type = transcribed RNA
                      organism = Homo sapiens
SEQUENCE: 445
ggtgcctcgg gagggcatgg gccaggccac ataatgagcc aaaccctgt ctacccgcag     60

SEQ ID NO: 446        moltype = RNA   length = 113
FEATURE               Location/Qualifiers
source                1..113
                      mol_type = transcribed RNA
                      organism = Homo sapiens
SEQUENCE: 446
gccgggtggg gcgggcggc ctcaggaggg gcccagctcc cctggatgtg ctgcggtggg     60
gccggagggg cgtcacgtgc acccaagtga cgccccttct gattctgcct cag          113

SEQ ID NO: 447        moltype = RNA   length = 98
FEATURE               Location/Qualifiers
source                1..98
                      mol_type = transcribed RNA
                      organism = Homo sapiens
SEQUENCE: 447
cgaggtaggg gcgtcccggg cgcgcgggcg ggtcccaggc tgggcccctc ggaggccggg    60
tgctcactgc cccgtcccgg cgcccgtgtc tcctccag                            98

SEQ ID NO: 448        moltype = RNA   length = 68
FEATURE               Location/Qualifiers
source                1..68
```

```
                        mol_type = transcribed RNA
                        organism = Homo sapiens
SEQUENCE: 448
gggcgcaggg ggactgggggg tgagcaggcc cagaacccag ctcgtgctca ctctcagtcc    60
ctccctag                                                              68

SEQ ID NO: 449          moltype = RNA   length = 62
FEATURE                 Location/Qualifiers
source                  1..62
                        mol_type = transcribed RNA
                        organism = Homo sapiens
SEQUENCE: 449
ttaccttgtg gggttggaga gctggctggt ccagcccctc agaagctctc ccctccccgc    60
ag                                                                    62

SEQ ID NO: 450          moltype = RNA   length = 72
FEATURE                 Location/Qualifiers
source                  1..72
                        mol_type = transcribed RNA
                        organism = Homo sapiens
SEQUENCE: 450
cagccaggag ggaaggggct gagaacagga cctgtgctca ctggggcctg catgacccct    60
ccctccccac ag                                                         72

SEQ ID NO: 451          moltype = RNA   length = 82
FEATURE                 Location/Qualifiers
source                  1..82
                        mol_type = transcribed RNA
                        organism = Homo sapiens
SEQUENCE: 451
acctgtaggt gacagtcagg ggcggggtgt ggtggggctg ggctggccc cctcctcaca     60
cctctcctgg catcgccccc ag                                              82

SEQ ID NO: 452          moltype = RNA   length = 65
FEATURE                 Location/Qualifiers
source                  1..65
                        mol_type = transcribed RNA
                        organism = Homo sapiens
SEQUENCE: 452
gagggctagg tgggggcttt gaagccccga gatgcctcac gtcttcaccc ctctcaccta    60
agcag                                                                 65

SEQ ID NO: 453          moltype = RNA   length = 65
FEATURE                 Location/Qualifiers
source                  1..65
                        mol_type = transcribed RNA
                        organism = Homo sapiens
SEQUENCE: 453
ctcctctggg ggtgggggc tgggcgtggt ggacagcgat gcatccctcg ccttctcacc     60
ctcag                                                                 65

SEQ ID NO: 454          moltype = RNA   length = 62
FEATURE                 Location/Qualifiers
source                  1..62
                        mol_type = transcribed RNA
                        organism = Homo sapiens
SEQUENCE: 454
tggcctaggg ggcggcttgt ggagtgtatg ggctgagcct tgctctgctc ccccgcccc     60
ag                                                                    62

SEQ ID NO: 455          moltype = RNA   length = 92
FEATURE                 Location/Qualifiers
source                  1..92
                        mol_type = transcribed RNA
                        organism = Homo sapiens
SEQUENCE: 455
gtgagccagt ggaatggaga ggctgtgggc aggggagat gtgaaggaaa gaactaggac      60
ccattcatcc actgcattcc tgcttggccc ag                                   92

SEQ ID NO: 456          moltype = RNA   length = 64
FEATURE                 Location/Qualifiers
source                  1..64
                        mol_type = transcribed RNA
                        organism = Homo sapiens
SEQUENCE: 456
tgaggatggg gtgagatggg gaggagcagc cagtcctgtc tcaccgctct tccctgacc      60
ccag                                                                  64

SEQ ID NO: 457          moltype = RNA   length = 61
```

```
FEATURE                 Location/Qualifiers
source                  1..61
                        mol_type = transcribed RNA
                        organism = Homo sapiens
SEQUENCE: 457
gagggttggg gtggagggcc aaggagctgg gtggggtgcc aagcctctgt ccccacccca    60
g                                                                    61

SEQ ID NO: 458          moltype = RNA  length = 61
FEATURE                 Location/Qualifiers
source                  1..61
                        mol_type = transcribed RNA
                        organism = Homo sapiens
SEQUENCE: 458
tggcccaggg aaccagttgg ggcttccgct ctgcagaggc tctaactggc tttccctgca    60
g                                                                    61

SEQ ID NO: 459          moltype = RNA  length = 63
FEATURE                 Location/Qualifiers
source                  1..63
                        mol_type = transcribed RNA
                        organism = Homo sapiens
SEQUENCE: 459
gaggtgtagg ggaggttggg ccagggatgc cttcactgtg tctctctggt cttgccaccc    60
cag                                                                  63

SEQ ID NO: 460          moltype = RNA  length = 98
FEATURE                 Location/Qualifiers
source                  1..98
                        mol_type = transcribed RNA
                        organism = Homo sapiens
SEQUENCE: 460
cttggtcaat aggaaagagg tgggacctcc tggcttttcc tctgcagcat ggctcggacc    60
tagtgcaatg tttaagctcc cctctctttc ctgttcag                            98

SEQ ID NO: 461          moltype = RNA  length = 61
FEATURE                 Location/Qualifiers
source                  1..61
                        mol_type = transcribed RNA
                        organism = Homo sapiens
SEQUENCE: 461
gtgcggaacg ctggccgggg cgggagggga agggacgccc ggccggaacg ccgcactcac    60
g                                                                    61

SEQ ID NO: 462          moltype = RNA  length = 67
FEATURE                 Location/Qualifiers
source                  1..67
                        mol_type = transcribed RNA
                        organism = Homo sapiens
SEQUENCE: 462
gtgaggaggg gctggcaggg acccctccaa gttggggacg gcagccagcc cctgctcacc    60
cctcgcc                                                              67

SEQ ID NO: 463          moltype = RNA  length = 64
FEATURE                 Location/Qualifiers
source                  1..64
                        mol_type = transcribed RNA
                        organism = Homo sapiens
SEQUENCE: 463
gaggcactgg gtaggtgggg ctccagggct cctgacacct ggacctctcc tccccaggcc    60
caca                                                                 64

SEQ ID NO: 464          moltype = RNA  length = 62
FEATURE                 Location/Qualifiers
source                  1..62
                        mol_type = transcribed RNA
                        organism = Homo sapiens
SEQUENCE: 464
gagggtggtg gaggaagagg gcagctccca tgactgcctg accgccttct ctcctccccc    60
ag                                                                   62

SEQ ID NO: 465          moltype = RNA  length = 80
FEATURE                 Location/Qualifiers
source                  1..80
                        mol_type = transcribed RNA
                        organism = Homo sapiens
SEQUENCE: 465
tgccgtcggc ctggggagga ggaagggcaa gtccaaaggt atacagttgg tctgttcatt    60
ctctctttt ggcctacaag                                                 80
```

```
SEQ ID NO: 466          moltype = RNA   length = 65
FEATURE                 Location/Qualifiers
source                  1..65
                        mol_type = transcribed RNA
                        organism = Homo sapiens
SEQUENCE: 466
gtctcctggg gggaggagac cctgctctcc ctggcagcaa gcctctcctg cccttccaga    60
ttagc                                                                65

SEQ ID NO: 467          moltype = RNA   length = 61
FEATURE                 Location/Qualifiers
source                  1..61
                        mol_type = transcribed RNA
                        organism = Homo sapiens
SEQUENCE: 467
tccgctctgt ggagtggggt gcctgtcccc tgccactggg tgacccaccc ctctccacca    60
g                                                                    61

SEQ ID NO: 468          moltype = RNA   length = 59
FEATURE                 Location/Qualifiers
source                  1..59
                        mol_type = transcribed RNA
                        organism = Homo sapiens
SEQUENCE: 468
cggggtcggc ggcgacgtgc tcagcttggc acccaagttc tgccgctccg acgcccggc     59

SEQ ID NO: 469          moltype = RNA   length = 96
FEATURE                 Location/Qualifiers
source                  1..96
                        mol_type = transcribed RNA
                        organism = Homo sapiens
SEQUENCE: 469
gccccgccgc ctggcctctg gcccgctggg gcgcgggctt tcgctttcag tcgagggcta    60
gcgagcgcag cggagcctgg agagaaggcg ctgggc                              96

SEQ ID NO: 470          moltype = RNA   length = 69
FEATURE                 Location/Qualifiers
source                  1..69
                        mol_type = transcribed RNA
                        organism = Homo sapiens
SEQUENCE: 470
tggagggctg cgggactgta gagggcatga gctcaggagc tcaggccagc tcatggtgca    60
aggcctctg                                                            69

SEQ ID NO: 471          moltype = RNA   length = 76
FEATURE                 Location/Qualifiers
source                  1..76
                        mol_type = transcribed RNA
                        organism = Homo sapiens
SEQUENCE: 471
tttaaatcct gttttcccca cttactattc tggtcagata tcccatgaag cagtgggtag    60
gaggacagga aaaagc                                                    76

SEQ ID NO: 472          moltype = RNA   length = 65
FEATURE                 Location/Qualifiers
source                  1..65
                        mol_type = transcribed RNA
                        organism = Homo sapiens
SEQUENCE: 472
cggccacatg gcccaggctc ttctccgagt gatctcggtg gactggagtg ggtggtaggt    60
ggcag                                                                65

SEQ ID NO: 473          moltype = RNA   length = 65
FEATURE                 Location/Qualifiers
source                  1..65
                        mol_type = transcribed RNA
                        organism = Homo sapiens
SEQUENCE: 473
cggccacatg gcccaggctc ttctccgagt gatctcggtg gactggagtg ggtggtaggt    60
ggcag                                                                65

SEQ ID NO: 474          moltype = RNA   length = 72
FEATURE                 Location/Qualifiers
source                  1..72
                        mol_type = transcribed RNA
                        organism = Homo sapiens
SEQUENCE: 474
gatttcagtg acctggcagc agggagcgtc gtcagtgttt gactgtttat ggtatgtcag    60
```

```
ggagctggtt cc                                                                72

SEQ ID NO: 475          moltype = RNA   length = 78
FEATURE                 Location/Qualifiers
source                  1..78
                        mol_type = transcribed RNA
                        organism = Homo sapiens
SEQUENCE: 475
ttagccctgc ggccccacgc accagggtaa gagagactct cgcttcctgc cctggcccga            60
gggaccgact ggctgggc                                                          78

SEQ ID NO: 476          moltype = RNA   length = 110
FEATURE                 Location/Qualifiers
source                  1..110
                        mol_type = transcribed RNA
                        organism = Homo sapiens
SEQUENCE: 476
ggctacagtc tttcttcatg tgactcgtgg acttcccttt gtcatcctat gcctgagaat            60
atatgaagga ggctgggaag gcaaagggac gttcaattgt catcactggc                      110

SEQ ID NO: 477          moltype = RNA   length = 84
FEATURE                 Location/Qualifiers
source                  1..84
                        mol_type = transcribed RNA
                        organism = Homo sapiens
SEQUENCE: 477
ggcccctcct tctcagcccc agctcccgct cacccctgcc acgtcaaagg aggcagaagg            60
ggagttggga gcagagaggg gacc                                                   84

SEQ ID NO: 478          moltype = RNA   length = 91
FEATURE                 Location/Qualifiers
source                  1..91
                        mol_type = transcribed RNA
                        organism = Homo sapiens
SEQUENCE: 478
ggcgccccgg ctccccgcgc ccccgatcgg ggccgccgct agtagtggcg gcggcggagg            60
cgggggcagc ggcggcggcg gcggaggcgc c                                           91

SEQ ID NO: 479          moltype = RNA   length = 58
FEATURE                 Location/Qualifiers
source                  1..58
                        mol_type = transcribed RNA
                        organism = Homo sapiens
SEQUENCE: 479
agaagggtgt gtgtgttttt cctgagaata agagaaggaa ggacagccaa attcttca              58

SEQ ID NO: 480          moltype = RNA   length = 58
FEATURE                 Location/Qualifiers
source                  1..58
                        mol_type = transcribed RNA
                        organism = Homo sapiens
SEQUENCE: 480
cttcccagct gccctaagtc aggagtggct ttcctgacac ggagggtggc ttgggaaa              58

SEQ ID NO: 481          moltype = RNA   length = 70
FEATURE                 Location/Qualifiers
source                  1..70
                        mol_type = transcribed RNA
                        organism = Homo sapiens
SEQUENCE: 481
aaaagcctgt ccctaagtcc ctcccagcct tccagagttg gtgccaggaa ggatttaggg            60
acaggctttg                                                                   70

SEQ ID NO: 482          moltype = RNA   length = 70
FEATURE                 Location/Qualifiers
source                  1..70
                        mol_type = transcribed RNA
                        organism = Homo sapiens
SEQUENCE: 482
aggacccagc ggggctgggc gcgcggagca gcgctgggtg cagcgcctgc gccggcagct            60
gcaagggccg                                                                   70

SEQ ID NO: 483          moltype = RNA   length = 80
FEATURE                 Location/Qualifiers
source                  1..80
                        mol_type = transcribed RNA
                        organism = Homo sapiens
SEQUENCE: 483
acctgaggag ccagccctcc tcccgcaccc aaacttggag cacttgacct ttggctgttg            60
```

```
gaggggggcag gctcgcgggt                                              80

SEQ ID NO: 484          moltype = RNA   length = 76
FEATURE                 Location/Qualifiers
source                  1..76
                        mol_type = transcribed RNA
                        organism = Homo sapiens
SEQUENCE: 484
gagggagctg tagagcaggg agcaggaagc tgtgtgtgtc cagccctgac ctgtcctgtt   60
ctgccccccag ccctc                                                   76

SEQ ID NO: 485          moltype = RNA   length = 74
FEATURE                 Location/Qualifiers
source                  1..74
                        mol_type = transcribed RNA
                        organism = Homo sapiens
SEQUENCE: 485
gctctagcct aattttagat ctggtctgct tcagtttcac tccaagcaga cttgacctac   60
aattagccta gagc                                                     74

SEQ ID NO: 486          moltype = RNA   length = 74
FEATURE                 Location/Qualifiers
source                  1..74
                        mol_type = transcribed RNA
                        organism = Homo sapiens
SEQUENCE: 486
gctctagcct aattttagat ctggtctgct tcagtttcac tccaagcaga cttgacctac   60
aattagccta gagc                                                     74

SEQ ID NO: 487          moltype = RNA   length = 97
FEATURE                 Location/Qualifiers
source                  1..97
                        mol_type = transcribed RNA
                        organism = Homo sapiens
SEQUENCE: 487
atctgagttg ggagggtccc tctccaaatg tgtcttgggg tgggggatca agacacattt   60
ggagagggaa cctcccaact cggcctctgc catcatt                            97

SEQ ID NO: 488          moltype = RNA   length = 60
FEATURE                 Location/Qualifiers
source                  1..60
                        mol_type = transcribed RNA
                        organism = Homo sapiens
SEQUENCE: 488
aggcctaggg ggtggcaggc tggccatcag tgtgggctaa ccctgtcctc tccctcccag   60

SEQ ID NO: 489          moltype = RNA   length = 68
FEATURE                 Location/Qualifiers
source                  1..68
                        mol_type = transcribed RNA
                        organism = Homo sapiens
SEQUENCE: 489
cagtgcaggg agaaggtgga agtgcagagt gggctcacct ctcgcccaca ctgtcccctt   60
ctccccag                                                            68

SEQ ID NO: 490          moltype = RNA   length = 69
FEATURE                 Location/Qualifiers
source                  1..69
                        mol_type = transcribed RNA
                        organism = Homo sapiens
SEQUENCE: 490
gaggagggga ggtgtgcagg gctggggtca ctgactctgc ttcccctgcc ctgcatggtg   60
tcccacag                                                            69

SEQ ID NO: 491          moltype = RNA   length = 62
FEATURE                 Location/Qualifiers
source                  1..62
                        mol_type = transcribed RNA
                        organism = Homo sapiens
SEQUENCE: 491
ccttctgcgg cagagctggg gtcaccagcc ctcatgtact tgtgacttct ccctgccac    60
ag                                                                  62

SEQ ID NO: 492          moltype = RNA   length = 74
FEATURE                 Location/Qualifiers
source                  1..74
                        mol_type = transcribed RNA
                        organism = Homo sapiens
SEQUENCE: 492
```

```
gtgcgtggtg gctcgaggcg ggggtggggg cctcgccctg cttgggccct ccctgacctc    60
tccgctccgc acag                                                      74

SEQ ID NO: 493          moltype = RNA   length = 67
FEATURE                 Location/Qualifiers
source                  1..67
                        mol_type = transcribed RNA
                        organism = Homo sapiens
SEQUENCE: 493
cagcgtgggc tgctgagaag gggcagggtc ctccagctca ttcctcctgc ctcctccgtg    60
gcctcag                                                              67

SEQ ID NO: 494          moltype = RNA   length = 69
FEATURE                 Location/Qualifiers
source                  1..69
                        mol_type = transcribed RNA
                        organism = Homo sapiens
SEQUENCE: 494
ccgggcaggc aggtgtaggg tggagcccac tgtggctcct gactcagccc tgctgccttc    60
acctgccag                                                            69

SEQ ID NO: 495          moltype = RNA   length = 87
FEATURE                 Location/Qualifiers
source                  1..87
                        mol_type = transcribed RNA
                        organism = Homo sapiens
SEQUENCE: 495
gtgtggccgg caggcgggtg ggcggggcg ccggtggga accccgcccc gccccgcgcc      60
cgcactcacc cgcccgtctc cccacag                                        87

SEQ ID NO: 496          moltype = RNA   length = 72
FEATURE                 Location/Qualifiers
source                  1..72
                        mol_type = transcribed RNA
                        organism = Homo sapiens
SEQUENCE: 496
ctgggggagg aaggacaggc catctgctat tcgtccacca acctgacttg atcctctctt    60
ccctcctccc ag                                                        72

SEQ ID NO: 497          moltype = RNA   length = 82
FEATURE                 Location/Qualifiers
source                  1..82
                        mol_type = transcribed RNA
                        organism = Homo sapiens
SEQUENCE: 497
aaggagcact cactccaatt tccctggact gggggcaggc tgccacctcc tggggacagg    60
ggattggggc aggatgttcc ag                                             82

SEQ ID NO: 498          moltype = RNA   length = 74
FEATURE                 Location/Qualifiers
source                  1..74
                        mol_type = transcribed RNA
                        organism = Homo sapiens
SEQUENCE: 498
ccgcactctc tccattacac taccctgcct cttctccatg agaggcagcg gggtgtagtg    60
gatagagcac gggt                                                      74

SEQ ID NO: 499          moltype = RNA   length = 96
FEATURE                 Location/Qualifiers
source                  1..96
                        mol_type = transcribed RNA
                        organism = Homo sapiens
SEQUENCE: 499
cgggcccgg gcgggcggga gggacgggac gcggtgcagt gttgtttttt cccccgccaa     60
tattgcactc gtcccggcct ccggccccc cggccc                               96

SEQ ID NO: 500          moltype = RNA   length = 84
FEATURE                 Location/Qualifiers
source                  1..84
                        mol_type = transcribed RNA
                        organism = Homo sapiens
SEQUENCE: 500
gctggcgtcg gtgctgggga gcggccccg ggtgggcctc tgctctggcc cctcctgggg     60
cccgcactct cgctctgggc ccgc                                           84

SEQ ID NO: 501          moltype = RNA   length = 63
FEATURE                 Location/Qualifiers
source                  1..63
                        mol_type = transcribed RNA
```

```
                              organism = Homo sapiens
SEQUENCE: 501
cttgcccggg agaaggaggt ggcctggaga gctgctgtct ccagccgccg cctgtctcca    60
cag                                                                  63

SEQ ID NO: 502          moltype = RNA   length = 90
FEATURE                 Location/Qualifiers
source                  1..90
                        mol_type = transcribed RNA
                        organism = Homo sapiens
SEQUENCE: 502
gagagaagca ctggacttag ggtcagaagg cctgagtctc tctgctgcag atgggctctc    60
tgtccctgag ccaagctttg tcctccctgg                                     90

SEQ ID NO: 503          moltype = RNA   length = 109
FEATURE                 Location/Qualifiers
source                  1..109
                        mol_type = transcribed RNA
                        organism = Homo sapiens
SEQUENCE: 503
ggtcgggctc accatgacac agtgtgagac ctcgggctac aacacaggac ccgggcgctg    60
ctctgacccc tcgtgtcttg tgttgcagcc ggagggacgg aggtccgca              109

SEQ ID NO: 504          moltype = RNA   length = 61
FEATURE                 Location/Qualifiers
source                  1..61
                        mol_type = transcribed RNA
                        organism = Homo sapiens
SEQUENCE: 504
gagggcagcg tgggtgtggc ggaggcaggc gtgaccgttt ccgccctct cgctgctcta     60
g                                                                    61

SEQ ID NO: 505          moltype = RNA   length = 67
FEATURE                 Location/Qualifiers
source                  1..67
                        mol_type = transcribed RNA
                        organism = Homo sapiens
SEQUENCE: 505
ccagacccct ggggctgggc aggcggaaag aggtctgaac tgcctctgcc tccttggtct    60
ccggcag                                                              67

SEQ ID NO: 506          moltype = RNA   length = 78
FEATURE                 Location/Qualifiers
source                  1..78
                        mol_type = transcribed RNA
                        organism = Homo sapiens
SEQUENCE: 506
tactgccctc ggcttcttta cagtgctgcc ttgttgcata tggatcaagc agcattgtac    60
agggctatga aggcattg                                                  78

SEQ ID NO: 507          moltype = RNA   length = 78
FEATURE                 Location/Qualifiers
source                  1..78
                        mol_type = transcribed RNA
                        organism = Homo sapiens
SEQUENCE: 507
ttgtgctttc agcttcttta cagtgctgcc ttgtagcatt caggtcaagc agcattgtac    60
agggctatga aagaacca                                                  78

SEQ ID NO: 508          moltype = RNA   length = 81
FEATURE                 Location/Qualifiers
source                  1..81
                        mol_type = transcribed RNA
                        organism = Homo sapiens
SEQUENCE: 508
ctctctgctt tcagcttctt tacagtgttg ccttgtggca tggagttcaa gcagcattgt    60
acagggctat caaagcacag a                                              81

SEQ ID NO: 509          moltype = RNA   length = 119
FEATURE                 Location/Qualifiers
source                  1..119
                        mol_type = transcribed RNA
                        organism = Homo sapiens
SEQUENCE: 509
agcctgcgcc ggagccgggg cctgagcccg ggccgcgcag gccgtgaact cgtcgagctg    60
cgcgtgcggc cggtgctcaa cctgccgggt cctggcccg cgctcccgcg cgccctgga    119

SEQ ID NO: 510          moltype = RNA   length = 90
FEATURE                 Location/Qualifiers
```

```
source              1..90
                    mol_type = transcribed RNA
                    organism = Homo sapiens
SEQUENCE: 510
gtgggtacgg cccagtgggg gggagaggga cacgccctgg gctctgccca gggtgcagcc    60
ggactgactg agccctgtg ccgccccag                                        90

SEQ ID NO: 511      moltype = RNA  length = 73
FEATURE             Location/Qualifiers
source              1..73
                    mol_type = transcribed RNA
                    organism = Homo sapiens
SEQUENCE: 511
gtgggcgggg gcaggtgtgt ggtgggtggt ggcctgcggt gagcagggcc ctcacacctg    60
cctcgccccc cag                                                        73

SEQ ID NO: 512      moltype = RNA  length = 69
FEATURE             Location/Qualifiers
source              1..69
                    mol_type = transcribed RNA
                    organism = Homo sapiens
SEQUENCE: 512
gtgggtaggg tttgggggag agcgtgggct ggggttcagg gacaccctct caccactgcc    60
ctcccacag                                                             69

SEQ ID NO: 513      moltype = RNA  length = 82
FEATURE             Location/Qualifiers
source              1..82
                    mol_type = transcribed RNA
                    organism = Homo sapiens
SEQUENCE: 513
gtgagtggga ggccaggca cggcagggg agctgcaggg ctatgggagg ggccccagcg      60
tctgagccct gtcctcccgc ag                                              82

SEQ ID NO: 514      moltype = RNA  length = 82
FEATURE             Location/Qualifiers
source              1..82
                    mol_type = transcribed RNA
                    organism = Homo sapiens
SEQUENCE: 514
gtgagtggga ggccagggca cggcagggg agctgcaggg ctatgggagg ggccccagcg     60
tctgagccct gtcctcccgc ag                                              82

SEQ ID NO: 515      moltype = RNA  length = 102
FEATURE             Location/Qualifiers
source              1..102
                    mol_type = transcribed RNA
                    organism = Homo sapiens
SEQUENCE: 515
gtgggagggc ccaggcgcgg gcaggggtgg gggtggcaga gcgctgtccc gggggcgggg    60
ccgaagcgcg gcgaccgtaa ctccttctgc tccgtccccc ag                       102

SEQ ID NO: 516      moltype = RNA  length = 136
FEATURE             Location/Qualifiers
source              1..136
                    mol_type = transcribed RNA
                    organism = Homo sapiens
SEQUENCE: 516
ccgcttgcct cgcccagcgc agccccggcc gctgggcgca cccgtcccgt tcgtccccgg    60
acgttgctct ctaccccggg aacgtcgaga ctggagcgcg cgaactgagc caccttcgcg   120
gaccccgaga gcggcg                                                    136

SEQ ID NO: 517      moltype = RNA  length = 97
FEATURE             Location/Qualifiers
source              1..97
                    mol_type = transcribed RNA
                    organism = Homo sapiens
SEQUENCE: 517
ggtgggagga ttgcttgagc ctggaagctg gagcctgcag tgaactatca ttgtgccact    60
gtactccagc ctaggcaaca aaatgaaatc ctgtcta                              97

SEQ ID NO: 518      moltype = RNA  length = 63
FEATURE             Location/Qualifiers
source              1..63
                    mol_type = transcribed RNA
                    organism = Homo sapiens
SEQUENCE: 518
ctgagcctgg aagctggagc ctgcagtgag ctatgatcat gtccctgtac tctagcctgg    60
gca                                                                   63
```

```
SEQ ID NO: 519          moltype = RNA  length = 89
FEATURE                 Location/Qualifiers
source                  1..89
                        mol_type = transcribed RNA
                        organism = Homo sapiens
SEQUENCE: 519
tctccgttta tcccaccact gccaccatta ttgctactgt tcagcaggtg ctgctggtgg    60
tgatggtgat agtctggtgg gggcggtgg                                     89

SEQ ID NO: 520          moltype = RNA  length = 52
FEATURE                 Location/Qualifiers
source                  1..52
                        mol_type = transcribed RNA
                        organism = Homo sapiens
SEQUENCE: 520
tagccgggcg tggtggtggg ggcctgtggt cccagctact ttggaggctg ag            52

SEQ ID NO: 521          moltype = RNA  length = 50
FEATURE                 Location/Qualifiers
source                  1..50
                        mol_type = transcribed RNA
                        organism = Homo sapiens
SEQUENCE: 521
acccgggcgt ggtggtgggg gtgggtgcct gtaattccag ctagttggga              50

SEQ ID NO: 522          moltype = RNA  length = 100
FEATURE                 Location/Qualifiers
source                  1..100
                        mol_type = transcribed RNA
                        organism = Homo sapiens
SEQUENCE: 522
gaggtgggag gattgcttga gtcagggtgg ttgaggctgc agtaagttgt gatcatacca    60
ctgcactcca gcctgagtga cagagcaaga ccttgtctca                        100

SEQ ID NO: 523          moltype = RNA  length = 82
FEATURE                 Location/Qualifiers
source                  1..82
                        mol_type = transcribed RNA
                        organism = Homo sapiens
SEQUENCE: 523
tgagctgttg gattcggggc cgtagcactg tctgagaggt ttacatttct cacagtgaac    60
cggtctcttt ttcagctgct tc                                            82

SEQ ID NO: 524          moltype = RNA  length = 84
FEATURE                 Location/Qualifiers
source                  1..84
                        mol_type = transcribed RNA
                        organism = Homo sapiens
SEQUENCE: 524
tgtgcagtgg gaaggggggc cgatacactg tacgagagtg agtagcaggt ctcacagtga    60
accggtctct ttccctactg tgtc                                          84

SEQ ID NO: 525          moltype = RNA  length = 78
FEATURE                 Location/Qualifiers
source                  1..78
                        mol_type = transcribed RNA
                        organism = Homo sapiens
SEQUENCE: 525
gagcgtcacg ttgacactca aaaagtttca gattttggaa catttcggat tttggatttt    60
tggatcaggg atgctcaa                                                 78

SEQ ID NO: 526          moltype = RNA  length = 84
FEATURE                 Location/Qualifiers
source                  1..84
                        mol_type = transcribed RNA
                        organism = Homo sapiens
SEQUENCE: 526
ctccccatgg ccctgtctcc caacccttgt accagtgctg ggctcagacc ctggtacagg    60
cctgggggac agggacctgg ggac                                          84

SEQ ID NO: 527          moltype = RNA  length = 84
FEATURE                 Location/Qualifiers
source                  1..84
                        mol_type = transcribed RNA
                        organism = Homo sapiens
SEQUENCE: 527
gtcagaataa tgtcaaagtg cttacagtgc aggtagtgat atgtgcatct actgcagtga    60
aggcacttgt agcattatgg tgac                                          84
```

| | | |
|---|---|---|
| SEQ ID NO: 528 | moltype = RNA length = 80 | |
| FEATURE | Location/Qualifiers | |
| source | 1..80 | |
| | mol_type = transcribed RNA | |
| | organism = Homo sapiens | |
| SEQUENCE: 528 | | |
| cgggaatgcc gcggcgggga cggcgattgg tccgtatgtg tggtgccacc ggccgccggc | | 60 |
| tccgccccgg ccccgcccc | | 80 |
| | | |
| SEQ ID NO: 529 | moltype = RNA length = 80 | |
| FEATURE | Location/Qualifiers | |
| source | 1..80 | |
| | mol_type = transcribed RNA | |
| | organism = Homo sapiens | |
| SEQUENCE: 529 | | |
| catccaggac aatggtgagt gccggtgcct gccctggggc cgtccctgcg caggggccgg | | 60 |
| gtgctcaccg catctgcccc | | 80 |
| | | |
| SEQ ID NO: 530 | moltype = RNA length = 80 | |
| FEATURE | Location/Qualifiers | |
| source | 1..80 | |
| | mol_type = transcribed RNA | |
| | organism = Homo sapiens | |
| SEQUENCE: 530 | | |
| cgtgtgagcc cgccctgtgc ccggcccact tctgcttcct cttagcgcag gaggggtccc | | 60 |
| gcactgggag gggccctcac | | 80 |
| | | |
| SEQ ID NO: 531 | moltype = RNA length = 80 | |
| FEATURE | Location/Qualifiers | |
| source | 1..80 | |
| | mol_type = transcribed RNA | |
| | organism = Homo sapiens | |
| SEQUENCE: 531 | | |
| tgagaggccg caccttgcct tgctgcccgg gccgtgcacc cgtgggcccc agggcgacgc | | 60 |
| ggcgggggcg gccctagcga | | 80 |
| | | |
| SEQ ID NO: 532 | moltype = RNA length = 92 | |
| FEATURE | Location/Qualifiers | |
| source | 1..92 | |
| | mol_type = transcribed RNA | |
| | organism = Homo sapiens | |
| SEQUENCE: 532 | | |
| cggctggaca gcgggcaacg gaatcccaaa agcagctgtt gtctccagag cattccagct | | 60 |
| gcgcttggat ttcgtcccct gctctcctgc ct | | 92 |
| | | |
| SEQ ID NO: 533 | moltype = RNA length = 85 | |
| FEATURE | Location/Qualifiers | |
| source | 1..85 | |
| | mol_type = transcribed RNA | |
| | organism = Homo sapiens | |
| SEQUENCE: 533 | | |
| ggctgagccg cagtagttct tcagtggcaa gctttatgtc ctgacccagc taaagctgcc | | 60 |
| agttgaagaa ctgttgccct ctgcc | | 85 |
| | | |
| SEQ ID NO: 534 | moltype = RNA length = 97 | |
| FEATURE | Location/Qualifiers | |
| source | 1..97 | |
| | mol_type = transcribed RNA | |
| | organism = Homo sapiens | |
| SEQUENCE: 534 | | |
| ctcaggtgct ctggctgctt gggttcctgg catgctgatt tgtgacttaa gattaaaatc | | 60 |
| acattgccag ggattaccac gcaaccacga ccttggc | | 97 |
| | | |
| SEQ ID NO: 535 | moltype = RNA length = 68 | |
| FEATURE | Location/Qualifiers | |
| source | 1..68 | |
| | mol_type = transcribed RNA | |
| | organism = Homo sapiens | |
| SEQUENCE: 535 | | |
| ctccggtgcc tactgagctg atatcagttc tcattttaca cactggctca gttcagcagg | | 60 |
| aacaggag | | 68 |
| | | |
| SEQ ID NO: 536 | moltype = RNA length = 73 | |
| FEATURE | Location/Qualifiers | |
| source | 1..73 | |
| | mol_type = transcribed RNA | |
| | organism = Homo sapiens | |
| SEQUENCE: 536 | | |

```
ctctgcctcc cgtgcctact gagctgaaac acagttggtt tgtgtacact ggctcagttc   60
agcaggaaca ggg                                                      73

SEQ ID NO: 537          moltype = RNA   length = 80
FEATURE                 Location/Qualifiers
source                  1..80
                        mol_type = transcribed RNA
                        organism = Homo sapiens
SEQUENCE: 537
aggacccttc cagagggccc ccctcaatc ctgttgtgcc taattcagag ggttgggtgg    60
aggctctcct gaagggctct                                               80

SEQ ID NO: 538          moltype = RNA   length = 63
FEATURE                 Location/Qualifiers
source                  1..63
                        mol_type = transcribed RNA
                        organism = Homo sapiens
SEQUENCE: 538
gagtcgagga ctggtggaag ggcctttccc ctcagaccaa ggccctggcc ccagcttctt   60
ctc                                                                 63

SEQ ID NO: 539          moltype = RNA   length = 82
FEATURE                 Location/Qualifiers
source                  1..82
                        mol_type = transcribed RNA
                        organism = Homo sapiens
SEQUENCE: 539
ctgactttt tagggagtag aagggtgggg agcatgaaca atgtttctca ctccctaccc    60
ctccactccc caaaaaagtc ag                                            82

SEQ ID NO: 540          moltype = RNA   length = 85
FEATURE                 Location/Qualifiers
source                  1..85
                        mol_type = transcribed RNA
                        organism = Homo sapiens
SEQUENCE: 540
ggcgcctcct gctctgctgt gccgccaggg cctcccctag cgcgccttct ggagaggctt   60
tgtgcggata cggggctgga ggcct                                         85

SEQ ID NO: 541          moltype = RNA   length = 64
FEATURE                 Location/Qualifiers
source                  1..64
                        mol_type = transcribed RNA
                        organism = Homo sapiens
SEQUENCE: 541
gggtggggc ggggcggcag gggcctcccc cagtgccagg ccccattctg cttctctccc    60
agct                                                                64

SEQ ID NO: 542          moltype = RNA   length = 73
FEATURE                 Location/Qualifiers
source                  1..73
                        mol_type = transcribed RNA
                        organism = Homo sapiens
SEQUENCE: 542
ggcgagggga ggcgcaggct cggaaaggcg cgcgaggctc caggctcctt cccgatccac   60
cgctctcctc gct                                                      73

SEQ ID NO: 543          moltype = RNA   length = 82
FEATURE                 Location/Qualifiers
source                  1..82
                        mol_type = transcribed RNA
                        organism = Homo sapiens
SEQUENCE: 543
gcttcgctcc cctccgcctt ctcttcccgg ttcttcccgg agtcgggaaa agctgggttg   60
agagggcgaa aaaggatgag gt                                            82

SEQ ID NO: 544          moltype = RNA   length = 99
FEATURE                 Location/Qualifiers
source                  1..99
                        mol_type = transcribed RNA
                        organism = Homo sapiens
SEQUENCE: 544
gaaactgggc tcaaggtgag gggtgctatc tgtgattgag ggacatggtt aatggaattg   60
tctcacacag aaatcgcacc cgtcaccttg gcctactta                          99

SEQ ID NO: 545          moltype = RNA   length = 85
FEATURE                 Location/Qualifiers
source                  1..85
                        mol_type = transcribed RNA
```

```
                            organism = Homo sapiens
SEQUENCE: 545
gtgagctgct ggggacgcgg gtcgggtct gcagggcggt gcggcagccg ccacctgacg    60
ccgcgccttt gtctgtgtcc cacag                                        85

SEQ ID NO: 546          moltype = RNA   length = 180
FEATURE                 Location/Qualifiers
source                  1..180
                        mol_type = transcribed RNA
                        organism = Homo sapiens
SEQUENCE: 546
cgcgactgcg gcggcggtgg tgggggagc cgcggggatc gccgagggcc ggtcggccgc    60
cccgggtgcc gcgcggtgcc gccggcggcg gtgaggcccc gcgcgtgtgt cccggctgcg   120
gtcggccgcg ctcgagggt ccccgtggcg tccccttccc gccggccgc ctttctcgcg     180

SEQ ID NO: 547          moltype = RNA   length = 69
FEATURE                 Location/Qualifiers
source                  1..69
                        mol_type = transcribed RNA
                        organism = Homo sapiens
SEQUENCE: 547
ctttcggcca gcgggacggc atccgaggtg ggctaggctc gggcccgtgg cgggtgcggg    60
ggtgggagg                                                           69

SEQ ID NO: 548          moltype = RNA   length = 87
FEATURE                 Location/Qualifiers
source                  1..87
                        mol_type = transcribed RNA
                        organism = Homo sapiens
SEQUENCE: 548
accgcaggga aaatgaggga cttttggggg cagatgtgtt tccattccac tatcataatg    60
cccctaaaaa tccttattgc tcttgca                                       87

SEQ ID NO: 549          moltype = RNA   length = 105
FEATURE                 Location/Qualifiers
source                  1..105
                        mol_type = transcribed RNA
                        organism = Homo sapiens
SEQUENCE: 549
gcggcggcg gcggcggcag cagcagcagg tgcggggcgg cggccgcgct ggccgctcga     60
ctccgcagct gctcgttctg cttctccagc ttgcgcacca gctcc                  105

SEQ ID NO: 550          moltype = RNA   length = 68
FEATURE                 Location/Qualifiers
source                  1..68
                        mol_type = transcribed RNA
                        organism = Homo sapiens
SEQUENCE: 550
cgtggtgagg atatggcagg gaagggagt ttccctctat tcccttcccc ccagtaatct    60
tcatcatg                                                           68

SEQ ID NO: 551          moltype = RNA   length = 67
FEATURE                 Location/Qualifiers
source                  1..67
                        mol_type = transcribed RNA
                        organism = Homo sapiens
SEQUENCE: 551
gtggcactca aactgtgggg gcactttctg ctctctggtg aaagtgccgc catcttttga    60
gtgttac                                                             67

SEQ ID NO: 552          moltype = RNA   length = 102
FEATURE                 Location/Qualifiers
source                  1..102
                        mol_type = transcribed RNA
                        organism = Homo sapiens
SEQUENCE: 552
gcttatcgag gaaaagatcg aggtgggttg gggcgggctc tggggatttg gtctcacagc    60
ccggatccca gcccacttac cttggttact ctccttcctt ct                     102

SEQ ID NO: 553          moltype = RNA   length = 94
FEATURE                 Location/Qualifiers
source                  1..94
                        mol_type = transcribed RNA
                        organism = Homo sapiens
SEQUENCE: 553
ataaaggaag ttaggctgag gggcagagag cgagactttt ctattttcca aaagctcggt    60
ctgaggcccc tcagtcttgc ttcctaaccc gcgc                               94

SEQ ID NO: 554          moltype = RNA   length = 86
```

| FEATURE | Location/Qualifiers |
|---|---|
| source | 1..86<br>mol_type = transcribed RNA<br>organism = Homo sapiens |

SEQUENCE: 554

```
ggcttagaaa cagtccctag gtaggatttg gggaggagct aagaagcccc tacagggccc   60
agaggtgggg actgagcctt agttgg                                        86
```

| SEQ ID NO: 555 | moltype = RNA length = 70 |
|---|---|
| FEATURE | Location/Qualifiers |
| source | 1..70<br>mol_type = transcribed RNA<br>organism = Homo sapiens |

SEQUENCE: 555

```
acaaatagct tcagggagtc aggggagggc agaaatagat ggccttcccc tgctgggaag   60
aaagtgggtc                                                          70
```

| SEQ ID NO: 556 | moltype = RNA length = 67 |
|---|---|
| FEATURE | Location/Qualifiers |
| source | 1..67<br>mol_type = transcribed RNA<br>organism = Homo sapiens |

SEQUENCE: 556

```
aaatctctct ccatatcttt cctgcagccc ccaggtgggg gggaagaaaa ggtggggaat   60
tagattc                                                             67
```

| SEQ ID NO: 557 | moltype = RNA length = 93 |
|---|---|
| FEATURE | Location/Qualifiers |
| source | 1..93<br>mol_type = transcribed RNA<br>organism = Homo sapiens |

SEQUENCE: 557

```
tacttatggc accccactcc tggtaccata gtcataagtt aggagatgtt agagctgtga   60
gtaccatgac ttaagtgtgg tggcttaaac atg                                93
```

| SEQ ID NO: 558 | moltype = RNA length = 73 |
|---|---|
| FEATURE | Location/Qualifiers |
| source | 1..73<br>mol_type = transcribed RNA<br>organism = Homo sapiens |

SEQUENCE: 558

```
ggggaggtac ctgggacagg aggaggaggc agccttgcct cagaaaccaa actgtcaaaa   60
gtgtaggttc cac                                                      73
```

| SEQ ID NO: 559 | moltype = RNA length = 73 |
|---|---|
| FEATURE | Location/Qualifiers |
| source | 1..73<br>mol_type = transcribed RNA<br>organism = Homo sapiens |

SEQUENCE: 559

```
gaaaacaacc aggtgggctt cccggagggc ggaacaccca gccccagcat ccagggctca   60
cctaccacgt ttg                                                      73
```

| SEQ ID NO: 560 | moltype = RNA length = 67 |
|---|---|
| FEATURE | Location/Qualifiers |
| source | 1..67<br>mol_type = transcribed RNA<br>organism = Homo sapiens |

SEQUENCE: 560

```
gcgccctccc tctctccccg gtgtgcaaat gtgtgtgtgc ggtgttatgc cggacaagag   60
ggaggtg                                                             67
```

| SEQ ID NO: 561 | moltype = RNA length = 67 |
|---|---|
| FEATURE | Location/Qualifiers |
| source | 1..67<br>mol_type = transcribed RNA<br>organism = Homo sapiens |

SEQUENCE: 561

```
ctggtccatt tccctgccat tcccttggct tcaatttact cccagggctg gcagtgacat   60
gggtcaa                                                             67
```

| SEQ ID NO: 562 | moltype = RNA length = 86 |
|---|---|
| FEATURE | Location/Qualifiers |
| source | 1..86<br>mol_type = transcribed RNA<br>organism = Homo sapiens |

SEQUENCE: 562

```
aggagtgacc aaaagacaag agtgcgagcc ttctattatg cccagacagg gccaccagag   60
ggctccttgg tctaggggta atgcca                                        86
```

```
SEQ ID NO: 563          moltype = RNA   length = 55
FEATURE                 Location/Qualifiers
source                  1..55
                        mol_type = transcribed RNA
                        organism = Homo sapiens
SEQUENCE: 563
ccggatccga gtcacggcac caaatttcat gcgtgtccgt gtgaagagac cacca              55

SEQ ID NO: 564          moltype = RNA   length = 63
FEATURE                 Location/Qualifiers
source                  1..63
                        mol_type = transcribed RNA
                        organism = Homo sapiens
SEQUENCE: 564
tggtggcggc ggtagttatg ggcttctctt tctcaccagc agccctggg ccgccgcctc          60
cct                                                                       63

SEQ ID NO: 565          moltype = RNA   length = 80
FEATURE                 Location/Qualifiers
source                  1..80
                        mol_type = transcribed RNA
                        organism = Homo sapiens
SEQUENCE: 565
tggcagaccc ttgctctctc actctcccta atgggctga agacagctca ggggcagggt          60
gggggtgtt gttttgttt                                                       80

SEQ ID NO: 566          moltype = RNA   length = 67
FEATURE                 Location/Qualifiers
source                  1..67
                        mol_type = transcribed RNA
                        organism = Homo sapiens
SEQUENCE: 566
tggtgggggt gggggtgtt gttttgtttt ttgagacaga gtcttgctcc gtcgcccagg          60
ccggagt                                                                   67

SEQ ID NO: 567          moltype = RNA   length = 52
FEATURE                 Location/Qualifiers
source                  1..52
                        mol_type = transcribed RNA
                        organism = Homo sapiens
SEQUENCE: 567
tctgggctga gccgagctgg gttaagccga gctgggttgg gctgggctgg gt                 52

SEQ ID NO: 568          moltype = RNA   length = 86
FEATURE                 Location/Qualifiers
source                  1..86
                        mol_type = transcribed RNA
                        organism = Homo sapiens
SEQUENCE: 568
agggagaagg gtcggggcag ggagggcagg gcaggctctg gggtgggggg tctgtgagtc         60
agccacggct ctgcccacgt ctcccc                                              86

SEQ ID NO: 569          moltype = RNA   length = 72
FEATURE                 Location/Qualifiers
source                  1..72
                        mol_type = transcribed RNA
                        organism = Homo sapiens
SEQUENCE: 569
cttgggaatg gcaaggaaac cgttaccatt actgagttta gtaatggtaa tggttctctt         60
gctatacccca ga                                                            72

SEQ ID NO: 570          moltype = RNA   length = 64
FEATURE                 Location/Qualifiers
source                  1..64
                        mol_type = transcribed RNA
                        organism = Homo sapiens
SEQUENCE: 570
tctgggcgag gggtgggctc tcagaggggc tggcagtact gctctgaggc ctgcctctcc         60
ccag                                                                      64

SEQ ID NO: 571          moltype = RNA   length = 73
FEATURE                 Location/Qualifiers
source                  1..73
                        mol_type = transcribed RNA
                        organism = Homo sapiens
SEQUENCE: 571
cggcgacggc gggtgggtg aggtcgggcc ccaagactcg ggtttgccg ggcgcctcag           60
ttcaccgcgg ccg                                                            73
```

```
SEQ ID NO: 572         moltype = RNA   length = 87
FEATURE                Location/Qualifiers
source                 1..87
                       mol_type = transcribed RNA
                       organism = Homo sapiens
SEQUENCE: 572
cccaggcgcc cgctcccgac ccacgccgcg ccgccgggtc cctcctcccc ggagaggctg    60
ggctcgggac gcgcggctca gctcggg                                       87

SEQ ID NO: 573         moltype = RNA   length = 77
FEATURE                Location/Qualifiers
source                 1..77
                       mol_type = transcribed RNA
                       organism = Homo sapiens
SEQUENCE: 573
catgagaaat cctgctggtc aaccatagcc ctggtcagac tctccggggc tgtgattgac    60
cagcaggact tctcatg                                                  77

SEQ ID NO: 574         moltype = RNA   length = 70
FEATURE                Location/Qualifiers
source                 1..70
                       mol_type = transcribed RNA
                       organism = Homo sapiens
SEQUENCE: 574
ggtttctcct tgaggagaca tggtgggggc cggtcaggca gcccatgcca tgtgtcctca    60
tggagaggcc                                                          70

SEQ ID NO: 575         moltype = RNA   length = 74
FEATURE                Location/Qualifiers
source                 1..74
                       mol_type = transcribed RNA
                       organism = Homo sapiens
SEQUENCE: 575
cctgcaggag gcagtgggcg agcaggcggg gcagcccaat gccatgggcc tgatctcacc    60
gctgcctcct tccc                                                     74

SEQ ID NO: 576         moltype = RNA   length = 78
FEATURE                Location/Qualifiers
source                 1..78
                       mol_type = transcribed RNA
                       organism = Homo sapiens
SEQUENCE: 576
gggcccagaa gggggcgcag tcactgacgt gaagggacca catcccgctt catgtcagtg    60
actcctgccc cttggtct                                                 78

SEQ ID NO: 577         moltype = RNA   length = 90
FEATURE                Location/Qualifiers
source                 1..90
                       mol_type = transcribed RNA
                       organism = Homo sapiens
SEQUENCE: 577
gtgtctctct ggagaccctg cagccttccc acccaccagg gagctttcca tgggctgtgg    60
ggaaggcgtc agtgtcgggt gagggaacac                                    90

SEQ ID NO: 578         moltype = RNA   length = 74
FEATURE                Location/Qualifiers
source                 1..74
                       mol_type = transcribed RNA
                       organism = Homo sapiens
SEQUENCE: 578
gggaggaaga agggaggagg agcggagggg cccttgtctt cccagagcct ctcccttcct    60
cccctccccc tccc                                                     74

SEQ ID NO: 579         moltype = RNA   length = 62
FEATURE                Location/Qualifiers
source                 1..62
                       mol_type = transcribed RNA
                       organism = Homo sapiens
SEQUENCE: 579
gtgagtgggg ctcccgggac ggcgcccgcc ctggccctgg cccggcgacg tctcacggtc    60
cc                                                                  62

SEQ ID NO: 580         moltype = RNA   length = 74
FEATURE                Location/Qualifiers
source                 1..74
                       mol_type = transcribed RNA
                       organism = Homo sapiens
SEQUENCE: 580
```

```
gcagcccggt gagcgctcgc tggcctggca gtgcgtcgga agaacagggc gggtggggcc    60
gcgcacatct ctgc                                                     74

SEQ ID NO: 581         moltype = RNA  length = 68
FEATURE                Location/Qualifiers
source                 1..68
                       mol_type = transcribed RNA
                       organism = Homo sapiens
SEQUENCE: 581
gcatcctgta ctgagctgcc ccgaggccct tcatgctgcc cagctcgggg cagctcagta    60
caggatac                                                            68

SEQ ID NO: 582         moltype = RNA  length = 64
FEATURE                Location/Qualifiers
source                 1..64
                       mol_type = transcribed RNA
                       organism = Homo sapiens
SEQUENCE: 582
tcctgtactg agctgccccg agctgggcag catgaagggc ctcggggcag ctcagtacag    60
gatg                                                                64

SEQ ID NO: 583         moltype = RNA  length = 100
FEATURE                Location/Qualifiers
source                 1..100
                       mol_type = transcribed RNA
                       organism = Homo sapiens
SEQUENCE: 583
agctcagggc ggctgcgcag agggctggac tcagcggcgg agctggctgc tggcctcagt    60
tctgcctctg tccaggtcct tgtgacccgc ccgctctcct                        100

SEQ ID NO: 584         moltype = RNA  length = 115
FEATURE                Location/Qualifiers
source                 1..115
                       mol_type = transcribed RNA
                       organism = Homo sapiens
SEQUENCE: 584
gagcaaaaac cagagaacaa catgggagcg ttcctaaccc ctaaggcaac tggatgggag    60
acctgaccca tccagttctc tgaggggggct cttgtgtgtt ctacaaggtt gttca      115

SEQ ID NO: 585         moltype = RNA  length = 97
FEATURE                Location/Qualifiers
source                 1..97
                       mol_type = transcribed RNA
                       organism = Homo sapiens
SEQUENCE: 585
tgatgctttg ctggctggtg cagtgcctga gggagtaaga gccctgttgt tgtaagatag    60
tgtcttactc cctcaggcac atctccaaca agtctct                            97

SEQ ID NO: 586         moltype = RNA  length = 97
FEATURE                Location/Qualifiers
source                 1..97
                       mol_type = transcribed RNA
                       organism = Homo sapiens
SEQUENCE: 586
tgatgctttg ctggctggtg cagtgcctga gggagtaaga gccctgttgt tgtcagatag    60
tgtcttactc cctcaggcac atctccagcg agtctct                            97

SEQ ID NO: 587         moltype = RNA  length = 72
FEATURE                Location/Qualifiers
source                 1..72
                       mol_type = transcribed RNA
                       organism = Homo sapiens
SEQUENCE: 587
ctgtgcacct gggggagtgc agtgattgtg gaatgcaaag tcccacaatc actgtactcc    60
ccaggtgcac ag                                                       72

SEQ ID NO: 588         moltype = RNA  length = 95
FEATURE                Location/Qualifiers
source                 1..95
                       mol_type = transcribed RNA
                       organism = Homo sapiens
SEQUENCE: 588
gacaccacat gctcctccag gcctgcctgc cctccaggtc atgttccagt gtcccacaga    60
tgcagcacca cggcccaggc ggcattggtg tcacc                              95

SEQ ID NO: 589         moltype = RNA  length = 51
FEATURE                Location/Qualifiers
source                 1..51
                       mol_type = transcribed RNA
```

-continued

```
                                organism = Homo sapiens
SEQUENCE: 589
agagatgaag cgggggggcg gggtcttgct ctattgccta cgctgatctc a        51

SEQ ID NO: 590          moltype = RNA  length = 64
FEATURE                 Location/Qualifiers
source                  1..64
                        mol_type = transcribed RNA
                        organism = Homo sapiens
SEQUENCE: 590
ccccgggccc ggcgttccct ccccttccgt gcgccagtgg aggccggggt ggggcgggc  60
gggg                                                              64

SEQ ID NO: 591          moltype = RNA  length = 64
FEATURE                 Location/Qualifiers
source                  1..64
                        mol_type = transcribed RNA
                        organism = Homo sapiens
SEQUENCE: 591
ccccgggccc ggcgttccct ccccttccgt gcgccagtgg aggccggggt ggggcgggc  60
gggg                                                              64

SEQ ID NO: 592          moltype = RNA  length = 96
FEATURE                 Location/Qualifiers
source                  1..96
                        mol_type = transcribed RNA
                        organism = Homo sapiens
SEQUENCE: 592
gctctgggc gtgccgccgc cgtcgctgcc acctccccta ccgctagtgg aagaagatgg   60
cggaaggcgg agcggcggat ctggacaccc agcggt                           96

SEQ ID NO: 593          moltype = RNA  length = 89
FEATURE                 Location/Qualifiers
source                  1..89
                        mol_type = transcribed RNA
                        organism = Homo sapiens
SEQUENCE: 593
agcctgtggg aaagagaaga gcagggcagg gtgaaggccc ggcggagaca ctctgcccac  60
cccacaccct gcctatgggc cacacagct                                   89

SEQ ID NO: 594          moltype = RNA  length = 90
FEATURE                 Location/Qualifiers
source                  1..90
                        mol_type = transcribed RNA
                        organism = Homo sapiens
SEQUENCE: 594
tctaagaaac gcagtggtct ctgaagcctg caggggcagg ccagccctgc actgaacgcc  60
tgttcttgcc aggtggcaga aggttgctgc                                  90

SEQ ID NO: 595          moltype = RNA  length = 96
FEATURE                 Location/Qualifiers
source                  1..96
                        mol_type = transcribed RNA
                        organism = Homo sapiens
SEQUENCE: 595
ctcgggaggg gcgggagggg ggtccccggt gctcggatct cgagggtgct tattgttcgg  60
tccgagcctg ggtctccctc ttccccccaa cccccc                           96

SEQ ID NO: 596          moltype = RNA  length = 99
FEATURE                 Location/Qualifiers
source                  1..99
                        mol_type = transcribed RNA
                        organism = Homo sapiens
SEQUENCE: 596
cgcccacctc agcctcccaa aatgctggga ttacaggcat gagccactgc ggtcgaccat  60
gacctggaca tgtttgtgcc cagtactgtc agtttgcag                        99

SEQ ID NO: 597          moltype = RNA  length = 100
FEATURE                 Location/Qualifiers
source                  1..100
                        mol_type = transcribed RNA
                        organism = Homo sapiens
SEQUENCE: 597
gtgagcgggc gcggcaggga tcgcgggcgg gtgcggcct agggcgcgga gggcggaccg   60
ggaatggcgc gccgtgcgcc gccggcgtaa ctgcggcgct                      100

SEQ ID NO: 598          moltype = RNA  length = 77
FEATURE                 Location/Qualifiers
source                  1..77
```

```
                        mol_type = transcribed RNA
                        organism = Homo sapiens
SEQUENCE: 598
gagttgggag gttccctctc caaatgtgtc ttgatccccc accccaagac acatttggag    60
agggaccctc ccaactc                                                   77

SEQ ID NO: 599          moltype = RNA   length = 96
FEATURE                 Location/Qualifiers
source                  1..96
                        mol_type = transcribed RNA
                        organism = Homo sapiens
SEQUENCE: 599
cagtgctggg gtctcaggag gcagcgctct caggacgtca ccaccatggc ctgggctctg    60
ctcctcctca ccctcctcac tcagggcaca ggtgat                              96

SEQ ID NO: 600          moltype = RNA   length = 93
FEATURE                 Location/Qualifiers
source                  1..93
                        mol_type = transcribed RNA
                        organism = Homo sapiens
SEQUENCE: 600
ccttccggcg tcccaggcgg ggcgccgcgg gaccgccctc gtgtctgtgg cggtgggatc    60
ccgcggccgt gttttcctgg tggcccggcc atg                                 93

SEQ ID NO: 601          moltype = RNA   length = 115
FEATURE                 Location/Qualifiers
source                  1..115
                        mol_type = transcribed RNA
                        organism = Homo sapiens
SEQUENCE: 601
ggtgccgagg gccgtccggc atcctaggcg ggtcgctgcg gtacctcct cctgtctgtg     60
gcggtgggat cccgtggccg tgttttcctg gtggcccggc cgtgcctgag gtttc        115

SEQ ID NO: 602          moltype = RNA   length = 73
FEATURE                 Location/Qualifiers
source                  1..73
                        mol_type = transcribed RNA
                        organism = Homo sapiens
SEQUENCE: 602
ctggtgtttg aggcgatgtg gggatgtaga gacaacttcc cagtctcatt tcctcatcct    60
gccaggccac cat                                                       73

SEQ ID NO: 603          moltype = RNA   length = 87
FEATURE                 Location/Qualifiers
source                  1..87
                        mol_type = transcribed RNA
                        organism = Homo sapiens
SEQUENCE: 603
ccctcatctc tgggcagggg cttattgtag gagtctctga agagagctgt ggactgacct    60
gctttaaccc ttccccaggt tcccatt                                        87

SEQ ID NO: 604          moltype = RNA   length = 61
FEATURE                 Location/Qualifiers
source                  1..61
                        mol_type = transcribed RNA
                        organism = Homo sapiens
SEQUENCE: 604
gggggcggga gctgggtct gcaggttcgc actgatgcct gctcgccctg tctcccgcta     60
g                                                                    61

SEQ ID NO: 605          moltype = RNA   length = 65
FEATURE                 Location/Qualifiers
source                  1..65
                        mol_type = transcribed RNA
                        organism = Homo sapiens
SEQUENCE: 605
gggtgctcgg ggcaggcggc tgggagcggc cctcacattg atggctcctg ccacctcctc    60
cgcag                                                                65

SEQ ID NO: 606          moltype = RNA   length = 64
FEATURE                 Location/Qualifiers
source                  1..64
                        mol_type = transcribed RNA
                        organism = Homo sapiens
SEQUENCE: 606
gaaggcgagg ggtagaagag cacaggggtt ctgataaacc cttctgcctg cattctactc    60
ccag                                                                 64

SEQ ID NO: 607          moltype = RNA   length = 63
```

```
FEATURE               Location/Qualifiers
source                1..63
                      mol_type = transcribed RNA
                      organism = Homo sapiens
SEQUENCE: 607
aatgggtggg tgctggtggg agccgtgccc tggccactca ttcggctctc tccctcaccc    60
tag                                                                  63

SEQ ID NO: 608        moltype = RNA   length = 69
FEATURE               Location/Qualifiers
source                1..69
                      mol_type = transcribed RNA
                      organism = Homo sapiens
SEQUENCE: 608
ggccctcggg cctggggttg ggggagctct gtcctgtctc actcattgct cctcccctgc    60
ctggcccag                                                            69

SEQ ID NO: 609        moltype = RNA   length = 71
FEATURE               Location/Qualifiers
source                1..71
                      mol_type = transcribed RNA
                      organism = Homo sapiens
SEQUENCE: 609
atggaggggg gtgtggagcc aggggggccca ggtctacagc ttctccccgc tccctgcccc   60
catactccca g                                                         71

SEQ ID NO: 610        moltype = RNA   length = 73
FEATURE               Location/Qualifiers
source                1..73
                      mol_type = transcribed RNA
                      organism = Homo sapiens
SEQUENCE: 610
cccagggtct ggtgcggaga gggcccacag tggacttggt gacgctgtat gccctcaccg    60
ctcagcccct ggg                                                       73

SEQ ID NO: 611        moltype = RNA   length = 69
FEATURE               Location/Qualifiers
source                1..69
                      mol_type = transcribed RNA
                      organism = Homo sapiens
SEQUENCE: 611
gggcttaggg atgggaggcc aggatgaaga ttaatcccta atccccaaca ctggccttgc    60
tatcccag                                                             69

SEQ ID NO: 612        moltype = RNA   length = 87
FEATURE               Location/Qualifiers
source                1..87
                      mol_type = transcribed RNA
                      organism = Homo sapiens
SEQUENCE: 612
gtgaggcggg gccaggaggg tgtgtggcgt gggtgctgcg gggccgtcag ggtgcctgcg    60
ggacgctcac ctggctggcc cgcccag                                        87

SEQ ID NO: 613        moltype = RNA   length = 69
FEATURE               Location/Qualifiers
source                1..69
                      mol_type = transcribed RNA
                      organism = Homo sapiens
SEQUENCE: 613
gaacctcggg gcatggggga gggaggctgg acaggagagg gctcacccag gccctgtcct    60
ctgccccag                                                            69

SEQ ID NO: 614        moltype = RNA   length = 79
FEATURE               Location/Qualifiers
source                1..79
                      mol_type = transcribed RNA
                      organism = Homo sapiens
SEQUENCE: 614
cagcctgggg aaggcttggc agggaagaca catgagcagt gcctccactt cacgcctctc    60
ccttgtctcc tttccctag                                                 79

SEQ ID NO: 615        moltype = RNA   length = 69
FEATURE               Location/Qualifiers
source                1..69
                      mol_type = transcribed RNA
                      organism = Homo sapiens
SEQUENCE: 615
tggggtaggg gtgggggaat tcaggggtgt cgaactcatg gctgccacct ttgtgtcccc    60
atcctgcag                                                            69
```

```
SEQ ID NO: 616         moltype = RNA   length = 67
FEATURE                Location/Qualifiers
source                 1..67
                       mol_type = transcribed RNA
                       organism = Homo sapiens
SEQUENCE: 616
tacaggccgg ggctttgggt gagggacccc cggagtctgt cacggtctca ccccaactct    60
gccccag                                                              67

SEQ ID NO: 617         moltype = RNA   length = 64
FEATURE                Location/Qualifiers
source                 1..64
                       mol_type = transcribed RNA
                       organism = Homo sapiens
SEQUENCE: 617
tgctctgtag gcatgaggca gggcccaggt tccatgtgat gctgaagctc tgacattcct    60
gcag                                                                 64

SEQ ID NO: 618         moltype = RNA   length = 71
FEATURE                Location/Qualifiers
source                 1..71
                       mol_type = transcribed RNA
                       organism = Homo sapiens
SEQUENCE: 618
tgaccacccc cgggcaaaga cctgcagatc ccctgttaga gacgggccca ggactttgtg    60
cggggtgccc a                                                         71

SEQ ID NO: 619         moltype = RNA   length = 70
FEATURE                Location/Qualifiers
source                 1..70
                       mol_type = transcribed RNA
                       organism = Homo sapiens
SEQUENCE: 619
gtccctgggg gctgggatgg gccatggtgt gctctgatcc ccctgtggtc tcttggcccc    60
caggaactcc                                                           70

SEQ ID NO: 620         moltype = RNA   length = 67
FEATURE                Location/Qualifiers
source                 1..67
                       mol_type = transcribed RNA
                       organism = Homo sapiens
SEQUENCE: 620
cagggaggag gtggtactag gggccagcaa cctgattacc cctctttggc cctttgtacc    60
cctccag                                                              67

SEQ ID NO: 621         moltype = RNA   length = 60
FEATURE                Location/Qualifiers
source                 1..60
                       mol_type = transcribed RNA
                       organism = Homo sapiens
SEQUENCE: 621
caaggtgggg gagatggggg ttgaacttca tttctcatgc tcatccccat ctcctttcag    60

SEQ ID NO: 622         moltype = RNA   length = 62
FEATURE                Location/Qualifiers
source                 1..62
                       mol_type = transcribed RNA
                       organism = Homo sapiens
SEQUENCE: 622
gtgggtctcg catcaggagg caaggccagg acccgctgac ccatgcctcc tgccgcggtc    60
ag                                                                   62

SEQ ID NO: 623         moltype = RNA   length = 72
FEATURE                Location/Qualifiers
source                 1..72
                       mol_type = transcribed RNA
                       organism = Homo sapiens
SEQUENCE: 623
gagtctgagg gacccaggac aggagaaggc ctatggtgat ttgcattctt cctgccctgg    60
ctccatcctc ag                                                        72

SEQ ID NO: 624         moltype = RNA   length = 64
FEATURE                Location/Qualifiers
source                 1..64
                       mol_type = transcribed RNA
                       organism = Homo sapiens
SEQUENCE: 624
agttcagggc cgaagggtgg aagctgctgg tgctcatctc agcctctgcc cttggcctcc    60
```

```
ccag                                                                              64

SEQ ID NO: 625          moltype = RNA   length = 66
FEATURE                 Location/Qualifiers
source                  1..66
                        mol_type = transcribed RNA
                        organism = Homo sapiens
SEQUENCE: 625
cagagcaggg cagggaaggt gggagagggg cccagctgac cctcctgtca cccgctcctt   60
gcccag                                                              66

SEQ ID NO: 626          moltype = RNA   length = 66
FEATURE                 Location/Qualifiers
source                  1..66
                        mol_type = transcribed RNA
                        organism = Homo sapiens
SEQUENCE: 626
cctggagggg ggcactgcgc aagcaaagcc agggaccctg agaggctttg cttcctgctc   60
ccctag                                                              66

SEQ ID NO: 627          moltype = RNA   length = 65
FEATURE                 Location/Qualifiers
source                  1..65
                        mol_type = transcribed RNA
                        organism = Homo sapiens
SEQUENCE: 627
gagaatgggg ggacagatgg agaggacaca ggctggcact gaggtcccct ccactttcct   60
cctag                                                               65

SEQ ID NO: 628          moltype = RNA   length = 76
FEATURE                 Location/Qualifiers
source                  1..76
                        mol_type = transcribed RNA
                        organism = Homo sapiens
SEQUENCE: 628
actgactttg agtctctcct cagggtgctg caggcaaagc tggggaccca gggagagacg   60
taagtgaggg gagatg                                                   76

SEQ ID NO: 629          moltype = RNA   length = 59
FEATURE                 Location/Qualifiers
source                  1..59
                        mol_type = transcribed RNA
                        organism = Homo sapiens
SEQUENCE: 629
ctccagggag acagtgtgtg aggcctcttg ccatggcctc cctgcccgcc tctctgcag    59

SEQ ID NO: 630          moltype = RNA   length = 98
FEATURE                 Location/Qualifiers
source                  1..98
                        mol_type = transcribed RNA
                        organism = Homo sapiens
SEQUENCE: 630
ttgggcaagg tgcggggcta gggctaacag cagtcttact gaaggtttcc tggaaaccac   60
gcacatgctg ttgccactaa cctcaacctt actcggtc                           98

SEQ ID NO: 631          moltype = RNA   length = 80
FEATURE                 Location/Qualifiers
source                  1..80
                        mol_type = transcribed RNA
                        organism = Homo sapiens
SEQUENCE: 631
ggcgcgtcgc cccctcagt ccaccagagc ccggatacct cagaaattcg gctctgggtc    60
tgtggggagc gaaatgcaac                                               80

SEQ ID NO: 632          moltype = RNA   length = 99
FEATURE                 Location/Qualifiers
source                  1..99
                        mol_type = transcribed RNA
                        organism = Homo sapiens
SEQUENCE: 632
gcaaggaca gggagggtcg tggcgacact cgcgccagct cccgggacgg ctgggctcgg    60
gctggtcgcc gacctccgac cctccactag atgcctggc                          99

SEQ ID NO: 633          moltype = RNA   length = 103
FEATURE                 Location/Qualifiers
source                  1..103
                        mol_type = transcribed RNA
                        organism = Homo sapiens
SEQUENCE: 633
```

```
gtgtcggctg tggcgtgact gtccctctgt gtcccccact aggcccactg ctcagtggag    60
cgtggaggac gaggaggagg ccgtccacga gcaatgccag cat                     103
```

| SEQ ID NO: 634 | moltype = RNA    length = 49 |
|---|---|
| FEATURE | Location/Qualifiers |
| source | 1..49 |
| | mol_type = transcribed RNA |
| | organism = Homo sapiens |

SEQUENCE: 634
```
ttcccagcca acgcaccaaa aatgatatgg gtctgttgtc tggagaaac              49
```

| SEQ ID NO: 635 | moltype = RNA    length = 81 |
|---|---|
| FEATURE | Location/Qualifiers |
| source | 1..81 |
| | mol_type = transcribed RNA |
| | organism = Homo sapiens |

SEQUENCE: 635
```
tacaggtgca ggggaactgt agatgaaaag gcttggcact tgagggaaag cctcagttca   60
ttctcatttt gctcacctgt t                                             81
```

| SEQ ID NO: 636 | moltype = RNA    length = 81 |
|---|---|
| FEATURE | Location/Qualifiers |
| source | 1..81 |
| | mol_type = transcribed RNA |
| | organism = Homo sapiens |

SEQUENCE: 636
```
tagaggcagt ttcaacagat gtgtagactt ttgatatgag aaattggttt caaaatcagg   60
agtcggggct ttactgcttt t                                             81
```

| SEQ ID NO: 637 | moltype = RNA    length = 80 |
|---|---|
| FEATURE | Location/Qualifiers |
| source | 1..80 |
| | mol_type = transcribed RNA |
| | organism = Homo sapiens |

SEQUENCE: 637
```
gcgtcaagat ggcggcgggg aggtaggcag agcaggacgc cgctgctgcc gccgccaccg   60
ccgcctccgc tccagtcgcc                                               80
```

| SEQ ID NO: 638 | moltype = RNA    length = 75 |
|---|---|
| FEATURE | Location/Qualifiers |
| source | 1..75 |
| | mol_type = transcribed RNA |
| | organism = Homo sapiens |

SEQUENCE: 638
```
tcatccctgg gtggggattt gttgcattac ttgtgttcta tataaagtat tgcacttgtc   60
ccggcctgtg gaaga                                                    75
```

| SEQ ID NO: 639 | moltype = RNA    length = 94 |
|---|---|
| FEATURE | Location/Qualifiers |
| source | 1..94 |
| | mol_type = transcribed RNA |
| | organism = Homo sapiens |

SEQUENCE: 639
```
gtgaggtgtg ggcccggccc caggagcggg gcctgggcag ccccgtgtgt tgaggaagga   60
aggcagggcc cccgctcccc gggcctgacc ccac                               94
```

| SEQ ID NO: 640 | moltype = RNA    length = 80 |
|---|---|
| FEATURE | Location/Qualifiers |
| source | 1..80 |
| | mol_type = transcribed RNA |
| | organism = Homo sapiens |

SEQUENCE: 640
```
cctctgtgag aaagggtgtg ggggagaggc tgtcttgtgt ctgtaagtat gccaaactta   60
ttttccccaa ggcagaggga                                               80
```

| SEQ ID NO: 641 | moltype = RNA    length = 149 |
|---|---|
| FEATURE | Location/Qualifiers |
| source | 1..149 |
| | mol_type = transcribed RNA |
| | organism = Homo sapiens |

SEQUENCE: 641
```
catcaagacc cagctgagtc actgtcactg cctaccaatc tcgaccggac ctcgaccggc   60
tcgtctgtgt tgccaatcga ctcggcgtgg cgtcggtcgt ggtagatagg cggtcatgca  120
tacgaatttt cagctcttgt tctggtgac                                    149
```

| SEQ ID NO: 642 | moltype = RNA    length = 73 |
|---|---|
| FEATURE | Location/Qualifiers |
| source | 1..73 |
| | mol_type = transcribed RNA |

```
                                    -continued
                      organism = Homo sapiens
SEQUENCE: 642
ggccggctgg ggttcctggg gatgggattt gcttcctgtc acaaatcaca ttgccaggga    60
tttccaaccg acc                                                       73

SEQ ID NO: 643         moltype = RNA   length = 81
FEATURE                Location/Qualifiers
source                 1..81
                       mol_type = transcribed RNA
                       organism = Homo sapiens
SEQUENCE: 643
cttcaggaag ctggtttcat atggtggttt agatttaaat agtgattgtc tagcaccatt    60
tgaaatcagt gttcttgggg g                                              81

SEQ ID NO: 644         moltype = RNA   length = 81
FEATURE                Location/Qualifiers
source                 1..81
                       mol_type = transcribed RNA
                       organism = Homo sapiens
SEQUENCE: 644
cttctggaag ctggtttcac atggtggctt agatttttcc atctttgtat ctagcaccat    60
ttgaaatcag tgtttttagga g                                             81

SEQ ID NO: 645         moltype = RNA   length = 68
FEATURE                Location/Qualifiers
source                 1..68
                       mol_type = transcribed RNA
                       organism = Homo sapiens
SEQUENCE: 645
tgcccaggct ggagcgagtg cagtggtgca gtcagtccta gctcactgca gcctcgaact    60
cctgggct                                                             68

SEQ ID NO: 646         moltype = RNA   length = 68
FEATURE                Location/Qualifiers
source                 1..68
                       mol_type = transcribed RNA
                       organism = Homo sapiens
SEQUENCE: 646
gaatggaaga agaaggcggt cggtctgcgg gagccaggcc gcagagccat ccgccttctg    60
tccatgtc                                                             68

SEQ ID NO: 647         moltype = RNA   length = 51
FEATURE                Location/Qualifiers
source                 1..51
                       mol_type = transcribed RNA
                       organism = Homo sapiens
SEQUENCE: 647
acagaccccg gggagcccgg cggtgaagct cctggtatcc tgggtgtctg a              51

SEQ ID NO: 648         moltype = RNA   length = 60
FEATURE                Location/Qualifiers
source                 1..60
                       mol_type = transcribed RNA
                       organism = Homo sapiens
SEQUENCE: 648
gagcaggcga ggctgggctg aacccgtggg tgaggagtgc agcccagctg aggcctctgc    60

SEQ ID NO: 649         moltype = RNA   length = 71
FEATURE                Location/Qualifiers
source                 1..71
                       mol_type = transcribed RNA
                       organism = Homo sapiens
SEQUENCE: 649
ggtgagtggg agccggtggg gctggagtaa gggcacgccc ggggctgccc cacctgctga    60
ccacccctccc c                                                        71

SEQ ID NO: 650         moltype = RNA   length = 82
FEATURE                Location/Qualifiers
source                 1..82
                       mol_type = transcribed RNA
                       organism = Homo sapiens
SEQUENCE: 650
gggaaagcgg agggcgcgcc cagctcccgg gctgattgcg ctaacagtgg ccccggtgtt    60
ggggcgcgtc tgccgctgcc cc                                             82

SEQ ID NO: 651         moltype = RNA   length = 109
FEATURE                Location/Qualifiers
source                 1..109
                       mol_type = transcribed RNA
```

```
                        organism = Homo sapiens
SEQUENCE: 651
tcccgcattc cctctgcttt ggtcaggtgg tgccctcctt ccatgggtag agccagagat    60
ggtgggttct ggctggtcag atgggagtgg acagagaccc ggggtcctc              109

SEQ ID NO: 652          moltype = RNA   length = 85
FEATURE                 Location/Qualifiers
source                  1..85
                        mol_type = transcribed RNA
                        organism = Homo sapiens
SEQUENCE: 652
agggtagagg gatgaggggg aaagttctat agtcctgtaa ttagatctca ggactataga    60
actttccccc tcatccctct gccct                                         85

SEQ ID NO: 653          moltype = RNA   length = 67
FEATURE                 Location/Qualifiers
source                  1..67
                        mol_type = transcribed RNA
                        organism = Homo sapiens
SEQUENCE: 653
cctgcaggca gaagtggggc tgacagggca gagggttgcg ccccctcacc atcccttctg    60
cctgcag                                                             67

SEQ ID NO: 654          moltype = RNA   length = 67
FEATURE                 Location/Qualifiers
source                  1..67
                        mol_type = transcribed RNA
                        organism = Homo sapiens
SEQUENCE: 654
cctgcaggca gaagtggggc tgacagggca gagggttgcg ccccctcacc atcccttctg    60
cctgcag                                                             67

SEQ ID NO: 655          moltype = RNA   length = 67
FEATURE                 Location/Qualifiers
source                  1..67
                        mol_type = transcribed RNA
                        organism = Homo sapiens
SEQUENCE: 655
cctgcaggca gaagtggggc tgacagggca gagggttgcg ccccctcacc atcccttctg    60
cctgcag                                                             67

SEQ ID NO: 656          moltype = RNA   length = 67
FEATURE                 Location/Qualifiers
source                  1..67
                        mol_type = transcribed RNA
                        organism = Homo sapiens
SEQUENCE: 656
cctgcaggca gaagtggggc tgacagggca gagggttgcg ccccctcacc atcccttctg    60
cctgcag                                                             67

SEQ ID NO: 657          moltype = RNA   length = 66
FEATURE                 Location/Qualifiers
source                  1..66
                        mol_type = transcribed RNA
                        organism = Homo sapiens
SEQUENCE: 657
ccgagtgggg cgggcaggt ccctgcaggg actgtgacac tgaaggacct gcaccttcgc    60
ccacag                                                              66

SEQ ID NO: 658          moltype = RNA   length = 66
FEATURE                 Location/Qualifiers
source                  1..66
                        mol_type = transcribed RNA
                        organism = Homo sapiens
SEQUENCE: 658
gggcatgggg aggtgtggag tcagcatggg gctaggaggc cccgcgctga cccgccttct    60
ccgcag                                                              66

SEQ ID NO: 659          moltype = RNA   length = 61
FEATURE                 Location/Qualifiers
source                  1..61
                        mol_type = transcribed RNA
                        organism = Homo sapiens
SEQUENCE: 659
aactgcgggg ccagagcaga gagcccttgc acaccaccag cctctcctcc ctgtgcccca    60
g                                                                   61

SEQ ID NO: 660          moltype = RNA   length = 94
FEATURE                 Location/Qualifiers
```

```
                              source          1..94
                                              mol_type = transcribed RNA
                                              organism = Homo sapiens
SEQUENCE: 660
cacggtgtcc cctggtggaa cctggcaggg ggagaggtaa ggtctttcag cctctccaaa    60
gcccatggtc aggtactcag gtgggggagc cctg                                94

SEQ ID NO: 661                moltype = RNA   length = 61
FEATURE                       Location/Qualifiers
source                        1..61
                              mol_type = transcribed RNA
                              organism = Homo sapiens
SEQUENCE: 661
tctcgtttga tctcggaagc taagcagggt tgggcctggt tagtacttgg atgggaaact    60
t                                                                    61

SEQ ID NO: 662                moltype = RNA   length = 53
FEATURE                       Location/Qualifiers
source                        1..53
                              mol_type = transcribed RNA
                              organism = Homo sapiens
SEQUENCE: 662
gtttgatctc ggaagctaag cagggtcggg cctggttagt acttggatgg gag            53

SEQ ID NO: 663                moltype = RNA   length = 68
FEATURE                       Location/Qualifiers
source                        1..68
                              mol_type = transcribed RNA
                              organism = Homo sapiens
SEQUENCE: 663
gtgcaaagag caggaggaca ggggatttat ctcccaaggg aggtcccctg atcctagtca    60
cggcacca                                                             68

SEQ ID NO: 664                moltype = RNA   length = 78
FEATURE                       Location/Qualifiers
source                        1..78
                              mol_type = transcribed RNA
                              organism = Homo sapiens
SEQUENCE: 664
ctttctacac aggttgggat cggttgcaat gctgtgtttc tgtatggtat tgcacttgtc    60
ccggcctgtt gagtttgg                                                  78

SEQ ID NO: 665                moltype = RNA   length = 17
FEATURE                       Location/Qualifiers
source                        1..17
                              mol_type = transcribed RNA
                              organism = Homo sapiens
SEQUENCE: 665
caggcacggg agctcag                                                   17

SEQ ID NO: 666                moltype = RNA   length = 23
FEATURE                       Location/Qualifiers
source                        1..23
                              mol_type = transcribed RNA
                              organism = Homo sapiens
SEQUENCE: 666
aatatacagg gggagactct tat                                            23

SEQ ID NO: 667                moltype = RNA   length = 15
FEATURE                       Location/Qualifiers
source                        1..15
                              mol_type = transcribed RNA
                              organism = Homo sapiens
SEQUENCE: 667
atatacaggg ggaga                                                     15

SEQ ID NO: 668                moltype = RNA   length = 21
FEATURE                       Location/Qualifiers
source                        1..21
                              mol_type = transcribed RNA
                              organism = Homo sapiens
SEQUENCE: 668
gtgagtcagg gtggggctgg c                                              21

SEQ ID NO: 669                moltype = RNA   length = 26
FEATURE                       Location/Qualifiers
source                        1..26
                              mol_type = transcribed RNA
                              organism = Homo sapiens
```

```
SEQUENCE: 669
caagatggtg gactacagcg tgtggg                                                26

SEQ ID NO: 670          moltype = RNA   length = 15
FEATURE                 Location/Qualifiers
source                  1..15
                        mol_type = transcribed RNA
                        organism = Homo sapiens
SEQUENCE: 670
aggcaagatg gtgga                                                            15

SEQ ID NO: 671          moltype = RNA   length = 24
FEATURE                 Location/Qualifiers
source                  1..24
                        mol_type = transcribed RNA
                        organism = Homo sapiens
SEQUENCE: 671
atatacaggg ggagactctc attt                                                  24

SEQ ID NO: 672          moltype = RNA   length = 15
FEATURE                 Location/Qualifiers
source                  1..15
                        mol_type = transcribed RNA
                        organism = Homo sapiens
SEQUENCE: 672
atatacaggg ggaga                                                            15

SEQ ID NO: 673          moltype = RNA   length = 21
FEATURE                 Location/Qualifiers
source                  1..21
                        mol_type = transcribed RNA
                        organism = Homo sapiens
SEQUENCE: 673
taggtcaccc gtttgactat c                                                     21

SEQ ID NO: 674          moltype = RNA   length = 21
FEATURE                 Location/Qualifiers
source                  1..21
                        mol_type = transcribed RNA
                        organism = Homo sapiens
SEQUENCE: 674
gaatggattt ttggagcagg a                                                     21

SEQ ID NO: 675          moltype = RNA   length = 15
FEATURE                 Location/Qualifiers
source                  1..15
                        mol_type = transcribed RNA
                        organism = Homo sapiens
SEQUENCE: 675
gaatggattt ttgga                                                            15

SEQ ID NO: 676          moltype = RNA   length = 26
FEATURE                 Location/Qualifiers
source                  1..26
                        mol_type = transcribed RNA
                        organism = Homo sapiens
SEQUENCE: 676
aggagggagg agatgggcca agttcc                                                26

SEQ ID NO: 677          moltype = RNA   length = 15
FEATURE                 Location/Qualifiers
source                  1..15
                        mol_type = transcribed RNA
                        organism = Homo sapiens
SEQUENCE: 677
gggaggaggg aggag                                                            15

SEQ ID NO: 678          moltype = RNA   length = 15
FEATURE                 Location/Qualifiers
source                  1..15
                        mol_type = transcribed RNA
                        organism = Homo sapiens
SEQUENCE: 678
cccgcgggac gcgcc                                                            15

SEQ ID NO: 679          moltype = RNA   length = 26
FEATURE                 Location/Qualifiers
source                  1..26
                        mol_type = transcribed RNA
```

```
                        organism = Homo sapiens
SEQUENCE: 679
cgggtagaga gggcagtggg aggtaa                                         26

SEQ ID NO: 680          moltype = RNA  length = 15
FEATURE                 Location/Qualifiers
source                  1..15
                        mol_type = transcribed RNA
                        organism = Homo sapiens
SEQUENCE: 680
cgggtagaga gggca                                                     15

SEQ ID NO: 681          moltype = RNA  length = 28
FEATURE                 Location/Qualifiers
source                  1..28
                        mol_type = transcribed RNA
                        organism = Homo sapiens
SEQUENCE: 681
ttggggaaac ggccgctgag tgaggcgt                                       28

SEQ ID NO: 682          moltype = RNA  length = 15
FEATURE                 Location/Qualifiers
source                  1..15
                        mol_type = transcribed RNA
                        organism = Homo sapiens
SEQUENCE: 682
ggggaaacgg ccgct                                                     15

SEQ ID NO: 683          moltype = RNA  length = 22
FEATURE                 Location/Qualifiers
source                  1..22
                        mol_type = transcribed RNA
                        organism = Homo sapiens
SEQUENCE: 683
ggcagggaca gcaaaggggt gc                                             22

SEQ ID NO: 684          moltype = RNA  length = 18
FEATURE                 Location/Qualifiers
source                  1..18
                        mol_type = transcribed RNA
                        organism = Homo sapiens
SEQUENCE: 684
gcagggacag caaaggg                                                   18

SEQ ID NO: 685          moltype = RNA  length = 23
FEATURE                 Location/Qualifiers
source                  1..23
                        mol_type = transcribed RNA
                        organism = Homo sapiens
SEQUENCE: 685
agcagaggca gagaggctca ggg                                            23

SEQ ID NO: 686          moltype = RNA  length = 15
FEATURE                 Location/Qualifiers
source                  1..15
                        mol_type = transcribed RNA
                        organism = Homo sapiens
SEQUENCE: 686
agcagaggca gagag                                                     15

SEQ ID NO: 687          moltype = RNA  length = 24
FEATURE                 Location/Qualifiers
source                  1..24
                        mol_type = transcribed RNA
                        organism = Homo sapiens
SEQUENCE: 687
gttgggacaa gaggacggtc ttct                                           24

SEQ ID NO: 688          moltype = RNA  length = 20
FEATURE                 Location/Qualifiers
source                  1..20
                        mol_type = transcribed RNA
                        organism = Homo sapiens
SEQUENCE: 688
gttgggacaa gaggacggtc                                                20

SEQ ID NO: 689          moltype = RNA  length = 15
FEATURE                 Location/Qualifiers
source                  1..15
```

```
                        mol_type = transcribed RNA
                        organism = Homo sapiens
SEQUENCE: 689
gcgggtggag gagga                                                    15

SEQ ID NO: 690          moltype = RNA  length = 21
FEATURE                 Location/Qualifiers
source                  1..21
                        mol_type = transcribed RNA
                        organism = Homo sapiens
SEQUENCE: 690
aaagatctgg aagtgggaga c                                             21

SEQ ID NO: 691          moltype = RNA  length = 22
FEATURE                 Location/Qualifiers
source                  1..22
                        mol_type = transcribed RNA
                        organism = Homo sapiens
SEQUENCE: 691
tcctgcagag aggaagccct tc                                            22

SEQ ID NO: 692          moltype = RNA  length = 18
FEATURE                 Location/Qualifiers
source                  1..18
                        mol_type = transcribed RNA
                        organism = Homo sapiens
SEQUENCE: 692
cctgcagaga ggaagccc                                                 18

SEQ ID NO: 693          moltype = RNA  length = 23
FEATURE                 Location/Qualifiers
source                  1..23
                        mol_type = transcribed RNA
                        organism = Homo sapiens
SEQUENCE: 693
tggggcggag cttccggagg ccc                                           23

SEQ ID NO: 694          moltype = RNA  length = 15
FEATURE                 Location/Qualifiers
source                  1..15
                        mol_type = transcribed RNA
                        organism = Homo sapiens
SEQUENCE: 694
gccccgggaa agcgt                                                    15

SEQ ID NO: 695          moltype = RNA  length = 20
FEATURE                 Location/Qualifiers
source                  1..20
                        mol_type = transcribed RNA
                        organism = Homo sapiens
SEQUENCE: 695
tggggacgta gctggccaga                                               20

SEQ ID NO: 696          moltype = RNA  length = 20
FEATURE                 Location/Qualifiers
source                  1..20
                        mol_type = transcribed RNA
                        organism = Homo sapiens
SEQUENCE: 696
agctctgctg ctcactggca                                               20

SEQ ID NO: 697          moltype = RNA  length = 24
FEATURE                 Location/Qualifiers
source                  1..24
                        mol_type = transcribed RNA
                        organism = Homo sapiens
SEQUENCE: 697
gaaaagctgg gttgagaggg caaa                                          24

SEQ ID NO: 698          moltype = RNA  length = 15
FEATURE                 Location/Qualifiers
source                  1..15
                        mol_type = transcribed RNA
                        organism = Homo sapiens
SEQUENCE: 698
gaaaagctgg gttga                                                    15

SEQ ID NO: 699          moltype = RNA  length = 22
FEATURE                 Location/Qualifiers
```

```
source                  1..22
                        mol_type = transcribed RNA
                        organism = Homo sapiens
SEQUENCE: 699
gggggggcagg aggggctcag gg                                              22

SEQ ID NO: 700          moltype = RNA  length = 16
FEATURE                 Location/Qualifiers
source                  1..16
                        mol_type = transcribed RNA
                        organism = Homo sapiens
SEQUENCE: 700
gtgggggggc aggagg                                                      16

SEQ ID NO: 701          moltype = RNA  length = 22
FEATURE                 Location/Qualifiers
source                  1..22
                        mol_type = transcribed RNA
                        organism = Homo sapiens
SEQUENCE: 701
tgagtgaatc ggaaaggagg cg                                               22

SEQ ID NO: 702          moltype = RNA  length = 15
FEATURE                 Location/Qualifiers
source                  1..15
                        mol_type = transcribed RNA
                        organism = Homo sapiens
SEQUENCE: 702
cggaaaggag gcgcc                                                       15

SEQ ID NO: 703          moltype = RNA  length = 23
FEATURE                 Location/Qualifiers
source                  1..23
                        mol_type = transcribed RNA
                        organism = Homo sapiens
SEQUENCE: 703
gtgggctggg ctgggctggg cca                                              23

SEQ ID NO: 704          moltype = RNA  length = 15
FEATURE                 Location/Qualifiers
source                  1..15
                        mol_type = transcribed RNA
                        organism = Homo sapiens
SEQUENCE: 704
gggctgggct gggct                                                       15

SEQ ID NO: 705          moltype = RNA  length = 23
FEATURE                 Location/Qualifiers
source                  1..23
                        mol_type = transcribed RNA
                        organism = Homo sapiens
SEQUENCE: 705
tgcctgctgg ggtggaacct ggt                                              23

SEQ ID NO: 706          moltype = RNA  length = 15
FEATURE                 Location/Qualifiers
source                  1..15
                        mol_type = transcribed RNA
                        organism = Homo sapiens
SEQUENCE: 706
gcctgctggg gtgga                                                       15

SEQ ID NO: 707          moltype = RNA  length = 29
FEATURE                 Location/Qualifiers
source                  1..29
                        mol_type = transcribed RNA
                        organism = Homo sapiens
SEQUENCE: 707
ggtcaggcgg ctcggactga gcaggtggg                                        29

SEQ ID NO: 708          moltype = RNA  length = 15
FEATURE                 Location/Qualifiers
source                  1..15
                        mol_type = transcribed RNA
                        organism = Homo sapiens
SEQUENCE: 708
agagtgtggt caggc                                                       15

SEQ ID NO: 709          moltype = RNA  length = 16
```

```
FEATURE                 Location/Qualifiers
source                  1..16
                        mol_type = transcribed RNA
                        organism = Homo sapiens
SEQUENCE: 709
ctgggggtcc cccgac                                                       16

SEQ ID NO: 710          moltype = RNA   length = 15
FEATURE                 Location/Qualifiers
source                  1..15
                        mol_type = transcribed RNA
                        organism = Homo sapiens
SEQUENCE: 710
gtgtggagct ggggc                                                        15

SEQ ID NO: 711          moltype = RNA   length = 15
FEATURE                 Location/Qualifiers
source                  1..15
                        mol_type = transcribed RNA
                        organism = Homo sapiens
SEQUENCE: 711
gaggctgaag gaaga                                                        15

SEQ ID NO: 712          moltype = RNA   length = 23
FEATURE                 Location/Qualifiers
source                  1..23
                        mol_type = transcribed RNA
                        organism = Homo sapiens
SEQUENCE: 712
caaggagacg ggaacatgga gcc                                               23

SEQ ID NO: 713          moltype = RNA   length = 22
FEATURE                 Location/Qualifiers
source                  1..22
                        mol_type = transcribed RNA
                        organism = Homo sapiens
SEQUENCE: 713
aaaagctggg ctgagaggcg ac                                                22

SEQ ID NO: 714          moltype = RNA   length = 15
FEATURE                 Location/Qualifiers
source                  1..15
                        mol_type = transcribed RNA
                        organism = Homo sapiens
SEQUENCE: 714
aaagctgggc tgaga                                                        15

SEQ ID NO: 715          moltype = RNA   length = 23
FEATURE                 Location/Qualifiers
source                  1..23
                        mol_type = transcribed RNA
                        organism = Homo sapiens
SEQUENCE: 715
acaggagtgg gggtgggaca taa                                               23

SEQ ID NO: 716          moltype = RNA   length = 20
FEATURE                 Location/Qualifiers
source                  1..20
                        mol_type = transcribed RNA
                        organism = Homo sapiens
SEQUENCE: 716
acaggagtgg gggtgggaca                                                   20

SEQ ID NO: 717          moltype = RNA   length = 26
FEATURE                 Location/Qualifiers
source                  1..26
                        mol_type = transcribed RNA
                        organism = Homo sapiens
SEQUENCE: 717
gtcccggggc tgcgcgaggc acaggc                                            26

SEQ ID NO: 718          moltype = RNA   length = 15
FEATURE                 Location/Qualifiers
source                  1..15
                        mol_type = transcribed RNA
                        organism = Homo sapiens
SEQUENCE: 718
ggcccggggg gcggg                                                        15
```

```
SEQ ID NO: 719           moltype = RNA  length = 23
FEATURE                  Location/Qualifiers
source                   1..23
                         mol_type = transcribed RNA
                         organism = Homo sapiens
SEQUENCE: 719
ccaggaggcg aggaggtgg agg                                                   23

SEQ ID NO: 720           moltype = RNA  length = 15
FEATURE                  Location/Qualifiers
source                   1..15
                         mol_type = transcribed RNA
                         organism = Homo sapiens
SEQUENCE: 720
acccaggagg cggag                                                           15

SEQ ID NO: 721           moltype = RNA  length = 24
FEATURE                  Location/Qualifiers
source                   1..24
                         mol_type = transcribed RNA
                         organism = Homo sapiens
SEQUENCE: 721
agaggcaccg cctgcccagt gaca                                                 24

SEQ ID NO: 722           moltype = RNA  length = 15
FEATURE                  Location/Qualifiers
source                   1..15
                         mol_type = transcribed RNA
                         organism = Homo sapiens
SEQUENCE: 722
gaggcaccgc ctgcc                                                           15

SEQ ID NO: 723           moltype = RNA  length = 19
FEATURE                  Location/Qualifiers
source                   1..19
                         mol_type = transcribed RNA
                         organism = Homo sapiens
SEQUENCE: 723
gctgggcgag gctggcatc                                                       19

SEQ ID NO: 724           moltype = RNA  length = 19
FEATURE                  Location/Qualifiers
source                   1..19
                         mol_type = transcribed RNA
                         organism = Homo sapiens
SEQUENCE: 724
aggggcggg ctccggcgc                                                        19

SEQ ID NO: 725           moltype = RNA  length = 15
FEATURE                  Location/Qualifiers
source                   1..15
                         mol_type = transcribed RNA
                         organism = Homo sapiens
SEQUENCE: 725
gtagggggcg ggctc                                                           15

SEQ ID NO: 726           moltype = RNA  length = 22
FEATURE                  Location/Qualifiers
source                   1..22
                         mol_type = transcribed RNA
                         organism = Homo sapiens
SEQUENCE: 726
ggtgggcta gtgatgcagg ac                                                    22

SEQ ID NO: 727           moltype = RNA  length = 19
FEATURE                  Location/Qualifiers
source                   1..19
                         mol_type = transcribed RNA
                         organism = Homo sapiens
SEQUENCE: 727
tggggctagt gatgcagga                                                       19

SEQ ID NO: 728           moltype = RNA  length = 30
FEATURE                  Location/Qualifiers
source                   1..30
                         mol_type = transcribed RNA
                         organism = Homo sapiens
SEQUENCE: 728
gctgggctgg gacggacacc cggcctccac                                           30
```

```
SEQ ID NO: 729          moltype = RNA  length = 19
FEATURE                 Location/Qualifiers
source                  1..19
                        mol_type = transcribed RNA
                        organism = Homo sapiens
SEQUENCE: 729
gaggctgggc tgggacgga                                                    19

SEQ ID NO: 730          moltype = RNA  length = 18
FEATURE                 Location/Qualifiers
source                  1..18
                        mol_type = transcribed RNA
                        organism = Homo sapiens
SEQUENCE: 730
tctaggtggg gagactga                                                     18

SEQ ID NO: 731          moltype = RNA  length = 16
FEATURE                 Location/Qualifiers
source                  1..16
                        mol_type = transcribed RNA
                        organism = Homo sapiens
SEQUENCE: 731
gtggggagac tgacgg                                                       16

SEQ ID NO: 732          moltype = RNA  length = 23
FEATURE                 Location/Qualifiers
source                  1..23
                        mol_type = transcribed RNA
                        organism = Homo sapiens
SEQUENCE: 732
aggactggac tcccggcagc ccc                                               23

SEQ ID NO: 733          moltype = RNA  length = 18
FEATURE                 Location/Qualifiers
source                  1..18
                        mol_type = transcribed RNA
                        organism = Homo sapiens
SEQUENCE: 733
gcgtggggag ctggtcct                                                     18

SEQ ID NO: 734          moltype = RNA  length = 21
FEATURE                 Location/Qualifiers
source                  1..21
                        mol_type = transcribed RNA
                        organism = Homo sapiens
SEQUENCE: 734
cccagcagga cgggagcgcg g                                                 21

SEQ ID NO: 735          moltype = RNA  length = 16
FEATURE                 Location/Qualifiers
source                  1..16
                        mol_type = transcribed RNA
                        organism = Homo sapiens
SEQUENCE: 735
aagctgggtc aaggag                                                       16

SEQ ID NO: 736          moltype = RNA  length = 25
FEATURE                 Location/Qualifiers
source                  1..25
                        mol_type = transcribed RNA
                        organism = Homo sapiens
SEQUENCE: 736
ctgggccagg gagcagctgg tgggt                                             25

SEQ ID NO: 737          moltype = RNA  length = 20
FEATURE                 Location/Qualifiers
source                  1..20
                        mol_type = transcribed RNA
                        organism = Homo sapiens
SEQUENCE: 737
tgggccaggg agcagctggt                                                   20

SEQ ID NO: 738          moltype = RNA  length = 26
FEATURE                 Location/Qualifiers
source                  1..26
                        mol_type = transcribed RNA
                        organism = Homo sapiens
SEQUENCE: 738
```

```
actgggaaga ggagctgagg gacatt                                         26

SEQ ID NO: 739         moltype = RNA   length = 19
FEATURE                Location/Qualifiers
source                 1..19
                       mol_type = transcribed RNA
                       organism = Homo sapiens
SEQUENCE: 739
actgggaaga ggagctgag                                                 19

SEQ ID NO: 740         moltype = RNA   length = 21
FEATURE                Location/Qualifiers
source                 1..21
                       mol_type = transcribed RNA
                       organism = Homo sapiens
SEQUENCE: 740
ctgggggacg cgtgagcgcg a                                              21

SEQ ID NO: 741         moltype = RNA   length = 21
FEATURE                Location/Qualifiers
source                 1..21
                       mol_type = transcribed RNA
                       organism = Homo sapiens
SEQUENCE: 741
agcggggagg aagtgggcgc t                                              21

SEQ ID NO: 742         moltype = RNA   length = 16
FEATURE                Location/Qualifiers
source                 1..16
                       mol_type = transcribed RNA
                       organism = Homo sapiens
SEQUENCE: 742
ggagccccgg cgcggg                                                    16

SEQ ID NO: 743         moltype = RNA   length = 22
FEATURE                Location/Qualifiers
source                 1..22
                       mol_type = transcribed RNA
                       organism = Homo sapiens
SEQUENCE: 743
aggagcaagg cggcatctct ct                                             22

SEQ ID NO: 744         moltype = RNA   length = 18
FEATURE                Location/Qualifiers
source                 1..18
                       mol_type = transcribed RNA
                       organism = Homo sapiens
SEQUENCE: 744
gagcaaggcg gcatctct                                                  18

SEQ ID NO: 745         moltype = RNA   length = 15
FEATURE                Location/Qualifiers
source                 1..15
                       mol_type = transcribed RNA
                       organism = Homo sapiens
SEQUENCE: 745
gggtgagggc aggtg                                                     15

SEQ ID NO: 746         moltype = RNA   length = 17
FEATURE                Location/Qualifiers
source                 1..17
                       mol_type = transcribed RNA
                       organism = Homo sapiens
SEQUENCE: 746
ggcaggaggg ctgtgcc                                                   17

SEQ ID NO: 747         moltype = RNA   length = 19
FEATURE                Location/Qualifiers
source                 1..19
                       mol_type = transcribed RNA
                       organism = Homo sapiens
SEQUENCE: 747
atagtgggaa gctggcaga                                                 19

SEQ ID NO: 748         moltype = RNA   length = 22
FEATURE                Location/Qualifiers
source                 1..22
                       mol_type = transcribed RNA
                       organism = Homo sapiens
```

```
SEQUENCE: 748
tggcggagcc cattccatgc ca                                              22

SEQ ID NO: 749          moltype = RNA   length = 21
FEATURE                 Location/Qualifiers
source                  1..21
                        mol_type = transcribed RNA
                        organism = Homo sapiens
SEQUENCE: 749
ctggcggagc ccattccatg c                                               21

SEQ ID NO: 750          moltype = RNA   length = 24
FEATURE                 Location/Qualifiers
source                  1..24
                        mol_type = transcribed RNA
                        organism = Homo sapiens
SEQUENCE: 750
gctgcgggct gcggtcaggg cgat                                            24

SEQ ID NO: 751          moltype = RNA   length = 20
FEATURE                 Location/Qualifiers
source                  1..20
                        mol_type = transcribed RNA
                        organism = Homo sapiens
SEQUENCE: 751
gctgcgggct gcggtcaggg                                                 20

SEQ ID NO: 752          moltype = RNA   length = 24
FEATURE                 Location/Qualifiers
source                  1..24
                        mol_type = transcribed RNA
                        organism = Homo sapiens
SEQUENCE: 752
ctgcggggac aggccagggc atct                                            24

SEQ ID NO: 753          moltype = RNA   length = 20
FEATURE                 Location/Qualifiers
source                  1..20
                        mol_type = transcribed RNA
                        organism = Homo sapiens
SEQUENCE: 753
ctgcggggac aggccagggc                                                 20

SEQ ID NO: 754          moltype = RNA   length = 22
FEATURE                 Location/Qualifiers
source                  1..22
                        mol_type = transcribed RNA
                        organism = Homo sapiens
SEQUENCE: 754
agccaggctc tgaagggaaa gt                                              22

SEQ ID NO: 755          moltype = RNA   length = 15
FEATURE                 Location/Qualifiers
source                  1..15
                        mol_type = transcribed RNA
                        organism = Homo sapiens
SEQUENCE: 755
gaagggaaag ttgaa                                                      15

SEQ ID NO: 756          moltype = RNA   length = 15
FEATURE                 Location/Qualifiers
source                  1..15
                        mol_type = transcribed RNA
                        organism = Homo sapiens
SEQUENCE: 756
gcccactgcc ccgcg                                                      15

SEQ ID NO: 757          moltype = RNA   length = 24
FEATURE                 Location/Qualifiers
source                  1..24
                        mol_type = transcribed RNA
                        organism = Homo sapiens
SEQUENCE: 757
caggggatg gcagagcaaa attc                                             24

SEQ ID NO: 758          moltype = RNA   length = 17
FEATURE                 Location/Qualifiers
source                  1..17
                        mol_type = transcribed RNA
```

```
                              organism = Homo sapiens
SEQUENCE: 758
aggggggatgg cagagca                                                  17

SEQ ID NO: 759         moltype = RNA   length = 22
FEATURE                Location/Qualifiers
source                 1..22
                       mol_type = transcribed RNA
                       organism = Homo sapiens
SEQUENCE: 759
gggagtgcag ggcagggttt cc                                             22

SEQ ID NO: 760         moltype = RNA   length = 18
FEATURE                Location/Qualifiers
source                 1..18
                       mol_type = transcribed RNA
                       organism = Homo sapiens
SEQUENCE: 760
agggagtgca gggcaggg                                                  18

SEQ ID NO: 761         moltype = RNA   length = 24
FEATURE                Location/Qualifiers
source                 1..24
                       mol_type = transcribed RNA
                       organism = Homo sapiens
SEQUENCE: 761
cccggggcag attggtgtag ggtg                                           24

SEQ ID NO: 762         moltype = RNA   length = 17
FEATURE                Location/Qualifiers
source                 1..17
                       mol_type = transcribed RNA
                       organism = Homo sapiens
SEQUENCE: 762
cggggcagat tggtgta                                                   17

SEQ ID NO: 763         moltype = RNA   length = 17
FEATURE                Location/Qualifiers
source                 1..17
                       mol_type = transcribed RNA
                       organism = Homo sapiens
SEQUENCE: 763
gatcccagcg gtgcctc                                                   17

SEQ ID NO: 764         moltype = RNA   length = 15
FEATURE                Location/Qualifiers
source                 1..15
                       mol_type = transcribed RNA
                       organism = Homo sapiens
SEQUENCE: 764
gatcccagcg gtgcc                                                     15

SEQ ID NO: 765         moltype = RNA   length = 25
FEATURE                Location/Qualifiers
source                 1..25
                       mol_type = transcribed RNA
                       organism = Homo sapiens
SEQUENCE: 765
gggacgaggg ttggggaaca ggtgg                                          25

SEQ ID NO: 766         moltype = RNA   length = 15
FEATURE                Location/Qualifiers
source                 1..15
                       mol_type = transcribed RNA
                       organism = Homo sapiens
SEQUENCE: 766
tggggaacag gtggt                                                     15

SEQ ID NO: 767         moltype = RNA   length = 23
FEATURE                Location/Qualifiers
source                 1..23
                       mol_type = transcribed RNA
                       organism = Homo sapiens
SEQUENCE: 767
gaaatcaagc gtgggtgaga cct                                            23

SEQ ID NO: 768         moltype = RNA   length = 20
FEATURE                Location/Qualifiers
source                 1..20
```

```
                                       mol_type = transcribed RNA
                                       organism = Homo sapiens
SEQUENCE: 768
gaaatcaagc gtgggtgaga                                                        20

SEQ ID NO: 769               moltype = RNA   length = 15
FEATURE                      Location/Qualifiers
source                       1..15
                             mol_type = transcribed RNA
                             organism = Homo sapiens
SEQUENCE: 769
ggcgcgggga ggtgc                                                             15

SEQ ID NO: 770               moltype = RNA   length = 18
FEATURE                      Location/Qualifiers
source                       1..18
                             mol_type = transcribed RNA
                             organism = Homo sapiens
SEQUENCE: 770
aaaaggaagg gggaggag                                                          18

SEQ ID NO: 771               moltype = RNA   length = 16
FEATURE                      Location/Qualifiers
source                       1..16
                             mol_type = transcribed RNA
                             organism = Homo sapiens
SEQUENCE: 771
aaggaagggg gaggag                                                            16

SEQ ID NO: 772               moltype = RNA   length = 23
FEATURE                      Location/Qualifiers
source                       1..23
                             mol_type = transcribed RNA
                             organism = Homo sapiens
SEQUENCE: 772
acagcagggc tggggattgc agt                                                    23

SEQ ID NO: 773               moltype = RNA   length = 19
FEATURE                      Location/Qualifiers
source                       1..19
                             mol_type = transcribed RNA
                             organism = Homo sapiens
SEQUENCE: 773
tgctgctccc agtcctgcc                                                         19

SEQ ID NO: 774               moltype = RNA   length = 21
FEATURE                      Location/Qualifiers
source                       1..21
                             mol_type = transcribed RNA
                             organism = Homo sapiens
SEQUENCE: 774
cagcagggga gagagaggag t                                                      21

SEQ ID NO: 775               moltype = RNA   length = 20
FEATURE                      Location/Qualifiers
source                       1..20
                             mol_type = transcribed RNA
                             organism = Homo sapiens
SEQUENCE: 775
cagcagggga gagagaggag                                                        20

SEQ ID NO: 776               moltype = RNA   length = 25
FEATURE                      Location/Qualifiers
source                       1..25
                             mol_type = transcribed RNA
                             organism = Homo sapiens
SEQUENCE: 776
ctgcaggcag aagtggggct gacag                                                  25

SEQ ID NO: 777               moltype = RNA   length = 19
FEATURE                      Location/Qualifiers
source                       1..19
                             mol_type = transcribed RNA
                             organism = Homo sapiens
SEQUENCE: 777
caggcagaag tggggctga                                                         19

SEQ ID NO: 778               moltype = RNA   length = 21
FEATURE                      Location/Qualifiers
```

```
source                  1..21
                        mol_type = transcribed RNA
                        organism = Homo sapiens
SEQUENCE: 778
caactctgat ctcttcatct a                                              21

SEQ ID NO: 779          moltype = RNA   length = 23
FEATURE                 Location/Qualifiers
source                  1..23
                        mol_type = transcribed RNA
                        organism = Homo sapiens
SEQUENCE: 779
tggtgggccg cagaacatgt gct                                            23

SEQ ID NO: 780          moltype = RNA   length = 21
FEATURE                 Location/Qualifiers
source                  1..21
                        mol_type = transcribed RNA
                        organism = Homo sapiens
SEQUENCE: 780
tggtgggccg cagaacatgt g                                              21

SEQ ID NO: 781          moltype = RNA   length = 22
FEATURE                 Location/Qualifiers
source                  1..22
                        mol_type = transcribed RNA
                        organism = Homo sapiens
SEQUENCE: 781
gcacgactca gggcggaggg aa                                             22

SEQ ID NO: 782          moltype = RNA   length = 15
FEATURE                 Location/Qualifiers
source                  1..15
                        mol_type = transcribed RNA
                        organism = Homo sapiens
SEQUENCE: 782
agggcggagg gaagt                                                     15

SEQ ID NO: 783          moltype = RNA   length = 25
FEATURE                 Location/Qualifiers
source                  1..25
                        mol_type = transcribed RNA
                        organism = Homo sapiens
SEQUENCE: 783
ttctgggccc gcggcgggcg tgggg                                          25

SEQ ID NO: 784          moltype = RNA   length = 15
FEATURE                 Location/Qualifiers
source                  1..15
                        mol_type = transcribed RNA
                        organism = Homo sapiens
SEQUENCE: 784
cgcggcgggc gtggg                                                     15

SEQ ID NO: 785          moltype = RNA   length = 22
FEATURE                 Location/Qualifiers
source                  1..22
                        mol_type = transcribed RNA
                        organism = Homo sapiens
SEQUENCE: 785
tcccccggcc tgctcatccc cc                                             22

SEQ ID NO: 786          moltype = RNA   length = 15
FEATURE                 Location/Qualifiers
source                  1..15
                        mol_type = transcribed RNA
                        organism = Homo sapiens
SEQUENCE: 786
acctctcctg gcatc                                                     15

SEQ ID NO: 787          moltype = RNA   length = 24
FEATURE                 Location/Qualifiers
source                  1..24
                        mol_type = transcribed RNA
                        organism = Homo sapiens
SEQUENCE: 787
gcggccccac gcaccagggt aaga                                           24

SEQ ID NO: 788          moltype = RNA   length = 19
```

```
FEATURE            Location/Qualifiers
source             1..19
                   mol_type = transcribed RNA
                   organism = Homo sapiens
SEQUENCE: 788
cggccccacg caccagggt                                                  19

SEQ ID NO: 789     moltype = RNA   length = 24
FEATURE            Location/Qualifiers
source             1..24
                   mol_type = transcribed RNA
                   organism = Homo sapiens
SEQUENCE: 789
gaggctggga aggcaaaggg acgt                                            24

SEQ ID NO: 790     moltype = RNA   length = 15
FEATURE            Location/Qualifiers
source             1..15
                   mol_type = transcribed RNA
                   organism = Homo sapiens
SEQUENCE: 790
gaaggaggct gggaa                                                      15

SEQ ID NO: 791     moltype = RNA   length = 16
FEATURE            Location/Qualifiers
source             1..16
                   mol_type = transcribed RNA
                   organism = Homo sapiens
SEQUENCE: 791
gaaggggagt tgggag                                                     16

SEQ ID NO: 792     moltype = RNA   length = 18
FEATURE            Location/Qualifiers
source             1..18
                   mol_type = transcribed RNA
                   organism = Homo sapiens
SEQUENCE: 792
ggcagcggcg gcggcggc                                                   18

SEQ ID NO: 793     moltype = RNA   length = 15
FEATURE            Location/Qualifiers
source             1..15
                   mol_type = transcribed RNA
                   organism = Homo sapiens
SEQUENCE: 793
gctccccgcg ccccc                                                      15

SEQ ID NO: 794     moltype = RNA   length = 19
FEATURE            Location/Qualifiers
source             1..19
                   mol_type = transcribed RNA
                   organism = Homo sapiens
SEQUENCE: 794
cgtcccaccc cccactcct                                                  19

SEQ ID NO: 795     moltype = RNA   length = 25
FEATURE            Location/Qualifiers
source             1..25
                   mol_type = transcribed RNA
                   organism = Homo sapiens
SEQUENCE: 795
caggaaggat ttagggacag gcttt                                           25

SEQ ID NO: 796     moltype = RNA   length = 19
FEATURE            Location/Qualifiers
source             1..19
                   mol_type = transcribed RNA
                   organism = Homo sapiens
SEQUENCE: 796
caggaaggat ttagggaca                                                  19

SEQ ID NO: 797     moltype = RNA   length = 18
FEATURE            Location/Qualifiers
source             1..18
                   mol_type = transcribed RNA
                   organism = Homo sapiens
SEQUENCE: 797
cagcggggct gggcgcgc                                                   18
```

```
SEQ ID NO: 798            moltype = RNA    length = 15
FEATURE                   Location/Qualifiers
source                    1..15
                          mol_type = transcribed RNA
                          organism = Homo sapiens
SEQUENCE: 798
cagcggggct gggcg                                                    15

SEQ ID NO: 799            moltype = RNA    length = 20
FEATURE                   Location/Qualifiers
source                    1..20
                          mol_type = transcribed RNA
                          organism = Homo sapiens
SEQUENCE: 799
tggctgttgg aggggcagg                                                20

SEQ ID NO: 800            moltype = RNA    length = 15
FEATURE                   Location/Qualifiers
source                    1..15
                          mol_type = transcribed RNA
                          organism = Homo sapiens
SEQUENCE: 800
ggaggggca ggctc                                                     15

SEQ ID NO: 801            moltype = RNA    length = 21
FEATURE                   Location/Qualifiers
source                    1..21
                          mol_type = transcribed RNA
                          organism = Homo sapiens
SEQUENCE: 801
cagccctcct cccgcaccca a                                             21

SEQ ID NO: 802            moltype = RNA    length = 15
FEATURE                   Location/Qualifiers
source                    1..15
                          mol_type = transcribed RNA
                          organism = Homo sapiens
SEQUENCE: 802
cagggagcag gaagc                                                    15

SEQ ID NO: 803            moltype = RNA    length = 22
FEATURE                   Location/Qualifiers
source                    1..22
                          mol_type = transcribed RNA
                          organism = Homo sapiens
SEQUENCE: 803
taattttaga tctggtctgc tt                                            22

SEQ ID NO: 804            moltype = RNA    length = 19
FEATURE                   Location/Qualifiers
source                    1..19
                          mol_type = transcribed RNA
                          organism = Homo sapiens
SEQUENCE: 804
aattttagat ctggtctgc                                                19

SEQ ID NO: 805            moltype = RNA    length = 24
FEATURE                   Location/Qualifiers
source                    1..24
                          mol_type = transcribed RNA
                          organism = Homo sapiens
SEQUENCE: 805
agacacattt ggagagggaa cctc                                          24

SEQ ID NO: 806            moltype = RNA    length = 16
FEATURE                   Location/Qualifiers
source                    1..16
                          mol_type = transcribed RNA
                          organism = Homo sapiens
SEQUENCE: 806
agacacattt ggagag                                                   16

SEQ ID NO: 807            moltype = RNA    length = 21
FEATURE                   Location/Qualifiers
source                    1..21
                          mol_type = transcribed RNA
                          organism = Homo sapiens
SEQUENCE: 807
aggcagcggg gtgtagtgga t                                             21
```

```
SEQ ID NO: 808          moltype = RNA   length = 24
FEATURE                 Location/Qualifiers
source                  1..24
                        mol_type = transcribed RNA
                        organism = Homo sapiens
SEQUENCE: 808
aatattgcac tcgtcccggc ctcc                                            24

SEQ ID NO: 809          moltype = RNA   length = 15
FEATURE                 Location/Qualifiers
source                  1..15
                        mol_type = transcribed RNA
                        organism = Homo sapiens
SEQUENCE: 809
tattgcactc gtccc                                                      15

SEQ ID NO: 810          moltype = RNA   length = 23
FEATURE                 Location/Qualifiers
source                  1..23
                        mol_type = transcribed RNA
                        organism = Homo sapiens
SEQUENCE: 810
ctcctggggc ccgcactctc gct                                             23

SEQ ID NO: 811          moltype = RNA   length = 18
FEATURE                 Location/Qualifiers
source                  1..18
                        mol_type = transcribed RNA
                        organism = Homo sapiens
SEQUENCE: 811
ctcctggggc ccgcactc                                                   18

SEQ ID NO: 812          moltype = RNA   length = 23
FEATURE                 Location/Qualifiers
source                  1..23
                        mol_type = transcribed RNA
                        organism = Homo sapiens
SEQUENCE: 812
ggctacaaca caggacccgg gcg                                             23

SEQ ID NO: 813          moltype = RNA   length = 21
FEATURE                 Location/Qualifiers
source                  1..21
                        mol_type = transcribed RNA
                        organism = Homo sapiens
SEQUENCE: 813
ggctacaaca caggacccgg g                                               21

SEQ ID NO: 814          moltype = RNA   length = 21
FEATURE                 Location/Qualifiers
source                  1..21
                        mol_type = transcribed RNA
                        organism = Homo sapiens
SEQUENCE: 814
gagggcagcg tgggtgtggc g                                               21

SEQ ID NO: 815          moltype = RNA   length = 29
FEATURE                 Location/Qualifiers
source                  1..29
                        mol_type = transcribed RNA
                        organism = Homo sapiens
SEQUENCE: 815
agcagcattg tacagggcta tgaaggcat                                       29

SEQ ID NO: 816          moltype = RNA   length = 15
FEATURE                 Location/Qualifiers
source                  1..15
                        mol_type = transcribed RNA
                        organism = Homo sapiens
SEQUENCE: 816
agcagcattg tacag                                                      15

SEQ ID NO: 817          moltype = RNA   length = 28
FEATURE                 Location/Qualifiers
source                  1..28
                        mol_type = transcribed RNA
                        organism = Homo sapiens
SEQUENCE: 817
```

```
agcagcattg tacagggcta tcaaagca                                          28

SEQ ID NO: 818           moltype = RNA   length = 15
FEATURE                  Location/Qualifiers
source                   1..15
                         mol_type = transcribed RNA
                         organism = Homo sapiens
SEQUENCE: 818
agcagcattg tacag                                                        15

SEQ ID NO: 819           moltype = RNA   length = 22
FEATURE                  Location/Qualifiers
source                   1..22
                         mol_type = transcribed RNA
                         organism = Homo sapiens
SEQUENCE: 819
gtgggcgggg gcaggtgtgt gg                                                22

SEQ ID NO: 820           moltype = RNA   length = 15
FEATURE                  Location/Qualifiers
source                   1..15
                         mol_type = transcribed RNA
                         organism = Homo sapiens
SEQUENCE: 820
cgggggcagg tgtgt                                                        15

SEQ ID NO: 821           moltype = RNA   length = 19
FEATURE                  Location/Qualifiers
source                   1..19
                         mol_type = transcribed RNA
                         organism = Homo sapiens
SEQUENCE: 821
agtgggaggc cagggcacg                                                    19

SEQ ID NO: 822           moltype = RNA   length = 15
FEATURE                  Location/Qualifiers
source                   1..15
                         mol_type = transcribed RNA
                         organism = Homo sapiens
SEQUENCE: 822
aggggggagct gcagg                                                       15

SEQ ID NO: 823           moltype = RNA   length = 15
FEATURE                  Location/Qualifiers
source                   1..15
                         mol_type = transcribed RNA
                         organism = Homo sapiens
SEQUENCE: 823
tggcagagcg ctgtc                                                        15

SEQ ID NO: 824           moltype = RNA   length = 22
FEATURE                  Location/Qualifiers
source                   1..22
                         mol_type = transcribed RNA
                         organism = Homo sapiens
SEQUENCE: 824
ccgggaacgt cgagactgga gc                                                22

SEQ ID NO: 825           moltype = RNA   length = 15
FEATURE                  Location/Qualifiers
source                   1..15
                         mol_type = transcribed RNA
                         organism = Homo sapiens
SEQUENCE: 825
cgggaacgtc gagac                                                        15

SEQ ID NO: 826           moltype = RNA   length = 24
FEATURE                  Location/Qualifiers
source                   1..24
                         mol_type = transcribed RNA
                         organism = Homo sapiens
SEQUENCE: 826
acgcccttcc cccccttctt cacc                                              24

SEQ ID NO: 827           moltype = RNA   length = 17
FEATURE                  Location/Qualifiers
source                   1..17
                         mol_type = transcribed RNA
                         organism = Homo sapiens
```

|  |  |  |
|---|---|---|
| SEQUENCE: 827 |  |  |
| acgcccttcc cccctt |  | 17 |
| SEQ ID NO: 828<br>FEATURE<br>source | moltype = RNA length = 27<br>Location/Qualifiers<br>1..27<br>mol_type = transcribed RNA<br>organism = Homo sapiens |  |
| SEQUENCE: 828 |  |  |
| agcctggaag ctggagcctg cagtgaa |  | 27 |
| SEQ ID NO: 829<br>FEATURE<br>source | moltype = RNA length = 15<br>Location/Qualifiers<br>1..15<br>mol_type = transcribed RNA<br>organism = Homo sapiens |  |
| SEQUENCE: 829 |  |  |
| ggtgggagga ttgct |  | 15 |
| SEQ ID NO: 830<br>FEATURE<br>source | moltype = RNA length = 20<br>Location/Qualifiers<br>1..20<br>mol_type = transcribed RNA<br>organism = Homo sapiens |  |
| SEQUENCE: 830 |  |  |
| atcccaccac tgccaccatt |  | 20 |
| SEQ ID NO: 831<br>FEATURE<br>source | moltype = RNA length = 15<br>Location/Qualifiers<br>1..15<br>mol_type = transcribed RNA<br>organism = Homo sapiens |  |
| SEQUENCE: 831 |  |  |
| atcccaccac tgcca |  | 15 |
| SEQ ID NO: 832<br>FEATURE<br>source | moltype = RNA length = 21<br>Location/Qualifiers<br>1..21<br>mol_type = transcribed RNA<br>organism = Homo sapiens |  |
| SEQUENCE: 832 |  |  |
| gccgggcgtg gtggtggggg c |  | 21 |
| SEQ ID NO: 833<br>FEATURE<br>source | moltype = RNA length = 15<br>Location/Qualifiers<br>1..15<br>mol_type = transcribed RNA<br>organism = Homo sapiens |  |
| SEQUENCE: 833 |  |  |
| tagccgggcg tggtg |  | 15 |
| SEQ ID NO: 834<br>FEATURE<br>source | moltype = RNA length = 24<br>Location/Qualifiers<br>1..24<br>mol_type = transcribed RNA<br>organism = Homo sapiens |  |
| SEQUENCE: 834 |  |  |
| cgggcgtggt ggtggggtg ggtg |  | 24 |
| SEQ ID NO: 835<br>FEATURE<br>source | moltype = RNA length = 15<br>Location/Qualifiers<br>1..15<br>mol_type = transcribed RNA<br>organism = Homo sapiens |  |
| SEQUENCE: 835 |  |  |
| cgggcgtggt ggtgg |  | 15 |
| SEQ ID NO: 836<br>FEATURE<br>source | moltype = RNA length = 21<br>Location/Qualifiers<br>1..21<br>mol_type = transcribed RNA<br>organism = Homo sapiens |  |
| SEQUENCE: 836 |  |  |
| cagcctgagt gacagagcaa g |  | 21 |
| SEQ ID NO: 837<br>FEATURE<br>source | moltype = RNA length = 15<br>Location/Qualifiers<br>1..15<br>mol_type = transcribed RNA |  |

```
                               organism = Homo sapiens
SEQUENCE: 837
actgcactcc agcct                                                       15

SEQ ID NO: 838            moltype = RNA   length = 20
FEATURE                   Location/Qualifiers
source                    1..20
                          mol_type = transcribed RNA
                          organism = Homo sapiens
SEQUENCE: 838
cggggccgta gcactgtctg                                                  20

SEQ ID NO: 839            moltype = RNA   length = 20
FEATURE                   Location/Qualifiers
source                    1..20
                          mol_type = transcribed RNA
                          organism = Homo sapiens
SEQUENCE: 839
ggggccgat acactgtacg                                                   20

SEQ ID NO: 840            moltype = RNA   length = 20
FEATURE                   Location/Qualifiers
source                    1..20
                          mol_type = transcribed RNA
                          organism = Homo sapiens
SEQUENCE: 840
ggatttttgg atcagggatg                                                  20

SEQ ID NO: 841            moltype = RNA   length = 15
FEATURE                   Location/Qualifiers
source                    1..15
                          mol_type = transcribed RNA
                          organism = Homo sapiens
SEQUENCE: 841
atttttggat caggg                                                       15

SEQ ID NO: 842            moltype = RNA   length = 24
FEATURE                   Location/Qualifiers
source                    1..24
                          mol_type = transcribed RNA
                          organism = Homo sapiens
SEQUENCE: 842
ctggtacagg cctgggggac aggg                                             24

SEQ ID NO: 843            moltype = RNA   length = 18
FEATURE                   Location/Qualifiers
source                    1..18
                          mol_type = transcribed RNA
                          organism = Homo sapiens
SEQUENCE: 843
ctggtacagg cctggggg                                                    18

SEQ ID NO: 844            moltype = RNA   length = 25
FEATURE                   Location/Qualifiers
source                    1..25
                          mol_type = transcribed RNA
                          organism = Homo sapiens
SEQUENCE: 844
actgcagtga aggcacttgt agcat                                            25

SEQ ID NO: 845            moltype = RNA   length = 15
FEATURE                   Location/Qualifiers
source                    1..15
                          mol_type = transcribed RNA
                          organism = Homo sapiens
SEQUENCE: 845
actgcagtga aggca                                                       15

SEQ ID NO: 846            moltype = RNA   length = 22
FEATURE                   Location/Qualifiers
source                    1..22
                          mol_type = transcribed RNA
                          organism = Homo sapiens
SEQUENCE: 846
cgcggcgggg acggcgattg gt                                               22

SEQ ID NO: 847            moltype = RNA   length = 17
FEATURE                   Location/Qualifiers
source                    1..17
```

```
                              mol_type = transcribed RNA
                              organism = Homo sapiens
SEQUENCE: 847
cggcggggac ggcgatt                                                        17

SEQ ID NO: 848               moltype = RNA   length = 23
FEATURE                      Location/Qualifiers
source                       1..23
                             mol_type = transcribed RNA
                             organism = Homo sapiens
SEQUENCE: 848
tgcgcagggg ccgggtgctc acc                                                 23

SEQ ID NO: 849               moltype = RNA   length = 19
FEATURE                      Location/Qualifiers
source                       1..19
                             mol_type = transcribed RNA
                             organism = Homo sapiens
SEQUENCE: 849
cgcaggggcc gggtgctca                                                      19

SEQ ID NO: 850               moltype = RNA   length = 23
FEATURE                      Location/Qualifiers
source                       1..23
                             mol_type = transcribed RNA
                             organism = Homo sapiens
SEQUENCE: 850
aggagggtc ccgcactggg agg                                                  23

SEQ ID NO: 851               moltype = RNA   length = 15
FEATURE                      Location/Qualifiers
source                       1..15
                             mol_type = transcribed RNA
                             organism = Homo sapiens
SEQUENCE: 851
tgggaggggc cctca                                                          15

SEQ ID NO: 852               moltype = RNA   length = 15
FEATURE                      Location/Qualifiers
source                       1..15
                             mol_type = transcribed RNA
                             organism = Homo sapiens
SEQUENCE: 852
cgcggcgggg gcggc                                                          15

SEQ ID NO: 853               moltype = RNA   length = 29
FEATURE                      Location/Qualifiers
source                       1..29
                             mol_type = transcribed RNA
                             organism = Homo sapiens
SEQUENCE: 853
caacggaatc ccaaaagcag ctgttgtct                                           29

SEQ ID NO: 854               moltype = RNA   length = 15
FEATURE                      Location/Qualifiers
source                       1..15
                             mol_type = transcribed RNA
                             organism = Homo sapiens
SEQUENCE: 854
caacggaatc ccaaa                                                          15

SEQ ID NO: 855               moltype = RNA   length = 25
FEATURE                      Location/Qualifiers
source                       1..25
                             mol_type = transcribed RNA
                             organism = Homo sapiens
SEQUENCE: 855
aagctgccag ttgaagaact gttgc                                               25

SEQ ID NO: 856               moltype = RNA   length = 15
FEATURE                      Location/Qualifiers
source                       1..15
                             mol_type = transcribed RNA
                             organism = Homo sapiens
SEQUENCE: 856
aagctgccag ttgaa                                                          15

SEQ ID NO: 857               moltype = RNA   length = 26
FEATURE                      Location/Qualifiers
```

-continued

```
source                  1..26
                        mol_type = transcribed RNA
                        organism = Homo sapiens
SEQUENCE: 857
aaaatcacat tgccagggat taccac                                              26

SEQ ID NO: 858          moltype = RNA   length = 15
FEATURE                 Location/Qualifiers
source                  1..15
                        mol_type = transcribed RNA
                        organism = Homo sapiens
SEQUENCE: 858
aatcacattg ccagg                                                          15

SEQ ID NO: 859          moltype = RNA   length = 24
FEATURE                 Location/Qualifiers
source                  1..24
                        mol_type = transcribed RNA
                        organism = Homo sapiens
SEQUENCE: 859
actggctcag ttcagcagga acag                                                24

SEQ ID NO: 860          moltype = RNA   length = 15
FEATURE                 Location/Qualifiers
source                  1..15
                        mol_type = transcribed RNA
                        organism = Homo sapiens
SEQUENCE: 860
tggctcagtt cagca                                                          15

SEQ ID NO: 861          moltype = RNA   length = 15
FEATURE                 Location/Qualifiers
source                  1..15
                        mol_type = transcribed RNA
                        organism = Homo sapiens
SEQUENCE: 861
gagggttggg tggag                                                          15

SEQ ID NO: 862          moltype = RNA   length = 23
FEATURE                 Location/Qualifiers
source                  1..23
                        mol_type = transcribed RNA
                        organism = Homo sapiens
SEQUENCE: 862
gagggccccc cctcaatcct gtt                                                 23

SEQ ID NO: 863          moltype = RNA   length = 16
FEATURE                 Location/Qualifiers
source                  1..16
                        mol_type = transcribed RNA
                        organism = Homo sapiens
SEQUENCE: 863
agggcccccc ctcaat                                                         16

SEQ ID NO: 864          moltype = RNA   length = 24
FEATURE                 Location/Qualifiers
source                  1..24
                        mol_type = transcribed RNA
                        organism = Homo sapiens
SEQUENCE: 864
tcgaggactg gtggaagggc cttt                                                24

SEQ ID NO: 865          moltype = RNA   length = 16
FEATURE                 Location/Qualifiers
source                  1..16
                        mol_type = transcribed RNA
                        organism = Homo sapiens
SEQUENCE: 865
tcgaggactg gtggaa                                                         16

SEQ ID NO: 866          moltype = RNA   length = 23
FEATURE                 Location/Qualifiers
source                  1..23
                        mol_type = transcribed RNA
                        organism = Homo sapiens
SEQUENCE: 866
agggagtaga agggtgggga gca                                                 23

SEQ ID NO: 867          moltype = RNA   length = 16
```

```
                           -continued
FEATURE                 Location/Qualifiers
source                  1..16
                        mol_type = transcribed RNA
                        organism = Homo sapiens
SEQUENCE: 867
tagggagtag aagggt                                                    16

SEQ ID NO: 868          moltype = RNA   length = 26
FEATURE                 Location/Qualifiers
source                  1..26
                        mol_type = transcribed RNA
                        organism = Homo sapiens
SEQUENCE: 868
ccttctggag aggctttgtg cggata                                         26

SEQ ID NO: 869          moltype = RNA   length = 15
FEATURE                 Location/Qualifiers
source                  1..15
                        mol_type = transcribed RNA
                        organism = Homo sapiens
SEQUENCE: 869
ccttctggag aggct                                                     15

SEQ ID NO: 870          moltype = RNA   length = 17
FEATURE                 Location/Qualifiers
source                  1..17
                        mol_type = transcribed RNA
                        organism = Homo sapiens
SEQUENCE: 870
gcggggcggc aggggcc                                                   17

SEQ ID NO: 871          moltype = RNA   length = 15
FEATURE                 Location/Qualifiers
source                  1..15
                        mol_type = transcribed RNA
                        organism = Homo sapiens
SEQUENCE: 871
gggggcgggg cggca                                                     15

SEQ ID NO: 872          moltype = RNA   length = 15
FEATURE                 Location/Qualifiers
source                  1..15
                        mol_type = transcribed RNA
                        organism = Homo sapiens
SEQUENCE: 872
gcaggctcgg aaagg                                                     15

SEQ ID NO: 873          moltype = RNA   length = 27
FEATURE                 Location/Qualifiers
source                  1..27
                        mol_type = transcribed RNA
                        organism = Homo sapiens
SEQUENCE: 873
gaaaagctgg gttgagaggg cgaaaaa                                        27

SEQ ID NO: 874          moltype = RNA   length = 15
FEATURE                 Location/Qualifiers
source                  1..15
                        mol_type = transcribed RNA
                        organism = Homo sapiens
SEQUENCE: 874
cttctcttcc cggtt                                                     15

SEQ ID NO: 875          moltype = RNA   length = 28
FEATURE                 Location/Qualifiers
source                  1..28
                        mol_type = transcribed RNA
                        organism = Homo sapiens
SEQUENCE: 875
aggggtgcta tctgtgattg agggacat                                       28

SEQ ID NO: 876          moltype = RNA   length = 15
FEATURE                 Location/Qualifiers
source                  1..15
                        mol_type = transcribed RNA
                        organism = Homo sapiens
SEQUENCE: 876
gctatctgtg attga                                                     15
```

```
SEQ ID NO: 877          moltype = RNA  length = 29
FEATURE                 Location/Qualifiers
source                  1..29
                        mol_type = transcribed RNA
                        organism = Homo sapiens
SEQUENCE: 877
gggagccgcg gggatcgccg agggccggt                                           29

SEQ ID NO: 878          moltype = RNA  length = 15
FEATURE                 Location/Qualifiers
source                  1..15
                        mol_type = transcribed RNA
                        organism = Homo sapiens
SEQUENCE: 878
ggcggcggtg gtggg                                                          15

SEQ ID NO: 879          moltype = RNA  length = 19
FEATURE                 Location/Qualifiers
source                  1..19
                        mol_type = transcribed RNA
                        organism = Homo sapiens
SEQUENCE: 879
tggcgggtgc gggggtggg                                                      19

SEQ ID NO: 880          moltype = RNA  length = 15
FEATURE                 Location/Qualifiers
source                  1..15
                        mol_type = transcribed RNA
                        organism = Homo sapiens
SEQUENCE: 880
tggcgggtgc ggggg                                                          15

SEQ ID NO: 881          moltype = RNA  length = 27
FEATURE                 Location/Qualifiers
source                  1..27
                        mol_type = transcribed RNA
                        organism = Homo sapiens
SEQUENCE: 881
tgagggactt ttgggggcag atgtgtt                                             27

SEQ ID NO: 882          moltype = RNA  length = 17
FEATURE                 Location/Qualifiers
source                  1..17
                        mol_type = transcribed RNA
                        organism = Homo sapiens
SEQUENCE: 882
ggactttttgg gggcaga                                                       17

SEQ ID NO: 883          moltype = RNA  length = 18
FEATURE                 Location/Qualifiers
source                  1..18
                        mol_type = transcribed RNA
                        organism = Homo sapiens
SEQUENCE: 883
gcggcggcgg cggcagca                                                       18

SEQ ID NO: 884          moltype = RNA  length = 15
FEATURE                 Location/Qualifiers
source                  1..15
                        mol_type = transcribed RNA
                        organism = Homo sapiens
SEQUENCE: 884
gcgggcggcg gcggc                                                          15

SEQ ID NO: 885          moltype = RNA  length = 19
FEATURE                 Location/Qualifiers
source                  1..19
                        mol_type = transcribed RNA
                        organism = Homo sapiens
SEQUENCE: 885
tgaggatatg gcagggaag                                                      19

SEQ ID NO: 886          moltype = RNA  length = 22
FEATURE                 Location/Qualifiers
source                  1..22
                        mol_type = transcribed RNA
                        organism = Homo sapiens
SEQUENCE: 886
actcaaactg tggggcact tt                                                   22
```

| | | |
|---|---|---|
| SEQ ID NO: 887<br>FEATURE<br>source | moltype = RNA   length = 19<br>Location/Qualifiers<br>1..19<br>mol_type = transcribed RNA<br>organism = Homo sapiens | |
| SEQUENCE: 887<br>actcaaactg tggggcac | | 19 |
| SEQ ID NO: 888<br>FEATURE<br>source | moltype = RNA   length = 19<br>Location/Qualifiers<br>1..19<br>mol_type = transcribed RNA<br>organism = Homo sapiens | |
| SEQUENCE: 888<br>gtgggttggg gcgggctct | | 19 |
| SEQ ID NO: 889<br>FEATURE<br>source | moltype = RNA   length = 30<br>Location/Qualifiers<br>1..30<br>mol_type = transcribed RNA<br>organism = Homo sapiens | |
| SEQUENCE: 889<br>tgagggcag agagcgagac ttttctattt | | 30 |
| SEQ ID NO: 890<br>FEATURE<br>source | moltype = RNA   length = 15<br>Location/Qualifiers<br>1..15<br>mol_type = transcribed RNA<br>organism = Homo sapiens | |
| SEQUENCE: 890<br>tgagggcag agagc | | 15 |
| SEQ ID NO: 891<br>FEATURE<br>source | moltype = RNA   length = 16<br>Location/Qualifiers<br>1..16<br>mol_type = transcribed RNA<br>organism = Homo sapiens | |
| SEQUENCE: 891<br>tggggggaa gaaaag | | 16 |
| SEQ ID NO: 892<br>FEATURE<br>source | moltype = RNA   length = 22<br>Location/Qualifiers<br>1..22<br>mol_type = transcribed RNA<br>organism = Homo sapiens | |
| SEQUENCE: 892<br>accccactcc tggtaccata gt | | 22 |
| SEQ ID NO: 893<br>FEATURE<br>source | moltype = RNA   length = 15<br>Location/Qualifiers<br>1..15<br>mol_type = transcribed RNA<br>organism = Homo sapiens | |
| SEQUENCE: 893<br>accccactcc tggta | | 15 |
| SEQ ID NO: 894<br>FEATURE<br>source | moltype = RNA   length = 15<br>Location/Qualifiers<br>1..15<br>mol_type = transcribed RNA<br>organism = Homo sapiens | |
| SEQUENCE: 894<br>aggaggagga ggcag | | 15 |
| SEQ ID NO: 895<br>FEATURE<br>source | moltype = RNA   length = 15<br>Location/Qualifiers<br>1..15<br>mol_type = transcribed RNA<br>organism = Homo sapiens | |
| SEQUENCE: 895<br>ggtgggcttc ccgga | | 15 |
| SEQ ID NO: 896<br>FEATURE<br>source | moltype = RNA   length = 20<br>Location/Qualifiers<br>1..20<br>mol_type = transcribed RNA<br>organism = Homo sapiens | |
| SEQUENCE: 896 | | |

```
ctccccggtg tgcaaatgtg                                                     20

SEQ ID NO: 897          moltype = RNA   length = 15
FEATURE                 Location/Qualifiers
source                  1..15
                        mol_type = transcribed RNA
                        organism = Homo sapiens
SEQUENCE: 897
gtgtgcggtg ttatg                                                          15

SEQ ID NO: 898          moltype = RNA   length = 23
FEATURE                 Location/Qualifiers
source                  1..23
                        mol_type = transcribed RNA
                        organism = Homo sapiens
SEQUENCE: 898
ccagggctgg cagtgacatg ggt                                                 23

SEQ ID NO: 899          moltype = RNA   length = 19
FEATURE                 Location/Qualifiers
source                  1..19
                        mol_type = transcribed RNA
                        organism = Homo sapiens
SEQUENCE: 899
cagggctggc agtgacatg                                                      19

SEQ ID NO: 900          moltype = RNA   length = 15
FEATURE                 Location/Qualifiers
source                  1..15
                        mol_type = transcribed RNA
                        organism = Homo sapiens
SEQUENCE: 900
cttggtctag gggta                                                          15

SEQ ID NO: 901          moltype = RNA   length = 21
FEATURE                 Location/Qualifiers
source                  1..21
                        mol_type = transcribed RNA
                        organism = Homo sapiens
SEQUENCE: 901
cggatccgag tcacggcacc a                                                   21

SEQ ID NO: 902          moltype = RNA   length = 15
FEATURE                 Location/Qualifiers
source                  1..15
                        mol_type = transcribed RNA
                        organism = Homo sapiens
SEQUENCE: 902
ggatccgagt cacgg                                                          15

SEQ ID NO: 903          moltype = RNA   length = 25
FEATURE                 Location/Qualifiers
source                  1..25
                        mol_type = transcribed RNA
                        organism = Homo sapiens
SEQUENCE: 903
tggcggcggt agttatgggc ttctc                                               25

SEQ ID NO: 904          moltype = RNA   length = 29
FEATURE                 Location/Qualifiers
source                  1..29
                        mol_type = transcribed RNA
                        organism = Homo sapiens
SEQUENCE: 904
gctgggttaa gccgagctgg gttgggctg                                           29

SEQ ID NO: 905          moltype = RNA   length = 19
FEATURE                 Location/Qualifiers
source                  1..19
                        mol_type = transcribed RNA
                        organism = Homo sapiens
SEQUENCE: 905
ctgggttggg ctgggctgg                                                      19

SEQ ID NO: 906          moltype = RNA   length = 23
FEATURE                 Location/Qualifiers
source                  1..23
                        mol_type = transcribed RNA
                        organism = Homo sapiens
```

| | | |
|---|---|---|
| SEQUENCE: 906 | | |
| agggtcgggg cagggagggc agg | | 23 |
| SEQ ID NO: 907<br>FEATURE<br>source | moltype = RNA   length = 15<br>Location/Qualifiers<br>1..15<br>mol_type = transcribed RNA<br>organism = Homo sapiens | |
| SEQUENCE: 907 | | |
| gggagaaggg tcggg | | 15 |
| SEQ ID NO: 908<br>FEATURE<br>source | moltype = RNA   length = 27<br>Location/Qualifiers<br>1..27<br>mol_type = transcribed RNA<br>organism = Homo sapiens | |
| SEQUENCE: 908 | | |
| aaaccgttac cattactgag tttagta | | 27 |
| SEQ ID NO: 909<br>FEATURE<br>source | moltype = RNA   length = 15<br>Location/Qualifiers<br>1..15<br>mol_type = transcribed RNA<br>organism = Homo sapiens | |
| SEQUENCE: 909 | | |
| gaaaccgtta ccatt | | 15 |
| SEQ ID NO: 910<br>FEATURE<br>source | moltype = RNA   length = 15<br>Location/Qualifiers<br>1..15<br>mol_type = transcribed RNA<br>organism = Homo sapiens | |
| SEQUENCE: 910 | | |
| tctgggcgag gggtg | | 15 |
| SEQ ID NO: 911<br>FEATURE<br>source | moltype = RNA   length = 23<br>Location/Qualifiers<br>1..23<br>mol_type = transcribed RNA<br>organism = Homo sapiens | |
| SEQUENCE: 911 | | |
| ggtgggtgag gtcgggcccc aag | | 23 |
| SEQ ID NO: 912<br>FEATURE<br>source | moltype = RNA   length = 22<br>Location/Qualifiers<br>1..22<br>mol_type = transcribed RNA<br>organism = Homo sapiens | |
| SEQUENCE: 912 | | |
| ctgggctcgg gacgcgcggc tc | | 22 |
| SEQ ID NO: 913<br>FEATURE<br>source | moltype = RNA   length = 19<br>Location/Qualifiers<br>1..19<br>mol_type = transcribed RNA<br>organism = Homo sapiens | |
| SEQUENCE: 913 | | |
| ctgggctcgg gacgcgcgg | | 19 |
| SEQ ID NO: 914<br>FEATURE<br>source | moltype = RNA   length = 21<br>Location/Qualifiers<br>1..21<br>mol_type = transcribed RNA<br>organism = Homo sapiens | |
| SEQUENCE: 914 | | |
| ttgaggagac atggtggggg c | | 21 |
| SEQ ID NO: 915<br>FEATURE<br>source | moltype = RNA   length = 15<br>Location/Qualifiers<br>1..15<br>mol_type = transcribed RNA<br>organism = Homo sapiens | |
| SEQUENCE: 915 | | |
| ttgaggagac atggt | | 15 |
| SEQ ID NO: 916<br>FEATURE<br>source | moltype = RNA   length = 21<br>Location/Qualifiers<br>1..21<br>mol_type = transcribed RNA | |

```
                              organism = Homo sapiens
SEQUENCE: 916
aggaggcagt gggcgagcag g                                              21

SEQ ID NO: 917           moltype = RNA  length = 23
FEATURE                  Location/Qualifiers
source                   1..23
                         mol_type = transcribed RNA
                         organism = Homo sapiens
SEQUENCE: 917
tggggaaggc gtcagtgtcg ggt                                            23

SEQ ID NO: 918           moltype = RNA  length = 16
FEATURE                  Location/Qualifiers
source                   1..16
                         mol_type = transcribed RNA
                         organism = Homo sapiens
SEQUENCE: 918
tggggaaggc gtcagt                                                    16

SEQ ID NO: 919           moltype = RNA  length = 23
FEATURE                  Location/Qualifiers
source                   1..23
                         mol_type = transcribed RNA
                         organism = Homo sapiens
SEQUENCE: 919
aagggaggag gagcggaggg gcc                                            23

SEQ ID NO: 920           moltype = RNA  length = 15
FEATURE                  Location/Qualifiers
source                   1..15
                         mol_type = transcribed RNA
                         organism = Homo sapiens
SEQUENCE: 920
gggaggagga gcgga                                                     15

SEQ ID NO: 921           moltype = RNA  length = 20
FEATURE                  Location/Qualifiers
source                   1..20
                         mol_type = transcribed RNA
                         organism = Homo sapiens
SEQUENCE: 921
tgagtggggc tcccgggacg                                                20

SEQ ID NO: 922           moltype = RNA  length = 15
FEATURE                  Location/Qualifiers
source                   1..15
                         mol_type = transcribed RNA
                         organism = Homo sapiens
SEQUENCE: 922
gggcgggggg cggcg                                                     15

SEQ ID NO: 923           moltype = RNA  length = 17
FEATURE                  Location/Qualifiers
source                   1..17
                         mol_type = transcribed RNA
                         organism = Homo sapiens
SEQUENCE: 923
ggtgagcgct cgctggc                                                   17

SEQ ID NO: 924           moltype = RNA  length = 15
FEATURE                  Location/Qualifiers
source                   1..15
                         mol_type = transcribed RNA
                         organism = Homo sapiens
SEQUENCE: 924
cggtgagcgc tcgct                                                     15

SEQ ID NO: 925           moltype = RNA  length = 23
FEATURE                  Location/Qualifiers
source                   1..23
                         mol_type = transcribed RNA
                         organism = Homo sapiens
SEQUENCE: 925
cggggcagct cagtacagga tac                                            23

SEQ ID NO: 926           moltype = RNA  length = 15
FEATURE                  Location/Qualifiers
source                   1..15
```

```
                        mol_type = transcribed RNA
                        organism = Homo sapiens
SEQUENCE: 926
agctcagtac aggat                                                     15

SEQ ID NO: 927          moltype = RNA   length = 26
FEATURE                 Location/Qualifiers
source                  1..26
                        mol_type = transcribed RNA
                        organism = Homo sapiens
SEQUENCE: 927
agggctggac tcagcggcgg agctgg                                         26

SEQ ID NO: 928          moltype = RNA   length = 17
FEATURE                 Location/Qualifiers
source                  1..17
                        mol_type = transcribed RNA
                        organism = Homo sapiens
SEQUENCE: 928
gcggcggagc tggctgc                                                   17

SEQ ID NO: 929          moltype = RNA   length = 15
FEATURE                 Location/Qualifiers
source                  1..15
                        mol_type = transcribed RNA
                        organism = Homo sapiens
SEQUENCE: 929
gagggagtaa gagcc                                                     15

SEQ ID NO: 930          moltype = RNA   length = 24
FEATURE                 Location/Qualifiers
source                  1..24
                        mol_type = transcribed RNA
                        organism = Homo sapiens
SEQUENCE: 930
tgggggagtg cagtgattgt ggaa                                           24

SEQ ID NO: 931          moltype = RNA   length = 19
FEATURE                 Location/Qualifiers
source                  1..19
                        mol_type = transcribed RNA
                        organism = Homo sapiens
SEQUENCE: 931
tgggggagtg cagtgattg                                                 19

SEQ ID NO: 932          moltype = RNA   length = 15
FEATURE                 Location/Qualifiers
source                  1..15
                        mol_type = transcribed RNA
                        organism = Homo sapiens
SEQUENCE: 932
tgaagcgggg gggcg                                                     15

SEQ ID NO: 933          moltype = RNA   length = 16
FEATURE                 Location/Qualifiers
source                  1..16
                        mol_type = transcribed RNA
                        organism = Homo sapiens
SEQUENCE: 933
cgggcccggc gttccc                                                    16

SEQ ID NO: 934          moltype = RNA   length = 15
FEATURE                 Location/Qualifiers
source                  1..15
                        mol_type = transcribed RNA
                        organism = Homo sapiens
SEQUENCE: 934
ccgggcccgg cgttc                                                     15

SEQ ID NO: 935          moltype = RNA   length = 23
FEATURE                 Location/Qualifiers
source                  1..23
                        mol_type = transcribed RNA
                        organism = Homo sapiens
SEQUENCE: 935
ctagtggaag aagatggcgg aag                                            23

SEQ ID NO: 936          moltype = RNA   length = 15
FEATURE                 Location/Qualifiers
```

```
source                  1..15
                        mol_type = transcribed RNA
                        organism = Homo sapiens
SEQUENCE: 936
tagtggaaga agatg                                                      15

SEQ ID NO: 937          moltype = RNA   length = 16
FEATURE                 Location/Qualifiers
source                  1..16
                        mol_type = transcribed RNA
                        organism = Homo sapiens
SEQUENCE: 937
gtgaaggccc ggcgga                                                     16

SEQ ID NO: 938          moltype = RNA   length = 15
FEATURE                 Location/Qualifiers
source                  1..15
                        mol_type = transcribed RNA
                        organism = Homo sapiens
SEQUENCE: 938
gtgaaggccc ggcgg                                                      15

SEQ ID NO: 939          moltype = RNA   length = 17
FEATURE                 Location/Qualifiers
source                  1..17
                        mol_type = transcribed RNA
                        organism = Homo sapiens
SEQUENCE: 939
tgcaggggca ggccagc                                                    17

SEQ ID NO: 940          moltype = RNA   length = 23
FEATURE                 Location/Qualifiers
source                  1..23
                        mol_type = transcribed RNA
                        organism = Homo sapiens
SEQUENCE: 940
gggggtcccc ggtgctcgga tct                                             23

SEQ ID NO: 941          moltype = RNA   length = 16
FEATURE                 Location/Qualifiers
source                  1..16
                        mol_type = transcribed RNA
                        organism = Homo sapiens
SEQUENCE: 941
tcgggagggg cgggag                                                     16

SEQ ID NO: 942          moltype = RNA   length = 24
FEATURE                 Location/Qualifiers
source                  1..24
                        mol_type = transcribed RNA
                        organism = Homo sapiens
SEQUENCE: 942
cccaaaatgc tgggattaca ggca                                            24

SEQ ID NO: 943          moltype = RNA   length = 15
FEATURE                 Location/Qualifiers
source                  1..15
                        mol_type = transcribed RNA
                        organism = Homo sapiens
SEQUENCE: 943
gcccacctca gcctc                                                      15

SEQ ID NO: 944          moltype = RNA   length = 16
FEATURE                 Location/Qualifiers
source                  1..16
                        mol_type = transcribed RNA
                        organism = Homo sapiens
SEQUENCE: 944
ggcgcggagg gcggac                                                     16

SEQ ID NO: 945          moltype = RNA   length = 15
FEATURE                 Location/Qualifiers
source                  1..15
                        mol_type = transcribed RNA
                        organism = Homo sapiens
SEQUENCE: 945
ggcgcggagg gcgga                                                      15

SEQ ID NO: 946          moltype = RNA   length = 20
```

```
FEATURE                 Location/Qualifiers
source                  1..20
                        mol_type = transcribed RNA
                        organism = Homo sapiens
SEQUENCE: 946
aagacacatt tggagaggga                                                   20

SEQ ID NO: 947          moltype = RNA   length = 16
FEATURE                 Location/Qualifiers
source                  1..16
                        mol_type = transcribed RNA
                        organism = Homo sapiens
SEQUENCE: 947
agacacattt ggagag                                                       16

SEQ ID NO: 948          moltype = RNA   length = 27
FEATURE                 Location/Qualifiers
source                  1..27
                        mol_type = transcribed RNA
                        organism = Homo sapiens
SEQUENCE: 948
gctggggtct caggaggcag cgctctc                                           27

SEQ ID NO: 949          moltype = RNA   length = 17
FEATURE                 Location/Qualifiers
source                  1..17
                        mol_type = transcribed RNA
                        organism = Homo sapiens
SEQUENCE: 949
gctggggtct caggagg                                                      17

SEQ ID NO: 950          moltype = RNA   length = 26
FEATURE                 Location/Qualifiers
source                  1..26
                        mol_type = transcribed RNA
                        organism = Homo sapiens
SEQUENCE: 950
cggtgggatc ccgcggccgt gttttc                                            26

SEQ ID NO: 951          moltype = RNA   length = 15
FEATURE                 Location/Qualifiers
source                  1..15
                        mol_type = transcribed RNA
                        organism = Homo sapiens
SEQUENCE: 951
ggggcgccgc gggac                                                        15

SEQ ID NO: 952          moltype = RNA   length = 23
FEATURE                 Location/Qualifiers
source                  1..23
                        mol_type = transcribed RNA
                        organism = Homo sapiens
SEQUENCE: 952
ggcccggccg tgcctgaggt ttc                                               23

SEQ ID NO: 953          moltype = RNA   length = 15
FEATURE                 Location/Qualifiers
source                  1..15
                        mol_type = transcribed RNA
                        organism = Homo sapiens
SEQUENCE: 953
ggcggtggga tcccg                                                        15

SEQ ID NO: 954          moltype = RNA   length = 21
FEATURE                 Location/Qualifiers
source                  1..21
                        mol_type = transcribed RNA
                        organism = Homo sapiens
SEQUENCE: 954
gaggcgatgt ggggatgtag a                                                 21

SEQ ID NO: 955          moltype = RNA   length = 20
FEATURE                 Location/Qualifiers
source                  1..20
                        mol_type = transcribed RNA
                        organism = Homo sapiens
SEQUENCE: 955
cccagtctca tttcctcatc                                                   20
```

```
SEQ ID NO: 956          moltype = RNA   length = 25
FEATURE                 Location/Qualifiers
source                  1..25
                        mol_type = transcribed RNA
                        organism = Homo sapiens
SEQUENCE: 956
tgggcagggg cttattgtag gagtc                                                 25

SEQ ID NO: 957          moltype = RNA   length = 19
FEATURE                 Location/Qualifiers
source                  1..19
                        mol_type = transcribed RNA
                        organism = Homo sapiens
SEQUENCE: 957
tgggcagggg cttattgta                                                        19

SEQ ID NO: 958          moltype = RNA   length = 15
FEATURE                 Location/Qualifiers
source                  1..15
                        mol_type = transcribed RNA
                        organism = Homo sapiens
SEQUENCE: 958
gggtctggtg cggag                                                            15

SEQ ID NO: 959          moltype = RNA   length = 16
FEATURE                 Location/Qualifiers
source                  1..16
                        mol_type = transcribed RNA
                        organism = Homo sapiens
SEQUENCE: 959
ggacccaggg agagac                                                           16

SEQ ID NO: 960          moltype = RNA   length = 25
FEATURE                 Location/Qualifiers
source                  1..25
                        mol_type = transcribed RNA
                        organism = Homo sapiens
SEQUENCE: 960
tgcggggcta gggctaacag cagtc                                                 25

SEQ ID NO: 961          moltype = RNA   length = 15
FEATURE                 Location/Qualifiers
source                  1..15
                        mol_type = transcribed RNA
                        organism = Homo sapiens
SEQUENCE: 961
tgcggggcta gggct                                                            15

SEQ ID NO: 962          moltype = RNA   length = 23
FEATURE                 Location/Qualifiers
source                  1..23
                        mol_type = transcribed RNA
                        organism = Homo sapiens
SEQUENCE: 962
tcggctctgg gtctgtgggg agc                                                   23

SEQ ID NO: 963          moltype = RNA   length = 15
FEATURE                 Location/Qualifiers
source                  1..15
                        mol_type = transcribed RNA
                        organism = Homo sapiens
SEQUENCE: 963
gcccggatac ctcag                                                            15

SEQ ID NO: 964          moltype = RNA   length = 24
FEATURE                 Location/Qualifiers
source                  1..24
                        mol_type = transcribed RNA
                        organism = Homo sapiens
SEQUENCE: 964
ctgccctggc ccgagggacc gact                                                  24

SEQ ID NO: 965          moltype = RNA   length = 15
FEATURE                 Location/Qualifiers
source                  1..15
                        mol_type = transcribed RNA
                        organism = Homo sapiens
SEQUENCE: 965
ctgccctggc ccgag                                                            15
```

```
SEQ ID NO: 966         moltype = RNA   length = 25
FEATURE                Location/Qualifiers
source                 1..25
                       mol_type = transcribed RNA
                       organism = Homo sapiens
SEQUENCE: 966
gggtggggat tgttgcatt acttg                                              25

SEQ ID NO: 967         moltype = RNA   length = 20
FEATURE                Location/Qualifiers
source                 1..20
                       mol_type = transcribed RNA
                       organism = Homo sapiens
SEQUENCE: 967
gggtggggat ttgttgcatt                                                   20

SEQ ID NO: 968         moltype = RNA   length = 26
FEATURE                Location/Qualifiers
source                 1..26
                       mol_type = transcribed RNA
                       organism = Homo sapiens
SEQUENCE: 968
agggacggga cgcggtgcag tgttgt                                            26

SEQ ID NO: 969         moltype = RNA   length = 15
FEATURE                Location/Qualifiers
source                 1..15
                       mol_type = transcribed RNA
                       organism = Homo sapiens
SEQUENCE: 969
ggcgggcggg aggga                                                        15

SEQ ID NO: 970         moltype = RNA   length = 25
FEATURE                Location/Qualifiers
source                 1..25
                       mol_type = transcribed RNA
                       organism = Homo sapiens
SEQUENCE: 970
aaggcagggc ccccgctccc cgggc                                             25

SEQ ID NO: 971         moltype = RNA   length = 15
FEATURE                Location/Qualifiers
source                 1..15
                       mol_type = transcribed RNA
                       organism = Homo sapiens
SEQUENCE: 971
gtgtgttgag gaagg                                                        15

SEQ ID NO: 972         moltype = RNA   length = 22
FEATURE                Location/Qualifiers
source                 1..22
                       mol_type = transcribed RNA
                       organism = Homo sapiens
SEQUENCE: 972
cctcacacct gcctcgcccc cc                                                22

SEQ ID NO: 973         moltype = RNA   length = 15
FEATURE                Location/Qualifiers
source                 1..15
                       mol_type = transcribed RNA
                       organism = Homo sapiens
SEQUENCE: 973
tcacacctgc ctcgc                                                        15

SEQ ID NO: 974         moltype = RNA   length = 23
FEATURE                Location/Qualifiers
source                 1..23
                       mol_type = transcribed RNA
                       organism = Homo sapiens
SEQUENCE: 974
gtgggggaga ggctgtcttg tgt                                               23

SEQ ID NO: 975         moltype = RNA   length = 15
FEATURE                Location/Qualifiers
source                 1..15
                       mol_type = transcribed RNA
                       organism = Homo sapiens
SEQUENCE: 975
```

-continued

```
gtgtggggga gaggc                                            15

SEQ ID NO: 976        moltype = RNA   length = 25
FEATURE               Location/Qualifiers
source                1..25
                      mol_type = transcribed RNA
                      organism = Homo sapiens
SEQUENCE: 976
actcggcgtg gcgtcggtcg tggta                                 25

SEQ ID NO: 977        moltype = RNA   length = 15
FEATURE               Location/Qualifiers
source                1..15
                      mol_type = transcribed RNA
                      organism = Homo sapiens
SEQUENCE: 977
actcggcgtg gcgtc                                            15

SEQ ID NO: 978        moltype = RNA   length = 27
FEATURE               Location/Qualifiers
source                1..27
                      mol_type = transcribed RNA
                      organism = Homo sapiens
SEQUENCE: 978
atcacattgc cagggatttc caaccga                               27

SEQ ID NO: 979        moltype = RNA   length = 15
FEATURE               Location/Qualifiers
source                1..15
                      mol_type = transcribed RNA
                      organism = Homo sapiens
SEQUENCE: 979
aatcacattg ccagg                                            15

SEQ ID NO: 980        moltype = RNA   length = 26
FEATURE               Location/Qualifiers
source                1..26
                      mol_type = transcribed RNA
                      organism = Homo sapiens
SEQUENCE: 980
tagcaccatt tgaaatcagt gttctt                                26

SEQ ID NO: 981        moltype = RNA   length = 15
FEATURE               Location/Qualifiers
source                1..15
                      mol_type = transcribed RNA
                      organism = Homo sapiens
SEQUENCE: 981
ctagcaccat ttgaa                                            15

SEQ ID NO: 982        moltype = RNA   length = 21
FEATURE               Location/Qualifiers
source                1..21
                      mol_type = transcribed RNA
                      organism = Homo sapiens
SEQUENCE: 982
cccaggctgg agcgagtgca g                                     21

SEQ ID NO: 983        moltype = RNA   length = 15
FEATURE               Location/Qualifiers
source                1..15
                      mol_type = transcribed RNA
                      organism = Homo sapiens
SEQUENCE: 983
agctcactgc agcct                                            15

SEQ ID NO: 984        moltype = RNA   length = 21
FEATURE               Location/Qualifiers
source                1..21
                      mol_type = transcribed RNA
                      organism = Homo sapiens
SEQUENCE: 984
aagaaggcgg tcggtctgcg g                                     21

SEQ ID NO: 985        moltype = RNA   length = 20
FEATURE               Location/Qualifiers
source                1..20
                      mol_type = transcribed RNA
                      organism = Homo sapiens
```

| | | |
|---|---|---|
| SEQUENCE: 985 ccccggggag cccggcggtg | | 20 |
| SEQ ID NO: 986 FEATURE source | moltype = RNA length = 15 Location/Qualifiers 1..15 mol_type = transcribed RNA organism = Homo sapiens | |
| SEQUENCE: 986 accccgggga gcccg | | 15 |
| SEQ ID NO: 987 FEATURE source | moltype = RNA length = 19 Location/Qualifiers 1..19 mol_type = transcribed RNA organism = Homo sapiens | |
| SEQUENCE: 987 gcaggcgagg ctgggctga | | 19 |
| SEQ ID NO: 988 FEATURE source | moltype = RNA length = 16 Location/Qualifiers 1..16 mol_type = transcribed RNA organism = Homo sapiens | |
| SEQUENCE: 988 aggcgaggct gggctg | | 16 |
| SEQ ID NO: 989 FEATURE source | moltype = RNA length = 24 Location/Qualifiers 1..24 mol_type = transcribed RNA organism = Homo sapiens | |
| SEQUENCE: 989 gtgagtggga gccggtgggg ctgg | | 24 |
| SEQ ID NO: 990 FEATURE source | moltype = RNA length = 15 Location/Qualifiers 1..15 mol_type = transcribed RNA organism = Homo sapiens | |
| SEQUENCE: 990 ggggctggag taagg | | 15 |
| SEQ ID NO: 991 FEATURE source | moltype = RNA length = 22 Location/Qualifiers 1..22 mol_type = transcribed RNA organism = Homo sapiens | |
| SEQUENCE: 991 ccccggtgtt ggggcgcgtc tg | | 22 |
| SEQ ID NO: 992 FEATURE source | moltype = RNA length = 21 Location/Qualifiers 1..21 mol_type = transcribed RNA organism = Homo sapiens | |
| SEQUENCE: 992 cccggtgttg gggcgcgtct g | | 21 |
| SEQ ID NO: 993 FEATURE source | moltype = RNA length = 20 Location/Qualifiers 1..20 mol_type = transcribed RNA organism = Homo sapiens | |
| SEQUENCE: 993 ggctggtcag atgggagtgg | | 20 |
| SEQ ID NO: 994 FEATURE source | moltype = RNA length = 26 Location/Qualifiers 1..26 mol_type = transcribed RNA organism = Homo sapiens | |
| SEQUENCE: 994 gactatagaa ctttccccct catccc | | 26 |
| SEQ ID NO: 995 FEATURE source | moltype = RNA length = 15 Location/Qualifiers 1..15 mol_type = transcribed RNA | |

| | | |
|---|---|---|
| SEQUENCE: 995 | organism = Homo sapiens | |
| aactttcccc ctcat | | 15 |
| SEQ ID NO: 996<br>FEATURE<br>source | moltype = RNA length = 25<br>Location/Qualifiers<br>1..25<br>mol_type = transcribed RNA<br>organism = Homo sapiens | |
| SEQUENCE: 996 | | |
| tgcaggcaga agtggggctg acagg | | 25 |
| SEQ ID NO: 997<br>FEATURE<br>source | moltype = RNA length = 20<br>Location/Qualifiers<br>1..20<br>mol_type = transcribed RNA<br>organism = Homo sapiens | |
| SEQUENCE: 997 | | |
| ctgcaggcag aagtggggct | | 20 |
| SEQ ID NO: 998<br>FEATURE<br>source | moltype = RNA length = 17<br>Location/Qualifiers<br>1..17<br>mol_type = transcribed RNA<br>organism = Homo sapiens | |
| SEQUENCE: 998 | | |
| tcctagtcac ggcacca | | 17 |
| SEQ ID NO: 999<br>FEATURE<br>source | moltype = RNA length = 28<br>Location/Qualifiers<br>1..28<br>mol_type = transcribed RNA<br>organism = Homo sapiens | |
| SEQUENCE: 999 | | |
| gtatggtatt gcacttgtcc cggcctgt | | 28 |
| SEQ ID NO: 1000<br>FEATURE<br>source | moltype = RNA length = 15<br>Location/Qualifiers<br>1..15<br>mol_type = transcribed RNA<br>organism = Homo sapiens | |
| SEQUENCE: 1000 | | |
| tattgcactt gtccc | | 15 |